US012180291B2

(12) United States Patent
Bender et al.

(10) Patent No.: US 12,180,291 B2
(45) **Date of Patent: *Dec. 31, 2024**

(54) ANTI-CCR7 ANTIBODY DRUG CONJUGATES

(71) Applicant: Novartis AG, Basel (CH)

(72) Inventors: Steven Bender, Oceanside, CA (US); Tracy Charlton, San Diego, CA (US); Anna Galkin, Encinitas, CA (US); Bernhard Hubert Geierstanger, Solana Beach, CA (US); Scott Martin Glaser, San Diego, CA (US); Shailaja Kasibhatla, San Diego, CA (US); Mark Knuth, El Cajon, CA (US); Sabine Rottmann, San Diego, CA (US); Sarah Rue, San Diego, CA (US); Glen Spraggon, San Diego, CA (US); Tetsuo Uno, San Diego, CA (US)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/164,519

(22) Filed: Feb. 3, 2023

(65) Prior Publication Data

US 2024/0092918 A1 Mar. 21, 2024

Related U.S. Application Data

(62) Division of application No. 16/482,173, filed as application No. PCT/IB2018/050639 on Feb. 1, 2018, now Pat. No. 11,634,497.

(51) Int. Cl.

| | |
|---|---|
| ***C07K 16/28*** | (2006.01) |
| ***A61K 39/00*** | (2006.01) |
| ***A61K 47/68*** | (2017.01) |
| ***A61P 35/00*** | (2006.01) |

(52) U.S. Cl.

CPC .... *C07K 16/2866* (2013.01); *A61K 47/68031* (2023.08); *A61K 47/68033* (2023.08); *A61K 47/6849* (2017.08); *A61P 35/00* (2018.01); *A61K 2039/505* (2013.01)

(58) Field of Classification Search

CPC ............ C07K 16/2866; A61K 47/6803; A61K 47/6849; A61K 2039/505; A61P 35/00

See application file for complete search history.

(56) References Cited

U.S. PATENT DOCUMENTS

| | | | |
|---|---|---|---|
| 5,759,804 | A | 6/1998 | Godiska et al. |
| 6,043,551 | A | 3/2000 | Seshan |
| 6,153,441 | A | 11/2000 | Appelbaum et al. |
| 8,066,996 | B2 | 11/2011 | Calleja et al. |
| 11,634,497 | B2 * | 4/2023 | Bender ............ A61K 39/39525 424/133.1 |
| 2002/0168358 | A1 | 11/2002 | Gladue et al. |
| 2002/0182624 | A1 | 12/2002 | Zlotnik |
| 2009/0123483 | A1 | 5/2009 | Munoz Calleja et al. |
| 2009/0175877 | A1 | 7/2009 | Mueller et al. |
| 2010/0285020 | A1 | 11/2010 | Aifantis et al. |
| 2011/0114651 | A1 | 5/2011 | Oltman |
| 2012/0114651 | A1 | 5/2012 | De Wildt et al. |
| 2012/0282654 | A1 * | 11/2012 | Yao .................... C07K 16/2863 435/69.6 |
| 2015/0017167 | A1 | 1/2015 | Nishiguchi et al. |
| 2015/0344580 | A1 | 12/2015 | Abbasova et al. |
| 2016/0031997 | A1 | 2/2016 | King et al. |
| 2017/0356284 | A1 * | 12/2017 | Veeningen ............ E21B 49/008 |
| 2020/0129632 | A1 | 4/2020 | Abrams et al. |

FOREIGN PATENT DOCUMENTS

| | | | |
|---|---|---|---|
| AU | 2018215701 | A1 | 7/2019 |
| AU | 2018215701 | B2 | 4/2021 |
| CN | 105007950 | A | 10/2015 |
| CN | 108064244 | A | 5/2018 |
| EP | 2623592 | A1 | 8/2013 |
| WO | 0004926 | A2 | 2/2000 |
| WO | 0009151 | A1 | 2/2000 |
| WO | 0138352 | A2 | 5/2001 |
| WO | 0210138 | A2 | 2/2002 |
| WO | 02062850 | A2 | 8/2002 |
| WO | 02067771 | A2 | 9/2002 |
| WO | 02101350 | A2 | 12/2002 |
| WO | 03047420 | A2 | 6/2003 |
| WO | 2004104574 | A2 | 12/2004 |
| WO | 2005015207 | A2 | 2/2005 |
| WO | 2006056061 | A1 | 6/2006 |

(Continued)

OTHER PUBLICATIONS

Duru, et al., Scientific Reports 2016 6:39572 (Year: 2016).*
Aatbio, et al., Product info Sheet (2016): https://www.aatbio.com/products/3-maleimidopropionic-acid-n-hydroxysuccinimide-ester-cas-55750-62-4; Accessed: Dec. 27, 2023 (Year: 2016).*
Birkenbach, et al., Epstein-Barr virus-induced genes: first lymphocyte-specific G protein-coupled peptide receptors, Journal of Virology, Apr. 1993, 2209-2220, 67(4).
Charest-Morin, et al., C—C chemokine receptor-7 mediated endocytosis of antibody cargoes into intact cells, Frontiers in Pharmacology, Sep. 24, 2013, Article 122, 4.

(Continued)

*Primary Examiner* — Julie Wu
*Assistant Examiner* — Sydney Van Druff
(74) *Attorney, Agent, or Firm* — Elizabeth T. Karnas

(57) ABSTRACT

This application discloses anti-CCR7 antibodies, antigen binding fragments thereof, and antibody drug conjugates of said antibodies or antigen binding fragments. The invention also relates to methods of treating or preventing cancer using the antibodies, antigen binding fragments, and antibody drug conjugates. Also disclosed herein are methods of making the antibodies, antigen binding fragments, and antibody drug conjugates, and methods of using the antibodies and antigen binding fragments as diagnostic reagents.

17 Claims, 16 Drawing Sheets

Specification includes a Sequence Listing.

(56) References Cited

FOREIGN PATENT DOCUMENTS

| | | | |
|---|---|---|---|
| WO | 2006099019 A2 | 9/2006 | |
| WO | 2007003216 A1 | 1/2007 | |
| WO | 2007003426 A1 | 1/2007 | |
| WO | 2007005605 A2 | 1/2007 | |
| WO | 2007041364 A2 | 4/2007 | |
| WO | 2007048022 A2 | 4/2007 | |
| WO | 2007051063 A2 | 5/2007 | |
| WO | 2008015694 A2 | 2/2008 | |
| WO | 2008034074 A2 | 3/2008 | |
| WO | 2008034076 A2 | 3/2008 | |
| WO | 2008080218 A1 | 7/2008 | |
| WO | 2009076696 A1 | 6/2009 | |
| WO | 2009139853 A2 | 11/2009 | |
| WO | 2011003833 A1 | 1/2011 | |
| WO | 2011123903 A1 | 10/2011 | |
| WO | 2012043533 A1 | 4/2012 | |
| WO | 2012088290 A2 | 6/2012 | |
| WO | 2012088302 A2 | 6/2012 | |
| WO | 2012148547 A1 | 11/2012 | |
| WO | 2012172337 A2 | 12/2012 | |
| WO | 2012172341 A2 | 12/2012 | |
| WO | 2012172343 A2 | 12/2012 | |
| WO | 2012172346 A2 | 12/2012 | |
| WO | 2012172347 A1 | 12/2012 | |
| WO | 2013014535 A1 | 1/2013 | |
| WO | 2013074044 A1 | 5/2013 | |
| WO | 2013123018 A1 | 8/2013 | |
| WO | 2013184200 A1 | 12/2013 | |
| WO | 2014093870 A2 | 6/2014 | |
| WO | 2014134483 A2 | 9/2014 | |
| WO | 2014150937 A1 | 9/2014 | |
| WO | 2014151834 A2 | 9/2014 | |
| WO | 2014153114 A1 | 9/2014 | |
| WO | 2015031698 A1 | 3/2015 | |
| WO | 2015033136 A1 | 3/2015 | |
| WO | 2015033137 A1 | 3/2015 | |
| WO | 2015036582 A2 | 3/2015 | |
| WO | 2015063187 A1 | 5/2015 | |
| WO | 2015138615 A2 | 9/2015 | |
| WO | 2015158855 A1 | 10/2015 | |
| WO | 2015177360 A1 | 11/2015 | |
| WO | 2016075670 A1 | 5/2016 | |
| WO | WO-2016067013 A1 * | 5/2016 | ......... A61K 47/6803 |
| WO | 2016179472 A2 | 11/2016 | |
| WO | 2017025569 A1 | 2/2017 | |
| WO | WO-2017134483 A1 * | 8/2017 | ......... H04B 10/5053 |
| WO | 2018142322 A1 | 8/2018 | |

OTHER PUBLICATIONS

Clinical trial NCT04240704, Jan. 27, 2020, available at https://www.clinicaltrials.gov/ct2/show/NCT04240704.

Cuesta-Mateos, et al., Preclinical activity of anti-CCR7 immunotherapy in patients with high-risk chronic lymphocytic leukemia, Cancer Immunology Immunotherapy, Feb. 28, 2015, 665-676, 64.

Itoh, et al., Presence of Three Distinct Molecular Species of G, Protein a Subunit, Strucutre of Rat cDNAs and Human Genomic DNAs, The Journal of Biological Chemistry, May 15, 1988, 6656-6664, 263(14).

Kim, et al., Strategies and Advancement in Antibody-Drug Conjugate Optimization for Targeted Cancer Therapeutics, Biomolecules and Therapeutics, Nov. 1, 2015, 493-509, 23(6).

Lo, et al., Effector-attenuating Substitutions That Maintain Antibody Stability and Reduce Toxicity in Mice, The Journal of Biological Chemistry, Mar. 3, 2017, 3900-3908, 292(9).

Sugimoto, et al., Follicular Lymphoma: The Role of the Tumor Microenvironment in Prognosis, J Clin Exp Hematop, Jun. 2016, 56.

Wilson, Anti-CCR7 antibodies for the treatment of cancer, Expert Opinion on Therapeutic Patents, Aug. 7, 2007, 871-874, 17(7).

* cited by examiner

ANTI-CCR7 ANTIBODY DRUG CONJUGATES

CROSS-REFERENCE TO RELATED APPLICATION

This application is a continuation of U.S. patent application Ser. No. 16/482,173 filed Jul. 30, 2019, which is a national phase application, filed under 35 U.S.C. 371, of the International Patent Application No. PCT/IB2018/050639 filed Feb. 1, 2018, which claims the benefit of U.S. Provisional Application No. 62/454,476 filed Feb. 3, 2017, the content of which is hereby incorporated by reference in its entirety.

SEQUENCE LISTING

The instant application contains a Sequence Listing which has been submitted electronically in XML format and is hereby incorporated by reference in its entirety. Said copy, created on Feb. 2, 2023, is named PAT057594-US-DIV_SL.xml and is 851,102 bytes in size.

FIELD OF THE INVENTION

The present invention generally relates to anti-CCR7 antibodies, antibody fragments, and immunoconjugates thereof, and their uses for the treatment or prevention of cancer.

BACKGROUND OF THE INVENTION

CC-chemokine receptor 7 (CCR7) was first identified in 1993 as a lymphocyte specific receptor (see, e.g., Birkenbach et al., J Virol. 1993 April; 67(4):2209-20). Its expression is restricted to subsets of immune cells, such as naïve T cells, central memory T cells (Tcm), regulatory T cells (Treg), naïve B cells, NK cells and mature antigen-presenting dendritic cells (DCs). CCR7 regulates homing of immune cells to and within lymphoid organs and thus plays a key role in balancing immunity and tolerance (see, e.g., Forster et al., Nat Rev Immunol. 2008 May; 8(5):362-71).

CCR7 is a class A, rhodopsin-like G-protein coupled receptor (GPCR), with two ligands, CCL21 and CCL19. The CCR7 structure has not been fully solved, however, certain motifs have been found essential for receptor activity (see, e.g., Legler et al., Int J Biochem Cell Biol. 2014 Jul. 1).

CCR7 and Cancer

CCR7 (also referred to as EBI1, BLR2, CC-CKR-7, CMKBR7, CD197 and CDw197) is also known to be overexpressed in a number of malignant tumors, including B cell malignancies (e.g., CLL, MCL, Burkitt's lymphoma), T cell malignancies (e.g., ATLL), HNSCC, ESCC, gastric carcinoma, NSCLC, colorectal carcinoma, pancreatic cancer, thyroid cancer, breast cancer, and cervical cancer, among others. The overexpression of CCR7 in, e.g., colorectal carcinoma, ESCC, pancreatic cancer, HNSCC, and gastric cancer was associated with advanced tumor stage, lymph node metastasis and poor survival (see, e.g., Malietzis et al., Journal of Surgical Oncology 2015; 112:86-92; Irino et al., BMC Cancer 2014, 14:291; Guo et al., Oncology Letters 5: 1572-1578, 2013; Xia et al., Oral Dis. 2015 January; 21(1):123-31; Du et al., Gastric Cancer. 2016 Mar. 16).

In addition, CCR7 expression in, e.g., HNSCC has been shown to play a role in resistance to chemotherapy (see, e.g., Wang et al., JNCI J Natl Cancer Inst (2008) 100 (7): 502-512.). In certain cancer types, such as pancreatic cancer and nasopharyngeal carcinoma (NPC), CCR7 is known to promote cancer stem-like cell metastasis and sphere formation (see, e.g., Zhang et al., PLOS ONE 11 (8); Lun et al., PLOS ONE 7(12)). CCR7's role in cell migration, invasiveness and EMT (epithelial-mesenchymal transition) is described in various cancer types, such as breast and pancreatic cancer in vitro and in vivo (see, e.g., Pang et al., Oncogene (2015), 1-13); Sperveslage et al., Int. J. Cancer: 131, E371-E381 (2012)). Key pathways that have been described to be essential for CCR7 signaling include b-Arrestin mediated p38/ERK1/2 and Rho signaling (see, e.g., Noor et al., J Neuroinflammation 2012 Apr. 25; 9:77).

Numerous cancer-related processes are known to induce CCR7 expression. In HNSCC, CCR7 expression is shown to be induced by NF-kB and AP1 transcription factors via direct binding to sites in the CCR7 promoter (Mburu et al., J. Biol. Chem. 2012, 287:3581-3590). In particular, CCR7 expression is regulated by various factors in the tumor microenvironment. In this context, it is known that CCR7 expression is induced via the b-Defensin 3/NF-kB pathway in HNSCC (see, e.g., Mburu et al., Carcinogenesis vol. 32 no. 2 pp. 168-174, 2010) and Endothelin Receptor A and Hypoxia-inducible factor-1 in breast tumor cells (see, e.g., Wilson et al., Cancer Res 2006; 66:11802-11807).

Antibody Drug Conjugates

Antibody drug conjugates ("ADCs") have been used for the local delivery of cytotoxic agents in the treatment of cancer (see, e.g., Lambert, Curr. Opinion In Pharmacology 5:543-549, 2005). ADCs allow targeted delivery of the drug moiety where maximum efficacy with minimal toxicity may be achieved. ADCs include an antibody selected for its ability to bind to a cell targeted for therapeutic intervention, linked to a drug selected for its cytostatic or cytotoxic activity. Binding of the antibody to the targeted cell thereby delivers the drug to the site where its therapeutic effect is needed.

Many antibodies that recognize and selectively bind to targeted cells, e.g., cancer cells, have been disclosed for use in ADCs. In spite of the extensive work on ADCs, antibody binding to a particular target of interest is not sufficient to predict success in ADC applications. Examples of factors that can effect therapeutic effectiveness of ADCs (besides target-intrinsic features) include various aspects that need customized fine-tuning, such as the optimal antibody affinity as a balance between target-mediated disposition (TMDD) and efficacy-driving exposure, evaluation of Fc-mediated functions (antibody-dependent cell-mediated cytotoxicity, ADCC), method of conjugation (site-specific or not), the ratio of the drug/payload molecules that conjugate to each antibody ("DAR" or "drug antibody ratio"), the cleavability or stability of the linker, stability of the ADC, and the tendency of an ADC to aggregate.

There remains a need for antibodies, attachment methods, and cytotoxic payloads with improved properties for use as effective ADC therapeutic compositions and methods.

SUMMARY OF THE INVENTION

The present application discloses an antibody or antigen binding fragment thereof that binds to human CCR7 protein, wherein the antibody or antigen binding fragment thereof has reduced or no significant effector function as compared to a wild-type antibody of the same isotype. In one embodiment, the antibody or antigen binding fragment thereof has a reduced or no significant level of antibody-dependent cell-mediated cytotoxicity (ADCC) activity. IN one embodiment, the antibody or antigen binding fragment thereof comprises a silenced Fc region. In some embodiments, the antibody comprises a mutation in the Fc region selected from: D265A; P329A; P329G; N297A; D265A and P329A; D265A and N297A; L234 and L235A; P329A, L234A and L235A; and P329G, L234A and L235A. In one embodiment, the antibody or antigen binding fragment thereof has no significant cell killing activity. In one embodiment, the antibody or antigen binding fragment thereof binds with greater affinity to cells expressing higher levels of CCR7 than cells expressing lower levels of CCR7. In some embodiments, the antibody or antigen binding fragment thereof binds with greater affinity to cancer cells that express higher levels of CCR7 than normal cells that express lower levels of CCR7. In some embodiments, the antibody or antigen binding fragment thereof does not significantly deplete normal hematopoietic cells that express CCR7.

In one embodiment, the present application discloses an antibody or antigen binding fragment thereof that binds CCR7 comprising:

a. a heavy chain variable region that comprises an HCDR1 (Heavy Chain Complementarity Determining Region 1) of SEQ ID NO:1, an HCDR2 (Heavy Chain Complementarity Determining Region 2) of SEQ ID NO:2, and an HCDR3 (Heavy Chain Complementarity Determining Region 3) of SEQ ID NO:3; and a light chain variable region that comprises an LCDR1 (Light Chain Complementarity Determining Region 1) of SEQ ID NO:17, an LCDR2 (Light Chain Complementarity Determining Region 2) of SEQ ID NO: 18, and an LCDR3 (Light Chain Complementarity Determining Region 3) of SEQ ID NO:19;

b. a heavy chain variable region that comprises an HCDR1 of SEQ ID NO:4, an HCDR2 of SEQ ID NO:5, and an HCDR3 of SEQ ID NO:6; and a light chain variable region that comprises an LCDR1 of SEQ ID NO: 20, an LCDR2 of SEQ ID NO:21, and an LCDR3 of SEQ ID NO:22;

c. a heavy chain variable region that comprises an HCDR1 of SEQ ID NO:7, an HCDR2 of SEQ ID NO:8, and an HCDR3 of SEQ ID NO:9; and a light chain variable region that comprises an LCDR1 of SEQ ID NO: 23, an LCDR2 of SEQ ID NO:24, and an LCDR3 of SEQ ID NO:25;

d. a heavy chain variable region that comprises an HCDR1 of SEQ ID NO:10, an HCDR2 of SEQ ID NO:11, and an HCDR3 of SEQ ID NO:12; and a light chain variable region that comprises an LCDR1 of SEQ ID NO:26, an LCDR2 of SEQ ID NO:27, and an LCDR3 of SEQ ID NO:28;

e. a heavy chain variable region that comprises an HCDR1 of SEQ ID NO:33, an HCDR2 of SEQ ID NO:34, and an HCDR3 of SEQ ID NO:35; and a light chain variable region that comprises an LCDR1 of SEQ ID NO:49, an LCDR2 of SEQ ID NO:50, and an LCDR3 of SEQ ID NO:51;

f. a heavy chain variable region that comprises an HCDR1 of SEQ ID NO:36, an HCDR2 of SEQ ID NO:37, and an HCDR3 of SEQ ID NO:38; and a light chain variable region that comprises an LCDR1 of SEQ ID NO:52, an LCDR2 of SEQ ID NO:53, and an LCDR3 of SEQ ID NO:54;

g. a heavy chain variable region that comprises an HCDR1 of SEQ ID NO:39, an HCDR2 of SEQ ID NO:40, and an HCDR3 of SEQ ID NO:41; and a light chain variable region that comprises an LCDR1 of SEQ ID NO:55, an LCDR2 of SEQ ID NO:56, and an LCDR3 of SEQ ID NO:57;

h. a heavy chain variable region that comprises an HCDR1 of SEQ ID NO:42, an HCDR2 of SEQ ID NO:43, and an HCDR3 of SEQ ID NO:44; and a light chain variable region that comprises an LCDR1 of SEQ ID NO:58, an LCDR2 of SEQ ID NO:59, and an LCDR3 of SEQ ID NO:60;

i. a heavy chain variable region that comprises an HCDR1 of SEQ ID NO:65, an HCDR2 of SEQ ID NO:66, and an HCDR3 of SEQ ID NO:67; and a light chain variable region that comprises an LCDR1 of SEQ ID NO:81, an LCDR2 of SEQ ID NO:82, and an LCDR3 of SEQ ID NO:83;

j. a heavy chain variable region that comprises an HCDR1 of SEQ ID NO:68, an HCDR2 of SEQ ID NO:69, and an HCDR3 of SEQ ID NO:70; and a light chain variable region that comprises an LCDR1 of SEQ ID NO:84, an LCDR2 of SEQ ID NO:85, and an LCDR3 of SEQ ID NO:86;

k. a heavy chain variable region that comprises an HCDR1 of SEQ ID NO:71, an HCDR2 of SEQ ID NO:72, and an HCDR3 of SEQ ID NO:73; and a light chain variable region that comprises an LCDR1 of SEQ ID NO:87, an LCDR2 of SEQ ID NO:88, and an LCDR3 of SEQ ID NO:89;

l. a heavy chain variable region that comprises an HCDR1 of SEQ ID NO:74, an HCDR2 of SEQ ID NO:75, and an HCDR3 of SEQ ID NO:76; and a light chain variable region that comprises an LCDR1 of SEQ ID NO:90, an LCDR2 of SEQ ID NO:91, and an LCDR3 of SEQ ID NO:92;

m. a heavy chain variable region that comprises an HCDR1 of SEQ ID NO:596, an HCDR2 of SEQ ID NO:597, and an HCDR3 of SEQ ID NO:598; and a light chain variable region that comprises an LCDR1 of SEQ ID NO:612, an LCDR2 of SEQ ID NO:613, and an LCDR3 of SEQ ID NO: 614;

n. a heavy chain variable region that comprises an HCDR1 of SEQ ID NO:599, an HCDR2 of SEQ ID NO:600, and an HCDR3 of SEQ ID NO: 601; and a light chain variable region that comprises an LCDR1 of SEQ ID NO:615, an LCDR2 of SEQ ID NO:616, and an LCDR3 of SEQ ID NO: 617;

o. a heavy chain variable region that comprises an HCDR1 of SEQ ID NO:602, an HCDR2 of SEQ ID NO:603, and an HCDR3 of SEQ ID NO: 604; and a light chain variable region that comprises an LCDR1 of SEQ ID NO:618, an LCDR2 of SEQ ID NO:619, and an LCDR3 of SEQ ID NO: 620; or p. a heavy chain variable region that comprises an HCDR1 of SEQ ID NO:605, an HCDR2 of SEQ ID NO:606, and an HCDR3 of SEQ ID NO: 607; and a light chain variable region that comprises an LCDR1 of SEQ ID NO:621, an LCDR2 of SEQ ID NO:622, and an LCDR3 of SEQ ID NO: 623.

An antibody or antigen binding fragment thereof that binds CCR7 of the present application may also comprise:

a. A heavy chain variable region (VH) comprising the amino acid sequence of SEQ ID NO:13, and a light chain variable region (VL) comprising the amino acid sequence of SEQ ID NO:29;

b. A heavy chain variable region (VH) comprising the amino acid sequence of SEQ ID NO:45, and a light chain variable region (VL) comprising the amino acid sequence of SEQ ID NO:61;

c. A heavy chain variable region (VH) comprising the amino acid sequence of SEQ ID NO:77, and a light chain variable region (VL) comprising the amino acid sequence of SEQ ID NO:93; or d. A heavy chain variable region (VH) comprising the amino acid sequence of SEQ ID NO:608, and a light chain variable region (VL) comprising the amino acid sequence of SEQ ID NO:624.

In another embodiment, the antibody or antigen binding fragment thereof that binds CCR7 comprises:

a. A heavy chain comprising the amino acid sequence of SEQ ID NO:15, and a light chain comprising the amino acid sequence of SEQ ID NO:31;

b. A heavy chain comprising the amino acid sequence of SEQ ID NO:47, and a light chain comprising the amino acid sequence of SEQ ID NO:63;

c. A heavy chain comprising the amino acid sequence of SEQ ID NO:79, and a light chain comprising the amino acid sequence of SEQ ID NO:95; or d. A heavy chain comprising the amino acid sequence of SEQ ID NO:610, and a light chain comprising the amino acid sequence of SEQ ID NO:626.

The antibody or antigen binding fragment thereof as described herein may comprise one or more cysteine substitutions. In one embodiment, the antibody or antigen binding fragment thereof comprises one or more cysteine substitutions selected from S152C, S375C, or both S152C and S375C of the heavy chain of the antibody or antigen binding fragment thereof, wherein the position is numbered according to the EU system. An antibody as disclosed herein can be a monoclonal antibody.

The present application discloses an antibody drug conjugate comprising the formula:

$$Ab\text{-}(L\text{-}(D)_m)_n$$

or a pharmaceutically acceptable salt thereof; wherein

Ab is an antibody or antigen binding antigen binding fragment thereof as disclosed herein;

L is a linker;

D is a drug moiety;

m is an integer from 1 to 8; and n is an integer from 1 to 12.

In some embodiments, m is 1. In one embodiment, n is about 3 to about 4. In one embodiment, the linker is selected from the group consisting of a cleavable linker, a non-cleavable linker, a hydrophilic linker, a procharged linker, and a dicarboxylic acid based linker.

In one embodiment, the linker is derived from a cross-linking reagent selected from the group consisting of N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl) aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC), and 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

In other embodiments, the linker has the following Formula (IIA):

(IIA)

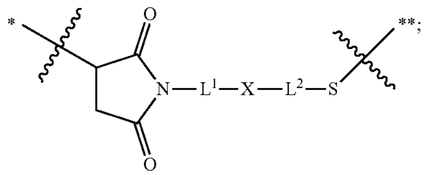

wherein * is linked to the thiol functionality on the antibody, and ** is linked to the thiol functionality of a drug moiety; and wherein:

$L^1$ is a $C_{1-6}$alkylene wherein one of the methylene groups may be replaced with oxygen;

$L^2$ is a $C_{1-6}$alkylene or is $—(CH_2CH_2O)_y—CH_2—CH_2—$ wherein y is 1 to 11;

X is —C(O)—NH—, —NHC(O)— or a triazole; and alkylene is linear or branched.

In another embodiment, the linker has the following Formula:

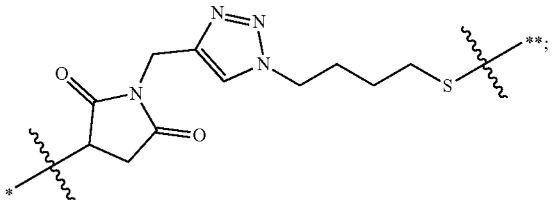

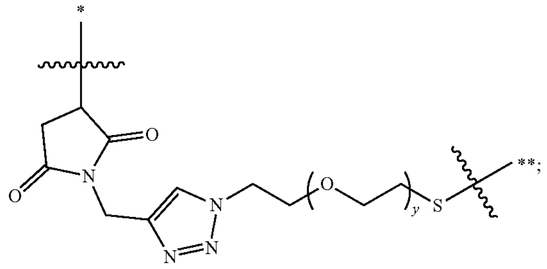

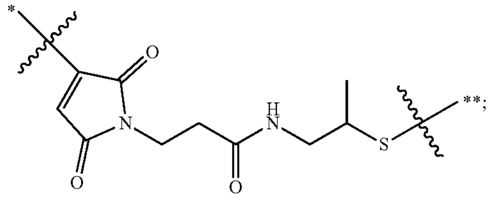

-continued

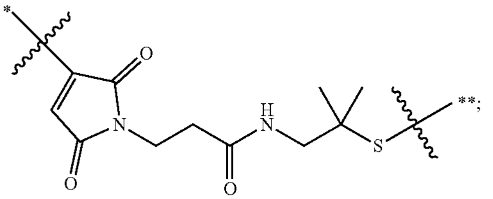

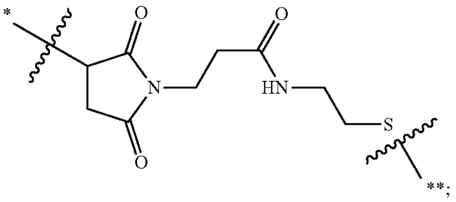

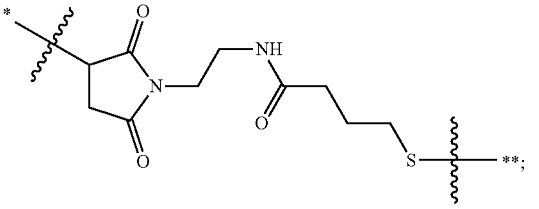

and

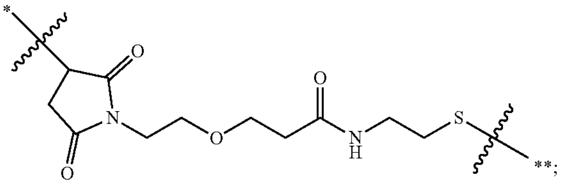

wherein y is 1 to 11; * is linked to the thiol functionality on the antibody, and ** is linked to the thiol functionality of the drug moiety.

In one embodiment, the drug moiety is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, an amanitin, a pyrrolobenzodiazepine, an RNA polymerase inhibitor, a dolastatin, a maytansinoid, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor. In some embodiments, the cytotoxic agent is a maytansinoid, wherein the maytansinoid is N(2')-deacetyl-N(2')-(3-mercapto-1-oxopropyl)-maytansine (DM1), N(2')-deacetyl-N(2')-(4-mercapto-1-oxopentyl)-maytansine (DM3) or N(2')-deacetyl-N2-(4-mercapto-4-methyl-1-oxopentyl)-maytansine (DM4).

In one embodiment, the antibody drug conjugates disclosed herein comprise the following formula (VIII):

(VIII)

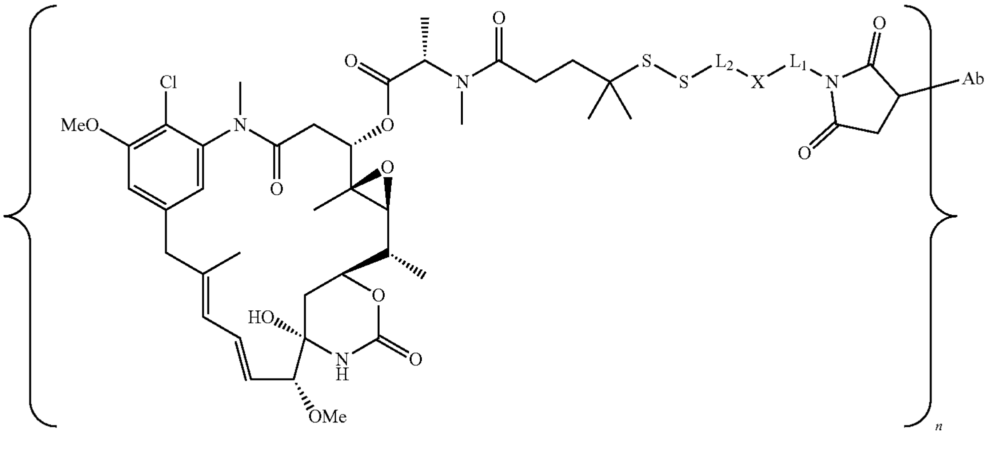

Ab-Maleimido linker-DM4 wherein $L^1$ is a $C_{1-6}$alkylene wherein one of the methylene groups may be replaced with oxygen;

$L^2$ is a $C_{1-6}$alkylene or is $-(CH_2CH_2O)_y-CH_2-CH_2-$ wherein y is 1 to 11;

X is $-C(O)-NH-$, $-NHC(O)-$ or a triazole; and alkylene is linear or branched; and wherein n is about 3 to about 4; or a pharmaceutically acceptable salt thereof In one embodiment, the antibody drug conjugates disclosed herein have the following formula:

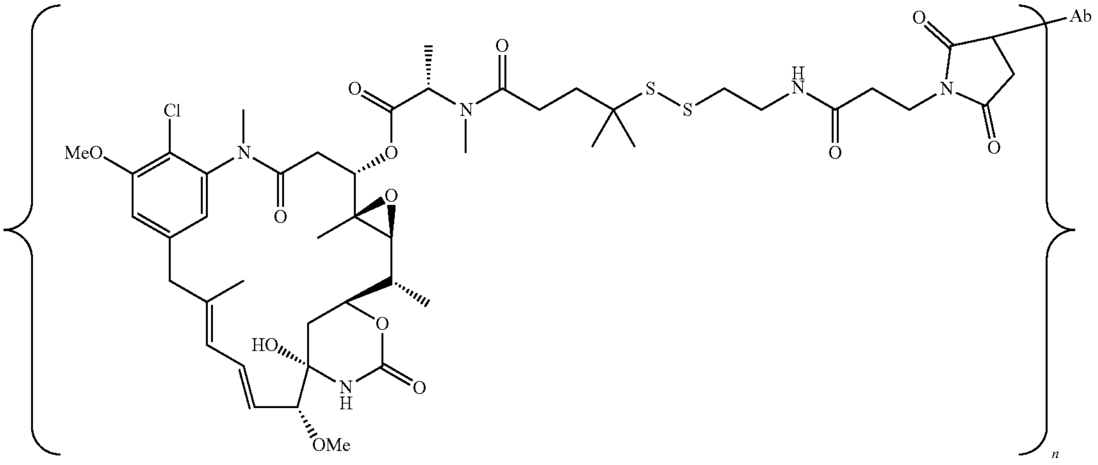

Ab-MPET-DM4 wherein n is about 3 to about 4, and Ab is an antibody comprising a heavy chain comprising the amino acid sequence of SEQ ID NO:47, and a light chain comprising the amino acid sequence of SEQ ID NO:63; or a pharmaceutically acceptable salt thereof.

The present application also discloses pharmaceutical composition comprising the antibodies, or antigen binding fragments thereof, disclosed herein and a pharmaceutically acceptable carrier. The present application also discloses pharmaceutical composition comprising the antibody drug conjugates as disclosed herein.

The present application also discloses methods of treating or preventing cancer in a patient in need thereof, comprising administering to said patient the antibody drug conjugates or the pharmaceutical compositions disclosed herein, wherein the cancer expresses CCR7.

In some embodiments of the methods of treatment or preventing cancer, the antibody drug conjugate or pharmaceutical composition are administered to the patient in combination with one or more additional therapeutic compounds. In one embodiment, the one or more additional therapeutic compounds is selected from a standard of care chemotherapeutic, a costimulatory molecule, or a checkpoint inhibitor. In one embodiment, the costimulatory molecule is selected from an agonist of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, STING, or CD83 ligand. In another embodiment, the checkpoint inhibitor is selected from an inhibitor of PD-1, PD-L1, PD-L2, CTLA4, TIM3, LAG3, VISTA, BTLA, TIGIT, LAIR1, CD160, 2B4 and/or TGFR beta.

The present application also discloses the antibody drug conjugates or the pharmaceutical compositions disclosed herein, for use as a medicament. In one embodiment, the antibody drug conjugates or the pharmaceutical compositions disclosed herein, are for use in the treatment or prevention of a CCR7 expressing cancer in a patient in need thereof.

In one embodiment, the application discloses use of the antibodies or antigen binding fragments thereof, the antibody drug conjugates, or the pharmaceutical composition as disclosed herein, to treat or prevent a CCR7 expressing cancer in a patient in need thereof.

In one embodiment, the application discloses use of the antibodies or antigen binding fragments thereof, the antibody drug conjugates, or the pharmaceutical compositions as disclosed herein, in the manufacture of a medicament.

In one embodiment, the cancer is selected from the group consisting of chronic lymphocytic leukemia (CLL), peripheral T cell lymphomas (PTCL) such as adult T-cell leukemia/lymphoma (ATLL) and anaplastic large-cell lymphoma (ALCL), Non-Hodgkin's lymphoma (NHL) such as mantle cell lymphoma (MCL), Burkitt's lymphoma and diffuse large B-cell lymphoma (DLBCL), gastric carcinoma, non-small cell lung cancer, small cell lung cancer, head and neck cancer, nasopharyngeal carcinoma (NPC), esophageal cancer, colorectal carcinoma, pancreatic cancer, thyroid cancer, breast cancer, renal cell cancer, and cervical cancer. In specific embodiments, the cancer is selected from the group consisting of chronic lymphocytic leukemia (CLL), peripheral T cell lymphomas (PTCL) such as adult T-cell leukemia/lymphoma (ATLL) and anaplastic large-cell lymphoma (ALCL), Non-Hodgkin's lymphoma (NHL) such as mantle cell lymphoma (MCL), Burkitt's lymphoma and diffuse large B-cell lymphoma (DLBCL), and non-small cell lung cancer.

The present application also discloses nucleic acids that encodes the antibodies or antigen binding fragments as disclosed herein. In one embodiment, the nucleic acid comprises the nucleotide sequence of SEQ ID NOs: 14, 16, 30, 32, 46, 48, 62, 64, 78, 80, 94, 96, 481, 483, 497, or 499. This application also discloses vectors comprising the nucleic acids, and host cells comprising the vectors or nucleic acids. This application also discloses a process for producing the antibodies or antigen binding fragments disclosed herein comprising cultivating the host cell and recovering the antibody from cell culture. In one embodiment, the process of recovering the antibody from cell culture comprises the steps of:

a) removing cells and filtering the culture;
b) purifying the culture by affinity chromatography;
c) inactivating any viruses in the culture by adjusting the pH to 3.4-3.6, then readjusting the pH to 5.8-6.2 and filtering the culture;
d) purifying the culture by cation exchange chromatography and performing on-column reduction of the culture;

e) performing anion exchange chromatography on the culture;

f) removing viruses by nanofiltration;

g) filtering the culture containing the antibody; and h) obtaining purified antibody.

In yet another embodiment, disclosed herein is a process for producing an anti-CCR7 antibody drug conjugate comprising:

(a) pre-forming a linker-drug moiety of the following Formula:

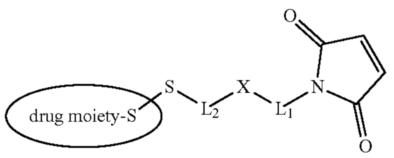

wherein:

the drug moiety is DM1, DM3 or DM4 and the drug moiety is attached to the linker via its thiol functionality;

$L^1$ is a $C_{1-6}$alkylene wherein one of the methylene groups may be replaced with oxygen;

$L^2$ is a $C_{1-6}$alkylene or is $-(CH_2CH_2O)_y-CH_2-CH_2-$ wherein y is 1 to 11;

X is —C(O)—NH—, —NHC(O)— or a triazole; and alkylene is linear or branched;

(b) conjugating said linker-drug moiety to the antibody recovered from the cell culture disclosed herein to produce an antibody drug conjugate; and (c) purifying the antibody drug conjugate.

In one embodiment, the process comprises:

(a) pre-forming a linker-drug moiety of the following Formula:

and (b) conjugating said linker-drug moiety to the antibody recovered from the cell culture disclosed herein to produce an antibody drug conjugate; and (c) purifying the antibody drug conjugate.

In another embodiment, the process for producing an anti-CCR7 antibody drug conjugate comprises:

(a) pre-forming a linker-drug moiety of the following Formula:

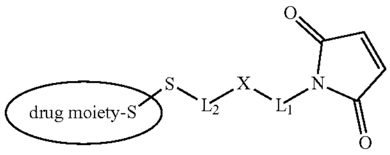

wherein:

the drug moiety is DM1, DM3 or DM4 and the drug moiety is attached to the linker via its thiol functionality;

$L^1$ is a $C_{1-6}$alkylene wherein one of the methylene groups may be replaced with oxygen;

$L^2$ is a $C_{1-6}$alkylene or is $-(CH_2CH_2O)_y-CH_2-CH_2-$ wherein y is 1 to 11;

X is —C(O)—NH—, —NHC(O)— or a triazole; and alkylene is linear or branched;

(b) conjugating said linker-drug moiety to an antibody as disclosed herein to produce an antibody drug conjugate; and (c) purifying the antibody drug conjugate.

In another embodiment, the process for producing an anti-CCR7 antibody drug conjugate comprises:

(a) pre-forming a linker-drug moiety of the following Formula:

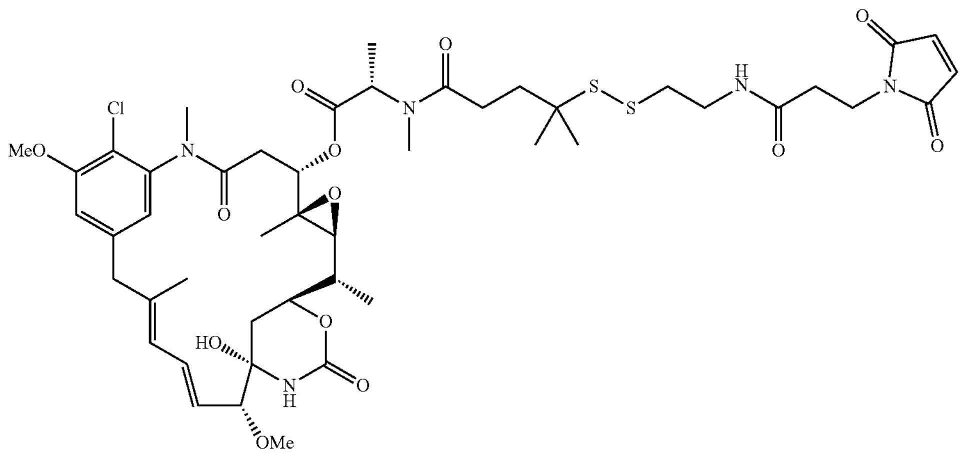 [SMILES: COc1cc2cc(c1Cl)N(C)C(=O)C[C@H](OC(=O)[C@H](C)N(C)C(=O)CCC(C)(C)SSCCNC(=O)CCN1C(=O)C=CC1=O)[C@]1(C)O[C@H]1[C@H](C)[C@@H]1C[C@@](O)(NC(=O)O1)[C@H](OC)/C=C/C=C(\C)C2]

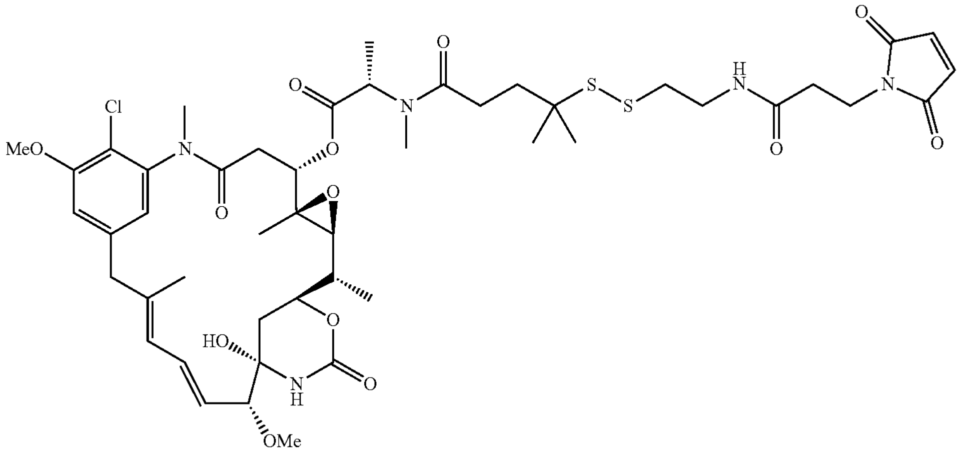 [SMILES: COc1cc2cc(c1Cl)N(C)C(=O)C[C@H](OC(=O)[C@H](C)N(C)C(=O)CCC(C)(C)SSCCNC(=O)CCN1C(=O)C=CC1=O)[C@]1(C)O[C@H]1[C@H](C)[C@@H]1C[C@@](O)(NC(=O)O1)[C@H](OC)/C=C/C=C(\C)C2]

(b) conjugating said linker-drug moiety to an antibody or antigen binding fragment thereof as disclosed herein, to produce an antibody drug conjugate; and (c) purifying the antibody drug conjugate.

In another embodiment, the step of pre-forming said linker-drug moiety comprises:

a) Reacting a drug moiety via its thiol functionality with:

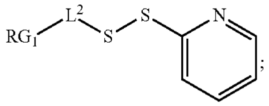

to form:

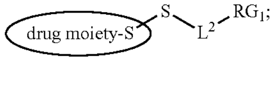

b) Reacting the formed

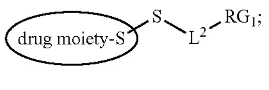

with:

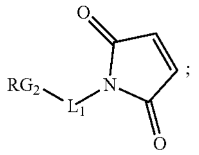

to form the linker-drug moiety:

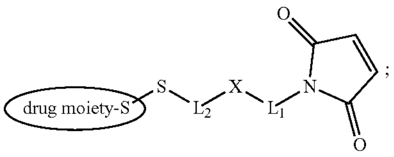

wherein:

$L^1$ is a $C_{1-6}$alkylene wherein one of the methylene groups may be replaced with oxygen;

$L^2$ is a $C_{1-6}$alkylene or is $-(CH_2CH_2O)_y-CH_2-CH_2-$ wherein y is 1 to 11; and X is —C(O)—NH—, —NHC(O)— or a triazole;

wherein the alkylene is linear or branched; and

RG1 and RG2 are 2 reactive groups forming group X.

In another embodiment, the step of pre-forming said linker-drug moiety comprises:

a) Reacting the drug moiety via its thiol functionality with:

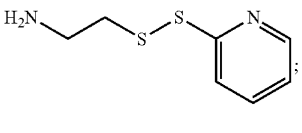 [SMILES: NCCSSc1ccccn1]

to form:
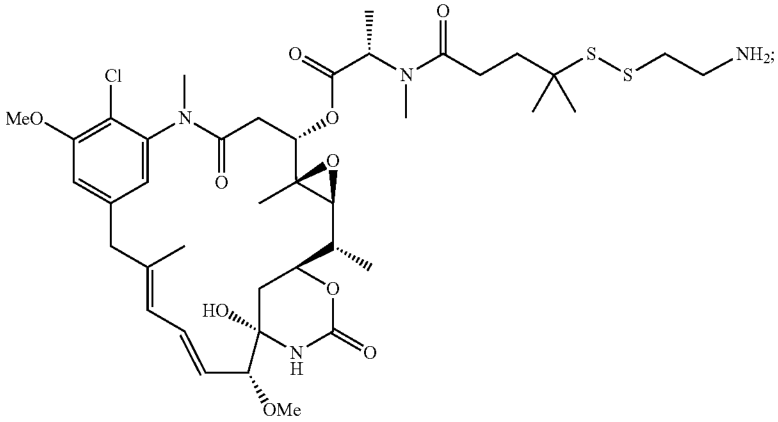 [SMILES: COc1cc2cc(c1Cl)N(C)C(=O)C[C@H](OC(=O)[C@H](C)N(C)C(=O)CCC(C)(C)SSCCN)[C@]1(C)O[C@H]1[C@H](C)[C@@H]1C[C@@](O)(NC(=O)O1)[C@H](OC)/C=C/C=C(\C)C2]
b) Reacting the formed
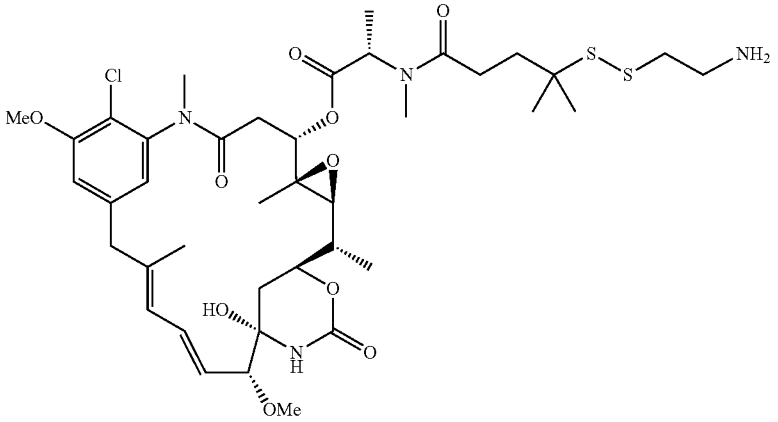 [SMILES: COc1cc2cc(c1Cl)N(C)C(=O)C[C@H](OC(=O)[C@H](C)N(C)C(=O)CCC(C)(C)SSCCN)[C@]1(C)O[C@H]1[C@H](C)[C@@H]1C[C@@](O)(NC(=O)O1)[C@H](OC)/C=C/C=C(\C)C2]
with:
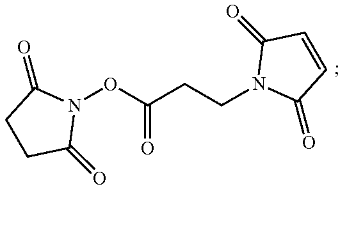 [SMILES: O=C(CCN1C(=O)C=CC1=O)ON1C(=O)CCC1=O]

to form the linker-drug moiety:

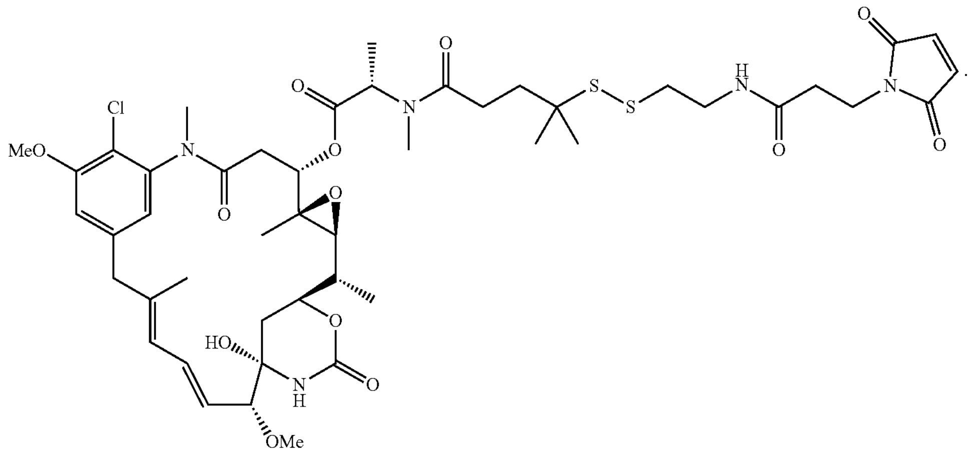 [SMILES: COc1cc2cc(c1Cl)N(C)C(=O)C[C@H](OC(=O)[C@H](C)N(C)C(=O)CCC(C)(C)SSCCNC(=O)CCN1C(=O)C=CC1=O)[C@]1(C)O[C@H]1[C@H](C)[C@@H]1C[C@@](O)(NC(=O)O1)[C@H](OC)/C=C/C=C(\C)C2]

In some embodiment, an antibody drug conjugate made according to above processes has an average DAR, measured with a UV spectrophotometer, of about 3 to about 4.

In another embodiment, this application discloses a process for producing an anti-CCR7 antibody drug conjugate comprising:

(a) chemically linking SMCC or MPET to a drug moiety DM-1 or DM-4 to form a linker-drug;

(b) conjugating said linker-drug to an antibody or antigen binding fragment thereof as disclosed herein; and (c) purifying the antibody drug conjugate.

In one embodiment, the antibody drug conjugate made according this process has an average DAR, measured with a UV spectrophotometer, of about 3 to about 4.

The present application also discloses a diagnostic reagent comprising an antibody or antigen binding fragment thereof as disclosed herein. In some embodiments, the antibody or antigen binding fragment thereof is labeled with a radiolabel, a fluorophore, a chromophore, an imaging agent, or a metal ion.

DETAILED DESCRIPTION OF THE INVENTION

Definitions

Figure 1:
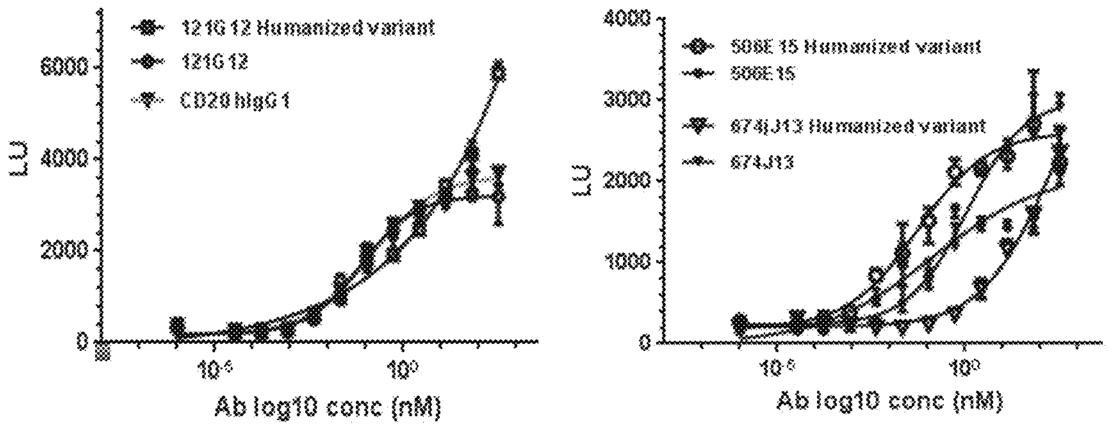
FIG. 1 depicts experimental data on in vitro ADCC activity of non-humanized and humanized anti-CCR7 antibodies in CysMab format using a surrogate ADCC reporter assay.

Unless stated otherwise, the following terms and phrases as used herein are intended to have the following meanings:

The term "alkyl" refers to a monovalent saturated hydrocarbon chain having the specified number of carbon atoms. For example, $C_{1-6}$ alkyl refers to an alkyl group having from 1 to 6 carbon atoms. Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl. The term "alkylene" is the bivalent form of "alkyl".

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" includes, but is not limited to, monoclonal antibodies, human antibodies, humanized antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementary-determining regions ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W. H. Freeman & Co., New York, 2000).

The positions of the CDRs and framework regions can be determined using various well known definitions in the art, e.g., Kabat, Chothia, international ImMunoGeneTics database (IMGT) (on the worldwide web at www.imgt.org/), and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), camelid antibodies, disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, single domain antibodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000). Also included are antibodies derived from human sequences wherein one or more CDRs has been mutated for affinity maturation or for manufacturing/payload conjugation purposes. See Kilpatrick et al., "Rapid development of affinity matured monoclonal antibodies using RIMMS," *Hybridoma.* 1997 August; 16(4):381-9.

The human antibodies of the invention may include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the invention specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)).

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementarity determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91, 92%, 93%, 94%, 95%, 96%, 97%, 98%, 99%, or 100% sequence identity with the reference variable region nucleic acid or amino acid sequence. Corresponding human germline sequences can be determined, for example, through the publicly available international ImMunoGeneTics database (IMGT) (on the worldwide web at www.imgt.org/) and V-base (on the worldwide web at vbase.mrc-cpe.cam.ac.uk).

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one embodiment, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some embodiments, antibodies or antibody fragments are selected that cross-react with certain desired molecules.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least 10 to 100 times over the background.

The term "equilibrium dissociation constant (KD, M)" refers to the dissociation rate constant (kd, time−1) divided by the association rate constant (ka, time−1, M−1). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than an antibody drug conjugate of the invention. In some embodiments, the phrase "consisting essentially of" expressly excludes the inclusion of one or more additional active agents other than an antibody drug conjugate of the invention and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17 (1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453 (1970) algorithm which has been incorporated into the GAP program in the GCG software package (available at www.gcg.com), using either a BLOSUM62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "antibody drug conjugate" or "immunoconjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the antibody drug conjugate. Additionally, the antibody drug conjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "cytotoxin", or "cytotoxic agent" as used herein, refers to any agent that is detrimental to the growth and proliferation of cells and may act to reduce, inhibit, or destroy a cell or malignancy.

The term "anti-cancer agent" as used herein refers to any agent that can be used to treat or prevent a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein refers to a chemical moiety that is conjugated to an antibody or antigen binding fragment of the invention, and can include any therapeutic or diagnostic agent, for example, an anti-cancer, anti-inflammatory, anti-infective (e.g., anti-fungal, antibacterial, anti-parasitic, anti-viral), or an anesthetic agent. For example, the drug moiety can be an anti-cancer agent, such as a cytotoxin. In certain embodiments, a drug moiety is selected from a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an RNA polymerase inhibitor, a pyrrolobenzodiazepine (PBD), an amanitin, an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Methods for attaching each of these to a linker compatible with the antibodies and method of the invention are known in the art. See, e.g., Singh et al., (2009) Therapeutic Antibodies: Methods and Protocols, vol. 525, 445-457. In addition, a payload can be a biophysical probe, a fluorophore, a spin label, an infrared probe, an affinity probe, a chelator, a spectroscopic probe, a radioactive probe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide.

The term "maytansinoid drug moiety" means the substructure of an antibody-drug conjugate that has the structure of a maytansinoid compound. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and maytansinol analogues have been reported. See U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, and Kawai et al., (1984) Chem. Pharm. Bull. 3441-3451), each of which are expressly incorporated by reference. Examples of specific maytansinoids useful for conjugation include DM1, DM3 and DM4.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. For example, anti-tumor activity can be shown by a decline in growth rate of abnormal cells that arises during therapy or tumor size stability or reduction, or longer survival due to therapy as compared to control without therapy. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

The term "CCR7" (also known as BLR2, CC-CKR-7, CCR-7, CD197, CDw197, CMKBR7, EBI1, or C—C motif chemokine receptor 7) refers to a member of the G protein-coupled receptor family. The nucleic acid and amino acid sequence of human CCR7 have been published in GenBank with the following Accession Nos.: NP_001829, NP_001288643, NP_001288645, NP_001288646, NP_001288647 (amino acid sequences), and NM_001838, NM_001301714, NM_001301716, NM_001301717, NM_001301718 (nucleotide sequences). As used herein, the term "CCR7" is used to refer collectively to all naturally occurring isoforms of CCR7 protein, or a variant thereof.

The term "variant" refers to a polypeptide that has a substantially identical amino acid sequence to a reference polypeptide, or is encoded by a substantially identical nucleotide sequence, and is capable of having one or more activities of the reference polypeptide. For example, a variant can have about 85%, 90%, 91%, 92%, 93%, 94%, 95%, 96%, 97%, 98%, 99% or higher sequence identity to a reference polypeptide, while retain one or more activities of the reference polypeptide.

As used herein, the terms "treat," "treating," or "treatment" of any disease or disorder refers in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both.

As used herein, the term "prevent", "preventing" or "prevention" of any disease or disorder refers to the prophylactic treatment of the disease or disorder; or delaying the onset or progression of the disease or disorder The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some embodiments, a therapeutically acceptable amount does not induce or cause undesirable side effects. In some embodiments, a therapeutically acceptable amount induces or causes side effects but only those that are acceptable by the healthcare providers in view of a patient's condition. A therapeutically acceptable amount can be determined by first administering a low dose, and then incrementally increasing that dose until the desired effect is achieved. A "prophylactically effective dosage," and a "therapeutically effective dosage," of the molecules of the invention can prevent the onset of, or result in a decrease in severity of, respectively, disease symptoms, including symptoms associated with cancer.

The term "co-administer" refers to the presence of two active agents in the blood of an individual. Active agents that are co-administered can be concurrently or sequentially delivered.

The present invention provides antibodies, antibody fragments (e.g., antigen binding fragments), and drug conjugates thereof, i.e., antibody drug conjugates or ADCs, that bind to CCR7. In particular, the present invention provides antibodies and antibody fragments (e.g., antigen binding fragments) that bind to CCR7, and internalize upon such binding. The antibodies and antibody fragments (e.g., antigen binding fragments) of the present invention can be used for producing antibody drug conjugates. Furthermore, the present invention provides antibody drug conjugates that have desirable pharmacokinetic characteristics and other desirable attributes, and thus can be used for treating or preventing a cancer expressing CCR7. The present invention further provides pharmaceutical compositions comprising the antibody drug conjugates of the invention, and methods of making and using such pharmaceutical compositions for the treatment or prevention of cancer.

Antibody Drug Conjugates

The present invention provides antibody drug conjugates also referred to as immunoconjugates, where an antibody, antigen binding fragment or its functional equivalent that specifically binds to CCR7 is linked to a drug moiety. In one aspect, the antibodies, antigen binding fragments or their functional equivalents of the invention are linked, via covalent attachment by a linker, to a drug moiety that is an anti-cancer agent. The antibody drug conjugates of the invention can deliver an effective dose of an anti-cancer agent (e.g., a cytotoxic agent) to tumor tissues expressing CCR7, whereby greater selectivity (and lower efficacious dose) may be achieved.

In one aspect, the invention provides an immunoconjugate of Formula (I):

$$Ab\text{-}(L\text{-}(D)_m)_n$$

Wherein Ab represents CCR7 binding antibody described herein;

L is a linker;

D is a drug moiety;

m is an integer from 1 to 8; and n is an integer from 1-20. In one embodiment, n is an integer from 1 to 10, 2 to 8, or 2 to 5. In a specific embodiment, n is 2, 3, or 4. In some embodiments, m is 1; in other embodiments m is 2, 3 or 4.

While the drug to antibody ratio has an exact value for a specific conjugate molecule (e.g., n multiplied by m in Formula (I)), it is understood that the value will often be an average value when used to describe a sample containing many molecules, due to some degree of heterogeneity, typically associated with the conjugation step. The average loading for a sample of an immunoconjugate is referred to herein as the drug to antibody ratio, or "DAR." In some embodiments, when the drug is a maytansinoid, it is referred to as "MAR." In some embodiments, the DAR is between about 2 and about 6, and typically is about 3, 3.5, 4, 4.5, 5, 5.5, 6, 6.5, 7.0, 7.5, 8.0. In some embodiments, at least 50% of a sample by weight is compound having the average DAR plus or minus 2, and preferably at least 50% of the sample is a conjugate that contains the average DAR plus or minus 1. Embodiments include immunoconjugates wherein the DAR is about 3.5, 3.6, 3.7, 3.8 or 3.9. In some embodiments, a DAR of 'about n' means the measured value for DAR is within 20% of n.

The present invention is also directed to immunoconjugates comprising the antibodies, antibody fragments (e.g., antigen binding fragments) and their functional equivalents as disclosed herein, linked or conjugated to a drug moiety. In one embodiment, the drug moiety D is a maytansinoid drug moiety, including those having the structure:

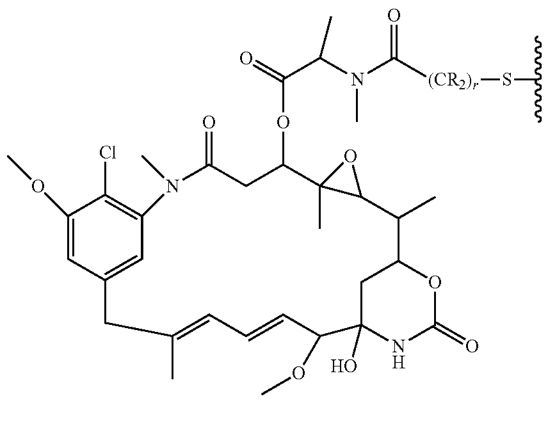

where the wavy line indicates the covalent attachment of the sulfur atom of the maytansinoid to a linker of an antibody drug conjugate. R at each occurrence is independently H or a $C_1$-$C_6$ alkyl. The alkylene chain attaching the amide group to the sulfur atom may be methanyl, ethanyl, or propyl, i.e., r is 1, 2, or 3. (U.S. Pat. No. 633,410, U.S. Pat. No. 5,208,020, Chari et al. (1992) Cancer Res. 52; 127-131, Lui et al. (1996) Proc. Natl. Acad. Sci. 93:8618-8623).

All stereoisomers of the maytansinoid drug moiety are contemplated for the immunoconjugates of the invention, i.e. any combination of R and S configurations at the chiral carbons of the maytansinoid. In one embodiment the maytansinoid drug moiety has the following stereochemistry.

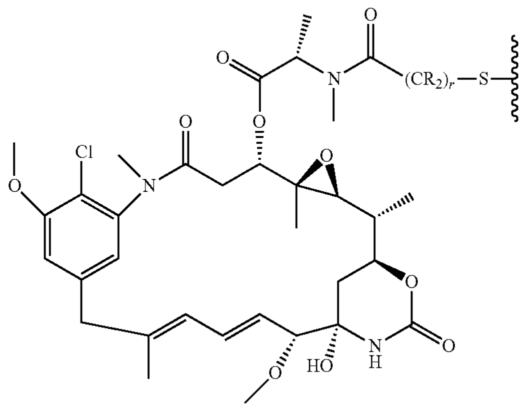

In one embodiment, the maytansinoid drug moiety is $N^{2'}$-deacetyl-$N^{2'}$-(3-mercapto-1-oxopropyl)-maytansine (also known as DM1). DM1 is represented by the following structural formula.

DM1

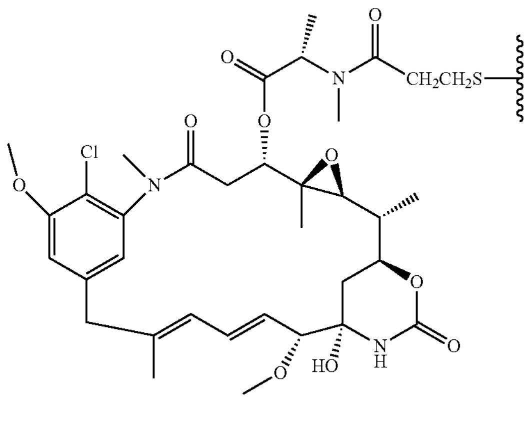

In another embodiment the maytansinoid drug moiety is $N^{2'}$-deacetyl-$N^{2'}$-(4-mercapto-1-oxopentyl)-maytansine (also known as DM3). DM3 is represented by the following structural formula.

DM3

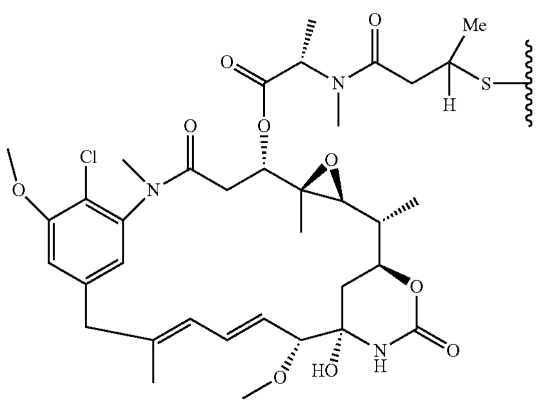

In another embodiment the maytansinoid drug moiety is $N^{2'}$-deacetyl-$N^{2'}$-(4-methyl-4-mercapto-1-oxopentyl)-maytansine (also known as DM4). DM4 is represented by the following structural formula.

DM4

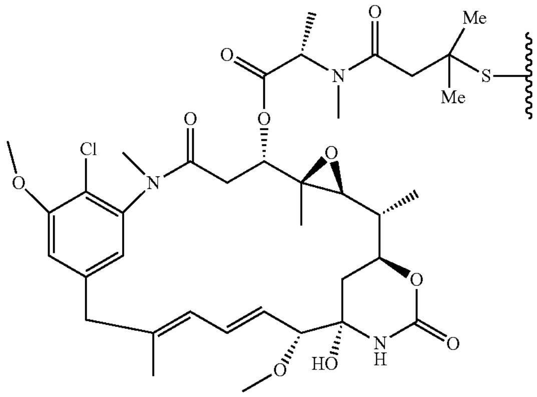

The drug moiety D can be linked to the antibody Ab through linker L. L is any chemical moiety capable of linking the drug moiety to the antibody through covalent bonds. A cross-linking reagent is a bifunctional or multifunctional reagent that can be used to link a drug moiety and an antibody to form antibody drug conjugates. Antibody drug conjugates can be prepared using a cross-linking reagent having a reactive functionality capable of binding to both the drug moiety and the antibody. For example, a cysteine, thiol or an amine, e.g. N-terminus or an amino acid side chain, such as lysine of the antibody, can form a bond with a functional group of a cross-linking reagent. Alternatively, the Antibody drug conjugates can be prepared by pre-forming a linker-drug moiety (or drug-linker moiety, both terms being used interchangeably), and reacting the linker-drug moiety with the antibody. In some instant, the linker moiety is built onto the drug stepwise using several linking moieties until obtaining the desired linker-drug moiety.

In one embodiment, L is a cleavable linker. In another embodiment, L is a non-cleavable linker. In some embodiments, L is an acid-labile linker, photo-labile linker, peptidase cleavable linker, esterase cleavable linker, a disulfide bond cleavable linker, a hydrophilic linker, a procharged linker, a glycosidase cleavable linker, a phosphodiesterase cleavable linker, a phosphatase cleavable linker, or a dicarboxylic acid based linker.

Suitable cross-linking reagents that form a non-cleavable linker between the drug moiety, for example maytansinoid, and the antibody are well known in the art, and can form non-cleavable linkers that comprise a sulfur atom (such as SMCC) or those that are without a sulfur atom. Preferred cross-linking reagents that form non-cleavable linkers between the drug moiety, for example maytansinoid, and the antibody comprise a maleimido- or haloacetyl-based moiety. According to the present invention, such non-cleavable linkers are said to be derived from maleimido- or haloacetyl-based moieties.

Cross-linking reagents comprising a maleimido-based moiety include but not limited to, N-succinimidyl-4-(maleimidomethyl)cyclohexanecarboxylate (SMCC), sulfosuccinimidyl 4-(N-maleimidomethyl) cyclohexane-1-carboxylate (sulfo-SMCC), N-succinimidyl-4-(maleimidomethyl) cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-succinimidyl ester (EMCS), m-maleimidobenzoyl-N-hydroxysuccinimide ester (MBS), N-(α-maleimidoacetoxy)-succinimide ester (AMSA), succinimidyl-6-(β-maleimidopropionamido)hexanoate (SMPH), N-succinimidyl-4-(p-maleimidophenyl)-butyrate (SMPB), N-(-p-maleomidophenyl)isocyanate (PMIP) and maleimido-based cross-linking reagents containing a polyethythene glycol spacer, such as MAL-PEG-NHS. These cross-linking reagents form non-cleavable linkers derived from maleimido-based moieties. Representative structures of maleimido-based cross-linking reagents are shown below.

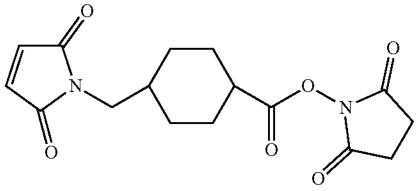

SMCC

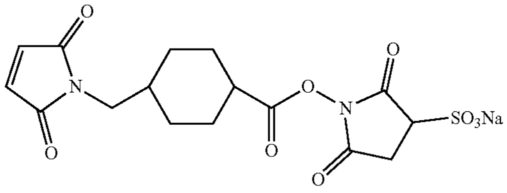

Sulfo-SMCC

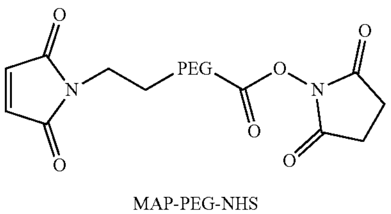

MAP-PEG-NHS

In another embodiment, the linker L is derived from N-succinimidyl-4-(maleimidomethyl)cyclohexanecarboxylate (SMCC), sulfosuccinimidyl 4-(N-maleimidomethyl) cyclohexane-1-carboxylate (sulfo-SMCC) or MAL-PEG-NHS.

Cross-linking reagents comprising a haloacetyle-based moiety include N-succinimidyl iodoacetate (SIA), N-succinimidyl(4-iodoacetyl)aminobenzoate (SIAB), N-succinimidyl bromoacetate (SBA) and N-succinimidyl 3-(bromoacetamido)propionate (SBAP). These cross-linking reagents form a non-cleavable linker derived from haloacetyl-based moieties. Representative structures of haloacetyl-based cross-linking reagents are shown below.

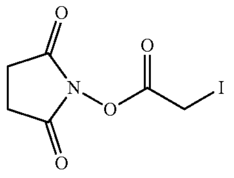

SIA

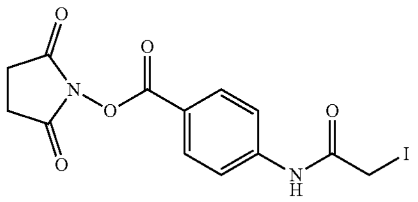

SIAB

In one embodiment, the linker L is derived from N-succinimidyl iodoacetate (SIA) or N-succinimidyl(4-iodoacetyl)aminobenzoate (SIAB).

Suitable cross-linking reagents that form a cleavable linker between the drug moiety, for example maytansinoid, and the antibody are well known in the art. Disulfide containing linkers are linkers cleavable through disulfide exchange, which can occur under physiological conditions. According to the present invention, such cleavable linkers are said to be derived from disulfide-based moieties. Suitable disulfide cross-linking reagents include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB) and N-succinimidyl-4-(2-pyridyldithio)-2-sulfo-butanoate (sulfo-SPDB), the structures of which are shown below. These disulfide cross-linking reagents form a cleavable linker derived from disulfide-based moieties.

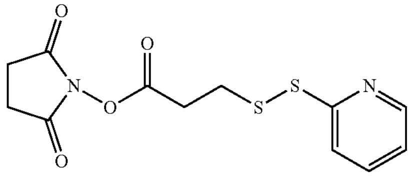 [SMILES: O=C(CCSSc1ccccn1)ON1C(=O)CCC1=O]

N-succinimidyl-3-(2-pyridyldithio)propionate (SPDP),

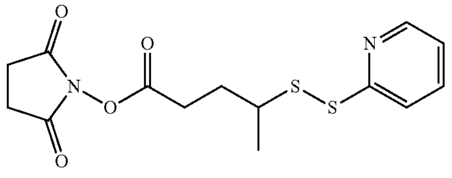 [SMILES: CC(CCC(=O)ON1C(=O)CCC1=O)SSc1ccccn1]

N-succinimidyl-4-(2-pyridyldithio)pentanoate (SPP),

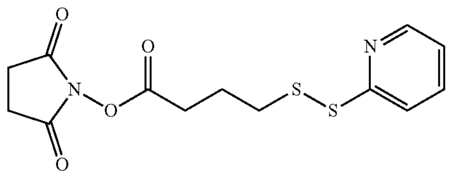 [SMILES: O=C(CCCSSc1ccccn1)ON1C(=O)CCC1=O]

N-succinimidyl-4-(2-pyridyldithio)butanoate (SPDB) and

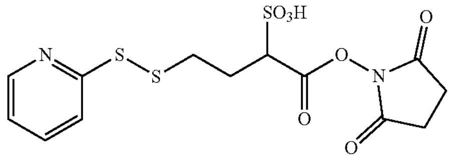 [SMILES: O=C(ON1C(=O)CCC1=O)C(CCSSc1ccccn1)S(=O)(=O)O]

N-succinimidyl-4-(2-pyridyldithio)-2-sulfo-butanoate (sulfo-SPDB).

In one embodiment, the linker L is derived from N-succinimidyl-4-(2-pyridyldithio) butanoate (SPDB).

Suitable cross-linking reagents that form a charged linker between the drug moiety, for example maytansinoid, and the antibody are known as procharged cross-linking reagents. In one embodiment, the linker L is derived from the procharged cross-linking reagent CX1-1. The structure of CX1-1 is below.

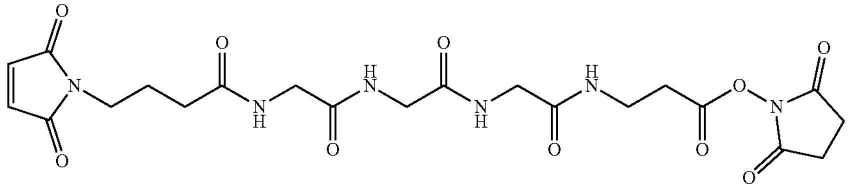 [SMILES: O=C(CCCN1C(=O)C=CC1=O)NCC(=O)NCC(=O)NCC(=O)NCCC(=O)ON1C(=O)CCC1=O]

2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1)

Each of the cross-linking reagents depicted above contains, at one end of the cross-linking reagent, a NHS-ester which reacts with a primary amine of the antibody to form an amide bond and, at the other end, a maleimide group or pyridinyldisulfide group which reacts with the sulfhydryl of the maytansionoid drug moiety to form a thioether or disulfide bond.

In another embodiment, suitable cross-linking moieties that form a cleavable linker between the drug moiety (for example maytansinoid) and the antibody are represented by the following formula (II):

(II)

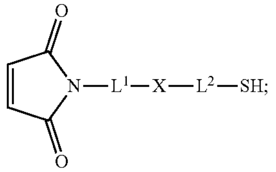

wherein:

$L^1$ is a $C_{1-6}$alkylene wherein one of the methylene groups may be replaced with oxygen;

$L^2$ is a $C_{1-6}$alkylene or is $—(CH_2CH_2O)_y—CH_2—CH_2—$ wherein y is 1 to 11; and X is —C(O)—NH—, —NHC(O)— or a triazole;

wherein the alkylene is linear or branched.

In one aspect of this embodiment y is 5, 7, 9 or 11. In another aspect of this embodiment y is less than 5.

In yet another embodiment, suitable cross-linking moieties according to formula I are selected from the group consisting of:

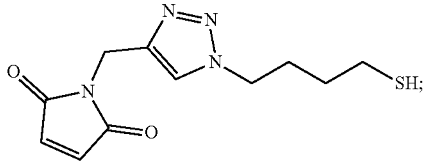

MaleimidoMethylTriazoleButaneThiol (MMTBT)

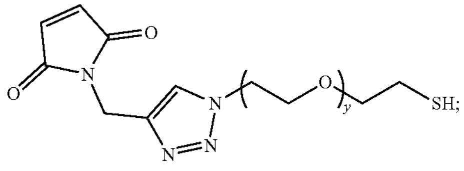

-continued

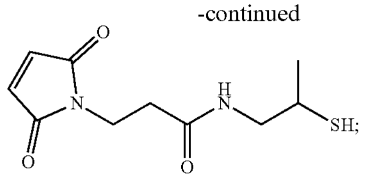

MPPT: MaleimidoPropionamidoPropaneThio

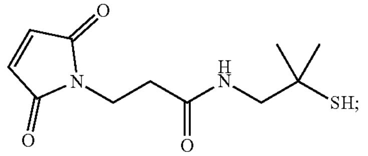

MPBT: maleimidoPropionamidoButylThio

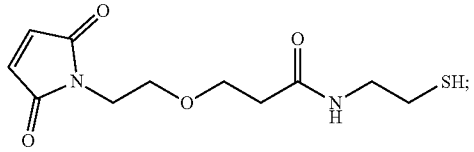

MEPET: MaleimidoEthoxyPropionamidoEthylThio

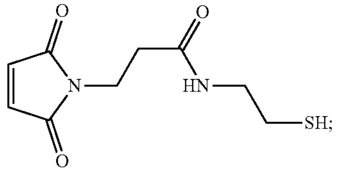

and

MPET: MaleimidoPropionamidoEthylThio

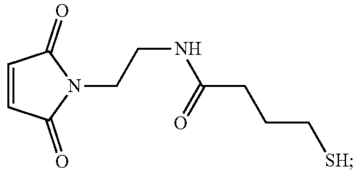

MBT: MaleimidoEthylButanamidoThio wherein y is 1 to 11.

For the cross-linking moieties depicted above (i.e. MBT, MPET, MEPET; MMTBT, MPPT, MPBT), the maleimide group allows for reaction with the sulfhydryl (or thiol) of a Cysteine in an antibody thereby forming a thioether bond; and the thiol functionality of the cross-linking moiety is connected to the thiol of the maytansinoid drug moiety to form a cleavable disulfide bond. In view of the cross-reactional nature of the linking moiety of Formula (I) (thiol and maleimide could cross react), one of ordinary skill in the art would appreciate that the linking moiety has to be built stepwise onto the drug moiety as depicted in Scheme 1.

According to the above embodiment, the linkers resulting from the cross linking moieties (i.e. MBT, MPET, MEPET) can be depicted as follow:

(IIA)

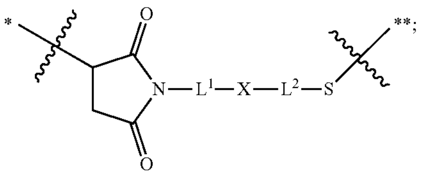

wherein * is linked to the thiol functionality on the antibody, and ** is linked to the thiol functionality of a drug moiety (e.g. maytansinoid drug moiety DM1, DM3 or DM4).

According to the above embodiment, the linkers resulting from the cross linking moieties (i.e. MBT, MPET, MEPET) can be depicted as follows:

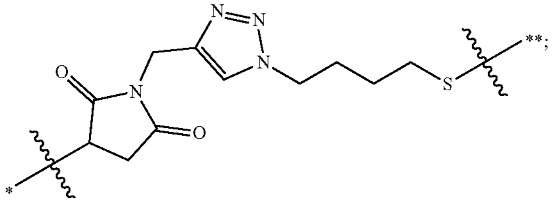

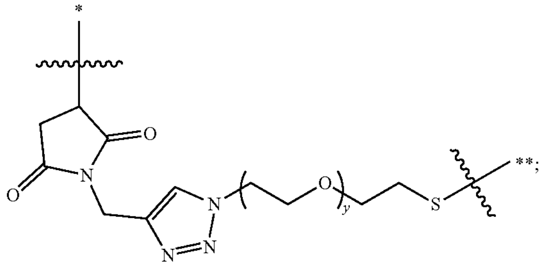

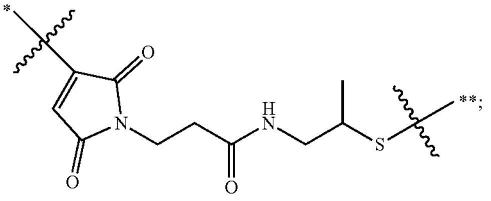

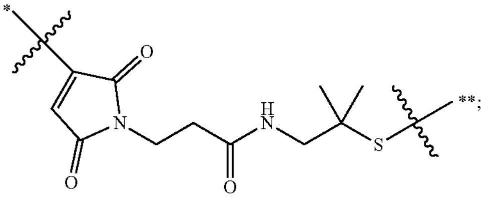

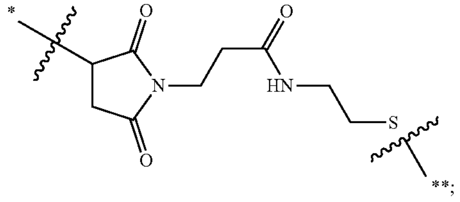

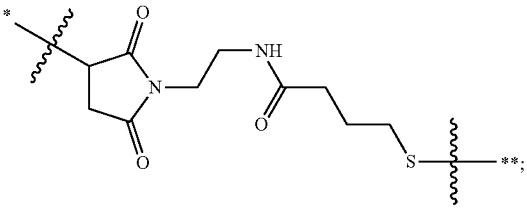

and

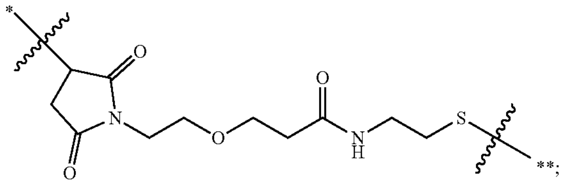

wherein y is 1 to 11; * is linked to the thiol functionality on the antibody, and ** is linked to the thiol functionality of the drug moiety (e.g. maytansinoid drug DM1, DM3 or DM4).

In a preferred embodiment, the linker has the following formula:

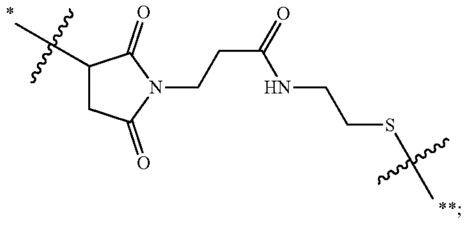 [SMILES: *SCCNC(=O)CCN1C(=O)CC(*)C1=O]

wherein * is linked to the thiol functionality on the antibody, and ** is linked to the thiol functionality of the maytansinoid drug (DM1, DM3 or DM4)

In one embodiment, the invention relates to the linker-drug moiety of Formula:

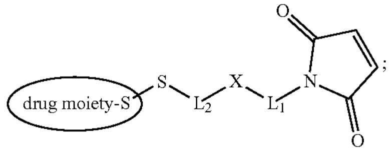

wherein $L^1$ is a $C_{1-6}$alkylene wherein one of the methylene groups may be replaced with oxygen;

$L^2$ is a $C_{1-6}$alkylene or is $-(CH_2CH_2O)_y-CH_2-CH_2-$ wherein y is 1 to 11; and X is —C(O)—NH—, —NHC(O)— or a triazole;

wherein the alkylene is linear or branched.

In another embodiment, the invention pertains to the stepwise formation of the above linker-drug conjugate as disclosed in Scheme 1 herein.

In one embodiment, the invention relates to the linker-drug moiety compounds having one of the following Formulae (III), (IV) and (V):

(III)

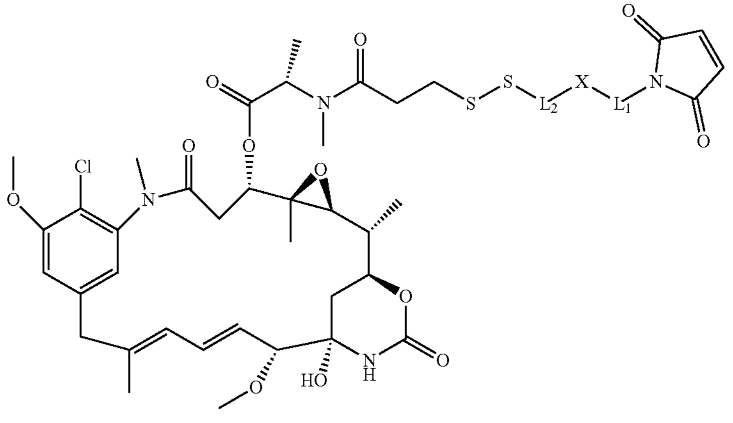

Maleimido Linker_DM1

(IV)

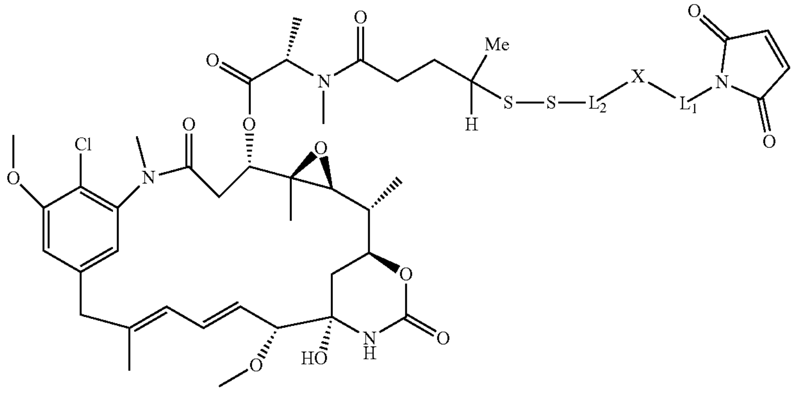

Maleimido Linker-DM3

-continued (V)

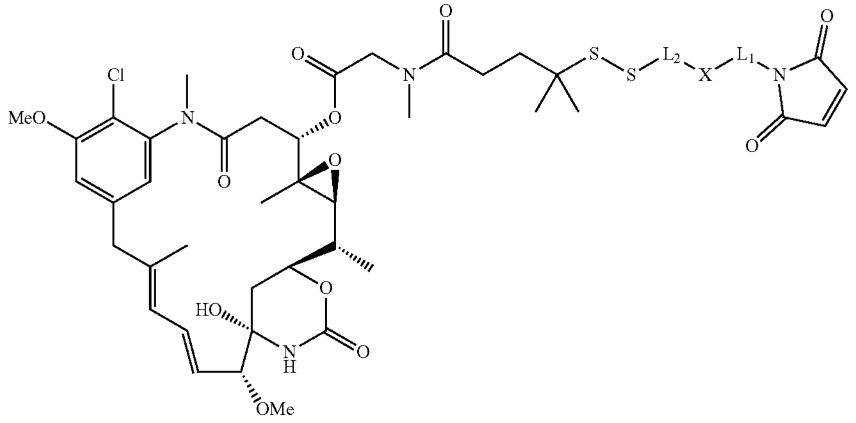

Maleimido linker-DM4 wherein $L^1$ is a $C_{1-6}$alkylene wherein one of the methylene groups may be replaced with oxygen;

$L^2$ is a $C_{1-6}$alkylene or is $-(CH_2CH_2O)_y-CH_2-CH_2-$ wherein y is 1 to 11; and X is $-C(O)-NH-$, $-NHC(O)-$ or a triazole;

Wherein the alkylene is linear or branched.

In one embodiment, the invention relates to the linker-drug moiety compounds which are selected from the following formulae:

MPET-DM4

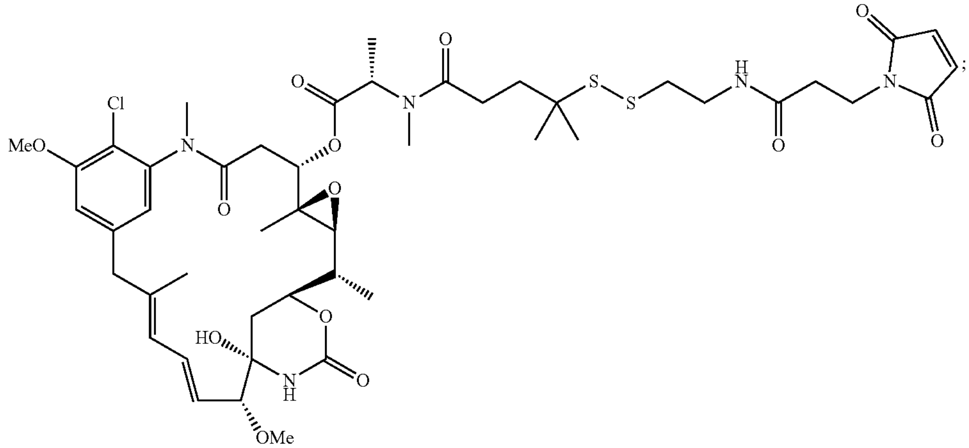

;

MPET-DM1

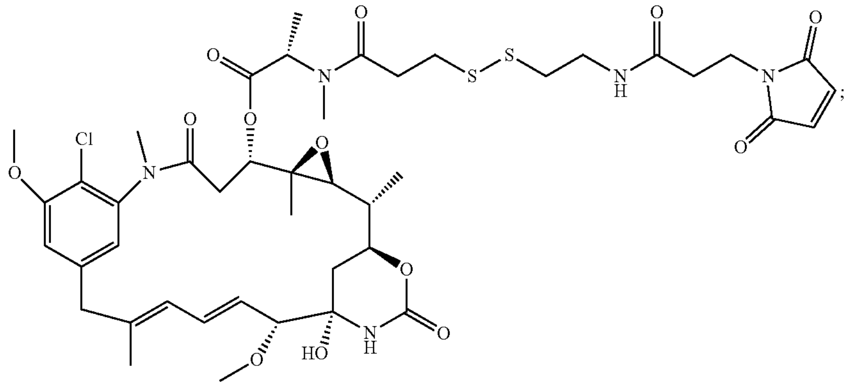

;

-continued
MPET-DM3
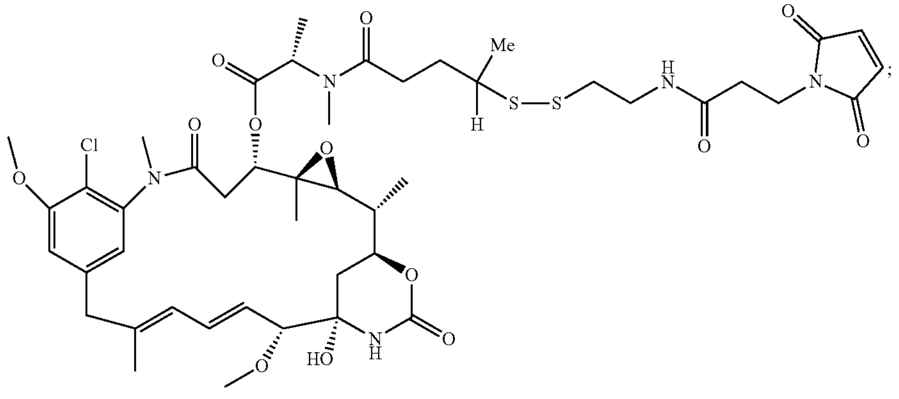
and
MPET-DM1
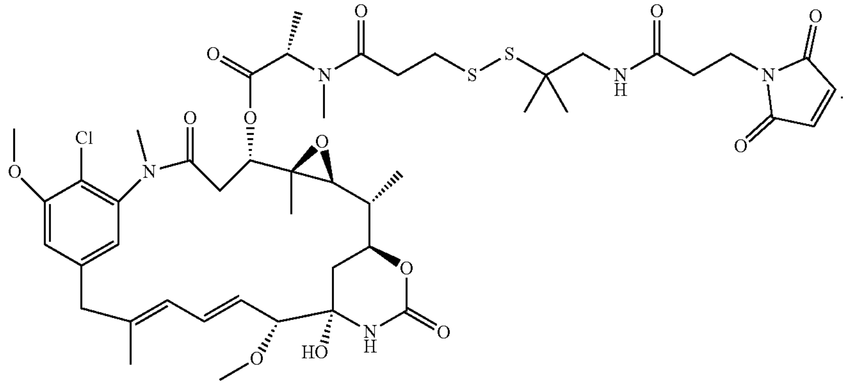
In another embodiment, the invention relates to the linker-drug moiety compounds which are selected from the following formulae:
MEPET-DM4
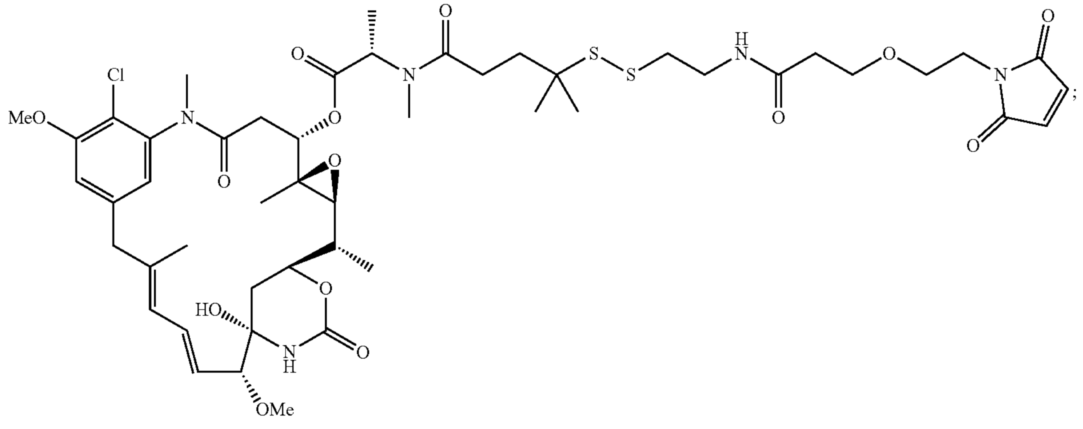

-continued
MEPET-DM1
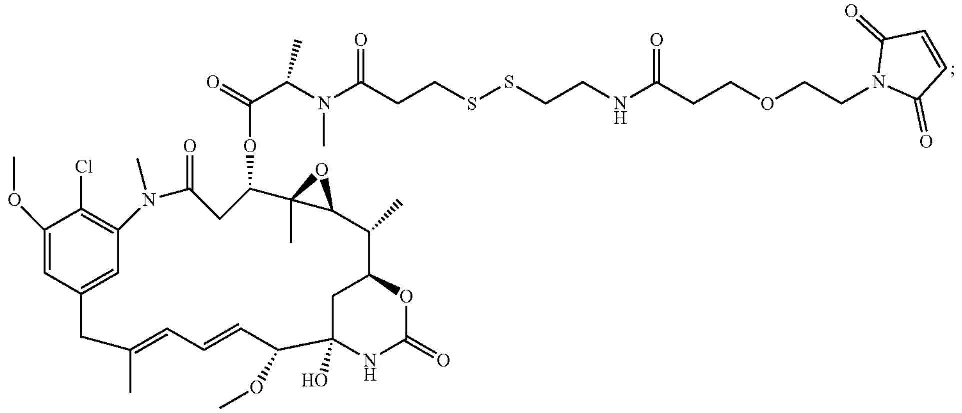
MEPET-DM3
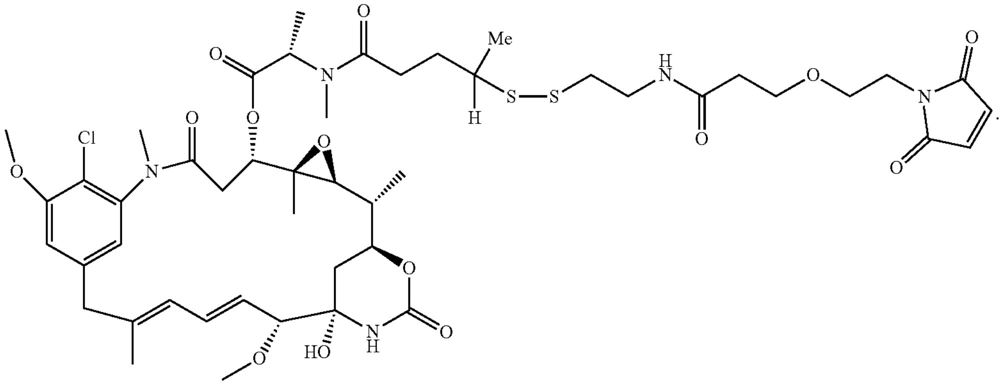
In another embodiment, the linker-drug of the present invention is represented by any one of the following formulae:
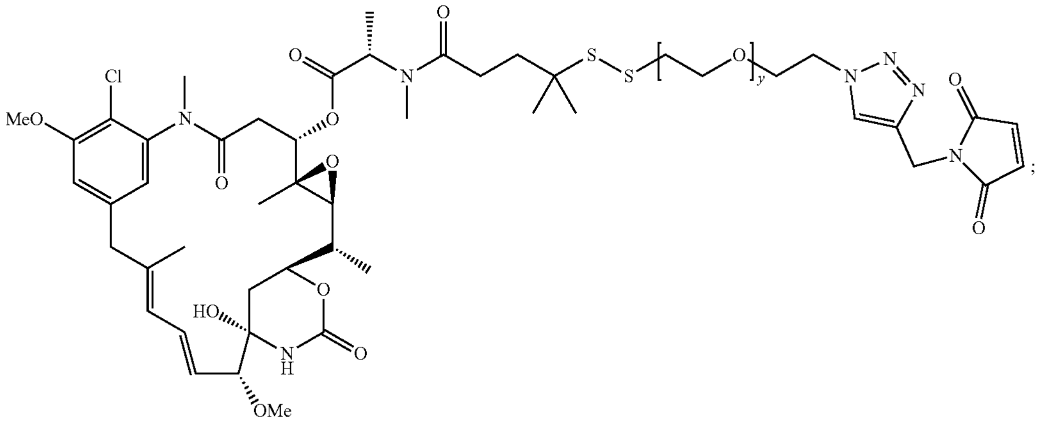

-continued
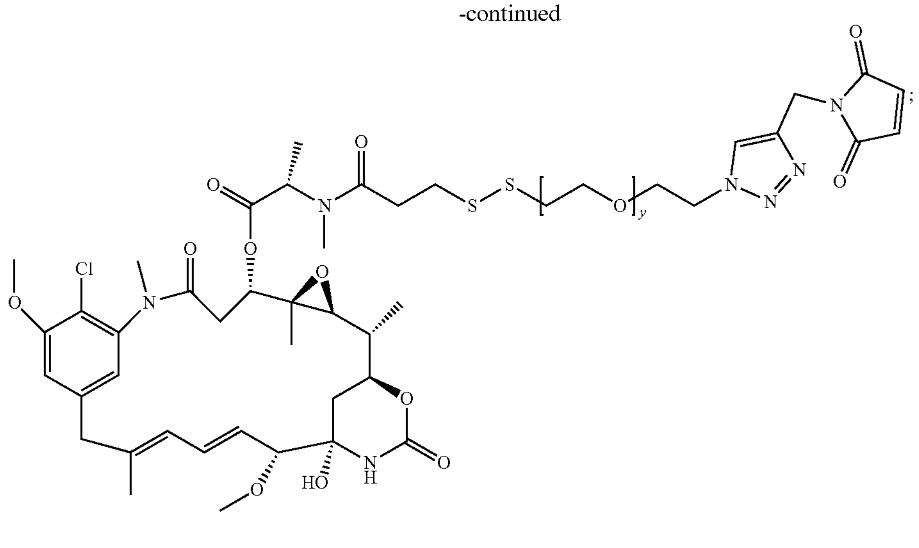
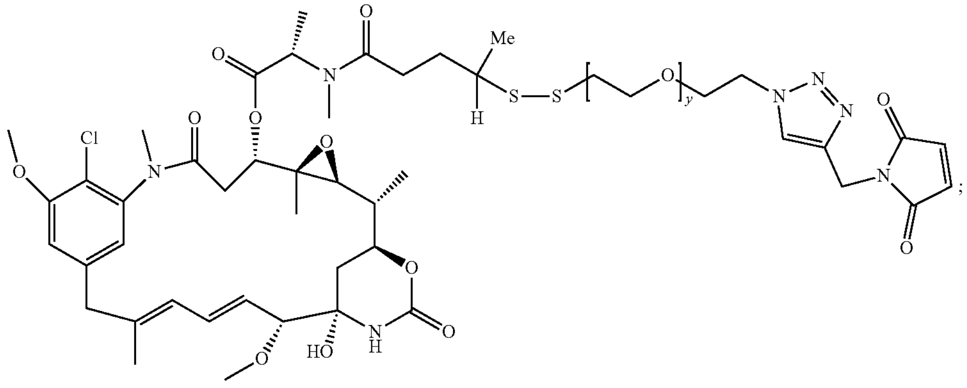
wherein y is 1 to 11, preferably 1 to 5.
In one embodiment, the linker-drug of the present invention is represented by any one of the following structural formulae:
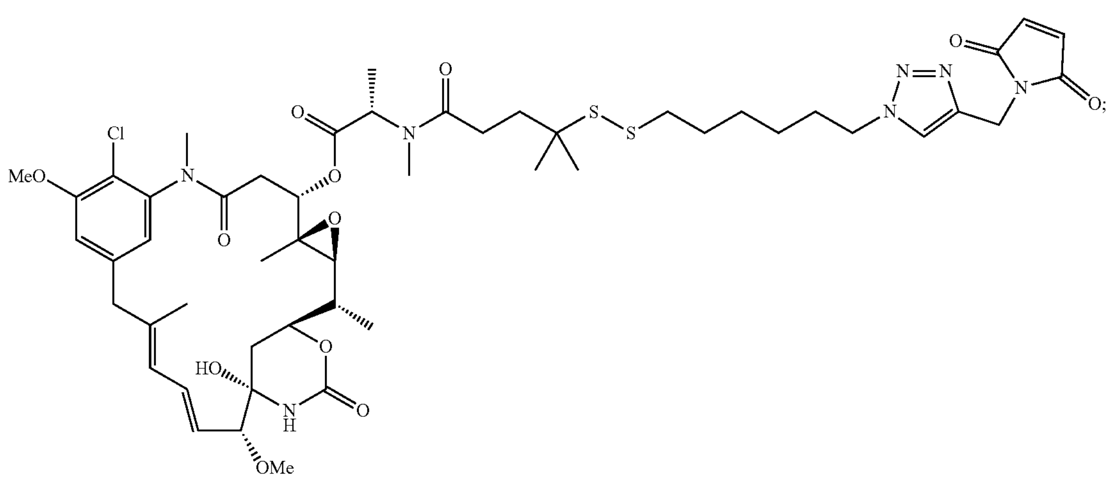

-continued
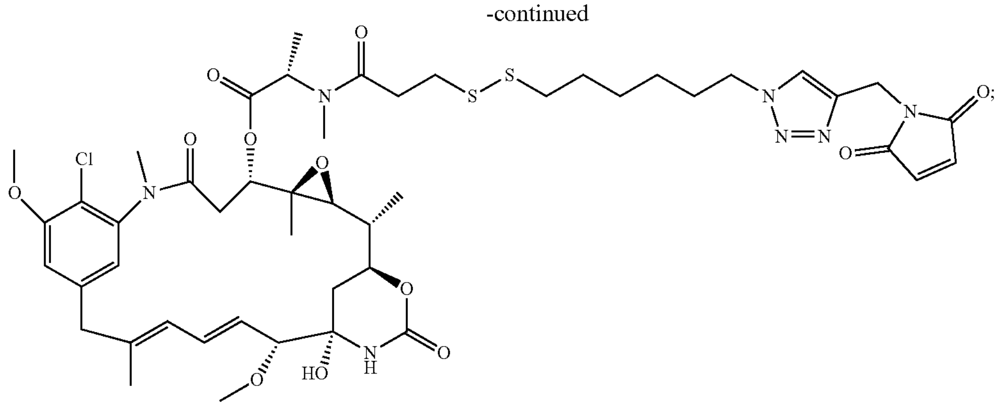
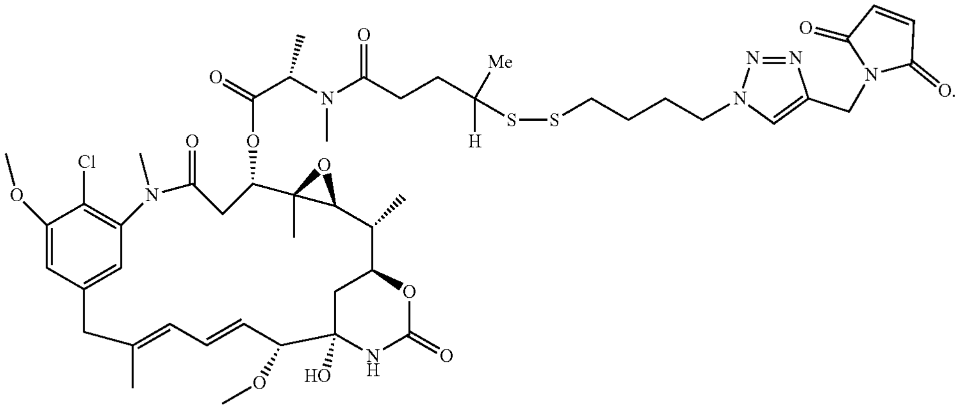
In one embodiment, the conjugate of the present invention is represented by any one of the following structural formulae:
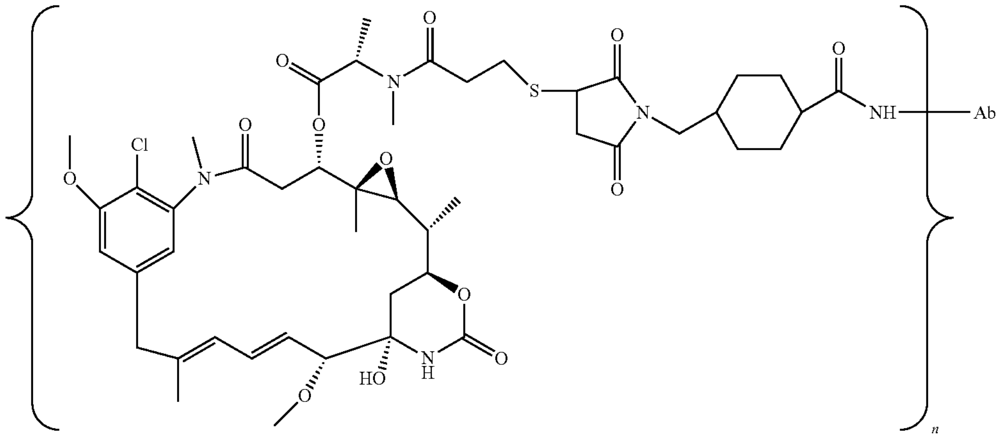
Ab-MCC-DM1

-continued

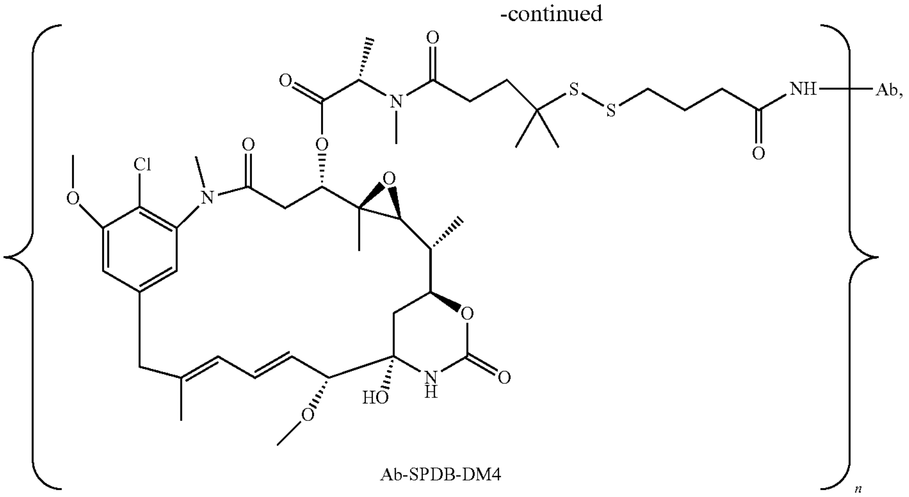

Ab-SPDB-DM4

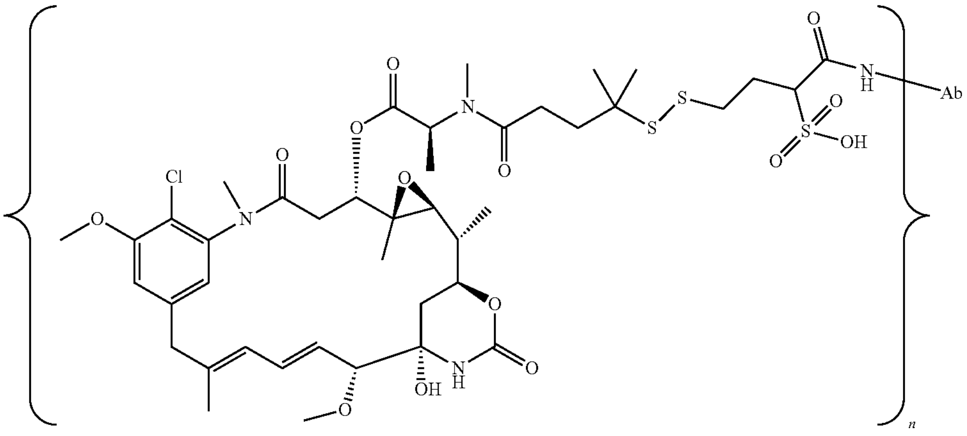

Ab-sSPDB-DM4

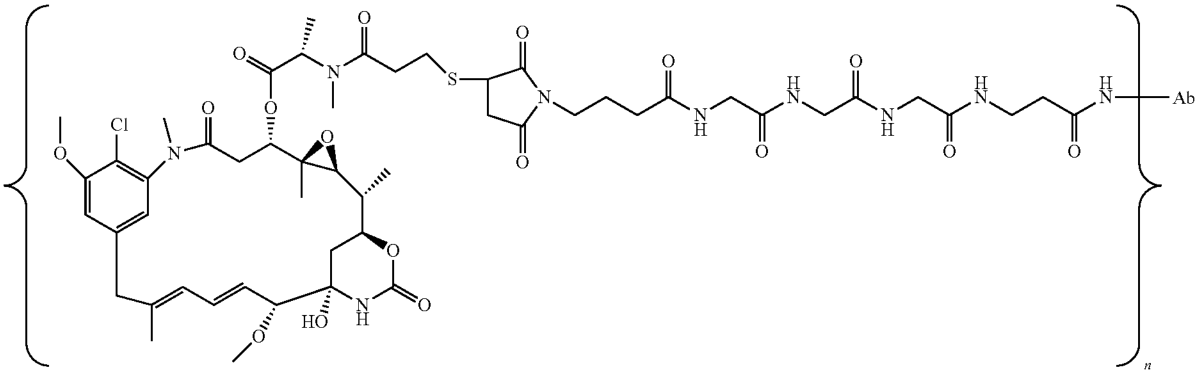

Ab-CX1-1-DM1 wherein:

Ab is an antibody or antigen binding fragment thereof that specifically binds CCR7;

n, which indicates the number of linker-drug (L-D-) groups attached to the Ab through the formation of an amide bond with a primary amine of the Ab, is an integer from 1 to 20. In one embodiment, n is an integer from 1 to 10, 2 to 8 or 2 to 5. In a specific embodiment, n is 3 or 4.

In another embodiment, the conjugate of the present invention is represented by any of the following Formulae (VI), (VII) and (VIII):

(VI)

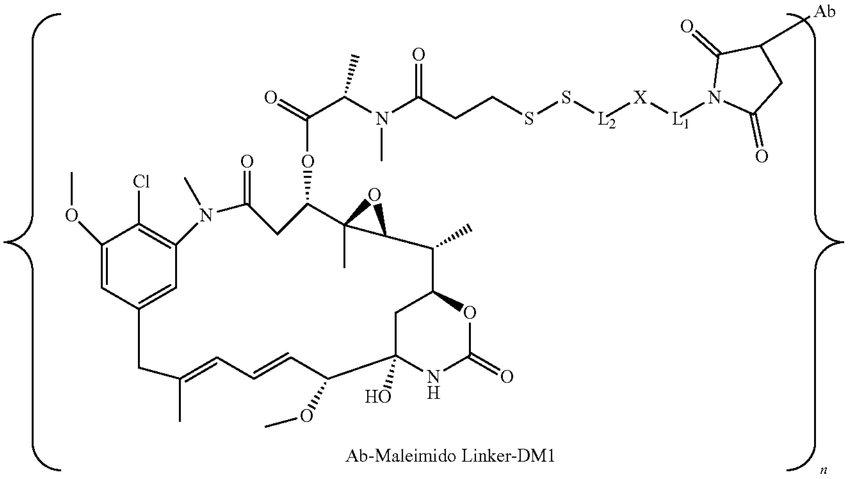

Ab-Maleimido Linker-DM1

(VII)

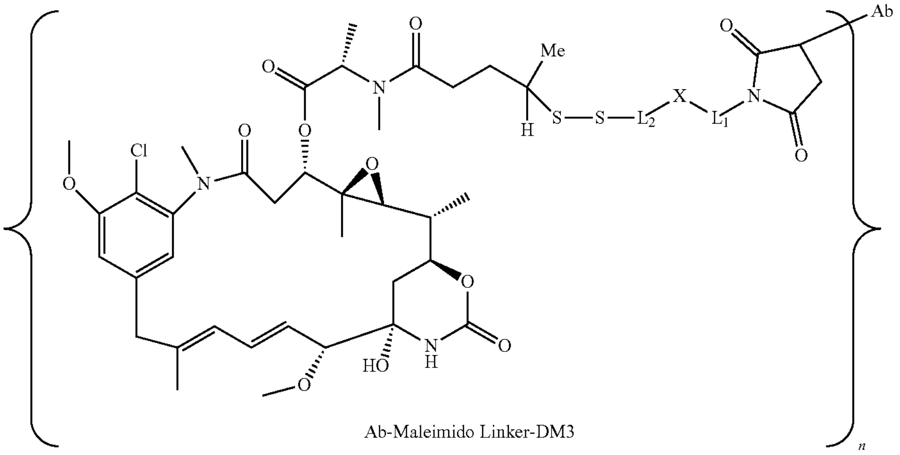

Ab-Maleimido Linker-DM3

(VIII)

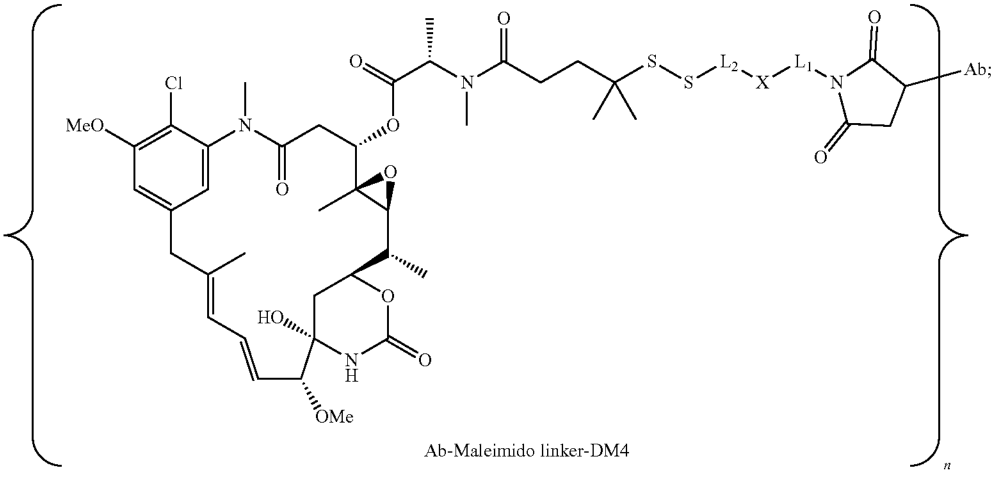

Ab-Maleimido linker-DM4 wherein:

$L^1$ is a $C_{1-6}$alkylene wherein one of the methylene groups may be replaced with oxygen;

$L^2$ is a $C_{1-6}$alkylene or is —$(CH_2CH_2O)_y$—$CH_2$—$CH_2$— wherein y is 1 to 11; and X is —C(O)—NH—, —NHC(O)— or a triazole;

wherein the alkylene is linear or branched; and

Ab is an antibody or antigen binding fragment thereof;

n, which indicates the number of linker-drug (L-D-) groups attached to the Ab through the formation of an amide bond with a primary amine of the Ab, is an integer from 1 to 20. In one embodiment, n is an integer from 1 to 10, 2 to 8 or 2 to 5. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In another embodiment, the conjugate of the present invention has the Formula (VIA) or (VIB) corresponding to the open forms of the succinimide of the conjugate of Formula (VI):

(VIA)

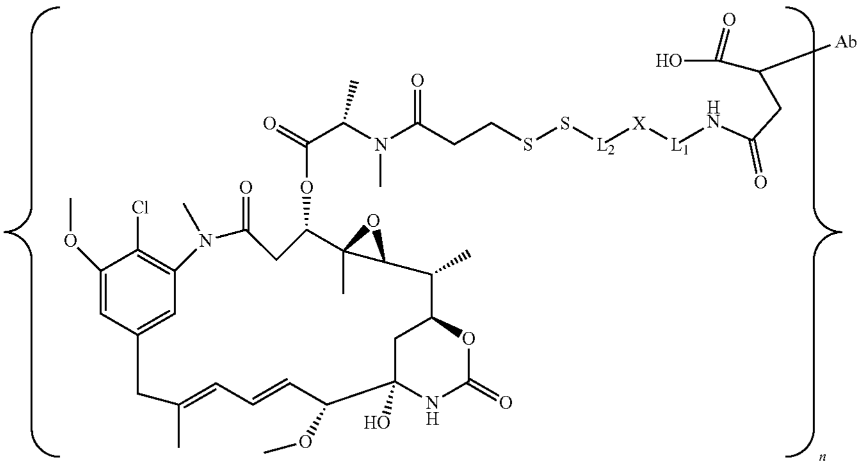

(VIB)

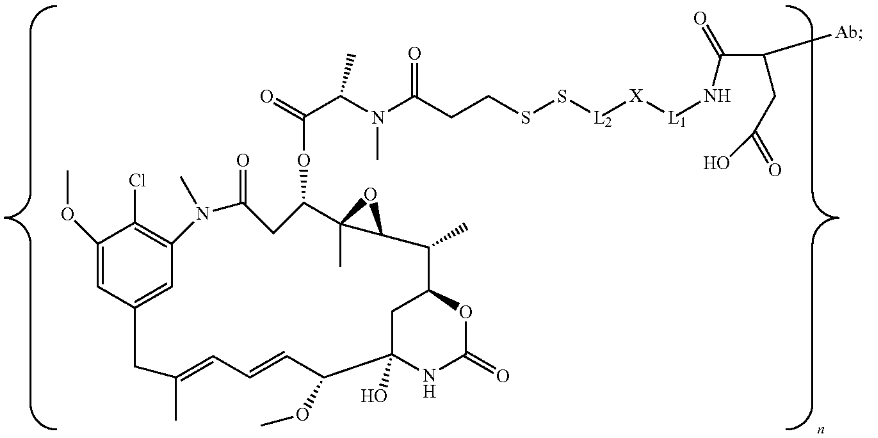

wherein:

$L^1$ is a $C_{1-6}$alkylene wherein one of the methylene groups may be replaced with oxygen;

$L^2$ is a $C_{1-6}$alkylene or is $-(CH_2CH_2O)_y-CH_2-CH_2-$ wherein y is 1 to 11; and X is —C(O)—NH—, —NHC(O)— or a triazole;

wherein the alkylene is linear or branched; and

Ab is an antibody or antigen binding fragment;

n, which indicates the number of linker-drug (L-D-) groups attached to the Ab through the formation of an amide bond with a primary amine of the Ab, is an integer from 1 to 20. In one embodiment, n is an integer from 1 to 10, 2 to 8 or 2 to 5. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In another embodiment, the conjugate of the present invention has the Formula (VIIA) or (VIIB) corresponding to the open forms of the succinimide of the conjugate of Formula (VII):

(VIIA)

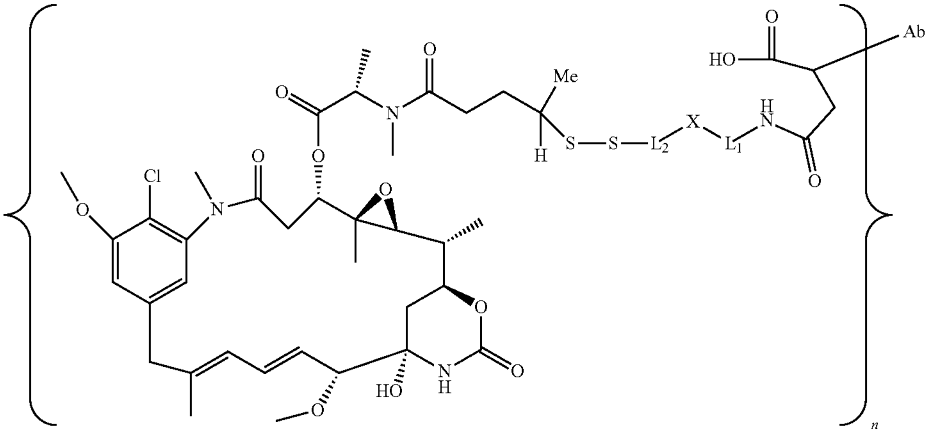

(VIIB)

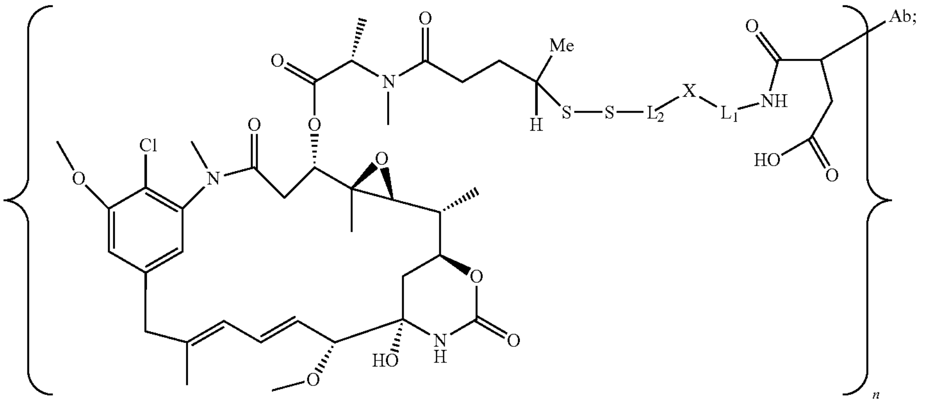

wherein:

$L^1$ is a $C_{1-6}$alkylene wherein one of the methylene groups may be replaced with oxygen;

$L^2$ is a $C_{1-6}$alkylene or is —$(CH_2CH_2O)_y$—$CH_2$—$CH_2$— wherein y is 1 to 11; and X is —C(O)—NH—, —NHC(O)— or a triazole;

wherein the alkylene is linear or branched; and

Ab is an antibody or antigen binding fragment thereof;

n, which indicates the number of linker-drug (L-D) groups attached to the Ab through the formation of an amide bond with a primary amine of the Ab, is an integer from 1 to 20. In one embodiment, n is an integer from 1 to 10, 2 to 8 or 2 to 5. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In another embodiment, the conjugate of the present invention has the Formula (VIIIA), (VIIIB) corresponding to the open forms of the succinimide of the conjugate of Formula (VIII):

(VIIIA)

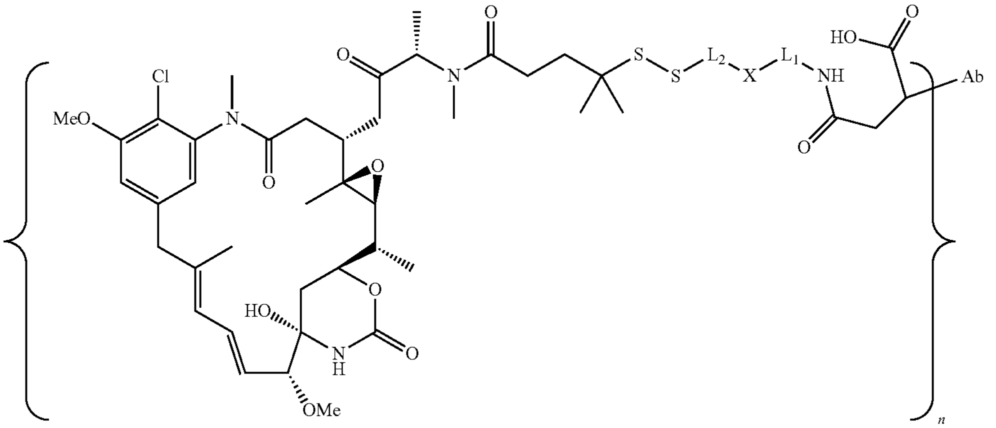

(VIIIB)

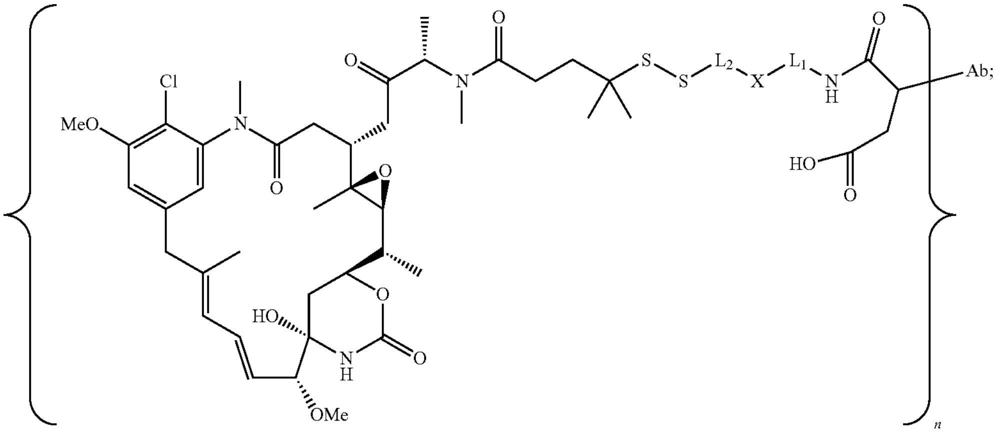

wherein:

$L^1$ is a $C_{1-6}$alkylene wherein one of the methylene groups may be replaced with oxygen;

$L^2$ is a $C_{1-6}$alkylene or is —$(CH_2CH_2O)_y$—$CH_2$—$CH_2$— wherein y is 1 to 11; and X is —C(O)—NH—, —NHC(O)— or a triazole;

wherein the alkylene is linear or branched; and

Ab is an antibody or antigen binding fragment thereof;

n, which indicates the number of linker-drug (L-D-) groups attached to the Ab through the formation of an amide bond with a primary amine of the Ab, is an integer from 1 to 20. In one embodiment, n is an integer from 1 to 10, 2 to 8 or 2 to 5. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In one embodiment, each antibody drug conjugate disclosed herein wherein the linker-drug moiety is attached to the antibody via a succimide, can also exist as the open forms of the succinimide as generally depicted in Formulae (VIA), (VIB), (VIIA), (VIIB), (VIIIA) and (VIIIB).

In yet another embodiment, the conjugate of the present invention is represented by any one of the following structural formulae:

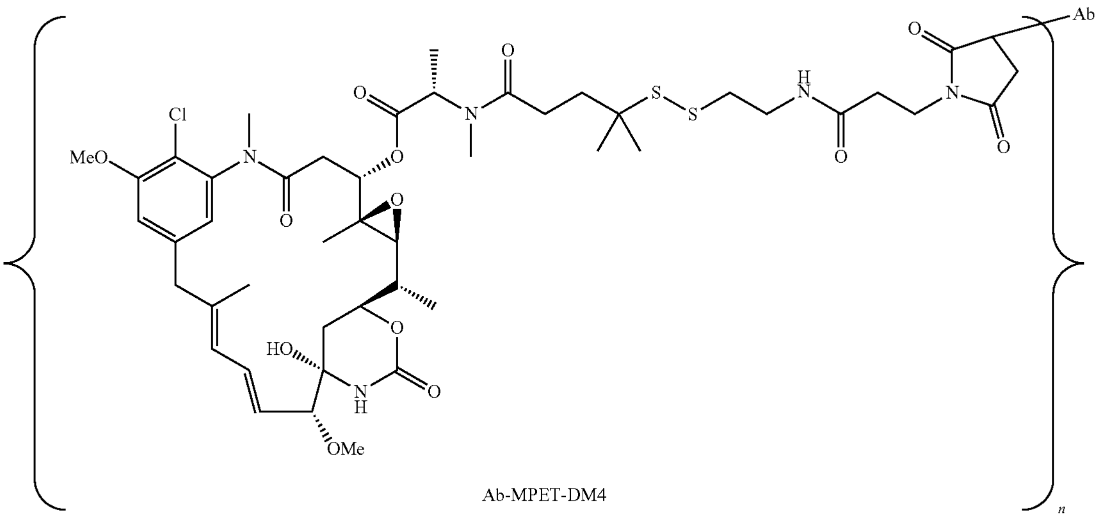
Ab-MPET-DM4
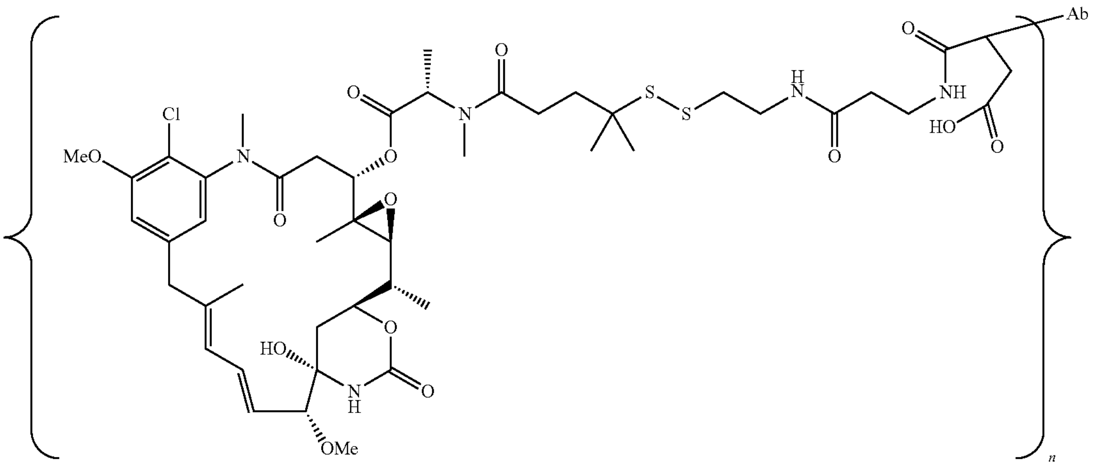
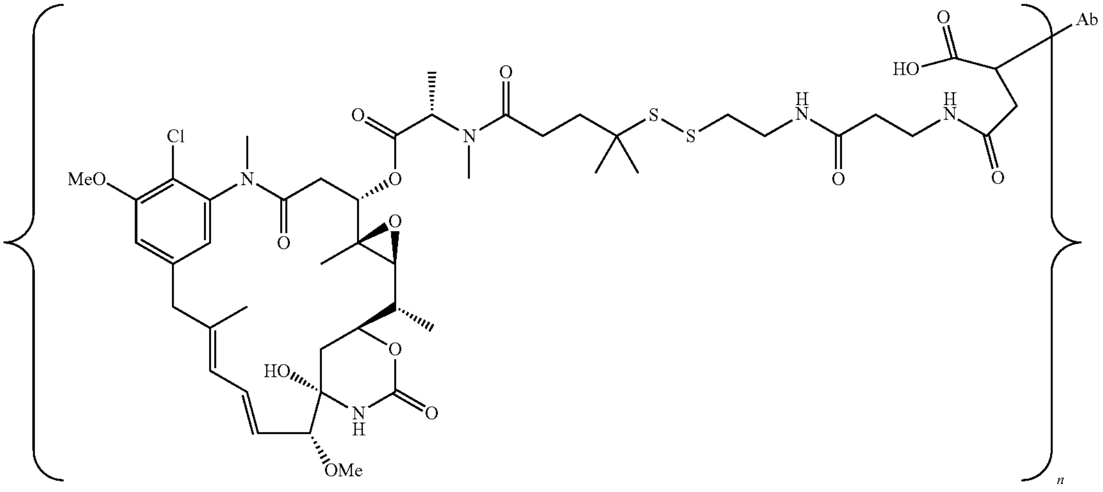

-continued
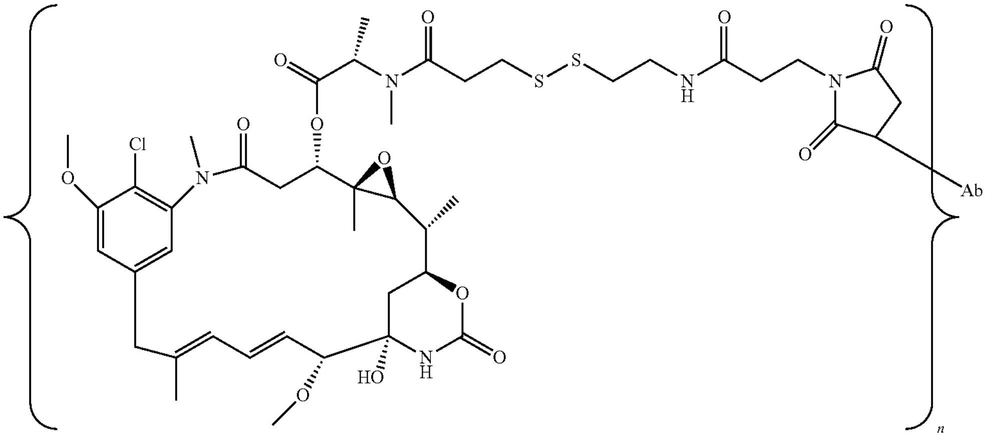
Ab-MPET-DM1
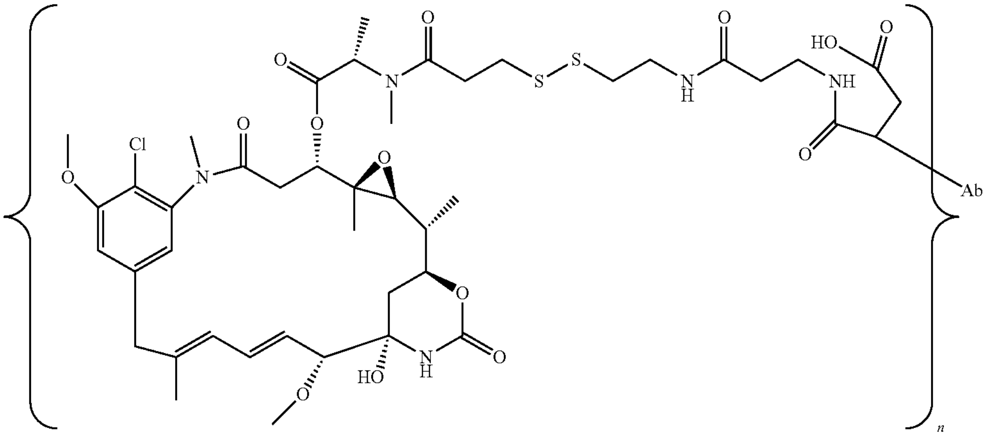
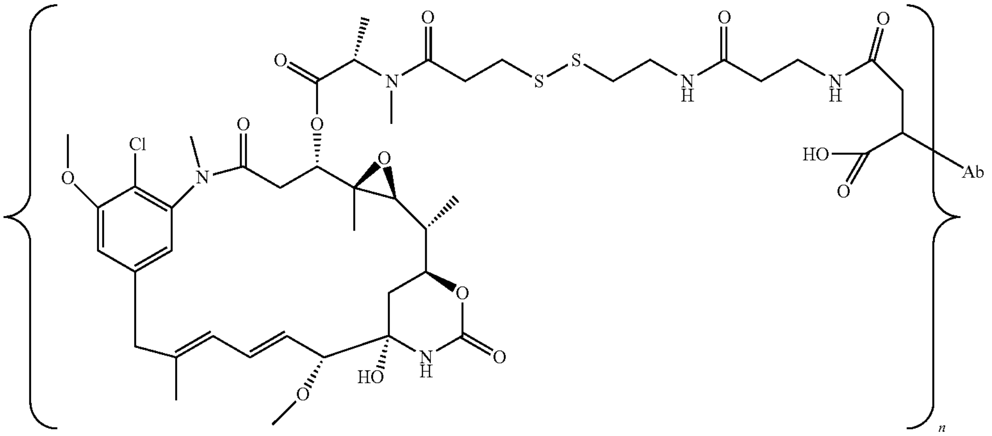

-continued

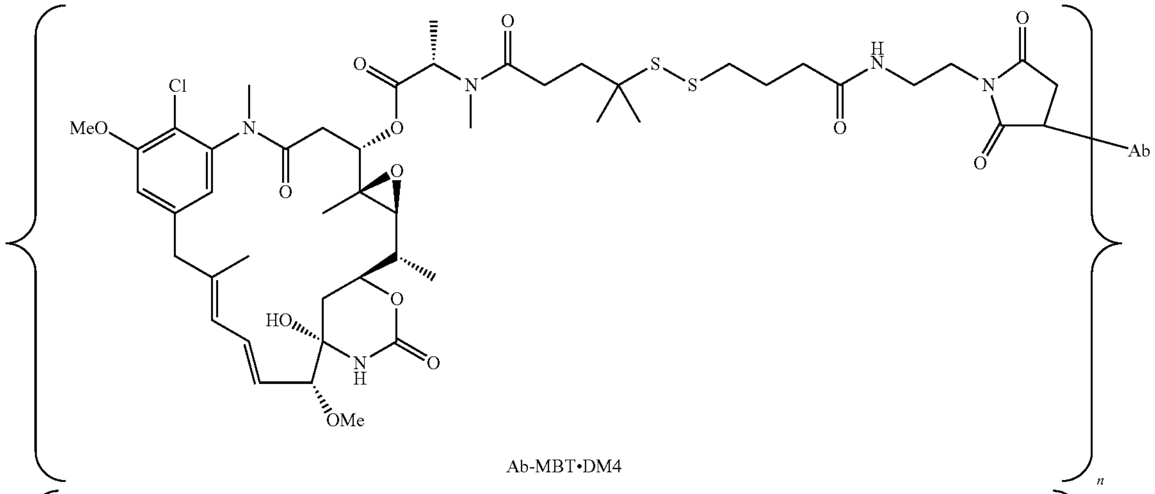

Ab-MBT•DM4

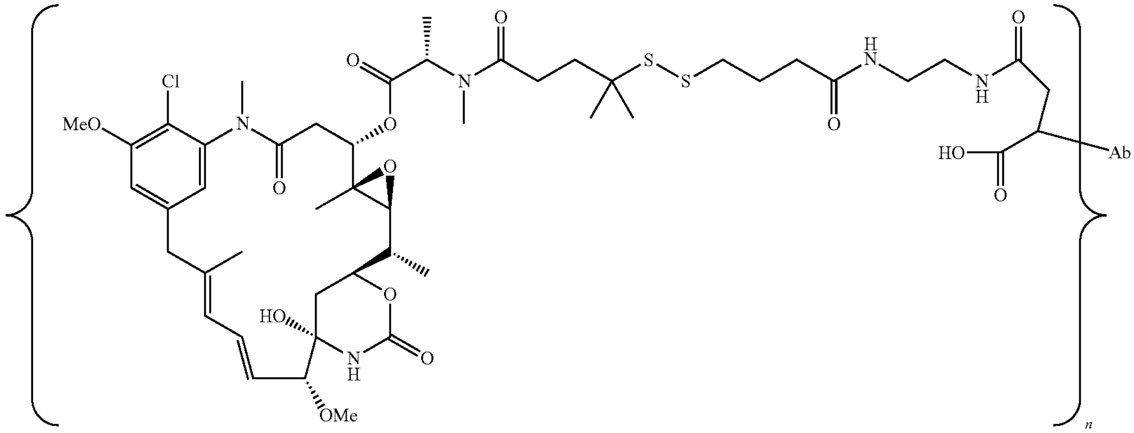

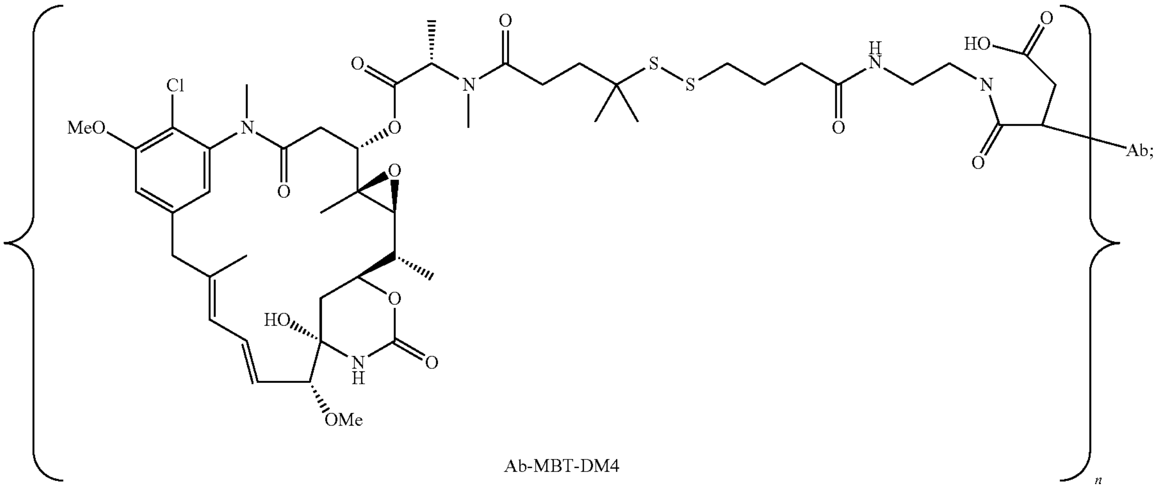

Ab-MBT-DM4 wherein:

Ab is an antibody or antigen binding fragment thereof;

n, which indicates the number of D-L groups attached to the Ab through the formation of a thioester bond with a sulfhydryl of the Ab, is an integer from 1 to 12, or 1 to 8, or preferably 1 to 4. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In another embodiment, the conjugate of the present invention is represented by any one of the following structural formulae:

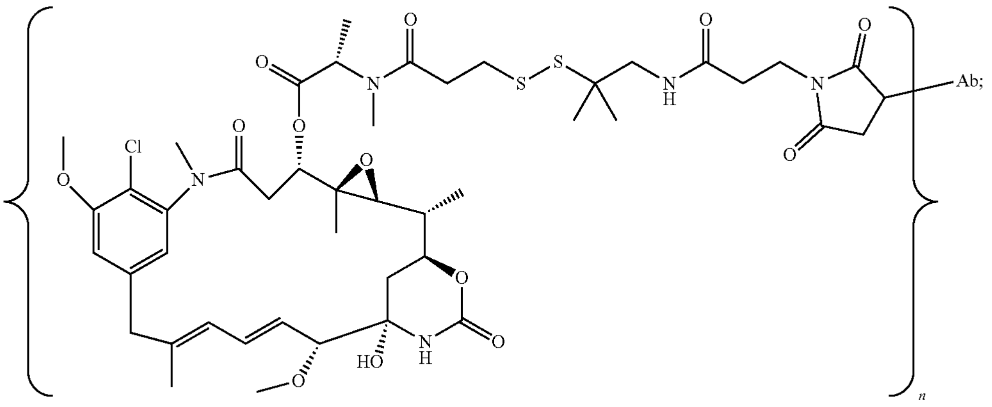
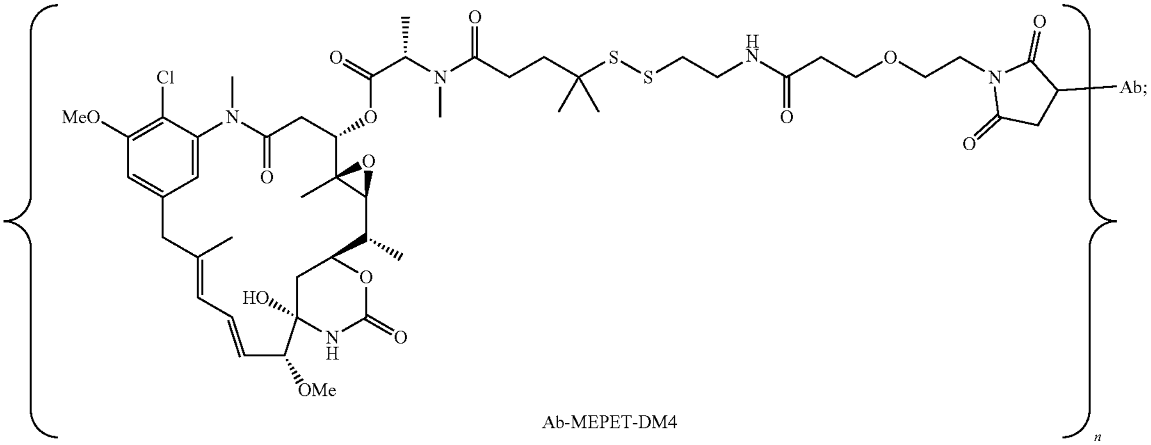
Ab-MEPET-DM4
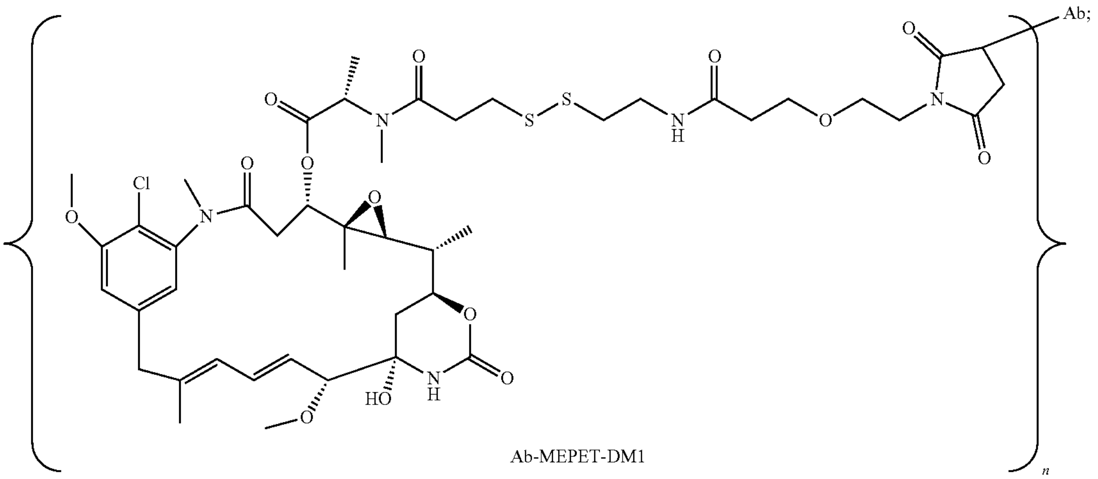
and
Ab-MEPET-DM1

-continued

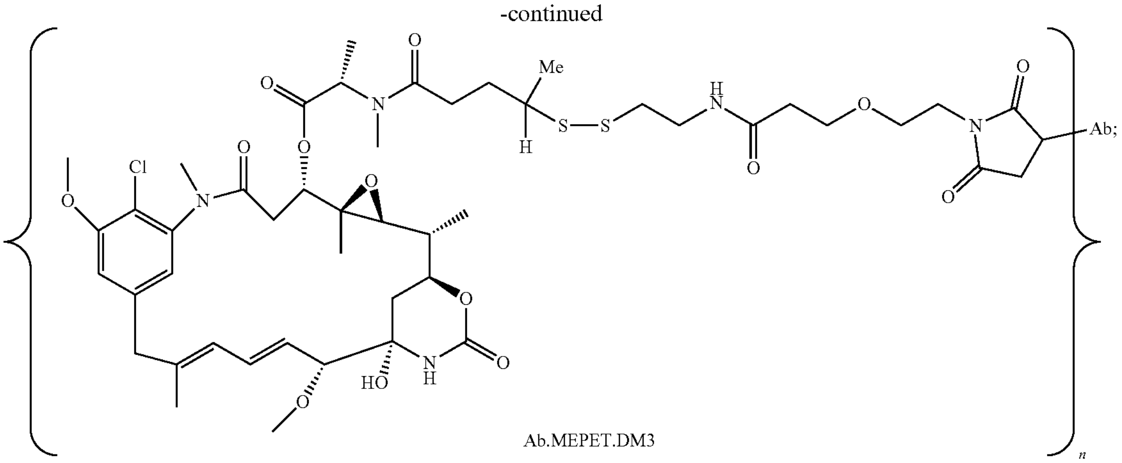

Ab.MEPET.DM3 as well as the corresponding open forms of the succinimide;

wherein:

Ab is an antibody or antigen binding fragment thereof;

n, which indicates the number of D-L groups attached to the Ab through the formation of a thioester bond with a sulfhydryl of the Ab, is an integer from 1 to 12, or 1 to 8, or preferably 1 to 4. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In another embodiment; the conjugate of the present invention is represented by any one of the following structural formulae:

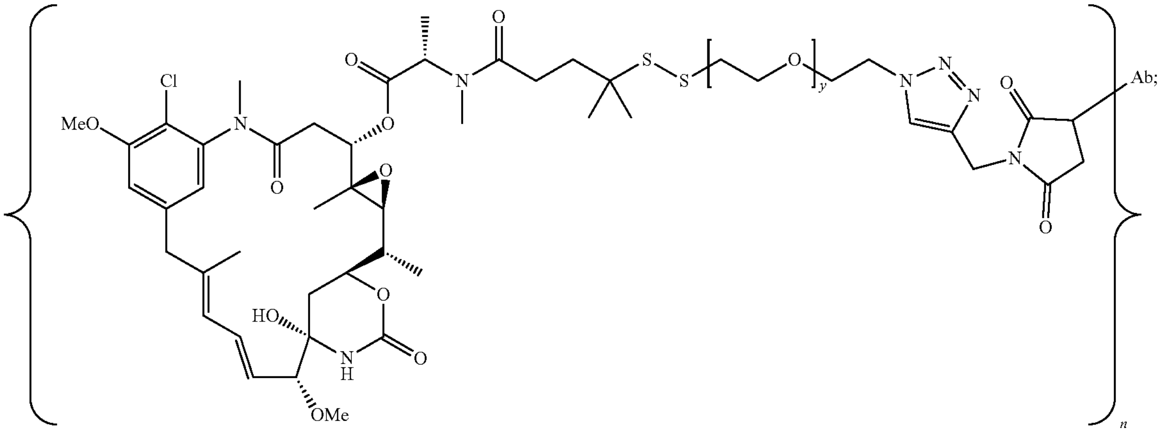

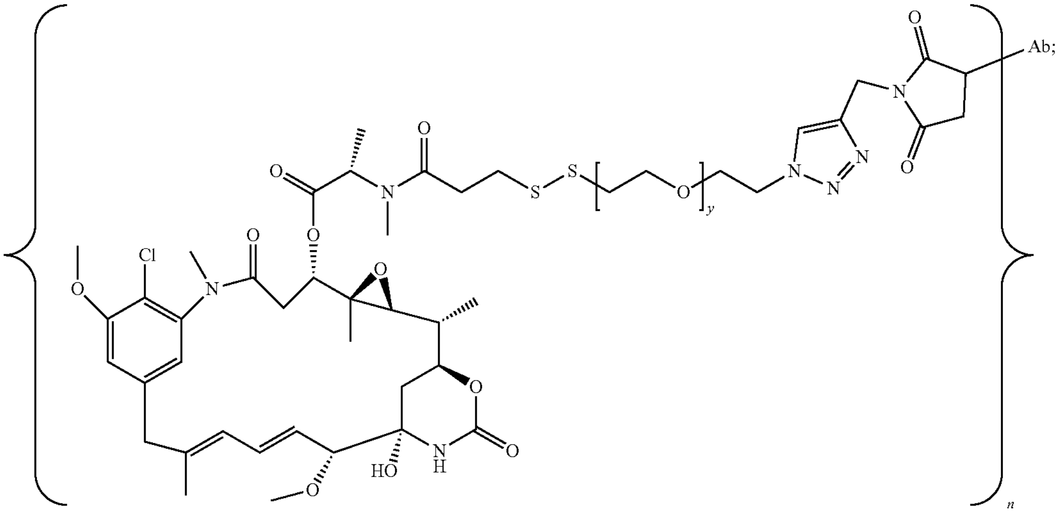

-continued

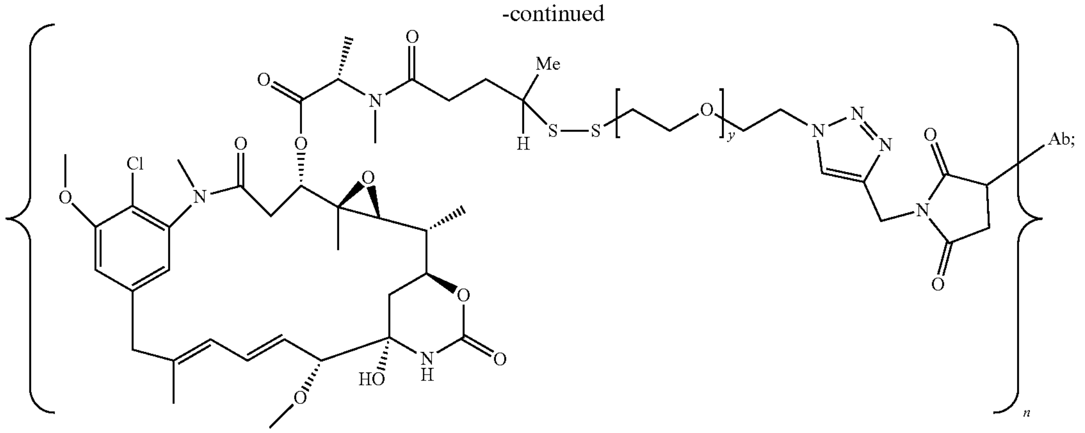

as well as the corresponding open forms of the succinimide;

wherein:

y is 1 to 11, preferably 1 to 5;

Ab is an antibody or antigen binding fragment thereof;

n, which indicates the number of D-L groups attached to the Ab through the formation of a thioester bond with a sulfhydryl of the Ab, is an integer from 1 to 12, or 1 to 8, or preferably 1 to 4. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In yet another embodiment; the conjugate of the present invention is represented by the following Formulae:

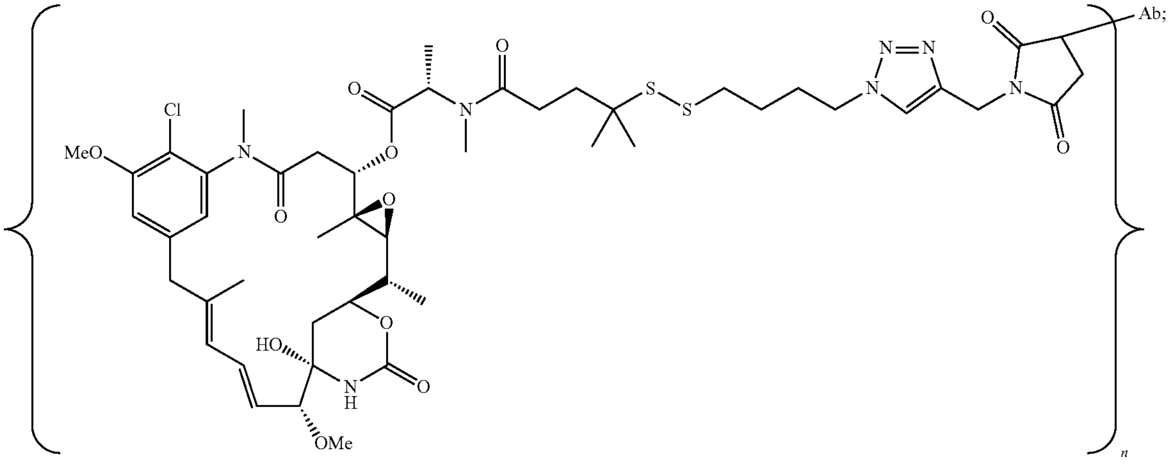

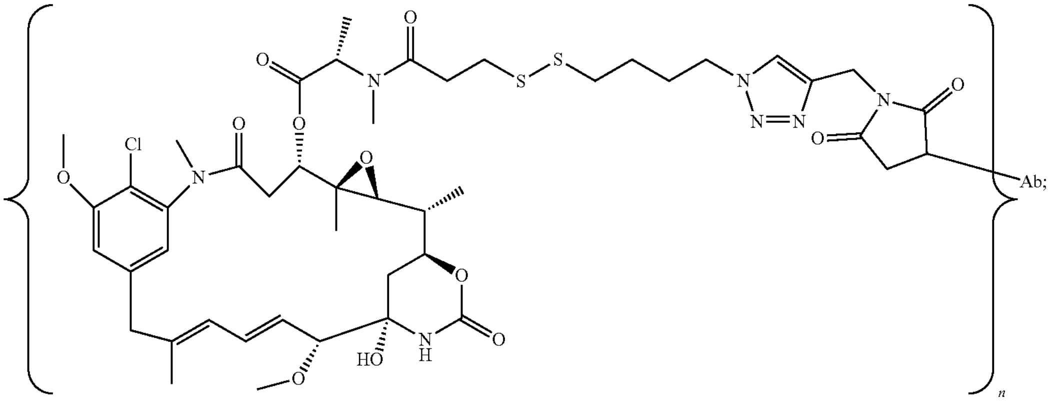

-continued

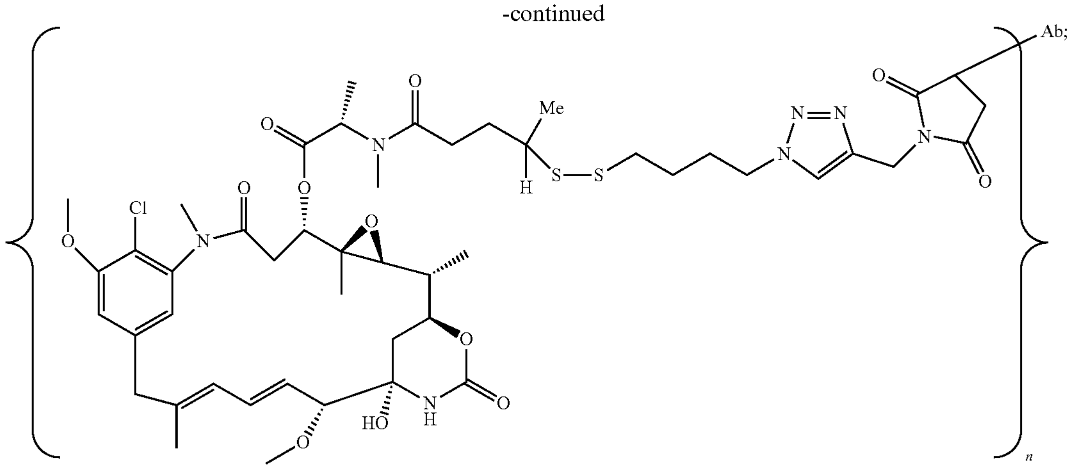

as well as the corresponding open forms of the succinimide;

wherein:

Ab is an antibody or antigen binding fragment thereof;

n, which indicates the number of D-L groups attached to the Ab through the formation of a thioester bond with a sulfhydryl of the Ab, is an integer from 1 to 12, or 1 to 8, or preferably 1 to 4. In a specific embodiment, n is 3 or 4. In some embodiments, the antibody or antigen binding fragment thereof binds to an antigen that is expressed on tumor cells. In one embodiment, the antibody or antigen binding fragment thereof specifically binds CCR7. In other embodiments, the antibody or antigen binding fragment thereof specifically binds P-cadherin, Cadherin 6, FGFR2, or FGFR4.

In a preferred embodiment, the conjugate of the present invention is represented by the following Formula:

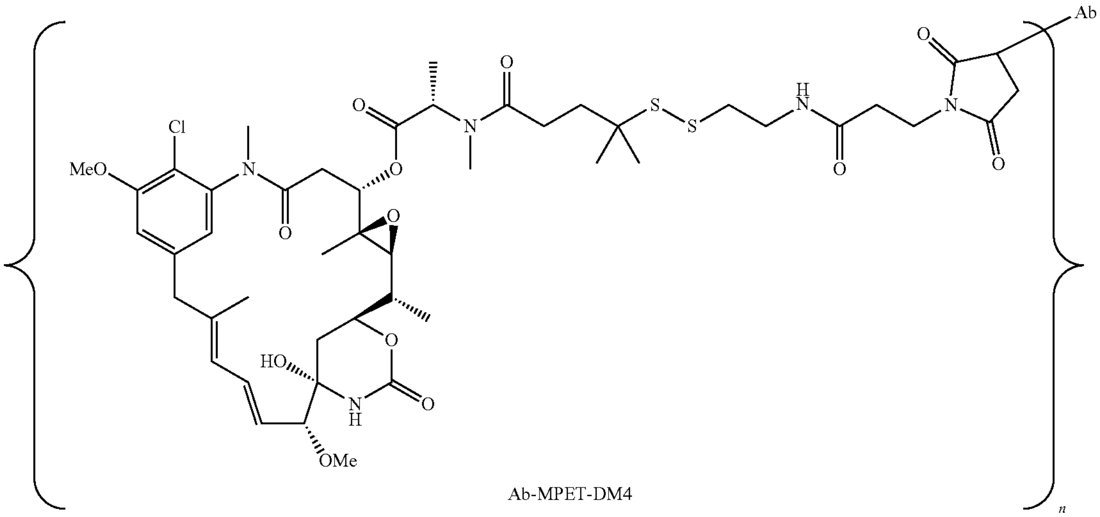

Ab-MPET-DM4 wherein:

Ab is an antibody or antigen binding fragment thereof;

n, which indicates the number of D-L groups attached to the Ab through the formation of a thioester bond with a sulfhydryl of the Ab, is an integer from 1 to 20. In some embodiments, n is an integer from 1 to 12. In some embodiments, n is an integer from 1 to 8. In some embodiments, n is an integer from 1 to 4. In a specific embodiment, n is 3 or 4. In another embodiment, the average n value is about 3 to about 4. In some embodiments, the antibody or antigen binding fragment thereof binds to an antigen that is expressed on tumor cells. In one embodiment, the antibody or antigen binding fragment thereof specifically binds CCR7. In other embodiments, the anti body or antigen binding fragment thereof specifically binds P-cadherin, Cadherin 6, FGFR2, or FGFR4.

In one embodiment, the average molar ratio of drug (e.g., DM1, DM3 or DM4) to the antibody in the conjugate (i.e., average n value, also known as Maytansinoid Antibody Ratio (MAR)) is about 1 to about 10, about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, or 8.1), about 2.5 to about 7, about 3 to about 5, about 2.5 to about 4.5 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5), about 3.0 to about 4.0, about 3.2 to about 4.2, or about 4.5 to 5.5 (e.g., about 4.5, about 4.6, about 4.7, about 4.8, about 4.9, about 5.0, about 5.1, about 5.2, about 5.3, about 5.4, or about 5.5).

In an aspect of the invention, the conjugate of the present invention has substantially high purity and has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free drug (e.g., DM1, DM3 or DM4) level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total cytotoxic agent) and/or (e) no substantial increase in the level of free drug (e.g., DM1, DM3 or DM4) occurs upon storage (e.g., after about 1 week, about 2 weeks, about 3 weeks, about 1 month, about 2 months, about 3 months, about 4 months, about 5 months, about 6 months, about 1 year, about 2 years, about 3 years, about 4 years, or about 5 years). "Substantial increase" in the level of free drug (e.g., DM1, DM3 or DM4) means that after certain storage time (e.g., about 1 week, about 2 weeks, about 3 weeks, about 1 month, about 2 months, about 3 months, about 4 months, about 5 months, about 6 months, about 1 year, about 2 years, about 3 years, about 4 years, or about 5 years), the increase in the level of free drug (e.g., DM1, DM3 or DM4) is less than about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.2%, about 2.5%, about 2.7%, about 3.0%, about 3.2%, about 3.5%, about 3.7%, or about 4.0%.

As used herein, the term "unconjugated linker" refers to the antibody that is covalently linked with a linker derived from a cross-linking reagent (e.g., SMCC, Sulfo-SMCC, SPDB, Sulfo-SPDB or CX1-1), wherein the antibody is not covalently coupled to the drug (e.g., DM1, DM3 or DM4) through a linker (i.e., the "unconjugated linker" can be represented by Ab-MCC, Ab-SPDB, or Ab-CX1-1).

1. Drug Moiety

The present invention provides immunoconjugates that specifically bind to CCR7. The antibody drug conjugates of the invention comprise anti-CCR7 antibodies, antibody fragments (e.g., antigen binding fragments) or functional equivalents that are conjugated to a drug moiety, e.g., an anti-cancer agent, an autoimmune treatment agent, an anti-inflammatory agent, an antifungal agent, an antibacterial agent, an anti-parasitic agent, an anti-viral agent, or an anesthetic agent. The antibodies, antibody fragments (e.g., antigen binding fragments) or functional equivalents of the invention can be conjugated to several identical or different drug moieties using any methods known in the art.

In certain embodiments, the drug moiety of the immunoconjugates of the present invention is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an RNA polymerase inhibitor, an amanitin, a pyrrolobenzodiazepine, an auristatin, a dolastatin, a maytansinoid, a MetAP (methionine aminopeptidase), an inhibitor of nuclear export of proteins CRM1, a DPPIV inhibitor, an Eg5 inhibitor, proteasome inhibitors, an inhibitor of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

In certain embodiment, the drug moiety of the immunoconjugates of the present invention is an auristatin disclosed in PCT Publication Numbers: WO 2015/095301 and WO2015/189791, both applications are hereby incorporated by reference. Non-limiting examples of auristatin drug moiety-linker constructs are:

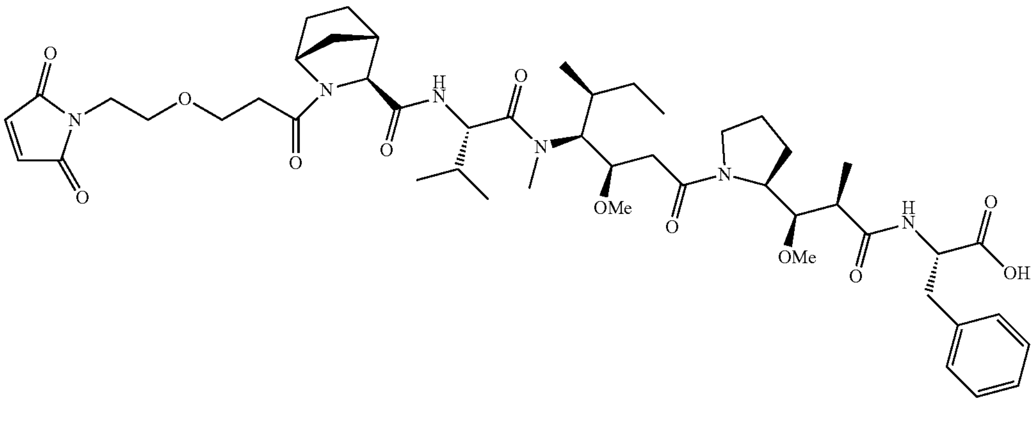 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H]1[C@H]2CC[C@H](C2)N1C(=O)CCOCCN1C(=O)C=CC1=O)C(C)C]

(which is AURIX2 as disclosed in instant application); and

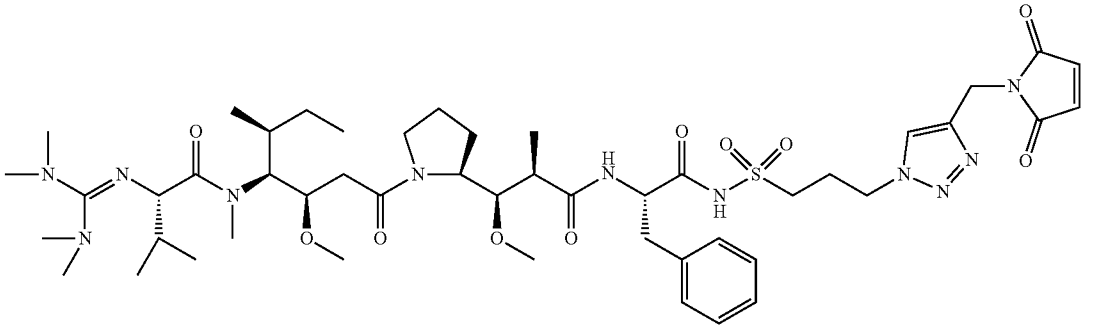 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)CCCn1cc(CN2C(=O)C=CC2=O)nn1)OC)N(C)C(=O)[C@@H](N=C(N(C)C)N(C)C)C(C)C]

(which is AURIX1 as disclosed in instant application).

In one embodiment, the drug moiety of the immunoconjugates of the present invention is a maytansinoid drug moiety, such as but not limited to, DM1, DM3 or DM4.

Further, the antibodies, antibody fragments (e.g., antigen binding fragments) or functional equivalents of the present invention may be conjugated to a drug moiety that modifies a given biological response. Drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or, a biological response modifier such as, for example, a lymphokine.

In one embodiment, the antibodies, antibody fragments (e.g., antigen binding fragments) or functional equivalents of the present invention are conjugated to a drug moiety, such as a cytotoxin, a drug (e.g., an immunosuppressant) or a radiotoxin. Examples of cytotoxins include but are not limited to, taxanes (see, e.g., International (PCT) Patent Application Nos. WO 01/38318 and PCT/US03/02675), DNA-alkylating agents (e.g., CC-1065 analogs), anthracyclines, tubulysin analogs, duocarmycin analogs, auristatin E, auristatin F, maytansinoids, and cytotoxic agents comprising a reactive polyethylene glycol moiety (see, e.g., Sasse et al., J. Antibiot. (Tokyo), 53, 879-85 (2000), Suzawa et al., Bioorg. Med. Chem., 8, 2175-84 (2000), Ichimura et al., J. Antibiot. (Tokyo), 44, 1045-53 (1991), Francisco et al., Blood (2003) (electronic publication prior to print publication), U.S. Pat. Nos. 5,475,092, 6,340,701, 6,372,738, and 6,436,931, U.S. Patent Application Publication No. 2001/0036923 A1, Pending U.S. patent application Ser. Nos. 10/024,290 and 10/116,053, and International (PCT) Patent Application No. WO 01/49698), taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thiotepa chlorambucil, meiphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). (See e.g., Seattle Genetics US20090304721).

Other examples of cytotoxins that can be conjugated to the antibodies, antibody fragments (antigen binding fragments) or functional equivalents of the invention include duocarmycins, calicheamicins, maytansines and auristatins, and derivatives thereof.

Various types of cytotoxins, linkers and methods for conjugating therapeutic agents to antibodies are known in the art, see, e.g., Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264.

The antibodies, antibody fragments (e.g., antigen binding fragments) or functional equivalents of the present invention can also be conjugated to a radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine-131, indium-111, yttrium-90, and lutetium-177. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention. In certain embodiments, the macrocyclic chelator is 1,4,7,10-tetraazacyclododecane-N,N',N",N"'-tetraacetic acid (DOTA) which can be attached to the antibody via a linker molecule. Such linker molecules are commonly known in the art and described in Denardo et al., (1998) Clin Cancer Res. 4(10):2483-90; Peterson et al., (1999) Bioconjug. Chem. 10(4):553-7; and Zimmerman et al., (1999) Nucl. Med. Biol. 26(8):943-50, each incorporated by reference in their entireties.

The antibodies, antibody fragments (e.g., antigen binding fragments) or functional equivalents of the present invention can also conjugated to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antibody fragment (e.g., antigen binding fragment) described herein (e.g., a Fab fragment, Fd fragment, Fv fragment, $F(ab)_2$ fragment, a VH domain, a VH CDR, a VL domain or a VL CDR) and a heterologous protein, polypeptide, or peptide.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2):76-82; Hansson et al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen may be recombined with one or more components, motifs, sections, parts, domains, fragments, etc. of one or more heterologous molecules.

Moreover, the antibodies, antibody fragments (e.g., antigen binding fragments) or functional equivalents of the present invention can be conjugated to marker sequences, such as a peptide, to facilitate purification. In preferred embodiments, the marker amino acid sequence is a hexa-histidine peptide (SEQ ID NO: 628), such as the tag provided in a pQE vector (QIAGEN, Inc., 9259 Eton Avenue, Chatsworth, CA, 91311), among others, many of which are commercially available. As described in Gentz et al., (1989) Proc. Natl. Acad. Sci. USA 86:821-824, for instance, hexa-histidine (SEQ ID NO: 628) provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "FLAG" tag (A. Einhauer et al., J. Biochem. Biophys. Methods 49: 455-465, 2001). According to the present invention, antibodies or antigen binding fragments can also be conjugated to tumor-penetrating peptides in order to enhance their efficacy.

In other embodiments, the antibodies, antibody fragments (e.g., antigen binding fragments) or functional equivalents of the present invention are conjugated to a diagnostic or detectable agent. Such immunoconjugates can be useful for monitoring or prognosing the onset, development, progression and/or severity of a disease or disorder as part of a clinical testing procedure, such as determining the efficacy of a particular therapy. Such diagnosis and detection can be accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, umbelliferone, fluorescein, fluorescein isothiocyanate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}I$, $^{125}I$, $^{123}I$, and $^{121}I$,), carbon ($^{14}C$), sulfur ($^{35}S$), tritium ($^{3}H$), indium ($^{115}In$, $^{113}In$ $^{112}In$, and $^{121}In$,), technetium ($^{99}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{64}Cu$, $^{113}Sn$, and $^{117}Sn$; and positron emitting metals using various positron emission tomographies, and non-radioactive paramagnetic metal ions.

The antibodies, antibody fragments (e.g., antigen binding fragments) or functional equivalents of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

2. Linker

As used herein, a "linker" is any chemical moiety that is capable of linking an antibody, antibody fragment (e.g., antigen binding fragments) or functional equivalent to another moiety, such as a drug moiety. Linkers can be susceptible to cleavage (cleavable linker), such as, acid-induced cleavage, photo-induced cleavage, peptidase-induced cleavage, esterase-induced cleavage, glycosidase induced cleavage, phosphodiesterase induced cleavage, phosphatase induced cleavage and disulfide bond cleavage, at conditions under which the compound or the antibody remains active. Alternatively, linkers can be substantially resistant to cleavage (e.g., stable linker or noncleavable linker). In some aspects, the linker is a procharged linker, a hydrophilic linker, or a dicarboxylic acid based linker.

In one aspect, the linker used in the present invention is derived from a crosslinking reagent such as N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodo-acetyl)aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

Non-cleavable linkers are any chemical moiety capable of linking a drug, such as a maytansinoid, to an antibody in a stable, covalent manner and does not fall under the categories listed above for cleavable linkers. Thus, non-cleavable linkers are substantially resistant to acid-induced cleavage, photo-induced cleavage, peptidase-induced cleavage, esterase-induced cleavage and disulfide bond cleavage. Furthermore, non-cleavable refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which the drug, such as maytansionoid or the antibody does not lose its activity.

Acid-labile linkers are linkers cleavable at acidic pH. For example, certain intracellular compartments, such as endosomes and lysosomes, have an acidic pH (pH 4-5), and provide conditions suitable to cleave acid-labile linkers.

Photo-labile linkers are linkers that are useful at the body surface and in many body cavities that are accessible to light. Furthermore, infrared light can penetrate tissue.

Some linkers can be cleaved by peptidases, i.e., peptidase cleavable linkers. Only certain peptides are readily cleaved inside or outside cells, see e.g., Trout et al., 79 Proc. Natl. Acad. Sci. USA, 626-629 (1982) and Umemoto et al. 43 Int. J. Cancer, 677-684 (1989). Furthermore, peptides are composed of α-amino acids and peptidic bonds, which chemically are amide bonds between the carboxylate of one amino acid and the amino group of a second amino acid. Other amide bonds, such as the bond between a carboxylate and the F-amino group of lysine, are understood not to be peptidic bonds and are considered non-cleavable.

Some linkers can be cleaved by esterases, i.e., esterase cleavable linkers. Again, only certain esters can be cleaved by esterases present inside or outside of cells. Esters are formed by the condensation of a carboxylic acid and an alcohol. Simple esters are esters produced with simple alcohols, such as aliphatic alcohols, and small cyclic and small aromatic alcohols.

Procharged linkers are derived from charged cross-linking reagents that retain their charge after incorporation into an antibody drug conjugate. Examples of procharged linkers can be found in US 2009/0274713.

3. Conjugation and Preparation of ADCs

Numerous methods of conjugating linker-payloads to antigen binding moiety are known in the art (reviewed in for example: Antibody-Drug Conjugate, Methods in Molecular Biology, Vol. 1045, Editor L. Ducry, Humana Press (2013)). Traditionally, drugs are conjugated to native lysine or native cysteine residues of the antibody. The resulting preparations are complex mixtures. More recently, site-specific conjugation methods are being employed to improve the therapeutic index and homogeneity of ADC preparations (For review: Panowski, S.; Bhakta, S.; Raab, H.; Polakis, P.; Junutula, J. R. *mAbs* 2014, 6, 34). Besides glycoengineering, (Zhou, Q. et al. *Bioconjugate chemistry* 2014, 25, 510; Zhu, Z. et al. *mAbs* 2014, 6, 1190); some of the more common methods of preparing site-specific ADCs are based on the incorporation of engineered cysteines, (Junutula, J. R. et al., *Nature biotechnology* 2008, 26, 925; Shinmi, D. et al., *Bioconjugate chemistry* 2016, 27, 1324), non-canonical amino acids (Tian, F. et al., *Proceedings National Academy of Sciences USA* 2014, 111, 1766; Axup, J. Y. et al., *Proceedings National Academy of Sciences USA* 2012, 109, 16101) or short peptide sequences into the antibody backbone (Drake, P. M. et al., *Bioconjugate chemistry* 2014, 25, 1331; Strop, P. et al., *Chemistry & biology* 2013, 20, 161; Beerli, R. R. et al., *PloS one* 2015, 10, e0131177; Grunewald, J. et al., *Bioconjugate chemistry* 2015, 26, 2554). These methods provide control over stoichiometry and attachment site of the cytotoxin resulting in better pharmacokinetic (PK), safety, and efficacy profiles of the conjugates relative to traditionally prepared ADCs.

The conjugates of the present invention can be prepared by any methods known in the art, such as those described in U.S. Pat. Nos. 7,811,572, 6,411,163, 7,368,565, and 8,163,888, US application publications 2011/0003969, 2011/0166319, 2012/0253021 and 2012/0259100, and PCT publications WO2014/124316 and WO2015/138615. The entire teachings of these patents and patent application publications are herein incorporated by reference.

Process for Conjugation to Engineered Cysteine Antibody Residues

Conjugates of the invention can be prepared using cysteine residues engineered into an antibody by, for example, site-directed mutagenesis. Such site-specific conjugates are homogenous and have improved properties (Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925-932.)

Because engineered cysteines in antibodies expressed in mammalian cells are modified by adducts (disulfides) such as glutathione (GSH) and/or cysteine during their biosynthesis (Chen et al. 2009), the engineered cysteine residues in the product as initially expressed are unreactive to thiol reactive reagents such as maleimido or bromo- or iodo-acetamide groups. To conjugate payload to an engineered cysteine after expression, glutathione or cysteine adducts need to be removed by reducing these disulfide adducts, which generally entails also reducing native disulfides in the expressed protein. Deprotection of adducted engineered cysteines can be accomplished by first exposing antibody to a reducing agent, e.g., dithiothreitol (DTT), TCEP, or reduced cysteine, followed by a procedure that allows for re-oxidation of all native disulfide bonds of an antibody to restore and/or stabilize the functional antibody structure.

Several methods can be employed to reduce and re-oxidize antibodies with engineered Cys residues for preparation of antibody drug conjugates. Attempts to follow re-oxidation protocols previously described in the literature using high concentration of $CuSO_4$ resulted in protein precipitation (Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925). We have successfully prepared and obtained antibody drug conjugates with several different methods for reduction and antibody re-oxidation.

In one example, freshly prepared DTT is added to purified Cys mutant antibodies to a final concentration of 10 mM. After incubation with DTT at room temperature for 1 hour, mixture is dialyzed at 4° C. against PBS for three days with daily buffer exchange to remove DTT and re-oxidize native disulfide bonds of the antibody. An alternative method is to remove reducing reagents through a desalting column such as Sephadex G-25, equilibrated with PBS. Once protein is fully reduced, 1 mM oxidized ascorbate (dehydro-ascorbic acid) is optionally added to desalted samples and re-oxidation incubations are carried out for 20-24 hours.

In another exemplary method, deprotection of engineered Cys residues is accomplished by adding fully reduced cysteine at 20 mM concentration to antibodies bound to protein A-Sepharose resin. Reduction of the Cys adducts is achieved by incubation for approximately 30-60 minutes at room temperature, then reductant is rapidly removed by washing resin with 50 beds of PBS. Re-oxidation of the reduced antibody is achieved by incubating washed slurry at room temperature with or without addition of 50-2000 nM $CuCl_2$ as an accelerant. With the exception of use of copper sulfate, examples herein use each of the protocols described herein with similar results. Reoxidation restores intra-chain disulfides, while dialysis, desalting or protein A chromatography removes reducing agent as well as cysteines and glutathiones initially connected to engineered cysteine(s) of the antibody. HPLC reverse phase chromatography is typically used to monitor the reoxidation process: Antibodies are loaded onto a PLRP-S column (4000 Å, 50 mm×2.1 mm, Agilent) heated to 80° C. and eluted using a linear gradient of 30-45% $CH_3CN$ in water containing 0.1% TFA at 1.5 mL/min. and peak detection at 215, 254, and 280 nm.

After re-oxidation, the antibody is conjugated to a pre-formed linker-drug moiety. By way of example, the pre-formed linker-drug moiety (such as for example MMTBT-DM4; MPET-DM4; MBT-DM4; MEPET-DM4, MPBT-DM1; and other linker-drug moieties as described herein), are added to re-oxidized Cys mutant antibody at 10 molar equivalents relative to antibody in PBS buffer (pH 7.2). Incubations are carried out for 1 hour. The conjugation process is monitored by reverse-phase HPLC, which is able to separate conjugated antibodies from non-conjugated ones. Conjugation reaction mixtures are analyzed on a PRLP-S column (4000 Å, 50 mm×2.1 mm, Agilent) heated to 80° C. and elution of the column are carried out by a linear gradient of 30-60% acetonitrile in water containing 0.1% TFA at a flow rate of 1.5 ml/min. Elution of proteins from the column is monitored at 280 nm, 254 nm and 215 nm.

In one embodiment, examples of linker-drug moiety for cysteine conjugation can be prepared according to Schemes 1 to 3:

Scheme 1

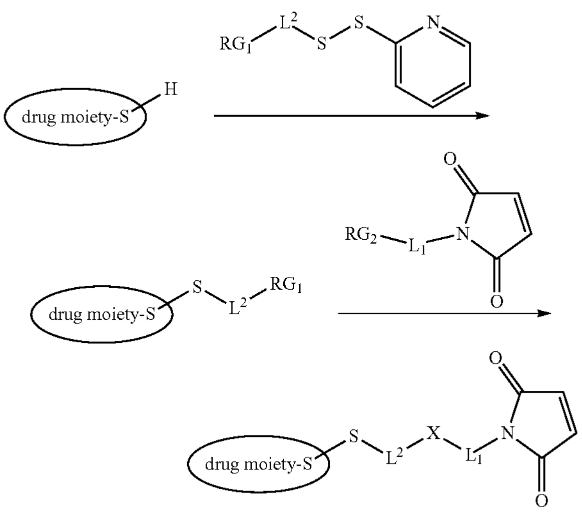

wherein:

the drug moiety is attached to the linker via a thiol functionality;

$L^1$ is a $C_{1-6}$alkylene wherein one of the methylene groups may be replaced with oxygen;

$L^2$ is a $C_{1-6}$alkylene or is $—(CH_2CH_2O)_y—CH_2—CH_2—$ wherein y is 1 to 11; and X is —C(O)—NH—, —NHC(O)— or a triazole;

wherein the alkylene is linear or branched; and

RG1 and RG2 are 2 reactive groups forming group X.

Reacting groups which form an amide or a triazole are well known in the art.

One example of pre-forming the linker-drug moiety is represented in Scheme 2 wherein the drug moiety is DM4; RG1 is an amino group and RG2 is an activated acid, resulting in the formation of the amide bond (X):

Scheme 2.

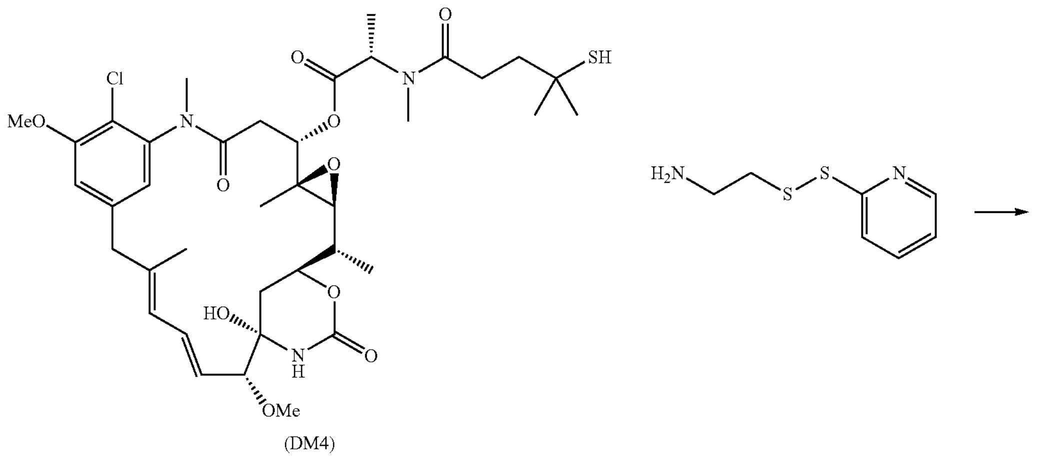

(DM4)

-continued
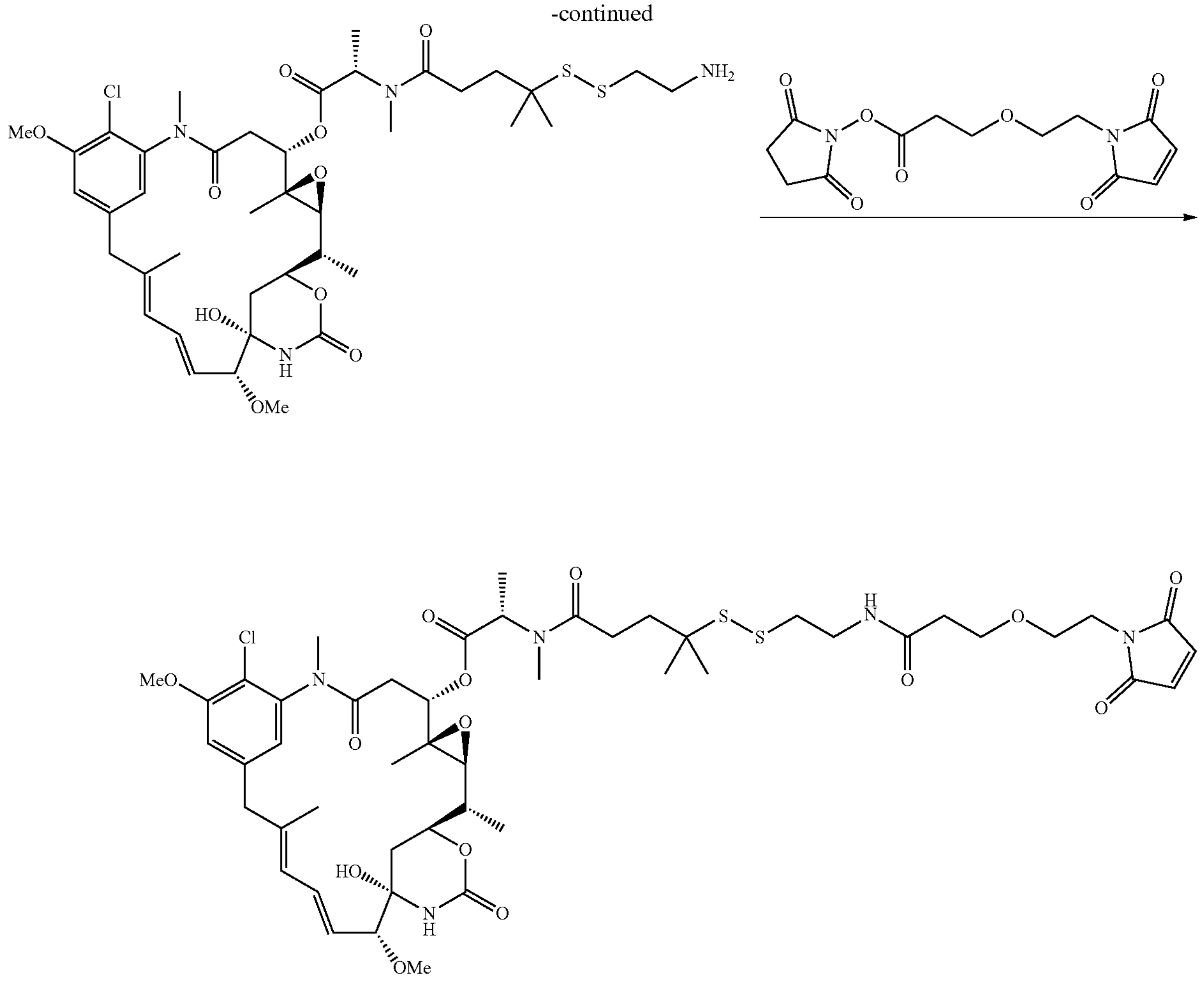
MEPET-DM4
Another example of pre-forming the linker-drug moiety is represented in Scheme 3 wherein the drug moiety is DM4; RG1 is an azide group and RG2 is an alkyne group, resulting in the formation of the tetrazole (X):
Scheme 3
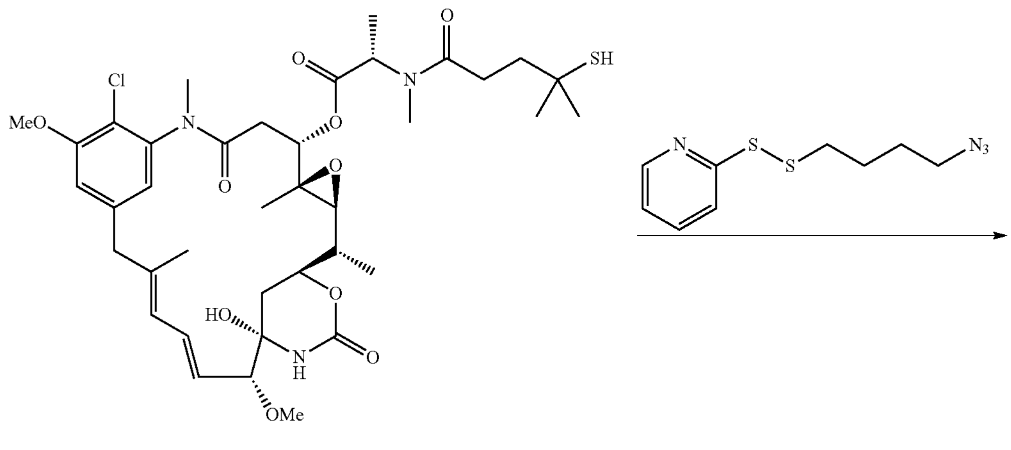
DM4

-continued

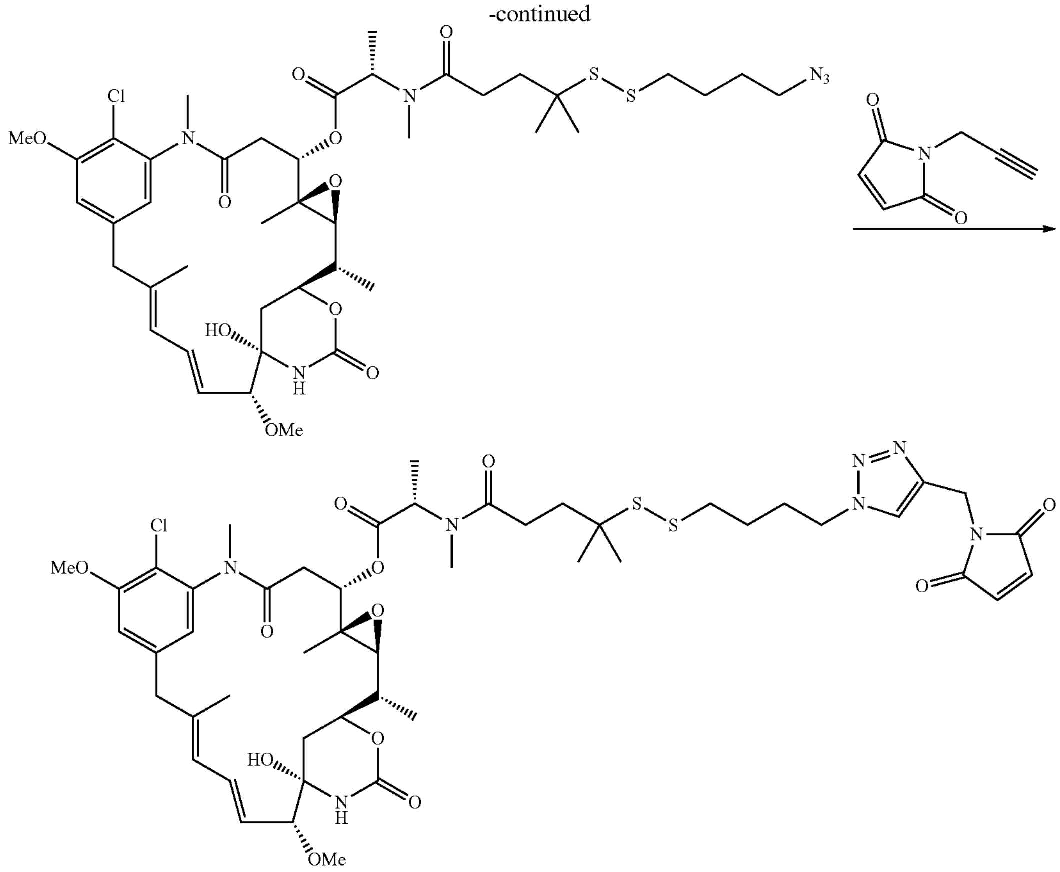

Conjugation efficiency of various drug moieties having a linked maleimide to a Cys mutant antibody vary depending on the solubility of the drug moieties used, however, many reactions result in more than 90% conjugate. To evaluate aggregation state, resulting conjugates are analyzed in a size exclusion chromatography column (GE, Superdex200, 3.2/30) at a flow rate of 0.1 ml/min in PBS. All conjugates are mainly monomeric. The majority of conjugates contain less than 3% dimeric and oligomeric material, indicating that conjugation of drug moiety having a linked maleimide to Cys mutant antibody does not cause aggregation.

Immunoconjugates are also characterized in terms of average loading of a drug moiety to antibody binding moiety, generally referred to as drug-to-antibody ratio (DAR). The DAR value is extrapolated, for example, from LC-MS data for reduced and deglycosylated samples. LC/MS allows quantitation of the average number of molecules of payload (drug moiety) attached to an antibody in an ADC. HPLC separates an antibody into light and heavy chains, and also separates heavy chain (HC) and light chain (LC) according to the number of Linker-Payload groups per chain. Mass spectral data enables identification of the component species in the mixture, e.g., LC, LC+1, LC+2, HC, HC+1, HC+2, etc. From average loading of LC and HC chains, the average DAR can be calculated for an ADC. The DAR for a given immunoconjugate sample represents the average number of drug (payload) molecules attached to a tetrameric antibody containing two light chains and two heavy chains.

Process for Conjugation to Native Cysteine Antibody Residues linker-drug moieties as described herein can also be conjugated to native cysteine residues of non-engineered antibodies using a procedure that involves partial reduction of the antibodies (Doronina, S. O., Toki, B. E., Torgov, M. Y., Mendelsohn, B. A., Cerveny, C. G., Chace, D. F., DeBlanc, R. L., Gearing, R. P., Bovee, T. D., Siegall, C. B., Francisco, J. A., Wahl, A. F., Meyer, D. L., and Senter, P. D. (2003) Development of potent monoclonal antibody auristatin conjugates for cancer therapy. *Nat. Biotechnol.* 21, 778-784). The following protocol is a non-limiting example how such conjugates can be prepared: Inter- and intra-chain disulfides bonds of the antibody (at a concentration of typically 5 to 10 mg/ml) are first partially reduced in PBS containing 2 mM EDTA by adding TCEP to a final concentration of 10 mM and incubating the mixture at 37° C. for 1 hour. After desalting and addition of 1% w/v PS-20 detergent, the partially reduced antibodies (1-2 mg/ml) is reacted overnight at 4° C. with 0.5 to 1 mg of a maleimide containing linker payload compound per 10 mg antibody. Resulting conjugates are purified by Protein A chromatography by standard methods and buffer exchanged to PBS, and are profiled typically by mass-spectrometry (MS), analytical size-exclusion chromatography (AnSEC), and analytical hydrophobic interaction chromatography (AnHIC) for their drug-to-antibody-ratio, aggregation propensity, and hydrophobicity as well as by activity assays.

One-Step Process for Cross-Linking to Lysine Antibody Residues

In one embodiment, the conjugates of the present invention can be prepared by a one-step process for cross-linking the drug to lysine residues on the antibody. The process comprises combining the antibody, drug and cross-linking agent in a substantially aqueous medium, optionally containing one or more co-solvents, at a suitable pH. In one embodiment, the process comprises the step of contacting the antibody of the present invention with a drug (e.g., DM1 or DM4) to form a first mixture comprising the antibody and the drug, and then contacting the first mixture comprising the antibody and the drug with a cross-linking agent (e.g., SMCC, Sulfo-SMCC, SPDB, Sulfo-SPDB or CX1-1) in a solution having a pH of about 4 to about 9 to provide a mixture comprising (i) the conjugate (e.g., Ab-MCC-DM1, Ab-SPDB-DM4, or Ab-CX1-1-DM1), (ii) free drug (e.g., DM1 or DM4), and (iii) reaction by-products.

In one embodiment, the one-step process comprises contacting the antibody with the drug (e.g., DM1 or DM4) and then the cross-linking agent (e.g., SMCC, Sulfo-SMCC, SPDB, Sulfo-SPDB or CX1-1) in a solution having a pH of about 6 or greater (e.g., about 6 to about 9, about 6 to about 7, about 7 to about 9, about 7 to about 8.5, about 7.5 to about 8.5, about 7.5 to about 8.0, about 8.0 to about 9.0, or about 8.5 to about 9.0). For example, the inventive process comprises contacting a cell-binding agent with the drug (DM1 or DM4) and then the cross-linking agent (e.g., SMCC, Sulfo-SMCC, SPDB, Sulfo-SPDB or CX1-1) in a solution having a pH of about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In a specific embodiment, the inventive process comprises contacting a cell-binding agent with the drug (e.g., DM1 or DM4) and then the cross-linking agent (e.g., SMCC, Sulfo-SMCC, SPDB, Sulfo-SPDB or CX1-1) in a solution having a pH of about 7.8 (e.g., a pH of 7.6 to 8.0 or a pH of 7.7 to 7.9).

The one-step process (i.e., contacting the antibody with the drug (e.g., DM1 or DM4) and then the cross-linking agent (e.g., SMCC, Sulfo-SMCC, SPDB, Sulfo-SPDB or CX1-1) can be carried out at any suitable temperature known in the art. For example, the one-step process can occur at about 20° C. or less (e.g., about −10° C. (provided that the solution is prevented from freezing, e.g., by the presence of organic solvent used to dissolve the cytotoxic agent and the bifunctional crosslinking reagent) to about 20° C., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, the one-step process occurs at a temperature of about 16° C. to about 24° C. (e.g., about 16° C., about 17° C., about 18° C., about 19° C., about 20° C., about 21° C., about 22° C., about 23° C., about 24° C., or about 25° C.). In another embodiment, the one-step process is carried out at a temperature of about 15° C. or less (e.g., about −10° C. to about 15° C., or about 0° C. to about 15° C.). For example, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about 15° C., about 14° C., about 13° C., about 12° C., about 11° C., about 10° C., about 9° C., about 8° C., about 7° C., about 6° C., about 5° C., about 4° C., about 3° C., about 2° C., about 1° C., about 0° C., about −1° C., about −2° C., about −3° C., about −4° C., about −5° C., about −6° C., about −7° C., about −8° C., about −9° C., or about −10° C., provided that the solution is prevented from freezing, e.g., by the presence of organic solvent(s) used to dissolve the cross-linking agent (e.g., SMCC, Sulfo-SMCC, Sulfo-SPDB SPDB, or CX1-1). In one embodiment, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about −10° C. to about 15° C., about 0° C. to about 15° C., about 0° C. to about 10° C., about 0° C. to about 5° C., about 5° C. to about 15° C., about 10° C. to about 15° C., or about 5° C. to about 10° C. In another embodiment, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about 10° C. (e.g., a temperature of 8° C. to 12° C. or a temperature of 9° C. to 11° C.).

In one embodiment, the contacting described above is effected by providing the antibody, then contacting the antibody with the drug (e.g., DM1 or DM4) to form a first mixture comprising the antibody and the drug (e.g., DM1 or DM4), and then contacting the first mixture comprising the antibody and the drug (e.g., DM1 or DM4) with the cross-linking agent (e.g., SMCC, Sulfo-SMCC, SPDB, Sulfo-SPDB or CX1-1). For example, in one embodiment, the antibody is provided in a reaction vessel, the drug (e.g., DM1 or DM4) is added to the reaction vessel (thereby contacting the antibody), and then the cross-linking agent (e.g., SMCC, Sulfo-SMCC, SPDB, Sulfo-SPDB or CX1-1) is added to the mixture comprising the antibody and the drug (e.g., DM1 or DM4) (thereby contacting the mixture comprising the antibody and the drug). In one embodiment, the antibody is provided in a reaction vessel, and the drug (e.g., DM1 or DM4) is added to the reaction vessel immediately following providing the antibody to the vessel. In another embodiment, the antibody is provided in a reaction vessel, and the drug (e.g., DM1 or DM4) is added to the reaction vessel after a time interval following providing the antibody to the vessel (e.g., about 5 minutes, about 10 minutes, about 20 minutes, about 30 minutes, about 40 minutes, about 50 minutes, about 1 hour, about 1 day or longer after providing the cell-binding agent to the space). The drug (e.g., DM1 or DM4) can be added quickly (i.e., within a short time interval, such as about 5 minutes, about 10 minutes) or slowly (such as by using a pump).

The mixture comprising the antibody and the drug (e.g., DM1 or DM4) can then be contacted with the cross-linking agent (e.g., SMCC, Sulfo-SMCC, SPDB, Sulfo-SPDB or CX1-1) either immediately after contacting the antibody with the drug (e.g., DM1 or DM4) or at some later point (e.g., about 5 minutes to about 8 hours or longer) after contacting the antibody with the drug (e.g., DM1 or DM4). For example, in one embodiment, the cross-linking agent (e.g., SMCC, Sulfo-SMCC, SPDB, Sulfo-SPDB or CX1-1) is added to the mixture comprising the antibody and the drug (e.g., DM1 or DM4) immediately after the addition of the drug (e.g., DM1 or DM4) to the reaction vessel comprising the antibody. Alternatively, the mixture comprising the antibody and the drug (e.g., DM1 or DM4) can be contacted with the cross-linking agent (e.g., SMCC, Sulfo-SMCC, SPDB, Sulfo-SPDB or CX1-1) at about 5 minutes, about 10 minutes, about 20 minutes, about 30 minutes, about 1 hour, about 2 hours, about 3 hours, about 4 hours, about 5 hours, about 6 hours, about 7 hours, about 8 hours, or longer after contacting the antibody with the drug (e.g., DM1 or DM4).

After the mixture comprising the antibody and the drug (e.g., DM1 or DM4) is contacted with the cross-linking agent (e.g., SMCC, Sulfo-SMCC, SPDB, Sulfo-SPDB or CX1-1) the reaction is allowed to proceed for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or longer (e.g., about 30 hours, about 35 hours, about 40 hours, about 45 hours, or about 48 hrs).

In one embodiment, the one-step process further comprises a quenching step to quench any unreacted drug (e.g., DM1 or DM4) and/or unreacted cross-linking agent (e.g., SMCC, Sulfo-SMCC, SPDB, Sulfo-SPDB or CX1-1). The quenching step is typically performed prior to purification of the conjugate. In one embodiment, the mixture is quenched by contacting the mixture with a quenching reagent. As used herein, the "quenching reagent" refers to a reagent that reacts with the free drug (e.g., DM1 or DM4) and/or cross-linking agent (e.g., SMCC, Sulfo-SMCC, SPDB, Sulfo-SPDB or CX1-1). In one embodiment, maleimide or haloacetamide quenching reagents, such as 4-maleimidobutyric acid, 3-maleimidopropionic acid, N-ethylmaleimide, iodoacetamide, or iodoacetamidopropionic acid, can be used to ensure that any unreacted group (such as thiol) in the drug (e.g., DM1 or DM4) is quenched. The quenching step can help prevent the dimerization of the drug (e.g., DM1). The dimerized DM1 can be difficult to remove. Upon quenching with polar, charged thiol-quenching reagents (such as 4-maleimidobutyric acid or 3-maleimidopropionic acid), the excess, unreacted DM1 is converted into a polar, charged, water-soluble adduct that can be easily separated from the covalently-linked conjugate during the purification step. Quenching with non-polar and neutral thiol-quenching reagents can also be used. In one embodiment, the mixture is quenched by contacting the mixture with a quenching reagent that reacts with the unreacted cross-linking agent (e.g., SMCC, Sulfo-SMCC, SPDB, Sulfo-SPDB or CX1-1). For example, nucleophiles can be added to the mixture in order to quench any unreacted SMCC. The nucleophile preferably is an amino group containing nucleophile, such as lysine, taurine and hydroxylamine.

In a preferred embodiment, the reaction (i.e., contacting the antibody with the drug (e.g., DM1 or DM4) and then cross-linking agent (e.g., SMCC, Sulfo-SMCC, SPDB, Sulfo-SPDB or CX1-1)) is allowed to proceed to completion prior to contacting the mixture with a quenching reagent. In this regard, the quenching reagent is added to the mixture about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 25 hours to about 48 hours) after the mixture comprising the antibody and the drug (e.g., DM1 or DM4) is contacted with the cross-linking agent (e.g., SMCC, Sulfo-SMCC, SPDB, Sulfo-SPDB or CX1-1).

Alternatively, the mixture is quenched by lowering the pH of the mixture to about 5.0 (e.g., 4.8, 4.9, 5.0, 5.1 or 5.2). In another embodiment, the mixture is quenched by lowering the pH to less than 6.0, less than 5.5, less than 5.0, less than 4.8, less than 4.6, less than 4.4, less than 4.2, less than 4.0. Alternatively, the pH is lowered to about 4.0 (e.g., 3.8, 3.9, 4.0, 4.1 or 4.2) to about 6.0 (e.g., 5.8, 5.9, 6.0, 6.1 or 6.2), about 4.0 to about 5.0, about 4.5 (e.g., 4.3, 4.4, 4.5, 4.6 or 4.7) to about 5.0. In one embodiment, the mixture is quenched by lowering the pH of the mixture to 4.8. In another embodiment, the mixture is quenched by lowering the pH of the mixture to 5.5.

In one embodiment, the one-step process further comprises a holding step to release the unstably bound linkers from the antibody. The holding step comprises holding the mixture prior to purification of the conjugate (e.g., after the reaction step, between the reaction step and the quenching step, or after the quenching step). For example, the process comprises (a) contacting the antibody with the drug (e.g., DM1, DM3 or DM4) to form a mixture comprising the antibody and the drug (e.g., DM1, DM3 or DM4); and then contacting the mixture comprising the antibody and drug (e.g., DM1, DM3 or DM4) with the cross-linking agent (e.g., SMCC, Sulfo-SMCC, SPDB, Sulfo-SPDB or CX1-1), in a solution having a pH of about 4 to about 9 to provide a mixture comprising (i) the conjugate (e.g., Ab-MCC-DM1, Ab-SPDB-DM4 or Ab-CX1-1-DM1), (ii) free drug (e.g., DM1, DM3 or DM4), and (iii) reaction by-products, (b) holding the mixture prepared in step (a) to release the unstably bound linkers from the cell-binding agent, and (c) purifying the mixture to provide a purified conjugate.

In another embodiment, the process comprises (a) contacting the antibody with the drug (e.g., DM1, DM3 or DM4) to form a mixture comprising the antibody and the drug (e.g., DM1, DM3 or DM4); and then contacting the mixture comprising the antibody and the drug (e.g., DM1, DM3 or DM4) with the cross-linking agent (e.g., SMCC, Sulfo-SMCC, SPDB, Sulfo-SPDB or CX1-1), in a solution having a pH of about 4 to about 9 to provide a mixture comprising (i) the conjugate, (ii) free drug (e.g., DM1, DM3 or DM4), and (iii) reaction by-products, (b) quenching the mixture prepared in step (a) to quench any unreacted drug (e.g., DM1, DM3 or DM4) and/or unreacted cross-linking agent (e.g., SMCC, Sulfo-SMCC, SPDB, Sulfo-SPDB or CX1-1), (c) holding the mixture prepared in step (b) to release the unstably bound linkers from the cell-binding agent, and (d) purifying the mixture to provide a purified conjugate (e.g., Ab-MCC-DM1, Ab-SPDB-DM4 or Ab-CX1-1-DM1).

Alternatively, the holding step can be performed after purification of the conjugate, followed by an additional purification step.

In a preferred embodiment, the reaction is allowed to proceed to completion prior to the holding step. In this regard, the holding step can be performed about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 24 hours to about 48 hours) after the mixture comprising the antibody and the drug (e.g., DM1, DM3 or DM4) is contacted with the cross-linking agent (e.g., SMCC, Sulfo-SMCC, SPDB, Sulfo-SPDB or CX1-1).

The holding step comprises maintaining the solution at a suitable temperature (e.g., about 0° C. to about 37° C.) for a suitable period of time (e.g., about 1 hour to about 1 week, about 1 hour to about 24 hours, about 1 hour to about 8 hours, or about 1 hour to about 4 hours) to release the unstably bound linkers from the antibody while not substantially releasing the stably bound linkers from the antibody. In one embodiment, the holding step comprises maintaining the solution at about 20° C. or less (e.g., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, the holding step comprises maintaining the solution at a temperature of about 16° C. to about 24° C. (e.g., about 15° C., about 16° C., about 17° C., about 18° C., about 19° C., about 20° C., about 21° C., about 22° C., about 23° C., about 24° C., or about 25° C.). In another embodiment, the holding step comprises maintaining the solution at a temperature of about 2° C. to about 8° C. (e.g., about 0° C., about 1° C., about 2° C., about 3° C., about 4° C., about 5° C., about 6° C., about 7° C., about 8° C., about 9° C., or about 10° C.). In another embodiment, the holding step comprises maintaining the solution at a temperature of about 37° C. (e.g., about 34° C., about 35° C., about 36° C., about 37° C., about 38° C., about 39° C., or about 40° C.).

The duration of the holding step depends on the temperature and the pH at which the holding step is performed. For example, the duration of the holding step can be substantially reduced by performing the holding step at elevated temperature, with the maximum temperature limited by the stability of the cell-binding agent-cytotoxic agent conjugate. The holding step can comprise maintaining the solution for about 1 hour to about 1 day (e.g., about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, or about 24 hours), about 10 hours to about 24 hours, about 12 hours to about 24 hours, about 14 hours to about 24 hours, about 16 hours to about 24 hours, about 18 hours to about 24 hours, about 20 hours to about 24 hours, about 5 hours to about 1 week, about 20 hours to about 1 week, about 12 hours to about 1 week (e.g., about 12 hours, about 16 hours, about 20 hours, about 24 hours, about 2 days, about 3 days, about 4 days, about 5 days, about 6 days, or about 7 days), or about 1 day to about 1 week.

In one embodiment, the holding step comprises maintaining the solution at a temperature of about 2° C. to about 8° C. for a period of at least about 12 hours for up to a week. In another embodiment, the holding step comprises maintaining the solution at a temperature of about 2° C. to about 8° C. overnight (e.g., about 12 to about 24 hours, preferably about 20 hours).

The pH value for the holding step preferably is about 4 to about 10. In one embodiment, the pH value for the holding step is about 4 or more, but less than about 6 (e.g., 4 to 5.9) or about 5 or more, but less than about 6 (e.g., 5 to 5.9). In another embodiment, the pH values for the holding step range from about 6 to about 10 (e.g., about 6.5 to about 9, about 6 to about 8). For example, pH values for the holding step can be about 6, about 6.5, about 7, about 7.5, about 8, about 8.5, about 9, about 9.5, or about 10.

In specific embodiments, the holding step can comprise incubating the mixture at 25° C. at a pH of about 6-7.5 for about 12 hours to about 1 week, incubating the mixture at 4° C. at a pH of about 4.5-5.9 for about 5 hours to about 5 days, or incubating the mixture at 25° C. at a pH of about 4.5-5.9 for about 5 hours to about 1 day.

The one-step process may optionally include the addition of sucrose to the reaction step to increase solubility and recovery of the conjugates. Desirably, sucrose is added at a concentration of about 0.1% (w/v) to about 20% (w/v) (e.g., about 0.1% (w/v), 1% (w/v), 5% (w/v), 10% (w/v), 15% (w/v), or 20% (w/v)). Preferably, sucrose is added at a concentration of about 1% (w/v) to about 10% (w/v) (e.g., about 0.5% (w/v), about 1% (w/v), about 1.5% (w/v), about 2% (w/v), about 3% (w/v), about 4% (w/v), about 5% (w/v), about 6% (w/v), about 7% (w/v), about 8% (w/v), about 9% (w/v), about 10% (w/v), or about 110% (w/v)). In addition, the reaction step also can comprise the addition of a buffering agent. Any suitable buffering agent known in the art can be used. Suitable buffering agents include, for example, a citrate buffer, an acetate buffer, a succinate buffer, and a phosphate buffer. In one embodiment, the buffering agent is selected from the group consisting of HEPPSO (N-(2-hydroxyethyl)piperazine-N'-(2-hydroxypropanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), HEPPS (EPPS) (4-(2-hydroxyethyl)piperazine-1-propanesulfonic acid), TES (N-[tris(hydroxymethyl)methyl]-2-aminoethanesulfonic acid), and a combination thereof.

In one embodiment, the one-step process can further comprise the step of purifying the mixture to provide purified conjugate (e.g., Ab-MCC-DM1, Ab-SPDB-DM4 or Ab-CX1-1-DM1). Any purification methods known in the art can be used to purify the conjugates of the present invention. In one embodiment, the conjugates of the present invention using tangential flow filtration (TFF), non-adsorptive chromatography, adsorptive chromatography, adsorptive filtration, selective precipitation, or any other suitable purification process, as well as combinations thereof. In another embodiment, prior to subjecting the conjugates to purification process described above, the conjugates are first filtered through one or more PVDF membranes. Alternatively, the conjugates are filtered through one or more PVDF membranes after subjecting the conjugates to the purification process described above. For example, in one embodiment, the conjugates are filtered through one or more PVDF membranes and then purified using tangential flow filtration. Alternatively, the conjugates are purified using tangential flow filtration and then filtered through one or more PVDF membranes.

Any suitable TFF systems may be utilized for purification, including a Pellicon type system (Millipore, Billerica, MA), a Sartocon Cassette system (Sartorius AG, Edgewood, NY), and a Centrasette type system (Pall Corp., East Hills, NY).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, CA), HA Ultrogel hydroxyapatite (Pall Corp., East Hills, NY), and ceramic fluoroapatite (CFT Type I and Type II, Bio-Rad Laboratories, Hercules, CA). An example of a suitable HCIC resin is MEP Hypercel resin (Pall Corp., East Hills, NY). Examples of suitable HIC resins include Butyl-Sepharose, Hexyl-Sepaharose, Phenyl-Sepharose, and Octyl Sepharose resins (all from GE Healthcare, Piscataway, NJ), as well as Macro-prep Methyl and Macro-Prep t-Butyl resins (Biorad Laboratories, Hercules, CA). Examples of suitable ion exchange resins include SP-Sepharose, CM-Sepharose, and Q-Sepharose resins (all from GE Healthcare, Piscataway, NJ), and Unosphere S resin (Bio-Rad Laboratories, Hercules, CA). Examples of suitable mixed mode ion exchangers include Bakerbond ABx resin (JT Baker, Phillipsburg N J). Examples of suitable IMAC resins include Chelating Sepharose resin (GE Healthcare, Piscataway, NJ) and Profinity IMAC resin (Bio-Rad Laboratories, Hercules, CA). Examples of suitable dye ligand resins include Blue Sepharose resin (GE Healthcare, Piscataway, NJ) and Affi-gel Blue resin (Bio-Rad Laboratories, Hercules, CA). Examples of suitable affinity resins include Protein A Sepharose resin (e.g., MabSelect, GE Healthcare, Piscataway, NJ) and lectin affinity resins, e.g. Lentil Lectin Sepharose resin (GE Healthcare, Piscataway, NJ), where the antibody bears appropriate lectin binding sites. Examples of suitable reversed phase resins include C4, C8, and C18 resins (Grace Vydac, Hesperia, CA).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

Two-Step Process and One-Pot Process for Cross-Linking to Lysine Antibody Residues In one embodiment, the conjugates of the present invention can be prepared as described in the U.S. Pat. No. 7,811,572 and U.S. Patent Application Publication No. 2006/0182750. The process comprises the steps of (a) contacting the antibody of the present invention with the cross-linking agent (e.g., SMCC, Sulfo-SMCC, SPDB, Sulfo-SPDB or CX1-1) to covalently attach the linker (i.e., Ab-SMCC, Ab-SPDB or Ab-CX1-1) to the antibody and thereby prepare a first mixture comprising the antibody having the linker bound thereto; (b) optionally subjecting the first mixture to a purification process to prepare a purified first mixture of the antibody having the linker bound thereto; (c) conjugating the drug (e.g., DM1, DM3, or DM4) to the antibody having the linker bound thereto in the first mixture by reacting the antibody having the linker bound thereto with the drug (e.g., DM1, DM3, or DM4) in a solution having a pH of about 4 to about 9 to prepare a second mixture comprising (i) conjugate (e.g., Ab-MCC-DM1, Ab-SPDB-DM4 or Ab-CX1-1-DM1), (ii) free drug (e.g., DM1, DM3 or DM4); and (iii) reaction by-products; and (d) subjecting the second mixture to a purification process to purify the conjugate from the other components of the second mixture. Alternatively, the purification step (b) can be omitted. Any purification methods described herein can be used for steps (b) and (d). In one embodiment, TFF is used for both steps (b) and (d). In another embodiment, TFF is used for step (b) and absorptive chromatography (e.g., CHT) is used for step (d).

One-Step Reagent and In-Situ Process for Cross-Linking to Lysine Antibody Residues In one embodiment, the conjugates of the present invention can be prepared by conjugating pre-formed linker-drug compound (e.g., SMCC-DM1, Sulfo-SMCC-DM1, SPDB-DM4 or CX1-1-DM1) to the antibody of the present invention, as described in U.S. Pat. No. 6,441,163 and U.S. Patent Application Publication Nos. 2011/0003969 and 2008/0145374, followed by a purification step. Any purification methods described herein can be used. The linker-drug compound is prepared by reacting the drug (e.g., DM1, DM3, or DM4) with the cross-linking agent (e.g., SMCC, Sulfo-SMCC, SPDB, Sulfo-SPDB or CX1-1). The linker-drug compound (e.g., SMCC-DM1, Sulfo-SMCC-DM1, SPDB-DM4 or CX1-1-DM1) is optionally subjected to purification before being conjugated to the antibody.

Anti-CCR7 Antibodies

The present invention provides antibodies or antibody fragments (e.g., antigen binding fragments) that specifically bind to CCR7. Antibodies or antibody fragments (e.g., antigen binding fragments) of the invention include, but are not limited to, the human monoclonal antibodies or fragments thereof, isolated as described in the Examples.

The present invention in certain embodiments provides antibodies or antibody fragments (e.g., antigen binding fragments) that specifically bind CCR7, said antibodies or antibody fragments (e.g., antigen binding fragments) comprise a VH domain having an amino acid sequence of SEQ ID NO: 13, 45, 77 or 608. The present invention in certain embodiments also provides antibodies or antibody fragments (e.g., antigen binding fragments) that specifically bind to CCR7, said antibodies or antibody fragments (e.g., antigen binding fragments) comprise a VH CDR having an amino acid sequence of any one of the VH CDRs listed in Tables 1 and 4, infra. In particular embodiments, the invention provides antibodies or antibody fragments (e.g., antigen binding fragments) that specifically bind to CCR7, said antibodies comprising (or alternatively, consist of) one, two, three, four, five or more VH CDRs having an amino acid sequence of any of the VH CDRs listed in Tables 1 and 4, infra.

The present invention provides antibodies or antibody fragments (e.g., antigen binding fragments) that specifically bind to CCR7, said antibodies or antibody fragments (e.g., antigen binding fragments) comprise a VL domain having an amino acid sequence of SEQ ID NO: 29, 61, 93 or 624. The present invention also provides antibodies or antibody fragments (e.g., antigen binding fragments) that specifically bind to CCR7, said antibodies or antibody fragments (e.g., antigen binding fragments) comprise a VL CDR having an amino acid sequence of any one of the VL CDRs listed in Tables 1 and 4, infra. In particular, the invention provides antibodies or antibody fragments (e.g., antigen binding fragments) that specifically bind to CCR7, said antibodies or antibody fragments (e.g., antigen binding fragments) comprise (or alternatively, consist of) one, two, three or more VL CDRs having an amino acid sequence of any of the VL CDRs listed in Tables 1 and 4, infra.

Other antibodies or antibody fragments (e.g., antigen binding fragments) of the invention include amino acids that have been mutated, yet have at least 60, 70, 80, 90 or 95 percent identity in the CDR regions with the CDR regions depicted in the sequences described in Tables 1 and 4. In some embodiments, the antibodies comprise mutant amino acid sequences wherein no more than 1, 2, 3, 4 or 5 amino acids have been mutated in the CDR regions when compared with the CDR regions depicted in the sequence described in Tables 1 and 4.

The present invention also provides nucleic acid sequences that encode the VH, VL, the full length heavy chain, and the full length light chain of the antibodies that specifically bind to CCR7. Such nucleic acid sequences can be optimized for expression in mammalian cells.

Throughout the text of this application, should there be a discrepancy between the text of the specification and the sequence listing, the text of the specification shall prevail.

TABLE 1

| Examples of Anti-CCR7 Antibodies of the Present Invention | | |
|---|---|---|
| 506E15 (Humanized CysMab DAPA) | | |
| SEQ ID NO: 1 | HCDR1 (Combined) | GFTFSSYAMS |
| SEQ ID NO: 2 | HCDR2 (Combined) | TISSGGSFTYYPDSVKG |
| SEQ ID NO: 3 | HCDR3 (Combined) | RASTVVGTDFDV |
| SEQ ID NO: 4 | HCDR1 (Kabat) | SYAMS |
| SEQ ID NO: 5 | HCDR2 (Kabat) | TISSGGSFTYYPDSVKG |
| SEQ ID NO: 6 | HCDR3 (Kabat) | RASTVVGTDFDV |
| SEQ ID NO: 7 | HCDR1 (Chothia) | GFTFSSY |
| SEQ ID NO: 8 | HCDR2 (Chothia) | SSGGSF |
| SEQ ID NO: 9 | HCDR3 (Chothia) | RASTVVGTDFDV |
| SEQ ID NO: 10 | HCDR1 (IMGT) | GFTFSSYA |
| SEQ ID NO: 11 | HCDR2 (IMGT) | ISSGGSFT |
| SEQ ID NO: 12 | HCDR3 (IMGT) | ARRASTVVGTDFDV |
| SEQ ID NO: 13 | VH | EVQLVESGGGLVKPGGSLRLSCAASGFTFSSYAMSWIRQ<br>APGKGLEWVATISSGGSFTYYPDSVKGRFTISRDNAKNSL<br>YLQMNSLRAEDTAVYYCARRASTVVGTDFDVWGQGTT<br>VTVSS |
| SEQ ID NO: 14 | DNA VH | GAAGTGCAGCTGGTGGAATCTGGCGGCGGACTGGTCA<br>AGCCTGGCGGCTCCCTGAGACTGTCTTGCGCCGCCTCC<br>GGCTTCACCTTCTCCAGCTACGCCATGTCCTGGATCCG<br>GCAGGCCCCTGGCAAGGGACTGGAGTGGGTGGCCAC<br>CATCTCCTCCGGCGGCAGCTTCACCTACTACCCCGACTC<br>CGTGAAGGGCCGGTTCACCATCTCCCGGGACAACGCC<br>AAGAACTCCCTGTACCTGCAGATGAACTCCCTGCGGGC<br>CGAGGACACCGCCGTGTACTACTGTGCCAGACGGGCC<br>TCCACCGTCGTGGGCACCGATTTCGATGTGTGGGGCCA<br>GGGCACAACCGTGACCGTGTCCTCC |
| SEQ ID NO: 15 | Heavy Chain (DAPA, CysMab mutations underlined) | EVQLVESGGGLVKPGGSLRLSCAASGFTFSSYAMSWIRQ<br>APGKGLEWVATISSGGSFTYYPDSVKGRFTISRDNAKNSL<br>YLQMNSLRAEDTAVYYCARRASTVVGTDFDVWGQGTT<br>VTVSSASTKGPSVFPLAPSSKSTSGGTAALGCLVKDYFP**C**P<br>VTVSWNSGALTSGVHTFPAVLQSSGLYSLSSVVTVPSSSL<br>GTQTYICNVNHKPSNTKVDKRVEPKSCDKTHTCPPCPAP<br>ELLGGPSVFLFPPKPKDTLMISRTPEVTCVVV**A**VSHEDPE<br>VKFNWYVDGVEVHNAKTKPREEQYNSTYRVVSVLTVLH<br>QDWLNGKEYKCKVSNKAL**A**APIEKTISKAKGQPREPQVY<br>TLPPSREEMTKNQVSLTCLVKGFYP**C**DIAVEWESNGQPE<br>NNYKTTPPVLDSDGSFFLYSKLTVDKSRWQQGNVFSCSV<br>MHEALHNHYTQKSLSLSPGK |
| SEQ ID NO: 16 | DNA Heavy Chain | GAAGTGCAGCTGGTGGAATCTGGCGGCGGACTGGTCA<br>AGCCTGGCGGCTCCCTGAGACTGTCTTGCGCCGCCTCC<br>GGCTTCACCTTCTCCAGCTACGCCATGTCCTGGATCCG<br>GCAGGCCCCTGGCAAGGGACTGGAGTGGGTGGCCAC<br>CATCTCCTCCGGCGGCAGCTTCACCTACTACCCCGACTC<br>CGTGAAGGGCCGGTTCACCATCTCCCGGGACAACGCC<br>AAGAACTCCCTGTACCTGCAGATGAACTCCCTGCGGGC<br>CGAGGACACCGCCGTGTACTACTGTGCCAGACGGGCC<br>TCCACCGTCGTGGGCACCGATTTCGATGTGTGGGGCCA<br>GGGCACAACCGTGACCGTGTCCTCCGCCTCCACCAAGG<br>GACCCTCCGTGTTCCCTCTGGCCCCTTCCAGCAAGTCCA |

TABLE 1-continued

Examples of Anti-CCR7 Antibodies of the Present Invention

| | | |
|---|---|---|
| | | CCTCTGGCGGCACCGCCGCTCTGGGCTGCCTGGTCAAG GACTACTTCCCCTGCCCTGTGACAGTGTCCTGGAACTC CGGCGCTCTGACCTCCGGCGTGCACACCTTCCCTGCCG TGCTGCAGTCCTCCGGCCTGTACTCCCTGTCCTCCGTCG TGACCGTGCCTTCCTCCAGCCTGGGCACCCAGACCTAC ATCTGCAACGTGAACCACAAGCCCTCCAACACCAAAGT GGACAAGCGGGTGGAACCCAAGTCCTGCGACAAGACC CACACCTGTCCTCCCTGCCCTGCCCCTGAGCTGCTGGG AGGCCCTTCCGTGTTCCTGTTCCCTCCAAAGCCCAAGG ACACCCTGATGATCTCCCGGACCCCTGAAGTGACCTGC GTGGTGGTGGCCGTGTCCCACGAGGATCCCGAAGTGA AGTTCAATTGGTACGTGGACGGCGTGGAAGTGCACAA TGCCAAGACCAAGCCCAGAGAGGAACAGTACAACTCC ACCTACCGGGTGGTGTCCGTGCTGACCGTGCTGCACCA GGACTGGCTGAACGGCAAAGAGTACAAGTGCAAAGT GTCCAACAAGGCCCTGGCCGCTCCCATCGAAAAGACC ATCTCCAAGGCCAAGGGCCAGCCCAGAGAGCCCCAAG TGTACACACTGCCTCCCAGCCGGGAAGAGATGACCAA GAACCAAGTGTCCCTGACCTGCCTCGTGAAGGGCTTCT ACCCCTGCGATATCGCCGTGGAGTGGGAGTCCAACGG CCAGCCCGAGAACAACTACAAGACCACCCCTCCCGTGC TGGACAGCGACGGCTCATTCTTCCTGTACTCCAAGCTG ACCGTGGACAAGTCCCGGTGGCAGCAGGGCAACGTGT TCTCCTGCTCCGTGATGCACGAGGCCCTGCACAACCAC TACACCCAGAAGTCCCTGTCCCTGAGCCCCGGCAAG |
| SEQ ID NO: 17 | LCDR1 (Combined) | RASQDIGSSLN |
| SEQ ID NO: 18 | LCD R2 (Combined) | ATSSLDS |
| SEQ ID NO: 19 | LCD R3 (Combined) | LQYASSPPT |
| SEQ ID NO: 20 | LCDR1 (Kabat) | RASQDIGSSLN |
| SEQ ID NO: 21 | LCDR2 (Kabat) | ATSSLDS |
| SEQ ID NO: 22 | LCDR3 (Kabat) | LQYASSPPT |
| SEQ ID NO: 23 | LCDR1 (Chothia) | SQDIGSS |
| SEQ ID NO: 24 | LCDR2 (Chothia) | ATS |
| SEQ ID NO: 25 | LCDR3 (Chothia) | YASSPP |
| SEQ ID NO: 26 | LCDR1 (IMGT) | QDIGSS |
| SEQ ID NO: 27 | LCDR2 (IMGT) | ATS |
| SEQ ID NO: 28 | LCDR3 (IMGT) | LQYASSPPT |
| SEQ ID NO: 29 | VL | DIQMTQSPSSLSASVGDRVTLTCRASQDIGSSLNWLQQK PGKAIKRLIYATSSLDSGVPSRFSGSRSGTDYTLTISSLQPE DFVVYYCLQYASSPPTFGGGTKLEIK |
| SEQ ID NO: 30 | DNA VL | GACATCCAGATGACCCAGAGCCCCTCCAGCCTGTCCGC CTCCGTGGGCGATAGAGTGACCCTGACCTGCCGGGCC TCCCAGGACATCGGCTCCTCCCTGAACTGGCTGCAGCA GAAGCCCGGCAAGGCCATCAAGCGGCTGATCTACGCC ACCTCCTCCCTGGACTCCGGCGTGCCCTCCCGGTTCTCT GGCTCCAGATCCGGCACCGACTACACCCTGACCATCTC CAGCCTGCAGCCCGAGGACTTCGTGGTGTACTACTGCC TGCAGTACGCCTCCAGCCCTCCCACCTTCGGCGGAGGC ACCAAGCTGGAAATCAAG |
| SEQ ID NO: 31 | Light Chain | DIQMTQSPSSLSASVGDRVTLTCRASQDIGSSLNWLQQK PGKAIKRLIYATSSLDSGVPSRFSGSRSGTDYTLTISSLQPE |

TABLE 1-continued

| Examples of Anti-CCR7 Antibodies of the Present Invention | | |
|---|---|---|
| | | DFVVYYCLQYASSPPTFGGGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQGL SSPVTKSFNRGEC |
| SEQ ID NO: 32 | DNA Light Chain | GACATCCAGATGACCCAGAGCCCCTCCAGCCTGTCCGC CTCCGTGGGCGATAGAGTGACCCTGACCTGCCGGGCC TCCCAGGACATCGGCTCCTCCCTGAACTGGCTGCAGCA GAAGCCCGGCAAGGCCATCAAGCGGCTGATCTACGCC ACCTCCTCCCTGGACTCCGGCGTGCCCTCCCGGTTCTCT GGCTCCAGATCCGGCACCGACTACACCCTGACCATCTC CAGCCTGCAGCCCGAGGACTTCGTGGTGTACTACTGCC TGCAGTACGCCTCCAGCCCTCCCACCTTCGGCGGAGGC ACCAAGCTGGAAATCAAGCGTACGGTGGCCGCTCCCA GCGTGTTCATCTTCCCCCCCAGCGACGAGCAGCTGAAG AGCGGCACCGCCAGCGTGGTGTGCCTGCTGAACAACT TCTACCCCCGGGAGGCCAAGGTGCAGTGGAAGGTGGA CAACGCCCTGCAGAGCGGCAACAGCCAGGAGAGCGTC ACCGAGCAGGACAGCAAGGACTCCACCTACAGCCTGA GCAGCACCCTGACCCTGAGCAAGGCCGACTACGAGAA GCATAAGGTGTACGCCTGCGAGGTGACCCACCAGGGC CTGTCCAGCCCCGTGACCAAGAGCTTCAACAGGGGCG AGTGC |
| | 121G12 | (Humanized CysMab, DAPA) |
| SEQ ID NO: 33 | HCDR1 (Combined) | GFTFSTYAMS |
| SEQ ID NO: 34 | HCDR2 (Combined) | TISDAGSYSYYPDNVKG |
| SEQ ID NO: 35 | HCDR3 (Combined) | RGSRYEEYYVMDY |
| SEQ ID NO: 36 | HCDR1 (Kabat) | TYAMS |
| SEQ ID NO: 37 | HCDR2 (Kabat) | TISDAGSYSYYPDNVKG |
| SEQ ID NO: 38 | HCDR3 (Kabat) | RGSRYEEYYVMDY |
| SEQ ID NO: 39 | HCDR1 (Chothia) | GFTFSTY |
| SEQ ID NO: 40 | HCDR2 (Chothia) | SDAGSY |
| SEQ ID NO: 41 | HCDR3 (Chothia) | RGSRYEEYYVMDY |
| SEQ ID NO: 42 | HCDR1 (IMGT) | GFTFSTYA |
| SEQ ID NO: 43 | HCDR2 (IMGT) | ISDAGSYS |
| SEQ ID NO: 44 | HCDR3 (IMGT) | ARRGSRYEEYYVMDY |
| SEQ ID NO: 45 | VH | EVQLVESGGGLVKPGGSLRLSCAASGFTFSTYAMSWVRQ APGKGLEWVATISDAGSYSYYPDNVKGRFTISRDNAKNSL YLQMNSLRAEDTAVYYCARRGSRYEEYYVMDYWGQGT TVTVSS |
| SEQ ID NO: 46 | DNA VH | GAAGTGCAGCTGGTGGAATCTGGCGGCGGACTGGTCA AGCCTGGCGGCTCCCTGAGACTGTCTTGCGCCGCCTCC GGCTTCACCTTCTCCACCTACGCCATGTCCTGGGTCCGA CAGGCCCCTGGAAAGGGCCTGGAGTGGGTGGCCACCA TCTCCGACGCCGGCTCCTACTCCTACTACCCCGACAAC GTGAAGGGCCGGTTCACCATCTCCCGGGACAACGCCA AGAACTCCCTGTACCTGCAGATGAACTCCCTGCGGGCC GAGGACACCGCCGTGTACTACTGCGCCAGACGGGGCT CCAGATACGAAGAGTACTACGTGATGGACTACTGGGG CCAGGGCACAACCGTGACCGTGTCCTCC |

TABLE 1-continued

| Examples of Anti-CCR7 Antibodies of the Present Invention | | |
|---|---|---|
| SEQ ID NO: 47 | Heavy Chain (DAPA, CysMab mutations underlined) | EVQLVESGGGLVKPGGSLRLSCAASGFTFSTYAMSWVRQ<br>APGKGLEWVATISDAGSYSYYPDNVKGRFTISRDNAKNSL<br>YLQMNSLRAEDTAVYYCARRGSRYEEYYVMDYWGQGT<br>TVTVSSASTKGPSVFPLAPSSKSTSGGTAALGCLVKDYFP**C**<br>PVTVSWNSGALTSGVHTFPAVLQSSGLYSLSSVVTVPSSS<br>LGTQTYICNVNHKPSNTKVDKRVEPKSCDKTHTCPPCPA<br>PELLGGPSVFLFPPKPKDTLMISRTPEVTCVVV**A**VSHEDPE<br>VKFNWYVDGVEVHNAKTKPREEQYNSTYRVVSVLTVLH<br>QDWLNGKEYKCKVSNKAL**A**APIEKTISKAKGQPREPQVY<br>TLPPSREEMTKNQVSLTCLVKGFYP**C**DIAVEWESNGQPE<br>NNYKTTPPVLDSDGSFFLYSKLTVDKSRWQQGNVFSCSV<br>MHEALHNHYTQKSLSLSPGK |
| SEQ ID NO: 48 | DNA Heavy Chain | GAAGTGCAGCTGGTGGAATCTGGCGGCGGACTGGTCA<br>AGCCTGGCGGCTCCCTGAGACTGTCTTGCGCCGCCTCC<br>GGCTTCACCTTCTCCACCTACGCCATGTCCTGGGTCCGA<br>CAGGCCCCTGGAAAGGGCCTGGAGTGGGTGGCCACCA<br>TCTCCGACGCCGGCTCCTACTCCTACTACCCCGACAAC<br>GTGAAGGGCCGGTTCACCATCTCCCGGGACAACGCCA<br>AGAACTCCCTGTACCTGCAGATGAACTCCCTGCGGGCC<br>GAGGACACCGCCGTGTACTACTGCGCCAGACGGGGCT<br>CCAGATACGAAGAGTACTACGTGATGGACTACTGGGG<br>CCAGGGCACAACCGTGACCGTGTCCTCCGCCTCCACCA<br>AGGGACCCTCCGTGTTCCCTCTGGCCCCTTCCAGCAAG<br>TCCACCTCTGGCGGCACCGCCGCTCTGGGCTGCCTGGT<br>CAAGGACTACTTCCCCTGCCCTGTGACAGTGTCCTGGA<br>ACTCCGGCGCTCTGACCTCCGGCGTGCACACCTTCCCT<br>GCCGTGCTGCAGTCCTCCGGCCTGTACTCCCTGTCCTCC<br>GTCGTGACCGTGCCTTCCTCCAGCCTGGGCACCCAGAC<br>CTACATCTGCAACGTGAACCACAAGCCCTCCAACACCA<br>AAGTGGACAAGCGGGTGGAACCCAAGTCCTGCGACAA<br>GACCCACACCTGTCCTCCCTGCCCTGCCCCTGAGCTGCT<br>GGGAGGCCCTTCCGTGTTCCTGTTCCCTCCAAAGCCCA<br>AGGACACCCTGATGATCTCCCGGACCCCTGAAGTGACC<br>TGCGTGGTGGTGGCCGTGTCCCACGAGGATCCCGAAG<br>TGAAGTTCAATTGGTACGTGGACGGCGTGGAAGTGCA<br>CAATGCCAAGACCAAGCCCAGAGAGGAACAGTACAAC<br>TCCACCTACCGGGTGGTGTCCGTGCTGACCGTGCTGCA<br>CCAGGACTGGCTGAACGGCAAAGAGTACAAGTGCAAA<br>GTGTCCAACAAGGCCCTGGCCGCTCCCATCGAAAAGA<br>CCATCTCCAAGGCCAAGGGCCAGCCCAGAGAGCCCCA<br>AGTGTACACACTGCCTCCCAGCCGGGAAGAGATGACC<br>AAGAACCAAGTGTCCCTGACCTGCCTCGTGAAGGGCTT<br>CTACCCCTGCGATATCGCCGTGGAGTGGGAGTCCAAC<br>GGCCAGCCCGAGAACAACTACAAGACCACCCCTCCCGT<br>GCTGGACTCCGACGGCTCATTCTTCCTGTACTCCAAGCT<br>GACCGTGGACAAGTCCCGGTGGCAGCAGGGCAACGT<br>GTTCTCCTGCTCCGTGATGCACGAGGCCCTGCACAACC<br>ACTACACCCAGAAGTCCCTGTCCCTGAGCCCCGGCAAG |
| SEQ ID NO: 49 | LCDR1 (Combined) | RASQSISNNLH |
| SEQ ID NO: 50 | LCDR2 (Combined) | YASQSIS |
| SEQ ID NO: 51 | LCDR3 (Combined) | QQSSSWLT |
| SEQ ID NO: 52 | LCDR1 (Kabat) | RASQSISNNLH |
| SEQ ID NO: 53 | LCDR2 (Kabat) | YASQSIS |
| SEQ ID NO: 54 | LCDR3 (Kabat) | QQSSSWLT |
| SEQ ID NO: 55 | LCDR1 (Chothia) | SQSISNN |
| SEQ ID NO: 56 | LCDR2 (Chothia) | YAS |
| SEQ ID NO: 57 | LCDR3 (Chothia) | SSSWL |

TABLE 1-continued

| Examples of Anti-CCR7 Antibodies of the Present Invention | | |
|---|---|---|
| SEQ ID NO: 58 | LCDR1 (IMGT) | QSISNN |
| SEQ ID NO: 59 | LCDR2 (IMGT) | YAS |
| SEQ ID NO: 60 | LCDR3 (IMGT) | QQSSSWLT |
| SEQ ID NO: 61 | VL | EIVLTQSPATLSVSPGERVTLSCRASQSISNNLHWYQQKP GQAPRLLIKYASQSISGIPARFSGSGSGTDFTLTISSVEPED FGVYFCQQSSSWLTFGQGTKLEIK |
| SEQ ID NO: 62 | DNA VL | GAGATCGTGCTGACACAGTCCCCTGCCACCCTGTCTGT GTCTCCCGGCGAGAGAGTGACCCTGTCCTGCCGGGCC TCCCAGTCCATCTCCAACAACCTGCACTGGTATCAGCA GAAGCCCGGCCAGGCCCCTCGGCTGCTGATTAAGTAC GCCTCCCAGAGCATCTCCGGCATCCCTGCCAGATTCTC CGGCTCCGGCAGCGGCACCGACTTCACCCTGACCATCT CCAGCGTGGAACCCGAGGACTTCGGCGTGTACTTCTGC CAGCAGTCCTCCTCCTGGCTGACCTTCGGCCAGGGCAC CAAGCTGGAAATCAAG |
| SEQ ID NO: 63 | Light Chain | EIVLTQSPATLSVSPGERVTLSCRASQSISNNLHWYQQKP GQAPRLLIKYASQSISGIPARFSGSGSGTDFTLTISSVEPED FGVYFCQQSSSWLTFGQGTKLEIKRTVAAPSVFIFPPSDE QLKSGTASVVCLLNNFYPREAKVQWKVDNALQSGNSQE SVTEQDSKDSTYSLSSTLTLSKADYEKHKVYACEVTHQGLS SPVTKSFNRGEC |
| SEQ ID NO: 64 | DNA Light Chain | GAGATCGTGCTGACACAGTCCCCTGCCACCCTGTCTGT GTCTCCCGGCGAGAGAGTGACCCTGTCCTGCCGGGCC TCCCAGTCCATCTCCAACAACCTGCACTGGTATCAGCA GAAGCCCGGCCAGGCCCCTCGGCTGCTGATTAAGTAC GCCTCCCAGAGCATCTCCGGCATCCCTGCCAGATTCTC CGGCTCCGGCAGCGGCACCGACTTCACCCTGACCATCT CCAGCGTGGAACCCGAGGACTTCGGCGTGTACTTCTGC CAGCAGTCCTCCTCCTGGCTGACCTTCGGCCAGGGCAC CAAGCTGGAAATCAAGCGTACGGTGGCCGCTCCCAGC GTGTTCATCTTCCCCCCCAGCGACGAGCAGCTGAAGAG CGGCACCGCCAGCGTGGTGTGCCTGCTGAACAACTTCT ACCCCCGGGAGGCCAAGGTGCAGTGGAAGGTGGACA ACGCCCTGCAGAGCGGCAACAGCCAGGAGAGCGTCAC CGAGCAGGACAGCAAGGACTCCACCTACAGCCTGAGC AGCACCCTGACCCTGAGCAAGGCCGACTACGAGAAGC ATAAGGTGTACGCCTGCGAGGTGACCCACCAGGGCCT GTCCAGCCCCGTGACCAAGAGCTTCAACAGGGGCGAG TGC |
| 674J13 (Humanized, CysMab DAPA) | | |
| SEQ ID NO: 65 | HCDR1 (Combined) | GYSITSGYSWH |
| SEQ ID NO: 66 | HCDR2 (Combined) | HIHSSGSTNYNPSLKS |
| SEQ ID NO: 67 | HCDR3 (Combined) | GGVQAFAY |
| SEQ ID NO: 68 | HCDR1 (Kabat) | SGYSWH |
| SEQ ID NO: 69 | HCDR2 (Kabat) | HIHSSGSTNYNPSLKS |
| SEQ ID NO: 70 | HCDR3 (Kabat) | GGVQAFAY |
| SEQ ID NO: 71 | HCDR1 (Chothia) | GYSITSGY |
| SEQ ID NO: 72 | HCDR2 (Chothia) | HSSGS |
| SEQ ID NO: 73 | HCDR3 (Chothia) | GGVQAFAY |

TABLE 1-continued

| Examples of Anti-CCR7 Antibodies of the Present Invention | | |
|---|---|---|
| SEQ ID NO: 74 | HCDR1<br>(IMGT) | GYSITSGYS |
| SEQ ID NO: 75 | HCDR2<br>(IMGT) | IHSSGST |
| SEQ ID NO: 76 | HCDR3<br>(IMGT) | ARGGVQAFAY |
| SEQ ID NO: 77 | VH | DVQLQESGPGLVKPSQTLSLTCTVSGYSITSGYSWHWIR<br>QHPGKGLEWMAHIHSSGSTNYNPSLKSRITISRDTSKNQ<br>FSLKLSSVTAADTAVYYCARGGVQAFAYWGQGTLVTVSS |
| SEQ ID NO: 78 | DNA VH | GACGTGCAGCTGCAGGAATCTGGCCCTGGCCTGGTCA<br>AGCCCTCCCAGACCCTGTCCCTGACCTGCACCGTGTCC<br>GGCTACTCTATCACCTCCGGCTACAGCTGGCACTGGAT<br>CCGGCAGCACCCCGGCAAGGGCCTGGAATGGATGGCC<br>CACATCCACTCCTCCGGCTCCACCAACTACAACCCCAGC<br>CTGAAGTCCCGGATCACCATCTCCCGGGACACCTCCAA<br>GAACCAGTTCTCCCTGAAGCTGTCCTCCGTGACCGCCG<br>CTGACACCGCCGTGTACTACTGTGCCAGAGGCGGCGT<br>GCAGGCCTTCGCTTATTGGGGCCAGGGAACCCTGGTC<br>ACCGTGTCCTCC |
| SEQ ID NO: 79 | Heavy<br>Chain<br>(DAPA,<br>CysMab<br>mutations<br>underlined) | DVQLQESGPGLVKPSQTLSLTCTVSGYSITSGYSWHWIR<br>QHPGKGLEWMAHIHSSGSTNYNPSLKSRITISRDTSKNQ<br>FSLKLSSVTAADTAVYYCARGGVQAFAYWGQGTLVTVSS<br>ASTKGPSVFPLAPSSKSTSGGTAALGCLVKDYFPCPVTVS<br>WNSGALTSGVHTFPAVLQSSGLYSLSSVVTVPSSSLGTQT<br>YICNVNHKPSNTKVDKRVEPKSCDKTHTCPPCPAPELLGG<br>PSVFLFPPKPKDTLMISRTPEVTCVVVAVSHEDPEVKFNW<br>YVDGVEVHNAKTKPREEQYNSTYRVVSVLTVLHQDWLN<br>GKEYKCKVSNKALAAPIEKTISKAKGQPREPQVYTLPPSRE<br>EMTKNQVSLTCLVKGFYPCDIAVEWESNGQPENNYKTTP<br>PVLDSDGSFFLYSKLTVDKSRWQQGNVFSCSVMHEALH<br>NHYTQKSLSLSPGK |
| SEQ ID NO: 80 | DNA Heavy<br>Chain | GACGTGCAGCTGCAGGAATCTGGCCCTGGCCTGGTCA<br>AGCCCTCCCAGACCCTGTCCCTGACCTGCACCGTGTCC<br>GGCTACTCTATCACCTCCGGCTACAGCTGGCACTGGAT<br>CCGGCAGCACCCCGGCAAGGGCCTGGAATGGATGGCC<br>CACATCCACTCCTCCGGCTCCACCAACTACAACCCCAGC<br>CTGAAGTCCCGGATCACCATCTCCCGGGACACCTCCAA<br>GAACCAGTTCTCCCTGAAGCTGTCCTCCGTGACCGCCG<br>CTGACACCGCCGTGTACTACTGTGCCAGAGGCGGCGT<br>GCAGGCCTTCGCTTATTGGGGCCAGGGAACCCTGGTC<br>ACCGTGTCCTCCGCCAGCACCAAGGGACCCTCCGTGTT<br>CCCTCTGGCCCCTTCCAGCAAGTCCACCTCTGGCGGCA<br>CCGCCGCTCTGGGCTGCCTCGTGAAGGACTACTTCCCC<br>TGCCCCGTGACCGTGTCCTGGAACTCCGGCGCTCTGAC<br>CTCCGGCGTGCACACCTTCCCTGCCGTGCTGCAGTCCT<br>CCGGCCTGTACTCCCTGTCCAGCGTCGTGACCGTGCCC<br>TCCAGCTCTCTGGGCACCCAGACCTACATCTGCAACGT<br>GAACCACAAGCCCTCCAACACCAAAGTGGACAAGCGG<br>GTGGAACCCAAGTCCTGCGACAAGACCCACACCTGTCC<br>TCCCTGCCCTGCCCCTGAGCTGCTGGGAGGCCCTTCCG<br>TGTTCCTGTTCCCTCCAAAGCCCAAGGACACCCTGATG<br>ATCTCCCGGACCCCTGAAGTGACCTGCGTGGTGGTGG<br>CCGTGTCCCACGAGGATCCCGAAGTGAAGTTCAATTG<br>GTACGTGGACGGCGTGGAAGTGCACAACGCCAAGACC<br>AAGCCCAGAGAGGAACAGTACAACTCCACCTACCGGG<br>TGGTGTCCGTGCTGACCGTGCTGCACCAGGACTGGCT<br>GAACGGCAAAGAGTACAAGTGCAAAGTGTCCAACAAG<br>GCCCTGGCCGCTCCCATCGAAAAGACCATCTCCAAGGC<br>CAAGGGCCAGCCCAGAGAGCCCCAAGTGTACACACTG<br>CCTCCCAGCCGGGAAGAGATGACCAAGAATCAAGTGT<br>CCCTGACCTGTCTGGTCAAGGGCTTCTACCCCTGCGAT<br>ATCGCCGTGGAGTGGGAGTCCAACGGCCAGCCCGAGA<br>ACAACTACAAGACCACCCCTCCCGTGCTGGACTCCGAC<br>GGCTCATTCTTCCTGTACTCCAAGCTGACCGTGGACAA<br>GTCCCGGTGGCAGCAGGGCAACGTGTTCTCCTGCTCCG<br>TGATGCACGAGGCCCTGCACAACCACTACACCCAGAA<br>GTCCCTGAGCCTGTCCCCTGGCAAG |
| SEQ ID NO: 81 | LCDR1<br>(Combined) | SASSSVIYMH |

TABLE 1-continued

| Examples of Anti-CCR7 Antibodies of the Present Invention | | |
|---|---|---|
| SEQ ID NO: 82 | LCDR2 (Combined) | DTSKLAS |
| SEQ ID NO: 83 | LCDR3 (Combined) | QQWSSNPLT |
| SEQ ID NO: 84 | LCDR1 (Kabat) | SASSSVIYMH |
| SEQ ID NO: 85 | LCDR2 (Kabat) | DTSKLAS |
| SEQ ID NO: 86 | LCDR3 (Kabat) | QQWSSNPLT |
| SEQ ID NO: 87 | LCDR1 (Chothia) | SSSVIY |
| SEQ ID NO: 88 | LCDR2 (Chothia) | DTS |
| SEQ ID NO: 89 | LCDR3 (Chothia) | WSSNPL |
| SEQ ID NO: 90 | LCDR1 (IMGT) | SSVIY |
| SEQ ID NO: 91 | LCDR2 (IMGT) | DTS |
| SEQ ID NO: 92 | LCDR3 (IMGT) | QQWSSNPLT |
| SEQ ID NO: 93 | VL | EIVLTQSPATLSASPGERVTMSCSASSSVIYMHWYQQKP GQAPRRWIYDTSKLASGVPARFSGSGSGTDYTLTISSMEP EDAAVYYCQQWSSNPLTFGQGTKLEIK |
| SEQ ID NO: 94 | DNA VL | GAGATCGTGCTGACACAGTCCCCTGCCACCCTGTCCGC CTCTCCAGGCGAGCGCGTGACAATGTCCTGCTCCGCCT CCTCCTCCGTGATCTACATGCACTGGTATCAGCAGAAG CCCGGCCAGGCCCCTCGGCGGTGGATCTACGATACCTC CAAGCTGGCCTCCGGCGTGCCCGCCAGATTCTCCGGCT CTGGCTCTGGCACCGACTACACCCTGACCATCTCCAGC ATGGAACCCGAGGACGCCGCCGTGTACTACTGCCAGC AGTGGTCCTCCAACCCTCTGACCTTCGGCCAGGGCACC AAGCTGGAAATCAAG |
| SEQ ID NO: 95 | Light Chain | EIVLTQSPATLSASPGERVTMSCSASSSVIYMHWYQQKP GQAPRRWIYDTSKLASGVPARFSGSGSGTDYTLTISSMEP EDAAVYYCQQWSSNPLTFGQGTKLEIKRTVAAPSVFIFPP SDEQLKSGTASVVCLLNNFYPREAKVQWKVDNALQSGN SQESVTEQDSKDSTYSLSSTLTLSKADYEKHKVYACEVTH QGLSSPVTKSFNRGEC |
| SEQ ID NO: 96 | DNA Light Chain | GAGATCGTGCTGACACAGTCCCCTGCCACCCTGTCCGC CTCTCCAGGCGAGCGCGTGACAATGTCCTGCTCCGCCT CCTCCTCCGTGATCTACATGCACTGGTATCAGCAGAAG CCCGGCCAGGCCCCTCGGCGGTGGATCTACGATACCTC CAAGCTGGCCTCCGGCGTGCCCGCCAGATTCTCCGGCT CTGGCTCTGGCACCGACTACACCCTGACCATCTCCAGC ATGGAACCCGAGGACGCCGCCGTGTACTACTGCCAGC AGTGGTCCTCCAACCCTCTGACCTTCGGCCAGGGCACC AAGCTGGAAATCAAGCGTACGGTGGCCGCTCCCAGCG TGTTCATCTTCCCCCCCAGCGACGAGCAGCTGAAGAGC GGCACCGCCAGCGTGGTGTGCCTGCTGAACAACTTCTA CCCCCGGGAGGCCAAGGTGCAGTGGAAGGTGGACAA CGCCCTGCAGAGCGGCAACAGCCAGGAGAGCGTCACC GAGCAGGACAGCAAGGACTCCACCTACAGCCTGAGCA GCACCCTGACCCTGAGCAAGGCCGACTACGAGAAGCA TAAGGTGTACGCCTGCGAGGTGACCCACCAGGGCCTG TCCAGCCCCGTGACCAAGAGCTTCAACAGGGGCGAGT GC |

Other antibodies of the invention include those where the amino acids or nucleic acids encoding the amino acids have been mutated, yet have at least 60, 70, 80, 90 or 95 percent identity to the sequences described in Tables 1 and 4. In some embodiments, 1, 2, 3, 4 or 5 amino acids have been mutated in the variable regions when compared with the variable regions depicted in the sequence described in Tables 1 and 4, while retaining substantially the same therapeutic activity as the antibodies listed in Tables 1 and 4.

Since each of these antibodies can bind to CCR7, the VH, VL, full length light chain, and full length heavy chain sequences (amino acid sequences and the nucleotide sequences encoding the amino acid sequences) can be "mixed and matched" to create other CCR7-binding antibodies of the invention. Such "mixed and matched" CCR7-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence. Accordingly, in one aspect, the invention provides an isolated monoclonal antibody or antigen binding region thereof having: a heavy chain variable region comprising an amino acid sequence selected from the group consisting of SEQ ID NOs: 13, 45, 77 and 608; and a light chain variable region comprising an amino acid sequence selected from the group consisting of SEQ ID NOs: 29, 61, 93 and 624; wherein the antibody specifically binds to CCR7.

In another aspect, the invention provides (i) an isolated monoclonal antibody having: a full length heavy chain comprising an amino acid sequence that has been optimized for expression in the cell of a mammalian expression system selected from the group consisting of SEQ ID NOs: 15, 47, 79 and 610; and a full length light chain comprising an amino acid sequence that has been optimized for expression in the cell of a mammalian selected from the group consisting of SEQ ID NOs: 31, 63, 95 and 626; or (ii) a functional protein comprising an antigen binding portion thereof.

In another aspect, the present invention provides CCR7-binding antibodies that comprise the heavy chain and light chain CDR1s, CDR2s and CDR3s as described in Tables 1 and 4, or combinations thereof. The amino acid sequences of the VH CDR1s of the antibodies are shown, for example, in SEQ ID NOs: 1, 4, 7, 10, 33, 36, 39, 42, 65, 68, 71 and 74. The amino acid sequences of the VH CDR2s of the antibodies and are shown, for example, in SEQ ID NOs: 2, 5, 8, 11, 34, 37, 40, 43, 66, 69, 72 and 75. The amino acid sequences of the VH CDR3s of the antibodies are shown, for example, in SEQ ID NOs: 3, 6, 9, 12, 35, 38, 41, 44, 67, 70, 73 and 76. The amino acid sequences of the VL CDR1s of the antibodies are shown, for example, in SEQ ID NOs: 17, 20, 23, 26, 49, 52, 55, 58, 81, 84, 87 and 90. The amino acid sequences of the VL CDR2s of the antibodies are shown, for example, in SEQ ID Nos: 18, 21, 24, 27, 50, 53, 56, 59, 82, 85, 88 and 91. The amino acid sequences of the VL CDR3s of the antibodies are shown, for example, in SEQ ID NOs: 19, 22, 25, 28, 51, 54, 57, 60, 83, 86, 89 and 92.

Given that each of these antibodies can bind to CCR7 and that antigen-binding specificity is provided primarily by the CDR1, 2 and 3 regions, the VH CDR1, CDR2 and CDR3 sequences and VL CDR1, CDR2 and CDR3 sequences can be "mixed and matched" (i.e., CDRs from different antibodies can be mixed and matched. Such "mixed and matched" CCR7-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention.

Accordingly, in some embodiments, the present invention provides an isolated monoclonal antibody or antigen binding region thereof comprising a heavy chain CDR1 comprising an amino acid sequence selected from the group consisting of SEQ ID NOs: 1, 4, 7, 10, 33, 36, 39, 42, 65, 68, 71, 74, 596, 599, 602 and 605; a heavy chain CDR2 comprising an amino acid sequence selected from the group consisting of SEQ ID NOs: 2, 5, 8, 11, 34, 37, 40, 43, 66, 69, 72, 75, 597, 600, 603 and 606; a heavy chain CDR3 comprising an amino acid sequence selected from the group consisting of SEQ ID NOs: 3, 6, 9, 12, 35, 38, 41, 44, 67, 70, 73, 76, 598, 601, 604 and 607; a light chain CDR1 comprising an amino acid sequence selected from the group consisting of SEQ ID NOs: 17, 20, 23, 26, 49, 52, 55, 58, 81, 84, 87, 90, 612, 615, 618 and 621; a light chain CDR2 comprising an amino acid sequence selected from the group consisting of SEQ ID NOs: 18, 21, 24, 27, 50, 53, 56, 59, 82, 85, 88, 91, 613, 616, 619 and 622; and a light chain CDR3 comprising an amino acid sequence selected from the group consisting of SEQ ID NOs: 19, 22, 25, 28, 51, 54, 57, 60, 83, 86, 89, 92, 614, 617, 620 and 623; wherein the antibody specifically binds CCR7.

In a specific embodiment, an antibody or antibody fragment (e.g., antigen binding fragments) that specifically binds to CCR7 comprises a heavy chain CDR1 of SEQ ID NO:1, a heavy chain CDR2 of SEQ ID NO:2; a heavy chain CDR3 of SEQ ID NO:3; a light chain CDR1 of SEQ ID NO:17; a light chain CDR2 of SEQ ID NO: 18; and a light chain CDR3 of SEQ ID NO:19.

In a specific embodiment, an antibody or antibody fragment (e.g., antigen binding fragments) that specifically binds to CCR7 comprises a heavy chain CDR1 of SEQ ID NO:4, a heavy chain CDR2 of SEQ ID NO:5; a heavy chain CDR3 of SEQ ID NO:6; a light chain CDR1 of SEQ ID NO:20; a light chain CDR2 of SEQ ID NO:21; and a light chain CDR3 of SEQ ID NO:22.

In a specific embodiment, an antibody or antibody fragment (e.g., antigen binding fragments) that specifically binds to CCR7 comprises a heavy chain CDR1 of SEQ ID NO:7, a heavy chain CDR2 of SEQ ID NO:8; a heavy chain CDR3 of SEQ ID NO:9; a light chain CDR1 of SEQ ID NO:23; a light chain CDR2 of SEQ ID NO:24; and a light chain CDR3 of SEQ ID NO:25.

In a specific embodiment, an antibody or antibody fragment (e.g., antigen binding fragments) that specifically binds to CCR7 comprises a heavy chain CDR1 of SEQ ID NO:10, a heavy chain CDR2 of SEQ ID NO: 11; a heavy chain CDR3 of SEQ ID NO: 12; a light chain CDR1 of SEQ ID NO:26; a light chain CDR2 of SEQ ID NO:27; and a light chain CDR3 of SEQ ID NO:28.

In a specific embodiment, an antibody or antibody fragment (e.g., antigen binding fragments) that specifically binds to CCR7 comprises a heavy chain CDR1 of SEQ ID NO:33, a heavy chain CDR2 of SEQ ID NO:34; a heavy chain CDR3 of SEQ ID NO:35; a light chain CDR1 of SEQ ID NO:49; a light chain CDR2 of SEQ ID NO:50; and a light chain CDR3 of SEQ ID NO:51.

In a specific embodiment, an antibody or antibody fragment (e.g., antigen binding fragments) that specifically binds to CCR7 comprises a heavy chain CDR1 of SEQ ID NO:36, a heavy chain CDR2 of SEQ ID NO:37; a heavy chain CDR3 of SEQ ID NO:38; a light chain CDR1 of SEQ ID NO:52; a light chain CDR2 of SEQ ID NO:53; and a light chain CDR3 of SEQ ID NO:54.

In a specific embodiment, an antibody or antibody fragment (e.g., antigen binding fragments) that specifically binds to CCR7 comprises a heavy chain CDR1 of SEQ ID NO:39, a heavy chain CDR2 of SEQ ID NO:40; a heavy chain CDR3 of SEQ ID NO:41; a light chain CDR1 of SEQ ID NO:55; a light chain CDR2 of SEQ ID NO:56; and a light chain CDR3 of SEQ ID NO:57.

In a specific embodiment, an antibody or antibody fragment (e.g., antigen binding fragments) that specifically binds to CCR7 comprises a heavy chain CDR1 of SEQ ID NO:42, a heavy chain CDR2 of SEQ ID NO:43; a heavy chain CDR3 of SEQ ID NO:44; a light chain CDR1 of SEQ ID NO:58; a light chain CDR2 of SEQ ID NO:59; and a light chain CDR3 of SEQ ID NO:60.

In a specific embodiment, an antibody or antibody fragment (e.g., antigen binding fragments) that specifically binds to CCR7 comprises a heavy chain CDR1 of SEQ ID NO:65, a heavy chain CDR2 of SEQ ID NO:66; a heavy chain CDR3 of SEQ ID NO:67; a light chain CDR1 of SEQ ID NO:81; a light chain CDR2 of SEQ ID NO:82; and a light chain CDR3 of SEQ ID NO:83.

In a specific embodiment, an antibody or antibody fragment (e.g., antigen binding fragments) that specifically binds to CCR7 comprises a heavy chain CDR1 of SEQ ID NO:68, a heavy chain CDR2 of SEQ ID NO:69; a heavy chain CDR3 of SEQ ID NO:70; a light chain CDR1 of SEQ ID NO:84; a light chain CDR2 of SEQ ID NO:85; and a light chain CDR3 of SEQ ID NO:86.

In a specific embodiment, an antibody or antibody fragment (e.g., antigen binding fragments) that specifically binds to CCR7 comprises a heavy chain CDR1 of SEQ ID NO:71, a heavy chain CDR2 of SEQ ID NO:72; a heavy chain CDR3 of SEQ ID NO:73; a light chain CDR1 of SEQ ID NO:87; a light chain CDR2 of SEQ ID NO:88; and a light chain CDR3 of SEQ ID NO:89.

In a specific embodiment, an antibody or antibody fragment (e.g., antigen binding fragments) that specifically binds to CCR7 comprises a heavy chain CDR1 of SEQ ID NO:74, a heavy chain CDR2 of SEQ ID NO:75; a heavy chain CDR3 of SEQ ID NO:76; a light chain CDR1 of SEQ ID NO:90; a light chain CDR2 of SEQ ID NO:91; and a light chain CDR3 of SEQ ID NO:92.

In a specific embodiment, an antibody or antibody fragment (e.g., antigen binding fragments) that specifically binds to CCR7 comprises a heavy chain variable region that comprises an HCDR1 of SEQ ID NO:596, an HCDR2 of SEQ ID NO:597, and an HCDR3 of SEQ ID NO:598; and a light chain variable region that comprises an LCDR1 of SEQ ID NO:612, an LCDR2 of SEQ ID NO:613, and an LCDR3 of SEQ ID NO:614.

In a specific embodiment, an antibody or antibody fragment (e.g., antigen binding fragments) that specifically binds to CCR7 comprises a heavy chain variable region that comprises an HCDR1 of SEQ ID NO:599, an HCDR2 of SEQ ID NO:600, and an HCDR3 of SEQ ID NO:601; and a light chain variable region that comprises an LCDR1 of SEQ ID NO:615, an LCDR2 of SEQ ID NO:616, and an LCDR3 of SEQ ID NO:617.

In a specific embodiment, an antibody or antibody fragment (e.g., antigen binding fragments) that specifically binds to CCR7 comprises a heavy chain variable region that comprises an HCDR1 of SEQ ID NO:602, an HCDR2 of SEQ ID NO:603, and an HCDR3 of SEQ ID NO:604; and a light chain variable region that comprises an LCDR1 of SEQ ID NO:618, an LCDR2 of SEQ ID NO:619, and an LCDR3 of SEQ ID NO:620.

In a specific embodiment, an antibody or antibody fragment (e.g., antigen binding fragments) that specifically binds to CCR7 comprises a heavy chain variable region that comprises an HCDR1 of SEQ ID NO:605, an HCDR2 of SEQ ID NO:606, and an HCDR3 of SEQ ID NO:607; and a light chain variable region that comprises an LCDR1 of SEQ ID NO:621, an LCDR2 of SEQ ID NO:622, and an LCDR3 of SEQ ID NO:623.

In a specific embodiment, an antibody or antibody fragment (e.g., antigen binding fragments) that specifically binds to CCR7 comprises a heavy chain variable region (VH) comprising the amino acid sequence of SEQ ID NO: 13, and a light chain variable region (VL) comprising the amino acid sequence of SEQ ID NO:29.

In a specific embodiment, an antibody or antibody fragment (e.g., antigen binding fragments) that specifically binds to CCR7 comprises a heavy chain variable region (VH) comprising the amino acid sequence of SEQ ID NO:45, and a light chain variable region (VL) comprising the amino acid sequence of SEQ ID NO:61.

In a specific embodiment, an antibody or antibody fragment (e.g., antigen binding fragments) that specifically binds to CCR7 comprises a heavy chain variable region (VH) comprising the amino acid sequence of SEQ ID NO:77, and a light chain variable region (VL) comprising the amino acid sequence of SEQ ID NO:93.

In a specific embodiment, an antibody or antibody fragment (e.g., antigen binding fragments) that specifically binds to CCR7 comprises a heavy chain variable region (VH) comprising the amino acid sequence of SEQ ID NO:608, and a light chain variable region (VL) comprising the amino acid sequence of SEQ ID NO:624.

In a specific embodiment, an antibody or antibody fragment (e.g., antigen binding fragments) that specifically binds to CCR7 comprises a heavy chain comprising the amino acid sequence of SEQ ID NO: 15, and a light chain comprising the amino acid sequence of SEQ ID NO:31.

In a specific embodiment, an antibody or antibody fragment (e.g., antigen binding fragments) that specifically binds to CCR7 comprises a heavy chain comprising the amino acid sequence of SEQ ID NO:47, and a light chain comprising the amino acid sequence of SEQ ID NO:63.

In a specific embodiment, an antibody or antibody fragment (e.g., antigen binding fragments) that specifically binds to CCR7 comprises a heavy chain comprising the amino acid sequence of SEQ ID NO:79, and a light chain comprising the amino acid sequence of SEQ ID NO:95.

In a specific embodiment, an antibody or antibody fragment (e.g., antigen binding fragments) that specifically binds to CCR7 comprises a heavy chain comprising the amino acid sequence of SEQ ID NO:610, and a light chain comprising the amino acid sequence of SEQ ID NO:626

In certain embodiments, an antibody that specifically binds to CCR7 is an antibody or antibody fragment (e.g., antigen binding fragment) that is described in Tables 1 and 4.

1. Identification of Epitopes and Antibodies that Bind to the Same Epitope

The present invention also provides antibodies and antibody fragments (e.g., antigen binding fragments) that specifically bind to the same epitope as the anti-CCR7 antibodies described in Tables 1 and 4, or cross compete with the antibodies described in Tables 1 and 4. Additional antibodies and antibody fragments (e.g., antigen binding fragments) can therefore be identified based on their ability to cross-compete (e.g., to competitively inhibit the binding of, in a statistically significant manner) with other antibodies of the invention in CCR7 binding assays, for example, via BIACORE or assays known to persons skilled in the art for measuring binding. The ability of a test antibody to inhibit the binding of antibodies and antibody fragments (e.g., antigen binding fragments) of the present invention to a CCR7 (e.g., human CCR7) demonstrates that the test antibody can compete with that antibody or antibody fragment (e.g., antigen binding fragments) for binding to CCR7; such an antibody may, according to non-limiting theory, bind to the same or a related (e.g., a structurally similar or spatially proximal or overlapping) epitope on the CCR7 protein as the antibody or antibody fragment (e.g., antigen binding fragments) with which it competes. In certain embodiments, the antibodies that bind to the same epitope on CCR7 as the antibodies or antibody fragments (e.g., antigen binding fragments) described in Tables 1 and 4 are human or humanized monoclonal antibodies. Such human or humanized monoclonal antibodies can be prepared and isolated as described herein.

2. Further Alteration of the Framework of Fc Region

The immunoconjugates of the invention may comprise modified antibodies or antigen binding fragments thereof that further comprise modifications to framework residues within VH and/or VL, e.g. to improve the properties of the antibody. In some embodiments, the framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 20030153043 by Carr et al.

In addition or in the alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity (ADCC). Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In some embodiments, the antibody or antibody fragment disclosed herein include modified or engineered amino acid residues, e.g., one or more cysteine residues, as sites for conjugation to a drug moiety (Junutula J R, et al., Nat Biotechnol 2008, 26:925-932). In one embodiment, the invention provides a modified antibody or antibody fragment comprising a substitution of one or more amino acids with cysteine at the positions described herein. Sites for cysteine substitution are in the constant regions of the antibody or antibody fragment and are thus applicable to a variety of antibody or antibody fragment, and the sites are selected to provide stable and homogeneous conjugates. A modified antibody or fragment can have one, two or more cysteine substitutions, and these substitutions can be used in combination with other modification and conjugation methods as described herein. Methods for inserting cysteine at specific locations of an antibody are known in the art, see, e.g., Lyons et al., (1990) Protein Eng., 3:703-708, WO 2011/005481, WO2014/124316, WO 2015/138615. In certain embodiments, a modified antibody comprises a substitution of one or more amino acids with cysteine on its constant region selected from positions 117, 119, 121, 124, 139, 152, 153, 155, 157, 164, 169, 171, 174, 189, 191, 195, 197, 205, 207, 246, 258, 269, 274, 286, 288, 290, 292, 293, 320, 322, 326, 333, 334, 335, 337, 344, 355, 360, 375, 382, 390, 392, 398, 400 and 422 of a heavy chain of the antibody, and wherein the positions are numbered according to the EU system. In some embodiments a modified antibody or antibody fragment comprises a substitution of one or more amino acids with cysteine on its constant region selected from positions 107, 108, 109, 114, 129, 142, 143, 145, 152, 154, 156, 159, 161, 165, 168, 169, 170, 182, 183, 197, 199, and 203 of a light chain of the antibody or antibody fragment, wherein the positions are numbered according to the EU system, and wherein the light chain is a human kappa light chain. In certain embodiments a modified antibody or antibody fragment thereof comprises a combination of substitution of two or more amino acids with cysteine on its constant regions wherein the combinations comprise substitutions at positions 375 of an antibody heavy chain, position 152 of an antibody heavy chain, position 360 of an antibody heavy chain, or position 107 of an antibody light chain and wherein the positions are numbered according to the EU system. In certain embodiments a modified antibody or antibody fragment thereof comprises a substitution of one amino acid with cysteine on its constant regions wherein the substitution is position 375 of an antibody heavy chain, position 152 of an antibody heavy chain, position 360 of an antibody heavy chain, position 107 of an antibody light chain, position 165 of an antibody light chain or position 159 of an antibody light chain and wherein the positions are numbered according to the EU system, and wherein the light chain is a kappa chain. In particular embodiments a modified antibody or antibody fragment thereof comprises a combination of substitution of two amino acids with cysteine on its constant regions wherein the combinations comprise substitutions at positions 375 of an antibody heavy chain and position 152 of an antibody heavy chain, wherein the positions are numbered according to the EU system. In particular embodiments a modified antibody or antibody fragment thereof comprises a substitution of one amino acid with cysteine at position 360 of an antibody heavy chain, wherein the positions are numbered according to the EU system. In other particular embodiments a modified antibody or antibody fragment thereof comprises a substitution of one amino acid with cysteine at position 107 of an antibody light chain and wherein the positions are numbered according to the EU system, and wherein the light chain is a kappa chain.

In additional embodiments antibodies or antibody fragments (e.g., antigen binding fragment) useful in immunoconjugates of the invention include modified or engineered antibodies, such as an antibody modified to introduce one or more other reactive amino acid (other than cysteine), including Pcl, pyrrolysine, peptide tags (such as S6, A1 and ybbR tags), and non-natural amino acids, in place of at least one amino acid of the native sequence, thus providing a reactive site on the antibody or antigen binding fragment for conjugation to a drug moiety or a linker-drug moiety with complementary reactivity. For example, the antibodies or antibody fragments can be modified to incorporate Pcl or pyrrolysine (W. Ou, et al., (2011) PNAS 108 (26), 10437-10442; WO2014124258) or unnatural amino acids (J. Y. Axup, et al., Proc Natl Acad Sci USA, 109 (2012), pp. 16101-16106; for review, see C. C. Liu and P. G. Schultz (2010) Annu Rev Biochem 79, 413-444; C. H. Kim, et al., (2013) Curr Opin Chem Biol. 17, 412-419) as sites for conjugation to a drug. Similarly, peptide tags for enzymatic conjugation methods can be introduced into an antibody (Strop P., et al., Chem Biol. 2013, 20(2):161-7; Rabuka D., Curr Opin Chem Biol. 2010 December; 14(6):790-6; Rabuka D, et al., Nat Protoc. 2012, 7(6):1052-67). One other example is the use of 4'-phosphopantetheinyl transferases (PPTase) for the conjugation of Co-enzyme A analogs (WO2013184514), and (Grünewald et al., (2015) Bioconjugate Chem. 26 (12), 2554-62). Methods for conjugating such modified or engineered antibodies with payloads or linker-payload combinations are known in the art.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another embodiment, one or more amino acid residues are altered to thereby alter the ability of the antibody to fix complement. This approach is described in, e.g., the PCT Publication WO 94/29351 by Bodmer et al. Allotypic amino acid residues include, but are not limited to, constant region of a heavy chain of the IgG1, IgG2, and IgG3 subclasses as well as constant region of a light chain of the kappa isotype as described by Jefferis et al., MAbs. 1:332-338 (2009).

Antibody fusion protein complexes containing such mutations mediate reduced or no antibody-dependent cellular cytotoxicity (ADCC) or complement-dependent cytotoxicity (CDC). In some embodiments, amino acid residues L234 and L235 of the IgG1 constant region are substituted to A234 and A235. In some embodiments, amino acid residue N267 of the IgG1 constant region is substituted to A267. In some embodiments, amino acid residues D265 and P329 of the IgG1 constant region are substituted to A265 and A329. In certain embodiments an immunoglobulin heavy chain optionally comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A. In particular embodiments, an immunoconjugate comprises an immunoglobulin heavy chain comprising a mutation or combination of mutations conferring reduced effector function selected from any of D265A, P329A, P329G, N297A, D265A/P329A, D265A/N297A, L234/L235A, P329A/L234A/L235A, and P329G/L234A/L235A In another embodiment, one or more amino acid residues are altered to thereby alter the ability of the antibody to fix complement. This approach is described in, e.g., the PCT Publication WO 94/29351 by Bodmer et al. In a specific embodiment, one or more amino acids of an antibody or antigen binding fragment thereof of the present invention are replaced by one or more allotypic amino acid residues. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In still another embodiment, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

3. Production of the CCR7 Antibodies

Anti-CCR7 antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The invention further provides polynucleotides encoding the antibodies described herein, e.g., polynucleotides encoding heavy or light chain variable regions or segments comprising the complementarity determining regions as described herein. In some embodiments, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 14, 46, 78 and 609. In some embodiments, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 30, 62, 94 and 625.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 16, 48, 80 or 611. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 32, 64, 96 or 627.

The polynucleotides of the invention can encode only the variable region sequence of an anti-CCR7 antibody. They can also encode both a variable region and a constant region of the antibody. Some of the polynucleotide sequences encode a polypeptide that comprises variable regions of both the heavy chain and the light chain of one of the exemplified mouse anti-CCR7 antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described in the Examples below) encoding an anti-CCR7 antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, C A, 1990; Mattila et al., Nucleic Acids Res. 19:967, 1991; and Eckert et al., PCR Methods and Applications 1:17, 1991.

Also provided in the invention are expression vectors and host cells for producing the anti-CCR7 antibodies described above. Various expression vectors can be employed to express the polynucleotides encoding the anti-CCR7 antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-CCR7 polynucleotides and polypeptides in mammalian (e.g., human) cells include pThioHis A, B & C, pcDNA™3.1/His, pEBVHis A, B & C (Invitrogen, San Diego, CA), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-CCR7 antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-CCR7 antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-CCR7 antibody sequences. More often, the inserted anti-CCR7 antibody sequences are linked to a signal sequences before inclusion in the vector. Vectors to be used to receive sequences encoding anti-CCR7 antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-CCR7 antibody chains can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-CCR7 polypeptides of the invention. Insect cells in combination with baculovirus vectors can also be used.

In some preferred embodiments, mammalian host cells are used to express and produce the anti-CCR7 polypeptides of the present invention. For example, they can be either a hybridoma cell line expressing endogenous immunoglobulin genes (e.g., the myeloma hybridoma clones as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., Molecular Cloning: A Laboratory Manual, $4^{th}$ ed.). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-CCR7 antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic Uses

The antibodies, antibody fragments (e.g., antigen binding fragments), and antibody drug conjugates of the invention are useful in a variety of applications including, but not limited to, treatment or prevention of cancer, such as solid cancers or heme malignancies. In certain embodiments, the antibodies, antibody fragments (e.g., antigen binding fragments), and antibody drug conjugates of the invention are useful for inhibiting tumor growth, inducing differentiation, reducing tumor volume, and/or reducing the tumorigenicity of a tumor. The methods of use can be in vitro, ex vivo, or in vivo methods.

In one aspect, the antibodies, antibody fragments (e.g., antigen binding fragments), and antibody drug conjugates of the invention are useful for detecting the presence of CCR7 in a biological sample. The term "detecting" as used herein encompasses quantitative or qualitative detection. In certain embodiments, a biological sample comprises a cell or tissue. In certain embodiments, such tissues include normal and/or cancerous tissues that express CCR7 at higher levels relative to other tissues.

In one aspect, the invention provides a method of detecting the presence of CCR7 in a biological sample. In certain embodiments, the method comprises contacting the biological sample with an anti-CCR7 antibody under conditions permissive for binding of the antibody to the antigen, and detecting whether a complex is formed between the antibody and the antigen.

In one aspect, the invention provides a method of diagnosing a disorder associated with increased expression of CCR7. In certain embodiments, the method comprises contacting a test cell with an anti-CCR7 antibody; determining the level of expression (either quantitatively or qualitatively) of CCR7 on the test cell by detecting binding of the anti-CCR7 antibody to the CCR7 antigen; and comparing the level of expression of CCR7 in the test cell with the level of expression of CCR7 on a control cell (e.g., a normal cell of the same tissue origin as the test cell or a cell that expresses CCR7 at levels comparable to such a normal cell), wherein a higher level of expression of CCR7 on the test cell as compared to the control cell indicates the presence of a disorder associated with increased expression of CCR7. In certain embodiments, the test cell is obtained from an individual suspected of having a disorder associated with increased expression of CCR7. In certain embodiments, the disorder is a cell proliferative disorder, such as a cancer or a tumor. In certain embodiments, the method comprises measuring the copy number of the CCR7 gene in a test cell.

In certain embodiments, a method of diagnosis or detection, such as those described above, comprises detecting binding of an anti-CCR7 antibody to CCR7 expressed on the surface of a cell or in a membrane preparation obtained from a cell expressing CCR7 on its surface. An exemplary assay for detecting binding of an anti-CCR7 antibody to CCR7 expressed on the surface of a cell is a "FACS" assay.

Certain other methods can be used to detect binding of anti-CCR7 antibodies to CCR7. Such methods include, but are not limited to, antigen-binding assays that are well known in the art, such as Western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-CCR7 antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, anti-CCR7 antibodies are immobilized on an insoluble matrix. Immobilization entails separating the anti-CCR7 antibody from any CCR7 protein that remains free in solution. This conventionally is accomplished by either insolubilizing the anti-CCR7 antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-CCR7 antibody after formation of a complex between the anti-CCR7 antibody and CCR7 protein, e.g., by immunoprecipitation.

Any of the above embodiments of diagnosis or detection can be carried out using an immunoconjugate of the invention in place of or in addition to an anti-CCR7 antibody.

In one embodiment, the invention provides a method of treating or preventing a disease comprising administering the antibodies, antibody fragments (e.g., antigen binding fragments), or antibody drug conjugates of the invention to a patient. The invention also provides use of the antibodies, antibody fragments (e.g., antigen binding fragments), or antibody drug conjugates of the invention to treat or prevent disease in a patient. In some embodiments, the invention provides antibodies, antibody fragments (e.g., antigen binding fragments), or antibody drug conjugates of the invention for use in the treatment or prevention of disease in a patient. In further embodiments, the invention provides use of the antibodies, antibody fragments (e.g., antigen binding fragments), or antibody drug conjugates of the invention in the manufacture of a medicament for treatment or prevention of disease in a patient.

In certain embodiments, the disease treated with the antibodies, antibody fragments (e.g., antigen binding fragments), and antibody drug conjugates of the invention is a cancer. In certain embodiments, the cancer is characterized by CCR7 expressing cells to which the antibodies, antibody fragments (e.g., antigen binding fragments), and antibody drug conjugates of the invention binds. In certain embodiments, the cancer is characterized by an increase in expression of CCR7 relative to a healthy patient. In some embodiments, the expression of CCR7 may be measured by an increase in CCR7 RNA. In other embodiments, the cancer is characterized by an increase in DNA copy number of CCR7. Other methods of measuring or determining levels of CCR7 expression are known to persons skilled in the art. Examples of diseases which can be treated and/or prevented include, but are not limited to, chronic lymphocytic leukemia (CLL), peripheral T cell lymphomas (PTCL) such as adult T-cell leukemia/lymphoma (ATLL) and anaplastic large-cell lymphoma (ALCL), Non-Hodgkin's lymphoma (NHL) such as mantle cell lymphoma (MCL), Burkitt's lymphoma and diffuse large B-cell lymphoma (DLBCL), gastric carcinoma, non-small cell lung cancer, small cell lung cancer, head and neck cancer, nasopharyngeal carcinoma (NPC), esophageal cancer, colorectal carcinoma, pancreatic cancer, thyroid cancer, breast cancer, renal cell cancer, and cervical cancer.

The present invention provides for methods of treating or preventing cancer comprising administering a therapeutically effective amount of the antibodies, antibody fragments (e.g., antigen binding fragments), or antibody drug conjugates of the invention. In certain embodiments, the cancer is a solid cancer. In certain embodiments, the subject is a human. In certain embodiments, the cancer is a resistant cancer and/or relapsed cancer. In certain aspects, for example, the resistant cancer is resistant to tyrosine kinase inhibitors, EGFR inhibitors, Her2 inhibitors, Her3 inhibitors, IGFR inhibitors and Met inhibitors.

In certain embodiments, the invention provides for methods of inhibiting tumor growth comprising administering to a subject a therapeutically effective amount of the antibodies, antibody fragments (e.g., antigen binding fragments), or antibody drug conjugates of the invention. In certain embodiments, the subject is a human. In certain embodiments, the subject has a tumor or has had a tumor removed. In certain embodiments, the tumor is resistant to other tyrosine kinase inhibitors, including but not limited to, EGFR inhibitors, Her2 inhibitors, Her3 inhibitors, IGFR inhibitors and Met inhibitors.

In certain embodiments, the tumor expresses the CCR7 to which the anti-CCR7 antibody binds. In certain embodiments, the tumor overexpresses the human CCR7. In certain embodiments, the tumor has an increase copy number of the CCR7 gene.

The present invention also provides for methods of selecting patients for treatment with antibodies, antibody fragments (e.g., antigen binding fragments), or antibody drug conjugates of the invention comprising administering a therapeutically effective amount of said antibodies, antibody fragments (e.g., antigen binding fragments), or antibody drug conjugates. In certain aspects the method comprises selecting patients with a tyrosine kinase inhibitor resistant cancer. In certain aspects it is contemplated that the tyrosine kinase inhibitor resistant cancer is resistant to EGFR inhibitors, Her2 inhibitors, Her3 inhibitors, IGFR inhibitors and/or Met inhibitors. In certain aspects it is contemplated that the resistant cancer is a Her2 resistant cancer. In certain aspects it is contemplated that the cancer is a de novo resistant cancer, and in still other aspects it is contemplated that the cancer is a relapsed cancer. In certain aspects of the invention the methods comprise selecting a patient with a de novo resistant or relapsed cancer and measuring for expression of CCR7. It is contemplated that in certain aspects the relapsed cancer or tumor was not initially a CCR7 expressing cancer or tumor, but becomes a CCR7 positive cancer that is a tyrosine kinase resistant or relapsed cancer or tumor after treatment with tyrosine kinase inhibitors.

For the treatment or prevention of the disease, the appropriate dosage of the antibodies, antibody fragments (e.g., antigen binding fragments), or antibody drug conjugates of the present invention depends on various factors, such as the type of disease to be treated, the severity and course of the disease, the responsiveness of the disease, previous therapy, patient's clinical history, and so on. The antibody or agent can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody, antibody fragment (e.g., antigen binding fragment), or antibody drug conjugates. The treating physician can estimate repetition rates for dosing based on measured residence times and concentrations of the drug in bodily fluids or tissues.

Combination Therapy

In certain instances, an antibody, antibody fragment (e.g., antigen binding fragment), or antibody drug conjugate of the present invention is combined with other therapeutic agents, such as other anti-cancer agents, anti-allergic agents, anti-nausea agents (or anti-emetics), pain relievers, cytoprotective agents, and combinations thereof.

In one embodiment, an antibody, antibody fragment (e.g., antigen binding fragment), or antibody drug conjugate of the present invention is combined in a pharmaceutical combination formulation, or dosing regimen as combination therapy, with a second compound having anti-cancer properties. The second compound of the pharmaceutical combination formulation or dosing regimen can have complementary activities to the antibody or immunoconjugate of the combination such that they do not adversely affect each other. For example, an antibody, antibody fragment (e.g., antigen binding fragment), or antibody drug conjugate of the present invention can be administered in combination with, but not limited to, a chemotherapeutic agent, a tyrosine kinase inhibitor, a CCR7 downstream signaling pathway inhibitor, IAP inhibitors, Bcl2 inhibitors, Mcl1 inhibitors, and other CCR7 inhibitors.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g., synergistic effect.

The term "combination therapy" refers to the administration of two or more therapeutic agents to treat or prevent a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating or preventing the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), and pemetrexed.

In one aspect, the present invention provides a method of treating or preventing cancer by administering to a subject in need thereof an antibody drug conjugate of the present invention in combination with one or more tyrosine kinase inhibitors, including but not limited to, BTK inhibitors, EGFR inhibitors, Her2 inhibitors, Her3 inhibitors, IGFR inhibitors, and Met inhibitors.

For example, tyrosine kinase inhibitors include but are not limited to, Ibrutinib (PCI-32765); Erlotinib hydrochloride (Tarceva®); Linifanib (N-[4-(3-amino-1H-indazol-4-yl) phenyl]-N'-(2-fluoro-5-methylphenyl)urea, also known as ABT 869, available from Genentech); Sunitinib malate (Sutent®); Bosutinib (4-[(2,4-dichloro-5-methoxyphenyl) amino]-6-methoxy-7-[3-(4-methylpiperazin-1-yl)propoxy] quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); and Imatinib or Imatinib mesylate (Gilvec® and Gleevec®).

Epidermal growth factor receptor (EGFR) inhibitors include but are not limited to, Erlotinib hydrochloride (Tarceva®), Gefitinib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-

[[(1R)-1-Phenylethyl]amino]-7H-pyrrolo[2,3-d]pyrimidin-6-yl]-phenol (PKI166, CAS 187724-61-4).

EGFR antibodies include but are not limited to, Cetuximab (Erbitux®); Panitumumab (Vectibix®); Matuzumab (EMD-72000); Nimotuzumab (hR3); Zalutumumab; TheraCIM h-R3; MDX0447 (CAS 339151-96-1); and ch806 (mAb-806, CAS 946414-09-1).

Human Epidermal Growth Factor Receptor 2 (Her2 receptor) (also known as Neu, ErbB-2, CD340, or p185) inhibitors include but are not limited to, Trastuzumab (Herceptin®); Pertuzumab (Omnitarg®); trastuzumab emtansine (Kadcyla®); Neratinib (HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443); Lapatinib or Lapatinib ditosylate (Tykerb®); (3R,4R)-4-amino-1-((4-((3-methoxyphenyl)amino)pyrrolo[2,1-f][1,2,4]triazin-5-yl)methyl)piperidin-3-ol (BMS690514); (2E)-N-[4-[(3-Chloro-4-fluorophenyl)amino]-7-[[(3S)-tetrahydro-3-furanyl]oxy]-6-quinazolinyl]-4-(dimethylamino)-2-butenamide (BIBW-2992, CAS 850140-72-6); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aα,5β, 6aα)-octahydro-2-methylcyclopenta[c]pyrrol-5-yl]methoxy]-4-quinazolinamine (XL647, CAS 781613-23-8).

Her3 inhibitors include but are not limited to, LJM716, MM-121, AMG-888, RG7116, REGN-1400, AV-203, MP-RM-1, MM-111, and MEHD-7945A.

MET inhibitors include but are not limited to, Cabozantinib (XL184, CAS 849217-68-1); Foretinib (GSK1363089, formerly XL880, CAS 849217-64-7); Tivantinib (ARQ197, CAS 1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-TH-pyrazole-4-carboxamide (AMG 458); Cryzotinib (Xalkori®, PF-02341066); (3Z)-5-(2,3-Dihydro-TH-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU11271); (3Z)—N-(3-Chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide (SU11274); (3Z)—N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU11606); 6-[Difluoro[6-(1-methyl-TH-pyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-TH-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin-3-yl]thio]-quinoline (SGX523, CAS 1022150-57-7); and (3Z)-5-[[(2,6-Dichlorophenyl)methyl]sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

IGF1R inhibitors include but are not limited to, BMS-754807, XL-228, OSI-906, GSK0904529A, A-928605, AXL1717, KW-2450, MK0646, AMG479, IMCA12, MEDI-573, and B1836845. See e.g., Yee, JNCI, 104; 975 (2012) for review.

In another aspect, the present invention provides a method of treating or preventing cancer by administering to a subject in need thereof an antibody drug conjugate of the present invention in combination with one or more CCR7 downstream signaling pathway inhibitors, including but not limited to, β-arrestin inhibitors, GRK inhibitors, MAPK inhibitors, PI3K inhibitors, JAK inhibitors, etc.

For example, phosphoinositide 3-kinase (PI3K) inhibitors include but are not limited to, Idelalisib (Zydelig, GS-1101, Cal-101), 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); and 8-Phenyl-2-(morpholin-4-yl)-chromen-4-one (LY294002, CAS 154447-36-6).

In yet another aspect, the present invention provides a method of treating or preventing cancer by administering to a subject in need thereof an antibody drug conjugate of the present invention in combination with one or more pro-apoptosis, including but not limited to, IAP inhibitors, Bcl2 inhibitors, MCl1 inhibitors, Trail agents, Chk inhibitors.

For examples, IAP inhibitors include but are not limited to, LCL161, GDC-0917, AEG-35156, AT406, and TL32711. Other examples of IAP inhibitors include but are not limited to those disclosed in WO04/005284, WO 04/007529, WO05/097791, WO 05/069894, WO 05/069888, WO 05/094818, US2006/0014700, US2006/0025347, WO 06/069063, WO 06/010118, WO 06/017295, and WO08/134679, all of which are incorporated herein by reference.

BCL-2 inhibitors include but are not limited to, Venetoclax (also known as GDC-0199, ABT-199, RG7601); 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386); Tetrocarcin A; Antimycin; Gossypol ((−)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (−)-Gossypol acetic acid (AT-101); 4-[4-[(4'-Chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-benzamide (ABT-737, CAS 852808-04-9); and Navitoclax (ABT-263, CAS 923564-51-6).

Proapoptotic receptor agonists (PARAs) including DR4 (TRAILR1) and DR5 (TRAILR2), including but are not limited to, Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab®); Conatumumab (AMG655, CAS 896731-82-1); and Tigatuzumab (CS1008, CAS 946415-34-5, available from Daiichi Sankyo).

Checkpoint Kinase (CHK) inhibitors include but are not limited to, 7-Hydroxystaurosporine (UCN-01); 6-Bromo-3-(1-methyl-1H-pyrazol-4-yl)-5-(3R)-3-piperidinyl-pyrazolo[1,5-a]pyrimidin-7-amine (SCH900776, CAS 891494-63-6); 5-(3-Fluorophenyl)-3-ureidothiophene-2-carboxylic acid N—[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (YGRKKRRQRRRLYRSPAMPENL (SEQ ID NO: 629)), and CBP501 ((d-Bpa)sws(d-Phe-F5)(d-Cha)rrrqrr).

In a further embodiment, the present invention provides a method of treating or preventing cancer by administering to a subject in need thereof an antibody drug conjugate of the present invention in combination with one or more immunomodulators (e.g., one or more of: an activator of a costimulatory molecule or an inhibitor of an immune checkpoint molecule).

In certain embodiments, the immunomodulator is an activator of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, STING, or CD83 ligand.

In certain embodiments, the immunomodulator is an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD160, 2B4 and/or TGFR beta. In one embodiment, the inhibitor of an immune checkpoint molecule inhibits PD-1, PD-L1, LAG-3, TIM-3 or CTLA4, or any combination thereof. The term "inhibition" or "inhibitor" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40%, 50% or more is included by this term. Thus, inhibition need not be 100%.

Inhibition of an inhibitory molecule can be performed at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof (also referred to herein as "an antibody molecule") that binds to PD-1, PD-L1, PD-L2, CTLA4, TIM3, LAG3, VISTA, BTLA, TIGIT, LAIR1, CD160, 2B4 and/or TGFR beta, or a combination thereof.

In one embodiment, the antibody molecule is a full antibody or fragment thereof (e.g., a Fab, F(ab')2, Fv, or a single chain Fv fragment (scFv)). In yet other embodiments, the antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG4 (e.g., human IgG1 or IgG4). In one embodiment, the heavy chain constant region is human IgG1 or human IgG4. In one embodiment, the constant region is altered, e.g., mutated, to modify the properties of the antibody molecule (e.g., to increase or decrease one or more of: Fc receptor binding, antibody glycosylation, the number of cysteine residues, effector cell function, or complement function).

In certain embodiments, the antibody molecule is in the form of a bispecific or multispecific antibody molecule. In one embodiment, the bispecific antibody molecule has a first binding specificity to PD-1 or PD-L1 and a second binding specificity, e.g., a second binding specificity to TIM-3, LAG-3, or PD-L2. In one embodiment, the bispecific antibody molecule binds to PD-1 or PD-L1 and TIM-3. In another embodiment, the bispecific antibody molecule binds to PD-1 or PD-L1 and LAG-3. In another embodiment, the bispecific antibody molecule binds to PD-1 and PD-L1. In yet another embodiment, the bispecific antibody molecule binds to PD-1 and PD-L2. In another embodiment, the bispecific antibody molecule binds to TIM-3 and LAG-3. Any combination of the aforesaid molecules can be made in a multispecific antibody molecule, e.g., a trispecific antibody that includes a first binding specificity to PD-1 or PD-1, and a second and third binding specificities to two or more of: TIM-3, LAG-3, or PD-L2.

In certain embodiments, the immunomodulator is an inhibitor of PD-1, e.g., human PD-1. In another embodiment, the immunomodulator is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immunomodulators, e.g., in combination with an inhibitor of LAG-3, TIM-3 or CTLA4. In an exemplary embodiment, the inhibitor of PD-1 or PD-L1, e.g., the anti-PD-1 or PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule. Other combinations of immunomodulators with a PD-1 inhibitor (e.g., one or more of PD-L2, CTLA4, TIM3, LAG3, VISTA, BTLA, TIGIT, LAIR1, CD160, 2B4 and/or TGFR) are also within the present invention. Any of the antibody molecules known in the art or disclosed herein can be used in the aforesaid combinations of inhibitors of checkpoint molecule.

In one embodiment, the PD-1 inhibitor is an anti-PD-1 antibody chosen from Nivolumab, Pembrolizumab or Pidilizumab. In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and PCT Publication No. WO2006/121168.

In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD1. Pembrolizumab is disclosed, e.g., in Hamid, O. et al. (2013) New England Journal of Medicine 369 (2): 134-44, PCT Publication No. WO2009/114335, and U.S. Pat. No. 8,354,509.

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in PCT Publication No. WO2009/101611. Other anti-PD1 antibodies are disclosed in U.S. Pat. No. 8,609,089, US Publication No. 2010028330, and/or US Publication No. 20120114649. Other anti-PD1 antibodies include AMP 514 (Amplimmune).

In some embodiments, the PD-1 inhibitor is PDR001 or any other anti-PD-1 antibody disclosed in WO2015/112900.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224.

In some embodiments, the PD-L1 inhibitor is anti-PD-L1 antibody. In some embodiments, the anti-PD-L1 inhibitor is chosen from YW243.55.S70, MPDL3280A, MEDI-4736, or MDX-1105MSB-0010718C (also referred to as A09-246-2) disclosed in, e.g., WO 2013/0179174, and having a sequence disclosed herein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in PCT Publication No. WO2007/005874.

In one embodiment, the PD-L1 inhibitor is YW243.55.S70. The YW243.55.S70 antibody is an anti-PD-L1 described in PCT Publication No. WO 2010/077634 (heavy and light chain variable region sequences shown in SEQ ID Nos. 20 and 21, respectively).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in PCT Publication Nos. WO2010/027827 and WO2011/066342).

In one embodiment, the LAG-3 inhibitor is an anti-LAG-3 antibody molecule. In one embodiment, the LAG-3 inhibitor is BMS-986016.

Pharmaceutical Compositions

To prepare pharmaceutical or sterile compositions including immunoconjugates, the immunoconjugates of the invention are mixed with a pharmaceutically acceptable carrier or excipient. The compositions can additionally contain one or more other therapeutic agents that are suitable for treating or preventing a CCR7 expressing cancer (including, but not limited to chronic lymphocytic leukemia (CLL), peripheral T cell lymphomas (PTCL) such as adult T-cell leukemia/lymphoma (ATLL) and anaplastic large-cell lymphoma (ALCL), Non-Hodgkin's lymphoma (NHL) such as mantle cell lymphoma (MCL), Burkitt's lymphoma and diffuse large B-cell lymphoma (DLBCL), gastric carcinoma, non-small cell lung cancer, small cell lung cancer, head and neck cancer, nasopharyngeal carcinoma (NPC), esophageal cancer, colorectal carcinoma, pancreatic cancer, thyroid cancer, breast cancer, renal cell cancer, and cervical cancer).

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N Y, 1993; Lieberman, et al. (eds.), Pharmaceutical Dosage Forms: tablets, Marcel Dekker, N Y, 1990; Lieberman, et al. (eds.) Pharmaceutical Dosage Forms: Disperse Systems, Marcel Dekker, N Y, 1990; Weiner and Kotkoskie, Excipient Toxicity and Safety, Marcel Dekker, Inc., New York, N.Y., 2000).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, U K, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or prevention or predicted to affect treatment or prevention. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof of the invention can be provided by continuous infusion, or by doses at intervals of, e.g., one day, one week, or 1-7 times per week, once every other week, once every three weeks, once every four weeks, once every five weeks, once every six weeks, once every seven weeks, or once very eight weeks. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the immunoconjugates of the invention, the dosage administered to a patient may be 0.0001 mg/kg to 100 mg/kg of the patient's body weight. The dosage may be between 0.0001 mg/kg and 30 mg/kg, 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof of the invention may be calculated using the patient's weight in kilograms (kg) multiplied by the dose to be administered in mg/kg.

Doses of the immunoconjugates the invention may be repeated and the administrations may be separated by less than 1 day, at least 1 day, 2 days, 3 days, 5 days, 10 days, 15 days, 30 days, 45 days, 2 months, 75 days, 3 months, 4 months, 5 months, or at least 6 months. In some embodiments, the immunoconjugates of the invention may be given twice weekly, once weekly, once every two weeks, once every three weeks, once every four weeks, or less frequently. In a specific embodiment, doses of the immunoconjugates of the invention are repeated every 2 weeks.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, U K, 2001).

The route of administration may be by, e.g., topical or cutaneous application, injection or infusion by subcutaneous, intravenous, intraperitoneal, intracerebral, intramuscular, intraocular, intraarterial, intracerebrospinal, intralesional administration, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present invention may also be administered via one or more routes of administration using one or more of a variety of methods known in the art. As will be appreciated by the skilled artisan, the route and/or mode of administration will vary depending upon the desired results. Selected routes of administration for the immunoconjugates of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the invention can be administered via a non-parenteral route, such as a topical, epidermal or mucosal route of administration, for example, intranasally, orally, vaginally, rectally, sublingually or topically. In one embodiment, the immunoconjugates of the invention is administered by infusion. In another embodiment, the immunoconjugates of the invention is administered subcutaneously.

If the immunoconjugates of the invention are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the invention (see, e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more immunoconjugates of the invention. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam et al., Proc. Int'l. Symp. Control Rel. Bioact. Mater. 24:759-760, 1997, each of which is incorporated herein by reference in their entirety.

If the immunoconjugates of the invention are administered topically, they can be formulated in the form of an ointment, cream, transdermal patch, lotion, gel, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the immunoconjugates are administered intranasally, it can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, $10^{th}$ ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the immunoconjugates of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the immunoconjugates of the invention. The two or more therapies may be administered within one same patient visit.

In certain embodiments, the immunoconjugates of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al., (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The invention provides protocols for the administration of pharmaceutical composition comprising immunoconjugates of the invention alone or in combination with other therapies to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the invention can be administered to a subject concurrently.

The term "concurrently" is not limited to the administration of therapies (e.g., prophylactic or therapeutic agents) at exactly the same time, but rather it is meant that a pharmaceutical composition comprising antibodies or fragments thereof the invention are administered to a subject in a sequence and within a time interval such that the antibody drug conjugates of the invention can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 5 minutes apart, less than 15 minutes apart, less than 30 minutes apart, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration. The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1: Generation of Anti-CCR7 Antibodies

Generation of Expression Constructs for Human, Rat, Mouse and Cynomolgus Monkey CCR7

Full length human, cyno and mouse CCR7 genes were synthesized based on amino acid sequences from the GenBank or Uniprot databases (SEQ ID NO: 97, SEQ ID NO: 99, SEQ ID NO: 101). The rat CCR7 cDNA template was gene synthesized based on amino acid sequence information generated using mRNA isolated from various rat tissues (SEQ ID NO: 103). All synthesized DNA fragments were cloned into appropriate expression vectors.

TABLE 2

| Amino Acid and Nucleotide Sequence Information for CCR7 | |
|---|---|
| **Human CCR7** | |
| SEQ ID NO: 97 | MDLGKPMKSVLVVALLVIFQVCLCQDEVTDDYIGDNTTVDYTLFESLCSKKDVRNFK<br>AWFLPIMYSIICFVGLLGNGLVVLTYIYFKRLKTMTDTYLLNLAVADILFLLTLPFWAYS<br>AAKSWVFGVHFCKLIFAIYKMSFFSGMLLLLCISIDRYVAIVQAVSAHRHRARVLLISK<br>LSCVGIWILATVLSIPELLYSDLQRSSSEQAMRCSLITEHVEAFITIQVAQMVIGFLVPL<br>LAMSFCYLVIIRTLLQARNFERNKAIKVIIAVVVVFIVFQLPYNGVVLAQTVANFNITSS<br>TCELSKQLNIAYDVTYSLACVRCCVNPFLYAFIGVKFRNDLFKLFKDLGCLSQEQLRQ<br>WSSCRHIRRSSMSVEAETTTTFSP |
| SEQ ID NO: 98 | ATGGACCTGGGGAAACCAATGAAAAGCGTGCTGGTGGTGGCTCTCCTTGTCATT<br>TTCCAGGTATGCCTGTGTCAAGATGAGGTCACGGACGATTACATCGGAGACAAC<br>ACCACAGTGGACTACACTTTGTTCGAGTCTTTGTGCTCCAAGAAGGACGTGCGG<br>AACTTTAAAGCCTGGTTCCTCCCTATCATGTACTCCATCATTTGTTTCGTGGGCCT<br>ACTGGGCAATGGGCTGGTCGTGTTGACCTATATCTATTTCAAGAGGCTCAAGAC<br>CATGACCGATACCTACCTGCTCAACCTGGCGGTGGCAGACATCCTCTTCCTCCTG<br>ACCCTTCCCTTCTGGGCCTACAGCGCGGCCAAGTCCTGGGTCTTCGGTGTCCACT<br>TTTGCAAGCTCATCTTTGCCATCTACAAGATGAGCTTCTTCAGTGGCATGCTCCTA<br>CTTCTTTGCATCAGCATTGACCGCTACGTGGCCATCGTCCAGGCTGTCTCAGCTC<br>ACCGCCACCGTGCCCGCGTCCTTCTCATCAGCAAGCTGTCCTGTGTGGGCATCTG<br>GATACTAGCCACAGTGCTCTCCATCCCAGAGCTCCTGTACAGTGACCTCCAGAGG<br>AGCAGCAGTGAGCAAGCGATGCGATGCTCTCTCATCACAGAGCATGTGGAGGC<br>CTTTATCACCATCCAGGTGGCCCAGATGGTGATCGGCTTTCTGGTCCCCCTGCTG<br>GCCATGAGCTTCTGTTACCTTGTCATCATCCGCACCCTGCTCCAGGCACGCAACT<br>TTGAGCGCAACAAGGCCATCAAGGTGATCATCGCTGTGGTCGTGGTCTTCATAG<br>TCTTCCAGCTGCCCTACAATGGGGTGGTCCTGGCCCAGACGGTGGCCAACTTCA<br>ACATCACCAGTAGCACCTGTGAGCTCAGTAAGCAACTCAACATCGCCTACGACG<br>TCACCTACAGCCTGGCCTGCGTCCGCTGCTGCGTCAACCCTTTCTTGTACGCCTTC<br>ATCGGCGTCAAGTTCCGCAACGATCTCTTCAAGCTCTTCAAGGACCTGGGCTGCC<br>TCAGCCAGGAGCAGCTCCGGCAGTGGTCTTCCTGTCGGCACATCCGGCGCTCCT<br>CCATGAGTGTGGAGGCCGAGACCACCACCACCTTCTCCCCA |
| **Cyno CCR7** | |
| SEQ ID NO: 99 | MDLGKPMKSVLVVALLVIFQVCLCQDEVTDDYIGDNTTVDYTLFESLCSKKDVRNFK<br>AWFLPIMYSIICFVGLLGNGLVVLTYIYFKRLKTMTDTYLLNLAVADILFLLTLPFWAYS<br>AAKSWVFGVHFCKLIFAIYKMSFFSGMLLLLCISIDRYVAIVQAVSAHRHRARVLLISK<br>LSCVGIWILATVLSIPELLYSGLQRSSSEQAMRCSLITEHVEAFITIQVAQMVIGFLVPL<br>LAMSFCYLVIIRTLLQARNFERNKAIKVIIAVVVVFIVFQLPYNGVVLAQTVANFNITSS<br>TCELSKQLNIAYDVTYSLACVRCCVNPFLYAFIGVKFRNDLFKLFKDLGCLSQEQLRQ<br>WSSCRHIRRSSMSVEAETTTTFSP |
| SEQ ID NO: 100 | ATGGACCTGGGGAAACCAATGAAAAGCGTGCTGGTGGTGGCTCTCCTTGTCATT<br>TTCCAGGTATGCCTGTGTCAAGATGAGGTCACGGACGATTACATCGGAGACAAC<br>ACCACAGTGGACTACACTTTGTTCGAGTCTTTGTGCTCCAAGAAGGACGTGCGG<br>AACTTTAAAGCCTGGTTCCTCCCTATCATGTACTCCATCATTTGTTTCGTGGGCCT<br>ACTGGGCAATGGGCTGGTCGTGTTGACCTATATCTATTTCAAGAGGCTCAAGAC<br>CATGACCGATACCTACCTGCTCAACCTGGCGGTGGCAGACATCCTCTTCCTCCTG |

TABLE 2-continued

| Amino Acid and Nucleotide Sequence Information for CCR7 | |
|---|---|
| | ACCCTTCCCTTCTGGGCCTACAGCGCGGCCAAGTCCTGGGTCTTCGGTGTCCACT<br>TTTGCAAGCTCATCTTTGCCATCTACAAGATGAGCTTCTTCAGTGGCATGCTCCTA<br>CTTCTTTGCATCAGCATTGACCGCTACGTGGCCATCGTCCAGGCTGTCTCAGCTC<br>ACCGCCACCGTGCCCGCGTCCTTCTCATCAGCAAGCTGTCCTGTGTGGGCATCTG<br>GATACTAGCCACAGTGCTCTCCATCCCAGAGCTCCTGTACAGTGGCCTCCAGAG<br>GAGCAGCAGTGAGCAAGCGATGCGATGCTCTCTCATCACAGAGCATGTGGAGG<br>CCTTTATCACCATCCAGGTGGCCCAGATGGTGATCGGCTTTCTGGTCCCCCTGCT<br>GGCCATGAGCTTCTGTTACCTTGTCATCATCCGCACCCTGCTCCAGGCACGCAAC<br>TTTGAGCGCAACAAGGCCATCAAGGTGATCATCGCTGTGGTCGTGGTCTTCATA<br>GTCTTCCAGCTGCCCTACAATGGGGTGGTCCTGGCCCAGACGGTGGCCAACTTC<br>AACATCACCAGTAGCACCTGTGAGCTCAGTAAGCAACTCAACATCGCCTACGAC<br>GTCACCTACAGCCTGGCCTGCGTCCGCTGCTGCGTCAACCCTTTCTTGTACGCCTT<br>CATCGGCGTCAAGTTCCGCAACGATCTCTTCAAGCTCTTCAAGGACCTGGGCTGC<br>CTCAGCCAGGAGCAGCTCCGGCAGTGGTCTTCCTGTCGGCACATCCGGCGCTCC<br>TCCATGAGTGTGGAGGCCGAGACCACCACCACCTTCTCCCCA |
| Mouse CCR7 | |
| SEQ ID NO: 101 | MDPGKPRKNVLVVALLVIFQVCFCQDEVTDDYIGENTTVDYTLYESVCFKKDVRNFK<br>AWFLPLMYSVICFVGLLGNGLVILTYIYFKRLKTMTDTYLLNLAVADILFLLILPFWAYS<br>EAKSWIFGVYLCKGIFGIYKLSFFSGMLLLLCISIDRYVAIVQAVSAHRHRARVLLISKLS<br>CVGIWMLALFLSIPELLYSGLQKNSGEDTLRCSLVSAQVEALITIQVAQMVFGFLVP<br>MLAMSFCYLIIIRTLLQARNFERNKAIKVIIAVVVVFIVFQLPYNGVVLAQTVANFNIT<br>NSSCETSKQLNIAYDVTYSLASVRCCVNPFLYAFIGVKFRSDLFKLFKDLGCLSQERLR<br>HWSSCRHVRNASVSMEAETTTTFSP |
| SEQ ID NO: 102 | ATGGACCCAGGGAAACCCAGGAAAAACGTGCTGGTGGTGGCTCTCCTTGTCATT<br>TTCCAGGTGTGCTTCTGCCAAGATGAGGTCACCGATGACTACATCGGCGAGAAT<br>ACCACGGTGGACTACACCCTGTACGAGTCGGTGTGCTTCAAGAAGGATGTGCGG<br>AACTTTAAGGCCTGGTTCCTGCCTCTCATGTATTCTGTCATCTGCTTCGTGGGCCT<br>GCTCGGCAACGGGCTGGTGATACTGACGTACATCTATTTCAAGAGGCTCAAGAC<br>CATGACGGATACCTACCTGCTCAACCTGGCCGTGGCAGACATCCTTTTCCTCCTG<br>ATTCTTCCCTTCTGGGCCTACAGCGAAGCCAAGTCCTGGATCTTTGGCGTCTACC<br>TGTGTAAGGGCATCTTTGGCATCTATAAGTTAAGCTTCTTCAGCGGGATGCTGCT<br>GCTCCTATGCATCAGCATTGACCGCTACGTAGCCATCGTCCAGGCCGTGTCGGCT<br>CATCGCCACCGCGCCCGCGTGCTTCTCATCAGCAAGCTGTCCTGTGTGGGCATCT<br>GGATGCTGGCCCTCTTCCTCTCCATCCCGGAGCTGCTCTACAGCGGCCTCCAGAA<br>GAACAGCGGCGAGGACACGCTGAGATGCTCACTGGTCAGTGCCCAAGTGGAGG<br>CCTTGATCACCATCCAAGTGGCCCAGATGGTTTTTGGGTTCCTAGTGCCTATGCT<br>GGCTATGAGTTTCTGCTACCTCATTATCATCCGTACCTTGCTCCAGGCACGCAACT<br>TTGAGCGGAACAAGGCCATCAAGGTGATCATTGCCGTGGTGGTAGTCTTCATAG<br>TCTTCCAGCTGCCCTACAATGGGGTGGTCCTGGCTCAGACGGTGGCCAACTTCA<br>ACATCACCAATAGCAGCTGCGAAACCAGCAAGCAGCTCAACATTGCCTATGACG<br>TCACCTACAGCCTGGCCTCCGTCCGCTGCTGCGTCAACCCTTTCTTGTATGCCTTC<br>ATCGGCGTCAAGTTCCGCAGCGACCTCTTCAAGCTCTTCAAGGACTTGGGCTGTC<br>TCAGCCAGGAACGGCTCCGGCACTGGTCTTCCTGCCGGCATGTACGGAACGCGT<br>CGGTGAGCATGGAGGCGGAGACCACCACAACCTTCTCCCCG |
| Rat CCR7 | |
| SEQ ID NO: 103 | MDLGKPTKNVLVVALLVIFQVCFCQDEVTDDYIGENTTVDYTLYESVCFKKDVRNFK<br>AWFLPLMYSVICFVGLLGNGLVVLTYIYFKRLKTMTDTYLLNLAVADILFLMILPFWA<br>YSEAKSWIFGAYLCKSIFGIYKLSFFSGMLLLLCISIDRYVAIVQAVSAHRHRARVLLISK<br>LSCIGIWTLAFFLSIPELLYSGLQKNSGEDTWRCSLVSAQVEALIAIQVAQMVVGFVL<br>PMLAMSFCYLVIIRTLLQARNFERNKAIKVIIAVVVVFVVFQLPYNGVVLAQTVANFN<br>ITNSSCEASKQLNIAYDVTYSLASVRCCVNPFLYAFIGVKFRSDLFKLFKDLGCLSQERL<br>RQWSSCRHVRHTSVSMEAETTTTFSP |
| SEQ ID NO: 104 | ATGGACCTGGGGAAGCCCACGAAAAACGTGCTGGTGGTGGCTCTCCTGGTCATT<br>TTCCAGGTGTGCTTCTGCCAAGATGAGGTCACAGACGACTACATCGGCGAGAAC<br>ACCACCGTGGACTACACCCTGTATGAGTCGGTGTGCTTCAAGAAGGATGTGCGG<br>AACTTTAAGGCCTGGTTCCTCCCTCTCATGTACTCAGTCATTTGCTTCGTGGGCCT<br>GCTAGGCAATGGGCTGGTGGTGCTGACATACATCTATTTCAAGAGACTGAAGAC<br>CATGACGGATACCTACCTGCTCAACCTGGCCGTGGCAGACATCCTCTTCCTCATG<br>ATCCTTCCCTTCTGGGCCTACAGCGAAGCCAAGTCCTGGATCTTTGGTGCCTACC<br>TGTGTAAGAGCATCTTTGGCATCTACAAGTTAAGCTTCTTCAGCGGGATGTTGCT<br>GCTCCTGTGTATCAGCATTGACCGCTATGTGGCCATCGTCCAGGCCGTGTCAGCC<br>CACCGGCACCGCGCCCGCGTGCTTCTCATCAGCAAGCTGTCCTGTATAGGCATCT<br>GGACGCTGGCCTTTTTCCTTTCTATCCCTGAGCTGCTCTACAGCGGCCTCCAGAA<br>GAACAGCGGCGAGGACACGTGGAGATGCTCCCTGGTCAGTGCCCAAGTGGAGG<br>CCTTGATCGCCATCCAAGTGGCCCAGATGGTTGTTGGGTTTGTACTGCCTATGCT<br>GGCTATGAGTTTCTGCTACCTGGTTATCATCCGCACTCTGCTCCAGGCGCGAAAC<br>TTCGAGCGGAACAAGGCCATCAAGGTGATCATCGCTGTGGTCGTAGTGTTCGTC<br>GTCTTCCAGCTGCCCTACAATGGGGTGGTCCTGGCCCAGACCGTGGCCAATTTC<br>AACATCACCAATAGCAGCTGCGAAGCCAGCAAGCAGCTCAACATTGCCTATGAC<br>GTCACCTACAGCCTGGCCTCCGTCCGCTGCTGTGTCAACCCTTTCTTGTATGCCTT<br>CATCGGCGTCAAGTTCCGCAGCGACCTCTTCAAGCTCTTCAAGGACTTGGGCTGC |

TABLE 2-continued

| Amino Acid and Nucleotide Sequence Information for CCR7 |
|---|
| CTCAGCCAGGAACGGCTCCGGCAGTGGTCTTCCTGCCGCCATGTACGGCACACG TCCGTGAGCATGGAGGCGGAGACTACCACCACCTTCTCCCCG |

Generation of Cell Lines Stably Expressing CCR7

Stable CCR7-expressing cell lines were generated using retroviral transduction. 293T cells were co-transfected with a CCR7 retroviral expression vector and a pCL-Eco or pCL-10A1 packaging vector (Novus, USA, cat #NBP2-29540 or NBP2-2952) using Fugene 6 transfection reagent (Promega, USA, cat #E2692) following manufacturer's recommendation. Cells were incubated in a 37° C. humidified $CO_2$ incubator and viral supernatant was collected 48 hours post-transfection. NIH/3T3 and 300.19 cells were grown to near confluent monolayer. Growth media was removed from the cells and viral supernatant was added in the presence of 8 ug polybrene/ml (final concentration) (EMD Millipore, cat #TR-1003-G). Following incubation for 3-6 hours at 37° C., fresh media was added. Cells were then cultured under appropriate selection conditions to produce stable CCR7-expressing cell lines.

Generation, Expression and Purification of Viral-Like Particles (VLPs)

HEK293T or NIH/3T3 cells were maintained in DMEM with 10% FBS. To make VLPs, cells were exchanged into DMEM with 4% FBS, then co-transfected with a CCR7 expression plasmid and a retroviral Gag expression plasmid at a μg ratio of 3:2. Forty-eight hours post-transfection, cell supernatant was collected and clarified by centrifugation at 2500×g for 5 min in a benchtop centrifuge and kept on ice. VLPs were purified by ultracentrifugation in at 100,000×g through a 20% sucrose cushion in Beckman Ultra-Clear 38 ml centrifugation tubes (catalog #344058) in a Beckman Coulter SW 32 Ti rotor in a Sorvall RC 6+ ultracentrifuge. Resulting pellets were resuspended in 300 μl of cold sterile PBS and quantitated using a BCA Assay (Pierce catalog #23225).

Structure Derived Generation of CCR7 Immunogen Scaffold

Members of the G coupled protein receptor family are membrane proteins that contain seven transmembrane helixes (TM1 . . . TM7) each connected by linking sequences of varying length. The amino terminus of the protein is on the ecto side of the cell surface which indicates that 4 regions of the protein are potentially exposed on the surface of the cell, the amino terminus (N-term) and 3 extracellular loop regions (EC1, EC2 and EC3). These regions are thus available as antigens for antibodies.

It was envisioned that a combination of one or more of these 4 entries could be inserted into a soluble protein scaffold to structurally approximate the extracellularly exposed region of CCR7.

To determine the optimal extracellular regions of CCR7, a model was built using the crystal structure of the close homologue CXCR4 (Wu et al., "Structures of the CXCR4 chemokine GPCR with small-molecule and cyclic peptide antagonists." (2010) Science 330: 1066-1071) using a combination of CXCR4 structure with Protein Data bank Entries (3FDU, 3OE0, 3OE6, 3OE8, 3OE9) and modelling software. Amino acids that were interstitial to the connecting transmembrane helices were inferred from the model to be exposed on the surface of the protein. These regions are identified in Table 3 below.

TABLE 3

Amino Acid and Nucleotide Sequence Information for CCR7 Immunogen Scaffold

| SEQ ID NO: | Description | | Comments |
|---|---|---|---|
| 105 | CCR7 (NP_001829.1\|C-C chemokine receptor type 7) | MDLGKPMKSVLVVALLVIFQVCLC**QDEVTDD YIGDNTTVDYTLFESLCSKKDVR**NFKAWFLPI MYSIICFVGLLGNGLVVLTYIYFKRLKTMTDTYL LNLAVADILFLLTLPFWAYSAA**KSWVFGVH**FC KLIFAIYKMSFFSGMLLLLCISIDRYVAIVQAVSA HRHRARVLLISKLSCVGIWILATVLSIPELL**YSDL QRSSSEQAMRCSLIT**EHVEAFITIQVAQMVIG FLVPLLAMSFCYLVIIRTLLQARNFERNKAIKVII AVVVVFIVFQLPYNGVVLAQTVAN**FNITSST**CE LSKQLNIAYDVTYSLACVRCCVNPFLYAFIGVKF RNDLFKLFKDLGCLSQEQLRQWSSCRHIRRSS MSVEAETTTTFSP | CCR7, precursor. Extracellular regions are highlighted in bold. Insert regions or derivatives thereof are in bold and underlined. |
| 106 | N-term | **QDEVTDDYIGDNTTVDYTLFESLCSKKDVR** | CCR7 N-terminal extracellular sequence |
| 107 | EC1 | **KSWVFGVH** | CCR7 Extracellular loop 1 |
| 108 | EC2 | **YSDLQRSSSEQAMRCSLIT** | CCR7 Extracellular loop 2 |

TABLE 3-continued

Amino Acid and Nucleotide Sequence Information for CCR7 Immunogen Scaffold

| SEQ ID NO: | Description | | Comments |
|---|---|---|---|
| 109 | EC3 | **FNITSST** | CCR7 Extracellular loop 3 |
| 110 | EC2_C24S | **YSDLQRSSSEQAMRSSLIT** | |
| 111 | H_MGFTX1 | EVQLVESGGGLVKPGGSLKLSCAASGFTFSDY<br>GMLWVRQAPEKGLEWIAYISSGSSTIYYADRV<br>KGRFTISRDNAKNTLFLQMTSLRSEDTAMYYC<br>STGTFAYWGQGTPVTVSSAKTTPPSVYPLAPG<br>SAAQTNSMVTLGCLVKGYFPEPVTVTWNSGS<br>LSSGVHTFPAVLQSDLYTLSSSVTVPSSTWPSE<br>TVTCNVAHPASSTKVDKKIVPRDC | Heavy chain of mouse Fab scaffold |
| 112 | L_MGFTX1 | DVVMTQNPLSLPVSLGDQASISCRSSQSLIYNN<br>GNTYLHWYRQKPGQSPKLLIYKVSNRFSGVPD<br>RFSGSGSGTDFTLKISRVEAEDLGVYFCSQSTH<br>VPFTFGSGTKLEIKRADAAPTVSIFPPSSEQLTS<br>GGASVVCFLNNFYPKDINVKWKIDGSERQNG<br>VLNSWTDQDSKDSTYSMSSTLTLTKDEYERHN<br>SYTCEATHKTSTSPIVKSFNRNEC | Light chain of mouse Fab scaffold |
| 113 | H_FabCCR7M1 | **QDEVTDDYIGDNTTVDYTLFESLCSKKDVR**EV<br>QLVESGGGLVKPGGSLKLSCAASGFTFSDYGM<br>LWVRQAPEKGLEWIAYISSGSSTIYYADRVKGR<br>FTISRDNAKNTLFLQMTSLRSEDTAMYYCSTG<br>T**YSDLQRSSSEQAMRSSLIT**FAYWGQGTPVT<br>VSSAKTTPPSVYPLAPGSAAQTNSMVTLGCLV<br>KGYFPEPVTVTWNSGSLSSGVHTFPAVLQSDL<br>YTLSSSVTVPSSTWPSETVTCNVAHPASSTKVD<br>KKIVPRDC | Heavy chain of Fab with N-term and EC2 inserted. Inserted sequences underlined and in bold |
| 114 | H_FabCCR7M1 | CAAGATGAGGTCACGGACGATTACATCGGA<br>GACAACACCACAGTGGACTACACTTTGTTCG<br>AGTCTTTGTGCTCCAAGAAGGACGTGCGGga<br>ggtgcagctggtggagtctggtggtggtctggtcaagcct<br>ggaggttccctgaaactgagttgtgccgcatctgggtttac<br>attctctgactacggaatgctgtgggtgaggcaggcacca<br>gagaagggcctggaatggatcgcttatatttccagcggat<br>ctagtactatctactatgcagacagggtcaagggccggtt<br>caccattagcagagataacgccaaaaataccctgtttctg<br>cagatgacatcactgaggtccgaggataccgctatgtatt<br>attgctccacagggactTACAGTGACCTCCAGAGG<br>AGCAGCAGTGAGCAAGCGATGCGATCCTCT<br>CTCATCACAtttgcttactggggacaggggacacccgt<br>gaccgtcagctcagccaagaccacccccccagcgtgtac<br>cctctggcccctggctctgccgcccagaccaacagcatgg<br>tgaccctgggctgcctggtgaagggctacttccccgagcc<br>cgtgaccgtgacctggaacagcggcagcctgagcagcgg<br>cgtgcacaccttccccgccgtgctgcagagcgacctgtac<br>accctgagcagctctgtgaccgtgcccagcagcacctggc<br>ccagcgagaccgtgacatgcaacgtggcccaccccgcca<br>gctccaccaaggtggacaagaaaatcgtgccccgggact<br>gc | DNA sequence of HFabCCR7M1 heavy chain. Inserted sequence in upper case |
| 115 | L_MGFTX1 | atgtcgtgatgactcagaatccactgtccctgcctgtgtcc<br>ctgggcgatcaggcttccattagctgtcgttcctctcagtcc<br>ctgatctacaacaatggtaacacctacctgcactggtata<br>gacagaagcccggccagtcccctaagctgctgatctacaa<br>agtgagtaataggttctcaggagtcccagaccggttttccg<br>gcagcggatctgggaccgatttcacactgaaaatctctag<br>ggtggaggccgaagacctgggcgtctacttttgtagtcag<br>agcactcacgtccccttcaccttcggcagcggaacaaaac<br>tggaaatcaagcgcgctgatgccgcccctaccgtgagcat<br>cttcccccccagcagcgagcagctgaccagcggcggagc<br>cagcgtggtgtgcttcctgaacaacttctaccccaaggac<br>atcaacgtgaagtggaagatcgacggcagcgagcggca<br>gaacggcgtgctgaacagctggaccgaccaggacagca<br>aggactccacctacagcatgagcagcaccctgaccctga<br>ccaaggacgagtacgagcggcacaacagctacacctgcg<br>aggccacccacaagaccagcaccagccccatcgtgaaga<br>gcttcaaccggaacgagtgc | DNA sequence of L_MGFTX1 |

The small size of loops EC1 and EC3 and the spatial separation of EC3 from the other three regions prioritized the use of N-term and EC2 loop as candidate epitopes.

Modelling the fusion of the N-term sequence into the crystal structure of a mouse Fab with the EC2 sequence inserted into various loop regions of the Fab such as in Framework 1, CDR-H3 or CDR3-H1, showed that if a degree of flexibility is assumed in the two sequences then these could be reasonable approximations to the structure of these regions in CCR7.

Immuno Scaffold Generation for Mouse Immunization

Engrafted constructs for mouse immunization were generated by fusing the N-terminal sequence from Table 3 to the N-terminus of the heavy chain of a mouse Fab scaffold (designated MGFTX1) and engrafting a modified version of EC2 sequence with the cysteine residue at position 24 mutated to a serine (Table 3 and underlined+emboldened sequences of SEQ ID NO: 113), into CDR3 of the MGFTX1 scaffold, then both heavy and light chain immunoglobulin chains were produced to generate final protein constructs. The constructs, designated FabCCR7M1, thus contained a mouse framework which should be immune tolerant combined with human sequence to which the mouse immune response was directed.

The N-term sequence was directly fused with the heavy chain of the MGFTX1 scaffold. Insertion points for EC2 were selected to be the mid-point of the CDR loop based on available structural or homology model data. Fab engrafted proteins were produced using standard molecular biology methodology utilizing recombinant DNA encoding the relevant sequences.

For example, a variable region of each antibody containing EC2 was inserted into heavy chain CDR3 was synthesized. DNA encoding variable region was amplified via PCR and the resulting fragment was sub-cloned into vector containing either the light chain constant region or the heavy chain constant and Fc regions. In this manner FabCCR7M1 proteins were made corresponding to fusion of N-term and insertion of EC2 into H3. Resulting constructs are shown in Table 3. Transfections of the appropriate combination of heavy and light chain vectors results in the expression of a recombinant Fab containing one N-term and one EC2 molecules.

The selection of which CDR is chosen for engraftment is determined based on the parameters of exposure of the loop and proximity to the N-terminal. At this time, modelling software is only partially useful in predicting which CDR and which location within the CDR will provide the desired parameters, due to the flexibility of the loops after fusion and engraftment. The structure of the MGFTX1 scaffold in combination with the EC2_C24S (Table 3, SEQ ID NO: 110) showed the sequence to be exposed and flexible as judged by lack of electron density for the majority of the sequence.

In summary, the insertion point in the CDR was chosen on a structural basis, with the hypothesis that grafting into the CDR would provide some level of structural semblance to the native antigen.

Hybridoma Generation

Bcl-2 transgenic mice (C57BL/6-Tgn (bcl-2) 22 WEHI strain) were immunized with antigen using a procedure that calls for Repetitive Immunization at Multiple Sites (RIMMS) (McIntyre G D. Hybridoma 1997). Briefly, mice were injected with 1-3 μg of CCR7 immunogen at 8 specific sites proximal to peripheral lymph nodes (PLNs). This procedure was repeated 8 times over a 12 day period. On Day 12, a test bleed was collected and the serum antibody titer was analyzed by FACS. In some instances, BALB/c and/or C57Bl/6 mice were immunized with NIH3T3 or 300.19 cells stably overexpressing human CCR7 (SEQ ID NO: 97). Animals were injected subcutaneously with $5\times10^6$ cells in PBS once a month for 3 months followed by an intravenous boost with 25 μg of human CCR7-expressing VLPs. Two days after the boost, a test bleed was collected and serum antibody titer was analyzed by FACS. Spleens and pooled PLNs were removed from high titer mice. To harvest lymphocytes, spleens and PLNs were washed twice with DMEM, and then dissociated by passage through a 70 micron screen (Falcon #352350). The resulting lymphocytes were washed 2 additional times prior to fusion in Cytofusion media (BTXpress Cytofusion® Electroporation Medium cat #47001).

For the fusion, F0 myeloma cells were mixed with lymphocytes at a 1:4 ratio. The cell mixture was centrifuged, suspended in Cytofusion media and subsequently added to an electrofusion chamber (Harvard Apparatus Coaxial chamber 9ML Part #470020). Electrofusion was carried out per manufacturer's instructions using the CEEF-50B Hybrimune/Hybridoma system (Cyto Pulse Sciences, Inc). Fused cells were allowed to recover 5 min in chamber, diluted 1/10 in Fusion media without HAT (DMEM+20% FBS, 1% Pen/Strep/Glu, 1×NEAA, 0.5×HFCS) and placed at 37° C. for one hour. 4×HAT media (DMEM+20% FBS, 1% Pen/Strep/Glu, 1×NEAA, 4×HAT, 0.5×HFCS) was added to make a 1× solution, and density was adjusted to $1.67\times10^4$ cells/ml. The cells were plated in 384-well plates at 60 μl/well.

FACS Screening

Ten days after fusion, hybridoma plates were screened for the presence of CCR7-specific antibodies using flow cytometry to confirm specific binding of candidate antibodies to cell lines stably overexpressing or endogenously expressing CCR7. Cells were rinsed thoroughly with PBS and treated with Accutase (Millipore #SCR005) to lift from growth plates and resuspended in cold PBS. Cells were biotinylated labeled with a fluorescent dye according to manufacturer's directions (FluoReporter Cell-Surface Biotinylation Kit, Thermo Fisher Scientific Cat #F-20650; PE-Cy7 Steptavidin, ThermoFisher Scientific Cat #SA1012). Cells were resuspended at approximately $1\times10^6$ cells/ml in FACS buffer (1×DPBS, 3% FBS, 5 mM EDTA, 0.1% Sodium Azide). In a 384-well plate, 20 μL of hybridoma supernatant was pre-seeded and 20 μL of cell suspension was added. Cells were incubated for 1 hour at 4° C., washed twice with cold FACS buffer and resuspended in 20 μL of 1:400 secondary antibody FACS buffer (Allophycocyanin conjugated F(ab')2 goat anti-human IgG, Fcγ specific; Jackson Immunoresearch, Cat #109-136-098). After additional incubation for 45 min at 4° C., cells were washed twice with FACS buffer and resuspended in 20 uL of FACS buffer+ with 2 μg/ml propidium iodide (Sigma Aldrich Cat #P4864-10ML). Geometric mean fluorescence intensity was calculated on live single cells using FlowJo™ software.

Antibody Purification

Chimeric antibodies comprising murine variable regions and human constant regions were prepared. Additionally, chimeric versions comprising cysteine mutations (e.g., cysteines at position K360C, or positions E152C and S375C of the heavy chain) were designed for conjugation of drug moiety and preparation of ADCs as described in further detail herein. Variable region (VH and VL) DNA sequences of hybridomas were obtained for generation of optimized sequences (e.g., humanization, preferred characteristics) for each of selected hybridomas mAb121G12, mAb506E15, mAb674J13 and mAb684E12. Variable region DNA from murine monoclonal antibodies was amplified by RACE from RNA obtained from each selected hybridoma cell line using standard methods. Polypeptide sequences for each of the murine variable heavy/light chains are shown in SEQ ID NO: 128/SEQ ID NO: 144, SEQ ID NO: 160/SEQ ID NO: 176, SEQ ID NO: 192/SEQ ID NO: 208, and SEQ ID NO: 224/SEQ ID NO: 240 respectively for each of 674J13, 121G12, 506E15 and 684E12 hybridomas. Corresponding derived variable heavy/light nucleotide sequences for each of the hybridomas are shown in SEQ ID NO: 129/SEQ ID NO: 145, SEQ ID NO: 161/SEQ ID NO: 177, SEQ ID NO: 193/SEQ ID NO: 209, and SEQ ID NO: 225/SEQ ID NO: 241. For preparation of chimeric antibodies, DNA sequences coding for the hybridoma VL and VH domain were subcloned into expression vectors containing the respective human wild type or engineered Cys or D265A/P329A (DAPA) mutation heavy chain and human light chain constant region sequences (IgG1, kappa).

Humanization of Antibodies

Variable region constructs were designed for humanization and optimization of sequences (e.g., removal of post-translational modifications, non-preferred sites, etc.), to include cysteine mutations (e.g., cysteines at position K360C, or positions E152C and S375C of the heavy chain) for conjugation of drug moiety and preparation of ADCs as described in further detail herein; as well as for modification of Fc effector mutations (e.g., D265A/P329A mutations in the Fc region) to include constructs having reduced Fc effector function, and combinations thereof.

DNA sequences coding for humanized VL and VH domains were ordered at GeneArt (Life Technologies Inc. Regensburg, Germany), including codon optimization for *Cricetulus griseus*. Sequences coding for VL and VH domains were subcloned from the GeneArt derived vectors into expression vectors suitable for protein production in mammalian cells. Heavy and light chains were cloned into individual expression vectors to allow co-transfection.

Recombinant antibodies (IgG1, kappa) were produced by co-transfection of vectors into Freestyle™ 293 expression cells (Invitrogen, USA) using PEI (polyethylenimine, MW 25,000 linear, Polysciences, USA, cat #23966) as transfection reagent. The PEI stock was prepared by dissolving 1 g of PEI in 900 ml cell culture grade water at room temperature (RT). To facilitate dissolution of PEI, the solution was acidified by addition of HCl to pH 3-5, followed by neutralization with NaOH to a final pH of 7.05. Finally, the volume was adjusted to 1 L and the solution was filter sterilized through a 0.22 um filter, aliquoted and frozen at −80° C. until further use.

Freestyle™ 293 cells (Gibco™, ThermoFisher scientific, USA, cat #R79007) were cultivated in Freestyle™ 293 media (Gibco™, ThermoFisher scientific, USA, cat #12338018) in shake flasks (Corning, Tewksbury, MA) on an orbital shaker (100-120 rpm) in a 37° C. humidified incubator at 5% $CO_2$. For transient transfections, cells were grown to a density or approximately $3\times10^6$ cells/ml, and then 1 ug of filter sterilized DNA/ml of culture (0.5 ug of heavy chain+0.5 ug of light chain) was added to 2 ug PEI/1 ug of DNA in OptiMem (ThermoFisher Scientific, USA, #11058021) solution and incubated at RT for 8 minutes. The mixture was the added to the Freestyle™ 293 cells dropwise with gently swirling. Following transfection, the cells were cultured for one to two weeks prior to antibody purification from supernatant. To generate stable cell lines for antibody production, vectors were co-transfected by nucleofection (Nucleofector™ 96-well Shuttle™; Lonza) into CHO cells using manufacturer's recommendations, and cultured under selection conditions for up to four weeks in shake flasks. Cells were harvested by centrifugation, and supernatant recovered for antibody purification. Antibody was purified using protein A, Protein G or MabSelect SuRe (GE Healthcare Life Sciences) columns. Prior to loading the supernatant, the resin was equilibrated with PBS. Following binding of the sample, the column was washed with PBS, and the antibody was eluted with Thermo (Pierce) IgG pH 2.8 (cat #21004). The eluate fractions were neutralized with sodium citrate tribasic dehydrate buffer, pH 8.5 (Sigma Aldrich cat #54641-1Kg) and then dialyzed overnight into PBS, pH 7.2.

Summary of Antibodies

Table 4 sets forth the relevant sequence information for parental and humanized anti-CCR7 antibodies derived from murine hybridomas. Throughout this application, when describing the antibodies, the terms "Hybridoma" and "Parental" are used interchangeably and refer to the Ab that is derived from the hybridoma.

TABLE 4

Amino Acid and Nucleotide Sequence Information for Hybridomas and Humanized Anti-CCR7 Antibodies

| | | |
|---|---|---|
| Parental 674J13 hIgG1 | | |
| SEQ ID NO: 116 | HCDR1 (Combined) | GYSITSGYSWH |
| SEQ ID NO: 117 | HCDR2 (Combined) | HIHSSGSTNYNPSLKS |
| SEQ ID NO: 118 | HCDR3 (Combined) | GGVQAFAY |
| SEQ ID NO: 119 | HCDR1 (Kabat) | SGYSWH |
| SEQ ID NO: 120 | HCDR2 (Kabat) | HIHSSGSTNYNPSLKS |
| SEQ ID NO: 121 | HCDR3 (Kabat) | GGVQAFAY |
| SEQ ID NO: 122 | HCDR1 (Chothia) | GYSITSGY |

TABLE 4-continued

| Amino Acid and Nucleotide Sequence Information for Hybridomas and Humanized Anti-CCR7 Antibodies | | |
|---|---|---|
| SEQ ID NO: 123 | HCDR2 (Chothia) | HSSGS |
| SEQ ID NO: 124 | HCDR3 (Chothia) | GGVQAFAY |
| SEQ ID NO: 125 | HCDR1 (IMGT) | GYSITSGYS |
| SEQ ID NO: 126 | HCDR2 (IMGT) | IHSSGST |
| SEQ ID NO: 127 | HCDR3 (IMGT) | ARGGVQAFAY |
| SEQ ID NO: 128 | VH | DVQLQESGPDLVKPSQSLSLTCTVTGYSITSGYSWHWIR<br>QFPGNKLEWMAHIHSSGSTNYNPSLKSRISIIRDTSKNLFF<br>LQLNSVTTEDTATYYCARGGVQAFAYWGQGTLVTVSA |
| SEQ ID NO: 129 | DNA VH | GATGTGCAGCTTCAGGAGTCAGGACCTGACCTGGTGA<br>AACCTTCTCAGTCACTTTCACTCACCTGCACTGTCACTG<br>GCTACTCCATCACCAGTGGTTATAGCTGGCACTGGATC<br>CGGCAGTTTCCAGGAAACAAACTGGAGTGGATGGCCC<br>ACATCCACTCCAGTGGTAGCACTAACTACAACCCATCT<br>CTCAAAAGTCGCATCTCTATCATTCGAGACACATCCAA<br>GAACCTGTTCTTCCTGCAGTTGAATTCTGTGACTACTGA<br>GGACACAGCCACATATTACTGTGCAAGAGGGGGGGTA<br>CAGGCCTTTGCTTACTGGGGCCAAGGGACTCTGGTCAC<br>TGTCTCTGCA |
| SEQ ID NO: 130 | Heavy Chain (WT Fc) | DVQLQESGPDLVKPSQSLSLTCTVTGYSITSGYSWHWIRQFPG<br>NKLEWMAHIHSSGSTNYNPSLKSRISIIRDTSKNLFFLQLNSVTT<br>EDTATYYCARGGVQAFAYWGQGTLVTVSAASTKGPSVFPLAP<br>SSKSTSGGTAALGCLVKDYFPEPVTVSWNSGALTSGVHTFPAV<br>LQSSGLYSLSSVVTVPSSSLGTQTYICNVNHKPSNTKVDKRVEP<br>KSCDKTHTCPPCPAPELLGGPSVFLFPPKPKDTLMISRTPEVTCV<br>VVDVSHEDPEVKFNWYVDGVEVHNAKTKPREEQYNSTYRVV<br>SVLTVLHQDWLNGKEYKCKVSNKALPAPIEKTISKAKGQPREP<br>QVYTLPPSREEMTKNQVSLTCLVKGFYPSDIAVEWESNGQPEN<br>NYKTTPPVLDSDGSFFLYSKLTVDKSRWQQGNVFSCSVMHEA<br>LHNHYTQKSLSLSPGK |
| SEQ ID NO: 131 | DNA Heavy Chain | gatgtgcagcttcaggagtcaggacctgacctggtgaaaccttctcagtcacttt<br>cactcacctgcactgtcactggctactccatcaccagtggttatagctggcactg<br>gatccggcagtttccaggaaacaaactggagtggatggcccacatccactcca<br>gtggtagcactaactacaacccatctctcaaaagtcgcatctctatcattcgag<br>acacatccaagaacctgttcttcctgcagttgaattctgtgactactgaggacac<br>agccacatattactgtgcaagagggggggtacaggcctttgcttactggggcc<br>aagggactctggtcactgtctctgcaGCTAGCACCAAGGGCCCAAGT<br>GTGTTTCCCCTGGCCCCCAGCAGCAAGTCTACTTCCGGCGG<br>AACTGCTGCCCTGGGTTGCCTGGTGAAGGACTACTTCCCCG<br>AGCCCGTGACAGTGTCCTGGAACTCTGGGGCTCTGACTTCC<br>GGCGTGCACACCTTCCCCGCCGTGCTGCAGAGCAGCGGCCT<br>GTACAGCCTGAGCAGCGTGGTGACAGTGCCCTCCAGCTCTC<br>TGGGAACCCAGACCTATATCTGCAACGTGAACCACAAGCCC<br>AGCAACACCAAGGTGGACAAGAGAGTGGAGCCCAAGAGCT<br>GCGACAAGACCCACACCTGCCCCCCCTGCCCAGCTCCAGAA<br>CTGCTGGGAGGGCCTTCCGTGTTCCTGTTCCCCCCCAAGCCC<br>AAGGACACCCTGATGATCAGCAGGACCCCCGAGGTGACCT<br>GCGTGGTGGTGGACGTGTCCCACGAGGACCCAGAGGTGAA<br>GTTCAACTGGTACGTGGACGGCGTGGAGGTGCACAACGCC<br>AAGACCAAGCCCAGAGAGGAGCAGTACAACAGCACCTACA<br>GGGTGGTGTCCGTGCTGACCGTGCTGCACCAGGACTGGCTG<br>AACGGCAAAGAATACAAGTGCAAAGTCTCCAACAAGGCCCT<br>GCCAGCCCCAATCGAAAAGACAATCAGCAAGGCCAAGGGC<br>CAGCCACGGGAGCCCCAGGTGTACACCCTGCCCCCCAGCCG<br>GGAGGAGATGACCAAGAACCAGGTGTCCCTGACCTGTCTG<br>GTGAAGGGCTTCTACCCCAGCGATATCGCCGTGGAGTGGG<br>AGAGCAACGGCCAGCCCGAGAACAACTACAAGACCACCCCC<br>CCAGTGCTGGACAGCGACGGCAGCTTCTTCCTGTACAGCAA<br>GCTGACCGTGGACAAGTCCAGGTGGCAGCAGGGCAACGTG<br>TTCAGCTGCAGCGTGATGCACGAGGCCCTGCACAACCACTA<br>CACCCAGAAGTCCCTGAGCCTGAGCCCCGGCAAG |
| SEQ ID NO: 132 | LCDR1 (Combined) | SASSSVIYMH |

TABLE 4-continued

| Amino Acid and Nucleotide Sequence Information for Hybridomas and Humanized Anti-CCR7 Antibodies | | |
|---|---|---|
| SEQ ID NO: 133 | LCDR2 (Combined) | DTSKLAS |
| SEQ ID NO: 134 | LCDR3 (Combined) | QQWSSNPLT |
| SEQ ID NO: 135 | LCDR1 (Kabat) | SASSSVIYMH |
| SEQ ID NO: 136 | LCDR2 (Kabat) | DTSKLAS |
| SEQ ID NO: 137 | LCDR3 (Kabat) | QQWSSNPLT |
| SEQ ID NO: 138 | LCDR1 (Chothia) | SSSVIY |
| SEQ ID NO: 139 | LCDR2 (Chothia) | DTS |
| SEQ ID NO: 140 | LCDR3 (Chothia) | WSSNPL |
| SEQ ID NO: 141 | LCDR1 (IMGT) | SSVIY |
| SEQ ID NO: 142 | LCDR2 (IMGT) | DTS |
| SEQ ID NO: 143 | LCDR3 (IMGT) | QQWSSNPLT |
| SEQ ID NO: 144 | VL | QIVLTQSPAIMSASPGEKVTMTCSASSSVIYMHWYQQKS<br>GTSPKRWIYDTSKLASGVPARFSGSGSGTSYSLTISSMEAE<br>DAATYYCQQWSSNPLTFGAGTTLELK |
| SEQ ID NO: 145 | DNA VL | CAAATTGTCCTCACCCAGTCTCCAGCAATCATGTCTGCA<br>TCTCCAGGGGAGAAGGTCACCATGACCTGCAGTGCCA<br>GTTCAAGTGTAATTTACATGCACTGGTACCAGCAGAAG<br>TCAGGCACCTCCCCCAAAAGATGGATTTATGACACATC<br>CAAACTGGCTTCTGGAGTCCCTGCTCGCTTCAGTGGTA<br>GTGGGTCTGGGACCTCTTACTCTCTCACAATCAGCAGC<br>ATGGAGGCTGAAGATGCTGCCACTTATTACTGCCAGCA<br>GTGGAGTAGTAACCCGCTCACGTTCGGTGCTGGGACC<br>ACGTTGGAGCTGAAA |
| SEQ ID NO: 146 | Light Chain | QIVLTQSPAIMSASPGEKVTMTCSASSSVIYMHWYQQKS<br>GTSPKRWIYDTSKLASGVPARFSGSGSGTSYSLTISSMEAE<br>DAATYYCQQWSSNPLTFGAGTTLELKRTVAAPSVFIFPPS<br>DEQLKSGTASVVCLLNNFYPREAKVQWKVDNALQSGNS<br>QESVTEQDSKDSTYSLSSTLTLSKADYEKHKVYACEVTHQ<br>GLSSPVTKSFNRGEC |
| SEQ ID NO: 147 | DNA Light Chain | CAAATTGTCCTCACCCAGTCTCCAGCAATCATGTCTGCA<br>TCTCCAGGGGAGAAGGTCACCATGACCTGCAGTGCCA<br>GTTCAAGTGTAATTTACATGCACTGGTACCAGCAGAAG<br>TCAGGCACCTCCCCCAAAAGATGGATTTATGACACATC<br>CAAACTGGCTTCTGGAGTCCCTGCTCGCTTCAGTGGTA<br>GTGGGTCTGGGACCTCTTACTCTCTCACAATCAGCAGC<br>ATGGAGGCTGAAGATGCTGCCACTTATTACTGCCAGCA<br>GTGGAGTAGTAACCCGCTCACGTTCGGTGCTGGGACC<br>ACGTTGGAGCTGAAACGTACGGTGGCCGCTCCCAGCG<br>TGTTCATCTTCCCCCCCAGCGACGAGCAGCTGAAGAGT<br>GGCACCGCCAGCGTGGTGTGCCTGCTGAACAACTTCTA<br>CCCCCGGGAGGCCAAGGTGCAGTGGAAGGTGGACAA<br>CGCCCTGCAGAGCGGCAACAGCCAGGAGAGCGTCACC<br>GAGCAGGACAGCAAGGACTCCACCTACAGCCTGAGCA<br>GCACCCTGACCCTGAGCAAGGCCGACTACGAGAAGCA<br>TAAGGTGTACGCCTGCGAGGTGACCCACCAGGGCCTG<br>TCCAGCCCCGTGACCAAGAGCTTCAACAGGGGCGAGT<br>GC |

TABLE 4-continued

Amino Acid and Nucleotide Sequence Information for Hybridomas and Humanized Anti-CCR7 Antibodies

| | | |
|---|---|---|
| | Parental 121G12 hIgG1 | |
| SEQ ID NO: 148 | HCDR1 (Combined) | GFTFSTYAMS |
| SEQ ID NO: 149 | HCDR2 (Combined) | TISDGGSYSYYPDNVKG |
| SEQ ID NO: 150 | HCDR3 (Combined) | RGSRYEEYYVMDY |
| SEQ ID NO: 151 | HCDR1 (Kabat) | TYAMS |
| SEQ ID NO: 152 | HCDR2 (Kabat) | TISDGGSYSYYPDNVKG |
| SEQ ID NO: 153 | HCDR3 (Kabat) | RGSRYEEYYVMDY |
| SEQ ID NO: 154 | HCDR1 (Chothia) | GFTFSTY |
| SEQ ID NO: 155 | HCDR2 (Chothia) | SDGGSY |
| SEQ ID NO: 156 | HCDR3 (Chothia) | RGSRYEEYYVMDY |
| SEQ ID NO: 157 | HCDR1 (IMGT) | GFTFSTYA |
| SEQ ID NO: 158 | HCDR2 (IMGT) | ISDGGSYS |
| SEQ ID NO: 159 | HCDR3 (IMGT) | ARRGSRYEEYYVMDY |
| SEQ ID NO: 160 | VH | EVQLVESGGGLVKPGGSLKLSCAASGFTFSTYAMSWVRQ TPEKRLEWVATISDGGSYSYYPDNVKGRFTISRDNAKNNL YLQMSHLKSEDTAMYYCARRGSRYEEYYVMDYWGQGT SVTVSS |
| SEQ ID NO: 161 | DNA VH | GAAGTGCAGCTGGTGGAGTCTGGGGGAGGCTTAGTG AAGCCTGGAGGGTCCCTGAAACTCTCCTGTGCAGCCTC TGGATTCACTTTCAGTACCTATGCCATGTCTTGGGTTCG CCAGACTCCGGAAAAGAGGCTGGAGTGGGTCGCAACC ATTAGTGATGGTGGTAGTTATTCGTACTATCCAGACAA TGTAAAGGGCCGATTCACCATCTCCAGAGACAATGCCA AGAACAACCTATACCTGCAAATGAGCCATCTGAAGTCT GAGGACACAGCCATGTATTACTGTGCAAGACGAGGTA GTAGGTACGAAGAGTACTATGTTATGGACTACTGGGG TCAAGGAACCTCAGTCACCGTCTCCTCA |
| SEQ ID NO: 162 | Heavy Chain (WT Fc) | EVQLVESGGGLVKPGGSLKLSCAASGFTFSTYAMSWVRQ TPEKRLEWVATISDGGSYSYYPDNVKGRFTISRDNAKNNL YLQMSHLKSEDTAMYYCARRGSRYEEYYVMDYWGQGT SVTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKRVEPKSCDKTHTCPPCPA PELLGGPSVFLFPPKPKDTLMISRTPEVTCVVVDVSHEDP EVKFNWYVDGVEVHNAKTKPREEQYNSTYRVVSVLTVL HQDWLNGKEYKCKVSNKALPAPIEKTISKAKGQPREPQV YTLPPSREEMTKNQVSLTCLVKGFYPSDIAVEWESNGQP ENNYKTTPPVLDSDGSFFLYSKLTVDKSRWQQGNVFSCS VMHEALHNHYTQKSLSLSPGK |
| SEQ ID NO: 163 | DNA Heavy Chain | GAAGTGCAGCTGGTGGAGTCTGGGGGAGGCTTAGTG AAGCCTGGAGGGTCCCTGAAACTCTCCTGTGCAGCCTC TGGATTCACTTTCAGTACCTATGCCATGTCTTGGGTTCG CCAGACTCCGGAAAAGAGGCTGGAGTGGGTCGCAACC ATTAGTGATGGTGGTAGTTATTCGTACTATCCAGACAA TGTAAAGGGCCGATTCACCATCTCCAGAGACAATGCCA AGAACAACCTATACCTGCAAATGAGCCATCTGAAGTCT GAGGACACAGCCATGTATTACTGTGCAAGACGAGGTA GTAGGTACGAAGAGTACTATGTTATGGACTACTGGGG |

TABLE 4-continued

| Amino Acid and Nucleotide Sequence Information for Hybridomas and Humanized Anti-CCR7 Antibodies | |
|---|---|
| | TCAAGGAACCTCAGTCACCGTCTCCTCAGCTAGCACCA AGGGCCCAAGTGTGTTTCCCCTGGCCCCCAGCAGCAA GTCTACTTCCGGCGGAACTGCTGCCCTGGGTTGCCTGG TGAAGGACTACTTCCCCGAGCCCGTGACAGTGTCCTGG AACTCTGGGGCTCTGACTTCCGGCGTGCACACCTTCCC CGCCGTGCTGCAGAGCAGCGGCCTGTACAGCCTGAGC AGCGTGGTGACAGTGCCCTCCAGCTCTCTGGGAACCCA GACCTATATCTGCAACGTGAACCACAAGCCCAGCAACA CCAAGGTGGACAAGAGAGTGGAGCCCAAGAGCTGCG ACAAGACCCACACCTGCCCCCCCTGCCCAGCTCCAGAA CTGCTGGGAGGGCCTTCCGTGTTCCTGTTCCCCCCCAA GCCCAAGGACACCCTGATGATCAGCAGGACCCCCGAG GTGACCTGCGTGGTGGTGGACGTGTCCCACGAGGACC CAGAGGTGAAGTTCAACTGGTACGTGGACGGCGTGGA GGTGCACAACGCCAAGACCAAGCCCAGAGAGGAGCA GTACAACAGCACCTACAGGGTGGTGTCCGTGCTGACC GTGCTGCACCAGGACTGGCTGAACGGCAAAGAATACA AGTGCAAAGTCTCCAACAAGGCCCTGCCAGCCCCAATC GAAAAGACAATCAGCAAGGCCAAGGGCCAGCCACGG GAGCCCCAGGTGTACACCCTGCCCCCCAGCCGGGAGG AGATGACCAAGAACCAGGTGTCCCTGACCTGTCTG GT GAAGGGCTTCTACCCCAGCGATATCGCCGTGGAGTGG GAGAGCAACGGCCAGCCCGAGAACAACTACAAGACCA CCCCCCCAGTGCTGGACAGCGACGGCAGCTTCTTCCTG TACAGCAAGCTGACCGTGGACAAGTCCAGGTGGCAGC AGGGCAACGTGTTCAGCTGCAGCGTGATGCACGAGGC CCTGCACAACCACTACACCCAGAAGTCCCTGAGCCTGA GCCCCGGCAAG |
| SEQ ID NO: 164 LCDR1 (Combined) | RASQSISNNLH |
| SEQ ID NO: 165 LCDR2 (Combined) | YASQSIS |
| SEQ ID NO: 166 LCDR3 (Combined) | QQSNSWLT |
| SEQ ID NO: 167 LCDR1 (Kabat) | RASQSISNNLH |
| SEQ ID NO: 168 LCDR2 (Kabat) | YASQSIS |
| SEQ ID NO: 169 LCDR3 (Kabat) | QQSNSWLT |
| SEQ ID NO: 170 LCDR1 (Chothia) | SQSISNN |
| SEQ ID NO: 171 LCDR2 (Chothia) | YAS |
| SEQ ID NO: 172 LCDR3 (Chothia) | SNSWL |
| SEQ ID NO: 173 LCDR1 (IMGT) | QSISNN |
| SEQ ID NO: 174 LCDR2 (IMGT) | YAS |
| SEQ ID NO: 175 LCDR3 (IMGT) | QQSNSWLT |
| SEQ ID NO: 176 VL | DIVLTQSPATLSVTPGDSVSLSCRASQSISNNLHWYQQKS HESPKLLIKYASQSISGIPSRFSGSGSGTDFTLSINSVETEDF GMYFCQQSNSWLTFGAGTKLGLK |
| SEQ ID NO: 177 DNA VL | GATATTGTGCTAACTCAGTCTCCAGCCACCCTGTCTGTG ACTCCAGGAGATAGCGTCAGTCTTTCCTGCAGGGCCAG CCAAAGTATTAGCAACAACCTACACTGGTATCAACAGA AATCACATGAGTCTCCAAAACTTCTCATCAAGTATGCTT CCCAGTCCATCTCTGGGATCCCCTCCAGGTTCAGTGGC AGTGGATCAGGGACAGATTTCACTCTCAGTATCAACAG TGTGGAGACTGAAGATTTTGGAATGTATTTCTGTCAAC |

TABLE 4-continued

| Amino Acid and Nucleotide Sequence Information for Hybridomas and Humanized Anti-CCR7 Antibodies | |
|---|---|
| | AGAGTAACAGCTGGCTCACGTTCGGTGCTGGGACCAA GCTGGGGCTGAAA |
| SEQ ID NO: 178 Light Chain | DIVLTQSPATLSVTPGDSVSLSCRASQSISNNLHWYQQKS HESPKLLIKYASQSISGIPSRFSGSGSGTDFTLSINSVETEDF GMYFCQQSNSWLTFGAGTKLGLKRTVAAPSVFIFPPSDE QLKSGTASVVCLLNNFYPREAKVQWKVDNALQSGNSQE SVTEQDSKDSTYSLSSTLTLSKADYEKHKVYACEVTHQGLS SPVTKSFNRGEC |
| SEQ ID NO: 179 DNA Light Chain | GATATTGTGCTAACTCAGTCTCCAGCCACCCTGTCTGTG ACTCCAGGAGATAGCGTCAGTCTTTCCTGCAGGGCCAG CCAAAGTATTAGCAACAACCTACACTGGTATCAACAGA AATCACATGAGTCTCCAAAACTTCTCATCAAGTATGCTT CCCAGTCCATCTCTGGGATCCCCTCCAGGTTCAGTGGC AGTGGATCAGGGACAGATTTCACTCTCAGTATCAACAG TGTGGAGACTGAAGATTTTGGAATGTATTTCTGTCAAC AGAGTAACAGCTGGCTCACGTTCGGTGCTGGGACCAA GCTGGGGCTGAAACGTACGGTGGCCGCTCCCAGCGTG TTCATCTTCCCCCCCAGCGACGAGCAGCTGAAGAGTGG CACCGCCAGCGTGGTGTGCCTGCTGAACAACTTCTACC CCCGGGAGGCCAAGGTGCAGTGGAAGGTGGACAACG CCCTGCAGAGCGGCAACAGCCAGGAGAGCGTCACCGA GCAGGACAGCAAGGACTCCACCTACAGCCTGAGCAGC ACCCTGACCCTGAGCAAGGCCGACTACGAGAAGCATA AGGTGTACGCCTGCGAGGTGACCCACCAGGGCCTGTC CAGCCCCGTGACCAAGAGCTTCAACAGGGGCGAGTGC |
| Parental 506E15 hIgG1 | |
| SEQ ID NO: 180 HCDR1 (Combined) | GFTFSSYAMS |
| SEQ ID NO: 181 HCDR2 (Combined) | TISSGGSFTYYPDSVKG |
| SEQ ID NO: 182 HCDR3 (Combined) | RASTVVGTDFDV |
| SEQ ID NO: 183 HCDR1 (Kabat) | SYAMS |
| SEQ ID NO: 184 HCDR2 (Kabat) | TISSGGSFTYYPDSVKG |
| SEQ ID NO: 185 HCDR3 (Kabat) | RASTVVGTDFDV |
| SEQ ID NO: 186 HCDR1 (Chothia) | GFTFSSY |
| SEQ ID NO: 187 HCDR2 (Chothia) | SSGGSF |
| SEQ ID NO: 188 HCDR3 (Chothia) | RASTVVGTDFDV |
| SEQ ID NO: 189 HCDR1 (IMGT) | GFTFSSYA |
| SEQ ID NO: 190 HCDR2 (IMGT) | ISSGGSFT |
| SEQ ID NO: 191 HCDR3 (IMGT) | ARRASTVVGTDFDV |
| SEQ ID NO: 192 VH | EVMLVESGGGLVKPGGSLKLSCAASGFTFSSYAMSWIRQ TPEKRLEWVATISSGGSFTYYPDSVKGRFTISRDNVKNTLY LQMSSLRSEDTAMYYCARRASTVVGTDFDVWGAGTTVT VSS |
| SEQ ID NO: 193 DNA VH | GAAGTGATGCTGGTGGAGTCTGGGGGAGGCTTAGTG AAGCCTGGAGGGTCCCTGAAACTCTCCTGTGCAGCCTC TGGATTCACTTTCAGTAGCTATGCCATGTCTTGGATTCG CCAGACTCCGGAGAAGAGACTGGAGTGGGTCGCAACC ATCAGTAGTGGTGGTAGTTTCACCTACTATCCAGACAG TGTGAAGGGGCGATTCACCATTTCTAGAGACAATGTCA |

TABLE 4-continued

| Amino Acid and Nucleotide Sequence Information for Hybridomas and Humanized Anti-CCR7 Antibodies | | |
|---|---|---|
| | | AGAACACCCTGTACCTGCAAATGAGCAGTCTGAGGTCT<br>GAAGACACGGCCATGTATTACTGTGCAAGACGGGCTT<br>CTACGGTAGTAGGTACGGACTTCGATGTCTGGGGCGC<br>AGGGACCACGGTCACCGTCTCCTCA |
| SEQ ID NO: 194 | Heavy Chain (WT Fc) | EVMLVESGGGLVKPGGSLKLSCAASGFTFSSYAMSWIRQ<br>TPEKRLEWVATISSGGSFTYYPDSVKGRFTISRDNVKNTLY<br>LQMSSLRSEDTAMYYCARRASTVVGTDFDVWGAGTTVT<br>VSSASTKGPSVFPLAPSSKSTSGGTAALGCLVKDYFPEPVT<br>VSWNSGALTSGVHTFPAVLQSSGLYSLSSVVTVPSSSLGT<br>QTYICNVNHKPSNTKVDKRVEPKSCDKTHTCPPCPAPELL<br>GGPSVFLFPPKPKDTLMISRTPEVTCVVVDVSHEDPEVKF<br>NWYVDGVEVHNAKTKPREEQYNSTYRVVSVLTVLHQD<br>WLNGKEYKCKVSNKALPAPIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVFSCSVMHE<br>ALHNHYTQKSLSLSPGK |
| SEQ ID NO: 195 | DNA Heavy Chain | GAAGTGATGCTGGTGGAGTCTGGGGGAGGCTTAGTG<br>AAGCCTGGAGGGTCCCTGAAACTCTCCTGTGCAGCCTC<br>TGGATTCACTTTCAGTAGCTATGCCATGTCTTGGATTCG<br>CCAGACTCCGGAGAAGAGACTGGAGTGGGTCGCAACC<br>ATCAGTAGTGGTGGTAGTTTCACCTACTATCCAGACAG<br>TGTGAAGGGGCGATTCACCATTTCTAGAGACAATGTCA<br>AGAACACCCTGTACCTGCAAATGAGCAGTCTGAGGTCT<br>GAAGACACGGCCATGTATTACTGTGCAAGACGGGCTT<br>CTACGGTAGTAGGTACGGACTTCGATGTCTGGGGCGC<br>AGGGACCACGGTCACCGTCTCCTCAGCTAGCACCAAG<br>GGCCCAAGTGTGTTTCCCCTGGCCCCCAGCAGCAAGTC<br>TACTTCCGGCGGAACTGCTGCCCTGGGTTGCCTGGTGA<br>AGGACTACTTCCCCGAGCCCGTGACAGTGTCCTGGAAC<br>TCTGGGGCTCTGACTTCCGGCGTGCACACCTTCCCCGC<br>CGTGCTGCAGAGCAGCGGCCTGTACAGCCTGAGCAGC<br>GTGGTGACAGTGCCCTCCAGCTCTCTGGGAACCCAGAC<br>CTATATCTGCAACGTGAACCACAAGCCCAGCAACACCA<br>AGGTGGACAAGAGAGTGGAGCCCAAGAGCTGCGACA<br>AGACCCACACCTGCCCCCCCTGCCCAGCTCCAGAACTG<br>CTGGGAGGGCCTTCCGTGTTCCTGTTCCCCCCCAAGCC<br>CAAGGACACCCTGATGATCAGCAGGACCCCCGAGGTG<br>ACCTGCGTGGTGGTGGACGTGTCCCACGAGGACCCAG<br>AGGTGAAGTTCAACTGGTACGTGGACGGCGTGGAGGT<br>GCACAACGCCAAGACCAAGCCCAGAGAGGAGCAGTAC<br>AACAGCACCTACAGGGTGGTGTCCGTGCTGACCGTGC<br>TGCACCAGGACTGGCTGAACGGCAAAGAATACAAGTG<br>CAAAGTCTCCAACAAGGCCCTGCCAGCCCCAATCGAAA<br>AGACAATCAGCAAGGCCAAGGGCCAGCCACGGGAGC<br>CCCAGGTGTACACCCTGCCCCCCAGCCGGGAGGAGAT<br>GACCAAGAACCAGGTGTCCCTGACCTGTCTGGTGAAG<br>GGCTTCTACCCCAGCGATATCGCCGTGGAGTGGGAGA<br>GCAACGGCCAGCCCGAGAACAACTACAAGACCACCCC<br>CCCAGTGCTGGACAGCGACGGCAGCTTCTTCCTGTACA<br>GCAAGCTGACCGTGGACAAGTCCAGGTGGCAGCAGG<br>GCAACGTGTTCAGCTGCAGCGTGATGCACGAGGCCCT<br>GCACAACCACTACACCCAGAAGTCCCTGAGCCTGAGCC<br>CCGGCAAG |
| SEQ ID NO: 196 | LCDR1 (Combined) | RASQDIGSSLN |
| SEQ ID NO: 197 | LCDR2 (Combined) | ATSSLDS |
| SEQ ID NO: 198 | LCDR3 (Combined) | LQYASSPPT |
| SEQ ID NO: 199 | LCDR1 (Kabat) | RASQDIGSSLN |
| SEQ ID NO: 200 | LCDR2 (Kabat) | ATSSLDS |
| SEQ ID NO: 201 | LCDR3 (Kabat) | LQYASSPPT |
| SEQ ID NO: 202 | LCDR1 (Chothia) | SQDIGSS |

TABLE 4-continued

Amino Acid and Nucleotide Sequence Information for Hybridomas and Humanized Anti-CCR7 Antibodies

| | | |
|---|---|---|
| SEQ ID NO: 203 | LCDR2 (Chothia) | ATS |
| SEQ ID NO: 204 | LCDR3 (Chothia) | YASSPP |
| SEQ ID NO: 205 | LCDR1 (IMGT) | QDIGSS |
| SEQ ID NO: 206 | LCDR2 (IMGT) | ATS |
| SEQ ID NO: 207 | LCDR3 (IMGT) | LQYASSPPT |
| SEQ ID NO: 208 | VL | DIQMTQSPSSLSASLGERVSLTCRASQDIGSSLNWLQQEP<br>DGTIKRLIYATSSLDSGVPKRFSGSRSGSDYSLTISSLESEDF<br>VVYYCLQYASSPPTFGGGTKLEIK |
| SEQ ID NO: 209 | DNA VL | GACATCCAGATGACCCAGTCTCCATCCTCCTTATCTGCC<br>TCTCTGGGAGAAAGAGTCAGTCTCACTTGTCGGGCAA<br>GTCAGGACATTGGTAGTAGCTTAAACTGGCTTCAGCAG<br>GAACCAGATGGAACTATTAAACGCCTGATCTATGCCAC<br>ATCCAGTTTAGATTCTGGTGTCCCCAAAAGGTTCAGTG<br>GCAGTAGGTCTGGGTCAGATTATTCTCTCACCATCAGC<br>AGCCTTGAGTCTGAAGATTTTGTAGTCTATTACTGTCTA<br>CAATATGCTAGTTCGCCTCCGACGTTCGGTGGAGGCAC<br>CAAGCTGGAAATCAAA |
| SEQ ID NO: 210 | Light Chain | DIQMTQSPSSLSASLGERVSLTCRASQDIGSSLNWLQQEP<br>DGTIKRLIYATSSLDSGVPKRFSGSRSGSDYSLTISSLESEDF<br>VVYYCLQYASSPPTFGGGTKLEIKRTVAAPSVFIFPPSDEQ<br>LKSGTASVVCLLNNFYPREAKVQWKVDNALQSGNSQES<br>VTEQDSKDSTYSLSSTLTLSKADYEKHKVYACEVTHQGLSS<br>PVTKSFNRGEC |
| SEQ ID NO: 211 | DNA Light Chain | GACATCCAGATGACCCAGTCTCCATCCTCCTTATCTGCC<br>TCTCTGGGAGAAAGAGTCAGTCTCACTTGTCGGGCAA<br>GTCAGGACATTGGTAGTAGCTTAAACTGGCTTCAGCAG<br>GAACCAGATGGAACTATTAAACGCCTGATCTATGCCAC<br>ATCCAGTTTAGATTCTGGTGTCCCCAAAAGGTTCAGTG<br>GCAGTAGGTCTGGGTCAGATTATTCTCTCACCATCAGC<br>AGCCTTGAGTCTGAAGATTTTGTAGTCTATTACTGTCTA<br>CAATATGCTAGTTCGCCTCCGACGTTCGGTGGAGGCAC<br>CAAGCTGGAAATCAAACGTACGGTGGCCGCTCCCAGC<br>GTGTTCATCTTCCCCCCCAGCGACGAGCAGCTGAAGAG<br>TGGCACCGCCAGCGTGGTGTGCCTGCTGAACAACTTCT<br>ACCCCCGGGAGGCCAAGGTGCAGTGGAAGGTGGACA<br>ACGCCCTGCAGAGCGGCAACAGCCAGGAGAGCGTCAC<br>CGAGCAGGACAGCAAGGACTCCACCTACAGCCTGAGC<br>AGCACCCTGACCCTGAGCAAGGCCGACTACGAGAAGC<br>ATAAGGTGTACGCCTGCGAGGTGACCCACCAGGGCCT<br>GTCCAGCCCCGTGACCAAGAGCTTCAACAGGGGCGAG<br>TGC |
| Parental 684E12 hIgG1 | | |
| SEQ ID NO: 212 | HCDR1 (Combined) | GFTFSNFAMS |
| SEQ ID NO: 213 | HCDR2 (Combined) | TISTGGTYTYYPDSVKG |
| SEQ ID NO: 214 | HCDR3 (Combined) | RGYDGVDK |
| SEQ ID NO: 215 | HCDR1 (Kabat) | SNFAMS |
| SEQ ID NO: 216 | HCDR2 (Kabat) | TISTGGTYTYYPDSVKG |
| SEQ ID NO: 217 | HCDR3 (Kabat) | RGYDGVDK |
| SEQ ID NO: 218 | HCDR1 (Chothia) | GFTFSNF |

TABLE 4-continued

Amino Acid and Nucleotide Sequence Information for Hybridomas and Humanized Anti-CCR7 Antibodies

| | | |
|---|---|---|
| SEQ ID NO: 219 | HCDR2 (Chothia) | STGGTY |
| SEQ ID NO: 220 | HCDR3 (Chothia) | RGYDGVDK |
| SEQ ID NO: 221 | HCDR1 (IMGT) | GFTFSNFA |
| SEQ ID NO: 222 | HCDR2 (IMGT) | ISTGGTYT |
| SEQ ID NO: 223 | HCDR3 (IMGT) | TRRGYDGVDK |
| SEQ ID NO: 224 | VH | EVHLVESGGGLVKPGGSLKLSCAASGFTFSNFAMSWVRQTPE KRLEWVATISTGGTYTYYPDSVKGRFTISRDNAKKTLYLQMSSL RSEDTAMYYCTRRGYDGVDKWGQGTTLTVSS |
| SEQ ID NO: 225 | DNA VH | gaagtgcatctggtggagtctgggggaggcttagtgaagcctggagggtccct gaaa ctctcctgtgcagcctctggattcactttcagtaactttgccatgtcttggg ttcgccagactccggagaagagactggagtgggtcgcaaccattagtactggt ggtacttacacctactatccagacagtgtgaagggtcgattcaccatctccaga gacaatgccaagaaaaccctgtacctgcaaatgagcagtctgaggtctgagg acacggccatgtattactgtacaagacgggggtacgacggcgtggacaaatg gggccaaggcaccactctcacagtctcctca |
| SEQ ID NO: 226 | Heavy Chain (WT Fc) | EVHLVESGGGLVKPGGSLKLSCAASGFTFSNFAMSWVRQTPE KRLEWVATISTGGTYTYYPDSVKGRFTISRDNAKKTLYLQMSSL RSEDTAMYYCTRRGYDGVDKWGQGTTLTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKRV EPKSCDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSREEMTKNQVSLTCLVKGFYPSDIAVEWESNGQP ENNYKTTPPVLDSDGSFFLYSKLTVDKSRWQQGNVFSCSVMH EALHNHYTQKSLSLSPGK |
| SEQ ID NO: 227 | DNA Heavy Chain | GAAGTGCATCTGGTGGAGTCTGGGGGAGGCTTAGTGAAGC CTGGAGGGTCCCTGAAACTCTCCTGTGCAGCCTCTGGATTCA CTTTCAGTAACTTTGCCATGTCTTGGGTTCGCCAGACTCCGG AGAAGAGACTGGAGTGGGTCGCAACCATTAGTACTGGTGG TACTTACACCTACTATCCAGACAGTGTGAAGGGTCGATTCAC CATCTCCAGAGACAATGCCAAGAAAACCCTGTACCTGCAAA TGAGCAGTCTGAGGTCTGAGGACACGGCCATGTATTACTGT ACAAGACGGGGGTACGACGGCGTGGACAAATGGGGCCAA GGCACCACTCTCACAGICTCCTCAgctagcaccaagggcccaagtgt gtttcccctggcccccagcagcaagtctacttccggcggaactgctgccctggg ttgcctggtgaaggactacttccccgagcccgtgacagtgtcctggaactctgg ggctctgacttccggcgtgcacaccttccccgccgtgctgcagagcagcggcct gtacagcctgagcagcgtggtgacagtgccctccagctctctgggaacccaga cctatatctgcaacgtgaaccacaagcccagcaacaccaaggtggacaagag agtggagcccaagagctgcgacaagacccacacctgccccccctgcccagctc cagaactgctgggagggccttccgtgttcctgttccccccaagcccaaggaca ccctgatgatcagcaggacccccgaggtgacctgcgtggtggtggacgtgtcc cacgaggacccagaggtgaagttcaactggtacgtggacggcgtggaggtgc acaacgccaagaccaagcccagagaggagcagtacaacagcacctacaggg tggtgtccgtgctgaccgtgctgcaccaggactggctgaacggcaaagaatac aagtgcaaagtctccaacaaggccctgccagccccaatcgaaaagacaatca gcaaggccaagggccagccacgggagccccaggtgtacaccctgccccccag ccgggaggagatgaccaagaaccaggtgtccctgacctgtctggtgaagggct tctaccccagcgatatcgccgtggagtgggagagcaacggccagcccgagaa caactacaagaccacccccccagtgctggacagcgacggcagcttcttcctgta cagcaagctgaccgtggacaagtccaggtggcagcagggcaacgtgttcagct gcagcgtgatgcacgaggccctgcacaaccactacacccagaagtccctgagc ctgagccccggcaag |
| SEQ ID NO: 228 | LCDR1 (Combined) | KSGQSLLDSDGKTYLN |
| SEQ ID NO: 229 | LCDR2 (Combined) | LVSKLDS |
| SEQ ID NO: 230 | LCDR3 (Combined) | WQGTHFPQT |

TABLE 4-continued

Amino Acid and Nucleotide Sequence Information for Hybridomas and Humanized Anti-CCR7 Antibodies

| | | |
|---|---|---|
| SEQ ID NO: 231 | LCDR1 (Kabat) | KSGQSLLDSDGKTYLN |
| SEQ ID NO: 232 | LCDR2 (Kabat) | LVSKLDS |
| SEQ ID NO: 233 | LCDR3 (Kabat) | WQGTHFPQT |
| SEQ ID NO: 234 | LCDR1 (Chothia) | GQSLLDSDGKTY |
| SEQ ID NO: 235 | LCDR2 (Chothia) | LVS |
| SEQ ID NO: 236 | LCDR3 (Chothia) | GTHFPQ |
| SEQ ID NO: 237 | LCDR1 (IMGT) | QSLLDSDGKTY |
| SEQ ID NO: 238 | LCDR2 (IMGT) | LVS |
| SEQ ID NO: 239 | LCDR3 (IMGT) | WQGTHFPQT |
| SEQ ID NO: 240 | VL | DVVMTQTPLTLSVTIGQPASISCKSGQSLLDSDGKTYLNWFLQ<br>RPGQSPKRLIYLVSKLDSGVPDRFTGSGSGTDFTLKISRVEAEDL<br>GVYYCWQGTHFPQTFGGGTKLEIK |
| SEQ ID NO: 241 | DNA VL | gatgttgtgatgacccagactccactcactttgtcggttaccattggacaaccag<br>cctccatctcttgcaagtcaggtcagagcctcttagatagtgatggaaagacat<br>atttgaattggtttttacagaggccaggccagtctccaaagcgcctaatctatct<br>ggtgtctaaactggactctggagtccctgacaggttcactggcagtggatcagg<br>gacagatttcacactgaaaatcagcagagtggaggctgaggatttgggagttt<br>attattgctggcaaggtacacattttcctcagacgttcggtggaggcaccaagc<br>tggaaatcaaa |
| SEQ ID NO: 242 | Light Chain | DVVMTQTPLTLSVTIGQPASISCKSGQSLLDSDGKTYLNWFLQ<br>RPGQSPKRLIYLVSKLDSGVPDRFTGSGSGTDFTLKISRVEAEDL<br>GVYYCWQGTHFPQTFGGGTKLEIKRTVAAPSVFIFPPSDEQLK<br>SGTASVVCLLNNFYPREAKVQWKVDNALQSGNSQESVTEQDS<br>KDSTYSLSSTLTLSKADYEKHKVYACEVTHQGLSSPVTKSFNRGE<br>C |
| SEQ ID NO: 243 | DNA Light Chain | GATGTTGTGATGACCCAGACTCCACTCACTTTGTCGGTTACC<br>ATTGGACAACCAGCCTCCATCTCTTGCAAGTCAGGTCAGAG<br>CCTCTTAGATAGTGATGGAAAGACATATTTGAATTGGTTTTT<br>ACAGAGGCCAGGCCAGTCTCCAAAGCGCCTAATCTATCTGG<br>TGTCTAAACTGGACTCTGGAGTCCCTGACAGGTTCACTGGC<br>AGTGGATCAGGGACAGATTTCACACTGAAAATCAGCAGAGT<br>GGAGGCTGAGGATTTGGGAGTTTATTATTGCTGGCAAGGTA<br>CACATTTTCCTCAGACGTTCGGTGGAGGCACCAAGCTGGAA<br>ATCAAAcgtacggtggccgctcccagcgtgttcatcttccccccagcgacg<br>agcagctgaagagtggcaccgccagcgtggtgtgcctgctgaacaacttctac<br>ccccgggaggccaaggtgcagtggaaggtggacaacgccctgcagagcggc<br>aacagccaggagagcgtcaccgagcaggacagcaaggactccacctacagc<br>ctgagcagcaccctgaccctgagcaaggccgactacgagaagcataaggtgt<br>acgcctgcgaggtgacccaccagggcctgtccagccccgtgaccaagagcttc<br>aacaggggcgagtgc |
| | | Parental 674J13 hIgG1 CysMab |
| SEQ ID NO: 244 | HCDR1 (Combined) | GYSITSGYSWH |
| SEQ ID NO: 245 | HCDR2 (Combined) | HIHSSGSTNYNPSLKS |
| SEQ ID NO: 246 | HCDR3 (Combined) | GGVQAFAY |
| SEQ ID NO: 247 | HCDR1 (Kabat) | SGYSWH |

TABLE 4-continued

| Amino Acid and Nucleotide Sequence Information for Hybridomas and Humanized Anti-CCR7 Antibodies | | |
|---|---|---|
| SEQ ID NO: 248 | HCDR2 (Kabat) | HIHSSGSTNYNPSLKS |
| SEQ ID NO: 249 | HCDR3 (Kabat) | GGVQAFAY |
| SEQ ID NO: 250 | HCDR1 (Chothia) | GYSITSGY |
| SEQ ID NO: 251 | HCDR2 (Chothia) | HSSGS |
| SEQ ID NO: 252 | HCDR3 (Chothia) | GGVQAFAY |
| SEQ ID NO: 253 | HCDR1 (IMGT) | GYSITSGYS |
| SEQ ID NO: 254 | HCDR2 (IMGT) | IHSSGST |
| SEQ ID NO: 255 | HCDR3 (IMGT) | ARGGVQAFAY |
| SEQ ID NO: 256 | VH | DVQLQESGPDLVKPSQSLSLTCTVTGYSITSGYSWHWIR<br>QFPGNKLEWMAHIHSSGSTNYNPSLKSRISIIRDTSKNLFF<br>LQLNSVTTEDTATYYCARGGVQAFAYWGQGTLVTVSA |
| SEQ ID NO: 257 | DNA VH | GATGTGCAGCTTCAGGAGTCAGGACCTGACCTGGTGA<br>AACCTTCTCAGTCACTTTCACTCACCTGCACTGTCACTG<br>GCTACTCCATCACCAGTGGTTATAGCTGGCACTGGATC<br>CGGCAGTTTCCAGGAAACAAACTGGAGTGGATGGCCC<br>ACATCCACTCCAGTGGTAGCACTAACTACAACCCATCT<br>CTCAAAAGTCGCATCTCTATCATTCGAGACACATCCAA<br>GAACCTGTTCTTCCTGCAGTTGAATTCTGTGACTACTGA<br>GGACACAGCCACATATTACTGTGCAAGAGGGGGGGTA<br>CAGGCCTTTGCTTACTGGGGCCAAGGGACTCTGGTCAC<br>TGTCTCTGCA |
| SEQ ID NO: 258 | Heavy Chain (Cys Mab mutations underlined) | DVQLQESGPDLVKPSQSLSLTCTVTGYSITSGYSWHWIR<br>QFPGNKLEWMAHIHSSGSTNYNPSLKSRISIIRDTSKNLFF<br>LQLNSVTTEDTATYYCARGGVQAFAYWGQGTLVTVSAA<br>STKGPSVFPLAPSSKSTSGGTAALGCLVKDYFP**C**PVTVSW<br>NSGALTSGVHTFPAVLQSSGLYSLSSVVTVPSS**S**LGTQTYI<br>CNVNHKPSNTKVDKRVEPKSCDKTHTCPPCPAPELLGGP<br>SVFLFPPKPKDTLMISRTPEVTCVVVDVSHEDPEVKFNWY<br>VDGVEVHNAKTKPREEQYNSTYRVVSVLTVLHQDWLNG<br>KEYKCKVSNKALPAPIEKTISKAKGQPREPQVYTLPPSREE<br>MTKNQVSLTCLVKGFYP**C**DIAVEWESNGQPENNYKTTP<br>PVLDSDGSFFLYSKLTV**D**KSRWQQGNVFSCSVMHEALH<br>NHYTQKSLSLSPGK |
| SEQ ID NO: 259 | DNA Heavy Chain | GATGTGCAGCTTCAGGAGTCAGGACCTGACCTGGTGA<br>AACCTTCTCAGTCACTTTCACTCACCTGCACTGTCACTG<br>GCTACTCCATCACCAGTGGTTATAGCTGGCACTGGATC<br>CGGCAGTTTCCAGGAAACAAACTGGAGTGGATGGCCC<br>ACATCCACTCCAGTGGTAGCACTAACTACAACCCATCT<br>CTCAAAAGTCGCATCTCTATCATTCGAGACACATCCAA<br>GAACCTGTTCTTCCTGCAGTTGAATTCTGTGACTACTGA<br>GGACACAGCCACATATTACTGTGCAAGAGGGGGGGTA<br>CAGGCCTTTGCTTACTGGGGCCAAGGGACTCTGGTCAC<br>TGTCTCTGCAgctagcaccaagggcccaagtgtgtttcccctggccc<br>ccagcagcaagtctacttccggcggaactgctgccctgggttgcctggtg<br>aaggactacttcccctgtcccgtgacagtgtcctggaactctggggctct<br>gacttccggcgtgcacaccttccccgccgtgctgcagagcagcggcctg<br>tacagcctgagcagcgtggtgacagtgccctccagctctctgggaaccc<br>agacctatatctgcaacgtgaaccacaagcccagcaacaccaaggtgg<br>acaagagagtggagcccaagagctgcgacaagacccacacctgcccc<br>ccctgcccagctccagaactgctgggagggccttccgtgttcctgttccc<br>ccccaagcccaaggacaccctgatgatcagcaggacccccgaggtgac<br>ctgcgtggtggtggacgtgtcccacgaggacccagaggtgaagttcaac<br>tggtacgtggacggcgtggaggtgcacaacgccaagaccaagcccag<br>agaggagcagtacaacagcacctacagggtggtgtccgtgctgaccgt<br>gctgcaccaggactggctgaacggcaaagaatacaagtgcaaagtctc<br>caacaaggccctgccagccccaatcgaaaagacaatcagcaaggcca<br>agggccagccacgggagccccaggtgtacaccctgcccccagccggg<br>aggagatgaccaagaaccaggtgtccctgacctgtctggtgaagggctt |

TABLE 4-continued

| Amino Acid and Nucleotide Sequence Information for Hybridomas and Humanized Anti-CCR7 Antibodies | |
|---|---|
| | ctacccctgtgatatcgccgtggagtgggagagcaacggccagcccga gaacaactacaagaccaccccccccagtgctggacagcgacggcagctt cttcctgtacagcaagctgaccgtggacaagtccaggtggcagcaggg caacgtgttcagctgcagcgtgatgcacgaggccctgcacaaccactac acccagaagtccctgagcctgagccccggcaag |
| SEQ ID NO: 260 LCDR1 (Combined) | SASSSVIYMH |
| SEQ ID NO: 261 LCDR2 (Combined) | DTSKLAS |
| SEQ ID NO: 262 LCDR3 (Combined) | QQWSSNPLT |
| SEQ ID NO: 263 LCDR1 (Kabat) | SASSSVIYMH |
| SEQ ID NO: 264 LCDR2 (Kabat) | DTSKLAS |
| SEQ ID NO: 265 LCDR3 (Kabat) | QQWSSNPLT |
| SEQ ID NO: 266 LCDR1 (Chothia) | SSSVIY |
| SEQ ID NO: 267 LCDR2 (Chothia) | DTS |
| SEQ ID NO: 268 LCDR3 (Chothia) | WSSNPL |
| SEQ ID NO: 269 LCDR1 (IMGT) | SSVIY |
| SEQ ID NO: 270 LCDR2 (IMGT) | DTS |
| SEQ ID NO: 271 LCDR3 (IMGT) | QQWSSNPLT |
| SEQ ID NO: 272 VL | QIVLTQSPAIMSASPGEKVTMTCSASSSVIYMHWYQQKS GTSPKRWIYDTSKLASGVPARFSGSGSGTSYSLTISSMEAE DAATYYCQQWSSNPLTFGAGTTLELK |
| SEQ ID NO: 273 DNA VL | CAAATTGTCCTCACCCAGTCTCCAGCAATCATGTCTGCA TCTCCAGGGGAGAAGGTCACCATGACCTGCAGTGCCA GTTCAAGTGTAATTTACATGCACTGGTACCAGCAGAAG TCAGGCACCTCCCCCAAAAGATGGATTTATGACACATC CAAACTGGCTTCTGGAGTCCCTGCTCGCTTCAGTG GTA GTGGGTCTGGGACCTCTTACTCTCTCACAATCAGCAGC ATGGAGGCTGAAGATGCTGCCACTTATTACTGCCAGCA GTGGAGTAGTAACCCGCTCACGTTCGGTGCTGGGACC ACGTTGGAGCTGAAA |
| SEQ ID NO: 274 Light Chain | QIVLTQSPAIMSASPGEKVTMTCSASSSVIYMHWYQQKS GTSPKRWIYDTSKLASGVPARFSGSGSGTSYSLTISSMEAE DAATYYCQQWSSNPLTFGAGTTLELKRTVAAPSVFIFPPS DEQLKSGTASVVCLLNNFYPREAKVQWKVDNALQSGNS QESVTEQDSKDSTYSLSSTLTLSKADYEKHKVYACEVTHQ GLSSPVTKSFNRGEC |
| SEQ ID NO: 275 DNA Light Chain | CAAATTGTCCTCACCCAGTCTCCAGCAATCATGTCTGCA TCTCCAGGGGAGAAGGTCACCATGACCTGCAGTGCCA GTTCAAGTGTAATTTACATGCACTGGTACCAGCAGAAG TCAGGCACCTCCCCCAAAAGATGGATTTATGACACATC CAAACTGGCTTCTGGAGTCCCTGCTCGCTTCAGTGGTA GTGGGTCTGGGACCTCTTACTCTCTCACAATCAGCAGC ATGGAGGCTGAAGATGCTGCCACTTATTACTGCCAGCA GTGGAGTAGTAACCCGCTCACGTTCGGTGCTGGGACC ACGTTGGAGCTGAAACGTACGGTGGCCGCTCCCAGCG TGTTCATCTTCCCCCCCAGCGACGAGCAGCTGAAGAGT GGCACCGCCAGCGTGGTGTGCCTGCTGAACAACTTCTA CCCCCGGGAGGCCAAGGTGCAGTGGAAGGTGGACAA CGCCCTGCAGAGCGGCAACAGCCAGGAGAGCGTCACC GAGCAGGACAGCAAGGACTCCACCTACAGCCTGAGCA |

TABLE 4-continued

| Amino Acid and Nucleotide Sequence Information for Hybridomas and Humanized Anti-CCR7 Antibodies | | |
|---|---|---|
| | | GCACCCTGACCCTGAGCAAGGCCGACTACGAGAAGCA<br>TAAGGTGTACGCCTGCGAGGTGACCCACCAGGGCCTG<br>TCCAGCCCCGTGACCAAGAGCTTCAACAGGGGCGAGT<br>GC |
| Parental 674J13 hIgG1 DAPA CysMab | | |
| SEQ ID NO: 276 | HCDR1 (Combined) | GYSITSGYSWH |
| SEQ ID NO: 277 | HCDR2 (Combined) | HIHSSGSTNYNPSLKS |
| SEQ ID NO: 278 | HCDR3 (Combined) | GGVQAFAY |
| SEQ ID NO: 279 | HCDR1 (Kabat) | SGYSWH |
| SEQ ID NO: 280 | HCDR2 (Kabat) | HIHSSGSTNYNPSLKS |
| SEQ ID NO: 281 | HCDR3 (Kabat) | GGVQAFAY |
| SEQ ID NO: 282 | HCDR1 (Chothia) | GYSITSGY |
| SEQ ID NO: 283 | HCDR2 (Chothia) | HSSGS |
| SEQ ID NO: 284 | HCDR3 (Chothia) | GGVQAFAY |
| SEQ ID NO: 285 | HCDR1 (IMGT) | GYSITSGYS |
| SEQ ID NO: 286 | HCDR2 (IMGT) | IHSSGST |
| SEQ ID NO: 287 | HCDR3 (IMGT) | ARGGVQAFAY |
| SEQ ID NO: 288 | VH | DVQLQESGPGLVKPSQTLSLTCTVSGYSITSGYSWHWIR<br>QHPGKGLEWMAHIHSSGSTNYNPSLKSRITISRDTSKNQ<br>FSLKLSSVTAADTAVYYCARGGVQAFAYWGQGTLVTVSS |
| SEQ ID NO: 289 | DNA VH | GACGTGCAGCTGCAGGAATCTGGCCCTGGCCTGGTGA<br>AACCCTCCCAGACCCTGTCCCTGACCTGCACCGTGTCC<br>GGCTACTCCATCACCTCCGGCTACAGCTGGCACTGGAT<br>CCGGCAGCACCCCGGCAAGGGCCTGGAATGGATGGCC<br>CACATCCACTCCTCCGGCTCCACCAACTACAACCCCAGC<br>CTGAAGTCCAGAATCACCATCAGCCGGGACACCTCCAA<br>GAACCAGTTCTCCCTGAAGCTGTCCTCCGTGACCGCCG<br>CTGACACCGCCGTGTACTACTGTGCCAGAGGCGGCGT<br>GCAGGCCTTCGCTTATTGGGGCCAGGGCACCCTGGTG<br>ACAGTGTCCTCC |
| SEQ ID NO: 290 | Heavy Chain (DAPA, CysMab mutations underlined) | DVQLQESGPGLVKPSQTLSLTCTVSGYSITSGYSWHWIR<br>QHPGKGLEWMAHIHSSGSTNYNPSLKSRITISRDTSKNQ<br>FSLKLSSVTAADTAVYYCARGGVQAFAYWGQGTLVTVSS<br>ASTKGPSVFPLAPSSKSTSGGTAALGCLVKDYFP**C**PVTVS<br>WNSGALTSGVHTFPAVLQSSGLYSLSSVVTVPSSSLGTQT<br>YICNVNHKPSNTKVDKRVEPKSCDKTHTCPPCPAPELLGG<br>PSVFLFPPKPKDTLMISRTPEVTCVVV**A**VSHEDPEVKFNW<br>YVDGVEVHNAKTKPREEQYNSTYRVVSVLTVLHQDWLN<br>GKEYKCKVSNKAL**A**APIEKTISKAKGQPREPQVYTLPPSRE<br>EMTKNQVSLTCLVKGFYP**C**DIAVEWESNGQPENNYKTTP<br>PVLDSDGSFFLYSKLTVDKSRWQQGNVFSCSVMHEALH<br>NHYTQKSLSLSPGK |
| SEQ ID NO: 291 | DNA Heavy Chain | GACGTGCAGCTGCAGGAATCTGGCCCTGGCCTGGTGA<br>AACCCTCCCAGACCCTGTCCCTGACCTGCACCGTGTCC<br>GGCTACTCCATCACCTCCGGCTACAGCTGGCACTGGAT<br>CCGGCAGCACCCCGGCAAGGGCCTGGAATGGATGGCC<br>CACATCCACTCCTCCGGCTCCACCAACTACAACCCCAGC<br>CTGAAGTCCAGAATCACCATCAGCCGGGACACCTCCAA |

TABLE 4-continued

Amino Acid and Nucleotide Sequence Information for Hybridomas and Humanized Anti-CCR7 Antibodies

| | | |
|---|---|---|
| | | GAACCAGTTCTCCCTGAAGCTGTCCTCCGTGACCGCCG<br>CTGACACCGCCGTGTACTACTGTGCCAGAGGCGGCGT<br>GCAGGCCTTCGCTTATTGGGGCCAGGGCACCCTGGTG<br>ACAGTGTCCTCCGCTAGCACCAAGGGCCCAAGTGTGTT<br>TCCCCTGGCCCCCAGCAGCAAGTCTACTTCCGGCGGAA<br>CTGCTGCCCTGGGTTGCCTGGTGAAGGACTACTTCCCC<br>TGTCCCGTGACAGTGTCCTGGAACTCTGGGGCTCTGAC<br>TTCCGGCGTGCACACCTTCCCCGCCGTGCTGCAGAGCA<br>GCGGCCTGTACAGCCTGAGCAGCGTGGTGACAGTGCC<br>CTCCAGCTCTCTGGGAACCCAGACCTATATCTGCAACG<br>TGAACCACAAGCCCAGCAACACCAAGGTGGACAAGAG<br>AGTGGAGCCCAAGAGCTGCGACAAGACCCACACCTGC<br>CCCCCCTGCCCAGCTCCAGAACTGCTGGGAGGGCCTTC<br>CGTGTTCCTGTTCCCCCCCAAGCCCAAGGACACCCTGA<br>TGATCAGCAGGACCCCCGAGGTGACCTGCGTGGTGGT<br>GGCCGTGTCCCACGAGGACCCAGAGGTGAAGTTCAAC<br>TGGTACGTGGACGGCGTGGAGGTGCACAACGCCAAG<br>ACCAAGCCCAGAGAGGAGCAGTACAACAGCACCTACA<br>GGGTGGTGTCCGTGCTGACCGTGCTGCACCAGGACTG<br>GCTGAACGGCAAAGAATACAAGTGCAAAGTCTCCAAC<br>AAGGCCCTGGCTGCCCCAATCGAAAAGACAATCAGCA<br>AGGCCAAGGGCCAGCCACGGGAGCCCCAGGTGTACAC<br>CCTGCCCCCCAGCCGGGAGGAGATGACCAAGAACCAG<br>GTGTCCCTGACCTGTCTGGTGAAGGGCTTCTACCCCTG<br>TGATATCGCCGTGGAGTGGGAGAGCAACGGCCAGCCC<br>GAGAACAACTACAAGACCACCCCCCCAGTGCTGGACA<br>GCGACGGCAGCTTCTTCCTGTACAGCAAGCTGACCGTG<br>GACAAGTCCAGGTGGCAGCAGGGCAACGTGTTCAGCT<br>GCAGCGTGATGCACGAGGCCCTGCACAACCACTACAC<br>CCAGAAGTCCCTGAGCCTGAGCCCCGGCAAG |
| SEQ ID NO: 292 | LCDR1 (Combined) | SASSSVIYMH |
| SEQ ID NO: 293 | LCDR2 (Combined) | DTSKLAS |
| SEQ ID NO: 294 | LCDR3 (Combined) | QQWSSNPLT |
| SEQ ID NO: 295 | LCDR1 (Kabat) | SASSSVIYMH |
| SEQ ID NO: 296 | LCDR2 (Kabat) | DTSKLAS |
| SEQ ID NO: 297 | LCDR3 (Kabat) | QQWSSNPLT |
| SEQ ID NO: 298 | LCDR1 (Chothia) | SSSVIY |
| SEQ ID NO: 299 | LCDR2 (Chothia) | DTS |
| SEQ ID NO: 300 | LCDR3 (Chothia) | WSSNPL |
| SEQ ID NO: 301 | LCDR1 (IMGT) | SSVIY |
| SEQ ID NO: 302 | LCDR2 (IMGT) | DTS |
| SEQ ID NO: 303 | LCDR3 (IMGT) | QQWSSNPLT |
| SEQ ID NO: 304 | VL | EIVLTQSPATLSASPGERVTMSCSASSSVIYMHWYQQKP<br>GQAPRRWIYDTSKLASGVPARFSGSGSGTDYTLTISSMEP<br>EDAAVYYCQQWSSNPLTFGQGTKLEIK |
| SEQ ID NO: 305 | DNA VL | GAGATCGTGCTGACCCAGTCCCCTGCCACCCTGTCTGC<br>TAGCCCTGGCGAGCGCGTGACAATGTCCTGCTCCGCCT<br>CCTCCTCCGTGATCTACATGCACTGGTATCAGCAGAAG<br>CCCGGCCAGGCCCCTCGGCGGTGGATCTACGATACCTC<br>CAAGCTGGCCTCCGGCGTGCCCGCCAGATTCTCCGGCT<br>CTGGCTCTGGCACCGACTACACCCTGACCATCTCCAGC |

TABLE 4-continued

| Amino Acid and Nucleotide Sequence Information for Hybridomas and Humanized Anti-CCR7 Antibodies | |
|---|---|
| | ATGGAACCCGAGGACGCCGCCGTGTACTACTGCCAGC<br>AGTGGTCCTCCAACCCCCTGACCTTCGGCCAGGGCACC<br>AAGCTGGAAATCAAG |
| SEQ ID NO: 306 Light Chain | EIVLTQSPATLSASPGERVTMSCSASSSVIYMHWYQQKP<br>GQAPRRWIYDTSKLASGVPARFSGSGSGTDYTLTISSMEP<br>EDAAVYYCQQWSSNPLTFGQGTKLEIKRTVAAPSVFIFPP<br>SDEQLKSGTASVVCLLNNFYPREAKVQWKVDNALQSGN<br>SQESVTEQDSKDSTYSLSSTLTLSKADYEKHKVYACEVTH<br>QGLSSPVTKSFNRGEC |
| SEQ ID NO: 307 DNA Light Chain | GAGATCGTGCTGACCCAGTCCCCTGCCACCCTGTCTGC<br>TAGCCCTGGCGAGCGCGTGACAATGTCCTGCTCCGCCT<br>CCTCCTCCGTGATCTACATGCACTGGTATCAGCAGAAG<br>CCCGGCCAGGCCCCTCGGCGGTGGATCTACGATACCTC<br>CAAGCTGGCCTCCGGCGTGCCCGCCAGATTCTCCGGCT<br>CTGGCTCTGGCACCGACTACACCCTGACCATCTCCAGC<br>ATGGAACCCGAGGACGCCGCCGTGTACTACTGCCAGC<br>AGTGGTCCTCCAACCCCCTGACCTTCGGCCAGGGCACC<br>AAGCTGGAAATCAAGCGTACGGTGGCCGCTCCCAGCG<br>TGTTCATCTTCCCCCCCAGCGACGAGCAGCTGAAGAGT<br>GGCACCGCCAGCGTGGTGTGCCTGCTGAACAACTTCTA<br>CCCCCGGGAGGCCAAGGTGCAGTGGAAGGTGGACAA<br>CGCCCTGCAGAGCGGCAACAGCCAGGAGAGCGTCACC<br>GAGCAGGACAGCAAGGACTCCACCTACAGCCTGAGCA<br>GCACCCTGACCCTGAGCAAGGCCGACTACGAGAAGCA<br>TAAGGTGTACGCCTGCGAGGTGACCCACCAGGGCCTG<br>TCCAGCCCCGTGACCAAGAGCTTCAACAGGGGCGAGT<br>GC |
| Parental 121G12 hIgG1 CysMab | |
| SEQ ID NO: 308 HCDR1 (Combined) | GFTFSTYAMS |
| SEQ ID NO: 309 HCDR2 (Combined) | TISDAGSYSYYPDNVKG |
| SEQ ID NO: 310 HCDR3 (Combined) | RGSRYEEYYVMDY |
| SEQ ID NO: 311 HCDR1 (Kabat) | TYAMS |
| SEQ ID NO: 312 HCDR2 (Kabat) | TISDAGSYSYYPDNVKG |
| SEQ ID NO: 313 HCDR3 (Kabat) | RGSRYEEYYVMDY |
| SEQ ID NO: 314 HCDR1 (Chothia) | GFTFSTY |
| SEQ ID NO: 315 HCDR2 (Chothia) | SDAGSY |
| SEQ ID NO: 316 HCDR3 (Chothia) | RGSRYEEYYVMDY |
| SEQ ID NO: 317 HCDR1 (IMGT) | GFTFSTYA |
| SEQ ID NO: 318 HCDR2 (IMGT) | ISDAGSYS |
| SEQ ID NO: 319 HCDR3 (IMGT) | ARRGSRYEEYYVMDY |
| SEQ ID NO: 320 VH | EVQLVESGGGLVKPGGSLKLSCAASGFTFSTYAMSWVRQ<br>TPEKRLEWVATISDGGSYSYYPDNVKGRFTISRDNAKNNL<br>YLQMSHLKSEDTAMYYCARRGSRYEEYYVMDYWGQGT<br>SVTVSS |
| SEQ ID NO: 321 DNA VH (CysMab mutations underlined) | GAAGTGCAGCTGGTGGAGTCTGGGGGAGGCTTAGTG<br>AAGCCTGGAGGGTCCCTGAAACTCTCCTGTGCAGCCTC<br>TGGATTCACTTTCAGTACCTATGCCATGTCTTGGGTTCG<br>CCAGACTCCGGAAAAGAGGCTGGAGTGGGTCGCAACC |

TABLE 4-continued

| Amino Acid and Nucleotide Sequence Information for Hybridomas and Humanized Anti-CCR7 Antibodies | | |
|---|---|---|
| | | ATTAGTGATGGTGGTAGTTATTCGTACTATCCAGACAA<br>TGTAAAGGGCCGATTCACCATCTCCAGAGACAATGCCA<br>AGAACAACCTATACCTGCAAATGAGCCATCTGAAGTCT<br>GAGGACACAGCCATGTATTACTGTGCAAGACGAGGTA<br>GTAGGTACGAAGAGTACTATGTTATGGACTACTGGGG<br>TCAAGGAACCTCAGTCACCGTCTCCTCA |
| SEQ ID NO: 322 | Heavy Chain (CysMab mutations underlined) | EVQLVESGGGLVKPGGSLKLSCAASGFTFSTYAMSWVRQTPE<br>KRLEWVATISDGGSYSYYPDNVKGRFTISRDNAKNNLYLQMSH<br>LKSEDTAMYYCARRGSRYEEYYVMDYWGQGTSVTVSSastkgp<br>svfplapsskstsggtaalgclykdyfp**C**pvtvswnsgaltsgvhtfpavlqss<br>glyslssvvtvpssslgtqtyicnvnhkpsntkvdkrvepkscdkthtcppcpa<br>pellggpsvflfppkpkdtlmisrtpevtcvvvdvshedpevkfnwyvdgve<br>vhnaktkpreeqynstyryysvltylhqdwlngkeykckvsnkalpapiekti<br>skakgqprepqvytlppsreemtknqvsltclvkgfyp**C**diavewesngqp<br>ennykttppvldsdgsfflyskltvdksrwqqgnvfscsvmhealhnhytqk<br>slslspgk |
| SEQ ID NO: 323 | DNA Heavy Chain | GAAGTGCAGCTGGTGGAGTCTGGGGGAGGCTTAGTG<br>AAGCCTGGAGGGTCCCTGAAACTCTCCTGTGCAGCCTC<br>TGGATTCACTTTCAGTACCTATGCCATGTCTTGGGTTCG<br>CCAGACTCCGGAAAAGAGGCTGGAGTGGGTCGCAACC<br>ATTAGTGATGGTGGTAGTTATTCGTACTATCCAGACAA<br>TGTAAAGGGCCGATTCACCATCTCCAGAGACAATGCCA<br>AGAACAACCTATACCTGCAAATGAGCCATCTGAAGTCT<br>GAGGACACAGCCATGTATTACTGTGCAAGACGAGGTA<br>GTAGGTACGAAGAGTACTATGTTATGGACTACTGGGG<br>TCAAGGAACCTCAGTCACCGTCTCCTCAgctagcaccaagg<br>gcccaagtgtgtttcccctggcccccagcagcaagtctacttccggcgga<br>actgctgccctgggttgcctggtgaaggactacttcccctgtcccgtgac<br>agtgtcctggaactctggggctctgacttccggcgtgcacaccttccccg<br>ccgtgctgcagagcagcggcctgtacagcctgagcagcgtggtgacag<br>tgccctccagctctctgggaacccagacctatatctgcaacgtgaacca<br>caagcccagcaacaccaaggtggacaagagagtggagcccaagagct<br>gcgacaagacccacacctgccccccctgcccagctccagaactgctgg<br>gagggccttccgtgttcctgttccccccaagcccaaggacaccctgatg<br>atcagcaggacccccgaggtgacctgcgtggtggtggacgtgtcccacg<br>aggacccagaggtgaagttcaactggtacgtggacggcgtggaggtgc<br>acaacgccaagaccaagcccagagaggagcagtacaacagcacctac<br>agggtggtgtccgtgctgaccgtgctgcaccaggactggctgaacggca<br>aagaatacaagtgcaaagtctccaacaaggccctgccagcccccaatcg<br>aaaagacaatcagcaaggccaagggccagccacgggagccccaggtg<br>tacaccctgcccccagccgggaggagatgaccaagaaccaggtgtcc<br>ctgacctgtctggtgaagggcttctacccctgtgatatcgccgtggagtg<br>ggagagcaacggccagcccgagaacaactacaagaccacccccccag<br>tgctggacagcgacggcagcttcttcctgtacagcaagctgaccgtgga<br>caagtccaggtggcagcagggcaacgtgttcagctgcagcgtgatgca<br>cgaggccctgcacaaccactacacccagaagtccctgagcctgagccc<br>cggcaag |
| SEQ ID NO: 324 | LCDR1 (Combined) | RASQSISNNLH |
| SEQ ID NO: 325 | LCDR2 (Combined) | YASQSIS |
| SEQ ID NO: 326 | LCDR3 (Combined) | QQSSSWLT |
| SEQ ID NO: 327 | LCDR1 (Kabat) | RASQSISNNLH |
| SEQ ID NO: 328 | LCDR2 (Kabat) | YASQSIS |
| SEQ ID NO: 329 | LCDR3 (Kabat) | QQSSSWLT |
| SEQ ID NO: 330 | LCDR1 (Chothia) | SQSISNN |
| SEQ ID NO: 331 | LCDR2 (Chothia) | YAS |
| SEQ ID NO: 332 | LCDR3 (Chothia) | SSSWL |

TABLE 4-continued

| Amino Acid and Nucleotide Sequence Information for Hybridomas and Humanized Anti-CCR7 Antibodies | | |
|---|---|---|
| SEQ ID NO: 333 | LCDR1 (IMGT) | QSISNN |
| SEQ ID NO: 334 | LCDR2 (IMGT) | YAS |
| SEQ ID NO: 335 | LCDR3 (IMGT) | QQSSSWLT |
| SEQ ID NO: 336 | VL | DIVLTQSPATLSVTPGDSVSLSCRASQSISNNLHWYQQKS HESPKLLIKYASQSISGIPSRFSGSGSGTDFTLSINSVETEDF GMYFCQQSNSWLTFGAGTKLGLK |
| SEQ ID NO: 337 | DNA VL | GATATTGTGCTAACTCAGTCTCCAGCCACCCTGTCTGTG ACTCCAGGAGATAGCGTCAGTCTTTCCTGCAGGGCCAG CCAAAGTATTAGCAACAACCTACACTGGTATCAACAGA AATCACATGAGTCTCCAAAACTTCTCATCAAGTATGCTT CCCAGTCCATCTCTGGGATCCCCTCCAGGTTCAGTGGC AGTGGATCAGGGACAGATTTCACTCTCAGTATCAACAG TGTGGAGACTGAAGATTTTGGAATGTATTTCTGTCAAC AGAGTAACAGCTGGCTCACGTTCGGTGCTGGGACCAA GCTGGGGCTGAAA |
| SEQ ID NO: 338 | Light Chain | DIVLTQSPATLSVTPGDSVSLSCRASQSISNNLHWYQQKS HESPKLLIKYASQSISGIPSRFSGSGSGTDFTLSINSVETEDF GMYFCQQSNSWLTFGAGTKLGLKRTVAAPSVFIFPPSDE QLKSGTASVVCLLNNFYPREAKVQWKVDNALQSGNSQE SVTEQDSKDSTYSLSSTLTLSKADYEKHKVYACEVTHQGLS SPVTKSFNRGEC |
| SEQ ID NO: 339 | DNA Light Chain | GATATTGTGCTAACTCAGTCTCCAGCCACCCTGTCTGTG ACTCCAGGAGATAGCGTCAGTCTTTCCTGCAGGGCCAG CCAAAGTATTAGCAACAACCTACACTGGTATCAACAGA AATCACATGAGTCTCCAAAACTTCTCATCAAGTATGCTT CCCAGTCCATCTCTGGGATCCCCTCCAGGTTCAGTGGC AGTGGATCAGGGACAGATTTCACTCTCAGTATCAACAG TGTGGAGACTGAAGATTTTGGAATGTATTTCTGTCAAC AGAGTAACAGCTGGCTCACGTTCGGTGCTGGGACCAA GCTGGGGCTGAAACGTACGGTGGCCGCTCCCAGCGTG TTCATCTTCCCCCCCAGCGACGAGCAGCTGAAGAGTGG CACCGCCAGCGTGGTGTGCCTGCTGAACAACTTCTACC CCCGGGAGGCCAAGGTGCAGTGGAAGGTGGACAACG CCCTGCAGAGCGGCAACAGCCAGGAGAGCGTCACCGA GCAGGACAGCAAGGACTCCACCTACAGCCTGAGCAGC ACCCTGACCCTGAGCAAGGCCGACTACGAGAAGCATA AGGTGTACGCCTGCGAGGTGACCCACCAGGGCCTGTC CAGCCCCGTGACCAAGAGCTTCAACAGGGGCGAGTGC |
| Parental 121G12 hIgG1 DAPA CysMab | | |
| SEQ ID NO: 340 | HCDR1 (Combined) | GFTFSTYAMS |
| SEQ ID NO: 341 | HCDR2 (Combined) | TISDAGSYSYYPDNVKG |
| SEQ ID NO: 342 | HCDR3 (Combined) | RGSRYEEYYVMDY |
| SEQ ID NO: 343 | HCDR1 (Kabat) | TYAMS |
| SEQ ID NO: 344 | HCDR2 (Kabat) | TISDAGSYSYYPDNVKG |
| SEQ ID NO: 345 | HCDR3 (Kabat) | RGSRYEEYYVMDY |
| SEQ ID NO: 346 | HCDR1 (Chothia) | GFTFSTY |
| SEQ ID NO: 347 | HCDR2 (Chothia) | SDAGSY |
| SEQ ID NO: 348 | HCDR3 (Chothia) | RGSRYEEYYVMDY |

TABLE 4-continued

| Amino Acid and Nucleotide Sequence Information for Hybridomas and Humanized Anti-CCR7 Antibodies | | |
|---|---|---|
| SEQ ID NO: 349 | HCDR1 (IMGT) | GFTFSTYA |
| SEQ ID NO: 350 | HCDR2 (IMGT) | ISDAGSYS |
| SEQ ID NO: 351 | HCDR3 (IMGT) | ARRGSRYEEYYVMDY |
| SEQ ID NO: 352 | VH | EVQLVESGGGLVKPGGSLRLSCAASGFTFSTYAMSWVRQ APGKGLEWVATISDAGSYSYYPDNVKGRFTISRDNAKNSL YLQMNSLRAEDTAVYYCARRGSRYEEYYVMDYWGQGT TVTVSS |
| SEQ ID NO: 353 | DNA VH | GAGGTGCAGCTGGTGGAATCTGGCGGAGGCCTGGTG AAACCCGGCGGATCCCTGAGACTGTCCTGCGCCGCCTC CGGCTTCACCTTCTCCACCTACGCCATGTCCTGGGTGC GGCAGGCTCCCGGCAAGGGCCTGGAATGGGTGGCCA CCATCTCCGACGCCGGCTCCTACTCCTACTACCCCGACA ACGTGAAGGGCAGATTCACCATCAGCCGGGACAACGC CAAGAACTCCCTGTACCTGCAGATGAACTCCCTGCGGG CCGAGGACACCGCCGTGTACTACTGTGCCAGACGGGG CTCCAGATACGAAGAGTACTACGTGATGGACTATTGG GGCCAGGGCACCACCGTGACAGTGTCCTCC |
| SEQ ID NO: 354 | Heavy Chain (DAPA, CysMab mutations underlined) | EVQLVESGGGLVKPGGSLRLSCAASGFTFSTYAMSWVRQ APGKGLEWVATISDAGSYSYYPDNVKGRFTISRDNAKNSL YLQMNSLRAEDTAVYYCARRGSRYEEYYVMDYWGQGT TVTVSSASTKGPSVFPLAPSSKSTSGGTAALGCLVKDYFP**C** PVTVSWNSGALTSGVHTFPAVLQSSGLYSLSSVVTVPSSS LGTQTYICNVNHKPSNTKVDKRVEPKSCDKTHTCPPCPA PELLGGPSVFLFPPKPKDTLMISRTPEVTCVVV**A**VSHEDPE VKFNWYVDGVEVHNAKTKPREEQYNSTYRVVSVLTVLH QDWLNGKEYKCKVSNKAL**A**APIEKTISKAKGQPREPQVY TLPPSREEMTKNQVSLTCLVKGFYP**C**DIAVEWESNGQPE NNYKTTPPVLDSDGSFFLYSKLTVDKSRWQQGNVFSCSV MHEALHNHYTQKSLSLSPGK |
| SEQ ID NO: 355 | DNA Heavy Chain | GAGGTGCAGCTGGTGGAATCTGGCGGAGGCCTGGTG AAACCCGGCGGATCCCTGAGACTGTCCTGCGCCGCCTC CGGCTTCACCTTCTCCACCTACGCCATGTCCTGGGTGC GGCAGGCTCCCGGCAAGGGCCTGGAATGGGTGGCCA CCATCTCCGACGCCGGCTCCTACTCCTACTACCCCGACA ACGTGAAGGGCAGATTCACCATCAGCCGGGACAACGC CAAGAACTCCCTGTACCTGCAGATGAACTCCCTGCGGG CCGAGGACACCGCCGTGTACTACTGTGCCAGACGGGG CTCCAGATACGAAGAGTACTACGTGATGGACTATTGG GGCCAGGGCACCACCGTGACAGTGTCCTCCGCTAGCA CCAAGGGCCCAAGTGTGTTTCCCCTGGCCCCCAGCAGC AAGTCTACTTCCGGCGGAACTGCTGCCCTGGGTTGCCT GGTGAAGGACTACTTCCCCTGTCCCGTGACAGTGTCCT GGAACTCTGGGGCTCTGACTTCCGGCGTGCACACCTTC CCCGCCGTGCTGCAGAGCAGCGGCCTGTACAGCCTGA GCAGCGTGGTGACAGTGCCCTCCAGCTCTCTGGGAAC CCAGACCTATATCTGCAACGTGAACCACAAGCCCAGCA ACACCAAGGTGGACAAGAGAGTGGAGCCCAAGAGCT GCGACAAGACCCACACCTGCCCCCCCTGCCCAGCTCCA GAACTGCTGGGAGGGCCTTCCGTGTTCCTGTTCCCCCC CAAGCCCAAGGACACCCTGATGATCAGCAGGACCCCC GAGGTGACCTGCGTGGTGGTGGCCGTGTCCCACGAGG ACCCAGAGGTGAAGTTCAACTGGTACGTGGACGGCGT GGAGGTGCACAACGCCAAGACCAAGCCCAGAGAGGA GCAGTACAACAGCACCTACAGGGTGGTGTCCGTGCTG ACCGTGCTGCACCAGGACTGGCTGAACGGCAAAGAAT ACAAGTGCAAAGTCTCCAACAAGGCCCTGGCTGCCCCA ATCGAAAAGACAATCAGCAAGGCCAAGGGCCAGCCAC GGGAGCCCCAGGTGTACACCCTGCCCCCCAGCCGGGA GGAGATGACCAAGAACCAGGTGTCCCTGACCTGTCTG GTGAAGGGCTTCTACCCCTGTGATATCGCCGTGGAGTG GGAGAGCAACGGCCAGCCCGAGAACAACTACAAGACC ACCCCCCCAGTGCTGGACAGCGACGGCAGCTTCTTCCT GTACAGCAAGCTGACCGTGGACAAGTCCAGGTGGCAG CAGGGCAACGTGTTCAGCTGCAGCGTGATGCACGAGG CCCTGCACAACCACTACACCCAGAAGTCCCTGAGCCTG AGCCCCGGCAAG |

TABLE 4-continued

| Amino Acid and Nucleotide Sequence Information for Hybridomas and Humanized Anti-CCR7 Antibodies | | |
|---|---|---|
| SEQ ID NO: 356 | LCDR1 (Combined) | RASQSISNNLH |
| SEQ ID NO: 357 | LCDR2 (Combined) | YASQSIS |
| SEQ ID NO: 358 | LCDR3 (Combined) | QQSSSWLT |
| SEQ ID NO: 359 | LCDR1 (Kabat) | RASQSISNNLH |
| SEQ ID NO: 360 | LCDR2 (Kabat) | YASQSIS |
| SEQ ID NO: 361 | LCDR3 (Kabat) | QQSSSWLT |
| SEQ ID NO: 362 | LCDR1 (Chothia) | SQSISNN |
| SEQ ID NO: 363 | LCDR2 (Chothia) | YAS |
| SEQ ID NO: 364 | LCDR3 (Chothia) | SSSWL |
| SEQ ID NO: 365 | LCDR1 (IMGT) | QSISNN |
| SEQ ID NO: 366 | LCDR2 (IMGT) | YAS |
| SEQ ID NO: 367 | LCDR3 (IMGT) | QQSSSWLT |
| SEQ ID NO: 368 | VL | EIVLTQSPATLSVSPGERVTLSCRASQSISNNLHWYQQKP<br>GQAPRLLIKYASQSISGIPARFSGSGSGTDFTLTISSVEPED<br>FGVYFCQQSSSWLTFGQGTKLEIK |
| SEQ ID NO: 369 | DNA VL | GAGATCGTGCTGACCCAGTCCCCTGCCACCCTGTCCGT<br>GTCTCCCGGCGAGAGAGTGACCCTGTCCTGCCGGGCC<br>TCCCAGTCCATCTCCAACAACCTGCACTGGTATCAGCA<br>GAAGCCCGGCCAGGCCCCTCGGCTGCTGATTAAGTAC<br>GCCTCCCAGAGCATCTCCGGCATCCCTGCCAGATTCTC<br>CGGCTCCGGCAGCGGCACCGACTTCACCCTGACCATCT<br>CCAGCGTGGAACCCGAGGACTTCGGCGTGTACTTCTGC<br>CAGCAGTCCTCATCCTGGCTGACCTTCGGCCAGGGCAC<br>CAAGCTGGAAATCAAG |
| SEQ ID NO: 370 | Light Chain | EIVLTQSPATLSVSPGERVTLSCRASQSISNNLHWYQQKP<br>GQAPRLLIKYASQSISGIPARFSGSGSGTDFTLTISSVEPED<br>FGVYFCQQSSSWLTFGQGTKLEIKRTVAAPSVFIFPPSDE<br>QLKSGTASVVCLLNNFYPREAKVQWKVDNALQSGNSQE<br>SVTEQDSKDSTYSLSSTLTLSKADYEKHKVYACEVTHQGLS<br>SPVTKSFNRGEC |
| SEQ ID NO: 371 | DNA Light Chain | GAGATCGTGCTGACCCAGTCCCCTGCCACCCTGTCCGT<br>GTCTCCCGGCGAGAGAGTGACCCTGTCCTGCCGGGCC<br>TCCCAGTCCATCTCCAACAACCTGCACTGGTATCAGCA<br>GAAGCCCGGCCAGGCCCCTCGGCTGCTGATTAAGTAC<br>GCCTCCCAGAGCATCTCCGGCATCCCTGCCAGATTCTC<br>CGGCTCCGGCAGCGGCACCGACTTCACCCTGACCATCT<br>CCAGCGTGGAACCCGAGGACTTCGGCGTGTACTTCTGC<br>CAGCAGTCCTCATCCTGGCTGACCTTCGGCCAGGGCAC<br>CAAGCTGGAAATCAAGCGTACGGTGGCCGCTCCCAGC<br>GTGTTCATCTTCCCCCCCAGCGACGAGCAGCTGAAGAG<br>TGGCACCGCCAGCGTGGTGTGCCTGCTGAACAACTTCT<br>ACCCCCGGGAGGCCAAGGTGCAGTGGAAGGTGGACA<br>ACGCCCTGCAGAGCGGCAACAGCCAGGAGAGCGTCAC<br>CGAGCAGGACAGCAAGGACTCCACCTACAGCCTGAGC<br>AGCACCCTGACCCTGAGCAAGGCCGACTACGAGAAGC<br>ATAAGGTGTACGCCTGCGAGGTGACCCACCAGGGCCT<br>GTCCAGCCCCGTGACCAAGAGCTTCAACAGGGGCGAG<br>TGC |

TABLE 4-continued

Amino Acid and Nucleotide Sequence Information for Hybridomas and Humanized Anti-CCR7 Antibodies

| Parental 506E15 hIgG1 CysMab | | |
|---|---|---|
| SEQ ID NO: 372 | HCDR1 (Combined) | GFTFSSYAMS |
| SEQ ID NO: 373 | HCDR2 (Combined) | TISSGGSFTYYPDSVKG |
| SEQ ID NO: 374 | HCDR3 (Combined) | RASTVVGTDFDV |
| SEQ ID NO: 375 | HCDR1 (Kabat) | SYAMS |
| SEQ ID NO: 376 | HCDR2 (Kabat) | TISSGGSFTYYPDSVKG |
| SEQ ID NO: 377 | HCDR3 (Kabat) | RASTVVGTDFDV |
| SEQ ID NO: 378 | HCDR1 (Chothia) | GFTFSSY |
| SEQ ID NO: 379 | HCDR2 (Chothia) | SSGGSF |
| SEQ ID NO: 380 | HCDR3 (Chothia) | RASTVVGTDFDV |
| SEQ ID NO: 381 | HCDR1 (IMGT) | GFTFSSYA |
| SEQ ID NO: 382 | HCDR2 (IMGT) | ISSGGSFT |
| SEQ ID NO: 383 | HCDR3 (IMGT) | ARRASTVVGTDFDV |
| SEQ ID NO: 384 | VH | EVMLVESGGGLVKPGGSLKLSCAASGFTFSSYAMSWIRQ<br>TPEKRLEWVATISSGGSFTYYPDSVKGRFTISRDNVKNTLY<br>LQMSSLRSEDTAMYYCARRASTVVGTDFDVWGAGTTVT<br>VSS |
| SEQ ID NO: 385 | DNA VH | GAAGTGATGCTGGTGGAGTCTGGGGGAGGCTTAGTG<br>AAGCCTGGAGGGTCCCTGAAACTCTCCTGTGCAGCCTC<br>TGGATTCACTTTCAGTAGCTATGCCATGTCTTGGATTCG<br>CCAGACTCCGGAGAAGAGACTGGAGTGGGTCGCAACC<br>ATCAGTAGTGGTGGTAGTTTCACCTACTATCCAGACAG<br>TGTGAAGGGGCGATTCACCATTTCTAGAGACAATGTCA<br>AGAACACCCTGTACCTGCAAATGAGCAGTCTGAGGTCT<br>GAAGACACGGCCATGTATTACTGTGCAAGACGGGCTT<br>CTACGGTAGTAGGTACGGACTTCGATGTCTGGGGCGC<br>AGGGACCACGGTCACCGTCTCCTCA |
| SEQ ID NO: 386 | Heavy Chain (CysMab mutations underlined) | EVMLVESGGGLVKPGGSLKLSCAASGFTFSSYAMSWIRQTPEK<br>RLEWVATISSGGSFTYYPDSVKGRFTISRDNVKNTLYLQMSSLR<br>SEDTAMYYCARRASTVVGTDFDVWGAGTTVTVSSastkgpsvfp<br>lapsskstsggtaalgclvkdyfpCpvtvswnsgaltsgvhtfpavlqssglysl<br>ssvvtvpssslgtqtyicnvnhkpsntkvdkrvepkscdkthtcppcpapell<br>ggpsvflfppkpkdtlmisrtpevtcvvvdvshedpevkfnwyvdgvevhn<br>aktkpreeqynstyrvvsvltvlhqdwlngkeykckvsnkalpapiektiska<br>kgqprepqvytlppsreemtknqvsltclvkgfypCdiavewesngqpen<br>nykttppvldsdgsfflyskltvdksrwqqgnvfscsvmhealhnhytqksls<br>lspgk |
| SEQ ID NO: 387 | DNA Heavy Chain | GAAGTGATGCTGGTGGAGTCTGGGGGAGGCTTAGTG<br>AAGCCTGGAGGGTCCCTGAAACTCTCCTGTGCAGCCTC<br>TGGATTCACTTTCAGTAGCTATGCCATGTCTTGGATTCG<br>CCAGACTCCGGAGAAGAGACTGGAGTGGGTCGCAACC<br>ATCAGTAGTGGTGGTAGTTTCACCTACTATCCAGACAG<br>TGTGAAGGGGCGATTCACCATTTCTAGAGACAATGTCA<br>AGAACACCCTGTACCTGCAAATGAGCAGTCTGAGGTCT<br>GAAGACACGGCCATGTATTACTGTGCAAGACGGGCTT<br>CTACGGTAGTAGGTACGGACTTCGATGTCTGGGGCGC<br>AGGGACCACGGTCACCGTCTCCTCAgctagcaccaagggcc<br>caagtgtgtttcccctggcccccagcagcaagtctacttccggcggaact<br>gctgccctgggttgcctggtgaaggactacttcccctgtcccgtgacagt |

TABLE 4-continued

| Amino Acid and Nucleotide Sequence Information for Hybridomas and Humanized Anti-CCR7 Antibodies | |
|---|---|
| | gtcctggaactctggggctctgacttccggcgtgcacaccttccccgccg tgctgcagagcagcggcctgtacagcctgagcagcgtggtgacagtgc cctccagctctctgggaacccagacctatatctgcaacgtgaaccacaa gcccagcaacaccaaggtggacaagagagtggagcccaagagctgcg acaagacccacacctgccccccctgcccagctccagaactgctgggag ggccttccgtgttcctgttccccccaagcccaaggacaccctgatgatc agcaggacccccgaggtgacctgcgtggtggtggacgtgtcccacgag gacccagaggtgaagttcaactggtacgtggacggcgtggaggtgcac aacgccaagaccaagcccagagaggagcagtacaacagcacctacag ggtggtgtccgtgctgaccgtgctgcaccaggactggctgaacggcaaa gaatacaagtgcaaagtctccaacaaggccctgccagccccaatcgaa aagacaatcagcaaggccaagggccagccacgggagccccaggtgta caccctgcccccccagccgggaggagatgaccaagaaccaggtgtccct gacctgtctggtgaagggcttctaccccgtgatatcgccgtggagtggg agagcaacggccagcccgagaacaactacaagaccacccccccagtg ctggacagcgacggcagcttcttcctgtacagcaagctgaccgtggaca agtccaggtggcagcagggcaacgtgttcagctgcagcgtgatgcacg aggccctgcacaaccactacacccagaagtccctgagcctgagccccg gcaag |
| SEQ ID NO: 388 LCDR1 (Combined) | RASQDIGSSLN |
| SEQ ID NO: 389 LCDR2 (Combined) | ATSSLDS |
| SEQ ID NO: 390 LCDR3 (Combined) | LQYASSPPT |
| SEQ ID NO: 391 LCDR1 (Kabat) | RASQDIGSSLN |
| SEQ ID NO: 392 LCDR2 (Kabat) | ATSSLDS |
| SEQ ID NO: 393 LCDR3 (Kabat) | LQYASSPPT |
| SEQ ID NO: 394 LCDR1 (Chothia) | SQDIGSS |
| SEQ ID NO: 395 LCDR2 (Chothia) | ATS |
| SEQ ID NO: 396 LCDR3 (Chothia) | YASSPP |
| SEQ ID NO: 397 LCDR1 (IMGT) | QDIGSS |
| SEQ ID NO: 398 LCDR2 (IMGT) | ATS |
| SEQ ID NO: 399 LCDR3 (IMGT) | LQYASSPPT |
| SEQ ID NO: 400 VL | DIQMTQSPSSLSASLGERVSLTCRASQDIGSSLNWLQQEP DGTIKRLIYATSSLDSGVPKRFSGSRSGSDYSLTISSLESEDF VVYYCLQYASSPPTFGGGTKLEIK |
| SEQ ID NO: 401 DNA VL | GACATCCAGATGACCCAGTCTCCATCCTCCTTATCTGCC TCTCTGGGAGAAAGAGTCAGTCTCACTTGTCGGGCAA GTCAGGACATTGGTAGTAGCTTAAACTGGCTTCAGCAG GAACCAGATGGAACTATTAAACGCCTGATCTATGCCAC ATCCAGTTTAGATTCTGGTGTCCCCAAAAGGTTCAGTG GCAGTAGGTCTGGGTCAGATTATTCTCTCACCATCAGC AGCCTTGAGTCTGAAGATTTTGTAGTCTATTACTGTCTA CAATATGCTAGTTCGCCTCCGACGTTCGGTGGAGGCAC CAAGCTGGAAATCAAA |
| SEQ ID NO: 402 Light Chain | DIQMTQSPSSLSASLGERVSLTCRASQDIGSSLNWLQQEP DGTIKRLIYATSSLDSGVPKRFSGSRSGSDYSLTISSLESEDF VVYYCLQYASSPPTFGGGTKLEIKRTVAAPSVFIFPPSDEQ LKSGTASVVCLLNNFYPREAKVQWKVDNALQSGNSQES VTEQDSKDSTYSLSSTLTLSKADYEKHKVYACEVTHQGLSS PVTKSFNRGEC |

TABLE 4-continued

| Amino Acid and Nucleotide Sequence Information for Hybridomas and Humanized Anti-CCR7 Antibodies | | |
|---|---|---|
| SEQ ID NO: 403 | DNA Light Chain | GACATCCAGATGACCCAGTCTCCATCCTCCTTATCTGCC TCTCTGGGAGAAAGAGTCAGTCTCACTTGTCGGGCAA GTCAGGACATTGGTAGTAGCTTAAACTGGCTTCAGCAG GAACCAGATGGAACTATTAAACGCCTGATCTATGCCAC ATCCAGTTTAGATTCTGGTGTCCCCAAAAGGTTCAGTG GCAGTAGGTCTGGGTCAGATTATTCTCTCACCATCAGC AGCCTTGAGTCTGAAGATTTTGTAGTCTATTACTGTCTA CAATATGCTAGTTCGCCTCCGACGTTCGGTGGAGGCAC CAAGCTGGAAATCAAACGTACGGTGGCCGCTCCCAGC GTGTTCATCTTCCCCCCCAGCGACGAGCAGCTGAAGAG TGGCACCGCCAGCGTGGTGTGCCTGCTGAACAACTTCT ACCCCCGGGAGGCCAAGGTGCAGTGGAAGGTGGACA ACGCCCTGCAGAGCGGCAACAGCCAGGAGAGCGTCAC CGAGCAGGACAGCAAGGACTCCACCTACAGCCTGAGC AGCACCCTGACCCTGAGCAAGGCCGACTACGAGAAGC ATAAGGTGTACGCCTGCGAGGTGACCCACCAGGGCCT GTCCAGCCCCGTGACCAAGAGCTTCAACAGGGGCGAG TGC |
| Parental 506E15 hIgG1 DAPA CysMab | | |
| SEQ ID NO: 404 | HCDR1 (Combined) | GFTFSSYAMS |
| SEQ ID NO: 405 | HCDR2 (Combined) | TISSGGSFTYYPDSVKG |
| SEQ ID NO: 406 | HCDR3 (Combined) | RASTVVGTDFDV |
| SEQ ID NO: 407 | HCDR1 (Kabat) | SYAMS |
| SEQ ID NO: 408 | HCDR2 (Kabat) | TISSGGSFTYYPDSVKG |
| SEQ ID NO: 409 | HCDR3 (Kabat) | RASTVVGTDFDV |
| SEQ ID NO: 410 | HCDR1 (Chothia) | GFTFSSY |
| SEQ ID NO: 411 | HCDR2 (Chothia) | SSGGSF |
| SEQ ID NO: 412 | HCDR3 (Chothia) | RASTVVGTDFDV |
| SEQ ID NO: 413 | HCDR1 (IMGT) | GFTFSSYA |
| SEQ ID NO: 414 | HCDR2 (IMGT) | ISSGGSFT |
| SEQ ID NO: 415 | HCDR3 (IMGT) | ARRASTVVGTDFDV |
| SEQ ID NO: 416 | VH | EVQLVESGGGLVKPGGSLRLSCAASGFTFSSYAMSWIRQ APGKGLEWVATISSGGSFTYYPDSVKGRFTISRDNAKNSL YLQMNSLRAEDTAVYYCARRASTVVGTDFDVWGQGTT VTVSS |
| SEQ ID NO: 417 | DNA VH | GAGGTGCAGCTGGTGGAATCTGGCGGAGGCCTGGTG AAACCCGGCGGATCCCTGAGACTGTCCTGCGCCGCCTC CGGCTTCACCTTCTCCAGCTACGCCATGTCCTGGATCCG GCAGGCTCCCGGCAAGGGCCTGGAATGGGTGGCCACC ATCTCCTCCGGCGGCAGCTTCACCTACTACCCCGACAG CGTGAAGGGCAGATTCACCATCAGCCGGGACAACGCC AAGAACTCCCTGTACCTGCAGATGAACTCCCTGCGGGC CGAGGACACCGCCGTGTACTACTGTGCCAGACGGGCC TCCACCGTCGTGGGAACCGACTTCGATGTGTGGGGCC AGGGCACCACCGTGACAGTGTCCTCC |
| SEQ ID NO: 418 | Heavy Chain (DAPA, CysMab | EVQLVESGGGLVKPGGSLRLSCAASGFTFSSYAMSWIRQ APGKGLEWVATISSGGSFTYYPDSVKGRFTISRDNAKNSL YLQMNSLRAEDTAVYYCARRASTVVGTDFDVWGQGTT VTVSSASTKGPSVFPLAPSSKSTSGGTAALGCLVKDYFPCP |

TABLE 4-continued

Amino Acid and Nucleotide Sequence Information for Hybridomas and Humanized Anti-CCR7 Antibodies

| | | |
|---|---|---|
| | mutations underlined) | VTVSWNSGALTSGVHTFPAVLQSSGLYSLSSVVTVPSSSL<br>GTQTYICNVNHKPSNTKVDKRVEPKSCDKTHTCPPCPAP<br>ELLGGPSVFLFPPKPKDTLMISRTPEVTCVVV**A**VSHEDPE<br>VKFNWYVDGVEVHNAKTKPREEQYNSTYRVVSVLTVLH<br>QDWLNGKEYKCKVSNKAL**A**APIEKTISKAKGQPREPQVY<br>TLPPSREEMTKNQVSLTCLVKGFYP**C**DIAVEWESNGQPE<br>NNYKTTPPVLDSDGSFFLYSKLTVDKSRWQQGNVFSCSV<br>MHEALHNHYTQKSLSLSPGK |
| SEQ ID NO: 419 | DNA Heavy Chain | GAGGTGCAGCTGGTGGAATCTGGCGGAGGCCTGGTG<br>AAACCCGGCGGATCCCTGAGACTGTCCTGCGCCGCCTC<br>CGGCTTCACCTTCTCCAGCTACGCCATGTCCTGGATCCG<br>GCAGGCTCCCGGCAAGGGCCTGGAATGGGTGGCCACC<br>ATCTCCTCCGGCGGCAGCTTCACCTACTACCCCGACAG<br>CGTGAAGGGCAGATTCACCATCAGCCGGGACAACGCC<br>AAGAACTCCCTGTACCTGCAGATGAACTCCCTGCGGGC<br>CGAGGACACCGCCGTGTACTACTGTGCCAGACGGGCC<br>TCCACCGTCGTGGGAACCGACTTCGATGTGTGGGGCC<br>AGGGCACCACCGTGACAGTGTCCTCCGCTAGCACCAA<br>GGGCCCAAGTGTGTTTCCCCTGGCCCCCAGCAGCAAGT<br>CTACTTCCGGCGGAACTGCTGCCCTGGGTTGCCTGGTG<br>AAGGACTACTTCCCCTGTCCCGTGACAGTGTCCTGGAA<br>CTCTGGGGCTCTGACTTCCGGCGTGCACACCTTCCCCG<br>CCGTGCTGCAGAGCAGCGGCCTGTACAGCCTGAGCAG<br>CGTGGTGACAGTGCCCTCCAGCTCTCTGGGAACCCAGA<br>CCTATATCTGCAACGTGAACCACAAGCCCAGCAACACC<br>AAGGTGGACAAGAGAGTGGAGCCCAAGAGCTGCGAC<br>AAGACCCACACCTGCCCCCCCTGCCCAGCTCCAGAACT<br>GCTGGGAGGGCCTTCCGTGTTCCTGTTCCCCCCCAAGC<br>CCAAGGACACCCTGATGATCAGCAGGACCCCCGAGGT<br>GACCTGCGTGGTGGTGGCCGTGTCCCACGAGGACCCA<br>GAGGTGAAGTTCAACTGGTACGTGGACGGCGTGGAG<br>GTGCACAACGCCAAGACCAAGCCCAGAGAGGAGCAGT<br>ACAACAGCACCTACAGGGTGGTGTCCGTGCTGACCGT<br>GCTGCACCAGGACTGGCTGAACGGCAAAGAATACAAG<br>TGCAAAGTCTCCAACAAGGCCCTGGCTGCCCCAATCGA<br>AAAGACAATCAGCAAGGCCAAGGGCCAGCCACGGGA<br>GCCCCAGGTGTACACCCTGCCCCCCAGCCGGGAGGAG<br>ATGACCAAGAACCAGGTGTCCCTGACCTGTCTGGTGAA<br>GGGCTTCTACCCCTGTGATATCGCCGTGGAGTGGGAG<br>AGCAACGGCCAGCCCGAGAACAACTACAAGACCACCC<br>CCCCAGTGCTGGACAGCGACGGCAGCTTCTTCCTGTAC<br>AGCAAGCTGACCGTGGACAAGTCCAGGTGGCAGCAG<br>GGCAACGTGTTCAGCTGCAGCGTGATGCACGAGGCCC<br>TGCACAACCACTACACCCAGAAGTCCCTGAGCCTGAGC<br>CCCGGCAAG |
| SEQ ID NO: 420 | LCDR1 (Combined) | RASQDIGSSLN |
| SEQ ID NO: 421 | LCDR2 (Combined) | ATSSLDS |
| SEQ ID NO: 422 | LCDR3 (Combined) | LQYASSPPT |
| SEQ ID NO: 423 | LCDR1 (Kabat) | RASQDIGSSLN |
| SEQ ID NO: 424 | LCDR2 (Kabat) | ATSSLDS |
| SEQ ID NO: 425 | LCDR3 (Kabat) | LQYASSPPT |
| SEQ ID NO: 426 | LCDR1 (Chothia) | SQDIGSS |
| SEQ ID NO: 427 | LCDR2 (Chothia) | ATS |
| SEQ ID NO: 428 | LCDR3 (Chothia) | YASSPP |
| SEQ ID NO: 429 | LCDR1 (IMGT) | QDIGSS |

TABLE 4-continued

Amino Acid and Nucleotide Sequence Information for Hybridomas and Humanized Anti-CCR7 Antibodies

| | | |
|---|---|---|
| SEQ ID NO: 430 | LCDR2 (IMGT) | ATS |
| SEQ ID NO: 431 | LCDR3 (IMGT) | LQYASSPPT |
| SEQ ID NO: 432 | VL | DIQMTQSPSSLSASVGDRVTLTCRASQDIGSSLNWLQQK<br>PGKAIKRLIYATSSLDSGVPSRFSGSRSGTDYTLTISSLQPE<br>DFVVYYCLQYASSPPTFGGGTKLEIK |
| SEQ ID NO: 433 | DNA VL | GACATCCAGATGACCCAGTCCCCCTCCAGCCTGTCCGC<br>CTCCGTGGGCGATAGAGTGACCCTGACCTGCCGGGCC<br>TCCCAGGACATCGGCTCCTCCCTGAACTGGCTGCAGCA<br>GAAGCCCGGCAAGGCCATCAAGCGGCTGATCTACGCC<br>ACCTCCTCCCTGGACTCCGGCGTGCCCTCCCGGTTCTCC<br>GGCTCTAGATCCGGCACCGACTACACCCTGACCATCTC<br>CAGCCTGCAGCCCGAGGACTTCGTGGTGTACTACTGCC<br>TGCAGTACGCCTCCAGCCCCCCCACCTTTGGCGGAGGC<br>ACCAAGCTGGAAATCAAG |
| SEQ ID NO: 434 | Light Chain | DIQMTQSPSSLSASVGDRVTLTCRASQDIGSSLNWLQQK<br>PGKAIKRLIYATSSLDSGVPSRFSGSRSGTDYTLTISSLQPE<br>DFVVYYCLQYASSPPTFGGGTKLEIKRTVAAPSVFIFPPSD<br>EQLKSGTASVVCLLNNFYPREAKVQWKVDNALQSGNSQ<br>ESVTEQDSKDSTYSLSSTLTLSKADYEKHKVYACEVTHQGL<br>SSPVTKSFNRGEC |
| SEQ ID NO: 435 | DNA Light Chain | GACATCCAGATGACCCAGTCCCCCTCCAGCCTGTCCGC<br>CTCCGTGGGCGATAGAGTGACCCTGACCTGCCGGGCC<br>TCCCAGGACATCGGCTCCTCCCTGAACTGGCTGCAGCA<br>GAAGCCCGGCAAGGCCATCAAGCGGCTGATCTACGCC<br>ACCTCCTCCCTGGACTCCGGCGTGCCCTCCCGGTTCTCC<br>GGCTCTAGATCCGGCACCGACTACACCCTGACCATCTC<br>CAGCCTGCAGCCCGAGGACTTCGTGGTGTACTACTGCC<br>TGCAGTACGCCTCCAGCCCCCCCACCTTTGGCGGAGGC<br>ACCAAGCTGGAAATCAAGCGTACGGTGGCCGCTCCCA<br>GCGTGTTCATCTTCCCCCCCAGCGACGAGCAGCTGAAG<br>AGTGGCACCGCCAGCGTGGTGTGCCTGCTGAACAACT<br>TCTACCCCCGGGAGGCCAAGGTGCAGTGGAAGGTGGA<br>CAACGCCCTGCAGAGCGGCAACAGCCAGGAGAGCGTC<br>ACCGAGCAGGACAGCAAGGACTCCACCTACAGCCTGA<br>GCAGCACCCTGACCCTGAGCAAGGCCGACTACGAGAA<br>GCATAAGGTGTACGCCTGCGAGGTGACCCACCAGGGC<br>CTGTCCAGCCCCGTGACCAAGAGCTTCAACAGGGGCG<br>AGTGC |
| | | Parental 684E12 hIgG1 CysMab |
| SEQ ID NO: 436 | HCDR1 (Combined) | GFTFSNFAMS |
| SEQ ID NO: 437 | HCDR2 (Combined) | TISTGGTYTYYPDSVKG |
| SEQ ID NO: 438 | HCDR3 (Combined) | RGYDGVDK |
| SEQ ID NO: 439 | HCDR1 (Kabat) | SNFAMS |
| SEQ ID NO: 440 | HCDR2 (Kabat) | TISTGGTYTYYPDSVKG |
| SEQ ID NO: 441 | HCDR3 (Kabat) | RGYDGVDK |
| SEQ ID NO: 442 | HCDR1 (Chothia) | GFTFSNF |
| SEQ ID NO: 443 | HCDR2 (Chothia) | STGGTY |
| SEQ ID NO: 444 | HCDR3 (Chothia) | RGYDGVDK |
| SEQ ID NO: 445 | HCDR1 (IMGT) | GFTFSNFA |

TABLE 4-continued

Amino Acid and Nucleotide Sequence Information for Hybridomas and Humanized Anti-CCR7 Antibodies

| | | |
|---|---|---|
| SEQ ID NO: 446 | HCDR2<br>(IMGT) | ISTGGTYT |
| SEQ ID NO: 447 | HCDR3<br>(IMGT) | TRRGYDGVDK |
| SEQ ID NO: 448 | VH | EVHLVESGGGLVKPGGSLKLSCAASGFTFSNFAMSWVRQTPE<br>KRLEWVATISTGGTYTYYPDSVKGRFTISRDNAKKTLYLQMSSL<br>RSEDTAMYYCTRRGYDGVDKWGQGTTLTVSS |
| SEQ ID NO: 449 | DNA VH | GAAGTGCATCTGGTGGAGTCTGGGGGAGGCTTAGTGAAGC<br>CTGGAGGGTCCCTGAAACTCTCCTGTGCAGCCTCTGGATTCA<br>CTTTCAGTAACTTTGCCATGTCTTGGGTTCGCCAGACTCCGG<br>AGAAGAGACTGGAGTGGGTCGCAACCATTAGTACTGGTGG<br>TACTTACACCTACTATCCAGACAGTGTGAAGGGTCGATTCAC<br>CATCTCCAGAGACAATGCCAAGAAAACCCTGTACCTGCAAA<br>TGAGCAGTCTGAGGTCTGAGGACACGGCCATGTATTACTGT<br>ACAAGACGGGGGTACGACGGCGTGGACAAATGGGGCCAA<br>GGCACCACTCTCACAGTCTCCTCA |
| SEQ ID NO: 450 | Heavy<br>Chain<br>(CysMab<br>mutations<br>underlined) | EVHLVESGGGLVKPGGSLKLSCAASGFTFSNFAMSWVRQTPE<br>KRLEWVATISTGGTYTYYPDSVKGRFTISRDNAKKTLYLQMSSL<br>RSEDTAMYYCTRRGYDGVDKWGQGTTLIVSSastkgpsvfplap<br>sskstsggtaalgclvkdyfpCpvtvswnsgaltsgvhtfpavlqssglyslssv<br>vtvpssslgtqtyicnvnhkpsntkvdkrvepkscdkthtcppcpapellggp<br>svflfppkpkdtlmisrtpevtcyvvdvshedpevkfnwyvdgvevhnakt<br>kpreeqynstyrvvsvltvlhqdwlngkeykckvsnkalpapiektiskakgq<br>prepqvytlppsreemtknqvsltclvkgfypCdiavewesngqpennykt<br>tppvldsdgsfflyskltvdksrwqqgnvfscsvmhealhnhytqkslslspg<br>k |
| SEQ ID NO: 451 | DNA Heavy<br>Chain<br>(CysMab<br>mutations<br>underlined) | GAAGTGCATCTGGTGGAGTCTGGGGGAGGCTTAGTGAAGC<br>CTGGAGGGTCCCTGAAACTCTCCTGTGCAGCCTCTGGATTCA<br>CTTTCAGTAACTTTGCCATGTCTTGGGTTCGCCAGACTCCGG<br>AGAAGAGACTGGAGTGGGTCGCAACCATTAGTACTGGTGG<br>TACTTACACCTACTATCCAGACAGTGTGAAGGGTCGATTCAC<br>CATCTCCAGAGACAATGCCAAGAAAACCCTGTACCTGCAAA<br>TGAGCAGTCTGAGGTCTGAGGACACGGCCATGTATTACTGT<br>ACAAGACGGGGGTACGACGGCGTGGACAAATGGGGCCAA<br>GGCACCACTCTCACAGTCTCCTCAgctagcaccaagggcccaagt<br>gtgtttcccctggcccccagcagcaagtctacttccggcggaactgctgc<br>cctgggttgcctggtgaaggactacttcccctgtcccgtgacagtgtcct<br>ggaactctggggctctgacttccggcgtgcacaccttccccgccgtgctg<br>cagagcagcggcctgtacagcctgagcagcgtggtgacagtgccctcc<br>agctctctgggaacccagacctatatctgcaacgtgaaccacaagccca<br>gcaacaccaaggtggacaagagagtggagcccaagagctgcgacaag<br>acccacacctgccccccctgcccagctccagaactgctgggagggcctt<br>ccgtgttcctgttccccccaagcccaaggacaccctgatgatcagcag<br>gacccccgaggtgacctgcgtggtggtggacgtgtcccacgaggaccc<br>agaggtgaagttcaactggtacgtggacggcgtggaggtgcacaacgc<br>caagaccaagcccagagaggagcagtacaacagcacctacagggtgg<br>tgtccgtgctgaccgtgctgcaccaggactggctgaacggcaaagaata<br>caagtgcaaagtctccaacaaggccctgccagcccccaatcgaaaagac<br>aatcagcaaggccaagggccagccacgggagccccaggtgtacaccct<br>gcccccccagccgggaggagatgaccaagaaccaggtgtccctgacctg<br>tctggtgaagggcttctaccccctgtgatatcgccgtggagtgggagagc<br>aacggccagcccgagaacaactacaagaccacccccccagtgctggac<br>agcgacggcagcttcttcctgtacagcaagctgaccgtggacaagtcca<br>ggtggcagcagggcaacgtgttcagctgcagcgtgatgcacgaggccc<br>tgcacaaccactacacccagaagtccctgagcctgagccccggcaag |
| SEQ ID NO: 452 | LCDR1<br>(Combined) | KSGQSLLDSDGKTYLN |
| SEQ ID NO: 453 | LCDR2<br>(Combined) | LVSKLDS |
| SEQ ID NO: 454 | LCDR3<br>(Combined) | WQGTHFPQT |
| SEQ ID NO: 455 | LCDR1<br>(Kabat) | KSGQSLLDSDGKTYLN |
| SEQ ID NO: 456 | LCDR2<br>(Kabat) | LVSKLDS |

TABLE 4-continued

| Amino Acid and Nucleotide Sequence Information for Hybridomas and Humanized Anti-CCR7 Antibodies | | |
|---|---|---|
| SEQ ID NO: 457 | LCDR3 (Kabat) | WQGTHFPQT |
| SEQ ID NO: 458 | LCDR1 (Chothia) | GQSLLDSDGKTY |
| SEQ ID NO: 459 | LCDR2 (Chothia) | LVS |
| SEQ ID NO: 460 | LCDR3 (Chothia) | GTHFPQ |
| SEQ ID NO: 461 | LCDR1 (IMGT) | QSLLDSDGKTY |
| SEQ ID NO: 462 | LCDR2 (IMGT) | LVS |
| SEQ ID NO: 463 | LCDR3 (IMGT) | WQGTHFPQT |
| SEQ ID NO: 464 | VL | DVVMTQTPLTLSVTIGQPASISCKSGQSLLDSDGKTYLNWFLQ RPGQSPKRLIYLVSKLDSGVPDRFTGSGSGTDFTLKISRVEAEDL GVYYCWQGTHFPQTFGGGTKLEIK |
| SEQ ID NO: 465 | DNA VL | gatgttgtgatgacccagactccactcactttgtcggttaccattggacaaccag cctccatctcttgcaagtcaggtcagagcctcttagatagtgatggaaagacat atttgaattggtttttacagaggccaggccagtctccaaagcgcctaatctatct ggtgtctaaactggactctggagtccctgacaggttcactggcagtggatcagg gacagatttcacactgaaaatcagcagagtggaggctgaggatttgggagttt attattgctggcaaggtacacattttcctcagacgttcggtggaggcaccaagc tggaaatcaaa |
| SEQ ID NO: 466 | Light Chain | DVVMTQTPLTLSVTIGQPASISCKSGQSLLDSDGKTYLNWFLQ RPGQSPKRLIYLVSKLDSGVPDRFTGSGSGTDFTLKISRVEAEDL GVYYCWQGTHFPQTFGGGTKLEIKRTVAAPSVFIFPPSDEQLK SGTASVVCLLNNFYPREAKVQWKVDNALQSGNSQESVTEQDS KDSTYSLSSTLTLSKADYEKHKVYACEVTHQGLSSPVTKSFNRGE C |
| SEQ ID NO: 467 | DNA Light Chain | GATGTTGTGATGACCCAGACTCCACTCACTTTGTCGGTTACC ATTGGACAACCAGCCTCCATCTCTTGCAAGTCAGGTCAGAG CCTCTTAGATAGTGATGGAAAGACATATTTGAATTGGTTTTT ACAGAGGCCAGGCCAGTCTCCAAAGCGCCTAATCTATCTGG TGTCTAAACTGGACTCTGGAGTCCCTGACAGGTTCACTGGC AGTGGATCAGGGACAGATTTCACACTGAAAATCAGCAGAGT GGAGGCTGAGGATTTGGGAGTTTATTATTGCTGGCAAGGTA CACATTTTCCTCAGACGTTCGGTGGAGGCACCAAGCTGGAA ATCAAAcgtacggtggccgctcccagcgtgttcatcttccccccagcgacg agcagctgaagagtggcaccgccagcgtggtgtgcctgctgaacaacttctac cccgggaggccaaggtgcagtggaaggtggacaacgccctgcagagcggc aacagccaggagagcgtcaccgagcaggacagcaaggactccacctacagc ctgagcagcaccctgaccctgagcaaggccgactacgagaagcataaggtgt acgcctgcgaggtgacccaccagggcctgtccagccccgtgaccaagagcttc aacaggggcgagtgc |
| Parental 684E12 hIgG1 DAPA CysMab | | |
| SEQ ID NO: 468 | HCDR1 (Combined) | GFTFSNFAMS |
| SEQ ID NO: 469 | HCDR2 (Combined) | TISTGGTYTYYPDSVKG |
| SEQ ID NO: 470 | HCDR3 (Combined) | RGYDGVDK |
| SEQ ID NO: 471 | HCDR1 (Kabat) | SNFAMS |
| SEQ ID NO: 472 | HCDR2 (Kabat) | TISTGGTYTYYPDSVKG |
| SEQ ID NO: 473 | HCDR3 (Kabat) | RGYDGVDK |

TABLE 4-continued

| Amino Acid and Nucleotide Sequence Information for Hybridomas and Humanized Anti-CCR7 Antibodies | | |
|---|---|---|
| SEQ ID NO: 474 | HCDR1 (Chothia) | GFTFSNF |
| SEQ ID NO: 475 | HCDR2 (Chothia) | STGGTY |
| SEQ ID NO: 476 | HCDR3 (Chothia) | RGYDGVDK |
| SEQ ID NO: 477 | HCDR1 (IMGT) | GFTFSNFA |
| SEQ ID NO: 478 | HCDR2 (IMGT) | ISTGGTYT |
| SEQ ID NO: 479 | HCDR3 (IMGT) | TRRGYDGVDK |
| SEQ ID NO: 480 | VH | EVHLVESGGGLVKPGGSLKLSCAASGFTFSNFAMSWVRQTPE<br>KRLEWVATISTGGTYTYYPDSVKGRFTISRDNAKKTLYLQMSSL<br>RSEDTAMYYCTRRGYDGVDKWGQGTTLTVSS |
| SEQ ID NO: 481 | DNA VH | GAAGTGCATCTGGTGGAGTCTGGGGGAGGCTTAGTGAAGC<br>CTGGAGGGTCCCTGAAACTCTCCTGTGCAGCCTCTGGATTCA<br>CTTTCAGTAACTTTGCCATGTCTTGGGTTCGCCAGACTCCGG<br>AGAAGAGACTGGAGTGGGTCGCAACCATTAGTACTGGTGG<br>TACTTACACCTACTATCCAGACAGTGTGAAGGGTCGATTCAC<br>CATCTCCAGAGACAATGCCAAGAAAACCCTGTACCTGCAAA<br>TGAGCAGTCTGAGGTCTGAGGACACGGCCATGTATTACTGT<br>ACAAGACGGGGGTACGACGGCGTGGACAAATGGGGCCAA<br>GGCACCACTCTCACAGTCTCCTCA |
| SEQ ID NO: 482 | Heavy Chain (DAPA, CysMab mutations underlined) | EVHLVESGGGLVKPGGSLKLSCAASGFTFSNFAMSWVRQTPE<br>KRLEWVATISTGGTYTYYPDSVKGRFTISRDNAKKTLYLQMSSL<br>RSEDTAMYYCTRRGYDGVDKWGQGTTLTVSSASTKGPSVFPL<br>APSSKSTSGGTAALGCLVKDYFP**C**PVTVSWNSGALTSGVHTFP<br>AVLQSSGLYSLSSVVTVPSSSLGTQTYICNVNHKPSNTKVDKRV<br>EPKSCDKTHTCPPCPAPELLGGPSVFLFPPKPKDTLMISRTPEVT<br>CVVV**A**VSHEDPEVKFNWYVDGVEVHNAKTKPREEQYNSTYR<br>VVSVLTVLHQDWLNGKEYKCKVSNKAL**A**APIEKTISKAKGQPR<br>EPQVYTLPPSREEMTKNQVSLTCLVKGFYP**C**DIAVEWESNGQP<br>ENNYKTTPPVLDSDGSFFLYSKLTVDKSRWQQGNVFSCSVMH<br>EALHNHYTQKSLSLSPGK |
| SEQ ID NO: 483 | DNA Heavy Chain | GAAGTGCATCTGGTGGAGTCTGGGGGAGGCTTAGTGAAGC<br>CTGGAGGGTCCCTGAAACTCTCCTGTGCAGCCTCTGGATTCA<br>CTTTCAGTAACTTTGCCATGTCTTGGGTTCGCCAGACTCCGG<br>AGAAGAGACTGGAGTGGGTCGCAACCATTAGTACTGGTGG<br>TACTTACACCTACTATCCAGACAGTGTGAAGGGTCGATTCAC<br>CATCTCCAGAGACAATGCCAAGAAAACCCTGTACCTGCAAA<br>TGAGCAGTCTGAGGTCTGAGGACACGGCCATGTATTACTGT<br>ACAAGACGGGGGTACGACGGCGTGGACAAATGGGGCCAA<br>GGCACCACTCTCACAGTCTCCTCAgctagcaccaagggcccaagt<br>gtgtttcccctggcccccagcagcaagtctacttccggcggaactgctgc<br>cctgggttgcctggtgaaggactacttcccctgtcccgtgacagtgtcct<br>ggaactctggggctctgacttccggcgtgcacaccttccccgccgtgctg<br>cagagcagcggcctgtacagcctgagcagcgtggtgacagtgccctcc<br>agctctctgggaacccagacctatatctgcaacgtgaaccacaagccca<br>gcaacaccaaggtggacaagagagtggagcccaagagctgcgacaag<br>acccacacctgccccccctgcccagctccagaactgctgggagggcctt<br>ccgtgttcctgttcccccccaagcccaaggacaccctgatgatcagcag<br>gacccccgaggtgacctgcgtggtggtggccgtgtcccacgaggaccc<br>agaggtgaagttcaactggtacgtggacggcgtggaggtgcacaacgc<br>caagaccaagcccagagaggagcagtacaacagcacctacagggtgg<br>tgtccgtgctgaccgtgctgcaccaggactggctgaacggcaaagaata<br>caagtgcaaagtctccaacaaggccctggctgccccaatcgaaaagac<br>aatcagcaaggccaagggccagccacgggagccccaggtgtacaccct<br>gcccccccagccgggaggagatgaccaagaaccaggtgtccctgacctg<br>tctggtgaagggcttctacccctgtgatatcgccgtggagtgggagagc<br>aacggccagcccgagaacaactacaagaccaccccccccagtgctggac<br>agcgacggcagcttcttcctgtacagcaagctgaccgtggacaagtcca<br>ggtggcagcagggcaacgtgttcagctgcagcgtgatgcacgaggccc<br>tgcacaaccactacacccagaagtccctgagcctgagccccggcaag |
| SEQ ID NO: 484 | LCDR1 (Combined) | KSGQSLLDSDGKTYLN |

TABLE 4-continued

| Amino Acid and Nucleotide Sequence Information for Hybridomas and Humanized Anti-CCR7 Antibodies | | |
|---|---|---|
| SEQ ID NO: 485 | LCDR2 (Combined) | LVSKLDS |
| SEQ ID NO: 486 | LCDR3 (Combined) | WQGTHFPQT |
| SEQ ID NO: 487 | LCDR1 (Kabat) | KSGQSLLDSDGKTYLN |
| SEQ ID NO: 488 | LCDR2 (Kabat) | LVSKLDS |
| SEQ ID NO: 489 | LCDR3 (Kabat) | WQGTHFPQT |
| SEQ ID NO: 490 | LCDR1 (Chothia) | GQSLLDSDGKTY |
| SEQ ID NO: 491 | LCDR2 (Chothia) | LVS |
| SEQ ID NO: 492 | LCDR3 (Chothia) | GTHFPQ |
| SEQ ID NO: 493 | LCDR1 (IMGT) | QSLLDSDGKTY |
| SEQ ID NO: 494 | LCDR2 (IMGT) | LVS |
| SEQ ID NO: 495 | LCDR3 (IMGT) | WQGTHFPQT |
| SEQ ID NO: 496 | VL | DVVMTQTPLTLSVTIGQPASISCKSGQSLLDSDGKTYLNWFLQ RPGQSPKRLIYLVSKLDSGVPDRFTGSGSGTDFTLKISRVEAEDL GVYYCWQGTHFPQTFGGGTKLEIK |
| SEQ ID NO: 497 | DNA VL | gatgttgtgatgacccagactccactcactttgtcggttaccattggacaaccag cctccatctcttgcaagtcaggtcagagcctcttagatagtgatggaaagacat atttgaattggtttttacagaggccaggccagtctccaaagcgcctaatctatct ggtgtctaaactggactctggagtccctgacaggttcactggcagtggatcagg gacagatttcacactgaaaatcagcagagtggaggctgaggatttgggagttt attattgctggcaaggtacacattttcctcagacgttcggtggaggcaccaagc tggaaatcaaa |
| SEQ ID NO: 498 | Light Chain | DVVMTQTPLTLSVTIGQPASISCKSGQSLLDSDGKTYLNWFLQ RPGQSPKRLIYLVSKLDSGVPDRFTGSGSGTDFTLKISRVEAEDL GVYYCWQGTHFPQTFGGGTKLEIKRTVAAPSVFIFPPSDEQLK SGTASVVCLLNNFYPREAKVQWKVDNALQSGNSQESVTEQDS KDSTYSLSSTLTLSKADYEKHKVYACEVTHQGLSSPVTKSFNRGE C |
| SEQ ID NO: 499 | DNA Light Chain | GATGTTGTGATGACCCAGACTCCACTCACTTTGTCGGTTACC ATTGGACAACCAGCCTCCATCTCTTGCAAGTCAGGTCAGAG CCTCTTAGATAGTGATGGAAAGACATATTTGAATTGGTTTTT ACAGAGGCCAGGCCAGTCTCCAAAGCGCCTAATCTATCTGG TGTCTAAACTGGACTCTGGAGTCCCTGACAGGTTCACTGGC AGTGGATCAGGGACAGATTTCACACTGAAAATCAGCAGAGT GGAGGCTGAGGATTTGGGAGTTTATTATTGCTGGCAAGGTA CACATTTTCCTCAGACGTTCGGTGGAGGCACCAAGCTGGAA ATCAAAcgtacggtggccgctcccagcgtgttcatcttccccccagcgacg agcagctgaagagtggcaccgccagcgtggtgtgcctgctgaacaacttctac cccgggaggccaaggtgcagtggaaggtggacaacgccctgcagagcggc aacagccaggagagcgtcaccgagcaggacagcaaggactccacctacagc ctgagcagcaccctgaccctgagcaaggccgactacgagaagcataaggtgt acgcctgcgaggtgacccaccagggcctgtccagccccgtgaccaagagcttc aacaggggcgagtgc |
| Humanized 674J13 higG1 DAPA | | |
| SEQ ID NO: 500 | HCDR1 (Combined) | GYSITSGYSWH |
| SEQ ID NO: 501 | HCDR2 (Combined) | HIHSSGSTNYNPSLKS |

TABLE 4-continued

| Amino Acid and Nucleotide Sequence Information for Hybridomas and Humanized Anti-CCR7 Antibodies | | |
|---|---|---|
| SEQ ID NO: 502 | HCDR3 (Combined) | GGVQAFAY |
| SEQ ID NO: 503 | HCDR1 (Kabat) | SGYSWH |
| SEQ ID NO: 504 | HCDR2 (Kabat) | HIHSSGSTNYNPSLKS |
| SEQ ID NO: 505 | HCDR3 (Kabat) | GGVQAFAY |
| SEQ ID NO: 506 | HCDR1 (Chothia) | GYSITSGY |
| SEQ ID NO: 507 | HCDR2 (Chothia) | HSSGS |
| SEQ ID NO: 508 | HCDR3 (Chothia) | GGVQAFAY |
| SEQ ID NO: 509 | HCDR1 (IMGT) | GYSITSGYS |
| SEQ ID NO: 510 | HCDR2 (IMGT) | IHSSGST |
| SEQ ID NO: 511 | HCDR3 (IMGT) | ARGGVQAFAY |
| SEQ ID NO: 512 | VH | DVQLQESGPGLVKPSQTLSLTCTVSGYSITSGYSWHWIR<br>QHPGKGLEWMAHIHSSGSTNYNPSLKSRITISRDTSKNQ<br>FSLKLSSVTAADTAVYYCARGGVQAFAYWGQGTLVTVSS |
| SEQ ID NO: 513 | DNA VH | GACGTGCAGCTGCAGGAATCTGGCCCTGGCCTGGTGA<br>AACCCTCCCAGACCCTGTCCCTGACCTGCACCGTGTCC<br>GGCTACTCCATCACCTCCGGCTACAGCTGGCACTGGAT<br>CCGGCAGCACCCCGGCAAGGGCCTGGAATGGATGGCC<br>CACATCCACTCCTCCGGCTCCACCAACTACAACCCCAGC<br>CTGAAGTCCAGAATCACCATCAGCCGGGACACCTCCAA<br>GAACCAGTTCTCCCTGAAGCTGTCCTCCGTGACCGCCG<br>CTGACACCGCCGTGTACTACTGTGCCAGAGGCGGCGT<br>GCAGGCCTTCGCTTATTGGGGCCAGGGCACCCTGGTG<br>ACAGTGTCCTCC |
| SEQ ID NO: 514 | Heavy Chain (DAPA mutations underlined) | DVQLQESGPGLVKPSQTLSLTCTVSGYSITSGYSWHWIR<br>QHPGKGLEWMAHIHSSGSTNYNPSLKSRITISRDTSKNQ<br>FSLKLSSVTAADTAVYYCARGGVQAFAYWGQGTLVTVSS<br>ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKRVEPKSCDKTHTCPPCPAPELLGG<br>PSVFLFPPKPKDTLMISRTPEVTCVVV**a**VSHEDPEVKFNW<br>YVDGVEVHNAKTKPREEQYNSTYRVVSVLTVLHQDWLN<br>GKEYKCKVSNKAL**a**APIEKTISKAKGQPREPQVYTLPPSRE<br>EMTKNQVSLTCLVKGFYPSDIAVEWESNGQPENNYKTTP<br>PVLDSDGSFFLYSKLTVDKSRWQQGNVFSCSVMHEALH<br>NHYTQKSLSLSPGK |
| SEQ ID NO: 515 | DNA Heavy Chain | GACGTGCAGCTGCAGGAATCTGGCCCTGGCCTGGTGA<br>AACCCTCCCAGACCCTGTCCCTGACCTGCACCGTGTCC<br>GGCTACTCCATCACCTCCGGCTACAGCTGGCACTGGAT<br>CCGGCAGCACCCCGGCAAGGGCCTGGAATGGATGGCC<br>CACATCCACTCCTCCGGCTCCACCAACTACAACCCCAGC<br>CTGAAGTCCAGAATCACCATCAGCCGGGACACCTCCAA<br>GAACCAGTTCTCCCTGAAGCTGTCCTCCGTGACCGCCG<br>CTGACACCGCCGTGTACTACTGTGCCAGAGGCGGCGT<br>GCAGGCCTTCGCTTATTGGGGCCAGGGCACCCTGGTG<br>ACAGTGTCCTCCGCTAGCACCAAGGGCCCAAGTGTGTT<br>TCCCCTGGCCCCCAGCAGCAAGTCTACTTCCGGCGGAA<br>CTGCTGCCCTGGGTTGCCTGGTGAAGGACTACTTCCCC<br>GAGCCCGTGACAGTGTCCTGGAACTCTGGGGCTCTGA<br>CTTCCGGCGTGCACACCTTCCCCGCCGTGCTGCAGAGC<br>AGCGGCCTGTACAGCCTGAGCAGCGTGGTGACAGTGC<br>CCTCCAGCTCTCTGGGAACCCAGACCTATATCTGCAAC<br>GTGAACCACAAGCCCAGCAACACCAAGGTGGACAAGA<br>GAGTGGAGCCCAAGAGCTGCGACAAGACCCACACCTG<br>CCCCCCCTGCCCAGCTCCAGAACTGCTGGGAGGGCCTT |

TABLE 4-continued

| Amino Acid and Nucleotide Sequence Information for Hybridomas and Humanized Anti-CCR7 Antibodies | |
|---|---|
| | CCGTGTTCCTGTTCCCCCCCAAGCCCAAGGACACCCTG ATGATCAGCAGGACCCCCGAGGTGACCTGCGTGGTGG TGGCCGTGTCCCACGAGGACCCAGAGGTGAAGTTCAA CTGGTACGTGGACGGCGTGGAGGTGCACAACGCCAAG ACCAAGCCCAGAGAGGAGCAGTACAACAGCACCTACA GGGTGGTGTCCGTGCTGACCGTGCTGCACCAGGACTG GCTGAACGGCAAAGAATACAAGTGCAAAGTCTCCAAC AAGGCCCTGGCTGCCCCAATCGAAAAGACAATCAGCA AGGCCAAGGGCCAGCCACGGGAGCCCCAGGTGTACAC CCTGCCCCCCAGCCGGGAGGAGATGACCAAGAACCAG GTGTCCCTGACCTGTCTGGTGAAGGGCTTCTACCCCAG CGATATCGCCGTGGAGTGGGAGAGCAACGGCCAGCCC GAGAACAACTACAAGACCACCCCCCCAGTGCTGGACA GCGACGGCAGCTTCTTCCTGTACAGCAAGCTGACCGTG GACAAGTCCAGGTGGCAGCAGGGCAACGTGTTCAGCT GCAGCGTGATGCACGAGGCCCTGCACAACCACTACAC CCAGAAGTCCCTGAGCCTGAGCCCCGGCAAG |
| SEQ ID NO: 516 LCDR1 (Combined) | SASSSVIYMH |
| SEQ ID NO: 517 LCDR2 (Combined) | DTSKLAS |
| SEQ ID NO: 518 LCDR3 (Combined) | QQWSSNPLT |
| SEQ ID NO: 519 LCDR1 (Kabat) | SASSSVIYMH |
| SEQ ID NO: 520 LCDR2 (Kabat) | DTSKLAS |
| SEQ ID NO: 521 LCDR3 (Kabat) | QQWSSNPLT |
| SEQ ID NO: 522 LCDR1 (Chothia) | SSSVIY |
| SEQ ID NO: 523 LCDR2 (Chothia) | DTS |
| SEQ ID NO: 524 LCDR3 (Chothia) | WSSNPL |
| SEQ ID NO: 525 LCDR1 (IMGT) | SSVIY |
| SEQ ID NO: 526 LCDR2 (IMGT) | DTS |
| SEQ ID NO: 527 LCDR3 (IMGT) | QQWSSNPLT |
| SEQ ID NO: 528 VL | EIVLTQSPATLSASPGERVTMSCSASSSVIYMHWYQQKP GQAPRRWIYDTSKLASGVPARFSGSGSGTDYTLTISSMEP EDAAVYYCQQWSSNPLTFGQGTKLEIK |
| SEQ ID NO: 529 DNA VL | GAGATCGTGCTGACCCAGTCCCCTGCCACCCTGTCTGC TAGCCCTGGCGAGCGCGTGACAATGTCCTGCTCCGCCT CCTCCTCCGTGATCTACATGCACTGGTATCAGCAGAAG CCCGGCCAGGCCCCTCGGCGGTGGATCTACGATACCTC CAAGCTGGCCTCCGGCGTGCCCGCCAGATTCTCCGGCT CTGGCTCTGGCACCGACTACACCCTGACCATCTCCAGC ATGGAACCCGAGGACGCCGCCGTGTACTACTGCCAGC AGTGGTCCTCCAACCCCCTGACCTTCGGCCAGGGCACC AAGCTGGAAATCAAG |
| SEQ ID NO: 530 Light Chain | EIVLTQSPATLSASPGERVTMSCSASSSVIYMHWYQQKP GQAPRRWIYDTSKLASGVPARFSGSGSGTDYTLTISSMEP EDAAVYYCQQWSSNPLTFGQGTKLEIKRTVAAPSVFIFPP SDEQLKSGTASVVCLLNNFYPREAKVQWKVDNALQSGN SQESVTEQDSKDSTYSLSSTLTLSKADYEKHKVYACEVTH QGLSSPVTKSFNRGEC |
| SEQ ID NO: 531 DNA Light Chain | GAGATCGTGCTGACCCAGTCCCCTGCCACCCTGTCTGC TAGCCCTGGCGAGCGCGTGACAATGTCCTGCTCCGCCT |

TABLE 4-continued

| Amino Acid and Nucleotide Sequence Information for Hybridomas and Humanized Anti-CCR7 Antibodies | | |
|---|---|---|
| | | CCTCCTCCGTGATCTACATGCACTGGTATCAGCAGAAG CCCGGCCAGGCCCCTCGGCGGTGGATCTACGATACCTC CAAGCTGGCCTCCGGCGTGCCCGCCAGATTCTCCGGCT CTGGCTCTGGCACCGACTACACCCTGACCATCTCCAGC ATGGAACCCGAGGACGCCGCCGTGTACTACTGCCAGC AGTGGTCCTCCAACCCCCTGACCTTCGGCCAGGGCACC AAGCTGGAAATCAAGCGTACGGTGGCCGCTCCCAGCG TGTTCATCTTCCCCCCCAGCGACGAGCAGCTGAAGAGT GGCACCGCCAGCGTGGTGTGCCTGCTGAACAACTTCTA CCCCCGGGAGGCCAAGGTGCAGTGGAAGGTGGACAA CGCCCTGCAGAGCGGCAACAGCCAGGAGAGCGTCACC GAGCAGGACAGCAAGGACTCCACCTACAGCCTGAGCA GCACCCTGACCCTGAGCAAGGCCGACTACGAGAAGCA TAAGGTGTACGCCTGCGAGGTGACCCACCAGGGCCTG TCCAGCCCCGTGACCAAGAGCTTCAACAGGGGCGAGT GC |
| | | Humanized 121G12 higG1 DAPA |
| SEQ ID NO: 532 | HCDR1 (Combined) | GFTFSTYAMS |
| SEQ ID NO: 533 | HCDR2 (Combined) | TISDAGSYSYYPDNVKG |
| SEQ ID NO: 534 | HCDR3 (Combined) | RGSRYEEYYVMDY |
| SEQ ID NO: 535 | HCDR1 (Kabat) | TYAMS |
| SEQ ID NO: 536 | HCDR2 (Kabat) | TISDAGSYSYYPDNVKG |
| SEQ ID NO: 537 | HCDR3 (Kabat) | RGSRYEEYYVMDY |
| SEQ ID NO: 538 | HCDR1 (Chothia) | GFTFSTY |
| SEQ ID NO: 539 | HCDR2 (Chothia) | SDAGSY |
| SEQ ID NO: 540 | HCDR3 (Chothia) | RGSRYEEYYVMDY |
| SEQ ID NO: 541 | HCDR1 (IMGT) | GFTFSTYA |
| SEQ ID NO: 542 | HCDR2 (IMGT) | ISDAGSYS |
| SEQ ID NO: 543 | HCDR3 (IMGT) | ARRGSRYEEYYVMDY |
| SEQ ID NO: 544 | VH | EVQLVESGGGLVKPGGSLRLSCAASGFTFSTYAMSWVRQ APGKGLEWVATISDAGSYSYYPDNVKGRFTISRDNAKNSL YLQMNSLRAEDTAVYYCARRGSRYEEYYVMDYWGQGT TVTVSS |
| SEQ ID NO: 545 | DNA VH | GAGGTGCAGCTGGTGGAATCTGGCGGAGGCCTGGTG AAACCCGGCGGATCCCTGAGACTGTCCTGCGCCGCCTC CGGCTTCACCTTCTCCACCTACGCCATGTCCTGGGTGC GGCAGGCTCCCGGCAAGGGCCTGGAATGGGTGGCCA CCATCTCCGACGCCGGCTCCTACTCCTACTACCCCGACA ACGTGAAGGGCAGATTCACCATCAGCCGGGACAACGC CAAGAACTCCCTGTACCTGCAGATGAACTCCCTGCGGG CCGAGGACACCGCCGTGTACTACTGTGCCAGACGGGG CTCCAGATACGAAGAGTACTACGTGATGGACTATTGG GGCCAGGGCACCACCGTGACAGTGTCCTCC |
| SEQ ID NO: 546 | Heavy Chain (DAPA mutations underlined) | EVQLVESGGGLVKPGGSLRLSCAASGFTFSTYAMSWVRQ APGKGLEWVATISDAGSYSYYPDNVKGRFTISRDNAKNSL YLQMNSLRAEDTAVYYCARRGSRYEEYYVMDYWGQGT TVTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKRVEPKSCDKTHTCPPCPA |

TABLE 4-continued

Amino Acid and Nucleotide Sequence Information for Hybridomas and Humanized Anti-CCR7 Antibodies

| | | |
|---|---|---|
| | | PELLGGPSVFLFPPKPKDTLMISRTPEVTCVVV**a**VSHEDPE<br>VKFNWYVDGVEVHNAKTKPREEQYNSTYRVVSVLTVLH<br>QDWLNGKEYKCKVSNKAL**a**APIEKTISKAKGQPREPQVY<br>TLPPSREEMTKNQVSLTCLVKGFYPSDIAVEWESNGQPE<br>NNYKTTPPVLDSDGSFFLYSKLTVDKSRWQQGNVFSCSV<br>MHEALHNHYTQKSLSLSPGK |
| SEQ ID NO: 547 | DNA Heavy Chain | GAGGTGCAGCTGGTGGAATCTGGCGGAGGCCTGGTG<br>AAACCCGGCGGATCCCTGAGACTGTCCTGCGCCGCCTC<br>CGGCTTCACCTTCTCCACCTACGCCATGTCCTGGGTGC<br>GGCAGGCTCCCGGCAAGGGCCTGGAATGGGTGGCCA<br>CCATCTCCGACGCCGGCTCCTACTCCTACTACCCCGACA<br>ACGTGAAGGGCAGATTCACCATCAGCCGGGACAACGC<br>CAAGAACTCCCTGTACCTGCAGATGAACTCCCTGCGGG<br>CCGAGGACACCGCCGTGTACTACTGTGCCAGACGGGG<br>CTCCAGATACGAAGAGTACTACGTGATGGACTATTGG<br>GGCCAGGGCACCACCGTGACAGTGTCCTCCGCTAGCA<br>CCAAGGGCCCAAGTGTGTTTCCCCTGGCCCCCAGCAGC<br>AAGTCTACTTCCGGCGGAACTGCTGCCCTGGGTTGCCT<br>GGTGAAGGACTACTTCCCCGAGCCCGTGACAGTGTCCT<br>GGAACTCTGGGGCTCTGACTTCCGGCGTGCACACCTTC<br>CCCGCCGTGCTGCAGAGCAGCGGCCTGTACAGCCTGA<br>GCAGCGTGGTGACAGTGCCCTCCAGCTCTCTGGGAAC<br>CCAGACCTATATCTGCAACGTGAACCACAAGCCCAGCA<br>ACACCAAGGTGGACAAGAGAGTGGAGCCCAAGAGCT<br>GCGACAAGACCCACACCTGCCCCCCCTGCCCAGCTCCA<br>GAACTGCTGGGAGGGCCTTCCGTGTTCCTGTTCCCCCC<br>CAAGCCCAAGGACACCCTGATGATCAGCAGGACCCCC<br>GAGGTGACCTGCGTGGTGGTGGCCGTGTCCCACGAGG<br>ACCCAGAGGTGAAGTTCAACTGGTACGTGGACGGCGT<br>GGAGGTGCACAACGCCAAGACCAAGCCCAGAGAGGA<br>GCAGTACAACAGCACCTACAGGGTGGTGTCCGTGCTG<br>ACCGTGCTGCACCAGGACTGGCTGAACGGCAAAGAAT<br>ACAAGTGCAAAGTCTCCAACAAGGCCCTGGCTGCCCCA<br>ATCGAAAAGACAATCAGCAAGGCCAAGGGCCAGCCAC<br>GGGAGCCCCAGGTGTACACCCTGCCCCCCAGCCGGGA<br>GGAGATGACCAAGAACCAGGTGTCCCTGACCTGTCTG<br>GTGAAGGGCTTCTACCCCAGCGATATCGCCGTGGAGT<br>GGGAGAGCAACGGCCAGCCCGAGAACAACTACAAGA<br>CCACCCCCCCAGTGCTGGACAGCGACGGCAGCTTCTTC<br>CTGTACAGCAAGCTGACCGTGGACAAGTCCAGGTG GC<br>AGCAGGGCAACGTGTTCAGCTGCAGCGTGATGCACGA<br>GGCCCTGCACAACCACTACACCCAGAAGTCCCTGAGCC<br>TGAGCCCCGGCAAG |
| SEQ ID NO: 548 | LCDR1 (Combined) | RASQSISNNLH |
| SEQ ID NO: 549 | LCDR2 (Combined) | YASQSIS |
| SEQ ID NO: 550 | LCDR3 (Combined) | QQSSSWLT |
| SEQ ID NO: 551 | LCDR1 (Kabat) | RASQSISNNLH |
| SEQ ID NO: 552 | LCDR2 (Kabat) | YASQSIS |
| SEQ ID NO: 553 | LCDR3 (Kabat) | QQSSSWLT |
| SEQ ID NO: 554 | LCDR1 (Chothia) | SQSISNN |
| SEQ ID NO: 555 | LCDR2 (Chothia) | YAS |
| SEQ ID NO: 556 | LCDR3 (Chothia) | SSSWL |
| SEQ ID NO: 557 | LCDR1 (IMGT) | QSISNN |
| SEQ ID NO: 558 | LCDR2 (IMGT) | YAS |

TABLE 4-continued

Amino Acid and Nucleotide Sequence Information for Hybridomas and Humanized Anti-CCR7 Antibodies

| | |
|---|---|
| SEQ ID NO: 559 LCDR3 (IMGT) | QQSSSWLT |
| SEQ ID NO: 560 VL | EIVLTQSPATLSVSPGERVTLSCRASQSISNNLHWYQQKP GQAPRLLIKYASQSISGIPARFSGSGSGTDFTLTISSVEPED FGVYFCQQSSSWLTFGQGTKLEIK |
| SEQ ID NO: 561 DNA VL | GAGATCGTGCTGACCCAGTCCCCTGCCACCCTGTCCGT GTCTCCCGGCGAGAGAGTGACCCTGTCCTGCCGGGCC TCCCAGTCCATCTCCAACAACCTGCACTGGTATCAGCA GAAGCCCGGCCAGGCCCCTCGGCTGCTGATTAAGTAC GCCTCCCAGAGCATCTCCGGCATCCCTGCCAGATTCTC CGGCTCCGGCAGCGGCACCGACTTCACCCTGACCATCT CCAGCGTGGAACCCGAGGACTTCGGCGTGTACTTCTGC CAGCAGTCCTCATCCTGGCTGACCTTCGGCCAGGGCAC CAAGCTGGAAATCAAG |
| SEQ ID NO: 562 Light Chain | EIVLTQSPATLSVSPGERVTLSCRASQSISNNLHWYQQKP GQAPRLLIKYASQSISGIPARFSGSGSGTDFTLTISSVEPED FGVYFCQQSSSWLTFGQGTKLEIKRTVAAPSVFIFPPSDE QLKSGTASVVCLLNNFYPREAKVQWKVDNALQSGNSQE SVTEQDSKDSTYSLSSTLTLSKADYEKHKVYACEVTHQGLS SPVTKSFNRGEC |
| SEQ ID NO: 563 DNA Light Chain | GAGATCGTGCTGACCCAGTCCCCTGCCACCCTGTCCGT GTCTCCCGGCGAGAGAGTGACCCTGTCCTGCCGGGCC TCCCAGTCCATCTCCAACAACCTGCACTGGTATCAGCA GAAGCCCGGCCAGGCCCCTCGGCTGCTGATTAAGTAC GCCTCCCAGAGCATCTCCGGCATCCCTGCCAGATTCTC CGGCTCCGGCAGCGGCACCGACTTCACCCTGACCATCT CCAGCGTGGAACCCGAGGACTTCGGCGTGTACTTCTGC CAGCAGTCCTCATCCTGGCTGACCTTCGGCCAGGGCAC CAAGCTGGAAATCAAGCGTACGGTGGCCGCTCCCAGC GTGTTCATCTTCCCCCCCAGCGACGAGCAGCTGAAGAG TGGCACCGCCAGCGTGGTGTGCCTGCTGAACAACTTCT ACCCCCGGGAGGCCAAGGTGCAGTGGAAGGTGGACA ACGCCCTGCAGAGCGGCAACAGCCAGGAGAGCGTCAC CGAGCAGGACAGCAAGGACTCCACCTACAGCCTGAGC AGCACCCTGACCCTGAGCAAGGCCGACTACGAGAAGC ATAAGGTGTACGCCTGCGAGGTGACCCACCAGGGCCT GTCCAGCCCCGTGACCAAGAGCTTCAACAGGGGCGAG TGC |
| Humanized 506E15 higG1 DAPA | |
| SEQ ID NO: 564 HCDR1 (Combined) | GFTFSSYAMS |
| SEQ ID NO: 565 HCDR2 (Combined) | TISSGGSFTYYPDSVKG |
| SEQ ID NO: 566 HCDR3 (Combined) | RASTVVGTDFDV |
| SEQ ID NO: 567 HCDR1 (Kabat) | SYAMS |
| SEQ ID NO: 568 HCDR2 (Kabat) | TISSGGSFTYYPDSVKG |
| SEQ ID NO: 569 HCDR3 (Kabat) | RASTVVGTDFDV |
| SEQ ID NO: 570 HCDR1 (Chothia) | GFTFSSY |
| SEQ ID NO: 571 HCDR2 (Chothia) | SSGGSF |
| SEQ ID NO: 572 HCDR3 (Chothia) | RASTVVGTDFDV |
| SEQ ID NO: 573 HCDR1 (IMGT) | GFTFSSYA |

TABLE 4-continued

| Amino Acid and Nucleotide Sequence Information for Hybridomas and Humanized Anti-CCR7 Antibodies | | |
|---|---|---|
| SEQ ID NO: 574 | HCDR2 (IMGT) | ISSGGSFT |
| SEQ ID NO: 575 | HCDR3 (IMGT) | ARRASTVVGTDFDV |
| SEQ ID NO: 576 | VH | EVQLVESGGGLVKPGGSLRLSCAASGFTFSSYAMSWIRQ<br>APGKGLEWVATISSGGSFTYYPDSVKGRFTISRDNAKNSL<br>YLQMNSLRAEDTAVYYCARRASTVVGTDFDVWGQGTT<br>VTVSS |
| SEQ ID NO: 577 | DNA VH | GAGGTGCAGCTGGTGGAATCTGGCGGAGGCCTGGTG<br>AAACCCGGCGGATCCCTGAGACTGTCCTGCGCCGCCTC<br>CGGCTTCACCTTCTCCAGCTACGCCATGTCCTGGATCCG<br>GCAGGCTCCCGGCAAGGGCCTGGAATGGGTGGCCACC<br>ATCTCCTCCGGCGGCAGCTTCACCTACTACCCCGACAG<br>CGTGAAGGGCAGATTCACCATCAGCCGGGACAACGCC<br>AAGAACTCCCTGTACCTGCAGATGAACTCCCTGCGGGC<br>CGAGGACACCGCCGTGTACTACTGTGCCAGACGGGCC<br>TCCACCGTCGTGGGAACCGACTTCGATGTGTGGGGCC<br>AGGGCACCACCGTGACAGTGTCCTCC |
| SEQ ID NO: 578 | Heavy Chain (DAPA mutations underlined) | EVQLVESGGGLVKPGGSLRLSCAASGFTFSSYAMSWIRQ<br>APGKGLEWVATISSGGSFTYYPDSVKGRFTISRDNAKNSL<br>YLQMNSLRAEDTAVYYCARRASTVVGTDFDVWGQGTT<br>VTVSSASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKRVEPKSCDKTHTCPPCPAP<br>ELLGGPSVFLFPPKPKDTLMISRTPEVTCVVV**a**VSHEDPEV<br>KFNWYVDGVEVHNAKTKPREEQYNSTYRVVSVLTVLHQ<br>DWLNGKEYKCKVSNKAL**a**APIEKTISKAKGQPREPQVYTL<br>PPSREEMTKNQVSLTCLVKGFYPSDIAVEWESNGQPENN<br>YKTTPPVLDSDGSFFLYSKLTVDKSRWQQGNVFSCSVMH<br>EALHNHYTQKSLSLSPGK |
| SEQ ID NO: 579 | DNA Heavy Chain | GAGGTGCAGCTGGTGGAATCTGGCGGAGGCCTGGTG<br>AAACCCGGCGGATCCCTGAGACTGTCCTGCGCCGCCTC<br>CGGCTTCACCTTCTCCAGCTACGCCATGTCCTGGATCCG<br>GCAGGCTCCCGGCAAGGGCCTGGAATGGGTGGCCACC<br>ATCTCCTCCGGCGGCAGCTTCACCTACTACCCCGACAG<br>CGTGAAGGGCAGATTCACCATCAGCCGGGACAACGCC<br>AAGAACTCCCTGTACCTGCAGATGAACTCCCTGCGGGC<br>CGAGGACACCGCCGTGTACTACTGTGCCAGACGGGCC<br>TCCACCGTCGTGGGAACCGACTTCGATGTGTGGGGCC<br>AGGGCACCACCGTGACAGTGTCCTCCGCTAGCACCAA<br>GGGCCCAAGTGTGTTTCCCCTGGCCCCCAGCAGCAAGT<br>CTACTTCCGGCGGAACTGCTGCCCTGGGTTGCCTGGTG<br>AAGGACTACTTCCCCGAGCCCGTGACAGTGTCCTGGAA<br>CTCTGGGGCTCTGACTTCCGGCGTGCACACCTTCCCCG<br>CCGTGCTGCAGAGCAGCGGCCTGTACAGCCTGAGCAG<br>CGTGGTGACAGTGCCCTCCAGCTCTCTGGGAACCCAGA<br>CCTATATCTGCAACGTGAACCACAAGCCCAGCAACACC<br>AAGGTGGACAAGAGAGTGGAGCCCAAGAGCTGCGAC<br>AAGACCCACACCTGCCCCCCCTGCCCAGCTCCAGAACT<br>GCTGGGAGGGCCTTCCGTGTTCCTGTTCCCCCCCAAGC<br>CCAAGGACACCCTGATGATCAGCAGGACCCCCGAGGT<br>GACCTGCGTGGTGGTGGCCGTGTCCCACGAGGACCCA<br>GAGGTGAAGTTCAACTGGTACGTGGACGGCGTGGAG<br>GTGCACAACGCCAAGACCAAGCCCAGAGAGGAGCAGT<br>ACAACAGCACCTACAGGGTGGTGTCCGTGCTGACCGT<br>GCTGCACCAGGACTGGCTGAACGGCAAAGAATACAAG<br>TGCAAAGTCTCCAACAAGGCCCTGGCTGCCCCAATCGA<br>AAAGACAATCAGCAAGGCCAAGGGCCAGCCACGGGA<br>GCCCCAGGTGTACACCCTGCCCCCCAGCCGGGAGGAG<br>ATGACCAAGAACCAGGTGTCCCTGACCTGTCTGGTGAA<br>GGGCTTCTACCCCAGCGATATCGCCGTGGAGTGGGAG<br>AGCAACGGCCAGCCCGAGAACAACTACAAGACCACCC<br>CCCCAGTGCTGGACAGCGACGGCAGCTTCTTCCTGTAC<br>AGCAAGCTGACCGTGGACAAGTCCAGGTGGCAGCAG<br>GGCAACGTGTTCAGCTGCAGCGTGATGCACGAGGCCC<br>TGCACAACCACTACACCCAGAAGTCCCTGAGCCTGAGC<br>CCCGGCAAG |
| SEQ ID NO: 580 | LCDR1 (Combined) | RASQDIGSSLN |

TABLE 4-continued

Amino Acid and Nucleotide Sequence Information for Hybridomas and Humanized Anti-CCR7 Antibodies

| | | |
|---|---|---|
| SEQ ID NO: 581 | LCD R2 (Combined) | ATSSLDS |
| SEQ ID NO: 582 | LCD R3 (Combined) | LQYASSPPT |
| SEQ ID NO: 583 | LCDR1 (Kabat) | RASQDIGSSLN |
| SEQ ID NO: 584 | LCD R2 (Kabat) | ATSSLDS |
| SEQ ID NO: 585 | LCD R3 (Kabat) | LQYASSPPT |
| SEQ ID NO: 586 | LCDR1 (Chothia) | SQDIGSS |
| SEQ ID NO: 587 | LCD R2 (Chothia) | ATS |
| SEQ ID NO: 588 | LCD R3 (Chothia) | YASSPP |
| SEQ ID NO: 589 | LCDR1 (IMGT) | QDIGSS |
| SEQ ID NO: 590 | LCD R2 (IMGT) | ATS |
| SEQ ID NO: 591 | LCD R3 (IMGT) | LQYASSPPT |
| SEQ ID NO: 592 | VL | DIQMTQSPSSLSASVGDRVTLTCRASQDIGSSLNWLQQK PGKAIKRLIYATSSLDSGVPSRFSGSRSGTDYTLTISSLQPE DFVVYYCLQYASSPPTFGGGTKLEIK |
| SEQ ID NO: 593 | DNA VL | GACATCCAGATGACCCAGTCCCCCTCCAGCCTGTCCGC CTCCGTGGGCGATAGAGTGACCCTGACCTGCCGGGCC TCCCAGGACATCGGCTCCTCCCTGAACTGGCTGCAGCA GAAGCCCGGCAAGGCCATCAAGCGGCTGATCTACGCC ACCTCCTCCCTGGACTCCGGCGTGCCCTCCCGGTTCTCC GGCTCTAGATCCGGCACCGACTACACCCTGACCATCTC CAGCCTGCAGCCCGAGGACTTCGTGGTGTACTACTGCC TGCAGTACGCCTCCAGCCCCCCCACCTTTGGCGGAGGC ACCAAGCTGGAAATCAAG |
| SEQ ID NO: 594 | Light Chain | DIQMTQSPSSLSASVGDRVTLTCRASQDIGSSLNWLQQK PGKAIKRLIYATSSLDSGVPSRFSGSRSGTDYTLTISSLQPE DFVVYYCLQYASSPPTFGGGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQGL SSPVTKSFNRGEC |
| SEQ ID NO: 595 | DNA Light Chain | GACATCCAGATGACCCAGTCCCCCTCCAGCCTGTCCGC CTCCGTGGGCGATAGAGTGACCCTGACCTGCCGGGCC TCCCAGGACATCGGCTCCTCCCTGAACTGGCTGCAGCA GAAGCCCGGCAAGGCCATCAAGCGGCTGATCTACGCC ACCTCCTCCCTGGACTCCGGCGTGCCCTCCCGGTTCTCC GGCTCTAGATCCGGCACCGACTACACCCTGACCATCTC CAGCCTGCAGCCCGAGGACTTCGTGGTGTACTACTGCC TGCAGTACGCCTCCAGCCCCCCCACCTTTGGCGGAGGC ACCAAGCTGGAAATCAAGCGTACGGTGGCCGCTCCCA GCGTGTTCATCTTCCCCCCCAGCGACGAGCAGCTGAAG AGTGGCACCGCCAGCGTGGTGTGCCTGCTGAACAACT TCTACCCCCGGGAGGCCAAGGTGCAGTGGAAGGTGGA CAACGCCCTGCAGAGCGGCAACAGCCAGGAGAGCGTC ACCGAGCAGGACAGCAAGGACTCCACCTACAGCCTGA GCAGCACCCTGACCCTGAGCAAGGCCGACTACGAGAA GCATAAGGTGTACGCCTGCGAGGTGACCCACCAGGGC CTGTCCAGCCCCGTGACCAAGAGCTTCAACAGGGGCG AGTGC |
| Humanized 684E12 hIgG1 DAPA CysMab | | |
| SEQ ID NO: 596 | HCDR1 (Combined) | GFTFSNFAMS |

TABLE 4-continued

Amino Acid and Nucleotide Sequence Information for Hybridomas and Humanized Anti-CCR7 Antibodies

| | | |
|---|---|---|
| SEQ ID NO: 597 | HCDR2 (Combined) | TISTGGTYTYYPDSVKG |
| SEQ ID NO: 598 | HCDR3 (Combined) | RGYSGVDK |
| SEQ ID NO: 599 | HCDR1 (Kabat) | SNFAMS |
| SEQ ID NO: 600 | HCDR2 (Kabat) | TISTGGTYTYYPDSVKG |
| SEQ ID NO: 601 | HCDR3 (Kabat) | RGYSGVDK |
| SEQ ID NO: 602 | HCDR1 (Chothia) | GFTFSNF |
| SEQ ID NO: 603 | HCDR2 (Chothia) | STGGTY |
| SEQ ID NO: 604 | HCDR3 (Chothia) | RGYSGVDK |
| SEQ ID NO: 605 | HCDR1 (IMGT) | GFTFSNFA |
| SEQ ID NO: 606 | HCDR2 (IMGT) | ISTGGTYT |
| SEQ ID NO: 607 | HCDR3 (IMGT) | TRRGYSGVDK |
| SEQ ID NO: 608 | VH | EVQLVESGGGLVKPGGSLRLSCAASGFTFSNFAMSWVRQAPG<br>KGLEWVSTISTGGTYTYYPDSVKGRFTISRDNAKNSLYLQMNSL<br>RAEDTAVYYCARRGYSGVDKWGQGTTVTVSS |
| SEQ ID NO: 609 | DNA VH | GAGGTGCAGCTGGTGGAATCTGGCGGAGGCCTGGTGAAAC<br>CCGGCGGATCCCTGAGACTGTCCTGCGCCGCCTCCGGCTTC<br>ACCTTCTCCAACTTCGCCATGTCCTGGGTGCGGCAGGCTCCC<br>GGCAAGGGCCTGGAATGGGTGTCCACCATCTCCACCGGCG<br>GCACCTACACCTACTACCCCGACAGCGTGAAGGGCAGATTC<br>ACCATCAGCCGGGACAACGCCAAGAACTCCCTGTACCTGCA<br>GATGAACTCCCTGCGGGCCGAGGACACCGCCGTGTACTACT<br>GTGCCAGACGGGGCTACTCAGGCGTGGACAAATGGGGCCA<br>GGGCACCACCGTGACAGTGTCCTCC |
| SEQ ID NO: 610 | Heavy Chain (DAPA, CysMab mutations underlined) | EVQLVESGGGLVKPGGSLRLSCAASGFTFSNFAMSWVRQAPG<br>KGLEWVSTISTGGTYTYYPDSVKGRFTISRDNAKNSLYLQMNSL<br>RAEDTAVYYCARRGYSGVDKWGQGTTVTVSSASTKGPSVFPL<br>APSSKSTSGGTAALGCLVKDYFP**C**PVTVSWNSGALTSGVHTFP<br>AVLQSSGLYSLSSVVTVPSSSLG**T**QTYICNVNHKPSNTKVDKRV<br>EPKSCDKTHTCPPCPAPELLGGPSVFLFPPKPKDTLMISRTPEVT<br>CVVV**A**VSHEDPEVKFNWYVDGVEVHNAKTKPREEQYNSTYR<br>VVSV**L**TVLHQDWLNGKEYKCKVSNKAL**A**APIEKTISKAKGQPR<br>EPQVYTLPPSREEMTKNQVSLTCLVKG**F**YP**C**DIAVEWESNGQP<br>ENNYKTTPPVLDSDGSFFLYSKLTVDKSRW**Q**QGNVFSCSVMH<br>EALHNHYTQKSLSLSPGK |
| SEQ ID NO: 611 | DNA Heavy Chain | GAGGTGCAGCTGGTGGAATCTGGCGGAGGCCTGGTG<br>AAACCCGGCGGATCCCTGAGACTGTCCTGCGCCGCCTC<br>CGGCTTCACCTTCTCCAACTTCGCCATGTCCTGGGTGCG<br>GCAGGCTCCCGGCAAGGGCCTGGAATGGGTGTCCACC<br>ATCTCCACCGGCGGCACCTACACCTACTACCCCGACAG<br>CGTGAAGGGCAGATTCACCATCAGCCGGGACAACGCC<br>AAGAACTCCCTGTACCTGCAGATGAACTCCCTGCGGGC<br>CGAGGACACCGCCGTGTACTACTGTGCCAGACGGGGC<br>TACTCAGGCGTGGACAAATGGGGCCAGGGCACCACCG<br>TGACAGTGTCCTCCgctagcaccaagggcccaagtgtgtttcccct<br>ggcccccagcagcaagtctacttccggcggaactgctgccctgggttgc<br>ctggtgaaggactacttcccctgtcccgtgacagtgtcctggaactctgg<br>ggctctgacttccggcgtgcacaccttccccgccgtgctgcagagcagc<br>ggcctgtacagcctgagcagcgtggtgacagtgccctccagctctctgg<br>gaacccagacctatatctgcaacgtgaaccacaagcccagcaacacca<br>aggtggacaagagagtggagcccaagagctgcgacaagacccacacc<br>tgccccccctgcccagctccagaactgctgggagggccttccgtgttcct |

TABLE 4-continued

| Amino Acid and Nucleotide Sequence Information for Hybridomas and Humanized Anti-CCR7 Antibodies | |
|---|---|
| | gttcccccccaagcccaaggacaccctgatgatcagcaggacccccga<br>ggtgacctgcgtggtggtggccgtgtcccacgaggacccagaggtgaa<br>gttcaactggtacgtggacggcgtggaggtgcacaacgccaagaccaa<br>gcccagagaggagcagtacaacagcacctacagggtggtgtccgtgct<br>gaccgtgctgcaccaggactggctgaacggcaaagaatacaagtgcaa<br>agtctccaacaaggccctggctgccccaatcgaaaagacaatcagcaa<br>ggccaagggccagccacgggagccccaggtgtacaccctgcccccccag<br>ccgggaggagatgaccaagaaccaggtgtccctgacctgtctggtgaa<br>gggcttctacccctgtgatatcgccgtggagtgggagagcaacggccag<br>cccgagaacaactacaagaccaccccccccagtgctggacagcgacggc<br>agcttcttcctgtacagcaagctgaccgtggacaagtccaggtggcagc<br>agggcaacgtgttcagctgcagcgtgatgcacgaggccctgcacaacc<br>actacacccagaagtccctgagcctgagccccggcaag |
| SEQ ID NO: 612 LCDR1 (Combined) | KSGQSLLDSTGKTYLN |
| SEQ ID NO: 613 LCDR2 (Combined) | LVSKLDS |
| SEQ ID NO: 614 LCDR3 (Combined) | WQGTHFPQT |
| SEQ ID NO: 615 LCDR1 (Kabat) | KSGQSLLDSTGKTYLN |
| SEQ ID NO: 616 LCDR2 (Kabat) | LVSKLDS |
| SEQ ID NO: 617 LCDR3 (Kabat) | WQGTHFPQT |
| SEQ ID NO: 618 LCDR1 (Chothia) | GQSLLDSTGKTY |
| SEQ ID NO: 619 LCDR2 (Chothia) | LVS |
| SEQ ID NO: 620 LCDR3 (Chothia) | GTHFPQ |
| SEQ ID NO: 621 LCDR1 (IMGT) | QSLLDSTGKTY |
| SEQ ID NO: 622 LCDR2 (IMGT) | LVS |
| SEQ ID NO: 623 LCDR3 (IMGT) | WQGTHFPQT |
| SEQ ID NO: 624 VL | DVVMTQSPLSLPVTLGQPASISCKSGQSLLDSTGKTYLNWFLQ<br>RPGQSPRRLIYLVSKLDSGVPDRFSGSGSGTDFTLKISRVEAEDV<br>GVYYCWQGTHFPQTFGGGTKLEIK |
| SEQ ID NO: 625 DNA VL | GACGTGGTGATGACCCAGTCCCCCCTGTCCCTGCCTGTGACC<br>CTGGGCCAGCCTGCCTCCATCTCCTGCAAGTCCGGCCAGTCC<br>CTGCTGGACTCCACTGGCAAGACCTACCTGAACTGGTTCCTG<br>CAGCGGCCTGGCCAGTCCCCTCGGCGGCTGATCTACCTGGT<br>GTCCAAGCTGGACAGCGGCGTGCCCGACAGATTCTCCGGCT<br>CTGGCTCCGGCACCGACTTCACCCTGAAGATCTCCCGGGTG<br>GAAGCCGAGGACGTGGGCGTGTACTACTGCTGGCAGGGCA<br>CCCACTTCCCCCAGACCTTCGGCGGAGGCACCAAGCTGGAA<br>ATCAAG |
| SEQ ID NO: 626 Light Chain | DVVMTQSPLSLPVTLGQPASISCKSGQSLLDSTGKTYLNWFLQ<br>RPGQSPRRLIYLVSKLDSGVPDRFSGSGSGTDFTLKISRVEAEDV<br>GVYYCWQGTHFPQTFGGGTKLEIKRTVAAPSVFIFPPSDEQLK<br>SGTASVVCLLNNFYPREAKVQWKVDNALQSGNSQESVTEQDS<br>KDSTYSLSSTLTLSKADYEKHKVYACEVTHQGLSSPVTKSFNRGE<br>C |
| SEQ ID NO: 627 DNA Light Chain | GACGTGGTGATGACCCAGTCCCCCCTGTCCCTGCCTGTGACC<br>CTGGGCCAGCCTGCCTCCATCTCCTGCAAGTCCGGCCAGTCC<br>CTGCTGGACTCCACTGGCAAGACCTACCTGAACTGGTTCCTG<br>CAGCGGCCTGGCCAGTCCCCTCGGCGGCTGATCTACCTGGT<br>GTCCAAGCTGGACAGCGGCGTGCCCGACAGATTCTCCGGCT<br>CTGGCTCCGGCACCGACTTCACCCTGAAGATCTCCCGGGTG |

TABLE 4-continued

| Amino Acid and Nucleotide Sequence Information for Hybridomas and Humanized Anti-CCR7 Antibodies | |
|---|---|
| | GAAGCCGAGGACGTGGGCGTGTACTACTGCTGGCAGGGCA CCCACTTCCCCCAGACCTTCGGCGGAGGCACCAAGCTGGAA ATCAAGcgtacggtggccgctcccagcgtgttcatcttccccccagcgacg agcagctgaagagtggcaccgccagcgtggtgtgcctgctgaacaacttctac ccccgggaggccaaggtgcagtggaaggtggacaacgccctgcagagcggc aacagccaggagagcgtcaccgagcaggacagcaaggactccacctacagc ctgagcagcaccctgaccctgagcaaggccgactacgagaagcataaggtgt acgcctgcgaggtgacccaccagggcctgtccagccccgtgaccaagagcttc aacaggggcgagtgc |

Example 2: In Vitro Assessment of Antibody Induced ADCC Activity

Capacity of candidate antibodies to mediate ADCC was assessed using a surrogate ADCC reporter assay. CCR7 and CD20 expressing JVM2 cells were used as target cells. JVM2 cells were washed and re-suspended at $8\times10^4$ cells/ml cells/ml. Effector cells in this assay were a Jurkat cell line stably expressing CD16V158 and an NFAT dependent luciferase reporter (Jurkat-V158); expression of luciferase is a surrogate for canonical ADCC signaling through CD16. Briefly, Jurkat-V158 cells grown in suspension were spun down to remove spent media, the pellet was resuspended in assay media and adjusted to $1.6\times10^6$ cells/ml cells/mL. Mix equal volumes of effector and target cells to make a master mix of cells yielding a target to effector cell ratio of 1:5 or 1:20. A titration of antibody was diluted in assay media with a final top concentration of 50 ug/mL in the assay well. 12.5 uL of Ab solution was added to a 384 well round bottom plate and then 12.5 ul of the master cell mix was added. Antibody and cells were mixed well by pipetting and incubated for 4 hours at 37° C. in 5% $CO_2$. Following incubation, 15 uL of Bright Glo substrate (Promega #G7572) was added to each well and shaken for 5 min at RT at 1050 rpm. Luminescent signal was read on the Envision plate reader (Perkin Elmer).

A CD20-targeting antibody was included as a positive control, and showed substantial NFAT signaling, as measured by luciferase activity. Similarly the candidate anti-CCR7 antibodies induced significant ADCC activity (FIG. 1).

The table below summarizes representative results for the various antibody formats run in the ADCC assay using JVM2 and Jurkat-V158 cells.

TABLE 5

ADCC activity of non-humanized and humanized anti-CCR7 antibodies

| | ADCC activity; IC50 (nM) |
|---|---|
| 121G12 non-humanized CysMab | 0.077 |
| 506E15 non-humanized CysMab | 0.131 |
| 674J13 non-humanized CysMab | 1.09 |
| 684E12 non-humanized CysMab | 2.63 |
| 121G12 humanized CysMab | Yes, but insufficient curve fitting |
| 506E15 humanized CysMab | 0.054 |
| 674J13 humanized CysMab | Yes, but insufficient curve fitting |
| CD20 control ADCC | 0.132 |

The ADCC assay was run with non-humanized 506E15 antibody as a representative ADCC-capable anti-CCR7 antibody across various cell lines with a range of CCR7 receptor numbers to determine the minimal receptor density needed for ADCC activity and if there is a sufficient safety margin over normal CCR7+ T cells. The table below summarizes some of the data.

TABLE 6

ADCC activity of non-humanized 506E15 antibody

| Cell line | CCR7 receptor # | 506E15 IC50 (nM) | 506E15 (max RLU) |
|---|---|---|---|
| JVM2 | 66,500 | 0.046 | 5840 |
| MOTN-1 | 64,600 | 0.077 | 5387 |
| DEL | 62,000 | 0.074 | 6480 |
| CMLT-1 | 29,000 | 0.011 | 4400 |
| SR786 | 27,800 | 0.011 | 4067 |
| PEER | 8,700 | 0.038 | 3360 |
| ALL-SIL | 6,200 | 0.008 | 3720 |
| Jurkat V158 | 3,400 | 0.004 | 3267 |
| DND-41 | 1,700 | 0.002 | 3733 |
| Normal T cells | <1.5K | depletion in vivo | n.a. |

The data show that even very low CCR7 receptor levels comparable to CCR7 receptor levels on normal T cells were sufficient to enable significant ADCC activity. ADCC was also assessed using a co-culture viability assay of NK cells with CCR7+ cancer cells and similar findings were collected (not discussed here).

This fits the observation described below that T cell depletion was seen in vivo and found to be ADCC-mechanism based. These findings demonstrate that the ADCC modality is not suitable for CCR7 from a safety perspective. As a consequence all candidates were switched to the Fc silent (DAPA) format to improve overall on-target safety.

Figure 2:
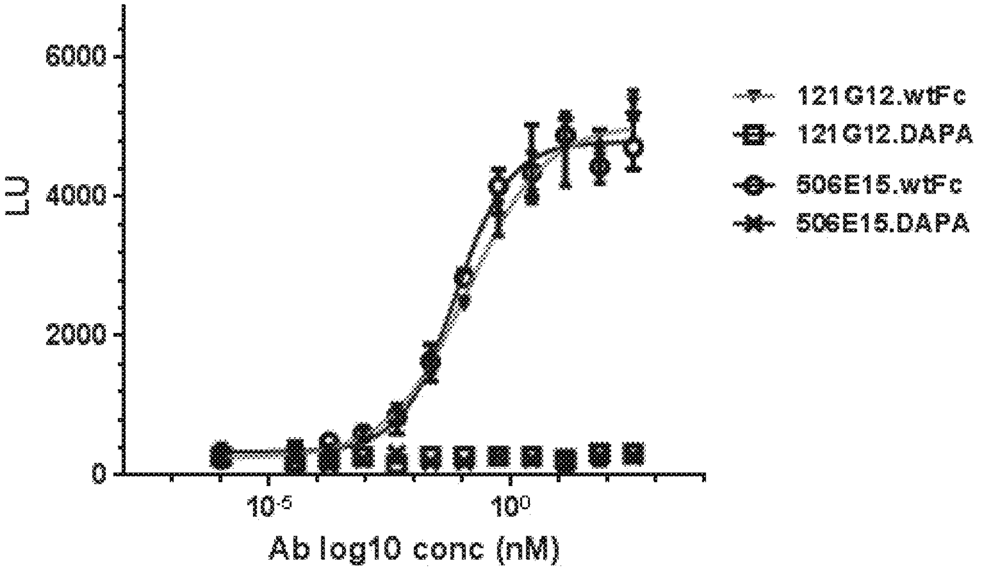
FIG. 2 depicts experimental data on in vitro ADCC activity of DAPA Fc-mutated versions of non-humanized anti-CCR7 antibodies using a surrogate ADCC reporter assay.

The ADCC in vitro reporter assay was repeated and confirmed lack of ADCC activity for the DAPA Fc-mutated versions of the non-humanized anti-CCR7 antibodies (FIG. 2).

Example 3: Biochemical Characterization of Antibodies

Affinities of Anti-CCR7 Antibodies to CCR7

The affinity of various antibodies and ADCs to CCR7 and its species orthologues was determined using FACS. Purified IgGs were titrated to determine EC50 values for binding to cell surface expressed CCR7.

For this purpose, CCR7 positive cells were harvested (adherent cells were detached with Accutase), washed twice with FACS buffer (PBS/3% FCS/0.02% sodium azide) and diluted to approximately $2\times10^6$ cells/ml in FACS buffer. All subsequent steps were done on ice to prevent internalization of the receptor. 100 µl cell suspension/well were transferred into 96-well U-bottom plates (Falcon). $2\times10^5$ cells/well were incubated with a serial dilution of antibody concentrations of the anti-CCR7 antibody-of-interest ranging across several logs, starting at a high of 100 nM for 60 minutes at 4° C., gently shaking. Following incubation, cells were spun down (1200 rpm, 2 min, 4° C.) and washed three times with FACS buffer. A fluorophore-conjugated anti-hFc gamma-APC (Jackson ImmunoResearch) detection antibody was added at 1:400 and samples were incubated for 1 h on ice in the dark, gently shaken. After a final wash, cells were resuspended in 100 µl of FACS buffer containing 0.2 µg/ml DAPI followed by readout on the flow cytometry machine (BD LSRFortessa Cell Analyzer; Cat #647177). Mean fluorescence intensity (MFI) of live, single cells was calculated in Flowjo 10.0.8 and exported into Graphpad Prism6 for EC50 determination.

Selectivity was assessed by measuring apparent binding affinities to isogenic cell pairs engineered to overexpress CCR7 as well as cell lines expressing CCR7 paralogs, e.g., CCR9, CCR6, CXCR4 and CCR8. All anti-CCR7 antibodies bind in a specific manner to CCR7 expressing cells only, as shown in Table 7 below.

TABLE 7

Binding of Various Anti-CCR7 Antibodies to CCR7 Expressing Cells

| Humanized CysMab | Apparent FACS binding (at 5 ug/ml) | | | |
|---|---|---|---|---|
| (Fc Wild Type) antibody | 121G12 | 506E15 | 674J13 | 684E12 |
| NIH3T3 cells | No binding | No binding | No binding | No binding |
| NIH3T3.hCCR7 | Binding | Binding | Binding | Binding |
| PF382 cells (CCR7−/CCR9+/CCR6+) | No binding | No binding | No binding | No binding |
| HEK293-CXCR4 | No binding | No binding | No binding | No binding |
| CHO-CCR8 | No binding | No binding | No binding | No binding |

In a similar experiment the antibodies were tested for cross-reactivity using engineered isogenic matched cell line sets (NIH3T3 series) and CD4+ T cells, which were purified from several PBMC batches from healthy donors as well as cynomolgus monkeys, Wistar rats and CD-1 mice. All antibodies were found to specifically bind human and cynomolgus monkey CCR7 at similar apparent affinities, as shown in Tables 8 & 9 below. Only the non-humanized 121G12 antibody is rodent cross-reactive.

TABLE 8

Cross-Reactivity of Various Non-Humanized Anti-CCR7 Antibodies

| Non-humanized | Apparent FACS Affinity; EC50 (nM) | | | |
|---|---|---|---|---|
| CysMab antibody | 121G12 | 506E15 | 674J13 | 684E12 |
| Human CD4+ T cells | 22-30 | 4.6-9.7 | 0.39-1.4 | n.d. |
| Cyno CD4+ T cells | 5.8-12 | 6.6 | 0.45 | n.d. |
| Mouse CD4+ T cells | 48-51 | No binding | No binding | n.d. |
| Rat CD4+ T cells | 18-31 | No binding | No binding | n.d. |
| NIH3T3.human CCR7 | 1.3 | n.d. | 3.6 | >30 |
| NIH3T3.cyno CCR7 | 1.3 | n.d. | n.d. | Binding |
| NIH3T3.mouse CCR7 | 2.5 | No binding | No binding | No binding |
| NIH3T3.rat CCR7 | 2.4 | No binding | No binding | No binding |
| Jeko-1 cancer cells (CCR7+) | 1.5 | n.d. | n.d. | 12 |

TABLE 9

Cross-Reactivity of Various Humanized Anti-CCR7 Antibodies

| Humanized | Apparent FACS Affinity; EC50 (nM) | | | |
|---|---|---|---|---|
| CysMab antibody | 121G12 | 506E15 | 674J13 | 684E12 |
| Human CD4+ T cells | 30-34 | 7.8-11 | 0.87-2.7 | 6.7 |
| Cyno CD4+ T cells | 12 | 7 | 0.5 | n.d. |
| NIH3T3.human CCR7 | 1 | n.d. | n.d. | n.d. |
| NIH3T3.cyno CCR7 | 0.9 | n.d. | n.d. | n.d. |

In order to determine receptor density impact on apparent affinity, and therefore the contribution avidity makes to cellular binding of antibody, FACS titration experiments were run on human CCR7 expressing cancer cell lines with varied expression levels and normal CCR7-positive PBMC-derived T cells. Receptor quantification was performed via FACS using microspheres from Bangs Laboratories as count standards and following the manufacturer's instructions. Exemplary results are shown in Table 10 below.

TABLE 10

Contribution of Avidity to Apparent Affinity in Correlation with Receptor Density

| Humanized CysMab.DAPA | CCR7 Receptor | Apparent FACS Affinity; EC50 (nM) | | | |
|---|---|---|---|---|---|
| antibody | density | 121G12 | 506E15 | 674J13 | 684E12 |
| NIH3T3.hCCR7 cells | >1,000,000 | 2.5 | 1.8 | 0.64 | n.d. |
| DEL cancer cells | ~100,000 | 1.78 | 3.09 | 0.47 | n.d. |
| Human CD4+ T cells | <2,000 | ~30 | ~10 | ~2 | ~7 |

All anti-CCR7 antibodies show substantial contribution of avidity to apparent affinity and the strength of binding decreased in correlation with receptor density. Especially 121G12 shows significantly weaker binding on low CCR7 expressing cells as represented by normal CD4+ T cells compared to indication-representative DEL cancer cells.

The relatively weak affinity of especially 121G12, which shows the strongest avidity effect among the anti-CCR7 antibodies, is optimal to utilize the receptor density difference between normal and cancer cells as a way to bias antibody binding to cancer cells.

Binding to Recombinant hCCR7 in ELISA

Binding and affinity was also assessed in an ELISA-based assay using recombinant CCR7 (Origene #TP306614). Maxisorp™ 384-well plates (Thermo Nunc) were coated with 3.5 μg/ml of recombinant CCR7 diluted in PBS. After blocking with 3% BSA (bovine serum albumin) in PBS for 1 hr at room temperature, washing plates 3× with PBS-T (0.01% Tween 20 in PBS), primary antibodies were added in a serial dilution and incubated for 1 hr at room temperature. Plates were washed again and bound antibodies were detected by incubation with 1:5000 anti-hFc gamma conjugated to horseradish peroxidase (HRP; Jackson ImmunoResearch, Cat #115-035-098) for 1 hr at room temperature followed by washing with PBS-T and afterwards addition of SureBlue Peroxidase substrate (KPL, #52-00-03) substrate. After 15 min, absorbance at 650 nM was recorded and analyzed in GraphPad Prism6.

Figure 3:
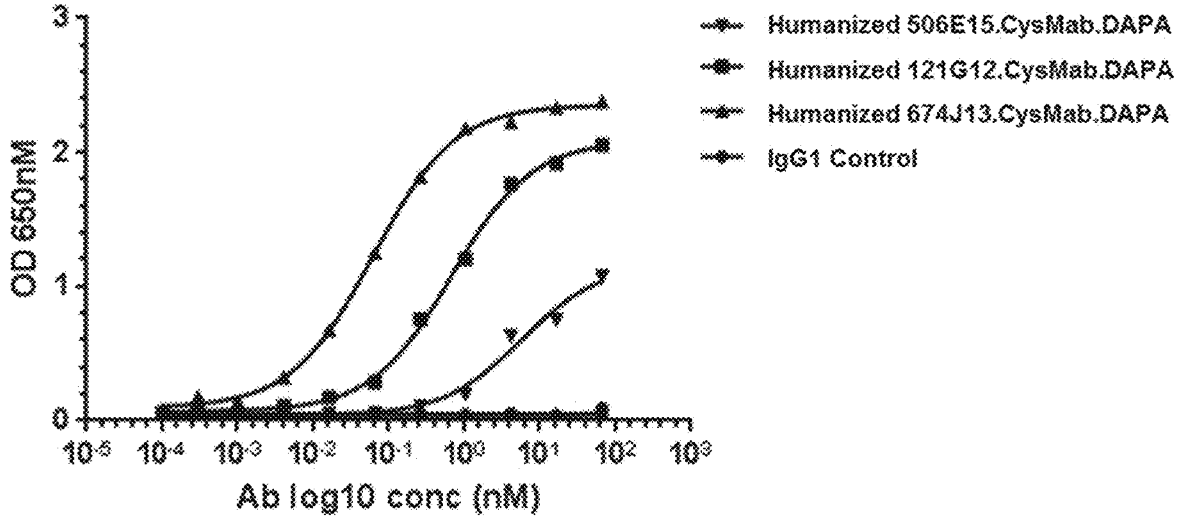
FIG. 3 depicts experimental data on binding to recombinant hCCR7 by anti-CCR7 antibodies in CysMab.DAPA format using an ELISA-based assay.

All tested anti-CCR7 antibodies are capable of binding recombinant hCCR7 (Table 11; FIG. 3).

TABLE 11

Binding Affinity of Humanized Anti-CCR7 Antibodies to Recombinant hCCR7

| Humanized CysMab antibody | Affinity, Kd (nM) |
|---|---|
| 121G12.DAPA | 0.677 |
| 506E15.DAPA | 5.731 |
| 674J13.DAPA | 0.006 |

Binding to Dual FabGraft

A FabGraft ELISA was performed to assess binding to a minimal epitope space, which comprises the N-terminus and EC2 of CCR7. In short, Maxisorp™ 384-well plates (Thermo Nunc) were coated with 5 μg/ml of FabGraft. Otherwise the generic ELISA protocol instructions as described above were followed. All anti-CCR7 antibodies are capable of binding the dual FabGraft as shown in Table 12 below.

TABLE 12

Binding Affinity of Humanized Anti-CCR7 Antibodies to FabGraft

| Humanized CysMab antibody | ELISA; Kd (nM) |
|---|---|
| 121G12.DAPA | 0.023 |
| 506E15.DAPA | 0.025 |
| 674J13.DAPA | 0.023 |

pH Dependency ELISA with VLPs

It is known that CCR7-bound CCL19 internalizes the receptor-ligand complex. However, while CCR7 recycles back to the cell surface, CCL19 is sorted to the lysososme for degradation, showing opposite fate for endocytosed CCR7 and its ligand (Otero et al., J Immunol 2006; 177: 2314-2323). For a successful anti-CCR7 ADC it is preferable that the antibody behaves similar to the ligand, e.g., internalizes rapidly, but does not recycle back out with CCR7. In order to accomplish this, we made sure to select ph-dependent antibodies, which would display weaker binding to CCR7 under low pH conditions.

To assess pH-dependency of the anti-CCR7 antibodies, an ELISA was performed using CCR7-expressing virus-like particles (VLPs). In short, Maxisorp™ 384-well plates (Thermo Nunc) were coated with 25 μg/ml of VLPs. Primary antibodies were incubated either in pH5.8 (1:1; $dH_2O$: 0.1M Citrate buffer, 150 mM NaCl) or pH7.4 buffer. Otherwise the generic ELISA protocol instructions as described above were followed.

Among a number of humanization variants for each candidates, comparison of antibody binding at neutral (7.4) and acidic (5.8) pH showed that all CCR7 candidate antibodies have improved affinity at pH 7.4 (Table 13). The entities below were chosen based on their superior ph-dependency among other features.

TABLE 13 pH Dependency of Humanized Anti-CCR7 Antibodies to CCR7-Expressing VLPs

| | ELISA; Kd (nM) | | |
|---|---|---|---|
| Humanized CysMab antibody | pH 7.4 buffer | pH 5.8 buffer | fold change (pH 5.8/7.4) |
| 121G12 | 0.1411 | 0.5207 | 4 |
| 506E15 | 0.0571 | 0.4942 | 9 |
| 674J13 | 0.0162 | 0.1657 | 10 |
| 684E12 | 0.0374 | 0.5041 | 13 |

bArrestin Assay

To determine functionality of the anti-CCR7 antibodies, the β-Arrestin assay was performed using the PathHunter Flash Detection Kit from DiscoverX (#93-0247) either in agonistic mode for assessment of agonistic function or antagonistic mode for assessment of antagonistic function.

In the agonistic mode, CHO-flpin-hCCR7 (cell line made by DiscoverX expressing hCCR7 tagged with ProLink, β-arrestin-EA) were seeded at $8\times10^4$ cell/well in 20 μl/well in growth medium (Ham's F-12/Glutamax medium; Invitrogen+10% FBS+0.5 mg/ml G418+0.2 mg/ml hygromycinB; Invitrogen+5 μg/ml Blasticidin; Gibco) with Dox 100 ng/ml in 384-well plates, covered with metal lids, incubated at 37° C. 5% $CO_2$ overnight. The next day, a serial dilution of a 5× working solution in 1× assay buffer (20 mM HEPES/0.1% BSA/1×HBSS pH7.4) was made with test antibodies or positive control, using the ligand hCCL19 (R&D, 361/MI-025/CF). 5 μl of the 5× working solution of antibodies or ligand were added to each well, briefly spun down, and incubated at 37° C./5% $CO_2$ for 2 h. Following incubation, 25 μl of detection reagent were added to each well, incubated at room temperature in the dark while shaking for 20 min. Then, the luminescence signal for enzyme activity was measured on the Envision machine. Finally, enzyme activity was analyzed using Excel.

In the antagonistic mode, CHO-flpin-hCCR7 cells were seeded as described above. The next day, a 6× working solution (0.5 μM×6=3.0 μM) in 1× assay buffer was made for each test antibody or positive control MAB197 (R&D reference antibody; ligand antagonist) or negative control hIgG. 5 μl of the 6× working solution of antibodies or controls were added to each well, briefly spun down, and incubated at 37° C./5% $CO_2$ for 30 min. During incubation, serial dilutions of a 6× working solution in 1× assay buffer were made for hCCL19. Following incubation, 5 μl of the 6× working solution of hCCL19 were added to each well, briefly spun down, and incubated at 37° C./5% $CO_2$ for 90 min. Following incubation, 25 μl of detection reagent were added to each well, incubated at room temperature in the dark while shaking for 20 min. Then, the luminescence signal for enzyme activity was measured on the Envision machine and analyzed in Excel.

Figure 4A:
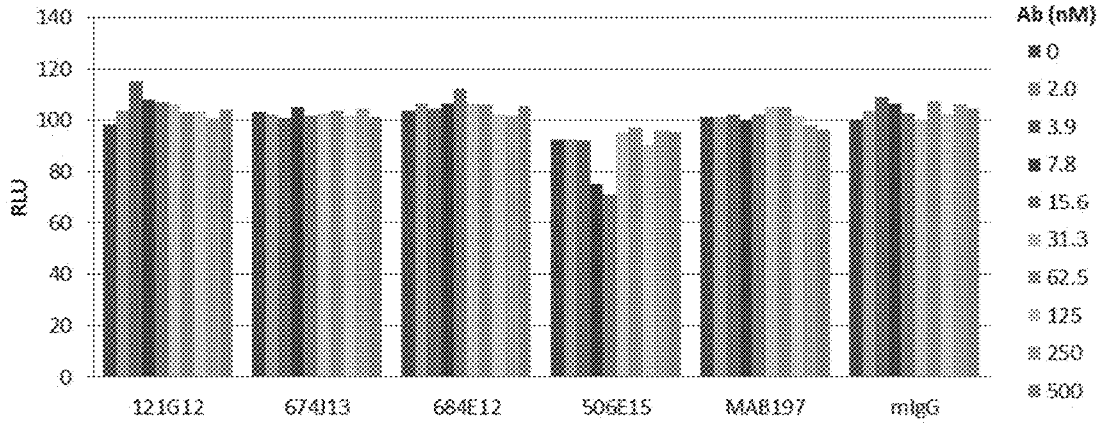
FIG. 4A-C depicts experimental data on functionality of parental anti-CCR7 antibodies using a β-Arrestin assay in agonistic mode (FIG. 4A) and antagonist mode (FIG. 4B, FIG. 4C).
Figure 4B:
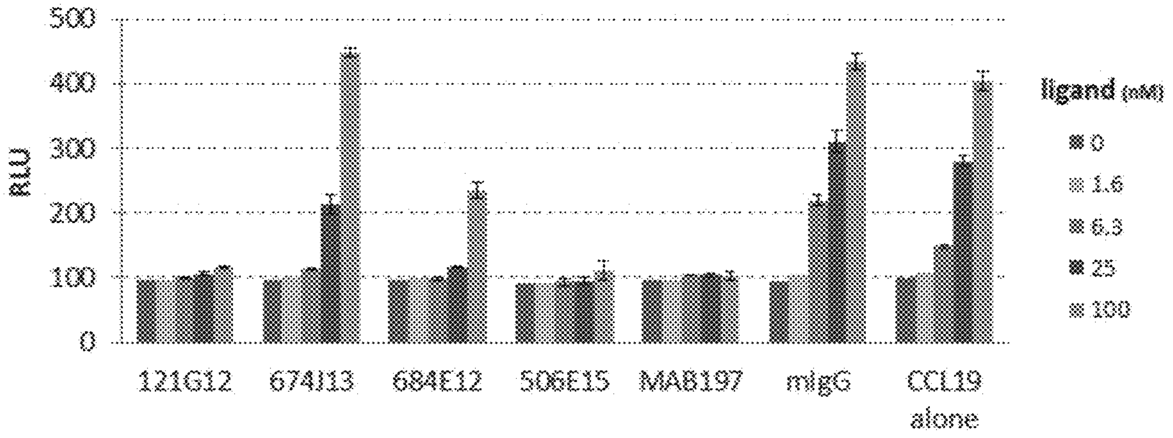
Figure 4C:
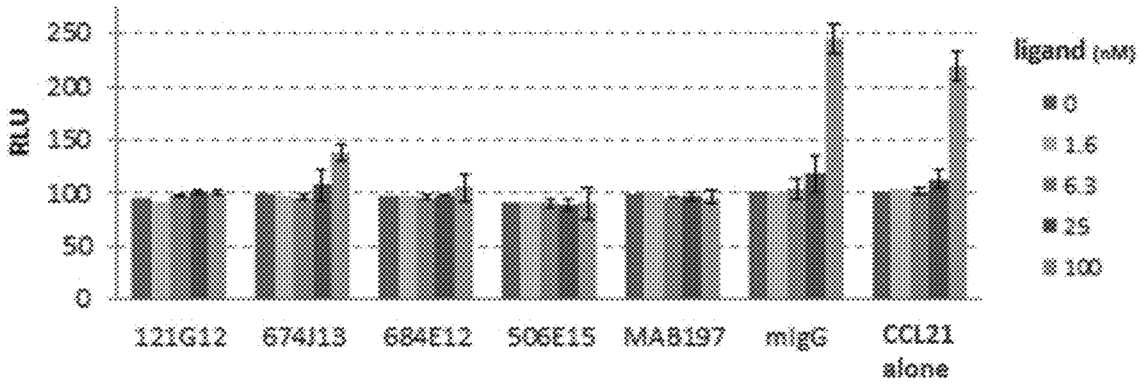

None of the parental anti-CCR7 antibodies showed activity in the agonistic model (FIG. 4A). However, when run in antagonistic format, 506E15 and 121G12 were identified as strong antagonists, e.g., ligand blocking antibodies (FIGS. 4B, 4C). 674J12 is a neutral, non-ligand blocking antibody. 684E12 is a weak antagonist.

FACS Competition Assay with Ligand

To confirm antibody competition with the CCR7 ligand, the FACS assay was run in presence of excess ligand concentration. The FACS assay was performed as described above. Some changes were made to the protocol, e.g., CCL19 was kept at a constant concentration of 1 μM, while the primary antibody was simultaneously applied to DEL cells ranging across several logs, starting at a high of 100 nM. After an incubation time of 30 min in ice-cold FACS buffer, cells were washed, secondary anti-hFc.PE antibody was applied for 15 min and MFI was determined as described above.

Figure 5:
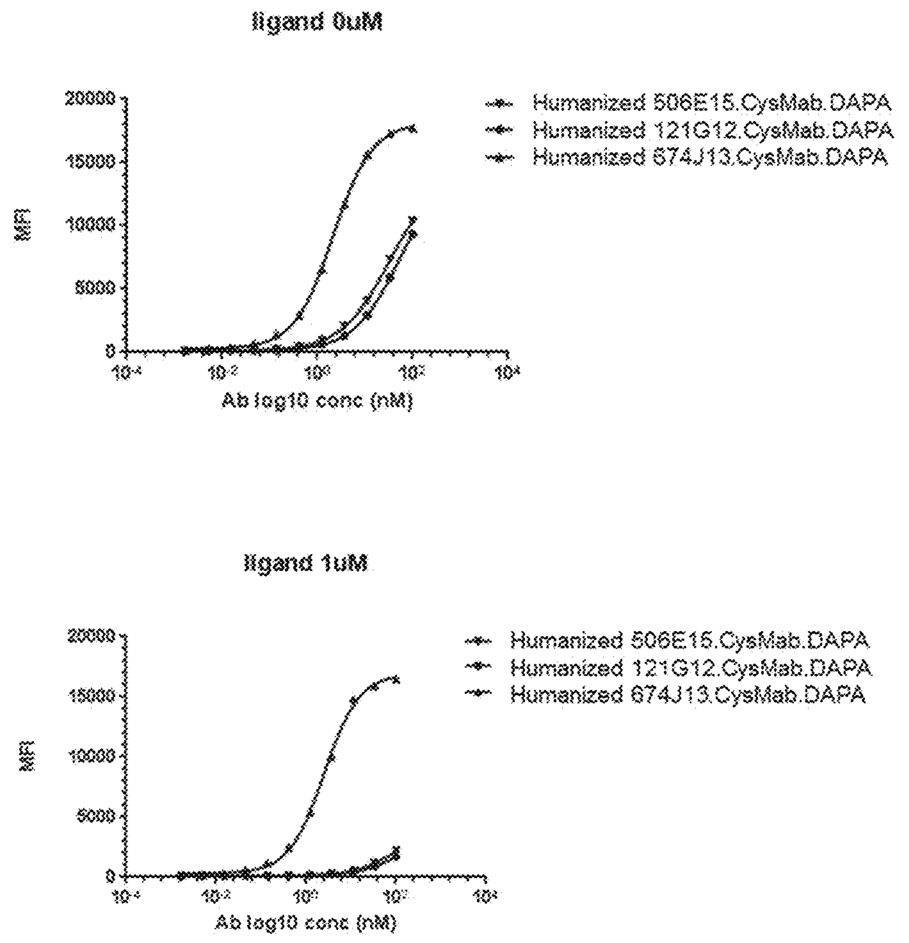
FIG. 5 depicts experimental data on competition with the CCR7 ligand by anti-CCR7 antibodies in CysMab.DAPA format using a FACS assay.

FIG. 5 shows that humanized CysMab.DAPA 674J13 is not impacted by the presence of excess CCL19, confirming its neutral functionality. Humanized CysMab.DAPA 121G12 and 506E15 are indeed strongly impacted in their binding affinity by the presence of excess ligand.

Internalization Capabilities Across Cell Lines with a Range of Receptor Densities Another aspect of a successful anti-CCR7 ADC is to ensure optimal usage of the differential expression distribution of CCR7. As a representative of normal CCR7 expressing cells, CD4+ T cells were isolated from healthy donor PBMCs. In addition, a number of CCR7-positive cancer cell lines were chosen displaying a range of receptor densities. We had purposely chosen antibodies with weaker apparent FACS binding affinities on CCR7+ T cells than CCR7+ cancer cells. In addition, the here described pHrodo assay utilizes a low pH-activated fluorophore-label on the anti-CCR7 antibodies to assess, if antibody uptake into cells as measured by fluorescence, correlates to receptor density. It is preferable to minimize antibody uptake to normal cells to maximize the therapeutic window.

Briefly, labeling of the anti-CCR7 antibodies in CysMab format with maleimide-pHrodo (ThermoFisher) was performed following the manufacturer's instructions yielding DAR=4 (drug, e.g., fluorophore to antibody ratio) entities. The FACS assay was performed as described above. Some changes were made to the protocol, e.g., to allow for internalization, the primary antibody was incubated at 5 μg/ml with cells at 37° C. in culture medium for 6 h, then washed with ice-cold FACS buffer containing sodium azide to stop the reaction.

Table 14 below summarizes the internalization capabilities of three antibodies across a panel of cell lines. A non-targeting pHrodo-labeled antibody was used as control and it was found that up to 400 MFI constitutes background noise of signal, e.g., non-target mediated antibody-conjugate uptake. The data show that all three anti-CCR7 antibodies require CCR7 receptor levels in the range that is typical for most CCR7+ cancer lines, e.g., above 20,000 receptors, to efficiently internalize and accumulate conjugated matter, while sparing normal CD4+ T cells.

TABLE 14

Internalization Capabilities of Various Anti-CCR7 Antibodies

| Cell Line | Receptor numbers | pHrodo (6 h MFI) Humanized 121G12.CysMab. DAPA | Humanized 506E15.CysMab. DAPA | Humanized 617J13.CysMab. DAPA |
|---|---|---|---|---|
| CD4+ T cells | 2000 | 278 | 429 | 402 |
| JVM3 | 8717 | 148 | 238 | 146 |
| CMLT1 | 19583 | 301 | 465 | 561 |
| Jeko-1 | 28852 | 450 | 908 | 1389 |
| Mec2 | 50840 | 1340 | 3089 | 3004 |
| L1236 | 61602 | 1237 | 3126 | 5824 |
| MOTN1 | 84200 | 1026 | 2899 | 2539 |
| DEL | 110685 | 1913 | 3058 | 3777 |
| MJ | 111121 | 1649 | 3870 | 3259 |
| KE97 | 152093 | 1567 | 2723 | 4416 |
| L540 | 167549 | 6836 | 16117 | 11800 |

Epitope Binning Using Octet Red96 System

Epitope binning of anti-hCCR7 parental antibodies was performed using the Octet Red96 system (ForteBio, USA) that measures biolayer interferometry (BLI). The CCR7 immunogen scaffold was biotinylated via an AviTag™ utilizing BirA biotin ligase according to Manufacturer's recommendations (Avidity, LLC, USA cat #BirA500). The biotinylated immunogen scaffold was loaded at 1.5 μg/ml onto pre-equilibrated streptavidin sensors (ForteBio, USA). The sensors were then transferred to a solution containing 100 nM antibody A in 1× kinetics buffer (ForteBio, USA). Sensors were briefly washed in 1× kinetics buffer and transferred to a second solution containing 100 nM of competitor antibody. Binding kinetics was determined from raw data using the Octet Red96 system analysis software (Version 6.3, ForteBio, USA). Antibodies were tested in all pairwise combinations, as both Antibody A and as competitor antibody.

TABLE 15

Antibody Binning Results

| Bin | Antibody |
|---|---|
| 1 | 684E12; MAB197 |
| 2 | 674J13 |
| 3 | 506E15 |
| 4 | 121G12 |

Epitope Mapping Using CCR7 Mutations

Additional epitope mapping was carried out utilizing mutant CCR7 cell lines. NIH/3T3 cell lines expressing mutated variants of human CCR7 were generated. Mutations were introduced at specific positions to exchange the human CCR7 residue into the corresponding murine CCR7 residue. Mutations generated included D35E, F44Y, L47V, S49F, D198G, R201K, S202N, S204G, Q206D, A207T, M208L, I213V, T214S, E215A, and H216Q. The mutant CCR7 plasmid constructs were generated by site-directed mutagenesis and introduced into NIH/3T3 cells to produce stable-expressing cell lines. Specific binding of candidate antibodies to each mutant CCR7 cell line was assessed by flow cytometry. Cells were rinsed thoroughly with PBS and treated with Accutase (Millipore #SCR005) to lift from growth plates and resuspended at approximately $1*10^5$ cells/90 μL in 1×FACS buffer (2% FBS+0.1% NaN3 in PBS). In a 96-well U-bottom plate, 10 μL of 10× antibody solution in FACS buffer was pre-seeded and 90 μL of cell suspension was added. Cell were incubated for 30 minutes at 4° C., washed 1× with cold PBS and resuspended in 100 μL of 1:500 secondary antibody 1×FACS buffer (Allophycocyanin conjugated F(ab')2 goat anti-human IgG, Fcγ specific; Jackson Immunoresearch, Cat #109-136-098). After additional incubation for 15 min at 4° C., cells were washed twice with PBS and resuspended in 100 μL of 1×FACS buffer+4 μg/mL propidium iodide (Life Technologies, Cat #P3566). Geometric mean fluorescence intensity was calculated on live single cells using FlowJo and plotted as % of WT CCR7 Geometric mean fluorescence intensity.

Figure 6:
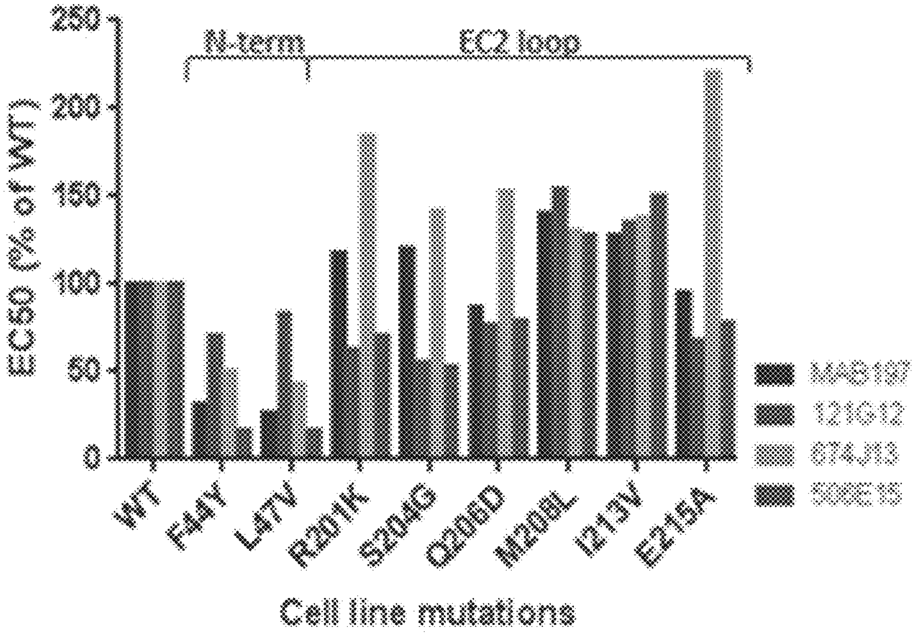
FIG. 6 depicts experimental data on epitope mapping of parental anti-CCR7 antibodies using mutated CCR7 proteins.

EC50-based affinities to point mutated CCR7 show that all tested antibodies have different binding profiles, implying different utilization of a conformational epitope (FIG. 6). Out of all shown antibodies, 506E15 has the most similar binding pattern to MAB197, e.g., both show a significant drop in binding affinity when residues F44 or L47 in the N-terminus of CCR7 are mutated, but not, when M208 or 1213 in the EC2 loop are mutated. 121G12 and 674J13 seem to utilize a different set of crucial contact points within the conformational epitope space, as they differ from MAB197 in at least 4 of the 8 tested point mutations.

Example 4: Generation and Characterization of CCR7 Antibody Drug Conjugates

In the section below, uL and μL are used interchangeably to refer to microliter. Similarly, uM and μM are used interchangeably to refer to microMolar: and um is used to refer to micrometer.

Example 4A: Preparation of Antibody Drug Conjugate 121G12.CysMab.DAPA.MPET.DM4

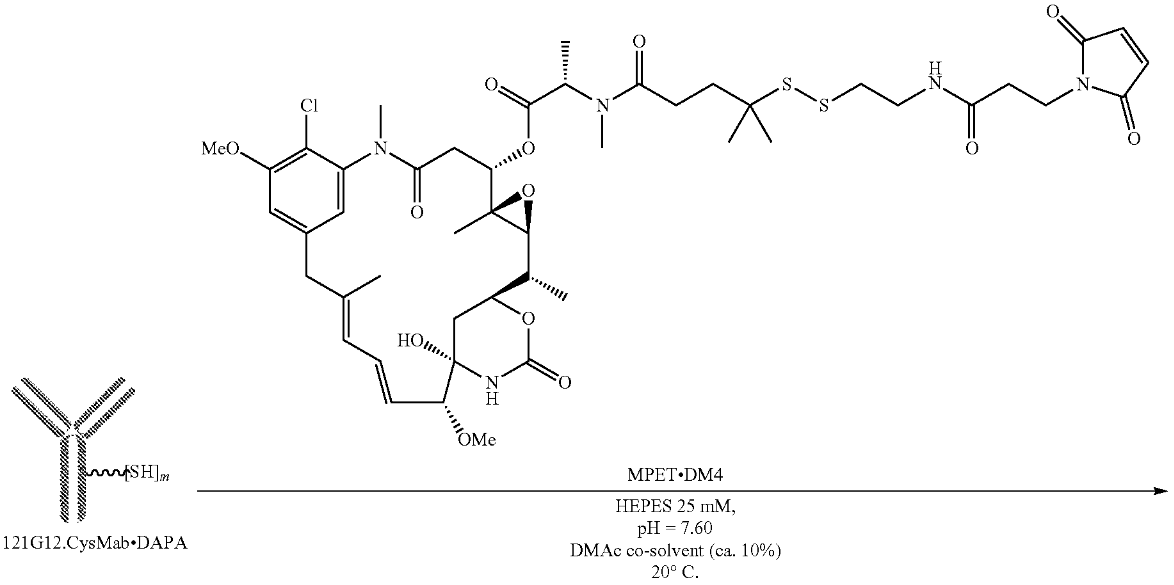

121G12.CysMab•DAPA

-continued

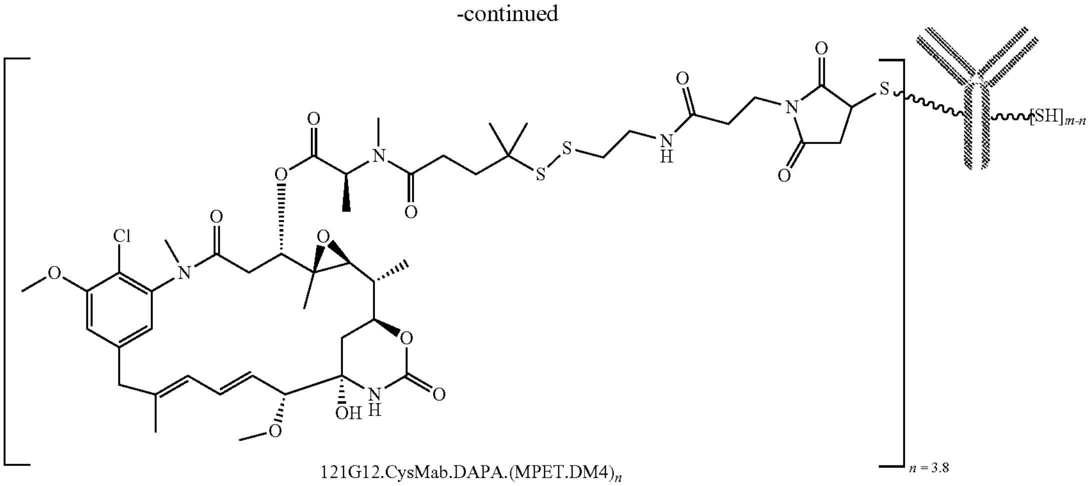

121G12.CysMab.DAPA.(MPET.DM4)$_n$

Conjugation of Purified 121G12.CysMab.DAPA and MPET.DM4:

Starting material was 121G12.CysMab.DAPA antibody at 127 mg/ml (OD280 with an extinction coefficient of 13.7 for a 10 mg/ml IgG solution) in 10 mM histidine hydrochloride buffer. To 7.9 ml of antibody (1003 mg) was added 16 ml of 0.5M sodium phosphate pH 8 (Teknova S1280), pH was verified as >7, then antibody was absorbed to 100.3 ml of RMP Protein A resin (GE Healthcare 1-223BPO/I) for 25 minutes with gentle swirling at room temperature. The resin, loaded at 10 mg Ab/ml bed was washed with 15 bed volumes of 1×PBS buffer (Hyclone SH30256.02) by vacuum filtration through a bottletop 0.2 um filter unit (Nalgene 567-0020), then re-suspended in 100.3 ml of 1×PBS to yield a 50% slurry.

To the slurry was added 4329 ul of 0.5M cysteine (Sigma G121-03) formulated in 0.5 M phosphate pH 8 to which NaOH (Alfa Aesar A16037) had been added at ratio of 13.6 g/L. Slurry was occasionally swirled at room temperature for 30 minutes, then washed by vacuum filtration through a bottletop 0.2 um filter unit with 50 bed volumes of 1×PBS in at least 10 cycles of filtration and addition. The washed resin was re-suspended in 100.3 ml of 1×PBS (50% slurry) and 1003 ul of 100 uM $CuCl_2$ (Aldrich 751944) was added (net 500 nM $Cu2^+$) to initiate reoxidation. The reoxidation of the antibody was tested by removing a 30 ul aliquot of slurry, adding 1 ul of a 20 mM stock of a reference maleimide (Example 3, page 110 of WO2015/095301), which is known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 μm particles, 4000 Å pore size) equilibrated to 0.1% trifluoroacetic acid in 29.5% $CH_3CN$/water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 60 minutes), 3010 ul of a 20 mM stock of MPET.DM4 in DMSO was added and slurry was occasionally gently swirled at room temperature for 30 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (201 ml) was neutralized with 20.1 ml of 0.5M sodium phosphate pH 8, then concentrated to 60 ml using spin concentrators (Amicon UFC905024) at 3,000×g. The concentrate was then applied to 24×PD-10 buffer exchange columns (GE Healthcare 17-0851-01) equilibrated to 1×PBS, loading 2.5 ml of concentrate and eluting with 3.5 ml of 1×PBS as per manufacturer.

For stability studies, material was pooled with an identically prepared batch to provide 2 grams of starting material. The pooled material was dialyzed extensively (Slidealyzer flask, Thermo Scientific 87762) against 10 mM histidine chloride buffer pH 5 (histidine from JTBaker 2080-05), concentrated to ~30 mg/ml, then sucrose (Millipore 1.00892.1003) and Tween 20 (JTBaker 4116-04) were added to 240 mM and 0.02% (v/v) respectively. Material in excess to that required for stability studies was back-exchanged to 1×PBS. Samples were aliquotted and flash-frozen with liquid nitrogen and stored at −80° C. Final concentrations were 23.9 mg/ml for the material formulated for stability testing and 18.9 mg/ml for the material formulated in 1×PBS.

Analytics on the resultant samples are as follows:

| Parameter | Stability sample | 1xPBS sample |
|---|---|---|
| Concentration (mg/ml) | 23.9 | 18.9 |
| Pyrogen (EU/ml) | 0.1 | 0.05 |
| % aggregate | <1 | <1 |
| DAR | 3.79 | 3.79 |

Analytics Methods: Concentration was determined by OD280 with an extinction coefficient of 13.7 for a 10 mg/ml IgG solution. Pyrogen was determined using Kinetic QCL assay (Lonza Walkersville 50-650H) read on a TECAN Safire plate reader. Percent aggregate was determined by analytical size exclusion chromatography on a Shodex KW-G guard (Thomson Instrument Company Cat #6960955) and KW-803 column (TIC Cat #6960940) equilibrated with mobile phase [20 mM Tris ~pH7.65 (prepped w/10 mM Tris pH7.4, 10 mM Tris pH8), 200 mM NaCl, 0.02% sodium azide], with data acquisition at 280 nm. An aliquot of the sample was prepared for DAR determination was prepareded by diluting the sample to 2 mg/ml in 1×PBS, deglycosylating the sample with PNGaseF (in-house) for 10 minutes at 50° C., removing the PNGaseF by binding to protein A, washing with 1×PBS, and eluting with 1% formic acid. Sample was then injected onto an 2.1×50 mm PLRP-S column (8 μm particles, 1000 Å poresize), equilibrated to 0.1% formic acid in 20% $CH_3CN$/water (Invitrogen) running at 0.5 ml/min. The column was washed at 20% $CH_3CN$/water for 3 minutes then eluted with a 0.1 minute gradient to 0.10% formic acid 90% $CH_3CN$/water which was maintained for 1.9 minutes. Mass spectral data was taken on an Agilent 1260 instrument and deconvoluted with MassHunter Qualitative Analysis B.05.00 in a range 110-180 kDa. Peak areas corresponding to various calculated DAR states were weighted according to DAR of each peak, then summed and weighted area of the DAR4 peak was divided by the sum of all weighted peaks to obtain the DAR value.

Preparation of the Linker Payload MPET.DM4:

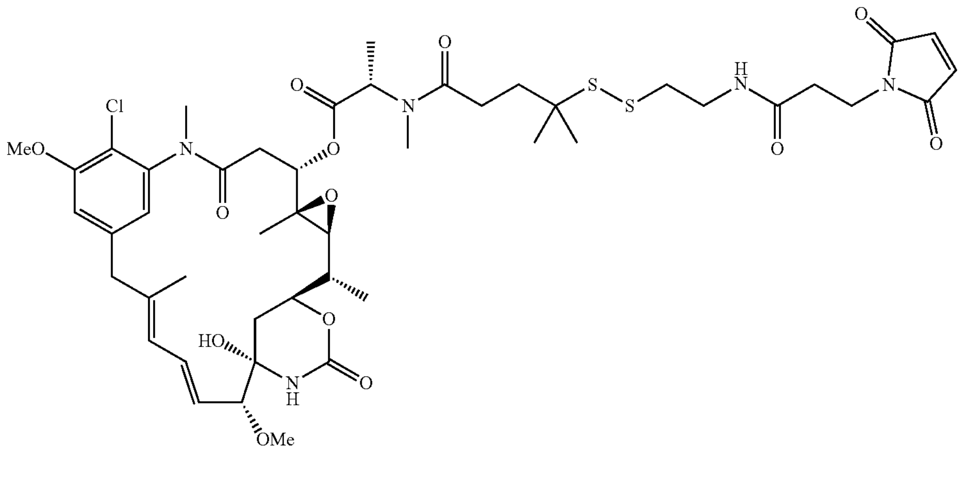 [SMILES: COc1cc2cc(c1Cl)N(C)C(=O)C[C@H](OC(=O)[C@H](C)N(C)C(=O)CCC(C)(C)SSCCNC(=O)CCN1C(=O)C=CC1=O)[C@]1(C)O[C@H]1[C@H](C)[C@@H]1C[C@@](O)(NC(=O)O1)[C@H](OC)/C=C/C=C(\C)C2]

Analytical Methods

Unless otherwise indicated, the following HPLC and HPLC/MS methods were used in the preparation of Intermediates and Examples.

LC/MS analysis was performed on an Agilent 1200sl/6140 system.

Column: Waters Acquity HSS T3 C18, 50×2.0, 1.8 um

Mobile Phase: A) $H_2O$+0.05% TFA; B: acetonitrile+0.035% TFA

Pump Method:

| Time | A % | B % | Flow (mL/min) |
|---|---|---|---|
| 0 | 90 | 10 | 0.9 |
| 1.35 | 0 | 100 | 0.9 |
| 1.36 | 0 | 100 | 0.9 |
| 1.95 | 0 | 100 | 0.9 |
| 1.96 | 90 | 10 | 0.9 |
| 2.0 | 90 | 10 | 0.9 |

Detection: UV Diode Array at 190 nm-400 nm

MS Scan: 200-1350 amu

ELSD: 60° C.

MS Parameters:

| | |
|---|---|
| Polarity | Positive |
| Drying Gas | 12 |
| Nebulizer Pressure | 50 |
| Drying Gas Temperature | 350 |
| Capillary Voltage | 3000 |

(14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-((2-(3-(2,5-dioxo-2,5-dihydro-1H-pyrrol-1-yl)propanamido)ethyl)disulfanyl)-4-methylpentanoyl)-N-methyl-L-alaninate
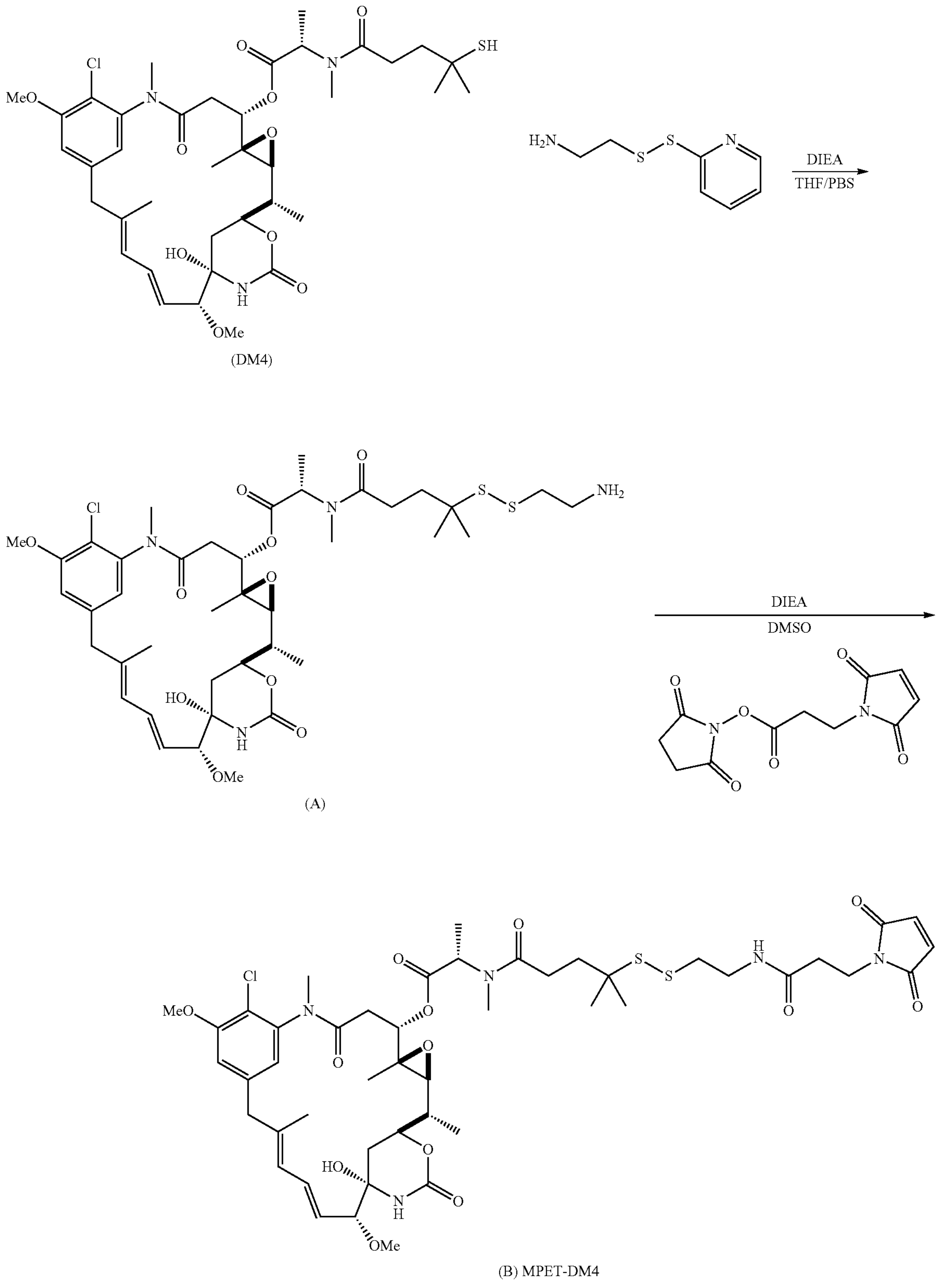
(DM4)
(A)
(B) MPET-DM4

Step 1: Preparation of (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-((2-aminoethyl)disulfanyl)-4-methylpentanoyl)-N-methyl-L-alaninate To DM4 (480 mg, 0.62 mmol) dissolved in PBS buffer (10.5 mL) and anhydrous THF (21 mL) were added 2-(pyridin-2-yldisulfanyl)ethan-1-amine (151 mg, 0.68 mmol) and DIEA (0.27 mL, 1.54 mmol) at room temperature. The reaction mixture was stirred at room temperature for 30 min and concentrated in vacuo. The aqueous residue was diluted with $CH_3CN$ (1 mL) and $H_2O$ (2 mL) and purified by reverse phase ISCO, eluted with 10-60% acetonitrile-$H_2O$ containing 0.05% TFA. Fractions containing desired product were lyophilized to obtain desired product (555 mg, 93% yield). $^1H$ NMR (400 MHz, MeOD-$d_4$) δ ppm 0.83 (s, 3H) 1.21 (d, J=5.0 Hz, 3H) 1.25 (s, 3H) 1.28 (s, 3H) 1.30 (d, J=5.0 Hz, 3H) 1.45-1.55 (m, 3H) 1.67 (s, 3H) 1.84-1.88 (m, 1H) 1.95-2.01 (m, 1H) 2.14 (dd, J=5.0 and 15.0 Hz, 1H) 2.37-2.43 (m, 1H) 2.53-2.59 (m, 1H) 2.64 (dd, J=10.0 and 15.0 Hz, 1H) 2.82-2.89 (m, 5H) 2.91 (d, J=10.0 Hz, 1H) 3.16 (dd, J=5.0 and 10.0 Hz, 2H) 3.20 (s, 3H) 3.23 (d, J=10.0 Hz, 1H) 3.35 (s, 3H) 3.55 (d, J=5.0 Hz, 1H) 3.58 (d, J=10.0 Hz, 1H) 4.15-4.20 (m, 1H) 4.64 (dd, J=5.0 and 10.0 Hz, 1H) 5.43 (q, J=5.0 Hz, 2H) 5.66 (dd, J=10.0 and 15.0 Hz, 1H)) 6.58 (dd, J=10.0 and 15.0 Hz, 1H) 6.65 (d, J=10.0 Hz, 1H) 6.66 (s, 1H) 7.11 (bs, 1H) 7.28 (bs, 1H); MS m/z 855.3 (M+H), Retention time 0.988 minutes.

Step 2: Preparation of (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-((2-(3-(2,5-dioxo-2,5-dihydro-1H-pyrrol-1-yl)propanamido)ethyl)disulfanyl)-4-methylpentanoyl)-N-methyl-L-alaninate To (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-((2-aminoethyl)disulfanyl)-4-methylpentanoyl)-N-methyl-L-alaninate (555 mg, 0.57 mmol) dissolved in anhydrous DMSO (7 mL) were added 2,5-dioxopyrrolidin-1-yl 3-(2,5-dioxo-2,5-dihydro-1H-pyrrol-1-yl)propanoate (171 mg, 0.63 mmol) and DIEA (249 mL, 1.43 mmol) at room temperature. The reaction mixture was stirred at room temperature for 15 min and neutralized using TFA. The mixture was cooled to 0° C. with iced bath, followed by addition of $CH_3CN$ (2 mL) and $H_2O$ (7 mL), and then purified by reverse phase ISCO, eluted with 10-70% acetonitrile-$H_2O$ containing 0.05% TFA. Fractions containing desired product were lyophilized to obtain desired product (430 mg, 66% yield).). $^1H$ NMR (400 MHz, $CDCl_3$) δ ppm 0.81 (s, 3H) 1.23 (s, 3H) 1.24 (s, 3H) 1.25 (s, 1H) 1.28 (d, J=5.0 Hz, 3H) 1.31 (d, J=5.0 Hz, 3H) 1.43-1.49 (m, 1H) 1.61 (d, J=15.0 Hz, 1H) 1.64 (s, 3H) 1.81-1.87 (m, 1H) 1.94-2.01 (m, 1H) 2.19 (dd, J=5.0 and 15.0 Hz, 1H) 2.30-2.36 (m, 1H) 2.54 (t, J=5.0 Hz, 2H) 2.61 (dd, J=10.0 and 15.0 Hz, 1H) 2.70 (t, J=5.0 Hz, 2H) 2.88 (s, 3H) 3.00 (d, J=10.0 Hz, 1H) 3.13 (d, J=10.0 Hz, 1H) 3.21 (s, 3H) 3.55 (s, 3H) 3.45 (q, J=5.0 Hz, 2H) 3.49 (d, J=5.0 Hz, 1H) 3.62 (d, J=10.0 Hz, 1H) 3.83 (t, J=5.0 Hz, 1H) 3.98 (s, 3H) 4.32 (m, 1H) 4.80 (dd, J=5.0 and 10.0 Hz, 1H) 5.28 (d, J=5.0 Hz, 1H) 5.66 (dd, J=10.0 and 15.0 Hz, 1H)) 6.22 (bs, 1H) 6.42 (dd, J=10.0 and 15.0 Hz, 1H) 6.50 (s, 1H) 6.63 (s, 1H) 6.66 (d, J=10.0 Hz, 1H) 6.70 (s, 2H) 6.83 (s, 1H); MS m/z 988.3 (M+H-$H_2O$), Retention time 1.145 minutes.

Example 4B: Preparation of Antibody Drug Conjugate 121G12.DAPA.sSPDB.DM4

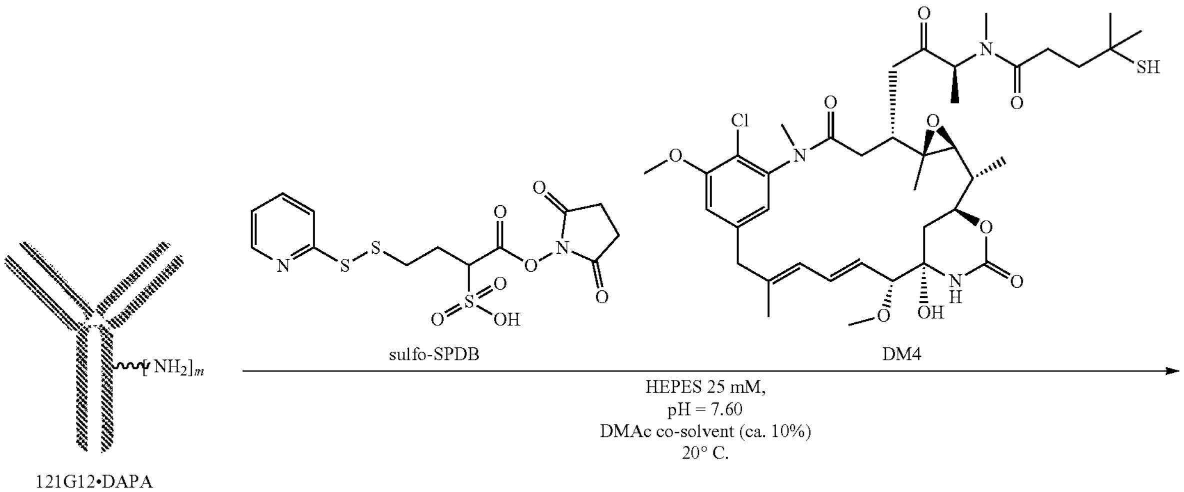

121G12•DAPA
(m = 86 lysine amines)

-continued

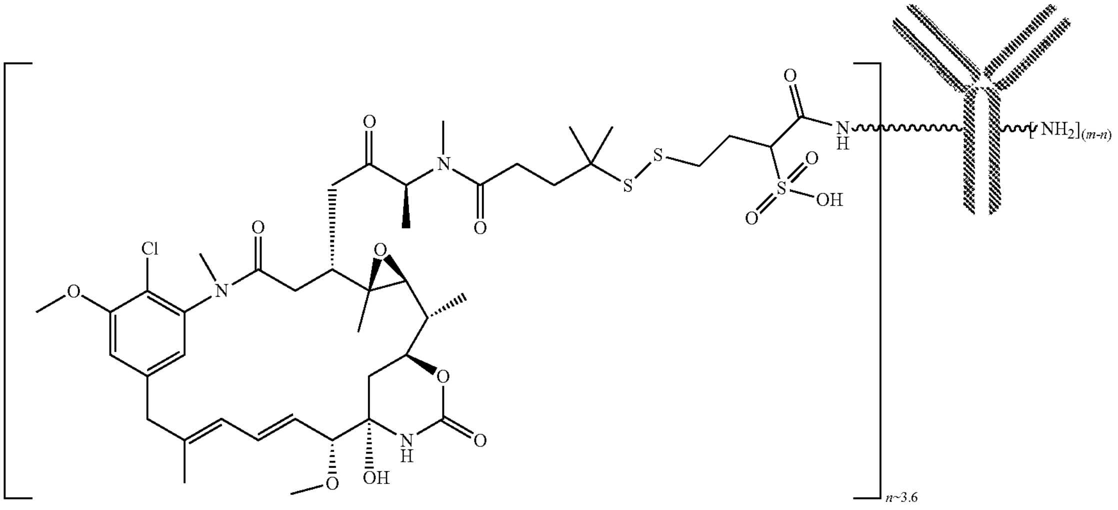

121G12•DAPA•(sSPDB•DM4)$_n$

To a stirred solution of 25 mM HEPES buffer pH 7.6 (3 ml; sterile) and dimethylacetamid (DMAc; 0.12 ml) at 22° C. a solution (1.695 ml) of 121G12.DAPA; MW-145546 g/mol; 62 mg (0.426 μmol)) in potassium phosphate buffer (10 mM, pH6; sterile) was added. Maytansinoid DM4 (2.42 mg (3.101 μmol) dissolved in 0.242 ml DMAc was added. Linker sulfoSPDB (0.970 mg (2.386 μmol, corrected for assay) dissolved in 0.970 ml DMAc was added. After 18 h the reaction mixture was analyzed for reaction completeness by SEC-UV and HPLC.

The reaction mixture was purified from small molecule by-products and buffer-exchanged by filtration over Amicon membrane cells; cut-off 30 kDa using 10 mM PBS-pH7.4 buffer (sterile) for washing. The obtained Amicon-retentate was combined and diluted to 10 mg/ml (UV) to give 2.9 ml solution of the antibody drug conjugate 121G12.DAPA.sSPDB-DM4 in 10 mM PBS-pH7.4 buffer (49% protein recovery).

By SEC-UV the drug antibody ratio was determined to be n=3.6 and the monomeric purity to be 98.7%. The Endotoxin-level was 0.14 EU/mg (BET Endosafe-test).

Example 4C: Preparation of Antibody Drug Conjugate 684E12.SMCC.DM1

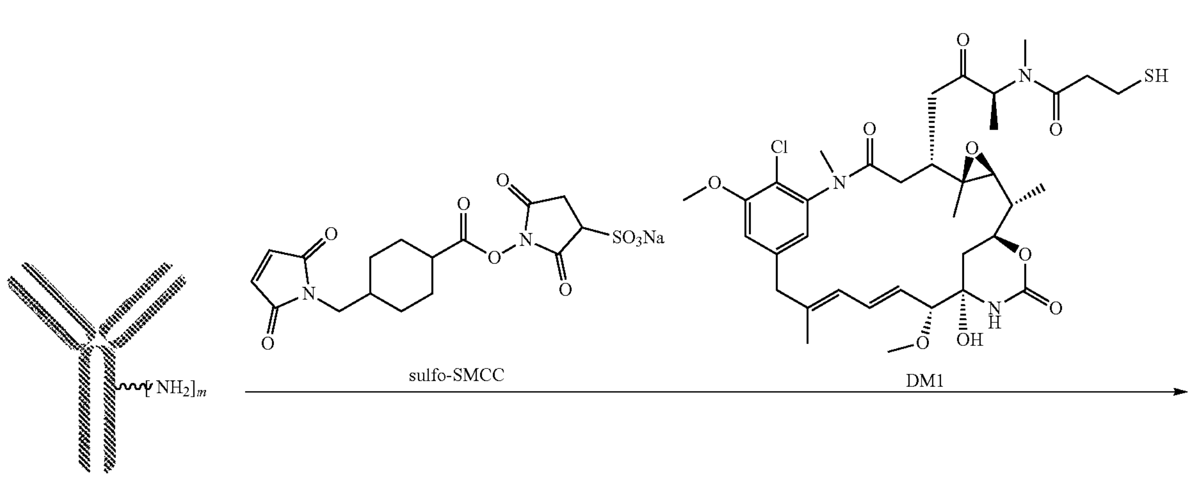

684E12

-continued

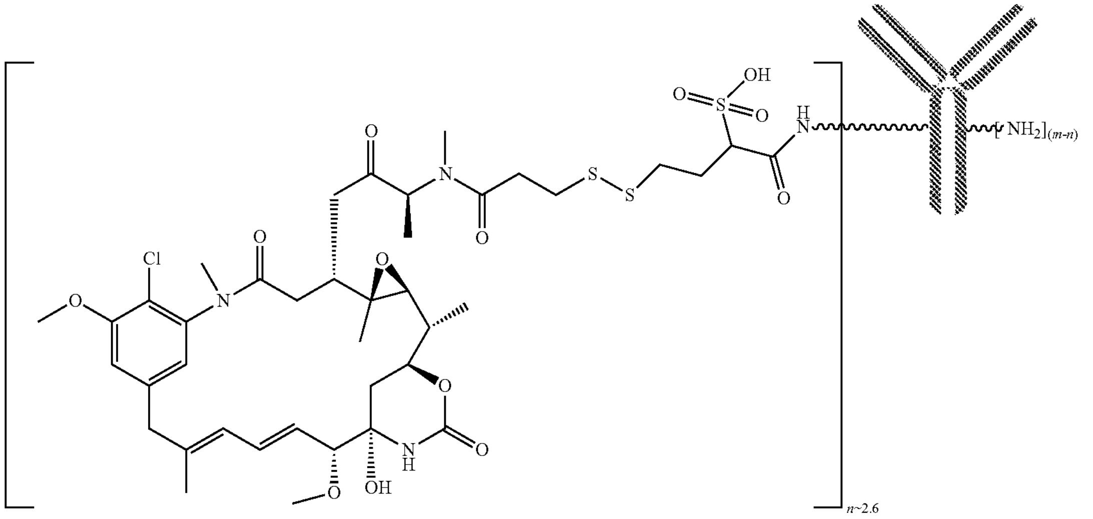

684E12•(SMCC•DM1)$_n$

To the antibody (parental 684E12) solution (7.1 mg/mL, 3.4 mL, ca 47 μM, PBS, pH 7.4) 100 μL of 2 mM DM1 (0.17 mg) in DMA and 50 μL of 4 mM sulfo-SMCC (0.15 mg) in DMA were added and the mixture was incubated and gently stirred at 4° C. overnight. After incubation the reaction mixture was purified via desalting on a HiPrep 26/10 Desalting column (GE Healthcare) using PBS, pH 7.4 as the running buffer and sterile filtered. The purified conjugate was analyzed by MALDI-MS and the DAR estimated to be 2.6. Analytical SEC showed 3.7% aggregation (or 96.3% monomer) present in the sample and LAL testing (PTS, Charles River Laboratories) determined the endotoxin value to be 0.36 EU/mg.

Example 4D: Preparation of Antibody Drug Conjugate 506E15.AURIX1

Starting material was 506E15.CysMab (WT Fc) antibody at 18.8 mg/ml (OD280 with an extinction coefficient of 13.7 for a 10 mg/ml IgG solution) in 1× phosphate buffered saline (1×PBS). 1.76 ml of antibody was absorbed to 3 ml of RMP Protein A resin (GE Healthcare 1-223BPO/I) and to resultant slurry was added 240 ul of 0.5M cysteine (Sigma G121-03) formulated in 0.5 M phosphate pH 8 to which NaOH (Alfa Aesar A16037) had been added at ratio of 13.6 g/L. Slurry was occasionally swirled at room temperature for 30 minutes, then washed by vacuum filtration through a bottletop 0.2 um filter unit with 50 bed volumes of 1×PBS in at least 10 cycles of filtration and addition. The washed resin was resuspended in 2 ml of 1×PBS (50% slurry) and 60 ul of 100 uM CuCl2 (Aldrich 751944) was added (net 100 nM $Cu2^+$) to initiate reoxidation. After 420 minutes, and additional 90 ul of 100 uM CuCl2 was added to further accelerate the reoxidation. The reoxidation of the antibody was tested by removing a 30 ul aliquot of slurry, adding 1 ul of a 20 mM stock of a reference maleimide: (Example 3, page 110 of WO2015/095301), which is known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 μm particles, 4000 Å poresize) equilibrated to 0.1% trifluoroacetic acid in 29.5% $CH_3CN$/water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 565 minutes), 220 ul of a 20 mM stock of AURIX1 in DMSO was added and slurry was occasionally gently swirled at room temperature for 70 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (6 ml) was neutralized with 0.6 ml of 0.5M sodium phosphate pH 8, concentrated to 2.5 ml using a spin concentrator (Amicon UFC905024) at 3,000×g, applied to a PD-10 buffer exchange column (GE Healthcare 17-0851-01) equilibrated to 1×PBS, loading 2.5 ml of concentrate and eluting with 3.5 ml of 1×PBS as per manufacturer. Yield was 22 mg (66%).

Example 4E: Preparation of Antibody Drug Conjugate 506E15.CysMab.DAPA.AURIX2

Starting material was 506E15.CysMab.DAPA antibody at 10 mg/ml (OD280 with an extinction coefficient of 13.7 for a 10 mg/ml IgG solution) in 1× phosphate buffered saline (1×PBS). 2.0 ml of antibody was absorbed to 2 ml of RMP Protein A resin (GE Healthcare 1-223BPO/I) and to resultant slurry was added 160 ul of 0.5M cysteine (Sigma G121-03) formulated in 0.5 M phosphate pH 8 to which NaOH (Alfa Aesar A16037) had been added at ratio of 13.6 g/L. Slurry was occasionally swirled at room temperature for 30 minutes, then washed by vacuum filtration through a bottletop 0.2 um filter unit with 50 bed volumes of 1×PBS in at least 10 cycles of filtration and addition. The washed resin was re-suspended in 2 ml of 1×PBS (50% slurry) and 10 ul of 100 uM $CuCl_2$ (Aldrich 751944) was added (net 250 nM $Cu2^+$) to initiate reoxidation. The reoxidation of the antibody was tested by removing a 30 ul aliquot of slurry, adding 1 ul of a 20 mM stock of a reference maleimide (Example 3, page 110 of WO2015/095301), which is known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 μm particles, 4000 Å pore size) equilibrated to 0.1% trifluoroacetic acid in 29.5% $CH_3CN$/water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 295 minutes), 80 ul of a 20 mM stock of AURIX2 in DMSO was added and slurry was occasionally gently swirled at room temperature for 85 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (4 ml) was neutralized with 0.4 ml of 0.5M sodium phosphate pH 8, applied to 2×PD-10 buffer exchange columns (GE Healthcare 17-0851-01) equilibrated to 1×PBS, loading 2.5 ml of eluate and eluting with 3.5 ml of 1×PBS as per manufacturer. Yield was 13.3 mg (67%).

Example 4F: Preparation of Antibody Drug Conjugate 674J13.CysMab.AURIX1

Starting material was 674J13.CysMab (WT Fc) antibody at 9 mg/ml (OD280 with an extinction coefficient of 13.7 for a 10 mg/ml IgG solution) in 1× phosphate buffered saline (1×PBS). To 57.6 ml of antibody was added DTT to 200 mM (Invitrogen 15508-013) and solution was incubated 75 minutes to strongly reduce the Ab. The reduced Abs were then applied to PD-10 buffer exchange columns (GE Healthcare 17-0851-01) equilibrated to 1×PBS, loading 2.5 ml of concentrate and eluting with 3.5 ml of 1×PBS as per manufacturer. The eluate from the PD10s was pooled then reapplied to fresh PD10 columns to more completely remove the DTT. Note that in separate experiments, PD10 columns are more effective at removal of DTT than would be seen just through size exclusion mechanism, provided the columns are used only once.

The reoxidation of the antibody was tested by removing a 30 ul aliquot of slurry, adding 1 ul of a 20 mM stock of AURIX1 known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 μm particles, 4000 Å poresize) equilibrated to 0.1% trifluoroacetic acid in 29.5% $CH_3CN$/water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 180 minutes), 290 ul of a 20 mM stock of AURIX1 in DMSO was added along with 6 ml of RMP Protein A resin (GE Healthcare 1-223BPO/I) resin. The slurry was occasionally gently swirled at room temperature for 40 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (11.5 ml) was neutralized with 1.2 ml of 0.5M sodium phosphate pH 8, concentrated to 2.5 ml using a spin concentrator (Amicon UFC905024) at 3,000×g, applied to a PD-10 buffer exchange column (GE Healthcare 17-0851-01) equilibrated to 1×PBS, loading 2.5 ml of concentrate and eluting with 3.5 ml of 1×PBS as per manufacturer. Yield was 26 mg (41%)

Example 4G: Preparation of Antibody Drug Conjugate 674J13.CysMab.DAPA.AURIX2

Starting material was 674J13.CysMab.DAR4.DAPA antibody at 31.7 mg/ml (OD280 with an extinction coefficient of 13.7 for a 10 mg/ml IgG solution) in 1× phosphate buffered saline (1×PBS). 9.5 ml of antibody was absorbed to 30.1 ml of RMP Protein A resin (GE Healthcare 1-223BPO/I) and to resultant slurry was added 1800 mg of DTT (Invitrogen 15508-013) to strongly reduce the Ab (net 200 mM DTT). Slurry was swirled at room temperature for 20 minutes, then washed by vacuum filtration through a bottletop 0.2 um filter unit with 50 bed volumes of 1×PBS in at least 10 cycles of filtration and addition. The washed resin was resuspended in 2 ml of 1×PBS and swirled at room temperature—no copper was added (this accelerated the reoxidation too severely). The reoxidation of the antibody was tested by removing a 30 ul aliquot of slurry, adding 1 ul of a 20 mM stock of a reference maleimide (Example 3, page 110 of WO2015/095301), which is known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 μm particles, 4000 Å poresize) equilibrated to 0.1% trifluoroacetic acid in 29.5% $CH_3CN$/water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 80 minutes), 903 ul of a 20 mM stock of AURIX2 in DMSO was added and slurry was occasionally gently swirled at room temperature for 50 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (60.2 ml) was neutralized with 6.0 ml of 0.5M sodium phosphate pH 8, concentrated to 17.5 ml using a spin concentrator (Amicon UFC905024) at 3,000×g, applied to 7 PD-10 buffer exchange columns (GE Healthcare 17-0851-01) equilibrated to 1×PBS, loading 2.5 ml of concentrate and eluting with 3.5 ml of 1×PBS as per manufacturer. Yield was 243 mg (81%)

Example 4H: Preparation of Antibody Drug Conjugate 121G12.CysMab.DAPA.AURIX1

Starting material was 121G12.CysMab.DAPA antibody at 16.7 mg/ml (OD280 with an extinction coefficient of 13.7 for a 10 mg/ml IgG solution) in 1× phosphate buffered saline (1×PBS). 3.6 ml of antibody was absorbed to 6 ml of RMP Protein A resin (GE Healthcare 1-223BPO/I) and resultant slurry was swirled at room temperature for 125 minutes then added 544 ul of 0.5M cysteine (Sigma G121-03) formulated in 0.5 M phosphate pH 8 to which NaOH (Alfa Aesar A16037) had been added at ratio of 13.6 g/L. Slurry was occasionally swirled at room temperature for 60 minutes, then washed by vacuum filtration through a bottletop 0.2 um filter unit with 50 bed volumes of 1×PBS in at least 10 cycles of filtration and addition. The washed resin was resuspended in 2 ml of 1×PBS (50% slurry) and 16 ul of 100 uM CuCl2 (Aldrich 751944) was added (net 250 nM $Cu2^{+}$) to initiate reoxidation. The reoxidation of the antibody was tested by removing a 30 ul aliquot of slurry, adding 1 ul of a 20 mM stock of AURIX1 known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 μm particles, 4000 Å poresize) equilibrated to 0.1% trifluoroacetic acid in 29.5% $CH_3CN$/water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 170 minutes), 67 ul of a 20 mM stock of AURIX1 in DMSO was added and slurry was occasionally gently swirled at room temperature for 120 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (15 ml) was neutralized with 1.5 ml of 0.5M sodium phosphate pH 8, concentrated to 5 ml using a spin concentrator (Amicon UFC905024) at 3,000×g, applied to 2×PD-10 buffer exchange columns (GE Healthcare 17-0851-01) equilibrated to 1×PBS, loading 2.5 ml of eluate and eluting with 3.5 ml of 1×PBS as per manufacturer. Yield was 54 mg (92%).

Example 4I: Preparation of Antibody Drug Conjugate 121G12.CysMab.AURIX1

Starting material was 121G12.CysMab (Fc WT) antibody at 12.5 mg/ml (OD280 with an extinction coefficient of 13.7 for a 10 mg/ml IgG solution) in 1× phosphate buffered saline (1×PBS). 4.8 ml of antibody was absorbed to 6 ml of RMP Protein A resin (GE Healthcare 1-223BPO/I) and resultant slurry was swirled at room temperature for 125 minutes then added 592 ul of 0.5M cysteine (Sigma G121-03) formulated in 0.5 M phosphate pH 8 to which NaOH (Alfa Aesar A16037) had been added at ratio of 13.6 g/L. Slurry was occasionally swirled at room temperature for 60 minutes, then washed by vacuum filtration through a bottletop 0.2 um filter unit with 50 bed volumes of 1×PBS in at least 10 cycles of filtration and addition. The washed resin was resuspended in 2 ml of 1×PBS (50% slurry) and 16 ul of 100 uM CuCl2 (Aldrich 751944) was added (net 250 nM $Cu2^{+}$) to initiate reoxidation. The reoxidation of the antibody was tested by removing a 30 ul aliquot of slurry, adding 1 ul of a 20 mM stock of AURIX1 known to shift the antibody peak by RPLC, mixing for 1 minute, spinning 7,000×g for 10 seconds, removing supernatant, adding 60 ul of Thermo IgG elution buffer (Thermo Scientific 21009), spinning 14,000×g for 10 seconds, sampling supernatant and analyzing products by RPLC as follows: 2 ul sample was injected onto a heated (80° C.) 4.6×50 mm Agilent PLRP-S column (5 μm particles, 4000 Å poresize) equilibrated to 0.1% trifluoroacetic acid in 29.5% $CH_3CN$/water (Millipore TX1280P-1, Burdick and Jackson 407-4) running at 1.5 ml/min. The column was eluted with a 5 minute gradient to 44.5% $CH_3CN$/water which was maintained for 1.9 minutes and peaks were detected at 280 nm. The optimal time for conjugation is defined as that time in which the main product peak is maximal, later-eluting peaks are minimized and earlier eluting peaks are not yet increasing.

When RPLC assay indicated reoxidation was optimal (in this case 160 minutes), 67 ul of a 20 mM stock of AURIX1 in DMSO was added and slurry was occasionally gently swirled at room temperature for 120 minutes. The slurry was then washed with 20 bed volumes of 1×PBS in at least 10 cycles of filtration and addition.

The slurry was then transferred to a fritted column (Pierce 7375021), pre-eluted with 0.5 bed volumes of Thermo IgG elution buffer (discarded), then eluted with 2 bed volumes of the same buffer. The entire eluate (15 ml) was neutralized with 1.5 ml of 0.5M sodium phosphate pH 8, concentrated to 5 ml using a spin concentrator (Amicon UFC905024) at 3,000×g, applied to 2×PD-10 buffer exchange columns (GE Healthcare 17-0851-01) equilibrated to 1×PBS, loading 2.5 ml of eluate and eluting with 3.5 ml of 1×PBS as per manufacturer. Yield was 52 mg (89%).

Analytics Methods: Concentration was determined by OD280 with an extinction coefficient of 13.7 for a 10 mg/ml IgG solution. Pyrogen was determined using Kinetic QCL assay (Lonza Walkersville 50-650H) read on a TECAN Safire plate reader. Percent aggregate was determined by analytical size exclusion chromatography on a Shodex KW-G guard (Thomson Instrument Company Cat #6960955) and KW-803 column (TIC Cat #6960940) equilibrated with mobile phase [20 mM Tris ~pH7.65 (prepped w/10 mM Tris pH7.4, 10 mM Tris pH8), 200 mM NaCl, 0.02% sodium azide], with data acquisition at 280 nm. An aliquot of the sample was prepared for DAR determination by diluting the sample to 2 mg/ml in 1×PBS, deglycosylating the sample with PNGaseF (in-house) for 10 minutes at 50° C., removing the PNGaseF by binding to protein A, washing with 1×PBS, and eluting with 1% formic acid. Sample was reduced by adding 14 volume of 5M ammonium acetate pH 5.0 containing 0.5M TCEP and incubating at room temperature for 30 minutes. Sample was then injected onto an 2.1×50 mm PLRP-S column (8 μm particles, 1000 Å poresize), equilibrated to 0.1% formic acid in 20% $CH_3CN$/water (Invitrogen) running at 0.5 ml/min. The column was washed at 20% $CH_3CN$/water for 3 minutes then eluted with a 0.1 minute gradient to 0.1% formic acid 90% $CH_3CN$/water which was maintained for 1.9 minutes. Mass spectral data was taken on an Agilent 1260 instrument and deconvoluted with MassHunter Qualitative Analysis B.05.00 in a range 15-60 kDa. Peak areas corresponding to various calculated DAR states were weighted according to DAR of each peak, then summed and weighted area of the DAR4 peak was divided by the sum of all weighted peaks to obtain the DAR value.

Analytics on the resultant sample is as follows:

| Parameter | 506E15.DAPA. AURIX2 | 506E15. AURIX1 | 674J13.DAPA. AURIX2 | 674J13. AURIX1 | 121G12. AURIX1 | 121G12.DAPA AURIX1 |
|---|---|---|---|---|---|---|
| Concentration (mg/ml) | 1.9 | 6.7 | 9 | 8.4 | 7.5 | 7.8 |
| Pyrogen (EU/ml) | 0.05 | 0.42 | 0.05 | <0.5 | 0.05 | 0.05 |
| % aggregate | <1 | <1 | 2.8 | <1 | 1.2 | 1.9 |
| DAR | 3.80 | 3.78 | HC 3.93<br>LC 0.03 | HC 3.8 | 3.80 | 3.80 |

Example 4J: Preparation of Additional Conjugates Using Other CysMab Antibodies The methods described in Example 4 Å are also used to produce MPET.DM4 conjugates with other cysteine engineered antibodies.

The methods are used to product anti-P-cadherin Ab.CysMab.MPET.DM4 conjugates using antibodies NOV169N31Q(E152C-S375C), NEG0012(E152C-S375C), NEG0013(E152C-S375C), NEG0016(E152C-S375C), NEG0064(E152C-S375C), NEG0067(E152C-S375C), NOV169N31Q(K360C(HC)-K107C(LC)), NEG0012 (K360C(HC)-K107C(LC)), NEG0013(K360C(HC)-K107C (LC)), NEG0016(K360C(HC)-K107C(LC)), NEG0064 (K360C(HC)-K107C(LC)), and NEG0067(K360C(HC)-K107C(LC)) disclosed in PCT Publication No. WO2016/203432.

Example 5: In Vitro ADC Characterization

Antibody drug conjugates (ADCs) were characterized by various functional and analytical methods. ADCs retained binding to target CCR7 protein on cells as assessed by FACS. For all ADCs, the geometric mean fluorescence intensity in FACS binding assay was within 20% of the value for the unconjugated antibody. By analytical SEC, ADCs were shown to be >95% material at desired molecular weight; in cases where this was not observed for initial reaction products, use of preparative SEC attained the necessary specification. Drug antibody ratio (DAR) was assessed by LCMS of the deglycosylated reduced antibody sample, summing the abundances of various DAR species and weighting by the number of drug molecules on each DAR species (e.g., a single DAR2 ion counts as 2, a single DAR1 ion counts as 1). Conjugates comprising constant regions containing two cysteine mutations were at least at or above DAR 3.4 and most commonly at or above DAR 3.8. This was consistent across reported conjugates.

Example 6: Inhibition of Cell Proliferation/Cellular Viability Assay

Above we showed that fluorophore-conjugated versions of all three anti-CCR7 antibodies can internalize CCR7 and effectively accumulate the conjugated fluorophore in the low-pH departments of cells across a panel of cell lines. Here we show the antibody's capability to internalize and accumulate conjugated matter intracellularly in a setting where the conjugated matter is a toxic payload.

In a piggyback ADC (pgADC) setting, cytotoxic effects of anti-CCR7 antibodies complexed with a payload-conjugated secondary antibody fragment were studied by assessing cell viability after four days of treatment. Three fold dilutions of the CCR7-specific IgGs were prepared and mixed with a constant amount of payload-coupled Fab fragment. The final concentration of payload-coupled Fab fragment was 0.5 µg/ml. The Fab reagent is an anti-mouseFc directed Fab conjugated either to MMAF or to Saporin (Advanced Targeting Systems, Fab-Zap). After pre-incubation for 30 min at room temperature, 10 µl/well of the antibody-payload complex was added to 384-well bottom white plates in triplicates. Respective CCR7(+) cells were seeded such that their density was less than $1\times10^6$ /ml for suspension cells and 80% confluency was reached for adherent cells. Cells were harvested (adherent cells were detached with Accutase) and resuspended to approximately $2\times10^4$ cells/ml. Cells were added to 384-well plates on top of the antibody-payload complex (20 µl/well). The plate was incubated for four days at 37° C. and 5% $CO_2$. Subsequently, 20 µl/well of CellTiter-Glo solution (CellTiter-Glo® Luminescent Cell Viability Assay; Promega, #G7571) were prepared and added to the cells. Only viable cells are producing ATP, which is needed for the luciferase reaction (provided by CellTiter-Glo) resulting in luminescence. According to this, the cell viability was determined by the luminescence signal, which was measured after 10 min of incubation at 22° C. and 400 rpm with the Envision 2104 Multilabel reader. IC50 values were calculated using the Graphpad Prism software.

Figure 7A:
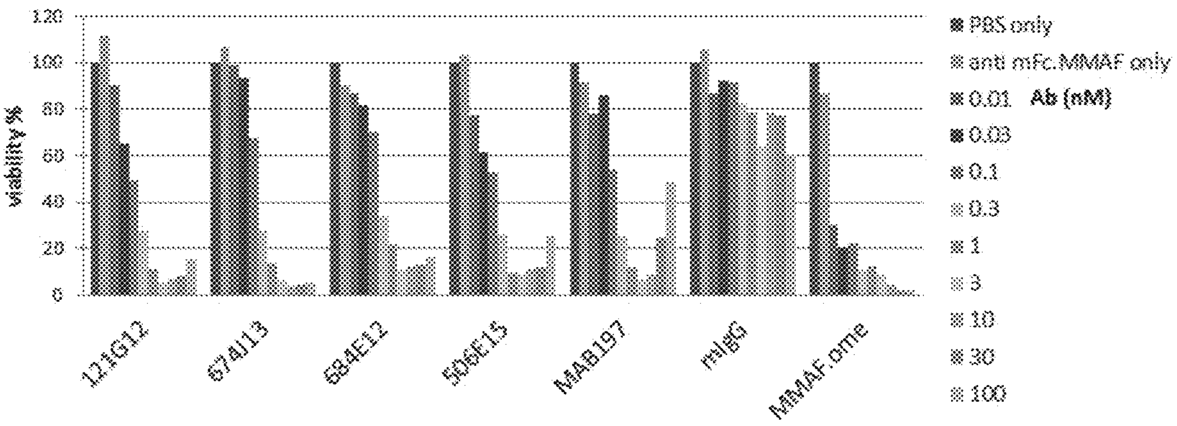
FIG. 7A-B depicts experimental data on piggyback ADC (pgADC) assays of parental anti-CCR7 antibodies complexed with a payload-conjugated secondary antibody fragment.
Figure 7B:
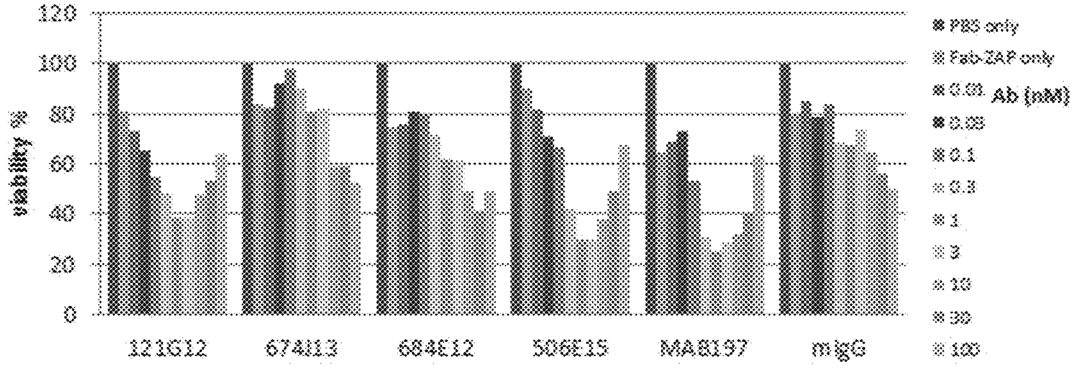

FIG. 7A and FIG. 7B shows that all four anti-CCR7 antibodies are capable of concentration-dependent cell killing of CCR7+KE97 cells in the piggyback assay format using the MMAF-conjugated reagent. The table below summarizes results from experiments using MMAF or Saporin as tool piggy-back payloads.

TABLE 16

IC50 and AMAX of anti-CCR7 antibodies in pgADC cytotoxic assay

| | Anti-mFc.MMAF | | Fab-ZAP | |
|---|---|---|---|---|
| | IC50 (nM) | AMAX (%) | IC50 (nM) | AMAX (%) |
| 121G12 Parental | 0.055 | 104 | 0.064 | 43 |
| 506E15 Parental | 0.070 | 95 | 0.135 | 60 |
| 674J13 Parental | 0.137 | 102 | 6.12 | 31 |
| 684E12 Parental | 0.214 | 80 | 2.60 | 33 |
| MAB197 (R&D) | 0.142 | 85 | 0.155 | 40 |

Figure 8:
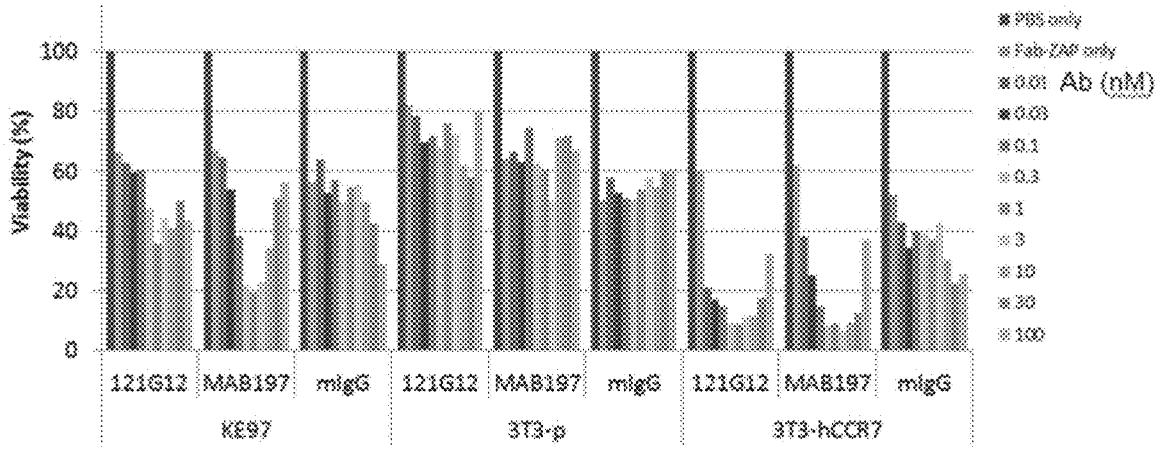
FIG. 8 depicts experimental data on piggyback ADC (pgADC) killing assay of cytotoxic effects of 121G12 parental Ab complexed with a payload-conjugated secondary antibody fragment using target negative cell lines.

Specificity of pgADC killing was assessed using target negative cell lines. An example is shown in FIG. 8 using the FabZap reagent. Specific CCR7-dependent increase in 121G12 pgADC activity is seen in KE97 and NIH3T3.hCCR7 cells in contrast to CCR7 negative NIH3T3 parental cells or mIgG control antibody.

Example 7: Impact of Mouse-Cross-Reactive Unconjugated or AURIX1 Conjugated Anti-CCR7 Antibodies on Normal Mouse Hematopoietic Cells In Vivo Normal tissue expression across species is restricted to cells of hematopoietic origin, including CD4+ and CD8+ T cells in blood and lymphoid organs, presenting a potential safety liability for CCR7 targeting ADC, especially in a wild type Fc format that could lead to ADCC and lymphoid cell depletion.

To determine impact of targeting CCR7 with an ADC on normal hematopoietic cells in vivo, a mouse cross-reactive 121G12 parental Ab either unconjugated or conjugated to AURIX1 was evaluated in healthy female 6-8 week-old CD-1 mice either in a wild type or silenced (DAPA) Fc format. Mice received a single IV treatment of 121G12 parental.Cys-Mab.wild type Fc.hIgG1 (121G12.wt.Fc), 121G12 parental.Cys-Mab.DAPA.hIgG1 (121G12.DAPA.Fc), 121G12 parental.Cys-Mab.wild type Fc.hIgG1.AURIX1 (121G12.wt.Fc.AURIX1) or 121G12.parental.Cys-Mab.DAPA.hIgG1.AURIX1 (121G12.DAPA.Fc.AURIX1) at a final dose of 10 mg/kg. All doses were adjusted to individual mouse body weights.

On day 25 post treatment spleens were extracted and dissociated into single cell suspensions using the gentleMACS Dissociator (Miltenyi Biotec Inc, San Diego, CA). 1 million cells for each sample were then stained with a cocktail of Abs, that included BUV737 Rat Anti-Mouse CD8a Antibody, clone 53-6.7 (1:100) (BD Biosciences, San Jose, CA, Cat #564297) and BV510 Rat Anti-Mouse CD4, clone RM4-5 (1:200) (BD Biosciences, San Jose, CA, Cat #563106) to determine impact of the individual treatments on CD4+ and CD8a+ T cells. Samples were incubated at 4° C. for 30 min, washed in ice-cold HyClone Phosphate Buffered Saline (Hyclone Laboratories, Logan, Utah) and evaluated on the BD LSRFortessa™ cell analyzer (BD Biosciences, San Jose, CA). Total splenocyte cell counts were used to determine CD4+ or CD8a+ T-cell depletion. T-Test was used to determine significance between groups.

Figure 9:
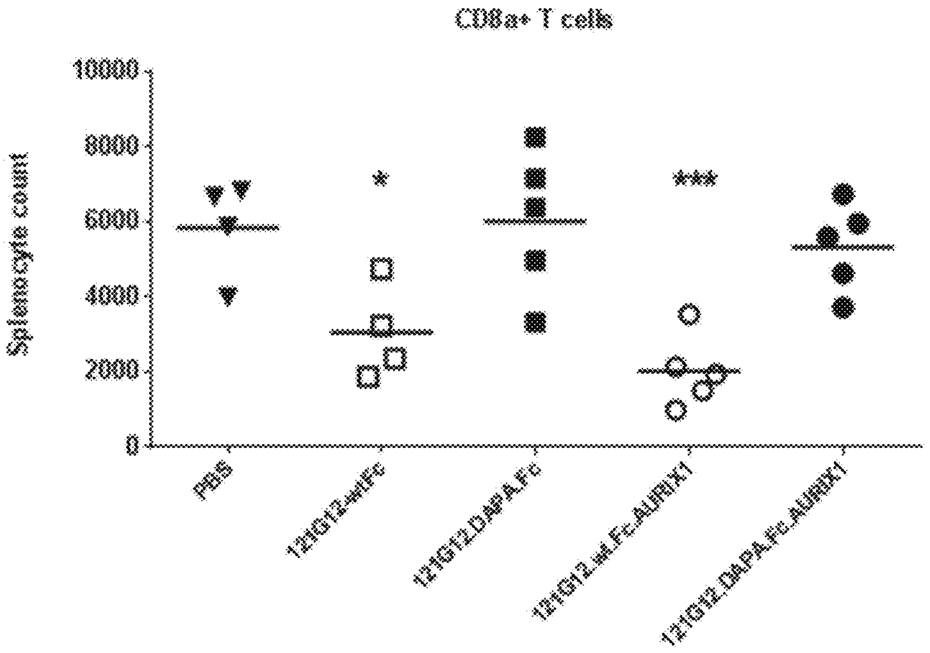
FIG. 9 depicts graphs illustrating CD4+ and CD8a+ T cell depletion with a mouse CCR7 cross-reactive 121G12 parental Ab in a CysMab wild type Fc format, either as an antibody alone or conjugated to an auristatin cytotoxin, the effects of which are rescued by switching to a DAPA silenced Fc format.
Figure 9:
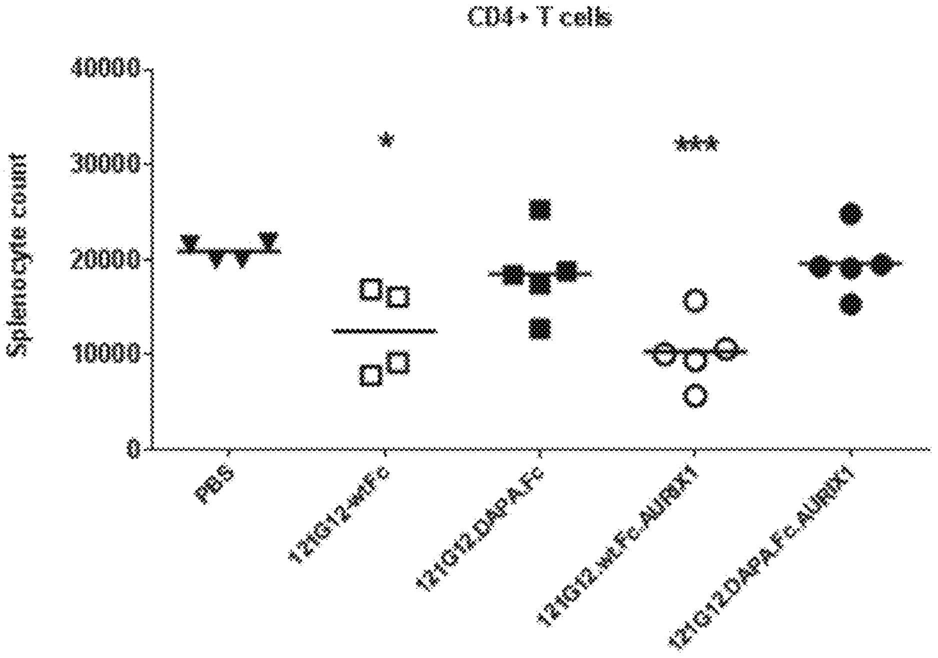

As shown in Table 17 and FIG. 9, a strong reduction of CD4+(FC 0.5-0.6) and CD8a+ T cells (FC 0.3-0.5) in the spleen was observed by Day 3 of treatment with either 121G12.wt.FC or 121G12.wt.Fc.AURIX1 Abs at 10 mg/kg, suggesting T cell depletion impact was independent of presence of AURIX1 payload. These effects were rescued by silencing the Fc through the introduction of DAPA mutations. Both 121G12.DAPA.Fc and 121G12.DAPA.Fc.AURIX1 failed to impact the T cell populations relative to No Treatment group. These data indicate that anti-CCR7 ADCs may have a T cell depletion safety liability that can be rescued through DAPA silencing of the Fc.

TABLE 17

Impact of 121G12 Antibody on CD4+ and CD8a+ T cell populations in CD-1 mice

| | No Treatment | 121G12-wtFc | 121G12.DAPA.Fc | 121G12.wt.Fc.AURIX1 | 121G12.DAPA.Fc.AURIX1 |
|---|---|---|---|---|---|
| | CD8+ T cells | | | | |
| Mean | 5833 | 3041 | 6003 | 2013 | 5317 |
| SE | 650 | 629 | 860 | 426 | 526 |
| Fold Change | | 0.5 | 1.0 | 0.3 | 0.9 |
| p value | | <0.05 | NS | <0.001 | NS |
| | CD4+ T cells | | | | |
| Mean | 20896 | 12512 | 18547 | 10324 | 19633 |
| SE | 480 | 2326 | 2004 | 1602 | 1520 |
| Fold Change | | 0.6 | 0.9 | 0.5 | 0.9 |
| p value | | <0.05 | NS | <0.001 | NS |

The experiment was evaluated on treatment Day 25. Fold change (FC) = Mean Splenocyte counts on Day 25 for indicated Treatment Group/Mean Splenocyte Counts for No Treatment Control Group on Day 3. T-Test was used to determine significance vs. No Treatment group (*$p < 0.05$, *** $p < 0.001$; NS = not significant).

Example 8: Anti-CCR7 ADC Activity of Direct Conjugates

Cytotoxic effects after binding of directly conjugated antibodies (ADCs) with various payloads and their internalization into CCR7(+) cells were studied by assessing cell viability after four days of treatment. Three fold dilutions of the ADCs were added to 384-well bottom white plates in triplicates (10 µl/ml). Respective CCR7(+) cells were seeded such that their density was less than $1\times10^6$/ml for suspension cells and 80% confluency was reached for adherent cells. Cells were harvested (adherent cells were detached with Accutase) and resuspended to approximately $2\times10^4$ cells/ml. Cells were added to 384-well plates on top of the antibody (20 µl/well). The plates were incubated for four days at 37° C. and 5% $CO_2$. Subsequently, 20 µl/well of CellTiter-Glo solution (CellTiter-Glo® Luminescent Cell Viability Assay; Promega, #G7571) was prepared and added to the cells. Cell viability was determined by the luminescence signal, which was measured after 10 min of incubation at 22° C. and 400 rpm with the Envision reader. IC50 values were calculated using the Graphpad Prism software.

The table below shows examples of cell viability effects measured with anti-CCR7 CysMab antibodies in either wild type Fc or silenced (DAPA) Fc format conjugated to AURIX1 or AURIX2.

TABLE 18

| IC50 of Anti-CCR7 ADCs in Cytotoxic Assay | | | | | |
|---|---|---|---|---|---|
| | | ADC activity in cell viability assay; IC50 (nM) | | | |
| Cell line | Cancer type | 506E15. CysMab. AURIX1 | 674J13. CysMab. AURIX1 | 506E15. CysMab.DAPA. AURIX2 | 674J13. CysMab.DAPA. AURIX2 |
| DEL | ALCL | 0.0029 | 0.0741 | 0.0084 | 0.1167 |
| KE97 | Multiple myeloma | 0.0031 | 0.03 | 0.0131 | 0.0658 |

To assess the ADCs for target-specificity and receptor-level dependency, ADC activity was tested across cell lines with different CCR7 receptor levels. The table below shows an example for the humanized 674J13 antibody in CysMab.DAPA format and conjugated to AURIX2. Cell lines were chosen based on similar sensitivity to payload.

TABLE 19

| IC50 of the humanized 674J13 antibody in DAPA format and conjugated to AURIX2 | | | |
|---|---|---|---|
| Cell line | Cancer type | CCR7 receptor levels | ADC activity in cell viability assay; IC50 (nM) 674J13.CysMab.DAPA.AURIX2 |
| DEL | ALCL | ~100,000 | 0.2417 (>95% AMAX) |
| KE97 | Multiple Myeloma | ~100,000 | 0.1018 (>95% AMAX) |
| SR786 | Anaplastic large T cell lymphoma | ~28,000 | 2.737 (90% AMAX) |
| CML-T1 | T cell leukemia | ~29,000 | 3.779 (60% AMAX) |
| DND-41 | T cell leukemia | 1,700 | <20% AMAX |
| NCI-H82 | Small cell lung cancer | 0 | No killing |

As seen in the pHrodo experiment, ADC activity requires a higher degree of receptor numbers than the ADCC modality. The exact receptor cut-off depends on various parameters (e.g., antibody avidity, payload potency), but the data shown here describe the general concept. Using an avidity-dependent anti-CCR7 antibody in DAPA-format, biases ADC activity towards cancer cells over normal CCR7+ PBMCs, which are here represented by cancer cell lines with less than 2,000 CCR7 receptors.

Example 9: Introduction of a Site-Specific MPET.DM4 ADC

DM4 conjugated ADCs are well established in the ADC field. Here we describe the generation and use of a site-specifically conjugated MPET.DM4 using the CysMab version of the antibodies, which has the advantage of yielding a reproducibly homogeneous, DAR-controlled ADC batch, where the DAR (drug to antibody ratio) is about 4. Non-site specific conjugates have been described to often contain significant populations with high DAR, which have been linked to unfavorable biophysical features including increased hydrophobicity, and consequentially more rapid clearance, poor PK profile and increased toxicity. Below we show various in vitro and in vivo assessments of an MPET.DM4 based anti-CCR7 ADC in comparison to its sSPDB.DM4 counterpart.

Example 10: FACS Binding Affinity of MPET.DM4 Versus sSPDB.DM4 ADCs

Another potential improvement of site-specific conjugation over non site-specific conjugation could be a potential interference of Lysine-conjugation sites that are structurally in the vicinity of essential CSD residues. Payload conjugation to such Lysine sites may be expected to impact binding affinity of the ADC. To test binding affinities of ADCs using the here described CysMab conjugated MPET.DM4 versus endogenous Lysine conjugated sSPDB.DM4, binding affinity was determined by FACS as described above. The table below summarizes some representative affinity data, which show a mild decrease in binding affinity of the sSPDB.DM4 ADC versus the MPET.DM4 ADC.

TABLE 20

| Binding affinity of anti-CCR7 ADCs | | | | |
|---|---|---|---|---|
| | | ADC affinity in FACS; EC50 (nM) | | |
| Cell line | CCR7 receptor levels | 121G12. CysMab.DAR4 unconjugated | 121G12. CysMab.DAPA. MPET.DM4 (DAR 3.8) | 121G12. DAPA.sSPDB.DM4 (DAR3.9) |
| DEL | ≥100,000 | 5.24 | 5.61 | 8.42 |

Example 11: In Vitro Activity of MPET.DM4 Versus sSPDB.DM4 ADCs

Cytotoxic effects of the ADCs 121G12.CysMab.DAPA.MPET.DM4 and 121G12.DAPA.sSPDB.DM4 (DAR3.9) were assessed in an in vitro viability assay as described above. The table below shows similar, slightly improved activity of the MPET.DM4 conjugate compared to sSPDB.DM4. This may be the consequence of better conserved affinity or other factors.

TABLE 21

| In vitro cytotoxic activity of anti-CCR7 ADCs | | |
|---|---|---|
| | ADC activity in cell viability assay; IC50 (nM) | |
| Cell line | 121G12.CysMab.DAPA.MPET.DM4 | 121G12.DAPA.sSPDB.DM4 (DAR3.9) |
| L540 | 2.944 | 3.905 |
| DEL | 2.286 | 2.983 |
| KE97 | 2.171 | 3.177 |

The 121G12.CysMab.DAPA.MPET.DM4 ADC was further tested in a variety of cancer cell lines covering various indication settings, where it achieved substantial cell killing that correlates to receptor densities.

TABLE 22

| In Vitro Cytotoxic Activity of Anti-CCR7 ADCs in Cell Lines | | | |
|---|---|---|---|
| Cell line | Cancer type | Relative receptor density (%) | 121G12.CysMab.DAPA.MPET.DM4 IC50 (nM) |
| SUPHD1 | Hodgkin's Lymphoma | 310 | 1.69 |
| L540 | Hodgkin's Lymphoma | 175 | 4.90 |
| KE97 | Multiple Myeloma | 100 | 2.24 |
| JVM2 | MCL | 79 | 4.62 |
| MOTN1 | CLL | 67 | 4.24 |
| DEL | ALCL | 67 | 2.28 |
| OCI-Ly3 | ABC-DLBCL | 43 | 6.42 |
| Toledo | DLBCL | 20 | n.d. |
| Mec-2 | CLL | 15 | >20 |
| PEER | T-ALL | 2 | >20 |

Example 12: Dose Dependent In Vivo Efficacy of 121G12.CysMab.DAPA.MPET.DM4 and 121G12.DAPA.sSPDB.DM4 Against KE97 Multiple Myeloma Xenograft Model in SCID-Beige Mice To demonstrate targeted anti-tumor activity of 121G12.CysMab.DAPA.MPET.DM4 and 121G12.DAPA.sSPDB.DM4 in vivo, KE97 xenograft model was established in female SCID-beige mice by subcutaneous injection of $3\times10^6$ cells into the right flank of each mouse. Once tumors reached approximately 135 $mm^3$, mice were randomized according to tumor volume into treatment groups (n=8 per group). Mice received an IV treatment of either 121G12.CysMab.DAPA.MPET.DM4 (DAR4) at a final dose of 0.5, 2 or 5 mg/kg, 121G12.DAPA.sSPDB.DM4 (DAR 3.9) at 0.5, 2 or 5 mg/kg, or a non-specific isotype control IgG1.CysMab.DAPA.MPET.DM4 at 5 mg/kg. All doses were adjusted to individual mouse body weights.

Figure 10:
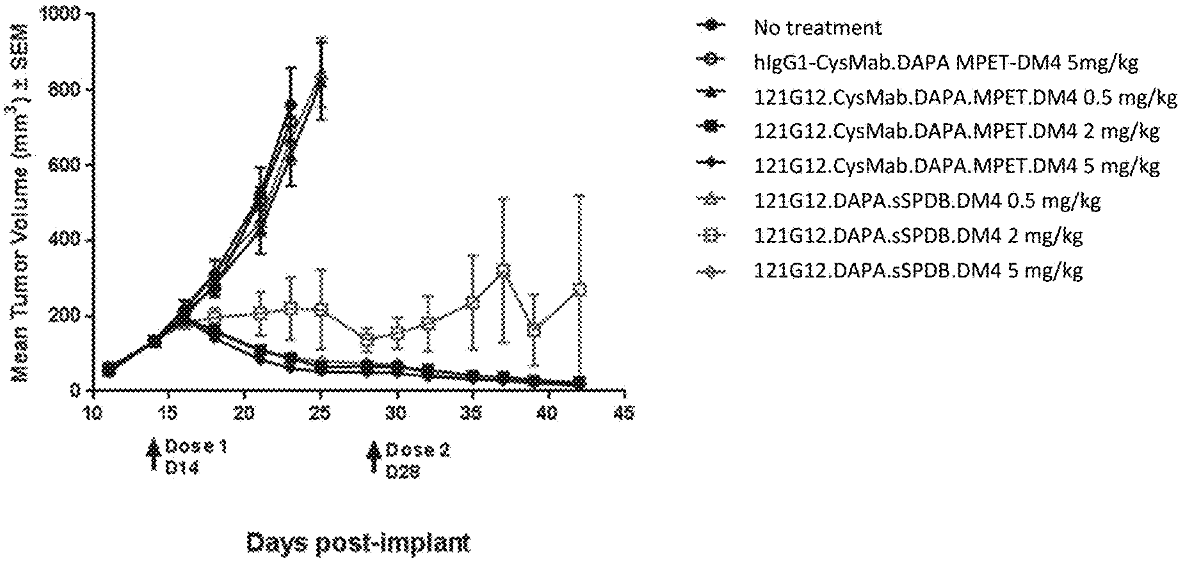
FIG. 10 depicts a graph illustrating dose response efficacy of antibody drug conjugates 121G12.CysMab.DAPA.MPET.DM4 and 121G12.DAPA.sSPDB.DM4 in a KE97 multiple myeloma xenograft model.

All test agents were tolerated on study and no overt clinical symptoms of toxicities or body weight loss were observed in any of the treatment groups (Table 23).

well as with 121G12.DAPA.sSPDB.DM4 at 5 mg/kg through to the end of study on D42 post implant. At 2 mg/kg with 121G12.DAPA.sSPDB.DM4 the response was more heterogeneous, with approximately 25% of the mice displaying sustained tumor regression, while the rest of the group showing either stable disease or tumor progression (FIG. 10, Table 23).

TABLE 23

Anti-CCR7 ADC dose response efficacy in KE97 xenograft model

| Treatment | Dose, schedule | Tumor Response: ΔT/ΔC (%) | Tumor Response: Regression (%) | Host Response: Δ body weight (%) | Host Response: Survival (alive/total) |
|---|---|---|---|---|---|
| No treatment | None | 100 | — | 2.09 | 8/8 |
| IgG1.CysMab.DAPA.MPET.DM4 | 5 mg/kg Single dose | 92.94 | — | 3.02 | 8/8 |
| 121G12.CysMab.DAPA.MPET.DM4 | 0.5 mg/kg Single dose | 78.62 | — | 1.05 | 8/8 |
| 121G12.CysMab.DAPA.MPET.DM4 | 2 mg/kg Single dose | — | 33.07* | 2.74 | 8/8 |
| 121G12.CysMab.DAPA.MPET.DM4 | 5 mg/kg Single dose | — | 53.66* | 0.46 | 8/8 |
| 121G12.DAPA.sSPDB.DM4 | 0.5 mg/kg Single dose | 85.38 | — | 1.84 | 8/8 |
| 121G12.DAPA.sSPDB.DM4 | 2 mg/kg Single dose | 13.77* | — | 0.59 | 8/8 |
| 121G12.DAPA.sSPDB.DM4 | 5 mg/kg Single dose | — | 32.63* | 3.63 | 8/8 |

The experiment was evaluated on treatment Day 9 (Day 23 post implant),

*$p < 0.001$ versus control No Treatment group (One-Way ANOVA/Tukey's Multiple Comparisons Test). % ΔT/ΔC = 100 ΔT/ΔC where: ΔT = mean tumor volume of the drug treated group on D23 of study-mean tumor volume of the drug treated group on initial day of dosing; ΔC = mean tumor volume of the control group on D23 of study-mean tumor volume of the control group on initial day of dosing D14. % Regression = (1-T final/T initial) x 100, where T final is mean tumor volume D23 and T initial is defined as tumor volume on D14 post implant. Δ body weight (%) = (Mean body weight D23-mean body weight D14) *100/Mean body weight D14 of treatment.

No significant anti-tumor efficacy was observed after treatment with the non-specific isotype control IgG1.CysMab.DAPA.MPET.DM4 at 5 mg/kg. 121G12.CysMab.DAPA.MPET.DM4 treatment resulted in dose-dependent anti-tumor efficacy, with ΔT/ΔC value of 78.62% (0.5 mg/kg), while doses of 2 and 5 mg/kg resulted in mean regression of 33% and 54% respectively by D9 post first dose (D23 post implant). 121G12.DAPA.sSPDB.DM4 treatment also demonstrated dose-dependent anti-tumor efficacy with ΔT/ΔC values of 85.38% (0.5 mg/kg) and 13.77% (2 mg/kg), while the 5 mg/kg dose resulted in mean regression of 33% by D9 post first dose (D23 post implant). By D23-D25 post implant, control groups and 0.5 mg/kg treatment groups were euthanized, and remaining groups received a second dose on D28 post implant of either 121G12.CysMab.DAPA.MPET.DM4 at 2 or 5 mg/kg or 121G12.DAPA.sSPDB.DM4 at 2 or 5 mg/kg. Sustained tumor regression was observed with 121G12.CysMab.DAPA.MPET.DM4 at 2 and 5 mg/kg, as

Example 13: Efficacy Assessment of 121G12.CysMab.DAPA.MPET.DM4 vs 121G12.DAPA.sSPDB.DM4 in the KE97 Multiple Myeloma Model at Larger Starting Tumor Volumes A higher bar in vivo model was set up using the KE97 multiple myeloma cell line to further differentiate the anti-tumor efficacy of the different cleavable linkers comparing efficacy of 121G12.CysMab.DAPA.MPET.DM4 121G12.DAPA.sSPDB.DM4 (DAR3.9) in tumors with larger starting tumor volumes at first dose. KE97 xenograft model was established in female SCID-beige mice by subcutaneous injection of $3\times10^6$ cells into the right flank of each mouse. Once tumors reached approximately 450 $mm^3$, mice were randomized according to tumor volume into two treatment groups (n=8). Mice received an IV treatment of 2 mg/kg of either 121G12.CysMab.DAPA.MPET.DM4 or 121G12.DAPA.sSPDB.DM4.

Figure 11:
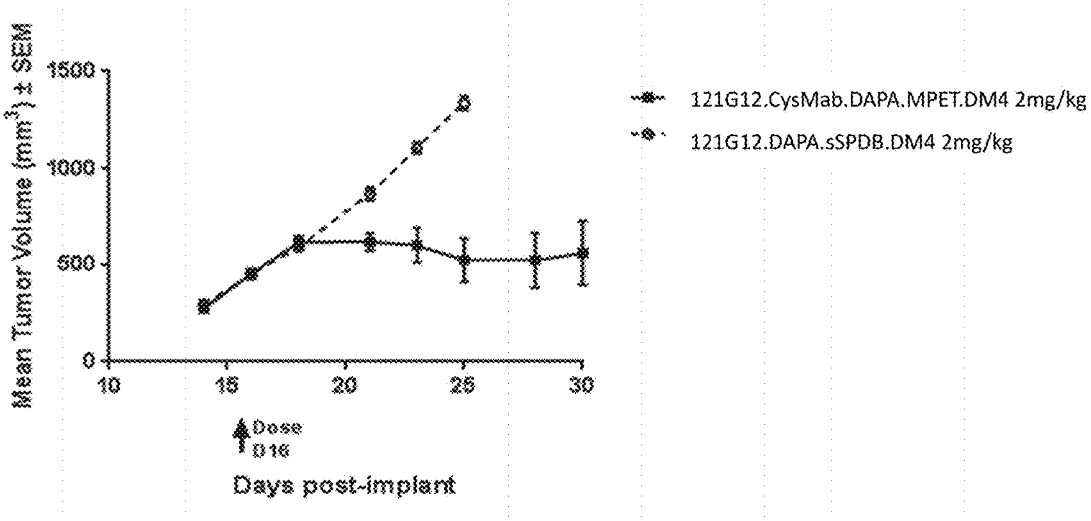
FIG. 11 depicts a graph illustrating activity of antibody drug conjugates 121G12.CysMab.DAPA.MPET.DM4 and 121G12.sSPDB.DM4 in a KE97 multiple myeloma model with dosing initiated at a larger starting tumor burden than FIG. 10.

No significant anti-tumor efficacy was observed after treatment with the 121G12.DAPA.sSPDB.DM4 at 2 mg/kg. 121G12.CysMab.DAPA.MPET.DM4 treatment resulted in partial regression/prolonged stasis in 75% (6 of 8) of the mice with a single dose treatment (FIG. 11). 121G12.CysMab.DAPA.MPET.DM4 strongly out-performed 121G12.DAPA.sSPDB.DM4 in this model (D25 Mean Tumor Volume 524.83±143.20 vs 1337.13±35.13 respectively, $p<0.001$; unpaired T-Test).

Example 14: In Vivo Efficacy of 121G12.CysMab.DAPA.MPET.DM4 Against Primary Patient Derived Non-Small Cell Lung Cancer HLUX1934 Tumor Model Anti-tumor activity of 121G12.CysMab.DAPA.MPET.DM4 was evaluated in the CCR7 expressing HLUX1934 primary non-small cell lung cancer xenograft model. Female athymic nude mice were implanted subcutaneously with tumor fragments into the right flank of each mouse. Once tumors reached approximately 100 $mm^3$, mice were randomized according to tumor volume into treatment groups (n=8). Mice received an IV treatment of either 121G12.CysMab.DAPA.MPET.DM4 (DAR4) at 10 mg/kg, or a non-specific isotype control IgG1.CysMab.DAPA.MPET.DM4 at 10 mg/kg. A second dose of each antibody was delivered 2 weeks later. All doses were adjusted to individual mouse body weights.

Figure 12:
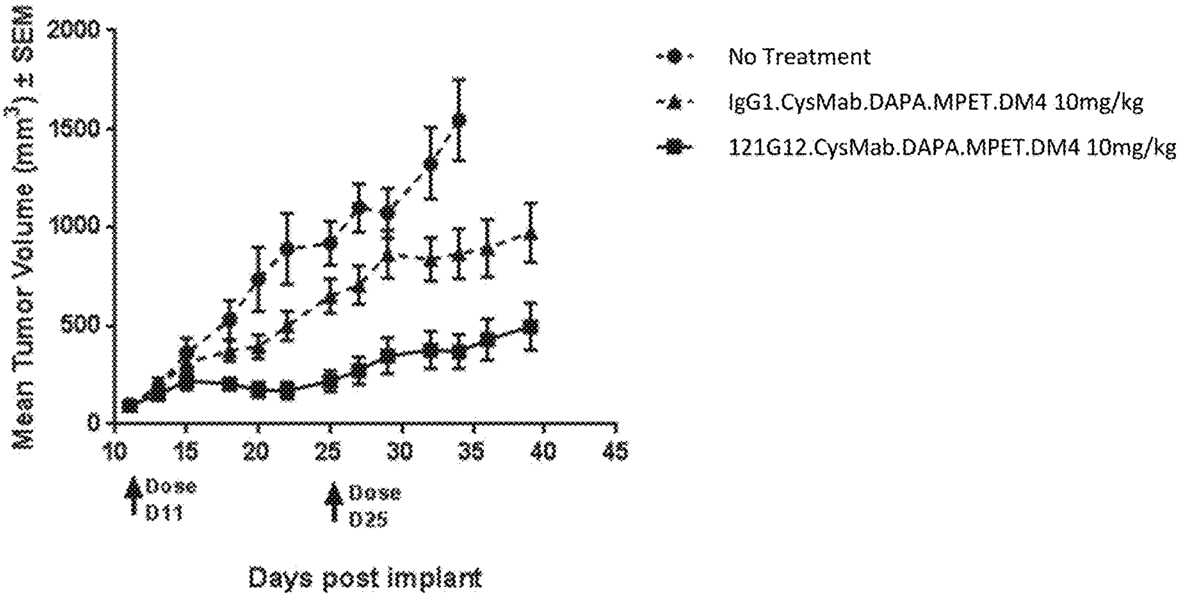
FIG. 12 depicts a graph illustrating in vivo activity of conjugate 121G12.CysMab.DAPA.MPET.DM4 in a primary non-small cell lung tumor model HLUX1934.

Non-specific isotype control IgG1.CysMab.DAPA.MPET.DM4 at 10 mg/kg appeared to slightly delay tumor growth relative to the No Treatment group (ΔT/ΔC value 53.07%) potentially due to non-specific binding of the antibody to an off-target in the HLUX1934 model. 121G12.CysMab.DAPA.MPET.DM4 treatment resulted in more pronounced efficacy that was sustained with the administration of the second dose. The 10 mg/kg dose of 121G12.CysMab.DAPA.MPET.DM4 treatment was well tolerated with no apparent body weight loss and ΔT/ΔC value of 18.83% on D34 post implant. (FIG. 12, Table 24).

TABLE 24

121G12.CysMab.DAPA.MPET.DM4 efficacy in the HLUX1934 NSCLC patient derived model. The experiment was evaluated on Day 34 post implant (D 23 post treatment).

| Treatment | Dose | Tumor Response ΔT/ΔC (%) | Host Response Δ body weight (%) | Host Response Survival (alive/total) |
|---|---|---|---|---|
| No treatment | None | 100 | 5.12 | 5/8** |
| IgG1.CysMab.DAPA.MPET.DM4 | 10 mg/kg | 53.07 | 2.81 | 8/8 |
| 121G12.CysMab.DAPA.MPET.DM4 | 10 mg/kg | 18.83* | 0.61 | 8/8 |

*$p < 0.001$ versus control No Treatment group (One-Way ANOVA/Tukey's Multiple Comparisons Test). % ΔT/ΔC = 100 ΔT/ΔC where: ΔT = mean tumor volume of the drug treated group on D34 of study-mean tumor volume of the drug treated group on initial day of dosing; ΔC = mean tumor volume of the control group on D34 of study-mean tumor volume of the control group on initial day of dosing. Δ body weight (%) = (Mean body weight D34-mean body weight D11) *100/Mean body weight D11 of treatment.

**Mice euthanized in the No Treatment group due to excessive tumor burden D25-D27 post treatment.

Example 15: In Vivo Efficacy of 684E12.SMCC.DM1 Against KE97 Multiple Myeloma Xenograft Model in SCID-Beige Mice To demonstrate targeted anti-tumor activity of 684E12.SMCC.DM1 in vivo, KE97 xenograft model was established in female SCID-beige mice by subcutaneous injection of $3\times10^6$ cells into the right flank of each mouse. Once tumors reached approximately 200 $mm^3$, mice were randomized according to tumor volume into treatment groups (n=8 per group). Mice received an IV treatment of either parental 684E12.SMCC.DM1 (DAR2.6) at a final dose of 2 or 6 mg/kg or a non-specific isotype control IgG1.SMCC.DM1 at 6 mg/kg. All doses were adjusted to individual mouse body weights.

Figure 13:
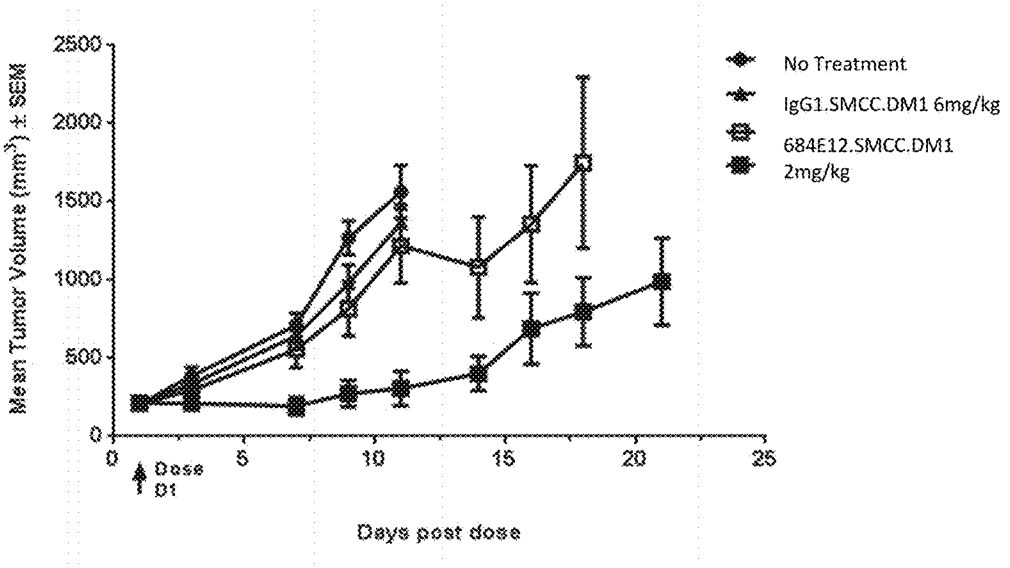
FIG. 13 depicts a graph illustrating activity of conjugated parental 684E12.SMCC.DM1 in a KE97 multiple myeloma xenograft model.

All test agents were tolerated on study and no overt clinical symptoms of toxicities or body weight loss were observed in any of the treatment groups. No significant anti-tumor efficacy was observed after treatment with the non-specific isotype control IgG1.SMCC.DM1 or parental 684E12.SMCC.DM1 at 2 mg/kg. Parental 684E12.SMCC.DM1 6 mg/kg treatment resulted in ΔT/ΔC value 6.72% on D11 post dose ($p<0.0001$, One-Way ANOVA/Tukey's Multiple Comparisons Test) (FIG. 13).

Example 16: In Vivo On-Target Pharmacodynamic Marker Modulation by 121G12.CysMab.DAPA.MPET.DM4 in the KE97 Tumor Model Accumulation of the phospho-histone H3 marker positive tumor cells post treatment with 121G12.CysMab.DAPA.MPET.DM4 was used to assess the ability of anti-CCR7 ADC to induce G2/M arrest in vivo.

A study was conducted where KE97 xenograft model was established in female SCID-beige mice by subcutaneous injection of $3\times10^6$ cells into the right flank of each mouse. Once tumors reached approximately 140 $mm^3$, mice were randomized according to tumor volume into treatment groups (n=3 per group). Mice received a single IV treatment of either 121G12.CysMab.DAPA.MPET.DM4 at a final dose of 2, 5 or 10 mg/kg, or a non-specific isotype control IgG1.CysMab.DAPA.MPET.DM4 at 10 mg/kg. All doses were adjusted to individual mouse body weights. 48 hr post treatment tumors were collected for assessment of phospho-histone H3 levels by immunohistochemical staining described below.

To measure accumulation of phospho-Histone H3 positive nuclei by immunohistochemistry a rabbit polyclonal antibody targeting residues surrounding phosphorylated Serine 10 of human histone H3 was obtained from Ventana Medical Systems (Tucson, AZ, Cat #760-4591). The IHC protocol included heat and mild exposure (32 min) to Ventana Discovery Cell Conditioner 1 antigen retrieval reagent. The samples were incubated for 60 min at room temperature with the primary antibody (pre-diluted by manufacturer). Subsequently incubation with OmniMap anti-rabbit HRP secondary Ab (Ventana, Tucson, AZ, Cat #760-4311) was performed for 12 min (pre-diluted by manufacturer).

Figure 14A:
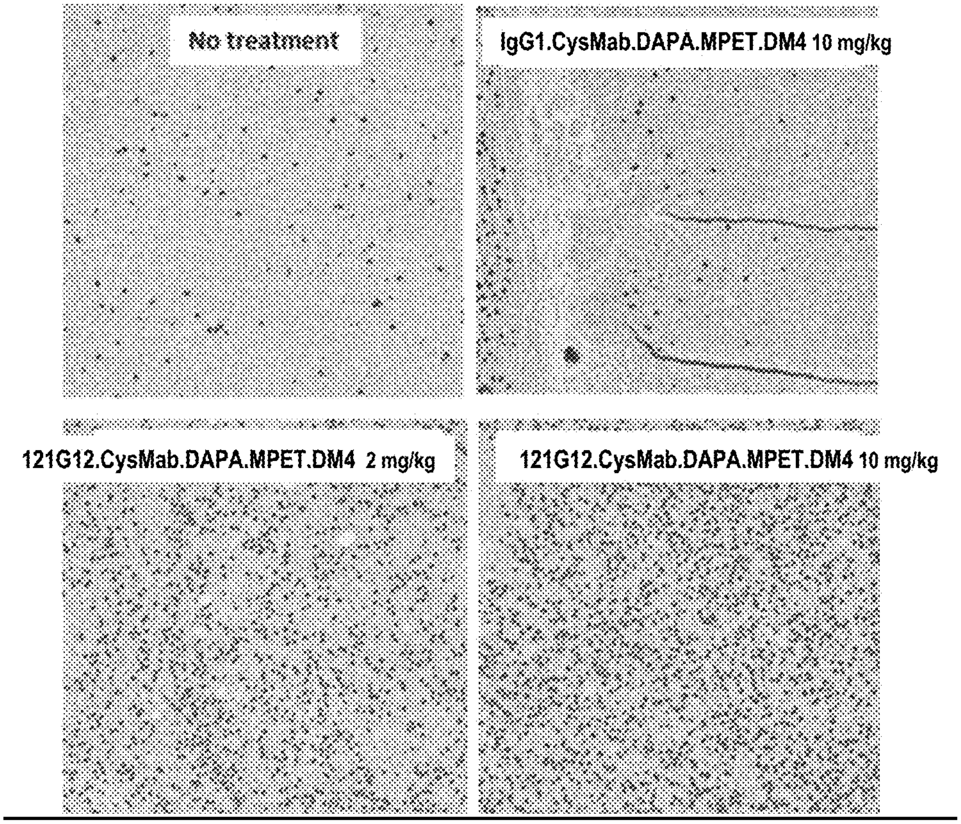
FIG. 14A-B depicts phospho-Histone H3 IHC images (FIG. 14A) and quantified phospho-Histone H3 signal (FIG. 14B) across KE97 tumors at 48 hr post treatment of single dose of either 121G12.CysMab.DAPA.MPET.DM4 at 2, 5, or 10 mg/kg or isotype control IgG1.CysMab.DAPA.MPET.DM4 at 10 mg/kg, demonstrating induction of mitotic arrest (phospho-histone H3) after treatment with anti-CCR7 ADC.
Figure 14B:
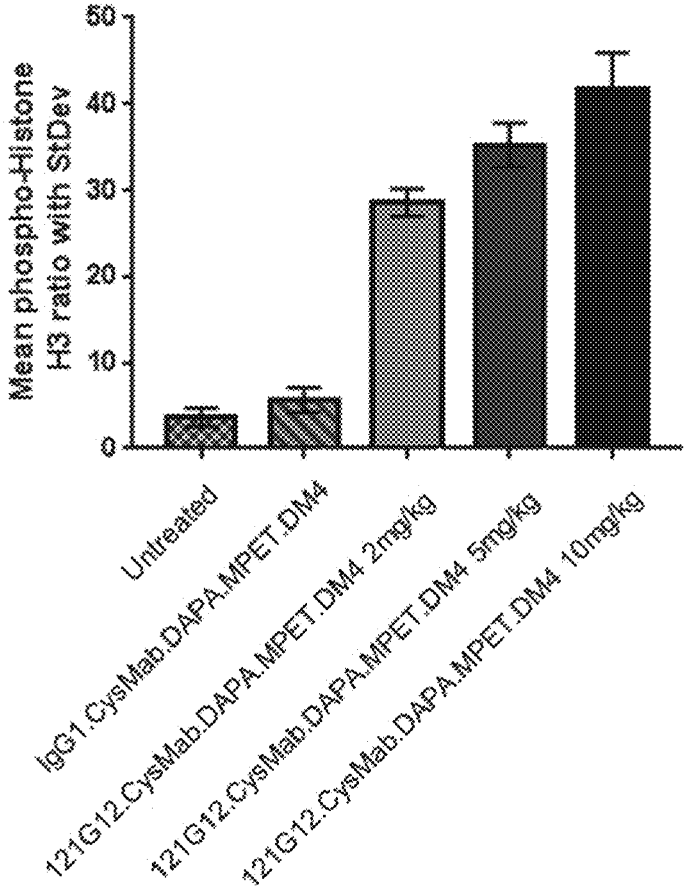

In FIG. 14A although the representative No Treatment and isotype control IgG1.CysMab.DAPA.MPET.DM4 show occasional tumor cells positive for phopho-histone H3, a robust dose-dependent increase in phopho-histone H3 immunostaining is detected 48 hr post administration of 121G12.CysMab.DAPA.MPET.DM4. Quantification of signal was done using MatLab (MathWorks, Natick M A) where total area of phospho-Histone H3 signal ($\mu m^2$) was normalized by total area of nuclei ($\mu m^2$), generating phospho-Histone H3 ratio (%) values shown below for each of the treatment groups. These data in FIG. 14B indicate that 121G12.CysMab.DAPA.MPET.DM4 is capable of eliciting a strong G2/M arrest in the tumor xenografts, consistent with the expected mechanism of action of the payload.

Example 17: Process for the Production of 121G12.CysMab.DAPA Antibody

This example describes a process for producing the CCR7 antibody 121G12.CysMab.DAPA from a cell culture, wherein the Ab is expressed from a vector that encodes the Ab. Once the Ab is expressed in the cell culture, the Ab is purified from the cell culture as follows:

The first step in the purification process of 121G12.CysMab.DAPA antibody drug substance intermediate consists of cell removal by inline depth filtration, followed by a 0.2 μm filtration.

The second step consists of a Protein A affinity liquid chromatography step. Depending on total amount of the bulk product, this step is performed in several runs. Each run allows a maximal loading of approximately 20 g/L column volume. The elution is performed with 50 mM acetic acid at approximately pH 3.0. The operation temperature is 18-28° C. All eluates are pooled and stored at 2-8° C. before the virus inactivation step.

Step three is a "low pH treatment" virus inactivation. The intermediate solution of step 2 is adjusted to 18-28° C. and an adjustment of the pH to 3.5 (range 3.4-3.6). The product intermediate solution is then held for virus inactivation for 70 minutes (range 60-90 minutes). After the holding time, the solution is adjusted to pH 6.0 (range 5.8-6.2). At the end of the step the solution is depth filtered in line with a 0.2 μm filtration and stored at 2-8° C.

The fourth step is a cation exchange chromatography in bind/elute mode which includes an integrated on-column reduction. Depending on the titer, this step is performed in several runs. Each run allows a loading of approximately 30 g/L column volume. The column is equilibrated with buffer A containing 20 mM sodium succinate, pH 6.0. On-column reduction is performed using 20 mM sodium phosphate, 1 mM EDTA, 7 mM L-cysteine, pH 7.1 as reduction buffer. The reduction buffer is removed with buffer A and the elution is performed with a linear gradient from 10% to 90% with buffer A and buffer B containing 10 mM sodium succinate, 300 mM sodium chloride, pH 6.0. Eluates and pools may be stored at 2-8° C. before the multimodal anion exchange chromatography step.

The fifth step of the process is an anion exchange chromatography in flow-through mode. Depending on the titer, this step is performed in several runs. Each run allows a maximal loading of approximately 350 g/L column volume. The operation temperature is 18-28° C. The equilibrium is performed with 20 mM sodium succinate, 119 mM sodium chloride, pH 6.0. The final percolate is stored at 2-8° C. before the virus removal step.

The virus filtration, step six, consists of a pre-filtration with a 0.1 μm filter followed by a virus filtration with a Planova 20N nanofilter. The temperature of the intermediate solution from Step 5 is adjusted to 18-28° C. before the virus filtration. The operation temperature is 18-28° C. After the nanofiltration the intermediate is stored at 2-8° C. or 18-28° C.

The seventh step, Ultrafiltration/Diafiltration, consists of an up-concentration step to approximately 70 g/L followed by a 1st diafiltration step with 10 mM potassium phosphate, pH 6.0. A diafiltration exchange factor of at least 7 is targeted followed by a dilution to approximately 50 g/L. The final drug substance intermediate is 0.2 μm filtered and stored at 2-8° C.

In the eighth and last step final bulk drug substance intermediate is filled in aliquots into suitable containers, and stored at below −60° C. after freezing.

TABLE 25

Flow diagram of the purification and reduction process

| Step | Operation |
|---|---|
| Step 1 | Harvesting, cell removal and filtration |
| Step 2 | Affinity Chromatography (MabSelect SuRE) |
| Step 3 | Virus inactivation at pH 3.5 |
| Step 4 | Cation Exchange Chromatography and On-column reduction (Fractogel EMD SO3 (M)) |
| Step 5 | Multimodal Anion Exchange Chromatography (Capto adhere) |
| Step 6 | Virus removal by nanofiltration (Planova 20N) |
| Step 7 | Ultrafiltration/Diafiltration and final filtration |
| Step 8 | Filling and deep-freezing |

Example 18: Dose Dependent In Vivo Efficacy of 121G12.CysMab.DAPA.MPET.DM4 Against OCI-LY3 ABC-DLBCL Xenograft Model in NSG Mice To demonstrate targeted anti-tumor activity of 121G12.CysMab.DAPA.MPET.DM4 in vivo in an ABC-DLBCL model, OCI-LY3 xenograft model was established in female NSG mice by subcutaneous injection of $10\times10^6$ cells into the right flank of each mouse. Once tumors reached approximately 140 $mm^3$, mice were randomized according to tumor volume into treatment groups (n=6 per group). Mice received an IV treatment of either 121G12.CysMab.DAPA.MPET.DM4 (DAR4) at a final dose of 0.5, 1 or 2 mg/kg or a non-specific isotype control hIgG1.CysMab.DAPA.MPET.DM4 at 2 mg/kg on day 1 and day 15 of study. All doses were adjusted to individual mouse body weights. All test agents were tolerated on study and no overt clinical symptoms of toxicities or body weight loss were observed in any of the treatment groups (Table 26).

Figure 15:
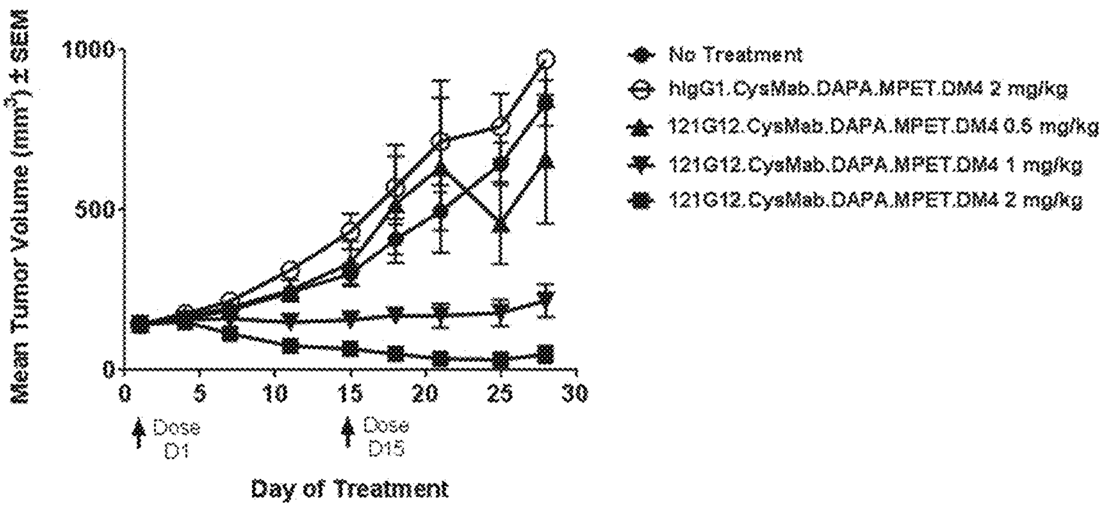
FIG. 15 depicts a graph illustrating dose response efficacy of 121G12.CysMab.DAPA.MPET.DM4 against OCI-LY3 ABC-DLBCL xenograft model.

No significant anti-tumor efficacy was observed after treatment with the non-specific isotype control hIgG1.CysMab.DAPA.MPET.DM4 at 2 mg/kg. 121G12.CysMab.DAPA.MPET.DM4 treatment resulted in dose-dependent anti-tumor efficacy with ΔT/ΔC value of 74.6% (0.5 mg/kg) and 10.7% (1 mg/kg), while the 2 mg/kg dose led to mean regression of 65.9% by day 28 of study. 3 of 6 mice in 121G12.CysMab.DAPA.MPET.DM4 2 mg/kg group displayed complete regression (FIG. 15).

TABLE 26

Anti-CCR7 ADC dose response efficacy in OCI-LY3 xenograft model on Day 28 of treatment.

| Treatment | Dose, schedule | Tumor Response $\Delta T/\Delta C$ (%) | Tumor Response Regression (%) | Host Response $\Delta$ body weight (%) | Host Response Survival (alive/total) |
|---|---|---|---|---|---|
| No treatment | None | 100.0 | — | 5.6 | 6/6 |
| hIgG1.CysMab.DAPA.MPET.DM4 | 2 mg/kg dosed D1 and D15 | 119.7 | — | 1.8 | 5/6 |
| 121G12.CysMab.DAPA.MPET.DM4 | 0.5 mg/kg dosed D1 and D15 | 74.6 | — | 3.5 | 5/6 |
| 121G12.CysMab.DAPA.MPET.DM4 | 1 mg/kg dosed D1 and D15 | 10.7** | | 2.9 | 6/6 |
| 121G12.CysMab.DAPA.MPET.DM4 | 2 mg/kg dosed D1 and D15 | — | 65.9** | −0.8 | 6/6 |

The experiment was evaluated on treatment Day 28,

**$p < 0.005$ versus control No Treatment group (One-Way ANOVA/Tukey's Multiple Comparisons Test). % $\Delta T/\Delta C$ = 100 $\Delta T/\Delta C$ where: $\Delta T$ = mean tumor volume of the drug treated group on D28 of study-mean tumor volume of the drug treated group on initial day of dosing; $\Delta C$ = mean tumor volume of the control group on D28 of study-mean tumor volume of the control group on initial day of dosing D1. % Regression = $(1 - T_{final}/T_{initial}) \times 100$ was calculated if $\Delta T < 0$, where $T_{final}$ is mean tumor volume D28 and $T_{initial}$ is defined as tumor volume on D1 of treatment. $\Delta$ body weight (%) = (Mean body weight D28-mean body weight D1) *100/Mean body weight D1 of treatment.

Example 19: Dose Dependent In Vivo Efficacy of 121G12.CysMab.DAPA.MPET.DM4 Against Toledo GCB-DLBCL Xenograft Model in SCID-Bg Mice To demonstrate targeted anti-tumor activity of 121G12.CysMab.DAPA.MPET.DM4 in vivo in a GCB-DLBCL model, Toledo xenograft model was established in female Scid-bg mice by subcutaneous injection of $3\times10^6$ cells into the right flank of each mouse. Once tumors reached approximately 100 $mm^3$, mice were randomized according to tumor volume into treatment groups (n=4 per group). Mice received an IV treatment of either 121G12.CysMab.DAPA.MPET.DM4 (DAR4) at a final dose of 2 or 5 mg/kg or a non-specific isotype control hIgG1.CysMab.DAPA.MPET.DM4 at 5 mg/kg on day 1 and day 15 of study. All doses were adjusted to individual mouse body weights. All test agents were tolerated on study and no overt clinical symptoms of toxicities or body weight loss were observed in any of the treatment groups (Table 27).

Figure 16:
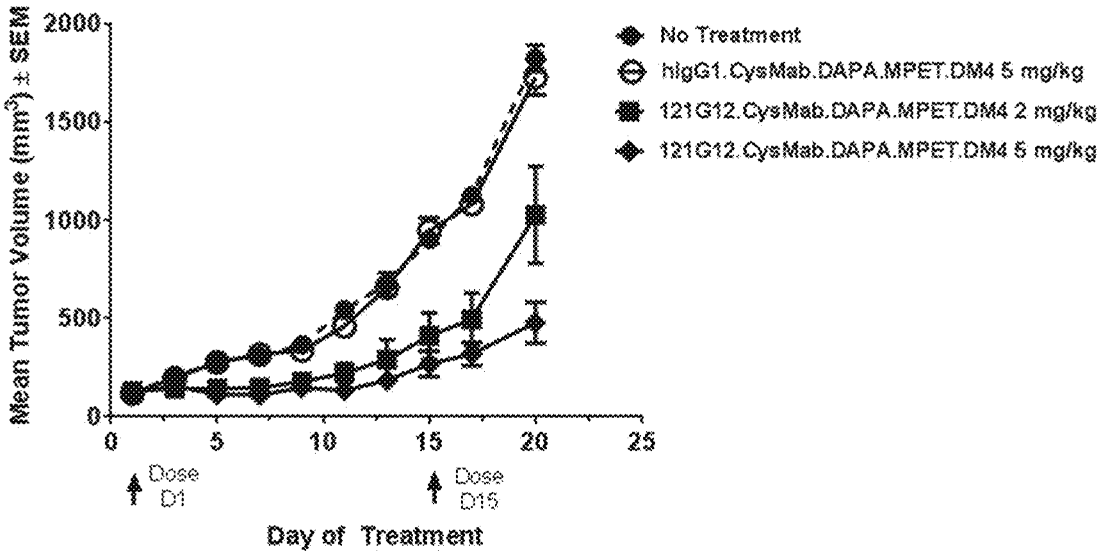
FIG. 16 depicts a graph illustrating dose response efficacy of 121G12.CysMab.DAPA.MPET.DM4 against Toledo GCB-DLBCL xenograft model.

No significant anti-tumor efficacy was observed after treatment with the non-specific isotype control hIgG1.CysMab.DAPA.MPET.DM4 at 5 mg/kg. 121G12.CysMab.DAPA.MPET.DM4 treatment resulted in dose-dependent anti-tumor efficacy, with $\Delta T/\Delta C$ value of 52.7% (2 mg/kg) and 20.6% (5 mg/kg) (FIG. 16, Table 27).

TABLE 27

Anti-CCR7 ADC dose response efficacy in Toledo xenograft model on Day 20 of treatment.

| Treatment | Dose, schedule | Tumor Response $\Delta T/\Delta C$ (%) | Host Response $\Delta$ body weight (%) | Host Response Survival (alive/total) |
|---|---|---|---|---|
| No treatment | None | 100.0 | 4.9 | 3/6 |
| hIgG1.CysMab.DAPA.MPET.DM4 | 5 mg/kg dosed D1 and D15 | 94.5 | 1.0 | 3/6 |
| 121G12.CysMab.DAPA.MPET.DM4 | 2 mg/kg dosed D1 and D15 | 52.7* | 3.2 | 4/6 |
| 121G12.CysMab.DAPA.MPET.DM4 | 5 mg/kg dosed D1 and D15 | 20.6 ** | 0.1 | 4/6 |

The experiment was evaluated on treatment Day 20,

*$p < 0.05$,

**$p < 0.005$ versus control No Treatment group (One-Way ANOVA/Tukey's Multiple Comparisons Test). % $\Delta T/\Delta C$ = 100 $\Delta T/\Delta C$ where: $\Delta T$ = mean tumor volume of the drug treated group on D20 of study-mean tumor volume of the drug treated group on initial day of dosing; $\Delta C$ = mean tumor volume of the control group on D20 of study-mean tumor volume of the control group on initial day of dosing D1. A body weight (%) = (Mean body weight D20-mean body weight D1) *100/Mean body weight D1 of treatment.

Example 20: In Vivo Efficacy of 121G12.CysMab.DAPA.MPET.DM4 Against DEL ALCL Xenograft Model in SCID-Bg Mice To demonstrate targeted anti-tumor activity of 121G12.CysMab.DAPA.MPET.DM4 in vivo in a CCR7 positive ALCL model, DEL xenograft model was established in female Scid-bg mice by subcutaneous injection of $3\times10^6$ cells into the right flank of each mouse. Once tumors reached approximately 100 $mm^3$, mice were randomized according to tumor volume into treatment groups (n=4 per group). Mice received an IV treatment of either 121G12.CysMab.DAPA.MPET.DM4 (DAR4) at a final dose of 2 mg/kg or a non-specific isotype control isotype.MPET.DM4 at 2 mg/kg on day 1 and day 15 of study. All doses were adjusted to individual mouse body weights.

Figure 17:
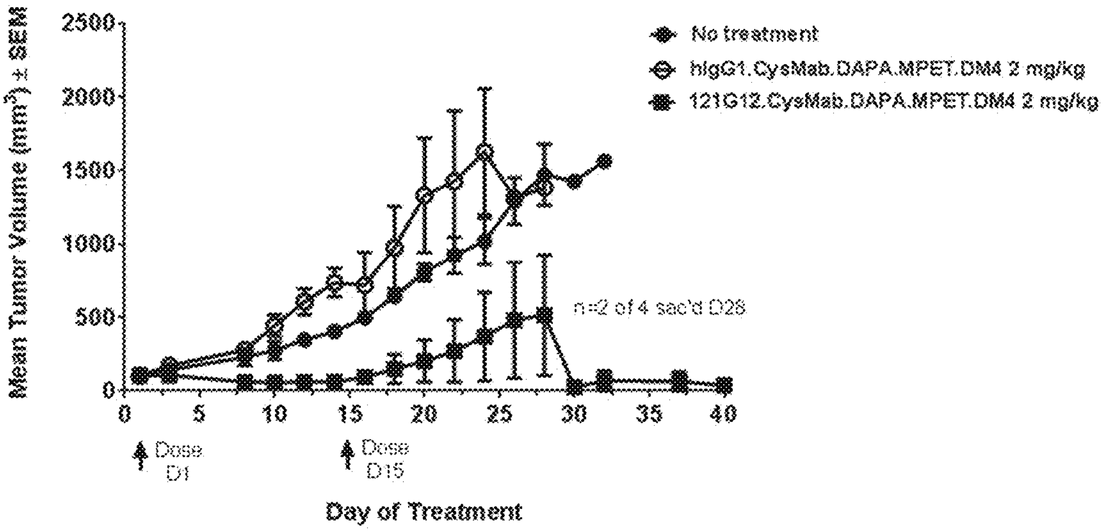
FIG. 17 depicts a graph illustrating efficacy of 121G12.CysMab.DAPA.MPET.DM4 against DEL ALCL xenograft model.

No significant anti-tumor efficacy was observed after treatment with the non-specific isotype control hIgG1.CysMab.DAPA.MPET.DM4 at 2 mg/kg. Treatment with 121G12.CysMab.DAPA.MPET.DM4 2 mg/kg resulted in mean regression of 40.2% by day 14 of study after a single dose ($p<0.01$). Mice received a second dose on day 15 and were monitored for three more weeks. One outlier animal failed to respond to a second dose of treatment and had to be euthanized by day 28 due to tumor burden. One additional animal showed slow disease progression and was also taken down on day 28 for target expression follow-up. Two of the four mice continued to display a sustained impact on tumor growth (FIG. 17). All treatments were well tolerated with no apparent body weight loss.

Example 21: In Vivo Efficacy of 121G12.CysMab.DAPA.MPET.DM4 Against Primary Patient Derived Non-Small Cell Lung Cancer HLUX1787 Tumor Model Anti-tumor activity of 121G12.CysMab.DAPA.MPET.DM4 was evaluated in the CCR7 expressing HLUX1787 primary non-small cell lung cancer xenograft model. Female NSG mice were implanted subcutaneously with tumor fragments into the right flank of each mouse. Once tumors reached approximately 150 $mm^3$, mice were randomized according to tumor volume into treatment groups (n=6 per group). Mice received an IV treatment of either 121G12.CysMab.DAPA.MPET.DM4 (DAR4) at 0.5, 2 or 5 mg/kg on day 1 and a second dose was delivered 2 weeks later on day 15. All doses were adjusted to individual mouse body weights.

Figure 18:
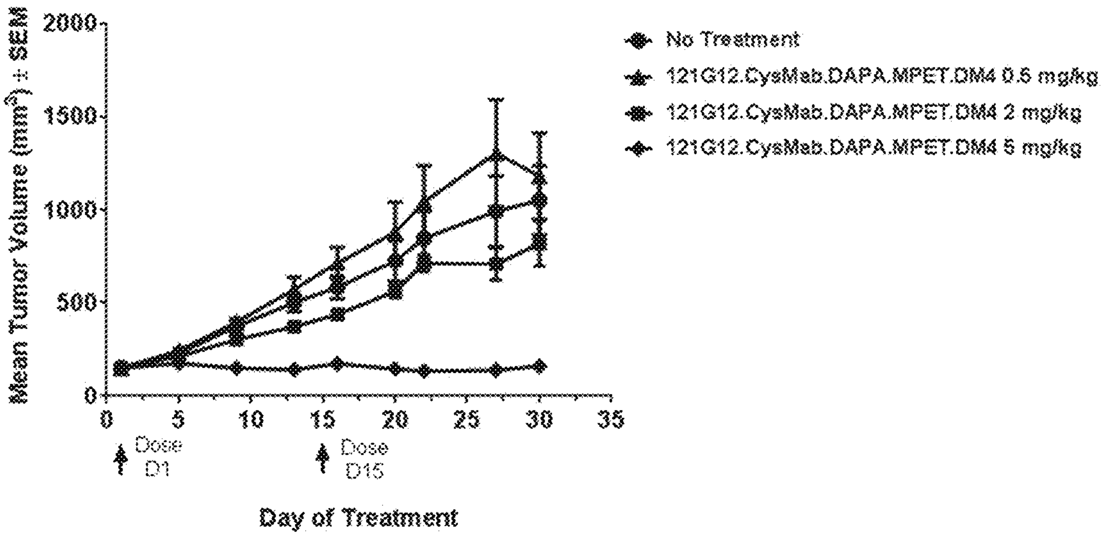
FIG. 18 depicts a graph illustrating dose response efficacy of 121G12.CysMab.DAPA.MPET.DM4 against HLUX1787 NSCLC patient derived xenograft model.

No significant anti-tumor efficacy was observed with the lower doses of the conjugated Ab, however partial regressions or stable disease were observed with 121G12.CysMab.DAPA.MPET.DM4 treatment at 5 mg/kg. Sustained tumor efficacy was observed two weeks after the second dose, resulting in $\Delta T/\Delta C$ value of 1.3% on D30 of treatment ($p<0.001$; One-Way ANOVA/Tukey's Multiple Comparisons Test) (FIG. 18) All treatments were well tolerated with no apparent body weight loss.

We claim:

1. A nucleic acid that encodes an antibody or antigen binding fragment comprising a. a heavy chain variable region that comprises an HCDR1 (Heavy Chain Complementarity Determining Region 1) of SEQ ID NO:1, an HCDR2 (Heavy Chain Complementarity Determining Region 2) of SEQ ID NO:2, and an HCDR3 (Heavy Chain Complementarity Determining Region 3) of SEQ ID NO:3; and a light chain variable region that comprises an LCDR1 (Light Chain Complementarity Determining Region 1) of SEQ ID NO:17, an LCDR2 (Light Chain Complementarity Determining Region 2) of SEQ ID NO: 18, and an LCDR3 (Light Chain Complementarity Determining Region 3) of SEQ ID NO: 19;

b. a heavy chain variable region that comprises an HCDR1 of SEQ ID NO:4, an HCDR2 of SEQ ID NO:5, and an HCDR3 of SEQ ID NO:6; and a light chain variable region that comprises an LCDR1 of SEQ ID NO:20, an LCDR2 of SEQ ID NO:21, and an LCDR3 of SEQ ID NO:22;

c. a heavy chain variable region that comprises an HCDR1 of SEQ ID NO:7, an HCDR2 of SEQ ID NO:8, and an HCDR3 of SEQ ID NO:9; and a light chain variable region that comprises an LCDR1 of SEQ ID NO:23, an LCDR2 of SEQ ID NO:24, and an LCDR3 of SEQ ID NO:25;

d. a heavy chain variable region that comprises an HCDR1 of SEQ ID NO: 10, an HCDR2 of SEQ ID NO:11, and an HCDR3 of SEQ ID NO:12; and a light chain variable region that comprises an LCDR1 of SEQ ID NO:26, an LCDR2 of SEQ ID NO: 27, and an LCDR3 of SEQ ID NO:28;

e. a heavy chain variable region that comprises an HCDR1 of SEQ ID NO: 33, an HCDR2 of SEQ ID NO:34, and an HCDR3 of SEQ ID NO:35; and a light chain variable region that comprises an LCDR1 of SEQ ID NO:49, an LCDR2 of SEQ ID NO: 50, and an LCDR3 of SEQ ID NO:51;

f. a heavy chain variable region that comprises an HCDR1 of SEQ ID NO: 36, an HCDR2 of SEQ ID NO:37, and an HCDR3 of SEQ ID NO:38; and a light chain variable region that comprises an LCDR1 of SEQ ID NO:52, an LCDR2 of SEQ ID NO: 53, and an LCDR3 of SEQ ID NO:54;

g. a heavy chain variable region that comprises an HCDR1 of SEQ ID NO: 39, an HCDR2 of SEQ ID NO:40, and an HCDR3 of SEQ ID NO:41; and a light chain variable region that comprises an LCDR1 of SEQ ID NO:55, an LCDR2 of SEQ ID NO: 56, and an LCDR3 of SEQ ID NO:57;

h. a heavy chain variable region that comprises an HCDR1 of SEQ ID NO: 42, an HCDR2 of SEQ ID NO:43, and an HCDR3 of SEQ ID NO:44; and a light chain variable region that comprises an LCDR1 of SEQ ID NO:58, an LCDR2 of SEQ ID NO: 59, and an LCDR3 of SEQ ID NO:60;

i. a heavy chain variable region that comprises an HCDR1 of SEQ ID NO: 65, an HCDR2 of SEQ ID NO:66, and an HCDR3 of SEQ ID NO:67; and a light chain variable region that comprises an LCDR1 of SEQ ID NO:81, an LCDR2 of SEQ ID NO: 82, and an LCDR3 of SEQ ID NO:83;

j. a heavy chain variable region that comprises an HCDR1 of SEQ ID NO: 68, an HCDR2 of SEQ ID NO:69, and an HCDR3 of SEQ ID NO:70; and a light chain variable region that comprises an LCDR1 of SEQ ID NO:84, an LCDR2 of SEQ ID NO: 85, and an LCDR3 of SEQ ID NO:86;

k. a heavy chain variable region that comprises an HCDR1 of SEQ ID NO: 71, an HCDR2 of SEQ ID NO:72, and an HCDR3 of SEQ ID NO:73; and a light chain variable region that comprises an LCDR1 of SEQ ID NO:87, an LCDR2 of SEQ ID NO: 88, and an LCDR3 of SEQ ID NO:89;

l. a heavy chain variable region that comprises an HCDR1 of SEQ ID NO: 74, an HCDR2 of SEQ ID NO:75, and an HCDR3 of SEQ ID NO:76; and a light chain variable region that comprises an LCDR1 of SEQ ID NO:90, an LCDR2 of SEQ ID NO: 91, and an LCDR3 of SEQ ID NO:92;

m. a heavy chain variable region that comprises an HCDR1 of SEQ ID NO: 596, an HCDR2 of SEQ ID NO:597, and an HCDR3 of SEQ ID NO:598; and a light chain variable region that comprises an LCDR1 of SEQ ID NO:612, an LCDR2 of SEQ ID NO: 613, and an LCDR3 of SEQ ID NO:614;

n. a heavy chain variable region that comprises an HCDR1 of SEQ ID NO: 599, an HCDR2 of SEQ ID NO:600, and an HCDR3 of SEQ ID NO:601; and a light chain variable region that comprises an LCDR1 of SEQ ID NO:615, an LCDR2 of SEQ ID NO: 616, and an LCDR3 of SEQ ID NO:617;

o. a heavy chain variable region that comprises an HCDR1 of SEQ ID NO: 602, an HCDR2 of SEQ ID NO:603, and an HCDR3 of SEQ ID NO:604; and a light chain variable region that comprises an LCDR1 of SEQ ID NO:618, an LCDR2 of SEQ ID NO: 619, and an LCDR3 of SEQ ID NO:620; or p. a heavy chain variable region that comprises an HCDR1 of SEQ ID NO: 605, an HCDR2 of SEQ ID NO:606, and an HCDR3 of SEQ ID NO:607; and a light chain variable region that comprises an LCDR1 of SEQ ID NO:621, an LCDR2 of SEQ ID NO: 622, and an LCDR3 of SEQ ID NO:623.

2. The nucleic acid of claim 1, wherein the nucleic acid comprises the nucleotide sequence of SEQ ID NOs: 14, 16, 30, 32, 46, 48, 62, 64, 78, 80, 94, 96, 481, 483, 497, or 499.

3. A vector comprising the nucleic acid of claim 1.

4. A host cell comprising the nucleic acid according to claim 1.

5. A process for producing an antibody or antigen binding fragment comprising cultivating the host cell of claim 4 and recovering the antibody from cell culture.

(b) conjugating said linker-drug moiety to the antibody recovered from the cell culture of claim 6 to produce an antibody drug conjugate; and (c) purifying the antibody drug conjugate.

8. The process according to claim 7 comprising:

(a) pre-forming a linker-drug moiety of the following Formula:

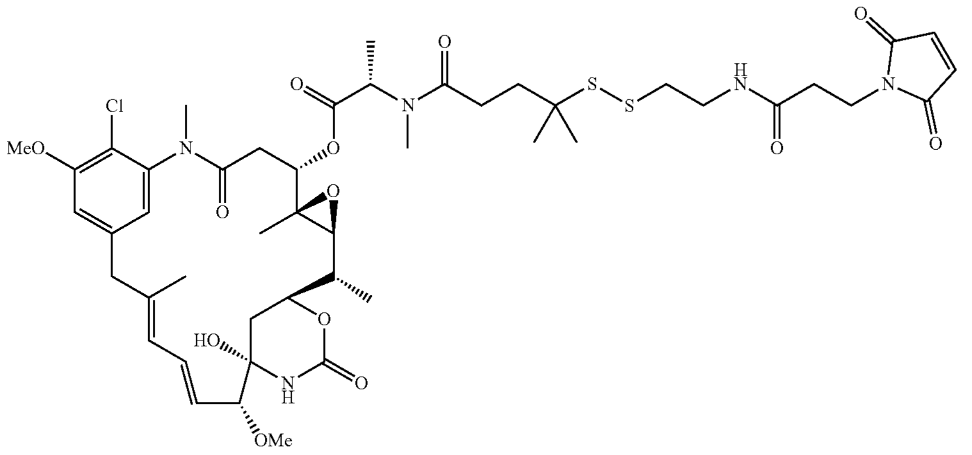 [SMILES: COc1cc2cc(c1Cl)N(C)C(=O)C[C@H](OC(=O)[C@H](C)N(C)C(=O)CCC(C)(C)SSCCNC(=O)CCN1C(=O)C=CC1=O)[C@]1(C)O[C@H]1[C@H](C)[C@@H]1C[C@@](O)(NC(=O)O1)[C@H](OC)/C=C/C=C(\C)C2]

and (b) conjugating said linker-drug moiety to the antibody recovered from the cell culture of claim 6 to produce an antibody drug conjugate; and (c) purifying the antibody drug conjugate.

6. The process of claim 5 wherein recovering the antibody from cell culture comprises the steps of:

a) removing cells and filtering the culture;

b) purifying the culture by affinity chromatography;

c) inactivating any viruses in the culture by adjusting the pH to 3.4-3.6, then readjusting the pH to 5.8-6.2 and filtering the culture;

d) purifying the culture by cation exchange chromatography and performing on-column reduction of the culture;

e) performing anion exchange chromatography on the culture;

f) removing viruses by nanofiltration;

g) filtering the culture containing the antibody; and h) obtaining purified antibody.

7. A process for producing an anti-CCR7 antibody drug conjugate comprising:

(a) pre-forming a linker-drug moiety of the following Formula:

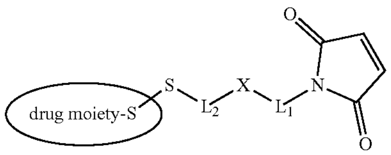

wherein:

the drug moiety is DM1, DM3 or DM4 and the drug moiety is attached to the linker via its thiol functionality;

$L^1$ is a $C_{1-6}$alkylene wherein one of the methylene groups may be replaced with oxygen;

$L^2$ is a $C_{1-6}$alkylene or is $-(CH_2CH_2O)_y-CH_2-CH_2-$ wherein y is 1 to 11;

X is —C(O)—NH—, —NHC(O)— or a triazole; and alkylene is linear or branched;

9. A process for producing an anti-CCR7 antibody drug conjugate comprising:

(a) pre-forming a linker-drug moiety of the following Formula:

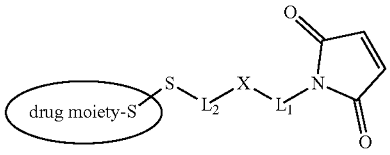

wherein:

the drug moiety is DM1, DM3 or DM4 and the drug moiety is attached to the linker via its thiol functionality;

$L^1$ is a $C_{1-6}$alkylene wherein one of the methylene groups may be replaced with oxygen;

$L^2$ is a $C_{1-6}$alkylene or is $-(CH_2CH_2O)_y-CH_2-CH_2-$ wherein y is 1 to 11;

X is —C(O)—NH—, —NHC(O)— or a triazole; and alkylene is linear or branched;

(b) conjugating said linker-drug moiety to an antibody or antigen binding fragment thereof to produce an antibody drug conjugate; and (c) purifying the antibody drug conjugate, wherein the antibody or antigen binding fragment thereof comprises:

a. a heavy chain variable region that comprises an HCDR1 (Heavy Chain Complementarity Determining Region 1) of SEQ ID NO:1, an HCDR2 (Heavy Chain Complementarity Determining Region 2) of SEQ ID NO:2, and an HCDR3 (Heavy Chain Complementarity Determining Region 3) of SEQ ID NO:3; and a light chain variable region that comprises an LCDR1 (Light Chain Complementarity Determining Region 1) of SEQ ID NO:17, an LCDR2 (Light Chain Complementarity Determining Region 2) of SEQ ID NO:18, and an LCDR3 (Light Chain Complementarity Determining Region 3) of SEQ ID NO:19;

b. a heavy chain variable region that comprises an HCDR1 of SEQ ID NO:4, an HCDR2 of SEQ ID NO:5, and an HCDR3 of SEQ ID NO:6; and a light chain variable region that comprises an LCDR1 of SEQ ID NO:20, an LCDR2 of SEQ ID NO:21, and an LCDR3 of SEQ ID NO:22;

c. a heavy chain variable region that comprises an HCDR1 of SEQ ID NO:7, an HCDR2 of SEQ ID NO:8, and an HCDR3 of SEQ ID NO:9; and a light chain variable region that comprises an LCDR1 of SEQ ID NO:23, an LCDR2 of SEQ ID NO:24, and an LCDR3 of SEQ ID NO:25;

d. a heavy chain variable region that comprises an HCDR1 of SEQ ID NO: 10, an HCDR2 of SEQ ID NO: 11, and an HCDR3 of SEQ ID NO: 12; and a light chain variable region that comprises an LCDR1 of SEQ ID NO:26, an LCDR2 of SEQ ID NO: 27, and an LCDR3 of SEQ ID NO:28;

e. a heavy chain variable region that comprises an HCDR1 of SEQ ID NO: 33, an HCDR2 of SEQ ID NO:34, and an HCDR3 of SEQ ID NO:35; and a light chain variable region that comprises an LCDR1 of SEQ ID NO:49, an LCDR2 of SEQ ID NO: 50, and an LCDR3 of SEQ ID NO:51;

f. a heavy chain variable region that comprises an HCDR1 of SEQ ID NO: 36, an HCDR2 of SEQ ID NO:37, and an HCDR3 of SEQ ID NO:38; and a light chain variable region that comprises an LCDR1 of SEQ ID NO:52, an LCDR2 of SEQ ID NO: 53, and an LCDR3 of SEQ ID NO:54;

g. a heavy chain variable region that comprises an HCDR1 of SEQ ID NO: 39, an HCDR2 of SEQ ID NO:40, and an HCDR3 of SEQ ID NO:41; and a light chain variable region that comprises an LCDR1 of SEQ ID NO:55, an LCDR2 of SEQ ID NO: 56, and an LCDR3 of SEQ ID NO:57;

h. a heavy chain variable region that comprises an HCDR1 of SEQ ID NO: 42, an HCDR2 of SEQ ID NO:43, and an HCDR3 of SEQ ID NO:44; and a light chain variable region that comprises an LCDR1 of SEQ ID NO:58, an LCDR2 of SEQ ID NO: 59, and an LCDR3 of SEQ ID NO:60;

i. a heavy chain variable region that comprises an HCDR1 of SEQ ID NO: 65, an HCDR2 of SEQ ID NO:66, and an HCDR3 of SEQ ID NO:67; and a light chain variable region that comprises an LCDR1 of SEQ ID NO:81, an LCDR2 of SEQ ID NO: 82, and an LCDR3 of SEQ ID NO:83;

j. a heavy chain variable region that comprises an HCDR1 of SEQ ID NO: 68, an HCDR2 of SEQ ID NO:69, and an HCDR3 of SEQ ID NO:70; and a light chain variable region that comprises an LCDR1 of SEQ ID NO:84, an LCDR2 of SEQ ID NO: 85, and an LCDR3 of SEQ ID NO:86;

k. a heavy chain variable region that comprises an HCDR1 of SEQ ID NO: 71, an HCDR2 of SEQ ID NO:72, and an HCDR3 of SEQ ID NO:73; and a light chain variable region that comprises an LCDR1 of SEQ ID NO:87, an LCDR2 of SEQ ID NO: 88, and an LCDR3 of SEQ ID NO:89;

l. a heavy chain variable region that comprises an HCDR1 of SEQ ID NO: 74, an HCDR2 of SEQ ID NO:75, and an HCDR3 of SEQ ID NO:76; and a light chain variable region that comprises an LCDR1 of SEQ ID NO:90, an LCDR2 of SEQ ID NO: 91, and an LCDR3 of SEQ ID NO:92;

m. a heavy chain variable region that comprises an HCDR1 of SEQ ID NO: 596, an HCDR2 of SEQ ID NO:597, and an HCDR3 of SEQ ID NO:598; and a light chain variable region that comprises an LCDR1 of SEQ ID NO:612, an LCDR2 of SEQ ID NO: 613, and an LCDR3 of SEQ ID NO:614;

n. a heavy chain variable region that comprises an HCDR1 of SEQ ID NO: 599, an HCDR2 of SEQ ID NO:600, and an HCDR3 of SEQ ID NO:601; and a light chain variable region that comprises an LCDR1 of SEQ ID NO:615, an LCDR2 of SEQ ID NO: 616, and an LCDR3 of SEQ ID NO:617;

o. a heavy chain variable region that comprises an HCDR1 of SEQ ID NO: 602, an HCDR2 of SEQ ID NO:603, and an HCDR3 of SEQ ID NO:604; and a light chain variable region that comprises an LCDR1 of SEQ ID NO:618, an LCDR2 of SEQ ID NO: 619, and an LCDR3 of SEQ ID NO:620; or p. a heavy chain variable region that comprises an HCDR1 of SEQ ID NO: 605, an HCDR2 of SEQ ID NO:606, and an HCDR3 of SEQ ID NO:607; and a light chain variable region that comprises an LCDR1 of SEQ ID NO:621, an LCDR2 of SEQ ID NO: 622, and an LCDR3 of SEQ ID NO:623.

10. A process for producing an anti-CCR7 antibody drug conjugate comprising:

(a) pre-forming a linker-drug moiety of the following Formula:

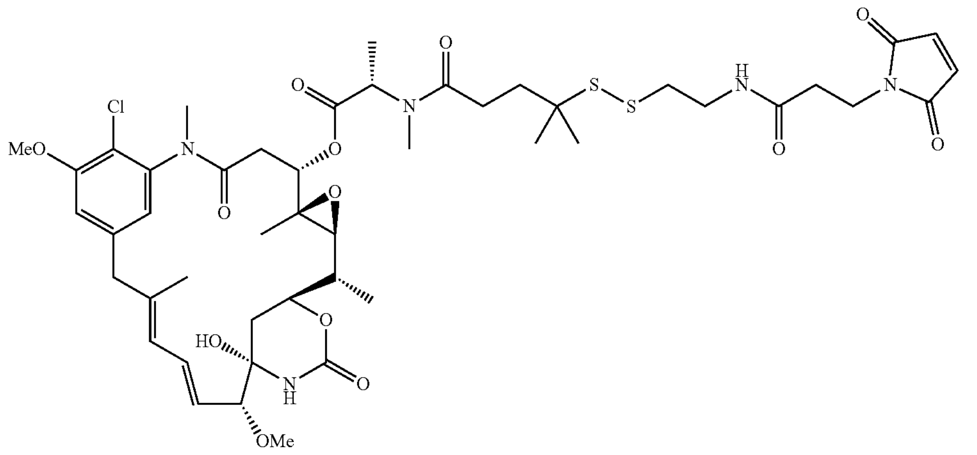 [SMILES: COc1cc2cc(c1Cl)N(C)C(=O)C[C@H](OC(=O)[C@H](C)N(C)C(=O)CCC(C)(C)SSCCNC(=O)CCN1C(=O)C=CC1=O)[C@]1(C)O[C@H]1[C@H](C)[C@@H]1C[C@@](O)(NC(=O)O1)[C@H](OC)/C=C/C=C(\C)C2]

(b) conjugating said linker-drug moiety to an antibody or antigen binding fragment thereof of to produce an antibody drug conjugate; and (c) purifying the antibody drug conjugate, wherein the antibody or antigen binding fragment thereof comprises:

a. a heavy chain variable region that comprises an HCDR1 (Heavy Chain Complementarity Determining Region 1) of SEQ ID NO:1, an HCDR2 (Heavy Chain Complementarity Determining Region 2) of SEQ ID NO:2, and an HCDR3 (Heavy Chain Complementarity Determining Region 3) of SEQ ID NO:3; and a light chain variable region that comprises an LCDR1 (Light Chain Complementarity Determining Region 1) of SEQ ID NO:17, an LCDR2 (Light Chain Complementarity Determining Region 2) of SEQ ID NO:18, and an LCDR3 (Light Chain Complementarity Determining Region 3) of SEQ ID NO:19;

b. a heavy chain variable region that comprises an HCDR1 of SEQ ID NO:4, an HCDR2 of SEQ ID NO:5, and an HCDR3 of SEQ ID NO:6; and a light chain variable region that comprises an LCDR1 of SEQ ID NO:20, an LCDR2 of SEQ ID NO:21, and an LCDR3 of SEQ ID NO:22;

c. a heavy chain variable region that comprises an HCDR1 of SEQ ID NO:7, an HCDR2 of SEQ ID NO:8, and an HCDR3 of SEQ ID NO:9; and a light chain variable region that comprises an LCDR1 of SEQ ID NO:23, an LCDR2 of SEQ ID NO:24, and an LCDR3 of SEQ ID NO:25;

d. a heavy chain variable region that comprises an HCDR1 of SEQ ID NO: 10, an HCDR2 of SEQ ID NO:11, and an HCDR3 of SEQ ID NO: 12; and a light chain variable region that comprises an LCDR1 of SEQ ID NO:26, an LCDR2 of SEQ ID NO: 27, and an LCDR3 of SEQ ID NO:28;

e. a heavy chain variable region that comprises an HCDR1 of SEQ ID NO: 33, an HCDR2 of SEQ ID NO:34, and an HCDR3 of SEQ ID NO:35; and a light chain variable region that comprises an LCDR1 of SEQ ID NO:49, an LCDR2 of SEQ ID NO: 50, and an LCDR3 of SEQ ID NO:51;

f. a heavy chain variable region that comprises an HCDR1 of SEQ ID NO: 36, an HCDR2 of SEQ ID NO:37, and an HCDR3 of SEQ ID NO:38; and a light chain variable region that comprises an LCDR1 of SEQ ID NO:52, an LCDR2 of SEQ ID NO: 53, and an LCDR3 of SEQ ID NO:54;

g. a heavy chain variable region that comprises an HCDR1 of SEQ ID NO: 39, an HCDR2 of SEQ ID NO:40, and an HCDR3 of SEQ ID NO:41; and a light chain variable region that comprises an LCDR1 of SEQ ID NO:55, an LCDR2 of SEQ ID NO: 56, and an LCDR3 of SEQ ID NO:57;

h. a heavy chain variable region that comprises an HCDR1 of SEQ ID NO: 42, an HCDR2 of SEQ ID NO:43, and an HCDR3 of SEQ ID NO:44; and a light chain variable region that comprises an LCDR1 of SEQ ID NO:58, an LCDR2 of SEQ ID NO: 59, and an LCDR3 of SEQ ID NO:60;

i. a heavy chain variable region that comprises an HCDR1 of SEQ ID NO: 65, an HCDR2 of SEQ ID NO:66, and an HCDR3 of SEQ ID NO:67; and a light chain variable region that comprises an LCDR1 of SEQ ID NO:81, an LCDR2 of SEQ ID NO: 82, and an LCDR3 of SEQ ID NO:83;

j. a heavy chain variable region that comprises an HCDR1 of SEQ ID NO: 68, an HCDR2 of SEQ ID NO:69, and an HCDR3 of SEQ ID NO:70; and a light chain variable region that comprises an LCDR1 of SEQ ID NO:84, an LCDR2 of SEQ ID NO: 85, and an LCDR3 of SEQ ID NO:86;

k. a heavy chain variable region that comprises an HCDR1 of SEQ ID NO: 71, an HCDR2 of SEQ ID NO:72, and an HCDR3 of SEQ ID NO:73; and a light chain variable region that comprises an LCDR1 of SEQ ID NO:87, an LCDR2 of SEQ ID NO: 88, and an LCDR3 of SEQ ID NO:89;

l. a heavy chain variable region that comprises an HCDR1 of SEQ ID NO: 74, an HCDR2 of SEQ ID NO:75, and an HCDR3 of SEQ ID NO: 76; and a light chain variable region that comprises an LCDR1 of SEQ ID NO:90, an LCDR2 of SEQ ID NO: 91, and an LCDR3 of SEQ ID NO:92;

m. a heavy chain variable region that comprises an HCDR1 of SEQ ID NO: 596, an HCDR2 of SEQ ID NO:597, and an HCDR3 of SEQ ID NO:598; and a light chain variable region that comprises an LCDR1 of SEQ ID NO:612, an LCDR2 of SEQ ID NO: 613, and an LCDR3 of SEQ ID NO:614;

n. a heavy chain variable region that comprises an HCDR1 of SEQ ID NO: 599, an HCDR2 of SEQ ID NO:600, and an HCDR3 of SEQ ID NO:601; and a light chain variable region that comprises an LCDR1 of SEQ ID NO:615, an LCDR2 of SEQ ID NO: 616, and an LCDR3 of SEQ ID NO:617;

o. a heavy chain variable region that comprises an HCDR1 of SEQ ID NO: 602, an HCDR2 of SEQ ID NO:603, and an HCDR3 of SEQ ID NO:604; and a light chain variable region that comprises an LCDR1 of SEQ ID NO:618, an LCDR2 of SEQ ID NO: 619, and an LCDR3 of SEQ ID NO:620; or p. a heavy chain variable region that comprises an HCDR1 of SEQ ID NO: 605, an HCDR2 of SEQ ID NO:606, and an HCDR3 of SEQ ID NO:607; and a light chain variable region that comprises an LCDR1 of SEQ ID NO:621, an LCDR2 of SEQ ID NO: 622, and an LCDR3 of SEQ ID NO:623.

11. The process according to claim 7, wherein the step of pre-forming said linker-drug moiety comprises:

a) Reacting a drug moiety via its thiol functionality with:

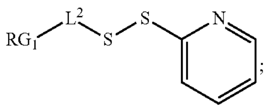

to form:

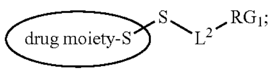

b) Reacting the formed

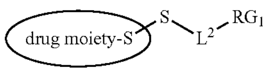

with:

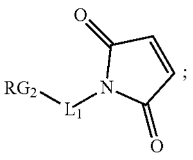

to form the linker-drug moiety:

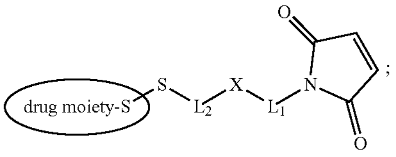

wherein:

$L^1$ is a $C_{1-6}$alkylene wherein one of the methylene groups may be replaced with oxygen;

$L^2$ is a $C_{1-6}$alkylene or is $—(CH_2CH_2O)_y—CH_2—CH_2—$ wherein y is 1 to 11; and X is —C(O)—NH—, —NHC(O)— or a triazole;

wherein the alkylene is linear or branched; and

RG1 and RG2 are 2 reactive groups forming group X.

12. The process according to claim 8, wherein the step of pre-forming said linker-drug moiety comprises:

c) Reacting the drug moiety via its thiol functionality with:

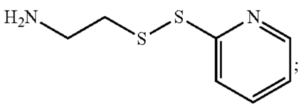 [SMILES: NCCSSc1ccccn1]

to form:

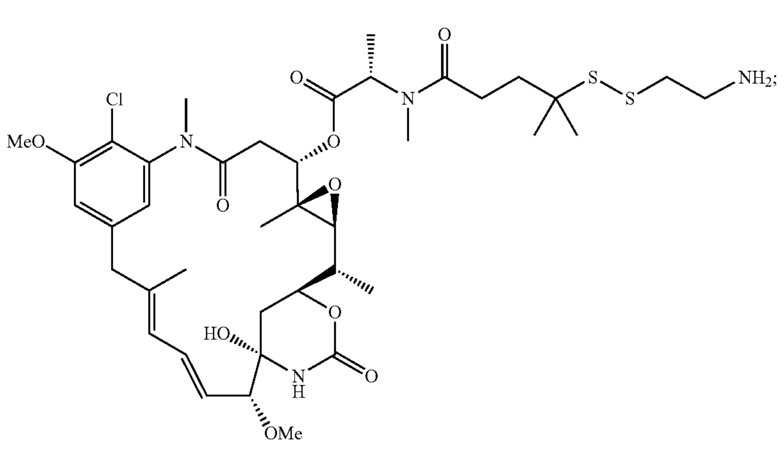 [SMILES: COc1cc2cc(c1Cl)N(C)C(=O)C[C@H](OC(=O)[C@H](C)N(C)C(=O)CCC(C)(C)SSCCN)[C@]1(C)O[C@H]1[C@H](C)[C@@H]1C[C@@](O)(NC(=O)O1)[C@H](OC)/C=C/C=C(\C)C2]

d) Reacting the formed

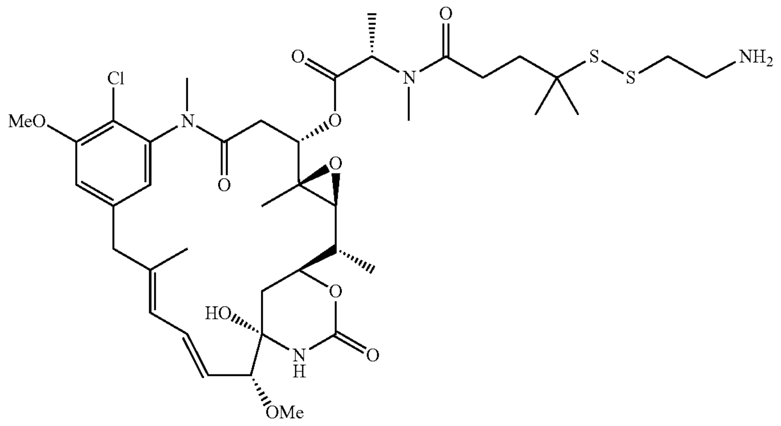 [SMILES: COc1cc2cc(c1Cl)N(C)C(=O)C[C@H](OC(=O)[C@H](C)N(C)C(=O)CCC(C)(C)SSCCN)[C@]1(C)O[C@H]1[C@H](C)[C@@H]1C[C@@](O)(NC(=O)O1)[C@H](OC)/C=C/C=C(\C)C2]

with:

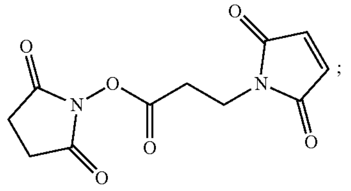 [SMILES: O=C(CCN1C(=O)C=CC1=O)ON1C(=O)CCC1=O]

to form the linker-drug moiety:

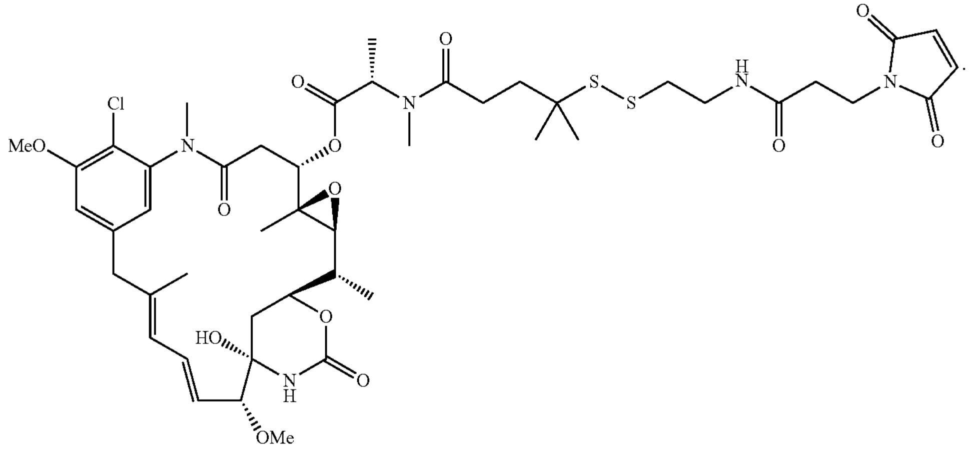 [SMILES: COc1cc2cc(c1Cl)N(C)C(=O)C[C@H](OC(=O)[C@H](C)N(C)C(=O)CCC(C)(C)SSCCNC(=O)CCN1C(=O)C=CC1=O)[C@]1(C)O[C@H]1[C@H](C)[C@@H]1C[C@@](O)(NC(=O)O1)[C@H](OC)/C=C/C=C(\C)C2]

13. The antibody drug conjugate made according to claim 7 having an average DAR, measured with a UV spectrophotometer, of about 3 to about 4.

14. A process for producing an anti-CCR7 antibody drug conjugate comprising:

(a) chemically linking SMCC or MPET to a drug moiety DM-1 or DM-4 to form a linker-drug;

(b) conjugating said linker-drug to an antibody or antigen binding fragment thereof; and (c) purifying the antibody drug conjugate, wherein the antibody or antigen binding fragment thereof comprises:

a. a heavy chain variable region that comprises an HCDR1 (Heavy Chain Complementarity Determining Region 1) of SEQ ID NO:1, an HCDR2 (Heavy Chain Complementarity Determining Region 2) of SEQ ID NO:2, and an HCDR3 (Heavy Chain Complementarity Determining Region 3) of SEQ ID NO:3; and a light chain variable region that comprises an LCDR1 (Light Chain Complementarity Determining Region 1) of SEQ ID NO:17, an LCDR2 (Light Chain Complementarity Determining Region 2) of SEQ ID NO:18, and an LCDR3 (Light Chain Complementarity Determining Region 3) of SEQ ID NO:19;

b. a heavy chain variable region that comprises an HCDR1 of SEQ ID NO:4, an HCDR2 of SEQ ID NO:5, and an HCDR3 of SEQ ID NO:6; and a light chain variable region that comprises an LCDR1 of SEQ ID NO:20, an LCDR2 of SEQ ID NO:21, and an LCDR3 of SEQ ID NO:22;

c. a heavy chain variable region that comprises an HCDR1 of SEQ ID NO:7, an HCDR2 of SEQ ID NO:8, and an HCDR3 of SEQ ID NO:9; and a light chain variable region that comprises an LCDR1 of SEQ ID NO:23, an LCDR2 of SEQ ID NO:24, and an LCDR3 of SEQ ID NO:25;

d. a heavy chain variable region that comprises an HCDR1 of SEQ ID NO: 10, an HCDR2 of SEQ ID NO:11, and an HCDR3 of SEQ ID NO: 12; and a light chain variable region that comprises an LCDR1 of SEQ ID NO:26, an LCDR2 of SEQ ID NO: 27, and an LCDR3 of SEQ ID NO:28;

e. a heavy chain variable region that comprises an HCDR1 of SEQ ID NO: 33, an HCDR2 of SEQ ID NO:34, and an HCDR3 of SEQ ID NO:35; and a light chain variable region that comprises an LCDR1 of SEQ ID NO:49, an LCDR2 of SEQ ID NO: 50, and an LCDR3 of SEQ ID NO:51;

f. a heavy chain variable region that comprises an HCDR1 of SEQ ID NO: 36, an HCDR2 of SEQ ID NO:37, and an HCDR3 of SEQ ID NO:38; and a light chain variable region that comprises an LCDR1 of SEQ ID NO:52, an LCDR2 of SEQ ID NO: 53, and an LCDR3 of SEQ ID NO:54;

g. a heavy chain variable region that comprises an HCDR1 of SEQ ID NO: 39, an HCDR2 of SEQ ID NO:40, and an HCDR3 of SEQ ID NO:41; and a light chain variable region that comprises an LCDR1 of SEQ ID NO:55, an LCDR2 of SEQ ID NO: 56, and an LCDR3 of SEQ ID NO:57;

h. a heavy chain variable region that comprises an HCDR1 of SEQ ID NO: 42, an HCDR2 of SEQ ID NO:43, and an HCDR3 of SEQ ID NO:44; and a light chain variable region that comprises an LCDR1 of SEQ ID NO:58, an LCDR2 of SEQ ID NO: 59, and an LCDR3 of SEQ ID NO:60;

i a heavy chain variable region that comprises an HCDR1 of SEQ ID NO: 65, an HCDR2 of SEQ ID NO:66, and an HCDR3 of SEQ ID NO:67; and a light chain variable region that comprises an LCDR1 of SEQ ID NO:81, an LCDR2 of SEQ ID NO: 82, and an LCDR3 of SEQ ID NO:83;

j. a heavy chain variable region that comprises an HCDR1 of SEQ ID NO: 68, an HCDR2 of SEQ ID NO:69, and an HCDR3 of SEQ ID NO: 70; and a light chain variable region that comprises an LCDR1 of SEQ ID NO:84, an LCDR2 of SEQ ID NO: 85, and an LCDR3 of SEQ ID NO:86;

k. a heavy chain variable region that comprises an HCDR1 of SEQ ID NO: 71, an HCDR2 of SEQ ID NO:72, and an HCDR3 of SEQ ID NO:73; and a light chain variable region that comprises an LCDR1 of SEQ ID NO:87, an LCDR2 of SEQ ID NO: 88, and an LCDR3 of SEQ ID NO:89;

l. a heavy chain variable region that comprises an HCDR1 of SEQ ID NO: 74, an HCDR2 of SEQ ID NO:75, and an HCDR3 of SEQ ID NO:76; and a light chain variable region that comprises an LCDR1 of SEQ ID NO:90, an LCDR2 of SEQ ID NO: 91, and an LCDR3 of SEQ ID NO:92;

m. a heavy chain variable region that comprises an HCDR1 of SEQ ID NO: 596, an HCDR2 of SEQ ID NO:597, and an HCDR3 of SEQ ID NO:598; and a light chain variable region that comprises an LCDR1 of SEQ ID NO:612, an LCDR2 of SEQ ID NO: 613, and an LCDR3 of SEQ ID NO:614;

n. a heavy chain variable region that comprises an HCDR1 of SEQ ID NO: 599, an HCDR2 of SEQ ID NO:600, and an HCDR3 of SEQ ID NO:601; and a light chain variable region that comprises an LCDR1 of SEQ ID NO:615, an LCDR2 of SEQ ID NO: 616, and an LCDR3 of SEQ ID NO:617;

o. a heavy chain variable region that comprises an HCDR1 of SEQ ID NO: 602, an HCDR2 of SEQ ID NO:603, and an HCDR3 of SEQ ID NO:604; and a light chain variable region that comprises an LCDR1 of SEQ ID NO:618, an LCDR2 of SEQ ID NO: 619, and an LCDR3 of SEQ ID NO:620; or p. a heavy chain variable region that comprises an HCDR1 of SEQ ID NO: 605, an HCDR2 of SEQ ID NO:606, and an HCDR3 of SEQ ID NO:607; and a light chain variable region that comprises an LCDR1 of SEQ ID NO:621, an LCDR2 of SEQ ID NO: 622, and an LCDR3 of SEQ ID NO:623.

15. The antibody drug conjugate made according to claim 14 having an average DAR, measured with a UV spectrophotometer, of about 3 to about 4.

16. A diagnostic reagent comprising an antibody or antigen binding fragment thereof comprising:

a. a heavy chain variable region that comprises an HCDR1 (Heavy Chain Complementarity Determining Region 1) of SEQ ID NO:1, an HCDR2 (Heavy Chain Complementarity Determining Region 2) of SEQ ID NO:2, and an HCDR3 (Heavy Chain Complementarity Determining Region 3) of SEQ ID NO:3; and a light chain variable region that comprises an LCDR1 (Light Chain Complementarity Determining Region 1) of SEQ ID NO:17, an LCDR2 (Light Chain Complementarity Determining Region 2) of SEQ ID NO:18, and an LCDR3 (Light Chain Complementarity Determining Region 3) of SEQ ID NO: 19;

b. a heavy chain variable region that comprises an HCDR1 of SEQ ID NO:4, an HCDR2 of SEQ ID NO:5, and an HCDR3 of SEQ ID NO:6; and a light chain variable region that comprises an LCDR1 of SEQ ID NO:20, an LCDR2 of SEQ ID NO:21, and an LCDR3 of SEQ ID NO:22;

c. a heavy chain variable region that comprises an HCDR1 of SEQ ID NO:7, an HCDR2 of SEQ ID NO:8, and an HCDR3 of SEQ ID NO:9; and a light chain variable region that comprises an LCDR1 of SEQ ID NO:23, an LCDR2 of SEQ ID NO:24, and an LCDR3 of SEQ ID NO:25;

d. a heavy chain variable region that comprises an HCDR1 of SEQ ID NO: 10, an HCDR2 of SEQ ID NO: 11, and an HCDR3 of SEQ ID NO: 12; and a light chain variable region that comprises an LCDR1 of SEQ ID NO:26, an LCDR2 of SEQ ID NO: 27, and an LCDR3 of SEQ ID NO:28;

e. a heavy chain variable region that comprises an HCDR1 of SEQ ID NO: 33, an HCDR2 of SEQ ID NO:34, and an HCDR3 of SEQ ID NO:35; and a light chain variable region that comprises an LCDR1 of SEQ ID NO:49, an LCDR2 of SEQ ID NO: 50, and an LCDR3 of SEQ ID NO:51;

f. a heavy chain variable region that comprises an HCDR1 of SEQ ID NO: 36, an HCDR2 of SEQ ID NO:37, and an HCDR3 of SEQ ID NO:38; and a light chain variable region that comprises an LCDR1 of SEQ ID NO:52, an LCDR2 of SEQ ID NO: 53, and an LCDR3 of SEQ ID NO:54;

g. a heavy chain variable region that comprises an HCDR1 of SEQ ID NO: 39, an HCDR2 of SEQ ID NO:40, and an HCDR3 of SEQ ID NO:41; and a light chain variable region that comprises an LCDR1 of SEQ ID NO:55, an LCDR2 of SEQ ID NO: 56, and an LCDR3 of SEQ ID NO:57;

h. a heavy chain variable region that comprises an HCDR1 of SEQ ID NO: 42, an HCDR2 of SEQ ID NO:43, and an HCDR3 of SEQ ID NO:44; and a light chain variable region that comprises an LCDR1 of SEQ ID NO:58, an LCDR2 of SEQ ID NO: 59, and an LCDR3 of SEQ ID NO:60;

i. a heavy chain variable region that comprises an HCDR1 of SEQ ID NO: 65, an HCDR2 of SEQ ID NO:66, and an HCDR3 of SEQ ID NO:67; and a light chain variable region that comprises an LCDR1 of SEQ ID NO:81, an LCDR2 of SEQ ID NO: 82, and an LCDR3 of SEQ ID NO:83;

j. a heavy chain variable region that comprises an HCDR1 of SEQ ID NO: 68, an HCDR2 of SEQ ID NO:69, and an HCDR3 of SEQ ID NO:70; and a light chain variable region that comprises an LCDR1 of SEQ ID NO:84, an LCDR2 of SEQ ID NO: 85, and an LCDR3 of SEQ ID NO:86;

k. a heavy chain variable region that comprises an HCDR1 of SEQ ID NO: 71, an HCDR2 of SEQ ID NO:72, and an HCDR3 of SEQ ID NO:73; and a light chain variable region that comprises an LCDR1 of SEQ ID NO:87, an LCDR2 of SEQ ID NO: 88, and an LCDR3 of SEQ ID NO:89;

l. a heavy chain variable region that comprises an HCDR1 of SEQ ID 1 NO: 74, an HCDR2 of SEQ ID NO:75, and an HCDR3 of SEQ ID NO:76; and a light chain variable region that comprises an LCDR1 of SEQ ID NO:90, an LCDR2 of SEQ ID NO: 91, and an LCDR3 of SEQ ID NO:92;

m. a heavy chain variable region that comprises an HCDR1 of SEQ ID NO: 596, an HCDR2 of SEQ ID NO:597, and an HCDR3 of SEQ ID NO:598; and a light chain variable region that comprises an LCDR1 of SEQ ID NO:612, an LCDR2 of SEQ ID NO: 613, and an LCDR3 of SEQ ID NO:614;

n. a heavy chain variable region that comprises an HCDR1 of SEQ ID NO: 599, an HCDR2 of SEQ ID NO:600, and an HCDR3 of SEQ ID NO:601; and a light chain variable region that comprises an LCDR1 of SEQ ID NO:615, an LCDR2 of SEQ ID NO: 616, and an LCDR3 of SEQ ID NO:617;

o. a heavy chain variable region that comprises an HCDR1 of SEQ ID NO: 602, an HCDR2 of SEQ ID NO:603, and an HCDR3 of SEQ ID NO:604; and a light chain variable region that comprises an LCDR1 of SEQ ID NO:618, an LCDR2 of SEQ ID NO: 619, and an LCDR3 of SEQ ID NO:620; or p. a heavy chain variable region that comprises an HCDR1 of SEQ ID NO: 605, an HCDR2 of SEQ ID NO:606, and an HCDR3 of SEQ ID NO:607; and a light chain variable region that comprises an LCDR1 of SEQ ID NO:621, an LCDR2 of SEQ ID NO: 622, and an LCDR3 of SEQ ID NO:623.

17. The diagnostic reagent of claim 16, wherein the antibody or antigen binding fragment thereof is labeled with a radiolabel, a fluorophore, a chromophore, an imaging agent, or a metal ion.

* * * * *

SEQUENCE LISTING

```
Sequence total quantity: 629
SEQ ID NO: 1            moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 1
GFTFSSYAMS                                                              10

SEQ ID NO: 2            moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 2
TISSGGSFTY YPDSVKG                                                      17

SEQ ID NO: 3            moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 3
RASTVVGTDF DV                                                           12

SEQ ID NO: 4            moltype = AA  length = 5
FEATURE                 Location/Qualifiers
REGION                  1..5
                        note = source = /note="Description of Artificial Sequence:
                         Synthetic peptide"
source                  1..5
                        mol_type = protein
```

```
                        organism = synthetic construct
SEQUENCE: 4
SYAMS                                                                5

SEQ ID NO: 5            moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 5
TISSGGSFTY YPDSVKG                                                   17

SEQ ID NO: 6            moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 6
RASTVVGTDF DV                                                        12

SEQ ID NO: 7            moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 7
GFTFSSY                                                              7

SEQ ID NO: 8            moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 8
SSGGSF                                                               6

SEQ ID NO: 9            moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 9
RASTVVGTDF DV                                                        12

SEQ ID NO: 10           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 10
GFTFSSYA                                                             8

SEQ ID NO: 11           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 11
```

```
ISSGGSFT                                                  8

SEQ ID NO: 12          moltype = AA  length = 14
FEATURE                Location/Qualifiers
REGION                 1..14
                       note = source = /note="Description of Artificial Sequence:
                        Synthetic peptide"
source                 1..14
                       mol_type = protein
                       organism = synthetic construct
SEQUENCE: 12
ARRASTVVGT DFDV                                           14

SEQ ID NO: 13          moltype = AA  length = 121
FEATURE                Location/Qualifiers
REGION                 1..121
                       note = source = /note="Description of Artificial Sequence:
                        Synthetic polypeptide"
source                 1..121
                       mol_type = protein
                       organism = synthetic construct
SEQUENCE: 13
EVQLVESGGG LVKPGGSLRL SCAASGFTFS SYAMSWIRQA PGKGLEWVAT ISSGGSFTYY  60
PDSVKGRFTI SRDNAKNSLY LQMNSLRAED TAVYYCARRA STVVGTDFDV WGQGTTVTVS  120
S                                                         121

SEQ ID NO: 14          moltype = DNA  length = 363
FEATURE                Location/Qualifiers
misc_feature           1..363
                       note = source = /note="Description of Artificial Sequence:
                        Synthetic polynucleotide"
source                 1..363
                       mol_type = other DNA
                       organism = synthetic construct
SEQUENCE: 14
gaagtgcagc tggtggaatc tggcggcgga ctggtcaagc ctggcggctc cctgagactg  60
tcttgcgccg cctccggctt caccttctcc agctacgcca tgtcctggat ccggcaggcc  120
cctggcaagg gactggagtg ggtggccacc atctcctccg gcggcagctt cacctactac  180
cccgactccg tgaagggccg gttcaccatc tcccgggaca acgccaagaa ctccctgtac  240
ctgcagatga actccctgcg ggccgaggac accgccgtgt actactgtgc cagacgggcc  300
tccaccgtcg tgggcaccga tttcgatgtg tggggccagg gcacaaccgt gaccgtgtcc  360
tcc                                                       363

SEQ ID NO: 15          moltype = AA  length = 451
FEATURE                Location/Qualifiers
REGION                 1..451
                       note = source = /note="Description of Artificial Sequence:
                        Synthetic polypeptide"
source                 1..451
                       mol_type = protein
                       organism = synthetic construct
SEQUENCE: 15
EVQLVESGGG LVKPGGSLRL SCAASGFTFS SYAMSWIRQA PGKGLEWVAT ISSGGSFTYY  60
PDSVKGRFTI SRDNAKNSLY LQMNSLRAED TAVYYCARRA STVVGTDFDV WGQGTTVTVS  120
SASTKGPSVF PLAPSSKSTS GGTAALGCLV KDYFPCPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVAV SHEDPEVKFN WYVDGVEVHN AKTKPREEQY  300
NSTYRVVSVL TVLHQDWLNG KEYKCKVSNK ALAAPIEKTI SKAKGQPREP QVYTLPPSRE  360
EMTKNQVSLT CLVKGFYPCD IAVEWESNGQ PENNYKTTPP VLDSDGSFFL YSKLTVDKSR  420
WQQGNVFSCS VMHEALHNHY TQKSLSLSPG K                        451

SEQ ID NO: 16          moltype = DNA  length = 1353
FEATURE                Location/Qualifiers
misc_feature           1..1353
                       note = source = /note="Description of Artificial Sequence:
                        Synthetic polynucleotide"
source                 1..1353
                       mol_type = other DNA
                       organism = synthetic construct
SEQUENCE: 16
gaagtgcagc tggtggaatc tggcggcgga ctggtcaagc ctggcggctc cctgagactg  60
tcttgcgccg cctccggctt caccttctcc agctacgcca tgtcctggat ccggcaggcc  120
cctggcaagg gactggagtg ggtggccacc atctcctccg gcggcagctt cacctactac  180
cccgactccg tgaagggccg gttcaccatc tcccgggaca acgccaagaa ctccctgtac  240
ctgcagatga actccctgcg ggccgaggac accgccgtgt actactgtgc cagacgggcc  300
tccaccgtcg tgggcaccga tttcgatgtg tggggccagg gcacaaccgt gaccgtgtcc  360
tccgcctcca ccaagggacc ctccgtgttc cctctggccc cttccagcaa gtccacctct  420
ggcggcaccg ccgctctggg ctgcctggtc aaggactact tcccctgccc tgtgacagtg  480
tcctggaact ccggcgctct gacctccggc gtgcacacct tccctgccgt gctgcagtcc  540
```

```
tccggcctgt actccctgtc ctccgtcgtg accgtgcctt cctccagcct gggcacccag  600
acctacatct gcaacgtgaa ccacaagccc tccaacacca aagtggacaa gcgggtggaa  660
cccaagtcct gcgacaagac ccacacctgt cctccctgcc ctgcccctga gctgctggga  720
ggcccttccg tgttcctgtt ccctccaaag cccaaggaca ccctgatgat ctcccggacc  780
cctgaagtga cctgcgtggt ggtggccgtg tcccacgagg atcccgaagt gaagttcaat  840
tggtacgtgg acggcgtgga agtgcacaat gccaagacca agcccagaga ggaacagtac  900
aactccacct accgggtggt gtccgtgctg accgtgctgc accaggactg gctgaacggc  960
aaagagtaca agtgcaaagt gtccaacaag gccctggccg ctcccatcga aaagaccatc  1020
tccaaggcca agggccagcc cagagagccc caagtgtaca cactgcctcc cagccgggaa  1080
gagatgacca agaaccaagt gtccctgacc tgcctcgtga agggcttcta cccctgcgat  1140
atcgccgtgg agtgggagtc caacggccag cccgagaaca actacaagac cacccctccc  1200
gtgctggaca gcgacggctc attcttcctg tactccaagc tgaccgtgga caagtcccgg  1260
tggcagcagg gcaacgtgtt ctcctgctcc gtgatgcacg aggccctgca caaccactac  1320
acccagaagt ccctgtccct gagccccggc aag                              1353

SEQ ID NO: 17           moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 17
RASQDIGSSL N                                                        11

SEQ ID NO: 18           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 18
ATSSLDS                                                             7

SEQ ID NO: 19           moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 19
LQYASSPPT                                                           9

SEQ ID NO: 20           moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 20
RASQDIGSSL N                                                        11

SEQ ID NO: 21           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 21
ATSSLDS                                                             7

SEQ ID NO: 22           moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 22
```

```
LQYASSPPT                                                 9

SEQ ID NO: 23           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 23
SQDIGSS                                                   7

SEQ ID NO: 24           moltype =   length =
SEQUENCE: 24
000

SEQ ID NO: 25           moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 25
YASSPP                                                    6

SEQ ID NO: 26           moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 26
QDIGSS                                                    6

SEQ ID NO: 27           moltype =   length =
SEQUENCE: 27
000

SEQ ID NO: 28           moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 28
LQYASSPPT                                                 9

SEQ ID NO: 29           moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 29
DIQMTQSPSS LSASVGDRVT LTCRASQDIG SSLNWLQQKP GKAIKRLIYA TSSLDSGVPS  60
RFSGSRSGTD YTLTISSLQP EDFVVYYCLQ YASSPPTFGG GTKLEIK                107

SEQ ID NO: 30           moltype = DNA  length = 321
FEATURE                 Location/Qualifiers
misc_feature            1..321
                        note = source = /note="Description of Artificial Sequence:
                         Synthetic polynucleotide"
source                  1..321
                        mol_type = other DNA
                        organism = synthetic construct
SEQUENCE: 30
gacatccaga tgacccagag cccctccagc ctgtccgcct ccgtgggcga tagagtgacc  60
ctgacctgcc gggcctccca ggacatcggc tcctccctga actggctgca gcagaagccc  120
ggcaaggcca tcaagcggct gatctacgcc acctcctccc tggactccgg cgtgccctcc  180
cggttctctg gctccagatc cggcaccgac tacaccctga ccatctccag cctgcagccc  240
```

```
gaggacttcg tggtgtacta ctgcctgcag tacgcctcca gccctcccac cttcggcgga  300
ggcaccaagc tggaaatcaa g                                            321

SEQ ID NO: 31          moltype = AA  length = 214
FEATURE                Location/Qualifiers
REGION                 1..214
                       note = source = /note="Description of Artificial Sequence:
                        Synthetic polypeptide"
source                 1..214
                       mol_type = protein
                       organism = synthetic construct
SEQUENCE: 31
DIQMTQSPSS LSASVGDRVT LTCRASQDIG SSLNWLQQKP GKAIKRLIYA TSSLDSGVPS  60
RFSGSRSGTD YTLTISSLQP EDFVVYYCLQ YASSPPTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 32          moltype = DNA  length = 642
FEATURE                Location/Qualifiers
misc_feature           1..642
                       note = source = /note="Description of Artificial Sequence:
                        Synthetic polynucleotide"
source                 1..642
                       mol_type = other DNA
                       organism = synthetic construct
SEQUENCE: 32
gacatccaga tgacccagag cccctccagc ctgtccgcct ccgtgggcga tagagtgacc  60
ctgacctgcc gggcctccca ggacatcggc tcctccctga actggctgca gcagaagccc  120
ggcaaggcca tcaagcggct gatctacgcc acctcctccc tggactccgg cgtgccctcc  180
cggttctctg gctccagatc cggcaccgac tacaccctga ccatctccag cctgcagccc  240
gaggacttcg tggtgtacta ctgcctgcag tacgcctcca gccctcccac cttcggcgga  300
ggcaccaagc tggaaatcaa gcgtacggtg gccgctccca gcgtgttcat cttccccccc  360
agcgacgagc agctgaagag cggcaccgcc agcgtggtgt gcctgctgaa caacttctac  420
cccgggagg ccaaggtgca gtggaaggtg gacaacgccc tgcagagcgg caacagccag  480
gagagcgtca ccgagcagga cagcaaggac tccacctaca gcctgagcag caccctgacc  540
ctgagcaagg ccgactacga gaagcataag gtgtacgcct gcgaggtgac ccaccagggc  600
ctgtccagcc ccgtgaccaa gagcttcaac aggggcgagt gc                      642

SEQ ID NO: 33          moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 33
GFTFSTYAMS                                                         10

SEQ ID NO: 34          moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 34
TISDAGSYSY YPDNVKG                                                 17

SEQ ID NO: 35          moltype = AA  length = 13
FEATURE                Location/Qualifiers
REGION                 1..13
                       note = source = /note="Description of Artificial Sequence:
                        Synthetic peptide"
source                 1..13
                       mol_type = protein
                       organism = synthetic construct
SEQUENCE: 35
RGSRYEEYYV MDY                                                     13

SEQ ID NO: 36          moltype = AA  length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
```

```
SEQUENCE: 36
TYAMS                                                       5

SEQ ID NO: 37          moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 37
TISDAGSYSY YPDNVKG                                          17

SEQ ID NO: 38          moltype = AA  length = 13
FEATURE                Location/Qualifiers
REGION                 1..13
                       note = source = /note="Description of Artificial Sequence:
                        Synthetic peptide"
source                 1..13
                       mol_type = protein
                       organism = synthetic construct
SEQUENCE: 38
RGSRYEEYYV MDY                                              13

SEQ ID NO: 39          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 39
GFTFSTY                                                     7

SEQ ID NO: 40          moltype = AA  length = 6
FEATURE                Location/Qualifiers
REGION                 1..6
                       note = source = /note="Description of Artificial Sequence:
                        Synthetic peptide"
source                 1..6
                       mol_type = protein
                       organism = synthetic construct
SEQUENCE: 40
SDAGSY                                                      6

SEQ ID NO: 41          moltype = AA  length = 13
FEATURE                Location/Qualifiers
REGION                 1..13
                       note = source = /note="Description of Artificial Sequence:
                        Synthetic peptide"
source                 1..13
                       mol_type = protein
                       organism = synthetic construct
SEQUENCE: 41
RGSRYEEYYV MDY                                              13

SEQ ID NO: 42          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 42
GFTFSTYA                                                    8

SEQ ID NO: 43          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 43
ISDAGSYS                                                    8
```

```
SEQ ID NO: 44           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 44
ARRGSRYEEY YVMDY                                                   15

SEQ ID NO: 45           moltype = AA  length = 122
FEATURE                 Location/Qualifiers
REGION                  1..122
                        note = source = /note="Description of Artificial Sequence:
                         Synthetic polypeptide"
source                  1..122
                        mol_type = protein
                        organism = synthetic construct
SEQUENCE: 45
EVQLVESGGG LVKPGGSLRL SCAASGFTFS TYAMSWVRQA PGKGLEWVAT ISDAGSYSYY  60
PDNVKGRFTI SRDNAKNSLY LQMNSLRAED TAVYYCARRG SRYEEYYVMD YWGQGTTVTV  120
SS                                                                 122

SEQ ID NO: 46           moltype = DNA  length = 366
FEATURE                 Location/Qualifiers
misc_feature            1..366
                        note = source = /note="Description of Artificial Sequence:
                         Synthetic polynucleotide"
source                  1..366
                        mol_type = other DNA
                        organism = synthetic construct
SEQUENCE: 46
gaagtgcagc tggtggaatc tggcggcgga ctggtcaagc ctggcggctc cctgagactg  60
tcttgcgccg cctccggctt caccttctcc acctacgcca tgtcctgggt ccgacaggcc  120
cctggaaagg gcctggagtg ggtggccacc atctccgacg ccggctccta ctcctactac  180
cccgacaacg tgaagggccg gttcaccatc tcccgggaca acgccaagaa ctccctgtac  240
ctgcagatga actccctgcg ggccgaggac accgccgtgt actactgcgc cagacggggc  300
tccagatacg aagagtacta cgtgatggac tactggggcc agggcacaac cgtgaccgtg  360
tcctcc                                                             366

SEQ ID NO: 47           moltype = AA  length = 452
FEATURE                 Location/Qualifiers
REGION                  1..452
                        note = source = /note="Description of Artificial Sequence:
                         Synthetic polypeptide"
source                  1..452
                        mol_type = protein
                        organism = synthetic construct
SEQUENCE: 47
EVQLVESGGG LVKPGGSLRL SCAASGFTFS TYAMSWVRQA PGKGLEWVAT ISDAGSYSYY  60
PDNVKGRFTI SRDNAKNSLY LQMNSLRAED TAVYYCARRG SRYEEYYVMD YWGQGTTVTV  120
SSASTKGPSV FPLAPSSKST SGGTAALGCL VKDYFPCPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLMISR TPEVTCVVVA VSHEDPEVKF NWYVDGVEVH NAKTKPREEQ  300
YNSTYRVVSV LTVLHQDWLN GKEYKCKVSN KALAAPIEKT ISKAKGQPRE PQVYTLPPSR  360
EEMTKNQVSL TCLVKGFYPC DIAVEWESNG QPENNYKTTP PVLDSDGSFF LYSKLTVDKS  420
RWQQGNVFSC SVMHEALHNH YTQKSLSLSP GK                                452

SEQ ID NO: 48           moltype = DNA  length = 1356
FEATURE                 Location/Qualifiers
misc_feature            1..1356
                        note = source = /note="Description of Artificial Sequence:
                         Synthetic polynucleotide"
source                  1..1356
                        mol_type = other DNA
                        organism = synthetic construct
SEQUENCE: 48
gaagtgcagc tggtggaatc tggcggcgga ctggtcaagc ctggcggctc cctgagactg  60
tcttgcgccg cctccggctt caccttctcc acctacgcca tgtcctgggt ccgacaggcc  120
cctggaaagg gcctggagtg ggtggccacc atctccgacg ccggctccta ctcctactac  180
cccgacaacg tgaagggccg gttcaccatc tcccgggaca acgccaagaa ctccctgtac  240
ctgcagatga actccctgcg ggccgaggac accgccgtgt actactgcgc cagacggggc  300
tccagatacg aagagtacta cgtgatggac tactggggcc agggcacaac cgtgaccgtg  360
tcctccgcct ccaccaaggg accctccgtg ttccctctgg ccccttccag caagtccacc  420
tctggcggca ccgccgctct gggctgcctg gtcaaggact acttccccctg ccctgtgaca  480
gtgtcctgga actccggcgc tctgacctcc ggcgtgcaca ccttccctgc cgtgctgcag  540
tcctccggcc tgtactccct gtcctccgtc gtgaccgtgc cttcctccag cctgggcacc  600
```

```
cagacctaca tctgcaacgt gaaccacaag ccctccaaca ccaaagtgga caagcgggtg  660
gaacccaagt cctgcgacaa gacccacacc tgtcctccct gccctgcccc tgagctgctg  720
ggaggccctt ccgtgttcct gttccctcca aagcccaagg acaccctgat gatctcccgg  780
acccctgaag tgacctgcgt ggtggtggcc gtgtcccacg aggatcccga agtgaagttc  840
aattggtacg tggacggcgt ggaagtgcac aatgccaaga ccaagcccag agaggaacag  900
tacaactcca cctaccgggt ggtgtccgtg ctgaccgtgc tgcaccagga ctggctgaac  960
ggcaaagagt acaagtgcaa agtgtccaac aaggccctgg ccgctcccat cgaaaagacc  1020
atctccaagg ccaagggcca gcccagagag ccccaagtgt acacactgcc tcccagccgg  1080
gaagagatga ccaagaacca agtgtccctg acctgcctcg tgaagggctt ctacccctgc  1140
gatatcgccg tggagtggga gtccaacggc cagcccgaga acaactacaa gaccacccct  1200
cccgtgctgg actccgacgg ctcattcttc ctgtactcca agctgaccgt ggacaagtcc  1260
cggtggcagc agggcaacgt gttctcctgc tccgtgatgc acgaggccct gcacaaccac  1320
tacacccaga agtccctgtc cctgagcccc ggcaag                           1356

SEQ ID NO: 49          moltype = AA  length = 11
FEATURE                Location/Qualifiers
REGION                 1..11
                       note = source = /note="Description of Artificial Sequence:
                        Synthetic peptide"
source                 1..11
                       mol_type = protein
                       organism = synthetic construct
SEQUENCE: 49
RASQSISNNL H                                                       11

SEQ ID NO: 50          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 50
YASQSIS                                                            7

SEQ ID NO: 51          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 51
QQSSSWLT                                                           8

SEQ ID NO: 52          moltype = AA  length = 11
FEATURE                Location/Qualifiers
REGION                 1..11
                       note = source = /note="Description of Artificial Sequence:
                        Synthetic peptide"
source                 1..11
                       mol_type = protein
                       organism = synthetic construct
SEQUENCE: 52
RASQSISNNL H                                                       11

SEQ ID NO: 53          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 53
YASQSIS                                                            7

SEQ ID NO: 54          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 54
QQSSSWLT                                                           8
```

```
SEQ ID NO: 55          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 55
SQSISNN                                                            7

SEQ ID NO: 56          moltype =   length =
SEQUENCE: 56
000

SEQ ID NO: 57          moltype = AA  length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 57
SSSWL                                                              5

SEQ ID NO: 58          moltype = AA  length = 6
FEATURE                Location/Qualifiers
REGION                 1..6
                       note = source = /note="Description of Artificial Sequence:
                        Synthetic peptide"
source                 1..6
                       mol_type = protein
                       organism = synthetic construct
SEQUENCE: 58
QSISNN                                                             6

SEQ ID NO: 59          moltype =   length =
SEQUENCE: 59
000

SEQ ID NO: 60          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 60
QQSSSWLT                                                           8

SEQ ID NO: 61          moltype = AA  length = 106
FEATURE                Location/Qualifiers
REGION                 1..106
                       note = source = /note="Description of Artificial Sequence:
                        Synthetic polypeptide"
source                 1..106
                       mol_type = protein
                       organism = synthetic construct
SEQUENCE: 61
EIVLTQSPAT LSVSPGERVT LSCRASQSIS NNLHWYQQKP GQAPRLLIKY ASQSISGIPA  60
RFSGSGSGTD FTLTISSVEP EDFGVYFCQQ SSSWLTFGQG TKLEIK                 106

SEQ ID NO: 62          moltype = DNA  length = 318
FEATURE                Location/Qualifiers
misc_feature           1..318
                       note = source = /note="Description of Artificial Sequence:
                        Synthetic polynucleotide"
source                 1..318
                       mol_type = other DNA
                       organism = synthetic construct
SEQUENCE: 62
gagatcgtgc tgacacagtc ccctgccacc ctgtctgtgt ctcccggcga gagagtgacc  60
ctgtcctgcc gggcctccca gtccatctcc aacaacctgc actggtatca gcagaagccc  120
ggccaggccc ctcggctgct gattaagtac gcctcccaga gcatctccgg catccctgcc  180
agattctccg gctccggcag cggcaccgac ttcaccctga ccatctccag cgtggaaccc  240
gaggacttcg gcgtgtactt ctgccagcag tcctcctcct ggctgacctt cggccagggc  300
```

```
accaagctgg aaatcaag                                           318

SEQ ID NO: 63          moltype = AA  length = 213
FEATURE                Location/Qualifiers
REGION                 1..213
                       note = source = /note="Description of Artificial Sequence:
                        Synthetic polypeptide"
source                 1..213
                       mol_type = protein
                       organism = synthetic construct
SEQUENCE: 63
EIVLTQSPAT LSVSPGERVT LSCRASQSIS NNLHWYQQKP GQAPRLLIKY ASQSISGIPA  60
RFSGSGSGTD FTLTISSVEP EDFGVYFCQQ SSSWLTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                          213

SEQ ID NO: 64          moltype = DNA  length = 639
FEATURE                Location/Qualifiers
misc_feature           1..639
                       note = source = /note="Description of Artificial Sequence:
                        Synthetic polynucleotide"
source                 1..639
                       mol_type = other DNA
                       organism = synthetic construct
SEQUENCE: 64
gagatcgtgc tgacacagtc ccctgccacc ctgtctgtgt ctcccggcga gagagtgacc  60
ctgtcctgcc gggcctccca gtccatctcc aacaacctgc actggtatca gcagaagccc  120
ggccaggccc ctcggctgct gattaagtac gcctcccaga gcatctccgg catccctgcc  180
agattctccg gctccggcag cggcaccgac ttcaccctga ccatctccag cgtggaaccc  240
gaggacttcg gcgtgtactt ctgccagcag tcctcctcct ggctgacctt cggccagggc  300
accaagctgg aaatcaagcg tacggtggcc gctcccagcg tgttcatctt cccccccagc  360
gacgagcagc tgaagagcgg caccgccagc gtggtgtgcc tgctgaacaa cttctacccc  420
cgggaggcca aggtgcagtg gaaggtggac aacgccctgc agagcggcaa cagccaggag  480
agcgtcaccg agcaggacag caaggactcc acctacagcc tgagcagcac cctgaccctg  540
agcaaggccg actacgagaa gcataaggtg tacgcctgcg aggtgaccca ccagggcctg  600
tccagccccg tgaccaagag cttcaacagg ggcgagtgc                    639

SEQ ID NO: 65          moltype = AA  length = 11
FEATURE                Location/Qualifiers
REGION                 1..11
                       note = source = /note="Description of Artificial Sequence:
                        Synthetic peptide"
source                 1..11
                       mol_type = protein
                       organism = synthetic construct
SEQUENCE: 65
GYSITSGYSW H                                                  11

SEQ ID NO: 66          moltype = AA  length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 66
HIHSSGSTNY NPSLKS                                             16

SEQ ID NO: 67          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 67
GGVQAFAY                                                      8

SEQ ID NO: 68          moltype = AA  length = 6
FEATURE                Location/Qualifiers
REGION                 1..6
                       note = source = /note="Description of Artificial Sequence:
                        Synthetic peptide"
source                 1..6
                       mol_type = protein
                       organism = synthetic construct
SEQUENCE: 68
```

```
SGYSWH                                                    6

SEQ ID NO: 69          moltype = AA  length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 69
HIHSSGSTNY NPSLKS                                         16

SEQ ID NO: 70          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 70
GGVQAFAY                                                  8

SEQ ID NO: 71          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 71
GYSITSGY                                                  8

SEQ ID NO: 72          moltype = AA  length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 72
HSSGS                                                     5

SEQ ID NO: 73          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 73
GGVQAFAY                                                  8

SEQ ID NO: 74          moltype = AA  length = 9
FEATURE                Location/Qualifiers
REGION                 1..9
                       note = source = /note="Description of Artificial Sequence:
                        Synthetic peptide"
source                 1..9
                       mol_type = protein
                       organism = synthetic construct
SEQUENCE: 74
GYSITSGYS                                                 9

SEQ ID NO: 75          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 75
IHSSGST                                                   7
```

```
SEQ ID NO: 76          moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 76
ARGGVQAFAY                                                         10

SEQ ID NO: 77          moltype = AA  length = 117
FEATURE                Location/Qualifiers
REGION                 1..117
                       note = source = /note="Description of Artificial Sequence:
                        Synthetic polypeptide"
source                 1..117
                       mol_type = protein
                       organism = synthetic construct
SEQUENCE: 77
DVQLQESGPG LVKPSQTLSL TCTVSGYSIT SGYSWHWIRQ HPGKGLEWMA HIHSSGSTNY  60
NPSLKSRITI SRDTSKNQFS LKLSSVTAAD TAVYYCARGG VQAFAYWGQG TLVTVSS     117

SEQ ID NO: 78          moltype = DNA  length = 351
FEATURE                Location/Qualifiers
misc_feature           1..351
                       note = source = /note="Description of Artificial Sequence:
                        Synthetic polynucleotide"
source                 1..351
                       mol_type = other DNA
                       organism = synthetic construct
SEQUENCE: 78
gacgtgcagc tgcaggaatc tggccctggc ctggtcaagc cctcccagac cctgtccctg  60
acctgcaccg tgtccggcta ctctatcacc tccggctaca gctggcactg gatccggcag  120
caccccggca agggcctgga atggatggcc cacatccact cctccggctc caccaactac  180
aaccccagcc tgaagtcccg gatcaccatc tcccgggaca cctccaagaa ccagttctcc  240
ctgaagctgt cctccgtgac cgccgctgac accgccgtgt actactgtgc cagaggcggc  300
gtgcaggcct tcgcttattg gggccaggga accctggtca ccgtgtcctc c           351

SEQ ID NO: 79          moltype = AA  length = 447
FEATURE                Location/Qualifiers
REGION                 1..447
                       note = source = /note="Description of Artificial Sequence:
                        Synthetic polypeptide"
source                 1..447
                       mol_type = protein
                       organism = synthetic construct
SEQUENCE: 79
DVQLQESGPG LVKPSQTLSL TCTVSGYSIT SGYSWHWIRQ HPGKGLEWMA HIHSSGSTNY  60
NPSLKSRITI SRDTSKNQFS LKLSSVTAAD TAVYYCARGG VQAFAYWGQG TLVTVSSAST  120
KGPSVFPLAP SSKSTSGGTA ALGCLVKDYF PCPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVAVSHED PEVKFNWYVD GVEVHNAKTK PREEQYNSTY  300
RVVSVLTVLH QDWLNGKEYK CKVSNKALAA PIEKTISKAK GQPREPQVYT LPPSREEMTK  360
NQVSLTCLVK GFYPCDIAVE WESNGQPENN YKTTPPVLDS DGSFFLYSKL TVDKSRWQQG  420
NVFSCSVMHE ALHNHYTQKS LSLSPGK                                      447

SEQ ID NO: 80          moltype = DNA  length = 1341
FEATURE                Location/Qualifiers
misc_feature           1..1341
                       note = source = /note="Description of Artificial Sequence:
                        Synthetic polynucleotide"
source                 1..1341
                       mol_type = other DNA
                       organism = synthetic construct
SEQUENCE: 80
gacgtgcagc tgcaggaatc tggccctggc ctggtcaagc cctcccagac cctgtccctg  60
acctgcaccg tgtccggcta ctctatcacc tccggctaca gctggcactg gatccggcag  120
caccccggca agggcctgga atggatggcc cacatccact cctccggctc caccaactac  180
aaccccagcc tgaagtcccg gatcaccatc tcccgggaca cctccaagaa ccagttctcc  240
ctgaagctgt cctccgtgac cgccgctgac accgccgtgt actactgtgc cagaggcggc  300
gtgcaggcct tcgcttattg gggccaggga accctggtca ccgtgtcctc cgccagcacc  360
aagggaccct ccgtgttccc tctggcccct tccagcaagt ccacctctgg cggcaccgcc  420
gctctgggct gcctcgtgaa ggactacttc cctgccccg tgaccgtgtc ctggaactcc  480
ggcgctctga cctccggcgt gcacaccttc cctgccgtgc tgcagtcctc cggcctgtac  540
tccctgtcca gcgtcgtgac cgtgccctcc agctctctgg gcacccagac ctacatctgc  600
aacgtgaacc acaagccctc caacaccaaa gtggacaagc gggtggaacc caagtcctgc  660
gacaagaccc acacctgtcc tccctgccct gcccctgagc tgctgggagg cccttccgtg  720
ttcctgttcc ctccaaagcc caaggacacc ctgatgatct cccggacccc tgaagtgacc  780
```

```
tgcgtggtgg tggccgtgtc ccacgaggat cccgaagtga agttcaattg gtacgtggac  840
ggcgtggaag tgcacaacgc caagaccaag cccagagagg aacagtacaa ctccacctac  900
cgggtggtgt ccgtgctgac cgtgctgcac caggactggc tgaacggcaa agagtacaag  960
tgcaaagtgt ccaacaaggc cctggccgct cccatcgaaa agaccatctc caaggccaag  1020
ggccagccca gagagcccca agtgtacaca ctgcctccca gccgggaaga gatgaccaag  1080
aatcaagtgt ccctgacctg tctggtcaag ggcttctacc cctgcgatat cgccgtggag  1140
tgggagtcca acggccagcc cgagaacaac tacaagacca cccctcccgt gctggactcc  1200
gacggctcat tcttcctgta ctccaagctg accgtggaca agtcccggtg gcagcagggc  1260
aacgtgttct cctgctccgt gatgcacgag gccctgcaca accactacac ccagaagtcc  1320
ctgagcctgt cccctggcaa g                                          1341

SEQ ID NO: 81          moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 81
SASSSVIYMH                                                       10

SEQ ID NO: 82          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 82
DTSKLAS                                                          7

SEQ ID NO: 83          moltype = AA  length = 9
FEATURE                Location/Qualifiers
REGION                 1..9
                       note = source = /note="Description of Artificial Sequence:
                        Synthetic peptide"
source                 1..9
                       mol_type = protein
                       organism = synthetic construct
SEQUENCE: 83
QQWSSNPLT                                                        9

SEQ ID NO: 84          moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 84
SASSSVIYMH                                                       10

SEQ ID NO: 85          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 85
DTSKLAS                                                          7

SEQ ID NO: 86          moltype = AA  length = 9
FEATURE                Location/Qualifiers
REGION                 1..9
                       note = source = /note="Description of Artificial Sequence:
                        Synthetic peptide"
source                 1..9
                       mol_type = protein
                       organism = synthetic construct
SEQUENCE: 86
QQWSSNPLT                                                        9

SEQ ID NO: 87          moltype = AA  length = 6
FEATURE                Location/Qualifiers
```

```
REGION                  1..6
                        note = source = /note="Description of Artificial Sequence:
                         Synthetic peptide"
source                  1..6
                        mol_type = protein
                        organism = synthetic construct
SEQUENCE: 87
SSSVIY                                                                            6

SEQ ID NO: 88           moltype =   length =
SEQUENCE: 88
000

SEQ ID NO: 89           moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 89
WSSNPL                                                                            6

SEQ ID NO: 90           moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 90
SSVIY                                                                             5

SEQ ID NO: 91           moltype =   length =
SEQUENCE: 91
000

SEQ ID NO: 92           moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 92
QQWSSNPLT                                                                         9

SEQ ID NO: 93           moltype = AA  length = 106
FEATURE                 Location/Qualifiers
REGION                  1..106
                        note = source = /note="Description of Artificial Sequence:
                         Synthetic polypeptide"
source                  1..106
                        mol_type = protein
                        organism = synthetic construct
SEQUENCE: 93
EIVLTQSPAT LSASPGERVT MSCSASSSVI YMHWYQQKPG QAPRRWIYDT SKLASGVPAR  60
FSGSGSGTDY TLTISSMEPE DAAVYYCQQW SSNPLTFGQG TKLEIK                106

SEQ ID NO: 94           moltype = DNA  length = 318
FEATURE                 Location/Qualifiers
misc_feature            1..318
                        note = source = /note="Description of Artificial Sequence:
                         Synthetic polynucleotide"
source                  1..318
                        mol_type = other DNA
                        organism = synthetic construct
SEQUENCE: 94
gagatcgtgc tgacacagtc ccctgccacc ctgtccgcct ctccaggcga gcgcgtgaca  60
atgtcctgct ccgcctcctc ctccgtgatc tacatgcact ggtatcagca gaagcccggc  120
caggcccctc ggcggtggat ctacgatacc tccaagctgg cctccggcgt gcccgccaga  180
ttctccggct ctggctctgg caccgactac accctgacca tctccagcat ggaacccgag  240
gacgccgccg tgtactactg ccagcagtgg tcctccaacc ctctgacctt cggccagggc  300
accaagctgg aaatcaag                                                318

SEQ ID NO: 95           moltype = AA  length = 213
```

```
FEATURE                Location/Qualifiers
REGION                 1..213
                       note = source = /note="Description of Artificial Sequence:
                        Synthetic polypeptide"
source                 1..213
                       mol_type = protein
                       organism = synthetic construct
SEQUENCE: 95
EIVLTQSPAT LSASPGERVT MSCSASSSVI YMHWYQQKPG QAPRRWIYDT SKLASGVPAR  60
FSGSGSGTDY TLTISSMEPE DAAVYYCQQW SSNPLTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 96          moltype = DNA  length = 639
FEATURE                Location/Qualifiers
misc_feature           1..639
                       note = source = /note="Description of Artificial Sequence:
                        Synthetic polynucleotide"
source                 1..639
                       mol_type = other DNA
                       organism = synthetic construct
SEQUENCE: 96
gagatcgtgc tgacacagtc ccctgccacc ctgtccgcct ctccaggcga gcgcgtgaca  60
atgtcctgct ccgcctcctc ctccgtgatc tacatgcact ggtatcagca gaagcccggc  120
caggcccctc ggcggtggat ctacgatacc tccaagctgg cctccggcgt gcccgccaga  180
ttctccggct ctggctctgg caccgactac accctgacca tctccagcat ggaacccgag  240
gacgccgccg tgtactactg ccagcagtgg tcctccaacc ctctgacctt cggccagggc  300
accaagctgg aaatcaagcg tacggtggcc gctcccagcg tgttcatctt ccccccccagc  360
gacgagcagc tgaagagcgg caccgccagc gtggtgtgcc tgctgaacaa cttctacccc  420
cgggaggcca aggtgcagtg gaaggtggac aacgccctgc agagcggcaa cagccaggag  480
agcgtcaccg agcaggacag caaggactcc acctacagcc tgagcagcac cctgaccctg  540
agcaaggccg actacgagaa gcataaggtg tacgcctgcg aggtgaccca ccagggcctg  600
tccagccccg tgaccaagag cttcaacagg ggcgagtgc                        639

SEQ ID NO: 97          moltype = AA  length = 378
FEATURE                Location/Qualifiers
source                 1..378
                       mol_type = protein
                       organism = Homo sapiens
SEQUENCE: 97
MDLGKPMKSV LVVALLVIFQ VCLCQDEVTD DYIGDNTTVD YTLFESLCSK KDVRNFKAWF  60
LPIMYSIICF VGLLGNGLVV LTYIYFKRLK TMTDTYLLNL AVADILFLLT LPFWAYSAAK  120
SWVFGVHFCK LIFAIYKMSF FSGMLLLLCI SIDRYVAIVQ AVSAHRHRAR VLLISKLSCV  180
GIWILATVLS IPELLYSDLQ RSSSEQAMRC SLITEHVEAF ITIQVAQMVI GFLVPLLAMS  240
FCYLVIIRTL LQARNFERNK AIKVIIAVVV VFIVFQLPYN GVVLAQTVAN FNITSSTCEL  300
SKQLNIAYDV TYSLACVRCC VNPFLYAFIG VKFRNDLFKL FKDLGCLSQE QLRQWSSCRH  360
IRRSSMSVEA ETTTTFSP                                               378

SEQ ID NO: 98          moltype = DNA  length = 1134
FEATURE                Location/Qualifiers
source                 1..1134
                       mol_type = unassigned DNA
                       organism = Homo sapiens
SEQUENCE: 98
atggacctgg ggaaaccaat gaaaagcgtg ctggtggtgg ctctccttgt cattttccag  60
gtatgcctgt gtcaagatga ggtcacggac gattacatcg gagacaacac cacagtggac  120
tacactttgt tcgagtcttt gtgctccaag aaggacgtgc ggaactttaa agcctggttc  180
ctccctatca tgtactccat catttgtttc gtgggcctac tgggcaatgg gctggtcgtg  240
ttgacctata tctatttcaa gaggctcaag accatgaccg atacctacct gctcaacctg  300
gcggtggcag acatcctctt cctcctgacc cttcccttct gggcctacag cgcggccaag  360
tcctgggtct tcggtgtcca cttttgcaag ctcatctttg ccatctacaa gatgagcttc  420
ttcagtggca tgctcctact tctttgcatc agcattgacc gctacgtggc catcgtccag  480
gctgtctcag ctcaccgcca ccgtgcccgc gtccttctca tcagcaagct gtcctgtgtg  540
ggcatctgga tactagccac agtgctctcc atcccagagc tcctgtacag tgacctccag  600
aggagcagca gtgagcaagc gatgcgatgc tctctcatca cagagcatgt ggaggccttt  660
atcaccatcc aggtggccca gatggtgatc ggctttctgg tcccccctgct ggccatgagc  720
ttctgttacc ttgtcatcat ccgcaccctg ctccaggcac gcaactttga gcgcaacaag  780
gccatcaagg tgatcatcgc tgtggtcgtg gtcttcatag tcttccagct gccctacaat  840
ggggtggtcc tggcccagac ggtggccaac ttcaacatca ccagtagcac ctgtgagctc  900
agtaagcaac tcaacatcgc ctacgacgtc acctacagcc tggcctgcgt ccgctgctgc  960
gtcaaccctt tcttgtacgc cttcatcggc gtcaagttcc gcaacgatct cttcaagctc  1020
ttcaaggacc tgggctgcct cagccaggag cagctccggc agtggtcttc ctgtcggcac  1080
atccggcgct cctccatgag tgtggaggcc gagaccacca ccaccttctc ccca        1134

SEQ ID NO: 99          moltype = AA  length = 378
FEATURE                Location/Qualifiers
source                 1..378
                       mol_type = protein
                       organism = Macaca fascicularis
```

-continued

```
SEQUENCE: 99
MDLGKPMKSV LVVALLVIFQ VCLCQDEVTD DYIGDNTTVD YTLFESLCSK KDVRNFKAWF  60
LPIMYSIICF VGLLGNGLVV LTYIYFKRLK TMTDTYLLNL AVADILFLLT LPFWAYSAAK  120
SWVFGVHFCK LIFAIYKMSF FSGMLLLLCI SIDRYVAIVQ AVSAHRHRAR VLLISKLSCV  180
GIWILATVLS IPELLYSGLQ RSSSEQAMRC SLITEHVEAF ITIQVAQMVI GFLVPLLAMS  240
FCYLVIIRTL LQARNFERNK AIKVIIAVVV VFIVFQLPYN GVVLAQTVAN FNITSSTCEL  300
SKQLNIAYDV TYSLACVRCC VNPFLYAFIG VKFRNDLFKL FKDLGCLSQE QLRQWSSCRH  360
IRRSSMSVEA ETTTTFSP                                              378

SEQ ID NO: 100         moltype = DNA  length = 1134
FEATURE                Location/Qualifiers
source                 1..1134
                       mol_type = unassigned DNA
                       organism = Macaca fascicularis
SEQUENCE: 100
atggacctgg ggaaaccaat gaaaagcgtg ctggtggtgg ctctccttgt cattttccag  60
gtatgcctgt gtcaagatga ggtcacggac gattacatcg gagacaacac cacagtggac  120
tacactttgt tcgagtcttt gtgctccaag aaggacgtgc ggaactttaa agcctggttc  180
ctccctatca tgtactccat catttgtttc gtgggcctac tgggcaatgg gctggtcgtg  240
ttgacctata tctatttcaa gaggctcaag accatgaccg atacctacct gctcaacctg  300
gcggtggcag acatcctctt cctcctgacc cttcccttct gggcctacag cgcggccaag  360
tcctgggtct tcggtgtcca cttttgcaag ctcatctttg ccatctacaa gatgagcttc  420
ttcagtggca tgctcctact tctttgcatc agcattgacc gctacgtggc catcgtccag  480
gctgtctcag ctcaccgcca ccgtgcccgc gtccttctca tcagcaagct gtcctgtgtg  540
ggcatctgga tactagccac agtgctctcc atcccagagc tcctgtacag tggcctccag  600
aggagcagca gtgagcaagc gatgcgatgc tctctcatca cagagcatgt ggaggccttt  660
atcaccatcc aggtggccca gatggtgatc ggctttctgg tccccctgct ggccatgagc  720
ttctgttacc ttgtcatcat ccgcaccctg ctccaggcac gcaactttga gcgcaacaag  780
gccatcaagg tgatcatcgc tgtggtcgtg gtcttcatag tcttccagct gccctacaat  840
ggggtggtcc tggcccagac ggtggccaac ttcaacatca ccagtagcac ctgtgagctc  900
agtaagcaac tcaacatcgc ctacgacgtc acctacagcc tggcctgcgt ccgctgctgc  960
gtcaaccctt tcttgtacgc cttcatcggc gtcaagttcc gcaacgatct cttcaagctc  1020
ttcaaggacc tgggctgcct cagccaggag cagctccggc agtggtcttc ctgtcggcac  1080
atccggcgct cctccatgag tgtggaggcc gagaccacca ccaccttctc ccca        1134

SEQ ID NO: 101         moltype = AA  length = 378
FEATURE                Location/Qualifiers
source                 1..378
                       mol_type = protein
                       organism = Mus sp.
SEQUENCE: 101
MDPGKPRKNV LVVALLVIFQ VCFCQDEVTD DYIGENTTVD YTLYESVCFK KDVRNFKAWF  60
LPLMYSVICF VGLLGNGLVI LTYIYFKRLK TMTDTYLLNL AVADILFLLI LPFWAYSEAK  120
SWIFGVYLCK GIFGIYKLSF FSGMLLLLCI SIDRYVAIVQ AVSAHRHRAR VLLISKLSCV  180
GIWMLALFLS IPELLYSGLQ KNSGEDTLRC SLVSAQVEAL ITIQVAQMVF GFLVPMLAMS  240
FCYLIIIRTL LQARNFERNK AIKVIIAVVV VFIVFQLPYN GVVLAQTVAN FNITNSSCET  300
SKQLNIAYDV TYSLASVRCC VNPFLYAFIG VKFRSDLFKL FKDLGCLSQE RLRHWSSCRH  360
VRNASVSMEA ETTTTFSP                                              378

SEQ ID NO: 102         moltype = DNA  length = 1134
FEATURE                Location/Qualifiers
source                 1..1134
                       mol_type = unassigned DNA
                       organism = Mus sp.
SEQUENCE: 102
atggacccag ggaaacccag gaaaaacgtg ctggtggtgg ctctccttgt cattttccag  60
gtgtgcttct gccaagatga ggtcaccgat gactacatcg gcgagaatac cacggtggac  120
tacaccctgt acgagtcggt gtgcttcaag aaggatgtgc ggaactttaa ggcctggttc  180
ctgcctctca tgtattctgt catctgcttc gtgggcctgc tcggcaacgg gctggtgata  240
ctgacgtaca tctatttcaa gaggctcaag accatgacgg atacctacct gctcaacctg  300
gccgtggcag acatcctttt cctcctgatt cttcccttct gggcctacag cgaagccaag  360
tcctggatct ttggcgtcta cctgtgtaag ggcatctttg gcatctataa gttaagcttc  420
ttcagcggga tgctgctgct cctatgcatc agcattgacc gctacgtagc catcgtccag  480
gccgtgtcgg ctcatcgcca ccgcgcccgc gtgcttctca tcagcaagct gtcctgtgtg  540
ggcatctgga tgctggccct cttcctctcc atcccggagc tgctctacag cggcctccag  600
aagaacagcg gcgaggacac gctgagatgc tcactggtca gtgcccaagt ggaggccttg  660
atcaccatcc aagtggccca gatggttttt gggttcctag tgcctatgct ggctatgagt  720
ttctgctacc tcattatcat ccgtaccttg ctccaggcac gcaactttga gcggaacaag  780
gccatcaagg tgatcattgc cgtggtggta gtcttcatag tcttccagct gccctacaat  840
ggggtggtcc tggctcagac ggtggccaac ttcaacatca ccaatagcag ctgcgaaacc  900
agcaagcagc tcaacattgc ctatgacgtc acctacagcc tggcctccgt ccgctgctgc  960
gtcaaccctt tcttgtatgc cttcatcggc gtcaagttcc gcagcgacct cttcaagctc  1020
ttcaaggact tgggctgtct cagccaggaa cggctccggc actggtcttc ctgccggcat  1080
gtacggaacg cgtcggtgag catggaggcg gagaccacca caaccttctc cccg        1134

SEQ ID NO: 103         moltype = AA  length = 378
FEATURE                Location/Qualifiers
source                 1..378
                       mol_type = protein
```

```
                         organism = Rattus sp.
SEQUENCE: 103
MDLGKPTKNV LVVALLVIFQ VCFCQDEVTD DYIGENTTVD YTLYESVCFK KDVRNFKAWF  60
LPLMYSVICF VGLLGNGLVV LTYIYFKRLK TMTDTYLLNL AVADILFLMI LPFWAYSEAK  120
SWIFGAYLCK SIFGIYKLSF FSGMLLLLCI SIDRYVAIVQ AVSAHRHRAR VLLISKLSCI  180
GIWTLAFFLS IPELLYSGLQ KNSGEDTWRC SLVSAQVEAL IAIQVAQMVV GFVLPMLAMS  240
FCYLVIIRTL LQARNFERNK AIKVIIAVVV VFVVFQLPYN GVVLAQTVAN FNITNSSCEA  300
SKQLNIAYDV TYSLASVRCC VNPFLYAFIG VKFRSDLFKL FKDLGCLSQE RLRQWSSCRH  360
VRHTSVSMEA ETTTTFSP                                              378

SEQ ID NO: 104           moltype = DNA  length = 1134
FEATURE                  Location/Qualifiers
source                   1..1134
                         mol_type = unassigned DNA
                         organism = Rattus sp.
SEQUENCE: 104
atggacctgg ggaagcccac gaaaaacgtg ctggtggtgg ctctcctggt cattttccag  60
gtgtgcttct gccaagatga ggtcacagac gactacatcg gcgagaacac caccgtggac  120
tacaccctgt atgagtcggt gtgcttcaag aaggatgtgc ggaactttaa ggcctggttc  180
ctccctctca tgtactcagt catttgcttc gtgggcctgc taggcaatgg gctggtggtg  240
ctgacataca tctatttcaa gagactgaag accatgacgg atacctacct gctcaacctg  300
gccgtggcag acatcctctt cctcatgatc cttcccttct gggcctacag cgaagccaag  360
tcctggatct ttggtgccta cctgtgtaag agcatctttg gcatctacaa gttaagcttc  420
ttcagcggga tgttgctgct cctgtgtatc agcattgacc gctatgtggc catcgtccag  480
gccgtgtcag cccaccggca ccgcgcccgc gtgcttctca tcagcaagct gtcctgtata  540
ggcatctgga cgctggcctt tttccttct atccctgagc tgctctacag cggcctccag  600
aagaacagcg gcgaggacac gtggagatgc tccctggtca gtgcccaagt ggaggccttg  660
atcgccatcc aagtggccca gatggttgtt gggtttgtac tgcctatgct ggctatgagt  720
ttctgctacc tggttatcat ccgcactctg ctccaggcgc gaaacttcga gcggaacaag  780
gccatcaagg tgatcatcgc tgtggtcgta gtgttcgtcg tcttccagct gccctacaat  840
ggggtggtcc tggcccagac cgtggccaat ttcaacatca ccaatagcag ctgcgaagcc  900
agcaagcagc tcaacattgc ctatgacgtc acctacagcc tggcctccgt ccgctgctgt  960
gtcaaccctt tcttgtatgc cttcatcggc gtcaagttcc gcagcgacct cttcaagctc  1020
ttcaaggact tgggctgcct cagccaggaa cggctccggc agtggtcttc ctgccgccat  1080
gtacggcaca cgtccgtgag catggaggcg gagactacca ccaccttctc cccg        1134

SEQ ID NO: 105           moltype = AA  length = 378
FEATURE                  Location/Qualifiers
source                   1..378
                         mol_type = protein
                         organism = Homo sapiens
SEQUENCE: 105
MDLGKPMKSV LVVALLVIFQ VCLCQDEVTD DYIGDNTTVD YTLFESLCSK KDVRNFKAWF  60
LPIMYSIICF VGLLGNGLVV LTYIYFKRLK TMTDTYLLNL AVADILFLLT LPFWAYSAAK  120
SWVFGVHFCK LIFAIYKMSF FSGMLLLLCI SIDRYVAIVQ AVSAHRHRAR VLLISKLSCV  180
GIWILATVLS IPELLYSDLQ RSSSEQAMRC SLITEHVEAF ITIQVAQMVI GFLVPLLAMS  240
FCYLVIIRTL LQARNFERNK AIKVIIAVVV VFIVFQLPYN GVVLAQTVAN FNITSSTCEL  300
SKQLNIAYDV TYSLACVRCC VNPFLYAFIG VKFRNDLFKL FKDLGCLSQE QLRQWSSCRH  360
IRRSSMSVEA ETTTTFSP                                              378

SEQ ID NO: 106           moltype = AA  length = 30
FEATURE                  Location/Qualifiers
source                   1..30
                         mol_type = protein
                         organism = Homo sapiens
SEQUENCE: 106
QDEVTDDYIG DNTTVDYTLF ESLCSKKDVR                                 30

SEQ ID NO: 107           moltype = AA  length = 8
FEATURE                  Location/Qualifiers
source                   1..8
                         mol_type = protein
                         organism = Homo sapiens
SEQUENCE: 107
KSWVFGVH                                                         8

SEQ ID NO: 108           moltype = AA  length = 19
FEATURE                  Location/Qualifiers
source                   1..19
                         mol_type = protein
                         organism = Homo sapiens
SEQUENCE: 108
YSDLQRSSSE QAMRCSLIT                                             19

SEQ ID NO: 109           moltype = AA  length = 7
FEATURE                  Location/Qualifiers
source                   1..7
                         mol_type = protein
                         organism = Homo sapiens
```

```
SEQUENCE: 109
FNITSST                                                     7

SEQ ID NO: 110          moltype = AA  length = 19
FEATURE                 Location/Qualifiers
source                  1..19
                        mol_type = protein
                        organism = Homo sapiens
SEQUENCE: 110
YSDLQRSSSE QAMRSSLIT                                        19

SEQ ID NO: 111          moltype = AA  length = 216
FEATURE                 Location/Qualifiers
REGION                  1..216
                        note = source = /note="Description of Artificial Sequence:
                         Synthetic polypeptide"
source                  1..216
                        mol_type = protein
                        organism = synthetic construct
SEQUENCE: 111
EVQLVESGGG LVKPGGSLKL SCAASGFTFS DYGMLWVRQA PEKGLEWIAY ISSGSSTIYY  60
ADRVKGRFTI SRDNAKNTLF LQMTSLRSED TAMYYCSTGT FAYWGQGTPV TVSSAKTTPP  120
SVYPLAPGSA AQTNSMVTLG CLVKGYFPEP VTVTWNSGSL SSGVHTFPAV LQSDLYTLSS  180
SVTVPSSTWP SETVTCNVAH PASSTKVDKK IVPRDC                      216

SEQ ID NO: 112          moltype = AA  length = 219
FEATURE                 Location/Qualifiers
REGION                  1..219
                        note = source = /note="Description of Artificial Sequence:
                         Synthetic polypeptide"
source                  1..219
                        mol_type = protein
                        organism = synthetic construct
SEQUENCE: 112
DVVMTQNPLS LPVSLGDQAS ISCRSSQSLI YNNGNTYLHW YRQKPGQSPK LLIYKVSNRF  60
SGVPDRFSGS GSGTDFTLKI SRVEAEDLGV YFCSQSTHVP FTFGSGTKLE IKRADAAPTV  120
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNEC                   219

SEQ ID NO: 113          moltype = AA  length = 265
FEATURE                 Location/Qualifiers
REGION                  1..265
                        note = source = /note="Description of Artificial Sequence:
                         Synthetic polypeptide"
source                  1..265
                        mol_type = protein
                        organism = synthetic construct
SEQUENCE: 113
QDEVTDDYIG DNTTVDYTLF ESLCSKKDVR EVQLVESGGG LVKPGGSLKL SCAASGFTFS  60
DYGMLWVRQA PEKGLEWIAY ISSGSSTIYY ADRVKGRFTI SRDNAKNTLF LQMTSLRSED  120
TAMYYCSTGT YSDLQRSSSE QAMRSSLITF AYWGQGTPVT VSSAKTTPPS VYPLAPGSAA  180
QTNSMVTLGC LVKGYFPEPV TVTWNSGSLS SGVHTFPAVL QSDLYTLSSS VTVPSSTWPS  240
ETVTCNVAHP ASSTKVDKKI VPRDC                                  265

SEQ ID NO: 114          moltype = DNA  length = 795
FEATURE                 Location/Qualifiers
misc_feature            1..795
                        note = source = /note="Description of Artificial Sequence:
                         Synthetic polynucleotide"
source                  1..795
                        mol_type = other DNA
                        organism = synthetic construct
SEQUENCE: 114
caagatgagg tcacggacga ttacatcgga gacaacacca cagtggacta cactttgttc  60
gagtctttgt gctccaagaa ggacgtgcgg gaggtgcagc tggtggagtc tggtggtggt  120
ctggtcaagc ctggaggttc cctgaaactg agttgtgccg catctgggtt tacattctct  180
gactacggaa tgctgtgggt gaggcaggca ccagagaagg gcctggaatg gatcgcttat  240
atttccagcg gatctagtac tatctactat gcagacaggg tcaagggccg gttcaccatt  300
agcagagata acgccaaaaa taccctgttt ctgcagatga catcactgag gtccgaggat  360
accgctatgt attattgctc cacagggact tacagtgacc tccagaggag cagcagtgag  420
caagcgatgc gatcctctct catcacattt gcttactggg gacaggggac acccgtgacc  480
gtcagctcag ccaagaccac ccccccagc gtgtaccctc tggcccctgg ctctgccgcc  540
cagaccaaca gcatggtgac cctgggctgc ctggtgaagg gctacttccc cgagcccgtg  600
accgtgacct ggaacagcgg cagcctgagc agcggcgtgc acaccttccc cgccgtgctg  660
cagagcgacc tgtacaccct gagcagctct gtgaccgtgc ccagcagcac ctggcccagc  720
gagaccgtga catgcaacgt ggcccacccc gccagctcca ccaaggtgga caagaaaatc  780
gtgccccggg actgc                                             795

SEQ ID NO: 115          moltype = DNA  length = 656
```

```
FEATURE                Location/Qualifiers
misc_feature           1..656
                       note = source = /note="Description of Artificial Sequence:
                        Synthetic polynucleotide"
source                 1..656
                       mol_type = other DNA
                       organism = synthetic construct
SEQUENCE: 115
atgtcgtgat gactcagaat ccactgtccc tgcctgtgtc cctgggcgat caggcttcca  60
ttagctgtcg ttcctctcag tccctgatct acaacaatgg taacacctac ctgcactggt  120
atagacagaa gcccggccag tcccctaagc tgctgatcta caaagtgagt aataggttct  180
caggagtccc agaccggttt tccggcagcg gatctgggac cgatttcaca ctgaaaatct  240
ctagggtgga ggccgaagac ctgggcgtct acttttgtag tcagagcact cacgtcccct  300
tcaccttcgg cagcggaaca aaactggaaa tcaagcgcgc tgatgccgcc cctaccgtga  360
gcatcttccc ccccagcagc gagcagctga ccagcggcgg agccagcgtg gtgtgcttcc  420
tgaacaactt ctaccccaag gacatcaacg tgaagtggaa gatcgacggc agcgagcggc  480
agaacggcgt gctgaacagc tggaccgacc aggacagcaa ggactccacc tacagcatga  540
gcagcaccct gaccctgacc aaggacgagt acgagcggca caacagctac acctgcgagg  600
ccacccacaa gaccagcacc agccccatcg tgaagagctt caaccggaac gagtgc      656

SEQ ID NO: 116         moltype = AA  length = 11
FEATURE                Location/Qualifiers
REGION                 1..11
                       note = source = /note="Description of Artificial Sequence:
                        Synthetic peptide"
source                 1..11
                       mol_type = protein
                       organism = synthetic construct
SEQUENCE: 116
GYSITSGYSW H                                                       11

SEQ ID NO: 117         moltype = AA  length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 117
HIHSSGSTNY NPSLKS                                                  16

SEQ ID NO: 118         moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 118
GGVQAFAY                                                           8

SEQ ID NO: 119         moltype = AA  length = 6
FEATURE                Location/Qualifiers
REGION                 1..6
                       note = source = /note="Description of Artificial Sequence:
                        Synthetic peptide"
source                 1..6
                       mol_type = protein
                       organism = synthetic construct
SEQUENCE: 119
SGYSWH                                                             6

SEQ ID NO: 120         moltype = AA  length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 120
HIHSSGSTNY NPSLKS                                                  16

SEQ ID NO: 121         moltype = AA  length = 8
FEATURE                Location/Qualifiers
REGION                 1..8
                       note = source = /note="Description of Artificial Sequence:
```

```
                        Synthetic peptide"
source                  1..8
                        mol_type = protein
                        organism = synthetic construct
SEQUENCE: 121
GGVQAFAY                                                                  8

SEQ ID NO: 122          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 122
GYSITSGY                                                                  8

SEQ ID NO: 123          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 123
HSSGS                                                                     5

SEQ ID NO: 124          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 124
GGVQAFAY                                                                  8

SEQ ID NO: 125          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 125
GYSITSGYS                                                                 9

SEQ ID NO: 126          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 126
IHSSGST                                                                   7

SEQ ID NO: 127          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 127
ARGGVQAFAY                                                                10

SEQ ID NO: 128          moltype = AA  length = 117
FEATURE                 Location/Qualifiers
REGION                  1..117
                        note = source = /note="Description of Artificial Sequence:
                         Synthetic polypeptide"
source                  1..117
```

```
                        mol_type = protein
                        organism = synthetic construct
SEQUENCE: 128
DVQLQESGPD LVKPSQSLSL TCTVTGYSIT SGYSWHWIRQ FPGNKLEWMA HIHSSGSTNY  60
NPSLKSRISI IRDTSKNLFF LQLNSVTTED TATYYCARGG VQAFAYWGQG TLVTVSA     117

SEQ ID NO: 129          moltype = DNA  length = 351
FEATURE                 Location/Qualifiers
misc_feature            1..351
                        note = source = /note="Description of Artificial Sequence:
                         Synthetic polynucleotide"
source                  1..351
                        mol_type = other DNA
                        organism = synthetic construct
SEQUENCE: 129
gatgtgcagc ttcaggagtc aggacctgac ctggtgaaac cttctcagtc actttcactc  60
acctgcactg tcactggcta ctccatcacc agtggttata gctggcactg gatccggcag  120
tttccaggaa acaaactgga gtggatggcc cacatccact ccagtggtag cactaactac  180
aacccatctc tcaaaagtcg catctctatc attcgagaca catccaagaa cctgttcttc  240
ctgcagttga attctgtgac tactgaggac acagccacat attactgtgc aagagggggg  300
gtacaggcct ttgcttactg gggccaaggg actctggtca ctgtctctgc a           351

SEQ ID NO: 130          moltype = AA  length = 447
FEATURE                 Location/Qualifiers
REGION                  1..447
                        note = source = /note="Description of Artificial Sequence:
                         Synthetic polypeptide"
source                  1..447
                        mol_type = protein
                        organism = synthetic construct
SEQUENCE: 130
DVQLQESGPD LVKPSQSLSL TCTVTGYSIT SGYSWHWIRQ FPGNKLEWMA HIHSSGSTNY  60
NPSLKSRISI IRDTSKNLFF LQLNSVTTED TATYYCARGG VQAFAYWGQG TLVTVSAAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 131          moltype = DNA  length = 1341
FEATURE                 Location/Qualifiers
misc_feature            1..1341
                        note = source = /note="Description of Artificial Sequence:
                         Synthetic polynucleotide"
source                  1..1341
                        mol_type = other DNA
                        organism = synthetic construct
SEQUENCE: 131
gatgtgcagc ttcaggagtc aggacctgac ctggtgaaac cttctcagtc actttcactc  60
acctgcactg tcactggcta ctccatcacc agtggttata gctggcactg gatccggcag  120
tttccaggaa acaaactgga gtggatggcc cacatccact ccagtggtag cactaactac  180
aacccatctc tcaaaagtcg catctctatc attcgagaca catccaagaa cctgttcttc  240
ctgcagttga attctgtgac tactgaggac acagccacat attactgtgc aagagggggg  300
gtacaggcct ttgcttactg gggccaaggg actctggtca ctgtctctgc agctagcacc  360
aagggcccaa gtgtgtttcc cctggccccc agcagcaagt ctacttccgg cggaactgct  420
gccctgggtt gcctggtgaa ggactacttc cccgagcccg tgacagtgtc ctggaactct  480
ggggctctga cttccggcgt gcacaccttc cccgccgtgc tgcagagcag cggcctgtac  540
agcctgagca gcgtggtgac agtgccctcc agctctctgg gaacccagac ctatatctgc  600
aacgtgaacc acaagcccag caacaccaag gtggacaaga gagtggagcc caagagctgc  660
gacaagaccc acacctgccc cccctgccca gctccagaac tgctgggagg gccttccgtg  720
ttcctgttcc cccccaagcc caaggacacc ctgatgatca gcaggacccc cgaggtgacc  780
tgcgtggtgg tggacgtgtc ccacgaggac ccagaggtga agttcaactg gtacgtggac  840
ggcgtggagg tgcacaacgc caagaccaag cccagagagg agcagtacaa cagcacctac  900
agggtggtgt ccgtgctgac cgtgctgcac caggactggc tgaacggcaa agaatacaag  960
tgcaaagtct ccaacaaggc cctgccagcc ccaatcgaaa agacaatcag caaggccaag  1020
ggccagccac gggagcccca ggtgtacacc ctgcccccca gccgggagga gatgaccaag  1080
aaccaggtgt ccctgacctg tctggtgaag ggcttctacc ccagcgatat cgccgtggag  1140
tgggagagca acggccagcc cgagaacaac tacaagacca ccccccccagt gctggacagc  1200
gacggcagct tcttcctgta cagcaagctg accgtggaca agtccaggtg gcagcagggc  1260
aacgtgttca gctgcagcgt gatgcacgag gccctgcaca accactacac ccagaagtcc  1320
ctgagcctga gccccggcaa g                                           1341

SEQ ID NO: 132          moltype = AA  length = 10
FEATURE                 Location/Qualifiers
REGION                  1..10
                        note = source = /note="Description of Artificial Sequence:
                         Synthetic peptide"
source                  1..10
```

```
                        mol_type = protein
                        organism = synthetic construct
SEQUENCE: 132
SASSSVIYMH                                                   10

SEQ ID NO: 133          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 133
DTSKLAS                                                      7

SEQ ID NO: 134          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 134
QQWSSNPLT                                                    9

SEQ ID NO: 135          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 135
SASSSVIYMH                                                   10

SEQ ID NO: 136          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 136
DTSKLAS                                                      7

SEQ ID NO: 137          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 137
QQWSSNPLT                                                    9

SEQ ID NO: 138          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 138
SSSVIY                                                       6

SEQ ID NO: 139          moltype =   length =
SEQUENCE: 139
000

SEQ ID NO: 140          moltype = AA  length = 6
FEATURE                 Location/Qualifiers
REGION                  1..6
                        note = source = /note="Description of Artificial Sequence:
```

```
                         Synthetic peptide"
source                   1..6
                         mol_type = protein
                         organism = synthetic construct
SEQUENCE: 140
WSSNPL                                                                6

SEQ ID NO: 141           moltype = AA  length = 5
FEATURE                  Location/Qualifiers
REGION                   1..5
                         note = source = /note="Description of Artificial Sequence:
                          Synthetic peptide"
source                   1..5
                         mol_type = protein
                         organism = synthetic construct
SEQUENCE: 141
SSVIY                                                                 5

SEQ ID NO: 142           moltype =   length =
SEQUENCE: 142
000

SEQ ID NO: 143           moltype = AA  length = 9
FEATURE                  Location/Qualifiers
REGION                   1..9
                         note = source = /note="Description of Artificial Sequence:
                          Synthetic peptide"
source                   1..9
                         mol_type = protein
                         organism = synthetic construct
SEQUENCE: 143
QQWSSNPLT                                                             9

SEQ ID NO: 144           moltype = AA  length = 106
FEATURE                  Location/Qualifiers
REGION                   1..106
                         note = source = /note="Description of Artificial Sequence:
                          Synthetic polypeptide"
source                   1..106
                         mol_type = protein
                         organism = synthetic construct
SEQUENCE: 144
QIVLTQSPAI MSASPGEKVT MTCSASSSVI YMHWYQQKSG TSPKRWIYDT SKLASGVPAR  60
FSGSGSGTSY SLTISSMEAE DAATYYCQQW SSNPLTFGAG TTLELK                 106

SEQ ID NO: 145           moltype = DNA  length = 318
FEATURE                  Location/Qualifiers
misc_feature             1..318
                         note = source = /note="Description of Artificial Sequence:
                          Synthetic polynucleotide"
source                   1..318
                         mol_type = other DNA
                         organism = synthetic construct
SEQUENCE: 145
caaattgtcc tcacccagtc tccagcaatc atgtctgcat ctccagggga gaaggtcacc  60
atgacctgca gtgccagttc aagtgtaatt tacatgcact ggtaccagca gaagtcaggc  120
acctccccca aaagatggat ttatgacaca tccaaactgg cttctggagt ccctgctcgc  180
ttcagtggta gtgggtctgg gacctcttac tctctcacaa tcagcagcat ggaggctgaa  240
gatgctgcca cttattactg ccagcagtgg agtagtaacc cgctcacgtt cggtgctggg  300
accacgttgg agctgaaa                                                318

SEQ ID NO: 146           moltype = AA  length = 213
FEATURE                  Location/Qualifiers
REGION                   1..213
                         note = source = /note="Description of Artificial Sequence:
                          Synthetic polypeptide"
source                   1..213
                         mol_type = protein
                         organism = synthetic construct
SEQUENCE: 146
QIVLTQSPAI MSASPGEKVT MTCSASSSVI YMHWYQQKSG TSPKRWIYDT SKLASGVPAR  60
FSGSGSGTSY SLTISSMEAE DAATYYCQQW SSNPLTFGAG TTLELKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 147           moltype = DNA  length = 639
FEATURE                  Location/Qualifiers
misc_feature             1..639
                         note = source = /note="Description of Artificial Sequence:
```

```
                          Synthetic polynucleotide"
source                   1..639
                         mol_type = other DNA
                         organism = synthetic construct
SEQUENCE: 147
caaattgtcc tcacccagtc tccagcaatc atgtctgcat ctccagggga gaaggtcacc  60
atgacctgca gtgccagttc aagtgtaatt tacatgcact ggtaccagca gaagtcaggc  120
acctccccca aaagatggat ttatgacaca tccaaactgg cttctggagt ccctgctcgc  180
ttcagtggta gtgggtctgg gacctcttac tctctcacaa tcagcagcat ggaggctgaa  240
gatgctgcca cttattactg ccagcagtgg agtagtaacc cgctcacgtt cggtgctggg  300
accacgttgg agctgaaacg tacggtggcc gctcccagcg tgttcatctt cccccccagc  360
gacgagcagc tgaagagtgg caccgccagc gtggtgtgcc tgctgaacaa cttctacccc  420
cgggaggcca aggtgcagtg gaaggtggac aacgccctgc agagcggcaa cagccaggag  480
agcgtcaccg agcaggacag caaggactcc acctacagcc tgagcagcac cctgaccctg  540
agcaaggccg actacgagaa gcataaggtg tacgcctgcg aggtgaccca ccagggcctg  600
tccagccccg tgaccaagag cttcaacagg ggcgagtgc                         639

SEQ ID NO: 148           moltype = AA  length = 10
FEATURE                  Location/Qualifiers
REGION                   1..10
                         note = source = /note="Description of Artificial Sequence:
                          Synthetic peptide"
source                   1..10
                         mol_type = protein
                         organism = synthetic construct
SEQUENCE: 148
GFTFSTYAMS                                                          10

SEQ ID NO: 149           moltype = AA  length = 17
FEATURE                  Location/Qualifiers
REGION                   1..17
                         note = source = /note="Description of Artificial Sequence:
                          Synthetic peptide"
source                   1..17
                         mol_type = protein
                         organism = synthetic construct
SEQUENCE: 149
TISDGGSYSY YPDNVKG                                                  17

SEQ ID NO: 150           moltype = AA  length = 13
FEATURE                  Location/Qualifiers
REGION                   1..13
                         note = source = /note="Description of Artificial Sequence:
                          Synthetic peptide"
source                   1..13
                         mol_type = protein
                         organism = synthetic construct
SEQUENCE: 150
RGSRYEEYYV MDY                                                      13

SEQ ID NO: 151           moltype = AA  length = 5
FEATURE                  Location/Qualifiers
REGION                   1..5
                         note = source = /note="Description of Artificial Sequence:
                          Synthetic peptide"
source                   1..5
                         mol_type = protein
                         organism = synthetic construct
SEQUENCE: 151
TYAMS                                                               5

SEQ ID NO: 152           moltype = AA  length = 17
FEATURE                  Location/Qualifiers
REGION                   1..17
                         note = source = /note="Description of Artificial Sequence:
                          Synthetic peptide"
source                   1..17
                         mol_type = protein
                         organism = synthetic construct
SEQUENCE: 152
TISDGGSYSY YPDNVKG                                                  17

SEQ ID NO: 153           moltype = AA  length = 13
FEATURE                  Location/Qualifiers
REGION                   1..13
                         note = source = /note="Description of Artificial Sequence:
                          Synthetic peptide"
source                   1..13
                         mol_type = protein
```

```
                         organism = synthetic construct
SEQUENCE: 153
RGSRYEEYYV MDY                                                 13

SEQ ID NO: 154           moltype = AA  length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 154
GFTFSTY                                                        7

SEQ ID NO: 155           moltype = AA  length = 6
FEATURE                  Location/Qualifiers
REGION                   1..6
                         note = source = /note="Description of Artificial Sequence:
                          Synthetic peptide"
source                   1..6
                         mol_type = protein
                         organism = synthetic construct
SEQUENCE: 155
SDGGSY                                                         6

SEQ ID NO: 156           moltype = AA  length = 13
FEATURE                  Location/Qualifiers
REGION                   1..13
                         note = source = /note="Description of Artificial Sequence:
                          Synthetic peptide"
source                   1..13
                         mol_type = protein
                         organism = synthetic construct
SEQUENCE: 156
RGSRYEEYYV MDY                                                 13

SEQ ID NO: 157           moltype = AA  length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 157
GFTFSTYA                                                       8

SEQ ID NO: 158           moltype = AA  length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 158
ISDGGSYS                                                       8

SEQ ID NO: 159           moltype = AA  length = 15
FEATURE                  Location/Qualifiers
REGION                   1..15
                         note = source = /note="Description of Artificial Sequence:
                          Synthetic peptide"
source                   1..15
                         mol_type = protein
                         organism = synthetic construct
SEQUENCE: 159
ARRGSRYEEY YVMDY                                               15

SEQ ID NO: 160           moltype = AA  length = 122
FEATURE                  Location/Qualifiers
REGION                   1..122
                         note = source = /note="Description of Artificial Sequence:
                          Synthetic polypeptide"
source                   1..122
                         mol_type = protein
                         organism = synthetic construct
SEQUENCE: 160
```

-continued

```
EVQLVESGGG LVKPGGSLKL SCAASGFTFS TYAMSWVRQT PEKRLEWVAT ISDGGSYSYY  60
PDNVKGRFTI SRDNAKNNLY LQMSHLKSED TAMYYCARRG SRYEEYYVMD YWGQGTSVTV  120
SS                                                               122

SEQ ID NO: 161         moltype = DNA  length = 366
FEATURE                Location/Qualifiers
misc_feature           1..366
                       note = source = /note="Description of Artificial Sequence:
                        Synthetic polynucleotide"
source                 1..366
                       mol_type = other DNA
                       organism = synthetic construct
SEQUENCE: 161
gaagtgcagc tggtggagtc tgggggaggc ttagtgaagc ctggagggtc cctgaaactc  60
tcctgtgcag cctctggatt cactttcagt acctatgcca tgtcttgggt tcgccagact  120
ccggaaaaga ggctggagtg ggtcgcaacc attagtgatg gtggtagtta ttcgtactat  180
ccagacaatg taaagggccg attcaccatc tccagagaca atgccaagaa caacctatac  240
ctgcaaatga gccatctgaa gtctgaggac acagccatgt attactgtgc aagacgaggt  300
agtaggtacg aagagtacta tgttatggac tactggggtc aaggaacctc agtcaccgtc  360
tcctca                                                           366

SEQ ID NO: 162         moltype = AA  length = 452
FEATURE                Location/Qualifiers
REGION                 1..452
                       note = source = /note="Description of Artificial Sequence:
                        Synthetic polypeptide"
source                 1..452
                       mol_type = protein
                       organism = synthetic construct
SEQUENCE: 162
EVQLVESGGG LVKPGGSLKL SCAASGFTFS TYAMSWVRQT PEKRLEWVAT ISDGGSYSYY  60
PDNVKGRFTI SRDNAKNNLY LQMSHLKSED TAMYYCARRG SRYEEYYVMD YWGQGTSVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                              452

SEQ ID NO: 163         moltype = DNA  length = 1356
FEATURE                Location/Qualifiers
misc_feature           1..1356
                       note = source = /note="Description of Artificial Sequence:
                        Synthetic polynucleotide"
source                 1..1356
                       mol_type = other DNA
                       organism = synthetic construct
SEQUENCE: 163
gaagtgcagc tggtggagtc tgggggaggc ttagtgaagc ctggagggtc cctgaaactc  60
tcctgtgcag cctctggatt cactttcagt acctatgcca tgtcttgggt tcgccagact  120
ccggaaaaga ggctggagtg ggtcgcaacc attagtgatg gtggtagtta ttcgtactat  180
ccagacaatg taaagggccg attcaccatc tccagagaca atgccaagaa caacctatac  240
ctgcaaatga gccatctgaa gtctgaggac acagccatgt attactgtgc aagacgaggt  300
agtaggtacg aagagtacta tgttatggac tactggggtc aaggaacctc agtcaccgtc  360
tcctcagcta gcaccaaggg cccaagtgtg tttcccctgg cccccagcag caagtctact  420
tccggcggaa ctgctgccct gggttgcctg gtgaaggact acttccccga gcccgtgaca  480
gtgtcctgga actctggggc tctgacttcc ggcgtgcaca ccttccccgc cgtgctgcag  540
agcagcggcc tgtacagcct gagcagcgtg gtgacagtgc cctccagctc tctgggaacc  600
cagacctata tctgcaacgt gaaccacaag cccagcaaca ccaaggtgga caagagagtg  660
gagcccaaga gctgcgacaa gacccacacc tgcccccct gcccagctcc agaactgctg  720
ggagggcctt ccgtgttcct gttccccccc aagcccaagg acaccctgat gatcagcagg  780
acccccgagg tgacctgcgt ggtggtggac gtgtcccacg aggacccaga ggtgaagttc  840
aactggtacg tggacggcgt ggaggtgcac aacgccaaga ccaagcccag agaggagcag  900
tacaacagca cctacagggt ggtgtccgtg ctgaccgtgc tgcaccagga ctggctgaac  960
ggcaaagaat acaagtgcaa agtctccaac aaggccctgc cagccccaat cgaaaagaca  1020
atcagcaagg ccaagggcca gccacgggag ccccaggtgt acaccctgcc ccccagccgg  1080
gaggagatga ccaagaacca ggtgtccctg acctgtctgg tgaagggctt ctaccccagc  1140
gatatcgccg tggagtggga gagcaacggc cagcccgaga acaactacaa gaccaccccc  1200
ccagtgctgg acagcgacgg cagcttcttc ctgtacagca agctgaccgt ggacaagtcc  1260
aggtggcagc agggcaacgt gttcagctgc agcgtgatgc acgaggccct gcacaaccac  1320
tacacccaga agtccctgag cctgagcccc ggcaag                          1356

SEQ ID NO: 164         moltype = AA  length = 11
FEATURE                Location/Qualifiers
REGION                 1..11
                       note = source = /note="Description of Artificial Sequence:
                        Synthetic peptide"
source                 1..11
                       mol_type = protein
```

```
                         organism = synthetic construct
SEQUENCE: 164
RASQSISNNL H                                                11

SEQ ID NO: 165           moltype = AA  length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 165
YASQSIS                                                     7

SEQ ID NO: 166           moltype = AA  length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 166
QQSNSWLT                                                    8

SEQ ID NO: 167           moltype = AA  length = 11
FEATURE                  Location/Qualifiers
REGION                   1..11
                         note = source = /note="Description of Artificial Sequence:
                          Synthetic peptide"
source                   1..11
                         mol_type = protein
                         organism = synthetic construct
SEQUENCE: 167
RASQSISNNL H                                                11

SEQ ID NO: 168           moltype = AA  length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 168
YASQSIS                                                     7

SEQ ID NO: 169           moltype = AA  length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 169
QQSNSWLT                                                    8

SEQ ID NO: 170           moltype = AA  length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 170
SQSISNN                                                     7

SEQ ID NO: 171           moltype =   length =
SEQUENCE: 171
000

SEQ ID NO: 172           moltype = AA  length = 5
FEATURE                  Location/Qualifiers
REGION                   1..5
                         note = source = /note="Description of Artificial Sequence:
                          Synthetic peptide"
```

```
source                  1..5
                        mol_type = protein
                        organism = synthetic construct
SEQUENCE: 172
SNSWL                                                                       5

SEQ ID NO: 173          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 173
QSISNN                                                                      6

SEQ ID NO: 174          moltype =   length =
SEQUENCE: 174
000

SEQ ID NO: 175          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 175
QQSNSWLT                                                                    8

SEQ ID NO: 176          moltype = AA  length = 106
FEATURE                 Location/Qualifiers
REGION                  1..106
                        note = source = /note="Description of Artificial Sequence:
                         Synthetic polypeptide"
source                  1..106
                        mol_type = protein
                        organism = synthetic construct
SEQUENCE: 176
DIVLTQSPAT LSVTPGDSVS LSCRASQSIS NNLHWYQQKS HESPKLLIKY ASQSISGIPS  60
RFSGSGSGTD FTLSINSVET EDFGMYFCQQ SNSWLTFGAG TKLGLK                 106

SEQ ID NO: 177          moltype = DNA  length = 318
FEATURE                 Location/Qualifiers
misc_feature            1..318
                        note = source = /note="Description of Artificial Sequence:
                         Synthetic polynucleotide"
source                  1..318
                        mol_type = other DNA
                        organism = synthetic construct
SEQUENCE: 177
gatattgtgc taactcagtc tccagccacc ctgtctgtga ctccaggaga tagcgtcagt  60
ctttcctgca gggccagcca aagtattagc aacaacctac actggtatca acagaaatca  120
catgagtctc caaaacttct catcaagtat gcttcccagt ccatctctgg gatcccctcc  180
aggttcagtg gcagtggatc agggacagat ttcactctca gtatcaacag tgtggagact  240
gaagattttg gaatgtattt ctgtcaacag agtaacagct ggctcacgtt cggtgctggg  300
accaagctgg ggctgaaa                                                 318

SEQ ID NO: 178          moltype = AA  length = 213
FEATURE                 Location/Qualifiers
REGION                  1..213
                        note = source = /note="Description of Artificial Sequence:
                         Synthetic polypeptide"
source                  1..213
                        mol_type = protein
                        organism = synthetic construct
SEQUENCE: 178
DIVLTQSPAT LSVTPGDSVS LSCRASQSIS NNLHWYQQKS HESPKLLIKY ASQSISGIPS  60
RFSGSGSGTD FTLSINSVET EDFGMYFCQQ SNSWLTFGAG TKLGLKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                                213

SEQ ID NO: 179          moltype = DNA  length = 639
FEATURE                 Location/Qualifiers
misc_feature            1..639
                        note = source = /note="Description of Artificial Sequence:
                         Synthetic polynucleotide"
```

```
source                  1..639
                        mol_type = other DNA
                        organism = synthetic construct
SEQUENCE: 179
gatattgtgc taactcagtc tccagccacc ctgtctgtga ctccaggaga tagcgtcagt  60
ctttcctgca gggccagcca aagtattagc aacaacctac actggtatca acagaaatca  120
catgagtctc caaaacttct catcaagtat gcttcccagt ccatctctgg gatcccctcc  180
aggttcagtg gcagtggatc agggacagat ttcactctca gtatcaacag tgtggagact  240
gaagattttg gaatgtattt ctgtcaacag agtaacagct ggctcacgtt cggtgctggg  300
accaagctgg ggctgaaacg tacggtggcc gctcccagcg tgttcatctt cccccccagc  360
gacgagcagc tgaagagtgg caccgccagc gtggtgtgcc tgctgaacaa cttctacccc  420
cgggaggcca aggtgcagtg gaaggtggac aacgccctgc agagcggcaa cagccaggag  480
agcgtcaccg agcaggacag caaggactcc acctacagcc tgagcagcac cctgaccctg  540
agcaaggccg actacgagaa gcataaggtg tacgcctgcg aggtgaccca ccagggcctg  600
tccagccccg tgaccaagag cttcaacagg ggcgagtgc                         639

SEQ ID NO: 180          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 180
GFTFSSYAMS                                                         10

SEQ ID NO: 181          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 181
TISSGGSFTY YPDSVKG                                                 17

SEQ ID NO: 182          moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 182
RASTVVGTDF DV                                                      12

SEQ ID NO: 183          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 183
SYAMS                                                              5

SEQ ID NO: 184          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 184
TISSGGSFTY YPDSVKG                                                 17

SEQ ID NO: 185          moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
```

```
SEQUENCE: 185
RASTVVGTDF DV                                                12

SEQ ID NO: 186          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 186
GFTFSSY                                                      7

SEQ ID NO: 187          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 187
SSGGSF                                                       6

SEQ ID NO: 188          moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 188
RASTVVGTDF DV                                                12

SEQ ID NO: 189          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 189
GFTFSSYA                                                     8

SEQ ID NO: 190          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 190
ISSGGSFT                                                     8

SEQ ID NO: 191          moltype = AA  length = 14
FEATURE                 Location/Qualifiers
REGION                  1..14
                        note = source = /note="Description of Artificial Sequence:
                         Synthetic peptide"
source                  1..14
                        mol_type = protein
                        organism = synthetic construct
SEQUENCE: 191
ARRASTVVGT DFDV                                              14

SEQ ID NO: 192          moltype = AA  length = 121
FEATURE                 Location/Qualifiers
REGION                  1..121
                        note = source = /note="Description of Artificial Sequence:
                         Synthetic polypeptide"
source                  1..121
                        mol_type = protein
                        organism = synthetic construct
SEQUENCE: 192
EVMLVESGGG LVKPGGSLKL SCAASGFTFS SYAMSWIRQT PEKRLEWVAT ISSGGSFTYY  60
```

-continued

```
PDSVKGRFTI SRDNVKNTLY LQMSSLRSED TAMYYCARRA STVVGTDFDV WGAGTTVTVS  120
S                                                                 121

SEQ ID NO: 193          moltype = DNA  length = 363
FEATURE                 Location/Qualifiers
misc_feature            1..363
                        note = source = /note="Description of Artificial Sequence:
                         Synthetic polynucleotide"
source                  1..363
                        mol_type = other DNA
                        organism = synthetic construct
SEQUENCE: 193
gaagtgatgc tggtggagtc tgggggaggc ttagtgaagc ctggagggtc cctgaaactc  60
tcctgtgcag cctctggatt cactttcagt agctatgcca tgtcttggat tcgccagact  120
ccggagaaga gactggagtg ggtcgcaacc atcagtagtg gtggtagttt cacctactat  180
ccagacagtg tgaaggggcg attcaccatt tctagagaca atgtcaagaa caccctgtac  240
ctgcaaatga gcagtctgag gtctgaagac acggccatgt attactgtgc aagacgggct  300
tctacggtag taggtacgga cttcgatgtc tggggcgcag ggaccacggt caccgtctcc  360
tca                                                               363

SEQ ID NO: 194          moltype = AA  length = 451
FEATURE                 Location/Qualifiers
REGION                  1..451
                        note = source = /note="Description of Artificial Sequence:
                         Synthetic polypeptide"
source                  1..451
                        mol_type = protein
                        organism = synthetic construct
SEQUENCE: 194
EVMLVESGGG LVKPGGSLKL SCAASGFTFS SYAMSWIRQT PEKRLEWVAT ISSGGSFTYY  60
PDSVKGRFTI SRDNVKNTLY LQMSSLRSED TAMYYCARRA STVVGTDFDV WGAGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 195          moltype = DNA  length = 1353
FEATURE                 Location/Qualifiers
misc_feature            1..1353
                        note = source = /note="Description of Artificial Sequence:
                         Synthetic polynucleotide"
source                  1..1353
                        mol_type = other DNA
                        organism = synthetic construct
SEQUENCE: 195
gaagtgatgc tggtggagtc tgggggaggc ttagtgaagc ctggagggtc cctgaaactc  60
tcctgtgcag cctctggatt cactttcagt agctatgcca tgtcttggat tcgccagact  120
ccggagaaga gactggagtg ggtcgcaacc atcagtagtg gtggtagttt cacctactat  180
ccagacagtg tgaaggggcg attcaccatt tctagagaca atgtcaagaa caccctgtac  240
ctgcaaatga gcagtctgag gtctgaagac acggccatgt attactgtgc aagacgggct  300
tctacggtag taggtacgga cttcgatgtc tggggcgcag ggaccacggt caccgtctcc  360
tcagctagca ccaagggccc aagtgtgttt cccctggccc ccagcagcaa gtctacttcc  420
ggcggaactg ctgccctggg ttgcctggtg aaggactact tccccgagcc cgtgacagtg  480
tcctggaact ctggggctct gacttccggc gtgcacacct tccccgccgt gctgcagagc  540
agcggcctgt acagcctgag cagcgtggtg acagtgccct ccagctctct gggaacccag  600
acctatatct gcaacgtgaa ccacaagccc agcaacacca aggtggacaa gagagtggag  660
cccaagagct gcgacaagac ccacacctgc ccccctgcc  cagctccaga actgctggga  720
gggccttccg tgttcctgtt ccccccaag  cccaaggaca ccctgatgat cagcaggacc  780
cccgaggtga cctgcgtggt ggtggacgtg tcccacgagg acccagaggt gaagttcaac  840
tggtacgtgg acggcgtgga ggtgcacaac gccaagacca agcccagaga ggagcagtac  900
aacagcacct acagggtggt gtccgtgctg accgtgctgc accaggactg gctgaacggc  960
aaagaataca agtgcaaagt ctccaacaag gccctgccag ccccaatcga aaagacaatc  1020
agcaaggcca agggccagcc acgggagccc caggtgtaca ccctgccccc cagccgggag  1080
gagatgacca agaaccaggt gtccctgacc tgtctggtga agggcttcta ccccagcgat  1140
atcgccgtgg agtgggagag caacggccag cccgagaaca actacaagac caccccccca  1200
gtgctggaca gcgacggcag cttcttcctg tacagcaagc tgaccgtgga caagtccagg  1260
tggcagcagg gcaacgtgtt cagctgcagc gtgatgcacg aggccctgca caaccactac  1320
acccagaagt ccctgagcct gagccccggc aag                              1353

SEQ ID NO: 196          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
```

```
SEQUENCE: 196
RASQDIGSSL N                                                    11

SEQ ID NO: 197          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 197
ATSSLDS                                                         7

SEQ ID NO: 198          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 198
LQYASSPPT                                                       9

SEQ ID NO: 199          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 199
RASQDIGSSL N                                                    11

SEQ ID NO: 200          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 200
ATSSLDS                                                         7

SEQ ID NO: 201          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 201
LQYASSPPT                                                       9

SEQ ID NO: 202          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 202
SQDIGSS                                                         7

SEQ ID NO: 203          moltype =   length =
SEQUENCE: 203
000

SEQ ID NO: 204          moltype = AA  length = 6
FEATURE                 Location/Qualifiers
REGION                  1..6
                        note = source = /note="Description of Artificial Sequence:
                         Synthetic peptide"
source                  1..6
```

```
                        mol_type = protein
                        organism = synthetic construct
SEQUENCE: 204
YASSPP                                                          6

SEQ ID NO: 205          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 205
QDIGSS                                                          6

SEQ ID NO: 206          moltype =   length =
SEQUENCE: 206
000

SEQ ID NO: 207          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 207
LQYASSPPT                                                       9

SEQ ID NO: 208          moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 208
DIQMTQSPSS LSASLGERVS LTCRASQDIG SSLNWLQQEP DGTIKRLIYA TSSLDSGVPK  60
RFSGSRSGSD YSLTISSLES EDFVVYYCLQ YASSPPTFGG GTKLEIK                107

SEQ ID NO: 209          moltype = DNA  length = 321
FEATURE                 Location/Qualifiers
misc_feature            1..321
                        note = source = /note="Description of Artificial Sequence:
                         Synthetic polynucleotide"
source                  1..321
                        mol_type = other DNA
                        organism = synthetic construct
SEQUENCE: 209
gacatccaga tgacccagtc tccatcctcc ttatctgcct ctctgggaga aagagtcagt  60
ctcacttgtc gggcaagtca ggacattggt agtagcttaa actggcttca gcaggaacca  120
gatggaacta ttaaacgcct gatctatgcc acatccagtt tagattctgg tgtccccaaa  180
aggttcagtg gcagtaggtc tgggtcagat tattctctca ccatcagcag ccttgagtct  240
gaagattttg tagtctatta ctgtctacaa tatgctagtt cgcctccgac gttcggtgga  300
ggcaccaagc tggaaatcaa a                                           321

SEQ ID NO: 210          moltype = AA  length = 214
FEATURE                 Location/Qualifiers
REGION                  1..214
                        note = source = /note="Description of Artificial Sequence:
                         Synthetic polypeptide"
source                  1..214
                        mol_type = protein
                        organism = synthetic construct
SEQUENCE: 210
DIQMTQSPSS LSASLGERVS LTCRASQDIG SSLNWLQQEP DGTIKRLIYA TSSLDSGVPK  60
RFSGSRSGSD YSLTISSLES EDFVVYYCLQ YASSPPTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 211          moltype = DNA  length = 642
FEATURE                 Location/Qualifiers
misc_feature            1..642
                        note = source = /note="Description of Artificial Sequence:
                         Synthetic polynucleotide"
source                  1..642
```

```
                        mol_type = other DNA
                        organism = synthetic construct
SEQUENCE: 211
gacatccaga tgacccagtc tccatcctcc ttatctgcct ctctgggaga aagagtcagt  60
ctcacttgtc gggcaagtca ggacattggt agtagcttaa actggcttca gcaggaacca  120
gatggaacta ttaaacgcct gatctatgcc acatccagtt tagattctgg tgtccccaaa  180
aggttcagtg gcagtaggtc tgggtcagat tattctctca ccatcagcag ccttgagtct  240
gaagattttg tagtctatta ctgtctacaa tatgctagtt cgcctccgac gttcggtgga  300
ggcaccaagc tggaaatcaa acgtacggtg gccgctccca gcgtgttcat cttccccccc  360
agcgacgagc agctgaagag tggcaccgcc agcgtggtgt gcctgctgaa caacttctac  420
ccccgggagg ccaaggtgca gtggaaggtg gacaacgccc tgcagagcgg caacagccag  480
gagagcgtca ccgagcagga cagcaaggac tccacctaca gcctgagcag caccctgacc  540
ctgagcaagg ccgactacga gaagcataag gtgtacgcct gcgaggtgac ccaccagggc  600
ctgtccagcc ccgtgaccaa gagcttcaac aggggcgagt gc                    642

SEQ ID NO: 212          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 212
GFTFSNFAMS                                                        10

SEQ ID NO: 213          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 213
TISTGGTYTY YPDSVKG                                                17

SEQ ID NO: 214          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 214
RGYDGVDK                                                          8

SEQ ID NO: 215          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 215
SNFAMS                                                            6

SEQ ID NO: 216          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 216
TISTGGTYTY YPDSVKG                                                17

SEQ ID NO: 217          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 217
```

```
RGYDGVDK                                                                    8

SEQ ID NO: 218          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 218
GFTFSNF                                                                     7

SEQ ID NO: 219          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 219
STGGTY                                                                      6

SEQ ID NO: 220          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 220
RGYDGVDK                                                                    8

SEQ ID NO: 221          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 221
GFTFSNFA                                                                    8

SEQ ID NO: 222          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 222
ISTGGTYT                                                                    8

SEQ ID NO: 223          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 223
TRRGYDGVDK                                                                  10

SEQ ID NO: 224          moltype = AA  length = 117
FEATURE                 Location/Qualifiers
REGION                  1..117
                        note = source = /note="Description of Artificial Sequence:
                         Synthetic polypeptide"
source                  1..117
                        mol_type = protein
                        organism = synthetic construct
SEQUENCE: 224
EVHLVESGGG LVKPGGSLKL SCAASGFTFS NFAMSWVRQT PEKRLEWVAT ISTGGTYTYY  60
PDSVKGRFTI SRDNAKKTLY LQMSSLRSED TAMYYCTRRG YDGVDKWGQG TTLTVSS     117
```

-continued

```
SEQ ID NO: 225          moltype = DNA  length = 351
FEATURE                Location/Qualifiers
misc_feature           1..351
                       note = source = /note="Description of Artificial Sequence:
                        Synthetic polynucleotide"
source                 1..351
                       mol_type = other DNA
                       organism = synthetic construct
SEQUENCE: 225
gaagtgcatc tggtggagtc tgggggaggc ttagtgaagc ctggagggtc cctgaaactc  60
tcctgtgcag cctctggatt cactttcagt aactttgcca tgtcttgggt tcgccagact  120
ccggagaaga gactggagtg ggtcgcaacc attagtactg gtggtactta cacctactat  180
ccagacagtg tgaagggtcg attcaccatc tccagagaca atgccaagaa aaccctgtac  240
ctgcaaatga gcagtctgag gtctgaggac acggccatgt attactgtac aagacggggg  300
tacgacggcg tggacaaatg gggccaaggc accactctca cagtctcctc a           351

SEQ ID NO: 226          moltype = AA  length = 447
FEATURE                Location/Qualifiers
REGION                 1..447
                       note = source = /note="Description of Artificial Sequence:
                        Synthetic polypeptide"
source                 1..447
                       mol_type = protein
                       organism = synthetic construct
SEQUENCE: 226
EVHLVESGGG LVKPGGSLKL SCAASGFTFS NFAMSWVRQT PEKRLEWVAT ISTGGTYTYY  60
PDSVKGRFTI SRDNAKKTLY LQMSSLRSED TAMYYCTRRG YDGVDKWGQG TTLTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 227          moltype = DNA  length = 1341
FEATURE                Location/Qualifiers
misc_feature           1..1341
                       note = source = /note="Description of Artificial Sequence:
                        Synthetic polynucleotide"
source                 1..1341
                       mol_type = other DNA
                       organism = synthetic construct
SEQUENCE: 227
gaagtgcatc tggtggagtc tgggggaggc ttagtgaagc ctggagggtc cctgaaactc  60
tcctgtgcag cctctggatt cactttcagt aactttgcca tgtcttgggt tcgccagact  120
ccggagaaga gactggagtg ggtcgcaacc attagtactg gtggtactta cacctactat  180
ccagacagtg tgaagggtcg attcaccatc tccagagaca atgccaagaa aaccctgtac  240
ctgcaaatga gcagtctgag gtctgaggac acggccatgt attactgtac aagacggggg  300
tacgacggcg tggacaaatg gggccaaggc accactctca cagtctcctc agctagcacc  360
aagggcccaa gtgtgtttcc cctggccccc agcagcaagt ctacttccgg cggaactgct  420
gccctgggtt gcctggtgaa ggactacttc cccgagcccg tgacagtgtc ctggaactct  480
ggggctctga cttccggcgt gcacaccttc cccgccgtgc tgcagagcag cggcctgtac  540
agcctgagca gcgtggtgac agtgccctcc agctctctgg gaacccagac ctatatctgc  600
aacgtgaacc acaagcccag caacaccaag gtggacaaga gagtggagcc caagagctgc  660
gacaagaccc acacctgccc cccctgccca gctccagaac tgctgggagg gccttccgtg  720
ttcctgttcc cccccaagcc caaggacacc ctgatgatca gcaggacccc cgaggtgacc  780
tgcgtggtgg tggacgtgtc ccacgaggac ccagaggtga agttcaactg gtacgtggac  840
ggcgtggagg tgcacaacgc caagaccaag cccagagagg agcagtacaa cagcacctac  900
agggtggtgt ccgtgctgac cgtgctgcac caggactggc tgaacggcaa agaatacaag  960
tgcaaagtct ccaacaaggc cctgccagcc ccaatcgaaa agacaatcag caaggccaag  1020
ggccagccac gggagcccca ggtgtacacc ctgcccccca gccgggagga gatgaccaag  1080
aaccaggtgt ccctgacctg tctggtgaag ggcttctacc ccagcgatat cgccgtggag  1140
tgggagagca acggccagcc cgagaacaac tacaagacca ccccccccagt gctggacagc  1200
gacggcagct tcttcctgta cagcaagctg accgtggaca agtccaggtg gcagcagggc  1260
aacgtgttca gctgcagcgt gatgcacgag gccctgcaca accactacac ccagaagtcc  1320
ctgagcctga gccccggcaa g                                           1341

SEQ ID NO: 228          moltype = AA  length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 228
KSGQSLLDSD GKTYLN                                                 16
```

-continued

```
SEQ ID NO: 229          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 229
LVSKLDS                                                    7

SEQ ID NO: 230          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 230
WQGTHFPQT                                                  9

SEQ ID NO: 231          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 231
KSGQSLLDSD GKTYLN                                          16

SEQ ID NO: 232          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 232
LVSKLDS                                                    7

SEQ ID NO: 233          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 233
WQGTHFPQT                                                  9

SEQ ID NO: 234          moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 234
GQSLLDSDGK TY                                              12

SEQ ID NO: 235          moltype =   length =
SEQUENCE: 235
000

SEQ ID NO: 236          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 236
```

```
GTHFPQ                                                      6

SEQ ID NO: 237          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 237
QSLLDSDGKT Y                                                11

SEQ ID NO: 238          moltype =   length =
SEQUENCE: 238
000

SEQ ID NO: 239          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 239
WQGTHFPQT                                                   9

SEQ ID NO: 240          moltype = AA  length = 112
FEATURE                 Location/Qualifiers
REGION                  1..112
                        note = source = /note="Description of Artificial Sequence:
                         Synthetic polypeptide"
source                  1..112
                        mol_type = protein
                        organism = synthetic construct
SEQUENCE: 240
DVVMTQTPLT LSVTIGQPAS ISCKSGQSLL DSDGKTYLNW FLQRPGQSPK RLIYLVSKLD  60
SGVPDRFTGS GSGTDFTLKI SRVEAEDLGV YYCWQGTHFP QTFGGGTKLE IK          112

SEQ ID NO: 241          moltype = DNA  length = 336
FEATURE                 Location/Qualifiers
misc_feature            1..336
                        note = source = /note="Description of Artificial Sequence:
                         Synthetic polynucleotide"
source                  1..336
                        mol_type = other DNA
                        organism = synthetic construct
SEQUENCE: 241
gatgttgtga tgacccagac tccactcact ttgtcggtta ccattggaca accagcctcc  60
atctcttgca agtcaggtca gagcctctta gatagtgatg gaaagacata tttgaattgg  120
tttttacaga ggccaggcca gtctccaaag cgcctaatct atctggtgtc taaactggac  180
tctggagtcc ctgacaggtt cactggcagt ggatcaggga cagatttcac actgaaaatc  240
agcagagtgg aggctgagga tttgggagtt tattattgct ggcaaggtac acattttcct  300
cagacgttcg gtggaggcac caagctggaa atcaaa                            336

SEQ ID NO: 242          moltype = AA  length = 219
FEATURE                 Location/Qualifiers
REGION                  1..219
                        note = source = /note="Description of Artificial Sequence:
                         Synthetic polypeptide"
source                  1..219
                        mol_type = protein
                        organism = synthetic construct
SEQUENCE: 242
DVVMTQTPLT LSVTIGQPAS ISCKSGQSLL DSDGKTYLNW FLQRPGQSPK RLIYLVSKLD  60
SGVPDRFTGS GSGTDFTLKI SRVEAEDLGV YYCWQGTHFP QTFGGGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 243          moltype = DNA  length = 657
FEATURE                 Location/Qualifiers
misc_feature            1..657
                        note = source = /note="Description of Artificial Sequence:
                         Synthetic polynucleotide"
source                  1..657
                        mol_type = other DNA
                        organism = synthetic construct
SEQUENCE: 243
```

-continued

```
gatgttgtga tgacccagac tccactcact ttgtcggtta ccattggaca accagcctcc  60
atctcttgca agtcaggtca gagcctctta gatagtgatg gaaagacata tttgaattgg  120
tttttacaga ggccaggcca gtctccaaag cgcctaatct atctggtgtc taaactggac  180
tctggagtcc ctgacaggtt cactggcagt ggatcaggga cagatttcac actgaaaatc  240
agcagagtgg aggctgagga tttgggagtt tattattgct ggcaaggtac acattttcct  300
cagacgttcg gtggaggcac caagctggaa atcaaacgta cggtggccgc tcccagcgtg  360
ttcatcttcc cccccagcga cgagcagctg aagagtggca ccgccagcgt ggtgtgcctg  420
ctgaacaact tctacccccg ggaggccaag gtgcagtgga aggtggacaa cgccctgcag  480
agcggcaaca gccaggagag cgtcaccgag caggacagca aggactccac ctacagcctg  540
agcagcaccc tgaccctgag caaggccgac tacgagaagc ataaggtgta cgcctgcgag  600
gtgacccacc agggcctgtc cagccccgtg accaagagct tcaacagggg cgagtgc     657

SEQ ID NO: 244         moltype = AA  length = 11
FEATURE                Location/Qualifiers
REGION                 1..11
                       note = source = /note="Description of Artificial Sequence:
                        Synthetic peptide"
source                 1..11
                       mol_type = protein
                       organism = synthetic construct
SEQUENCE: 244
GYSITSGYSW H                                                       11

SEQ ID NO: 245         moltype = AA  length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 245
HIHSSGSTNY NPSLKS                                                  16

SEQ ID NO: 246         moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 246
GGVQAFAY                                                           8

SEQ ID NO: 247         moltype = AA  length = 6
FEATURE                Location/Qualifiers
REGION                 1..6
                       note = source = /note="Description of Artificial Sequence:
                        Synthetic peptide"
source                 1..6
                       mol_type = protein
                       organism = synthetic construct
SEQUENCE: 247
SGYSWH                                                             6

SEQ ID NO: 248         moltype = AA  length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 248
HIHSSGSTNY NPSLKS                                                  16

SEQ ID NO: 249         moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 249
GGVQAFAY                                                           8

SEQ ID NO: 250         moltype = AA  length = 8
```

```
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 250
GYSITSGY                                                    8

SEQ ID NO: 251         moltype = AA  length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 251
HSSGS                                                       5

SEQ ID NO: 252         moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 252
GGVQAFAY                                                    8

SEQ ID NO: 253         moltype = AA  length = 9
FEATURE                Location/Qualifiers
REGION                 1..9
                       note = source = /note="Description of Artificial Sequence:
                        Synthetic peptide"
source                 1..9
                       mol_type = protein
                       organism = synthetic construct
SEQUENCE: 253
GYSITSGYS                                                   9

SEQ ID NO: 254         moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 254
IHSSGST                                                     7

SEQ ID NO: 255         moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 255
ARGGVQAFAY                                                  10

SEQ ID NO: 256         moltype = AA  length = 117
FEATURE                Location/Qualifiers
REGION                 1..117
                       note = source = /note="Description of Artificial Sequence:
                        Synthetic polypeptide"
source                 1..117
                       mol_type = protein
                       organism = synthetic construct
SEQUENCE: 256
DVQLQESGPD LVKPSQSLSL TCTVTGYSIT SGYSWHWIRQ FPGNKLEWMA HIHSSGSTNY  60
NPSLKSRISI IRDTSKNLFF LQLNSVTTED TATYYCARGG VQAFAYWGQG TLVTVSA     117

SEQ ID NO: 257         moltype = DNA  length = 351
FEATURE                Location/Qualifiers
```

```
misc_feature           1..351
                       note = source = /note="Description of Artificial Sequence:
                        Synthetic polynucleotide"
source                 1..351
                       mol_type = other DNA
                       organism = synthetic construct
SEQUENCE: 257
gatgtgcagc ttcaggagtc aggacctgac ctggtgaaac cttctcagtc actttcactc  60
acctgcactg tcactggcta ctccatcacc agtggttata gctggcactg gatccggcag  120
tttccaggaa acaaactgga gtggatggcc cacatccact ccagtggtag cactaactac  180
aacccatctc tcaaaagtcg catctctatc attcgagaca catccaagaa cctgttcttc  240
ctgcagttga attctgtgac tactgaggac acagccacat attactgtgc aagagggggg  300
gtacaggcct ttgcttactg gggccaaggg actctggtca ctgtctctgc a           351

SEQ ID NO: 258         moltype = AA  length = 447
FEATURE                Location/Qualifiers
REGION                 1..447
                       note = source = /note="Description of Artificial Sequence:
                        Synthetic polypeptide"
source                 1..447
                       mol_type = protein
                       organism = synthetic construct
SEQUENCE: 258
DVQLQESGPD LVKPSQSLSL TCTVTGYSIT SGYSWHWIRQ FPGNKLEWMA HIHSSGSTNY  60
NPSLKSRISI IRDTSKNLFF LQLNSVTTED TATYYCARGG VQAFAYWGQG TLVTVSAAST  120
KGPSVFPLAP SSKSTSGGTA ALGCLVKDYF PCPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPCDIAVE WESNGQPENN YKTTPPVLDS DGSFFLYSKL TVDKSRWQQG  420
NVFSCSVMHE ALHNHYTQKS LSLSPGK                                     447

SEQ ID NO: 259         moltype = DNA  length = 1341
FEATURE                Location/Qualifiers
misc_feature           1..1341
                       note = source = /note="Description of Artificial Sequence:
                        Synthetic polynucleotide"
source                 1..1341
                       mol_type = other DNA
                       organism = synthetic construct
SEQUENCE: 259
gatgtgcagc ttcaggagtc aggacctgac ctggtgaaac cttctcagtc actttcactc  60
acctgcactg tcactggcta ctccatcacc agtggttata gctggcactg gatccggcag  120
tttccaggaa acaaactgga gtggatggcc cacatccact ccagtggtag cactaactac  180
aacccatctc tcaaaagtcg catctctatc attcgagaca catccaagaa cctgttcttc  240
ctgcagttga attctgtgac tactgaggac acagccacat attactgtgc aagagggggg  300
gtacaggcct ttgcttactg gggccaaggg actctggtca ctgtctctgc agctagcacc  360
aagggcccaa gtgtgtttcc cctggccccc agcagcaagt ctacttccgg cggaactgct  420
gccctgggtt gcctggtgaa ggactacttc ccctgtcccg tgacagtgtc ctggaactct  480
ggggctctga cttccggcgt gcacaccttc cccgccgtgc tgcagagcag cggcctgtac  540
agcctgagca gcgtggtgac agtgccctcc agctctctgg gaacccagac ctatatctgc  600
aacgtgaacc acaagcccag caacaccaag gtggacaaga gagtggagcc caagagctgc  660
gacaagaccc acacctgccc cccctgccca gctccagaac tgctgggagg gccttccgtg  720
ttcctgttcc cccccaagcc caaggacacc ctgatgatca gcaggacccc cgaggtgacc  780
tgcgtggtgg tggacgtgtc ccacgaggac ccagaggtga agttcaactg gtacgtggac  840
ggcgtggagg tgcacaacgc caagaccaag cccagagagg agcagtacaa cagcacctac  900
agggtggtgt ccgtgctgac cgtgctgcac caggactggc tgaacggcaa agaatacaag  960
tgcaaagtct ccaacaaggc cctgccagcc ccaatcgaaa agacaatcag caaggccaag  1020
ggccagccac gggagcccca ggtgtacacc ctgcccccca gccgggagga gatgaccaag  1080
aaccaggtgt ccctgacctg tctggtgaag ggcttctacc cctgtgatat cgccgtggag  1140
tgggagagca acggccagcc cgagaacaac tacaagacca cccccccagt gctggacagc  1200
gacggcagct tcttcctgta cagcaagctg accgtggaca agtccaggtg gcagcagggc  1260
aacgtgttca gctgcagcgt gatgcacgag gccctgcaca accactacac ccagaagtcc  1320
ctgagcctga gccccggcaa g                                           1341

SEQ ID NO: 260         moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 260
SASSSVIYMH                                                        10

SEQ ID NO: 261         moltype = AA  length = 7
FEATURE                Location/Qualifiers
REGION                 1..7
```

```
                        note = source = /note="Description of Artificial Sequence:
                         Synthetic peptide"
source                  1..7
                        mol_type = protein
                        organism = synthetic construct
SEQUENCE: 261
DTSKLAS                                                                      7

SEQ ID NO: 262          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 262
QQWSSNPLT                                                                    9

SEQ ID NO: 263          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 263
SASSSVIYMH                                                                   10

SEQ ID NO: 264          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 264
DTSKLAS                                                                      7

SEQ ID NO: 265          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 265
QQWSSNPLT                                                                    9

SEQ ID NO: 266          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 266
SSSVIY                                                                       6

SEQ ID NO: 267          moltype =   length =
SEQUENCE: 267
000

SEQ ID NO: 268          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 268
WSSNPL                                                                       6

SEQ ID NO: 269          moltype = AA  length = 5
```

```
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 269
SSVIY                                                                       5

SEQ ID NO: 270         moltype =   length =
SEQUENCE: 270
000

SEQ ID NO: 271         moltype = AA  length = 9
FEATURE                Location/Qualifiers
REGION                 1..9
                       note = source = /note="Description of Artificial Sequence:
                        Synthetic peptide"
source                 1..9
                       mol_type = protein
                       organism = synthetic construct
SEQUENCE: 271
QQWSSNPLT                                                                   9

SEQ ID NO: 272         moltype = AA  length = 106
FEATURE                Location/Qualifiers
REGION                 1..106
                       note = source = /note="Description of Artificial Sequence:
                        Synthetic polypeptide"
source                 1..106
                       mol_type = protein
                       organism = synthetic construct
SEQUENCE: 272
QIVLTQSPAI MSASPGEKVT MTCSASSSVI YMHWYQQKSG TSPKRWIYDT SKLASGVPAR  60
FSGSGSGTSY SLTISSMEAE DAATYYCQQW SSNPLTFGAG TTLELK                  106

SEQ ID NO: 273         moltype = DNA  length = 318
FEATURE                Location/Qualifiers
misc_feature           1..318
                       note = source = /note="Description of Artificial Sequence:
                        Synthetic polynucleotide"
source                 1..318
                       mol_type = other DNA
                       organism = synthetic construct
SEQUENCE: 273
caaattgtcc tcacccagtc tccagcaatc atgtctgcat ctccagggga gaaggtcacc  60
atgacctgca gtgccagttc aagtgtaatt tacatgcact ggtaccagca gaagtcaggc  120
acctccccca aaagatggat ttatgacaca tccaaactgg cttctggagt ccctgctcgc  180
ttcagtggta gtgggtctgg gacctcttac tctctcacaa tcagcagcat ggaggctgaa  240
gatgctgcca cttattactg ccagcagtgg agtagtaacc cgctcacgtt cggtgctggg  300
accacgttgg agctgaaa                                                 318

SEQ ID NO: 274         moltype = AA  length = 213
FEATURE                Location/Qualifiers
REGION                 1..213
                       note = source = /note="Description of Artificial Sequence:
                        Synthetic polypeptide"
source                 1..213
                       mol_type = protein
                       organism = synthetic construct
SEQUENCE: 274
QIVLTQSPAI MSASPGEKVT MTCSASSSVI YMHWYQQKSG TSPKRWIYDT SKLASGVPAR  60
FSGSGSGTSY SLTISSMEAE DAATYYCQQW SSNPLTFGAG TTLELKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                                213

SEQ ID NO: 275         moltype = DNA  length = 639
FEATURE                Location/Qualifiers
misc_feature           1..639
                       note = source = /note="Description of Artificial Sequence:
                        Synthetic polynucleotide"
source                 1..639
                       mol_type = other DNA
                       organism = synthetic construct
SEQUENCE: 275
caaattgtcc tcacccagtc tccagcaatc atgtctgcat ctccagggga gaaggtcacc  60
atgacctgca gtgccagttc aagtgtaatt tacatgcact ggtaccagca gaagtcaggc  120
acctccccca aaagatggat ttatgacaca tccaaactgg cttctggagt ccctgctcgc  180
```

-continued

```
ttcagtggta gtgggtctgg gacctcttac tctctcacaa tcagcagcat ggaggctgaa  240
gatgctgcca cttattactg ccagcagtgg agtagtaacc cgctcacgtt cggtgctggg  300
accacgttgg agctgaaacg tacggtggcc gctcccagcg tgttcatctt cccccccagc  360
gacgagcagc tgaagagtgg caccgccagc gtggtgtgcc tgctgaacaa cttctacccc  420
cgggaggcca aggtgcagtg gaaggtggac aacgccctgc agagcggcaa cagccaggag  480
agcgtcaccg agcaggacag caaggactcc acctacagcc tgagcagcac cctgaccctg  540
agcaaggccg actacgagaa gcataaggtg tacgcctgcg aggtgaccca ccagggcctg  600
tccagccccg tgaccaagag cttcaacagg ggcgagtgc                         639

SEQ ID NO: 276         moltype = AA  length = 11
FEATURE                Location/Qualifiers
REGION                 1..11
                       note = source = /note="Description of Artificial Sequence:
                        Synthetic peptide"
source                 1..11
                       mol_type = protein
                       organism = synthetic construct
SEQUENCE: 276
GYSITSGYSW H                                                          11

SEQ ID NO: 277         moltype = AA  length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 277
HIHSSGSTNY NPSLKS                                                     16

SEQ ID NO: 278         moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 278
GGVQAFAY                                                              8

SEQ ID NO: 279         moltype = AA  length = 6
FEATURE                Location/Qualifiers
REGION                 1..6
                       note = source = /note="Description of Artificial Sequence:
                        Synthetic peptide"
source                 1..6
                       mol_type = protein
                       organism = synthetic construct
SEQUENCE: 279
SGYSWH                                                                6

SEQ ID NO: 280         moltype = AA  length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 280
HIHSSGSTNY NPSLKS                                                     16

SEQ ID NO: 281         moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 281
GGVQAFAY                                                              8

SEQ ID NO: 282         moltype = AA  length = 8
FEATURE                Location/Qualifiers
REGION                 1..8
                       note = source = /note="Description of Artificial Sequence:
```

```
                         Synthetic peptide"
source                  1..8
                        mol_type = protein
                        organism = synthetic construct
SEQUENCE: 282
GYSITSGY                                                          8

SEQ ID NO: 283          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 283
HSSGS                                                             5

SEQ ID NO: 284          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 284
GGVQAFAY                                                          8

SEQ ID NO: 285          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 285
GYSITSGYS                                                         9

SEQ ID NO: 286          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 286
IHSSGST                                                           7

SEQ ID NO: 287          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 287
ARGGVQAFAY                                                        10

SEQ ID NO: 288          moltype = AA  length = 117
FEATURE                 Location/Qualifiers
REGION                  1..117
                        note = source = /note="Description of Artificial Sequence:
                         Synthetic polypeptide"
source                  1..117
                        mol_type = protein
                        organism = synthetic construct
SEQUENCE: 288
DVQLQESGPG LVKPSQTLSL TCTVSGYSIT SGYSWHWIRQ HPGKGLEWMA HIHSSGSTNY  60
NPSLKSRITI SRDTSKNQFS LKLSSVTAAD TAVYYCARGG VQAFAYWGQG TLVTVSS     117

SEQ ID NO: 289          moltype = DNA  length = 351
FEATURE                 Location/Qualifiers
misc_feature            1..351
                        note = source = /note="Description of Artificial Sequence:
                         Synthetic polynucleotide"
```

```
source                  1..351
                        mol_type = other DNA
                        organism = synthetic construct
SEQUENCE: 289
gacgtgcagc tgcaggaatc tggccctggc ctggtgaaac cctcccagac cctgtccctg  60
acctgcaccg tgtccggcta ctccatcacc tccggctaca gctggcactg gatccggcag  120
caccccggca agggcctgga atggatggcc cacatccact cctccggctc caccaactac  180
aaccccagcc tgaagtccag aatcaccatc agccgggaca cctccaagaa ccagttctcc  240
ctgaagctgt cctccgtgac cgccgctgac accgccgtgt actactgtgc cagaggcggc  300
gtgcaggcct tcgcttattg gggccagggc accctggtga cagtgtcctc c           351

SEQ ID NO: 290          moltype = AA  length = 447
FEATURE                 Location/Qualifiers
REGION                  1..447
                        note = source = /note="Description of Artificial Sequence:
                         Synthetic polypeptide"
source                  1..447
                        mol_type = protein
                        organism = synthetic construct
SEQUENCE: 290
DVQLQESGPG LVKPSQTLSL TCTVSGYSIT SGYSWHWIRQ HPGKGLEWMA HIHSSGSTNY  60
NPSLKSRITI SRDTSKNQFS LKLSSVTAAD TAVYYCARGG VQAFAYWGQG TLVTVSSAST  120
KGPSVFPLAP SSKSTSGGTA ALGCLVKDYF PCPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVAVSHED PEVKFNWYVD GVEVHNAKTK PREEQYNSTY  300
RVVSVLTVLH QDWLNGKEYK CKVSNKALAA PIEKTISKAK GQPREPQVYT LPPSREEMTK  360
NQVSLTCLVK GFYPCDIAVE WESNGQPENN YKTTPPVLDS DGSFFLYSKL TVDKSRWQQG  420
NVFSCSVMHE ALHNHYTQKS LSLSPGK                                     447

SEQ ID NO: 291          moltype = DNA  length = 1341
FEATURE                 Location/Qualifiers
misc_feature            1..1341
                        note = source = /note="Description of Artificial Sequence:
                         Synthetic polynucleotide"
source                  1..1341
                        mol_type = other DNA
                        organism = synthetic construct
SEQUENCE: 291
gacgtgcagc tgcaggaatc tggccctggc ctggtgaaac cctcccagac cctgtccctg  60
acctgcaccg tgtccggcta ctccatcacc tccggctaca gctggcactg gatccggcag  120
caccccggca agggcctgga atggatggcc cacatccact cctccggctc caccaactac  180
aaccccagcc tgaagtccag aatcaccatc agccgggaca cctccaagaa ccagttctcc  240
ctgaagctgt cctccgtgac cgccgctgac accgccgtgt actactgtgc cagaggcggc  300
gtgcaggcct tcgcttattg gggccagggc accctggtga cagtgtcctc cgctagcacc  360
aagggcccaa gtgtgtttcc cctggccccc agcagcaagt ctacttccgg cggaactgct  420
gccctgggtt gcctggtgaa ggactacttc ccctgtcccg tgacagtgtc ctggaactct  480
ggggctctga cttccggcgt gcacaccttc cccgccgtgc tgcagagcag cggcctgtac  540
agcctgagca gcgtggtgac agtgccctcc agctctctgg gaacccagac ctatatctgc  600
aacgtgaacc acaagcccag caacaccaag gtggacaaga gagtggagcc caagagctgc  660
gacaagaccc acacctgccc cccctgccca gctccagaac tgctgggagg gccttccgtg  720
ttcctgttcc cccccaagcc caaggacacc ctgatgatca gcaggacccc cgaggtgacc  780
tgcgtggtgg tggccgtgtc ccacgaggac ccagaggtga agttcaactg gtacgtggac  840
ggcgtggagg tgcacaacgc caagaccaag cccagagagg agcagtacaa cagcacctac  900
agggtggtgt ccgtgctgac cgtgctgcac caggactggc tgaacggcaa agaatacaag  960
tgcaaagtct ccaacaaggc cctggctgcc cccatcgaaa agacaatcag caaggccaag  1020
ggccagccac gggagcccca ggtgtacacc ctgcccccca gccgggagga gatgaccaag  1080
aaccaggtgt ccctgacctg tctggtgaag ggcttctacc cctgtgatat cgccgtggag  1140
tgggagagca acggccagcc cgagaacaac tacaagacca cccccccagt gctggacagc  1200
gacggcagct tcttcctgta cagcaagctg accgtggaca agtccaggtg gcagcagggc  1260
aacgtgttca gctgcagcgt gatgcacgag gccctgcaca accactacac ccagaagtcc  1320
ctgagcctga gccccggcaa g                                           1341

SEQ ID NO: 292          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 292
SASSSVIYMH                                                        10

SEQ ID NO: 293          moltype = AA  length = 7
FEATURE                 Location/Qualifiers
REGION                  1..7
                        note = source = /note="Description of Artificial Sequence:
                         Synthetic peptide"
source                  1..7
```

```
                        mol_type = protein
                        organism = synthetic construct
SEQUENCE: 293
DTSKLAS                                                       7

SEQ ID NO: 294          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 294
QQWSSNPLT                                                     9

SEQ ID NO: 295          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 295
SASSSVIYMH                                                    10

SEQ ID NO: 296          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 296
DTSKLAS                                                       7

SEQ ID NO: 297          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 297
QQWSSNPLT                                                     9

SEQ ID NO: 298          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 298
SSSVIY                                                        6

SEQ ID NO: 299          moltype =   length =
SEQUENCE: 299
000

SEQ ID NO: 300          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 300
WSSNPL                                                        6

SEQ ID NO: 301          moltype = AA  length = 5
FEATURE                 Location/Qualifiers
REGION                  1..5
                        note = source = /note="Description of Artificial Sequence:
```

```
                          Synthetic peptide"
source                    1..5
                          mol_type = protein
                          organism = synthetic construct
SEQUENCE: 301
SSVIY                                                            5

SEQ ID NO: 302            moltype =   length =
SEQUENCE: 302
000

SEQ ID NO: 303            moltype = AA  length = 9
FEATURE                   Location/Qualifiers
REGION                    1..9
                          note = source = /note="Description of Artificial Sequence:
                           Synthetic peptide"
source                    1..9
                          mol_type = protein
                          organism = synthetic construct
SEQUENCE: 303
QQWSSNPLT                                                        9

SEQ ID NO: 304            moltype = AA  length = 106
FEATURE                   Location/Qualifiers
REGION                    1..106
                          note = source = /note="Description of Artificial Sequence:
                           Synthetic polypeptide"
source                    1..106
                          mol_type = protein
                          organism = synthetic construct
SEQUENCE: 304
EIVLTQSPAT LSASPGERVT MSCSASSSVI YMHWYQQKPG QAPRRWIYDT SKLASGVPAR  60
FSGSGSGTDY TLTISSMEPE DAAVYYCQQW SSNPLTFGQG TKLEIK                106

SEQ ID NO: 305            moltype = DNA  length = 318
FEATURE                   Location/Qualifiers
misc_feature              1..318
                          note = source = /note="Description of Artificial Sequence:
                           Synthetic polynucleotide"
source                    1..318
                          mol_type = other DNA
                          organism = synthetic construct
SEQUENCE: 305
gagatcgtgc tgacccagtc ccctgccacc ctgtctgcta gccctggcga gcgcgtgaca  60
atgtcctgct ccgcctcctc ctccgtgatc tacatgcact ggtatcagca gaagcccggc  120
caggcccctc ggcggtggat ctacgatacc tccaagctgg cctccggcgt gcccgccaga  180
ttctccggct ctggctctgg caccgactac accctgacca tctccagcat ggaacccgag  240
gacgccgccg tgtactactg ccagcagtgg tcctccaacc ccctgacctt cggccagggc  300
accaagctgg aaatcaag                                                318

SEQ ID NO: 306            moltype = AA  length = 213
FEATURE                   Location/Qualifiers
REGION                    1..213
                          note = source = /note="Description of Artificial Sequence:
                           Synthetic polypeptide"
source                    1..213
                          mol_type = protein
                          organism = synthetic construct
SEQUENCE: 306
EIVLTQSPAT LSASPGERVT MSCSASSSVI YMHWYQQKPG QAPRRWIYDT SKLASGVPAR  60
FSGSGSGTDY TLTISSMEPE DAAVYYCQQW SSNPLTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 307            moltype = DNA  length = 639
FEATURE                   Location/Qualifiers
misc_feature              1..639
                          note = source = /note="Description of Artificial Sequence:
                           Synthetic polynucleotide"
source                    1..639
                          mol_type = other DNA
                          organism = synthetic construct
SEQUENCE: 307
gagatcgtgc tgacccagtc ccctgccacc ctgtctgcta gccctggcga gcgcgtgaca  60
atgtcctgct ccgcctcctc ctccgtgatc tacatgcact ggtatcagca gaagcccggc  120
caggcccctc ggcggtggat ctacgatacc tccaagctgg cctccggcgt gcccgccaga  180
ttctccggct ctggctctgg caccgactac accctgacca tctccagcat ggaacccgag  240
gacgccgccg tgtactactg ccagcagtgg tcctccaacc ccctgacctt cggccagggc  300
accaagctgg aaatcaagcg tacggtggcc gctcccagcg tgttcatctt cccccccagc  360
```

-continued

```
gacgagcagc tgaagagtgg caccgccagc gtggtgtgcc tgctgaacaa cttctacccc  420
cgggaggcca aggtgcagtg gaaggtggac aacgccctgc agagcggcaa cagccaggag  480
agcgtcaccg agcaggacag caaggactcc acctacagcc tgagcagcac cctgaccctg  540
agcaaggccg actacgagaa gcataaggtg tacgcctgcg aggtgaccca ccagggcctg  600
tccagccccg tgaccaagag cttcaacagg ggcgagtgc                         639

SEQ ID NO: 308          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 308
GFTFSTYAMS                                                          10

SEQ ID NO: 309          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 309
TISDAGSYSY YPDNVKG                                                  17

SEQ ID NO: 310          moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 310
RGSRYEEYYV MDY                                                      13

SEQ ID NO: 311          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 311
TYAMS                                                               5

SEQ ID NO: 312          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 312
TISDAGSYSY YPDNVKG                                                  17

SEQ ID NO: 313          moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 313
RGSRYEEYYV MDY                                                      13

SEQ ID NO: 314          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
```

```
                         organism = synthetic construct
SEQUENCE: 314
GFTFSTY                                                                 7

SEQ ID NO: 315           moltype = AA  length = 6
FEATURE                  Location/Qualifiers
REGION                   1..6
                         note = source = /note="Description of Artificial Sequence:
                          Synthetic peptide"
source                   1..6
                         mol_type = protein
                         organism = synthetic construct
SEQUENCE: 315
SDAGSY                                                                  6

SEQ ID NO: 316           moltype = AA  length = 13
FEATURE                  Location/Qualifiers
REGION                   1..13
                         note = source = /note="Description of Artificial Sequence:
                          Synthetic peptide"
source                   1..13
                         mol_type = protein
                         organism = synthetic construct
SEQUENCE: 316
RGSRYEEYYV MDY                                                          13

SEQ ID NO: 317           moltype = AA  length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 317
GFTFSTYA                                                                8

SEQ ID NO: 318           moltype = AA  length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 318
ISDAGSYS                                                                8

SEQ ID NO: 319           moltype = AA  length = 15
FEATURE                  Location/Qualifiers
REGION                   1..15
                         note = source = /note="Description of Artificial Sequence:
                          Synthetic peptide"
source                   1..15
                         mol_type = protein
                         organism = synthetic construct
SEQUENCE: 319
ARRGSRYEEY YVMDY                                                        15

SEQ ID NO: 320           moltype = AA  length = 122
FEATURE                  Location/Qualifiers
REGION                   1..122
                         note = source = /note="Description of Artificial Sequence:
                          Synthetic polypeptide"
source                   1..122
                         mol_type = protein
                         organism = synthetic construct
SEQUENCE: 320
EVQLVESGGG LVKPGGSLKL SCAASGFTFS TYAMSWVRQT PEKRLEWVAT ISDGGSYSYY  60
PDNVKGRFTI SRDNAKNNLY LQMSHLKSED TAMYYCARRG SRYEEYYVMD YWGQGTSVTV  120
SS                                                                 122

SEQ ID NO: 321           moltype = DNA  length = 366
FEATURE                  Location/Qualifiers
misc_feature             1..366
                         note = source = /note="Description of Artificial Sequence:
                          Synthetic polynucleotide"
source                   1..366
                         mol_type = other DNA
```

```
                         organism = synthetic construct
SEQUENCE: 321
gaagtgcagc tggtggagtc tgggggaggc ttagtgaagc ctggagggtc cctgaaactc  60
tcctgtgcag cctctggatt cactttcagt acctatgcca tgtcttgggt tcgccagact  120
ccggaaaaga ggctggagtg ggtcgcaacc attagtgatg gtggtagtta ttcgtactat  180
ccagacaatg taaagggccg attcaccatc tccagagaca atgccaagaa caacctatac  240
ctgcaaatga gccatctgaa gtctgaggac acagccatgt attactgtgc aagacgaggt  300
agtaggtacg aagagtacta tgttatggac tactggggtc aaggaacctc agtcaccgtc  360
tcctca                                                            366

SEQ ID NO: 322          moltype = AA  length = 452
FEATURE                 Location/Qualifiers
REGION                  1..452
                        note = source = /note="Description of Artificial Sequence:
                         Synthetic polypeptide"
source                  1..452
                        mol_type = protein
                        organism = synthetic construct
SEQUENCE: 322
EVQLVESGGG LVKPGGSLKL SCAASGFTFS TYAMSWVRQT PEKRLEWVAT ISDGGSYSYY  60
PDNVKGRFTI SRDNAKNNLY LQMSHLKSED TAMYYCARRG SRYEEYYVMD YWGQGTSVTV  120
SSASTKGPSV FPLAPSSKST SGGTAALGCL VKDYFPCPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPC DIAVEWESNG QPENNYKTTP PVLDSDGSFF LYSKLTVDKS  420
RWQQGNVFSC SVMHEALHNH YTQKSLSLSP GK                                452

SEQ ID NO: 323          moltype = DNA  length = 1356
FEATURE                 Location/Qualifiers
misc_feature            1..1356
                        note = source = /note="Description of Artificial Sequence:
                         Synthetic polynucleotide"
source                  1..1356
                        mol_type = other DNA
                        organism = synthetic construct
SEQUENCE: 323
gaagtgcagc tggtggagtc tgggggaggc ttagtgaagc ctggagggtc cctgaaactc  60
tcctgtgcag cctctggatt cactttcagt acctatgcca tgtcttgggt tcgccagact  120
ccggaaaaga ggctggagtg ggtcgcaacc attagtgatg gtggtagtta ttcgtactat  180
ccagacaatg taaagggccg attcaccatc tccagagaca atgccaagaa caacctatac  240
ctgcaaatga gccatctgaa gtctgaggac acagccatgt attactgtgc aagacgaggt  300
agtaggtacg aagagtacta tgttatggac tactggggtc aaggaacctc agtcaccgtc  360
tcctcagcta gcaccaaggg cccaagtgtg tttcccctgg cccccagcag caagtctact  420
tccggcggaa ctgctgccct gggttgcctg gtgaaggact acttcccctg tcccgtgaca  480
gtgtcctgga actctggggc tctgacttcc ggcgtgcaca ccttccccgc cgtgctgcag  540
agcagcggcc tgtacagcct gagcagcgtg gtgacagtgc cctccagctc tctgggaacc  600
cagacctata tctgcaacgt gaaccacaag cccagcaaca ccaaggtgga caagagagtg  660
gagcccaaga gctgcgacaa gacccacacc tgcccccct gcccagctcc agaactgctg  720
ggagggcctt ccgtgttcct gttcccccc aagcccaagg acaccctgat gatcagcagg  780
acccccgagg tgacctgcgt ggtggtggac gtgtcccacg aggacccaga ggtgaagttc  840
aactggtacg tggacggcgt ggaggtgcac aacgccaaga ccaagcccag agaggagcag  900
tacaacagca cctacagggt ggtgtccgtg ctgaccgtgc tgcaccagga ctggctgaac  960
ggcaaagaat acaagtgcaa agtctccaac aaggccctgc cagccccaat cgaaaagaca  1020
atcagcaagg ccaagggcca gccacgggag ccccaggtgt acaccctgcc ccccagccgg  1080
gaggagatga ccaagaacca ggtgtccctg acctgtctgg tgaagggctt ctacccctgt  1140
gatatcgccg tggagtggga gagcaacggc cagcccgaga acaactacaa gaccaccccc  1200
ccagtgctgg acagcgacgg cagcttcttc ctgtacagca agctgaccgt ggacaagtcc  1260
aggtggcagc agggcaacgt gttcagctgc agcgtgatgc acgaggccct gcacaaccac  1320
tacacccaga agtccctgag cctgagcccc ggcaag                           1356

SEQ ID NO: 324          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 324
RASQSISNNL H                                                       11

SEQ ID NO: 325          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
```

```
                        organism = synthetic construct
SEQUENCE: 325
YASQSIS                                                                    7

SEQ ID NO: 326          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 326
QQSSSWLT                                                                   8

SEQ ID NO: 327          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 327
RASQSISNNL H                                                               11

SEQ ID NO: 328          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 328
YASQSIS                                                                    7

SEQ ID NO: 329          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 329
QQSSSWLT                                                                   8

SEQ ID NO: 330          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 330
SQSISNN                                                                    7

SEQ ID NO: 331          moltype =   length =
SEQUENCE: 331
000

SEQ ID NO: 332          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 332
SSSWL                                                                      5

SEQ ID NO: 333          moltype = AA  length = 6
FEATURE                 Location/Qualifiers
REGION                  1..6
                        note = source = /note="Description of Artificial Sequence:
                         Synthetic peptide"
```

```
source                  1..6
                        mol_type = protein
                        organism = synthetic construct
SEQUENCE: 333
QSISNN                                                                6

SEQ ID NO: 334          moltype =   length =
SEQUENCE: 334
000

SEQ ID NO: 335          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 335
QQSSSWLT                                                              8

SEQ ID NO: 336          moltype = AA  length = 106
FEATURE                 Location/Qualifiers
REGION                  1..106
                        note = source = /note="Description of Artificial Sequence:
                         Synthetic polypeptide"
source                  1..106
                        mol_type = protein
                        organism = synthetic construct
SEQUENCE: 336
DIVLTQSPAT LSVTPGDSVS LSCRASQSIS NNLHWYQQKS HESPKLLIKY ASQSISGIPS  60
RFSGSGSGTD FTLSINSVET EDFGMYFCQQ SNSWLTFGAG TKLGLK                106

SEQ ID NO: 337          moltype = DNA  length = 318
FEATURE                 Location/Qualifiers
misc_feature            1..318
                        note = source = /note="Description of Artificial Sequence:
                         Synthetic polynucleotide"
source                  1..318
                        mol_type = other DNA
                        organism = synthetic construct
SEQUENCE: 337
gatattgtgc taactcagtc tccagccacc ctgtctgtga ctccaggaga tagcgtcagt  60
ctttcctgca gggccagcca aagtattagc aacaacctac actggtatca acagaaatca  120
catgagtctc caaaacttct catcaagtat gcttcccagt ccatctctgg gatcccctcc  180
aggttcagtg gcagtggatc agggacagat ttcactctca gtatcaacag tgtggagact  240
gaagattttg gaatgtattt ctgtcaacag agtaacagct ggctcacgtt cggtgctggg  300
accaagctgg ggctgaaa                                               318

SEQ ID NO: 338          moltype = AA  length = 213
FEATURE                 Location/Qualifiers
REGION                  1..213
                        note = source = /note="Description of Artificial Sequence:
                         Synthetic polypeptide"
source                  1..213
                        mol_type = protein
                        organism = synthetic construct
SEQUENCE: 338
DIVLTQSPAT LSVTPGDSVS LSCRASQSIS NNLHWYQQKS HESPKLLIKY ASQSISGIPS  60
RFSGSGSGTD FTLSINSVET EDFGMYFCQQ SNSWLTFGAG TKLGLKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 339          moltype = DNA  length = 639
FEATURE                 Location/Qualifiers
misc_feature            1..639
                        note = source = /note="Description of Artificial Sequence:
                         Synthetic polynucleotide"
source                  1..639
                        mol_type = other DNA
                        organism = synthetic construct
SEQUENCE: 339
gatattgtgc taactcagtc tccagccacc ctgtctgtga ctccaggaga tagcgtcagt  60
ctttcctgca gggccagcca aagtattagc aacaacctac actggtatca acagaaatca  120
catgagtctc caaaacttct catcaagtat gcttcccagt ccatctctgg gatcccctcc  180
aggttcagtg gcagtggatc agggacagat ttcactctca gtatcaacag tgtggagact  240
gaagattttg gaatgtattt ctgtcaacag agtaacagct ggctcacgtt cggtgctggg  300
accaagctgg ggctgaaacg tacggtggcc gctcccagcg tgttcatctt cccccccagc  360
gacgagcagc tgaagagtgg caccgccagc gtggtgtgcc tgctgaacaa cttctacccc  420
```

```
cgggaggcca aggtgcagtg gaaggtggac aacgccctgc agagcggcaa cagccaggag  480
agcgtcaccg agcaggacag caaggactcc acctacagcc tgagcagcac cctgaccctg  540
agcaaggccg actacgagaa gcataaggtg tacgcctgcg aggtgaccca ccagggcctg  600
tccagccccg tgaccaagag cttcaacagg ggcgagtgc                         639

SEQ ID NO: 340         moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 340
GFTFSTYAMS                                                         10

SEQ ID NO: 341         moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 341
TISDAGSYSY YPDNVKG                                                 17

SEQ ID NO: 342         moltype = AA  length = 13
FEATURE                Location/Qualifiers
REGION                 1..13
                       note = source = /note="Description of Artificial Sequence:
                        Synthetic peptide"
source                 1..13
                       mol_type = protein
                       organism = synthetic construct
SEQUENCE: 342
RGSRYEEYYV MDY                                                     13

SEQ ID NO: 343         moltype = AA  length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 343
TYAMS                                                              5

SEQ ID NO: 344         moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 344
TISDAGSYSY YPDNVKG                                                 17

SEQ ID NO: 345         moltype = AA  length = 13
FEATURE                Location/Qualifiers
REGION                 1..13
                       note = source = /note="Description of Artificial Sequence:
                        Synthetic peptide"
source                 1..13
                       mol_type = protein
                       organism = synthetic construct
SEQUENCE: 345
RGSRYEEYYV MDY                                                     13

SEQ ID NO: 346         moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
```

```
SEQUENCE: 346
GFTFSTY                                                        7

SEQ ID NO: 347          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 347
SDAGSY                                                         6

SEQ ID NO: 348          moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 348
RGSRYEEYYV MDY                                                 13

SEQ ID NO: 349          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 349
GFTFSTYA                                                       8

SEQ ID NO: 350          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 350
ISDAGSYS                                                       8

SEQ ID NO: 351          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 351
ARRGSRYEEY YVMDY                                               15

SEQ ID NO: 352          moltype = AA  length = 122
FEATURE                 Location/Qualifiers
REGION                  1..122
                        note = source = /note="Description of Artificial Sequence:
                         Synthetic polypeptide"
source                  1..122
                        mol_type = protein
                        organism = synthetic construct
SEQUENCE: 352
EVQLVESGGG LVKPGGSLRL SCAASGFTFS TYAMSWVRQA PGKGLEWVAT ISDAGSYSYY  60
PDNVKGRFTI SRDNAKNSLY LQMNSLRAED TAVYYCARRG SRYEEYYVMD YWGQGTTVTV  120
SS                                                             122

SEQ ID NO: 353          moltype = DNA  length = 366
FEATURE                 Location/Qualifiers
misc_feature            1..366
                        note = source = /note="Description of Artificial Sequence:
                         Synthetic polynucleotide"
source                  1..366
                        mol_type = other DNA
                        organism = synthetic construct
```

```
SEQUENCE: 353
gaggtgcagc tggtggaatc tggcggaggc ctggtgaaac ccggcggatc cctgagactg  60
tcctgcgccg cctccggctt caccttctcc acctacgcca tgtcctgggt gcggcaggct  120
cccggcaagg gcctggaatg ggtggccacc atctccgacg ccggctccta ctcctactac  180
cccgacaacg tgaagggcag attcaccatc agccgggaca acgccaagaa ctccctgtac  240
ctgcagatga actccctgcg ggccgaggac accgccgtgt actactgtgc cagacggggc  300
tccagatacg aagagtacta cgtgatggac tattggggcc agggcaccac cgtgacagtg  360
tcctcc                                                             366

SEQ ID NO: 354         moltype = AA  length = 452
FEATURE                Location/Qualifiers
REGION                 1..452
                       note = source = /note="Description of Artificial Sequence:
                        Synthetic polypeptide"
source                 1..452
                       mol_type = protein
                       organism = synthetic construct
SEQUENCE: 354
EVQLVESGGG LVKPGGSLRL SCAASGFTFS TYAMSWVRQA PGKGLEWVAT ISDAGSYSYY  60
PDNVKGRFTI SRDNAKNSLY LQMNSLRAED TAVYYCARRG SRYEEYYVMD YWGQGTTVTV  120
SSASTKGPSV FPLAPSSKST SGGTAALGCL VKDYFPCPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLMISR TPEVTCVVVA VSHEDPEVKF NWYVDGVEVH NAKTKPREEQ  300
YNSTYRVVSV LTVLHQDWLN GKEYKCKVSN KALAAPIEKT ISKAKGQPRE PQVYTLPPSR  360
EEMTKNQVSL TCLVKGFYPC DIAVEWESNG QPENNYKTTP PVLDSDGSFF LYSKLTVDKS  420
RWQQGNVFSC SVMHEALHNH YTQKSLSLSP GK                                452

SEQ ID NO: 355         moltype = DNA  length = 1356
FEATURE                Location/Qualifiers
misc_feature           1..1356
                       note = source = /note="Description of Artificial Sequence:
                        Synthetic polynucleotide"
source                 1..1356
                       mol_type = other DNA
                       organism = synthetic construct
SEQUENCE: 355
gaggtgcagc tggtggaatc tggcggaggc ctggtgaaac ccggcggatc cctgagactg  60
tcctgcgccg cctccggctt caccttctcc acctacgcca tgtcctgggt gcggcaggct  120
cccggcaagg gcctggaatg ggtggccacc atctccgacg ccggctccta ctcctactac  180
cccgacaacg tgaagggcag attcaccatc agccgggaca acgccaagaa ctccctgtac  240
ctgcagatga actccctgcg ggccgaggac accgccgtgt actactgtgc cagacggggc  300
tccagatacg aagagtacta cgtgatggac tattggggcc agggcaccac cgtgacagtg  360
tcctccgcta gcaccaaggg cccaagtgtg tttcccctgg cccccagcag caagtctact  420
tccggcggaa ctgctgccct gggttgcctg gtgaaggact acttcccctg tcccgtgaca  480
gtgtcctgga actctggggc tctgacttcc ggcgtgcaca ccttccccgc cgtgctgcag  540
agcagcggcc tgtacagcct gagcagcgtg gtgacagtgc cctccagctc tctgggaacc  600
cagacctata tctgcaacgt gaaccacaag cccagcaaca ccaaggtgga caagagagtg  660
gagcccaaga gctgcgacaa gacccacacc tgccccccct gcccagctcc agaactgctg  720
ggagggcctt ccgtgttcct gttcccccc aagcccaagg acaccctgat gatcagcagg  780
acccccgagg tgacctgcgt ggtggtggcc gtgtcccacg aggacccaga ggtgaagttc  840
aactggtacg tggacggcgt ggaggtgcac aacgccaaga ccaagcccag agaggagcag  900
tacaacagca cctacagggt ggtgtccgtg ctgaccgtgc tgcaccagga ctggctgaac  960
ggcaaagaat acaagtgcaa agtctccaac aaggccctgg ctgccccaat cgaaaagaca  1020
atcagcaagg ccaagggcca gccacgggag ccccaggtgt acaccctgcc ccccagccgg  1080
gaggagatga ccaagaacca ggtgtccctg acctgtctgg tgaagggctt ctacccctgt  1140
gatatcgccg tggagtggga gagcaacggc cagcccgaga acaactacaa gaccaccccc  1200
ccagtgctgg acagcgacgg cagcttcttc ctgtacagca agctgaccgt ggacaagtcc  1260
aggtggcagc agggcaacgt gttcagctgc agcgtgatgc acgaggccct gcacaaccac  1320
tacacccaga agtccctgag cctgagcccc ggcaag                             1356

SEQ ID NO: 356         moltype = AA  length = 11
FEATURE                Location/Qualifiers
REGION                 1..11
                       note = source = /note="Description of Artificial Sequence:
                        Synthetic peptide"
source                 1..11
                       mol_type = protein
                       organism = synthetic construct
SEQUENCE: 356
RASQSISNNL H                                                       11

SEQ ID NO: 357         moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
```

```
SEQUENCE: 357
YASQSIS                                                    7

SEQ ID NO: 358          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 358
QQSSSWLT                                                   8

SEQ ID NO: 359          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 359
RASQSISNNL H                                               11

SEQ ID NO: 360          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 360
YASQSIS                                                    7

SEQ ID NO: 361          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 361
QQSSSWLT                                                   8

SEQ ID NO: 362          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 362
SQSISNN                                                    7

SEQ ID NO: 363          moltype =   length =
SEQUENCE: 363
000

SEQ ID NO: 364          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 364
SSSWL                                                      5

SEQ ID NO: 365          moltype = AA  length = 6
FEATURE                 Location/Qualifiers
REGION                  1..6
                        note = source = /note="Description of Artificial Sequence:
                         Synthetic peptide"
source                  1..6
```

```
                        mol_type = protein
                        organism = synthetic construct
SEQUENCE: 365
QSISNN                                                     6

SEQ ID NO: 366          moltype =   length =
SEQUENCE: 366
000

SEQ ID NO: 367          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 367
QQSSSWLT                                                   8

SEQ ID NO: 368          moltype = AA  length = 106
FEATURE                 Location/Qualifiers
REGION                  1..106
                        note = source = /note="Description of Artificial Sequence:
                         Synthetic polypeptide"
source                  1..106
                        mol_type = protein
                        organism = synthetic construct
SEQUENCE: 368
EIVLTQSPAT LSVSPGERVT LSCRASQSIS NNLHWYQQKP GQAPRLLIKY ASQSISGIPA  60
RFSGSGSGTD FTLTISSVEP EDFGVYFCQQ SSSWLTFGQG TKLEIK                 106

SEQ ID NO: 369          moltype = DNA  length = 318
FEATURE                 Location/Qualifiers
misc_feature            1..318
                        note = source = /note="Description of Artificial Sequence:
                         Synthetic polynucleotide"
source                  1..318
                        mol_type = other DNA
                        organism = synthetic construct
SEQUENCE: 369
gagatcgtgc tgacccagtc ccctgccacc ctgtccgtgt ctcccggcga gagagtgacc  60
ctgtcctgcc gggcctccca gtccatctcc aacaacctgc actggtatca gcagaagccc  120
ggccaggccc ctcggctgct gattaagtac gcctcccaga gcatctccgg catccctgcc  180
agattctccg gctccggcag cggcaccgac ttcaccctga ccatctccag cgtggaaccc  240
gaggacttcg gcgtgtactt ctgccagcag tcctcatcct ggctgacctt cggccagggc  300
accaagctgg aaatcaag                                                318

SEQ ID NO: 370          moltype = AA  length = 213
FEATURE                 Location/Qualifiers
REGION                  1..213
                        note = source = /note="Description of Artificial Sequence:
                         Synthetic polypeptide"
source                  1..213
                        mol_type = protein
                        organism = synthetic construct
SEQUENCE: 370
EIVLTQSPAT LSVSPGERVT LSCRASQSIS NNLHWYQQKP GQAPRLLIKY ASQSISGIPA  60
RFSGSGSGTD FTLTISSVEP EDFGVYFCQQ SSSWLTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 371          moltype = DNA  length = 639
FEATURE                 Location/Qualifiers
misc_feature            1..639
                        note = source = /note="Description of Artificial Sequence:
                         Synthetic polynucleotide"
source                  1..639
                        mol_type = other DNA
                        organism = synthetic construct
SEQUENCE: 371
gagatcgtgc tgacccagtc ccctgccacc ctgtccgtgt ctcccggcga gagagtgacc  60
ctgtcctgcc gggcctccca gtccatctcc aacaacctgc actggtatca gcagaagccc  120
ggccaggccc ctcggctgct gattaagtac gcctcccaga gcatctccgg catccctgcc  180
agattctccg gctccggcag cggcaccgac ttcaccctga ccatctccag cgtggaaccc  240
gaggacttcg gcgtgtactt ctgccagcag tcctcatcct ggctgacctt cggccagggc  300
accaagctgg aaatcaagcg tacggtggcc gctcccagcg tgttcatctt cccccccagc  360
gacgagcagc tgaagagtgg caccgccagc gtggtgtgcc tgctgaacaa cttctacccc  420
cgggaggcca aggtgcagtg gaaggtggac aacgccctgc agagcggcaa cagccaggag  480
```

-continued

```
agcgtcaccg agcaggacag caaggactcc acctacagcc tgagcagcac cctgaccctg  540
agcaaggccg actacgagaa gcataaggtg tacgcctgcg aggtgaccca ccagggcctg  600
tccagccccg tgaccaagag cttcaacagg ggcgagtgc                         639

SEQ ID NO: 372         moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 372
GFTFSSYAMS                                                         10

SEQ ID NO: 373         moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 373
TISSGGSFTY YPDSVKG                                                 17

SEQ ID NO: 374         moltype = AA  length = 12
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 374
RASTVVGTDF DV                                                      12

SEQ ID NO: 375         moltype = AA  length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 375
SYAMS                                                              5

SEQ ID NO: 376         moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 376
TISSGGSFTY YPDSVKG                                                 17

SEQ ID NO: 377         moltype = AA  length = 12
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 377
RASTVVGTDF DV                                                      12

SEQ ID NO: 378         moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 378
```

```
GFTFSSY                                                      7

SEQ ID NO: 379          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 379
SSGGSF                                                       6

SEQ ID NO: 380          moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 380
RASTVVGTDF DV                                                12

SEQ ID NO: 381          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 381
GFTFSSYA                                                     8

SEQ ID NO: 382          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 382
ISSGGSFT                                                     8

SEQ ID NO: 383          moltype = AA  length = 14
FEATURE                 Location/Qualifiers
REGION                  1..14
                        note = source = /note="Description of Artificial Sequence:
                         Synthetic peptide"
source                  1..14
                        mol_type = protein
                        organism = synthetic construct
SEQUENCE: 383
ARRASTVVGT DFDV                                              14

SEQ ID NO: 384          moltype = AA  length = 121
FEATURE                 Location/Qualifiers
REGION                  1..121
                        note = source = /note="Description of Artificial Sequence:
                         Synthetic polypeptide"
source                  1..121
                        mol_type = protein
                        organism = synthetic construct
SEQUENCE: 384
EVMLVESGGG LVKPGGSLKL SCAASGFTFS SYAMSWIRQT PEKRLEWVAT ISSGGSFTYY  60
PDSVKGRFTI SRDNVKNTLY LQMSSLRSED TAMYYCARRA STVVGTDFDV WGAGTTVTVS  120
S                                                            121

SEQ ID NO: 385          moltype = DNA  length = 363
FEATURE                 Location/Qualifiers
misc_feature            1..363
                        note = source = /note="Description of Artificial Sequence:
                         Synthetic polynucleotide"
source                  1..363
                        mol_type = other DNA
                        organism = synthetic construct
SEQUENCE: 385
```

```
gaagtgatgc tggtggagtc tgggggaggc ttagtgaagc ctggagggtc cctgaaactc  60
tcctgtgcag cctctggatt cactttcagt agctatgcca tgtcttggat tcgccagact  120
ccggagaaga gactggagtg ggtcgcaacc atcagtagtg gtggtagttt cacctactat  180
ccagacagtg tgaaggggcg attcaccatt tctagagaca atgtcaagaa caccctgtac  240
ctgcaaatga gcagtctgag gtctgaagac acggccatgt attactgtgc aagacgggct  300
tctacggtag taggtacgga cttcgatgtc tggggcgcag ggaccacggt caccgtctcc  360
tca                                                                363

SEQ ID NO: 386          moltype = AA  length = 451
FEATURE                 Location/Qualifiers
REGION                  1..451
                        note = source = /note="Description of Artificial Sequence:
                         Synthetic polypeptide"
source                  1..451
                        mol_type = protein
                        organism = synthetic construct
SEQUENCE: 386
EVMLVESGGG LVKPGGSLKL SCAASGFTFS SYAMSWIRQT PEKRLEWVAT ISSGGSFTYY  60
PDSVKGRFTI SRDNVKNTLY LQMSSLRSED TAMYYCARRA STVVGTDFDV WGAGTTVTVS  120
SASTKGPSVF PLAPSSKSTS GGTAALGCLV KDYFPCPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPCD IAVEWESNGQ PENNYKTTPP VLDSDGSFFL YSKLTVDKSR  420
WQQGNVFSCS VMHEALHNHY TQKSLSLSPG K                                 451

SEQ ID NO: 387          moltype = DNA  length = 1353
FEATURE                 Location/Qualifiers
misc_feature            1..1353
                        note = source = /note="Description of Artificial Sequence:
                         Synthetic polynucleotide"
source                  1..1353
                        mol_type = other DNA
                        organism = synthetic construct
SEQUENCE: 387
gaagtgatgc tggtggagtc tgggggaggc ttagtgaagc ctggagggtc cctgaaactc  60
tcctgtgcag cctctggatt cactttcagt agctatgcca tgtcttggat tcgccagact  120
ccggagaaga gactggagtg ggtcgcaacc atcagtagtg gtggtagttt cacctactat  180
ccagacagtg tgaaggggcg attcaccatt tctagagaca atgtcaagaa caccctgtac  240
ctgcaaatga gcagtctgag gtctgaagac acggccatgt attactgtgc aagacgggct  300
tctacggtag taggtacgga cttcgatgtc tggggcgcag ggaccacggt caccgtctcc  360
tcagctagca ccaagggccc aagtgtgttt cccctggccc ccagcagcaa gtctacttcc  420
ggcggaactg ctgccctggg ttgcctggtg aaggactact tcccctgtcc cgtgacagtg  480
tcctggaact ctggggctct gacttccggc gtgcacacct tccccgccgt gctgcagagc  540
agcggcctgt acagcctgag cagcgtggtg acagtgccct ccagctctct gggaacccag  600
acctatatct gcaacgtgaa ccacaagccc agcaacacca aggtggacaa gagagtggag  660
cccaagagct gcgacaagac ccacacctgc ccccctgcc cagctccaga actgctggga  720
gggccttccg tgttcctgtt ccccccaag cccaaggaca ccctgatgat cagcaggacc  780
cccgaggtga cctgcgtggt ggtggacgtg tcccacgagg acccagaggt gaagttcaac  840
tggtacgtgg acggcgtgga ggtgcacaac gccaagacca agcccagaga ggagcagtac  900
aacagcacct acagggtggt gtccgtgctg accgtgctgc accaggactg gctgaacggc  960
aaagaataca agtgcaaagt ctccaacaag gccctgccag ccccaatcga aaagacaatc  1020
agcaaggcca agggccagcc acgggagccc caggtgtaca ccctgccccc cagccgggag  1080
gagatgacca agaaccaggt gtccctgacc tgtctggtga agggcttcta cccctgtgat  1140
atcgccgtgg agtgggagag caacggccag cccgagaaca actacaagac cacccccca  1200
gtgctggaca gcgacggcag cttcttcctg tacagcaagc tgaccgtgga caagtccagg  1260
tggcagcagg gcaacgtgtt cagctgcagc gtgatgcacg aggccctgca caaccactac  1320
acccagaagt ccctgagcct gagccccggc aag                               1353

SEQ ID NO: 388          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 388
RASQDIGSSL N                                                       11

SEQ ID NO: 389          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 389
```

```
ATSSLDS                                                    7

SEQ ID NO: 390          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 390
LQYASSPPT                                                  9

SEQ ID NO: 391          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 391
RASQDIGSSL N                                               11

SEQ ID NO: 392          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 392
ATSSLDS                                                    7

SEQ ID NO: 393          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 393
LQYASSPPT                                                  9

SEQ ID NO: 394          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 394
SQDIGSS                                                    7

SEQ ID NO: 395          moltype =   length =
SEQUENCE: 395
000

SEQ ID NO: 396          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 396
YASSPP                                                     6

SEQ ID NO: 397          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
```

```
                        organism = synthetic construct
SEQUENCE: 397
QDIGSS                                                        6

SEQ ID NO: 398          moltype =   length =
SEQUENCE: 398
000

SEQ ID NO: 399          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 399
LQYASSPPT                                                     9

SEQ ID NO: 400          moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 400
DIQMTQSPSS LSASLGERVS LTCRASQDIG SSLNWLQQEP DGTIKRLIYA TSSLDSGVPK  60
RFSGSRSGSD YSLTISSLES EDFVVYYCLQ YASSPPTFGG GTKLEIK                107

SEQ ID NO: 401          moltype = DNA  length = 321
FEATURE                 Location/Qualifiers
misc_feature            1..321
                        note = source = /note="Description of Artificial Sequence:
                         Synthetic polynucleotide"
source                  1..321
                        mol_type = other DNA
                        organism = synthetic construct
SEQUENCE: 401
gacatccaga tgacccagtc tccatcctcc ttatctgcct ctctgggaga aagagtcagt  60
ctcacttgtc gggcaagtca ggacattggt agtagcttaa actggcttca gcaggaacca  120
gatggaacta ttaaacgcct gatctatgcc acatccagtt tagattctgg tgtccccaaa  180
aggttcagtg gcagtaggtc tgggtcagat tattctctca ccatcagcag ccttgagtct  240
gaagattttg tagtctatta ctgtctacaa tatgctagtt cgcctccgac gttcggtgga  300
ggcaccaagc tggaaatcaa a                                            321

SEQ ID NO: 402          moltype = AA  length = 214
FEATURE                 Location/Qualifiers
REGION                  1..214
                        note = source = /note="Description of Artificial Sequence:
                         Synthetic polypeptide"
source                  1..214
                        mol_type = protein
                        organism = synthetic construct
SEQUENCE: 402
DIQMTQSPSS LSASLGERVS LTCRASQDIG SSLNWLQQEP DGTIKRLIYA TSSLDSGVPK  60
RFSGSRSGSD YSLTISSLES EDFVVYYCLQ YASSPPTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 403          moltype = DNA  length = 642
FEATURE                 Location/Qualifiers
misc_feature            1..642
                        note = source = /note="Description of Artificial Sequence:
                         Synthetic polynucleotide"
source                  1..642
                        mol_type = other DNA
                        organism = synthetic construct
SEQUENCE: 403
gacatccaga tgacccagtc tccatcctcc ttatctgcct ctctgggaga aagagtcagt  60
ctcacttgtc gggcaagtca ggacattggt agtagcttaa actggcttca gcaggaacca  120
gatggaacta ttaaacgcct gatctatgcc acatccagtt tagattctgg tgtccccaaa  180
aggttcagtg gcagtaggtc tgggtcagat tattctctca ccatcagcag ccttgagtct  240
gaagattttg tagtctatta ctgtctacaa tatgctagtt cgcctccgac gttcggtgga  300
ggcaccaagc tggaaatcaa acgtacggtg gccgctccca gcgtgttcat cttccccccc  360
agcgacgagc agctgaagag tggcaccgcc agcgtggtgt gcctgctgaa caacttctac  420
ccccgggagg ccaaggtgca gtggaaggtg gacaacgccc tgcagagcgg caacagccag  480
gagagcgtca ccgagcagga cagcaaggac tccacctaca gcctgagcag caccctgacc  540
```

```
ctgagcaagg ccgactacga gaagcataag gtgtacgcct gcgaggtgac ccaccagggc  600
ctgtccagcc ccgtgaccaa gagcttcaac aggggcgagt gc                     642

SEQ ID NO: 404         moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 404
GFTFSSYAMS                                                         10

SEQ ID NO: 405         moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 405
TISSGGSFTY YPDSVKG                                                 17

SEQ ID NO: 406         moltype = AA  length = 12
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 406
RASTVVGTDF DV                                                      12

SEQ ID NO: 407         moltype = AA  length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 407
SYAMS                                                              5

SEQ ID NO: 408         moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 408
TISSGGSFTY YPDSVKG                                                 17

SEQ ID NO: 409         moltype = AA  length = 12
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 409
RASTVVGTDF DV                                                      12

SEQ ID NO: 410         moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 410
GFTFSSY                                                            7
```

```
SEQ ID NO: 411          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 411
SSGGSF                                                                      6

SEQ ID NO: 412          moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 412
RASTVVGTDF DV                                                               12

SEQ ID NO: 413          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 413
GFTFSSYA                                                                    8

SEQ ID NO: 414          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 414
ISSGGSFT                                                                    8

SEQ ID NO: 415          moltype = AA  length = 14
FEATURE                 Location/Qualifiers
REGION                  1..14
                        note = source = /note="Description of Artificial Sequence:
                         Synthetic peptide"
source                  1..14
                        mol_type = protein
                        organism = synthetic construct
SEQUENCE: 415
ARRASTVVGT DFDV                                                             14

SEQ ID NO: 416          moltype = AA  length = 121
FEATURE                 Location/Qualifiers
REGION                  1..121
                        note = source = /note="Description of Artificial Sequence:
                         Synthetic polypeptide"
source                  1..121
                        mol_type = protein
                        organism = synthetic construct
SEQUENCE: 416
EVQLVESGGG LVKPGGSLRL SCAASGFTFS SYAMSWIRQA PGKGLEWVAT ISSGGSFTYY  60
PDSVKGRFTI SRDNAKNSLY LQMNSLRAED TAVYYCARRA STVVGTDFDV WGQGTTVTVS  120
S                                                                   121

SEQ ID NO: 417          moltype = DNA  length = 363
FEATURE                 Location/Qualifiers
misc_feature            1..363
                        note = source = /note="Description of Artificial Sequence:
                         Synthetic polynucleotide"
source                  1..363
                        mol_type = other DNA
                        organism = synthetic construct
SEQUENCE: 417
gaggtgcagc tggtggaatc tggcggaggc ctggtgaaac ccggcggatc cctgagactg  60
```

```
tcctgcgccg cctccggctt caccttctcc agctacgcca tgtcctggat ccggcaggct  120
cccggcaagg gcctggaatg ggtggccacc atctcctccg gcggcagctt cacctactac  180
cccgacagcg tgaagggcag attcaccatc agccgggaca acgccaagaa ctccctgtac  240
ctgcagatga actccctgcg ggccgaggac accgccgtgt actactgtgc cagacgggcc  300
tccaccgtcg tgggaaccga cttcgatgtg tggggccagg gcaccaccgt gacagtgtcc  360
tcc                                                               363

SEQ ID NO: 418         moltype = AA  length = 451
FEATURE                Location/Qualifiers
REGION                 1..451
                       note = source = /note="Description of Artificial Sequence:
                        Synthetic polypeptide"
source                 1..451
                       mol_type = protein
                       organism = synthetic construct
SEQUENCE: 418
EVQLVESGGG LVKPGGSLRL SCAASGFTFS SYAMSWIRQA PGKGLEWVAT ISSGGSFTYY  60
PDSVKGRFTI SRDNAKNSLY LQMNSLRAED TAVYYCARRA STVVGTDFDV WGQGTTVTVS  120
SASTKGPSVF PLAPSSKSTS GGTAALGCLV KDYFPCPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVAV SHEDPEVKFN WYVDGVEVHN AKTKPREEQY  300
NSTYRVVSVL TVLHQDWLNG KEYKCKVSNK ALAAPIEKTI SKAKGQPREP QVYTLPPSRE  360
EMTKNQVSLT CLVKGFYPCD IAVEWESNGQ PENNYKTTPP VLDSDGSFFL YSKLTVDKSR  420
WQQGNVFSCS VMHEALHNHY TQKSLSLSPG K                                 451

SEQ ID NO: 419         moltype = DNA  length = 1353
FEATURE                Location/Qualifiers
misc_feature           1..1353
                       note = source = /note="Description of Artificial Sequence:
                        Synthetic polynucleotide"
source                 1..1353
                       mol_type = other DNA
                       organism = synthetic construct
SEQUENCE: 419
gaggtgcagc tggtggaatc tggcggaggc ctggtgaaac ccggcggatc cctgagactg  60
tcctgcgccg cctccggctt caccttctcc agctacgcca tgtcctggat ccggcaggct  120
cccggcaagg gcctggaatg ggtggccacc atctcctccg gcggcagctt cacctactac  180
cccgacagcg tgaagggcag attcaccatc agccgggaca acgccaagaa ctccctgtac  240
ctgcagatga actccctgcg ggccgaggac accgccgtgt actactgtgc cagacgggcc  300
tccaccgtcg tgggaaccga cttcgatgtg tggggccagg gcaccaccgt gacagtgtcc  360
tccgctagca ccaagggccc aagtgtgttt cccctggccc ccagcagcaa gtctacttcc  420
ggcggaactg ctgccctggg ttgcctggtg aaggactact tcccctgtcc cgtgacagtg  480
tcctggaact ctggggctct gacttccggc gtgcacacct tccccgccgt gctgcagagc  540
agcggcctgt acagcctgag cagcgtggtg acagtgccct ccagctctct gggaacccag  600
acctatatct gcaacgtgaa ccacaagccc agcaacacca aggtggacaa gagagtggag  660
cccaagagct gcgacaagac ccacacctgc ccccccctgcc cagctccaga actgctggga  720
gggccttccg tgttcctgtt cccccccaag cccaaggaca ccctgatgat cagcaggacc  780
cccgaggtga cctgcgtggt ggtggccgtg tcccacgagg acccagaggt gaagttcaac  840
tggtacgtgg acggcgtgga ggtgcacaac gccaagacca agcccagaga ggagcagtac  900
aacagcacct acagggtggt gtccgtgctg accgtgctgc accaggactg gctgaacggc  960
aaagaataca agtgcaaagt ctccaacaag gccctggctg ccccaatcga aaagacaatc  1020
agcaaggcca agggccagcc acgggagccc caggtgtaca ccctgccccc cagccgggag  1080
gagatgacca agaaccaggt gtccctgacc tgtctggtga agggcttcta cccctgtgat  1140
atcgccgtgg agtgggagag caacggccag cccgagaaca actacaagac caccccccca  1200
gtgctggaca gcgacggcag cttcttcctg tacagcaagc tgaccgtgga caagtccagg  1260
tggcagcagg gcaacgtgtt cagctgcagc gtgatgcacg aggccctgca caaccactac  1320
acccagaagt ccctgagcct gagccccggc aag                              1353

SEQ ID NO: 420         moltype = AA  length = 11
FEATURE                Location/Qualifiers
REGION                 1..11
                       note = source = /note="Description of Artificial Sequence:
                        Synthetic peptide"
source                 1..11
                       mol_type = protein
                       organism = synthetic construct
SEQUENCE: 420
RASQDIGSSL N                                                      11

SEQ ID NO: 421         moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 421
ATSSLDS                                                           7
```

```
SEQ ID NO: 422          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 422
LQYASSPPT                                                                9

SEQ ID NO: 423          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 423
RASQDIGSSL N                                                             11

SEQ ID NO: 424          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 424
ATSSLDS                                                                  7

SEQ ID NO: 425          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 425
LQYASSPPT                                                                9

SEQ ID NO: 426          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 426
SQDIGSS                                                                  7

SEQ ID NO: 427          moltype =   length =
SEQUENCE: 427
000

SEQ ID NO: 428          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 428
YASSPP                                                                   6

SEQ ID NO: 429          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
```

```
SEQUENCE: 429
QDIGSS                                                                      6

SEQ ID NO: 430          moltype =    length =
SEQUENCE: 430
000

SEQ ID NO: 431          moltype = AA   length = 9
FEATURE                 Location/Qualifiers
REGION                  1..9
                        note = source = /note="Description of Artificial Sequence:
                        Synthetic peptide"
source                  1..9
                        mol_type = protein
                        organism = synthetic construct
SEQUENCE: 431
LQYASSPPT                                                                   9

SEQ ID NO: 432          moltype = AA   length = 107
FEATURE                 Location/Qualifiers
REGION                  1..107
                        note = source = /note="Description of Artificial Sequence:
                        Synthetic polypeptide"
source                  1..107
                        mol_type = protein
                        organism = synthetic construct
SEQUENCE: 432
DIQMTQSPSS LSASVGDRVT LTCRASQDIG SSLNWLQQKP GKAIKRLIYA TSSLDSGVPS    60
RFSGSRSGTD YTLTISSLQP EDFVVYYCLQ YASSPPTFGG GTKLEIK                 107

SEQ ID NO: 433          moltype = DNA  length = 321
FEATURE                 Location/Qualifiers
misc_feature            1..321
                        note = source = /note="Description of Artificial Sequence:
                        Synthetic polynucleotide"
source                  1..321
                        mol_type = other DNA
                        organism = synthetic construct
SEQUENCE: 433
gacatccaga tgacccagtc cccctccagc ctgtccgcct ccgtgggcga tagagtgacc    60
ctgacctgcc gggcctccca ggacatcggc tcctccctga actggctgca gcagaagccc   120
ggcaaggcca tcaagcggct gatctacgcc acctcctccc tggactccgg cgtgccctcc   180
cggttctccg gctctagatc cggcaccgac tacaccctga ccatctccag cctgcagccc   240
gaggacttcg tggtgtacta ctgcctgcag tacgcctcca gcccccccac ctttggcgga   300
ggcaccaagc tggaaatcaa g                                             321

SEQ ID NO: 434          moltype = AA   length = 214
FEATURE                 Location/Qualifiers
REGION                  1..214
                        note = source = /note="Description of Artificial Sequence:
                        Synthetic polypeptide"
source                  1..214
                        mol_type = protein
                        organism = synthetic construct
SEQUENCE: 434
DIQMTQSPSS LSASVGDRVT LTCRASQDIG SSLNWLQQKP GKAIKRLIYA TSSLDSGVPS    60
RFSGSRSGTD YTLTISSLQP EDFVVYYCLQ YASSPPTFGG GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 435          moltype = DNA  length = 642
FEATURE                 Location/Qualifiers
misc_feature            1..642
                        note = source = /note="Description of Artificial Sequence:
                        Synthetic polynucleotide"
source                  1..642
                        mol_type = other DNA
                        organism = synthetic construct
SEQUENCE: 435
gacatccaga tgacccagtc cccctccagc ctgtccgcct ccgtgggcga tagagtgacc    60
ctgacctgcc gggcctccca ggacatcggc tcctccctga actggctgca gcagaagccc   120
ggcaaggcca tcaagcggct gatctacgcc acctcctccc tggactccgg cgtgccctcc   180
cggttctccg gctctagatc cggcaccgac tacaccctga ccatctccag cctgcagccc   240
gaggacttcg tggtgtacta ctgcctgcag tacgcctcca gcccccccac ctttggcgga   300
ggcaccaagc tggaaatcaa gcgtacggtg gccgctccca gcgtgttcat cttccccccc   360
agcgacgagc agctgaagag tggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga gaagcataag gtgtacgcct gcgaggtgac ccaccagggc   600
```

```
ctgtccagcc ccgtgaccaa gagcttcaac aggggcgagt gc                  642

SEQ ID NO: 436          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 436
GFTFSNFAMS                                                      10

SEQ ID NO: 437          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 437
TISTGGTYTY YPDSVKG                                              17

SEQ ID NO: 438          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 438
RGYDGVDK                                                        8

SEQ ID NO: 439          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 439
SNFAMS                                                          6

SEQ ID NO: 440          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 440
TISTGGTYTY YPDSVKG                                              17

SEQ ID NO: 441          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 441
RGYDGVDK                                                        8

SEQ ID NO: 442          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 442
GFTFSNF                                                         7
```

```
SEQ ID NO: 443          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 443
STGGTY                                                                      6

SEQ ID NO: 444          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 444
RGYDGVDK                                                                    8

SEQ ID NO: 445          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 445
GFTFSNFA                                                                    8

SEQ ID NO: 446          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 446
ISTGGTYT                                                                    8

SEQ ID NO: 447          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 447
TRRGYDGVDK                                                                  10

SEQ ID NO: 448          moltype = AA  length = 117
FEATURE                 Location/Qualifiers
REGION                  1..117
                        note = source = /note="Description of Artificial Sequence:
                         Synthetic polypeptide"
source                  1..117
                        mol_type = protein
                        organism = synthetic construct
SEQUENCE: 448
EVHLVESGGG LVKPGGSLKL SCAASGFTFS NFAMSWVRQT PEKRLEWVAT ISTGGTYTYY  60
PDSVKGRFTI SRDNAKKTLY LQMSSLRSED TAMYYCTRRG YDGVDKWGQG TTLTVSS     117

SEQ ID NO: 449          moltype = DNA  length = 351
FEATURE                 Location/Qualifiers
misc_feature            1..351
                        note = source = /note="Description of Artificial Sequence:
                         Synthetic polynucleotide"
source                  1..351
                        mol_type = other DNA
                        organism = synthetic construct
SEQUENCE: 449
gaagtgcatc tggtggagtc tgggggaggc ttagtgaagc ctggagggtc cctgaaactc  60
tcctgtgcag cctctggatt cactttcagt aactttgcca tgtcttgggt tcgccagact  120
ccggagaaga gactggagtg ggtcgcaacc attagtactg gtggtactta cacctactat  180
```

-continued

```
ccagacagtg tgaagggtcg attcaccatc tccagagaca atgccaagaa aaccctgtac  240
ctgcaaatga gcagtctgag gtctgaggac acggccatgt attactgtac aagacggggg  300
tacgacggcg tggacaaatg ggccaaggc accactctca cagtctcctc a           351

SEQ ID NO: 450          moltype = AA  length = 447
FEATURE                 Location/Qualifiers
REGION                  1..447
                        note = source = /note="Description of Artificial Sequence:
                         Synthetic polypeptide"
source                  1..447
                        mol_type = protein
                        organism = synthetic construct
SEQUENCE: 450
EVHLVESGGG LVKPGGSLKL SCAASGFTFS NFAMSWVRQT PEKRLEWVAT ISTGGTYTYY  60
PDSVKGRFTI SRDNAKKTLY LQMSSLRSED TAMYYCTRRG YDGVDKWGQG TTLTVSSAST  120
KGPSVFPLAP SSKSTSGGTA ALGCLVKDYF PCPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPCDIAVE WESNGQPENN YKTTPPVLDS DGSFFLYSKL TVDKSRWQQG  420
NVFSCSVMHE ALHNHYTQKS LSLSPGK                                     447

SEQ ID NO: 451          moltype = DNA  length = 1341
FEATURE                 Location/Qualifiers
misc_feature            1..1341
                        note = source = /note="Description of Artificial Sequence:
                         Synthetic polynucleotide"
source                  1..1341
                        mol_type = other DNA
                        organism = synthetic construct
SEQUENCE: 451
gaagtgcatc tggtggagtc tgggggaggc ttagtgaagc ctggagggtc cctgaaactc  60
tcctgtgcag cctctggatt cactttcagt aactttgcca tgtcttgggt tcgccagact  120
ccggagaaga gactggagtg ggtcgcaacc attagtactg gtggtactta cacctactat  180
ccagacagtg tgaagggtcg attcaccatc tccagagaca atgccaagaa aaccctgtac  240
ctgcaaatga gcagtctgag gtctgaggac acggccatgt attactgtac aagacggggg  300
tacgacggcg tggacaaatg ggccaaggc accactctca cagtctcctc agctagcacc  360
aagggcccaa gtgtgtttcc cctggccccc agcagcaagt ctacttccgg cggaactgct  420
gccctgggtt gcctggtgaa ggactacttc ccctgtcccg tgacagtgtc ctggaactct  480
ggggctctga cttccggcgt gcacaccttc cccgccgtgc tgcagagcag cggcctgtac  540
agcctgagca gcgtggtgac agtgccctcc agctctctgg gaacccagac ctatatctgc  600
aacgtgaacc acaagcccag caacaccaag gtggacaaga gagtggagcc caagagctgc  660
gacaagaccc acacctgccc cccctgccca gctccagaac tgctgggagg gccttccgtg  720
ttcctgttcc cccccaagcc caaggacacc ctgatgatca gcaggacccc cgaggtgacc  780
tgcgtggtgg tggacgtgtc ccacgaggac ccagaggtga agttcaactg gtacgtggac  840
ggcgtggagg tgcacaacgc caagaccaag cccagagagg agcagtacaa cagcacctac  900
agggtggtgt ccgtgctgac cgtgctgcac caggactggc tgaacggcaa agaatacaag  960
tgcaaagtct ccaacaaggc cctgccagcc cccatcgaaa agacaatcag caaggccaag  1020
ggccagccac gggagcccca ggtgtacacc ctgcccccca gccgggagga gatgaccaag  1080
aaccaggtgt ccctgacctg tctggtgaag ggcttctacc cctgtgatat cgccgtggag  1140
tgggagagca acggccagcc cgagaacaac tacaagacca cccccccagt gctggacagc  1200
gacggcagct tcttcctgta cagcaagctg accgtggaca agtccaggtg gcagcagggc  1260
aacgtgttca gctgcagcgt gatgcacgag gccctgcaca accactacac ccagaagtcc  1320
ctgagcctga gccccggcaa g                                           1341

SEQ ID NO: 452          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 452
KSGQSLLDSD GKTYLN                                                 16

SEQ ID NO: 453          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 453
LVSKLDS                                                           7

SEQ ID NO: 454          moltype = AA  length = 9
FEATURE                 Location/Qualifiers
```

```
REGION                  1..9
                        note = source = /note="Description of Artificial Sequence:
                         Synthetic peptide"
source                  1..9
                        mol_type = protein
                        organism = synthetic construct
SEQUENCE: 454
WQGTHFPQT                                                                  9

SEQ ID NO: 455          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 455
KSGQSLLDSD GKTYLN                                                          16

SEQ ID NO: 456          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 456
LVSKLDS                                                                    7

SEQ ID NO: 457          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 457
WQGTHFPQT                                                                  9

SEQ ID NO: 458          moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 458
GQSLLDSDGK TY                                                              12

SEQ ID NO: 459          moltype =   length =
SEQUENCE: 459
000

SEQ ID NO: 460          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 460
GTHFPQ                                                                     6

SEQ ID NO: 461          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 461
QSLLDSDGKT Y                                                               11
```

```
SEQ ID NO: 462         moltype =   length =
SEQUENCE: 462
000

SEQ ID NO: 463         moltype = AA  length = 9
FEATURE                Location/Qualifiers
REGION                 1..9
                       note = source = /note="Description of Artificial Sequence:
                        Synthetic peptide"
source                 1..9
                       mol_type = protein
                       organism = synthetic construct
SEQUENCE: 463
WQGTHFPQT                                                         9

SEQ ID NO: 464         moltype = AA  length = 112
FEATURE                Location/Qualifiers
REGION                 1..112
                       note = source = /note="Description of Artificial Sequence:
                        Synthetic polypeptide"
source                 1..112
                       mol_type = protein
                       organism = synthetic construct
SEQUENCE: 464
DVVMTQTPLT LSVTIGQPAS ISCKSGQSLL DSDGKTYLNW FLQRPGQSPK RLIYLVSKLD  60
SGVPDRFTGS GSGTDFTLKI SRVEAEDLGV YYCWQGTHFP QTFGGGTKLE IK          112

SEQ ID NO: 465         moltype = DNA  length = 336
FEATURE                Location/Qualifiers
misc_feature           1..336
                       note = source = /note="Description of Artificial Sequence:
                        Synthetic polynucleotide"
source                 1..336
                       mol_type = other DNA
                       organism = synthetic construct
SEQUENCE: 465
gatgttgtga tgacccagac tccactcact ttgtcggtta ccattggaca accagcctcc  60
atctcttgca agtcaggtca gagcctctta gatagtgatg gaaagacata tttgaattgg  120
tttttacaga ggccaggcca gtctccaaag cgcctaatct atctggtgtc taaactggac  180
tctggagtcc ctgacaggtt cactggcagt ggatcaggga cagatttcac actgaaaatc  240
agcagagtgg aggctgagga tttgggagtt tattattgct ggcaaggtac acattttcct  300
cagacgttcg gtggaggcac caagctggaa atcaaa                           336

SEQ ID NO: 466         moltype = AA  length = 219
FEATURE                Location/Qualifiers
REGION                 1..219
                       note = source = /note="Description of Artificial Sequence:
                        Synthetic polypeptide"
source                 1..219
                       mol_type = protein
                       organism = synthetic construct
SEQUENCE: 466
DVVMTQTPLT LSVTIGQPAS ISCKSGQSLL DSDGKTYLNW FLQRPGQSPK RLIYLVSKLD  60
SGVPDRFTGS GSGTDFTLKI SRVEAEDLGV YYCWQGTHFP QTFGGGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 467         moltype = DNA  length = 657
FEATURE                Location/Qualifiers
misc_feature           1..657
                       note = source = /note="Description of Artificial Sequence:
                        Synthetic polynucleotide"
source                 1..657
                       mol_type = other DNA
                       organism = synthetic construct
SEQUENCE: 467
gatgttgtga tgacccagac tccactcact ttgtcggtta ccattggaca accagcctcc  60
atctcttgca agtcaggtca gagcctctta gatagtgatg gaaagacata tttgaattgg  120
tttttacaga ggccaggcca gtctccaaag cgcctaatct atctggtgtc taaactggac  180
tctggagtcc ctgacaggtt cactggcagt ggatcaggga cagatttcac actgaaaatc  240
agcagagtgg aggctgagga tttgggagtt tattattgct ggcaaggtac acattttcct  300
cagacgttcg gtggaggcac caagctggaa atcaaacgta cggtggccgc tcccagcgtg  360
ttcatcttcc cccccagcga cgagcagctg aagagtggca ccgccagcgt ggtgtgcctg  420
ctgaacaact tctacccccg ggaggccaag gtgcagtgga aggtggacaa cgccctgcag  480
agcggcaaca gccaggagag cgtcaccgag caggacagca aggactccac ctacagcctg  540
agcagcaccc tgaccctgag caaggccgac tacgagaagc ataaggtgta cgcctgcgag  600
gtgacccacc agggcctgtc cagccccgtg accaagagct tcaacagggg cgagtgc     657

SEQ ID NO: 468         moltype = AA  length = 10
```

```
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 468
GFTFSNFAMS                                                                   10

SEQ ID NO: 469          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 469
TISTGGTYTY YPDSVKG                                                           17

SEQ ID NO: 470          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 470
RGYDGVDK                                                                     8

SEQ ID NO: 471          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 471
SNFAMS                                                                       6

SEQ ID NO: 472          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 472
TISTGGTYTY YPDSVKG                                                           17

SEQ ID NO: 473          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 473
RGYDGVDK                                                                     8

SEQ ID NO: 474          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 474
GFTFSNF                                                                      7

SEQ ID NO: 475          moltype = AA  length = 6
FEATURE                 Location/Qualifiers
REGION                  1..6
```

```
                         note = source = /note="Description of Artificial Sequence:
                          Synthetic peptide"
source                   1..6
                         mol_type = protein
                         organism = synthetic construct
SEQUENCE: 475
STGGTY                                                                    6

SEQ ID NO: 476           moltype = AA  length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 476
RGYDGVDK                                                                  8

SEQ ID NO: 477           moltype = AA  length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 477
GFTFSNFA                                                                  8

SEQ ID NO: 478           moltype = AA  length = 8
FEATURE                  Location/Qualifiers
REGION                   1..8
                         note = source = /note="Description of Artificial Sequence:
                          Synthetic peptide"
source                   1..8
                         mol_type = protein
                         organism = synthetic construct
SEQUENCE: 478
ISTGGTYT                                                                  8

SEQ ID NO: 479           moltype = AA  length = 10
FEATURE                  Location/Qualifiers
REGION                   1..10
                         note = source = /note="Description of Artificial Sequence:
                          Synthetic peptide"
source                   1..10
                         mol_type = protein
                         organism = synthetic construct
SEQUENCE: 479
TRRGYDGVDK                                                                10

SEQ ID NO: 480           moltype = AA  length = 117
FEATURE                  Location/Qualifiers
REGION                   1..117
                         note = source = /note="Description of Artificial Sequence:
                          Synthetic polypeptide"
source                   1..117
                         mol_type = protein
                         organism = synthetic construct
SEQUENCE: 480
EVHLVESGGG LVKPGGSLKL SCAASGFTFS NFAMSWVRQT PEKRLEWVAT ISTGGTYTYY  60
PDSVKGRFTI SRDNAKKTLY LQMSSLRSED TAMYYCTRRG YDGVDKWGQG TTLTVSS     117

SEQ ID NO: 481           moltype = DNA  length = 351
FEATURE                  Location/Qualifiers
misc_feature             1..351
                         note = source = /note="Description of Artificial Sequence:
                          Synthetic polynucleotide"
source                   1..351
                         mol_type = other DNA
                         organism = synthetic construct
SEQUENCE: 481
gaagtgcatc tggtggagtc tgggggaggc ttagtgaagc ctggagggtc cctgaaactc  60
tcctgtgcag cctctggatt cactttcagt aactttgcca tgtcttgggt tcgccagact  120
ccggagaaga gactggagtg ggtcgcaacc attagtactg gtggtactta cacctactat  180
ccagacagtg tgaagggtcg attcaccatc tccagagaca atgccaagaa aaccctgtac  240
ctgcaaatga gcagtctgag gtctgaggac acggccatgt attactgtac aagacggggg  300
tacgacggcg tggacaaatg gggccaaggc accactctca cagtctcctc a           351
```

```
SEQ ID NO: 482         moltype = AA  length = 447
FEATURE                Location/Qualifiers
REGION                 1..447
                       note = source = /note="Description of Artificial Sequence:
                        Synthetic polypeptide"
source                 1..447
                       mol_type = protein
                       organism = synthetic construct
SEQUENCE: 482
EVHLVESGGG LVKPGGSLKL SCAASGFTFS NFAMSWVRQT PEKRLEWVAT ISTGGTYTYY  60
PDSVKGRFTI SRDNAKKTLY LQMSSLRSED TAMYYCTRRG YDGVDKWGQG TTLTVSSAST  120
KGPSVFPLAP SSKSTSGGTA ALGCLVKDYF PCPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVAVSHED PEVKFNWYVD GVEVHNAKTK PREEQYNSTY  300
RVVSVLTVLH QDWLNGKEYK CKVSNKALAA PIEKTISKAK GQPREPQVYT LPPSREEMTK  360
NQVSLTCLVK GFYPCDIAVE WESNGQPENN YKTTPPVLDS DGSFFLYSKL TVDKSRWQQG  420
NVFSCSVMHE ALHNHYTQKS LSLSPGK                                     447

SEQ ID NO: 483         moltype = DNA  length = 1341
FEATURE                Location/Qualifiers
misc_feature           1..1341
                       note = source = /note="Description of Artificial Sequence:
                        Synthetic polynucleotide"
source                 1..1341
                       mol_type = other DNA
                       organism = synthetic construct
SEQUENCE: 483
gaagtgcatc tggtggagtc tgggggaggc ttagtgaagc ctggagggtc cctgaaactc  60
tcctgtgcag cctctggatt cactttcagt aactttgcca tgtcttgggt tcgccagact  120
ccggagaaga gactggagtg ggtcgcaacc attagtactg gtggtactta cacctactat  180
ccagacagtg tgaagggtcg attcaccatc tccagagaca atgccaagaa aaccctgtac  240
ctgcaaatga gcagtctgag gtctgaggac acggccatgt attactgtac aagacggggg  300
tacgacggcg tggacaaatg gggccaaggc accactctca cagtctcctc agctagcacc  360
aagggcccaa gtgtgtttcc cctggccccc agcagcaagt ctacttccgg cggaactgct  420
gccctgggtt gcctggtgaa ggactacttc cctgtcccg tgacagtgtc ctggaactct  480
ggggctctga cttccggcgt gcacaccttc cccgccgtgc tgcagagcag cggcctgtac  540
agcctgagca gcgtggtgac agtgccctcc agctctctgg gaacccagac ctatatctgc  600
aacgtgaacc acaagcccag caacaccaag gtggacaaga gagtggagcc caagagctgc  660
gacaagaccc acacctgccc cccctgccca gctccagaac tgctgggagg gccttccgtg  720
ttcctgttcc cccccaagcc caaggacacc ctgatgatca gcaggacccc cgaggtgacc  780
tgcgtggtgg tggccgtgtc ccacgaggac ccagaggtga agttcaactg gtacgtggac  840
ggcgtggagg tgcacaacgc caagaccaag cccagagagg agcagtacaa cagcacctac  900
agggtggtgt ccgtgctgac cgtgctgcac caggactggc tgaacggcaa agaatacaag  960
tgcaaagtct ccaacaaggc cctggctgcc ccaatcgaaa agacaatcag caaggccaag  1020
ggccagccac gggagcccca ggtgtacacc ctgcccccca gccgggagga gatgaccaag  1080
aaccaggtgt ccctgacctg tctggtgaag ggcttctacc cctgtgatat cgccgtggag  1140
tgggagagca acggccagcc cgagaacaac tacaagacca ccccccccagt gctggacagc  1200
gacggcagct tcttcctgta cagcaagctg accgtggaca agtccaggtg gcagcagggc  1260
aacgtgttca gctgcagcgt gatgcacgag gccctgcaca accactacac ccagaagtcc  1320
ctgagcctga gccccggcaa g                                           1341

SEQ ID NO: 484         moltype = AA  length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 484
KSGQSLLDSD GKTYLN                                                 16

SEQ ID NO: 485         moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 485
LVSKLDS                                                           7

SEQ ID NO: 486         moltype = AA  length = 9
FEATURE                Location/Qualifiers
REGION                 1..9
                       note = source = /note="Description of Artificial Sequence:
                        Synthetic peptide"
```

```
source                  1..9
                        mol_type = protein
                        organism = synthetic construct
SEQUENCE: 486
WQGTHFPQT                                                                     9

SEQ ID NO: 487          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 487
KSGQSLLDSD GKTYLN                                                             16

SEQ ID NO: 488          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 488
LVSKLDS                                                                       7

SEQ ID NO: 489          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 489
WQGTHFPQT                                                                     9

SEQ ID NO: 490          moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 490
GQSLLDSDGK TY                                                                 12

SEQ ID NO: 491          moltype =   length =
SEQUENCE: 491
000

SEQ ID NO: 492          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 492
GTHFPQ                                                                        6

SEQ ID NO: 493          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 493
QSLLDSDGKT Y                                                                  11

SEQ ID NO: 494          moltype =   length =
SEQUENCE: 494
000
```

```
SEQ ID NO: 495         moltype = AA  length = 9
FEATURE                Location/Qualifiers
REGION                 1..9
                       note = source = /note="Description of Artificial Sequence:
                        Synthetic peptide"
source                 1..9
                       mol_type = protein
                       organism = synthetic construct
SEQUENCE: 495
WQGTHFPQT                                                         9

SEQ ID NO: 496         moltype = AA  length = 112
FEATURE                Location/Qualifiers
REGION                 1..112
                       note = source = /note="Description of Artificial Sequence:
                        Synthetic polypeptide"
source                 1..112
                       mol_type = protein
                       organism = synthetic construct
SEQUENCE: 496
DVVMTQTPLT LSVTIGQPAS ISCKSGQSLL DSDGKTYLNW FLQRPGQSPK RLIYLVSKLD  60
SGVPDRFTGS GSGTDFTLKI SRVEAEDLGV YYCWQGTHFP QTFGGGTKLE IK          112

SEQ ID NO: 497         moltype = DNA  length = 336
FEATURE                Location/Qualifiers
misc_feature           1..336
                       note = source = /note="Description of Artificial Sequence:
                        Synthetic polynucleotide"
source                 1..336
                       mol_type = other DNA
                       organism = synthetic construct
SEQUENCE: 497
gatgttgtga tgacccagac tccactcact ttgtcggtta ccattggaca accagcctcc  60
atctcttgca agtcaggtca gagcctctta gatagtgatg gaaagacata tttgaattgg  120
tttttacaga ggccaggcca gtctccaaag cgcctaatct atctggtgtc taaactggac  180
tctggagtcc ctgacaggtt cactggcagt ggatcaggga cagatttcac actgaaaatc  240
agcagagtgg aggctgagga tttgggagtt tattattgct ggcaaggtac acattttcct  300
cagacgttcg gtggaggcac caagctggaa atcaaa                           336

SEQ ID NO: 498         moltype = AA  length = 219
FEATURE                Location/Qualifiers
REGION                 1..219
                       note = source = /note="Description of Artificial Sequence:
                        Synthetic polypeptide"
source                 1..219
                       mol_type = protein
                       organism = synthetic construct
SEQUENCE: 498
DVVMTQTPLT LSVTIGQPAS ISCKSGQSLL DSDGKTYLNW FLQRPGQSPK RLIYLVSKLD  60
SGVPDRFTGS GSGTDFTLKI SRVEAEDLGV YYCWQGTHFP QTFGGGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 499         moltype = DNA  length = 657
FEATURE                Location/Qualifiers
misc_feature           1..657
                       note = source = /note="Description of Artificial Sequence:
                        Synthetic polynucleotide"
source                 1..657
                       mol_type = other DNA
                       organism = synthetic construct
SEQUENCE: 499
gatgttgtga tgacccagac tccactcact ttgtcggtta ccattggaca accagcctcc  60
atctcttgca agtcaggtca gagcctctta gatagtgatg gaaagacata tttgaattgg  120
tttttacaga ggccaggcca gtctccaaag cgcctaatct atctggtgtc taaactggac  180
tctggagtcc ctgacaggtt cactggcagt ggatcaggga cagatttcac actgaaaatc  240
agcagagtgg aggctgagga tttgggagtt tattattgct ggcaaggtac acattttcct  300
cagacgttcg gtggaggcac caagctggaa atcaaacgta cggtggccgc tcccagcgtg  360
ttcatcttcc cccccagcga cgagcagctg aagagtggca ccgccagcgt ggtgtgcctg  420
ctgaacaact tctacccccg ggaggccaag gtgcagtgga aggtggacaa cgccctgcag  480
agcggcaaca gccaggagag cgtcaccgag caggacagca aggactccac ctacagcctg  540
agcagcaccc tgaccctgag caaggccgac tacgagaagc ataaggtgta cgcctgcgag  600
gtgacccacc agggcctgtc cagccccgtg accaagagct tcaacagggg cgagtgc     657

SEQ ID NO: 500         moltype = AA  length = 11
FEATURE                Location/Qualifiers
REGION                 1..11
                       note = source = /note="Description of Artificial Sequence:
```

```
                         Synthetic peptide"
source                  1..11
                        mol_type = protein
                        organism = synthetic construct
SEQUENCE: 500
GYSITSGYSW H                                                    11

SEQ ID NO: 501          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 501
HIHSSGSTNY NPSLKS                                               16

SEQ ID NO: 502          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 502
GGVQAFAY                                                        8

SEQ ID NO: 503          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 503
SGYSWH                                                          6

SEQ ID NO: 504          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 504
HIHSSGSTNY NPSLKS                                               16

SEQ ID NO: 505          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 505
GGVQAFAY                                                        8

SEQ ID NO: 506          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 506
GYSITSGY                                                        8

SEQ ID NO: 507          moltype = AA  length = 5
FEATURE                 Location/Qualifiers
REGION                  1..5
                        note = source = /note="Description of Artificial Sequence:
                         Synthetic peptide"
source                  1..5
```

```
                        mol_type = protein
                        organism = synthetic construct
SEQUENCE: 507
HSSGS                                                                5

SEQ ID NO: 508          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 508
GGVQAFAY                                                             8

SEQ ID NO: 509          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 509
GYSITSGYS                                                            9

SEQ ID NO: 510          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 510
IHSSGST                                                              7

SEQ ID NO: 511          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 511
ARGGVQAFAY                                                           10

SEQ ID NO: 512          moltype = AA  length = 117
FEATURE                 Location/Qualifiers
REGION                  1..117
                        note = source = /note="Description of Artificial Sequence:
                         Synthetic polypeptide"
source                  1..117
                        mol_type = protein
                        organism = synthetic construct
SEQUENCE: 512
DVQLQESGPG LVKPSQTLSL TCTVSGYSIT SGYSWHWIRQ HPGKGLEWMA HIHSSGSTNY  60
NPSLKSRITI SRDTSKNQFS LKLSSVTAAD TAVYYCARGG VQAFAYWGQG TLVTVSS     117

SEQ ID NO: 513          moltype = DNA  length = 351
FEATURE                 Location/Qualifiers
misc_feature            1..351
                        note = source = /note="Description of Artificial Sequence:
                         Synthetic polynucleotide"
source                  1..351
                        mol_type = other DNA
                        organism = synthetic construct
SEQUENCE: 513
gacgtgcagc tgcaggaatc tggccctggc ctggtgaaac cctcccagac cctgtccctg  60
acctgcaccg tgtccggcta ctccatcacc tccggctaca gctggcactg gatccggcag  120
caccccggca agggcctgga atggatggcc cacatccact cctccggctc caccaactac  180
aaccccagcc tgaagtccag aatcaccatc agccgggaca cctccaagaa ccagttctcc  240
ctgaagctgt cctccgtgac cgccgctgac accgccgtgt actactgtgc cagaggcggc  300
gtgcaggcct tcgcttattg gggccagggc accctggtga cagtgtcctc c           351

SEQ ID NO: 514          moltype = AA  length = 447
FEATURE                 Location/Qualifiers
```

-continued

```
REGION                  1..447
                        note = source = /note="Description of Artificial Sequence:
                         Synthetic polypeptide"
source                  1..447
                        mol_type = protein
                        organism = synthetic construct
SEQUENCE: 514
DVQLQESGPG LVKPSQTLSL TCTVSGYSIT SGYSWHWIRQ HPGKGLEWMA HIHSSGSTNY  60
NPSLKSRITI SRDTSKNQFS LKLSSVTAAD TAVYYCARGG VQAFAYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVAVSHED PEVKFNWYVD GVEVHNAKTK PREEQYNSTY  300
RVVSVLTVLH QDWLNGKEYK CKVSNKALAA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                    447

SEQ ID NO: 515          moltype = DNA  length = 1341
FEATURE                 Location/Qualifiers
misc_feature            1..1341
                        note = source = /note="Description of Artificial Sequence:
                         Synthetic polynucleotide"
source                  1..1341
                        mol_type = other DNA
                        organism = synthetic construct
SEQUENCE: 515
gacgtgcagc tgcaggaatc tggccctggc ctggtgaaac cctcccagac cctgtccctg  60
acctgcaccg tgtccggcta ctccatcacc tccggctaca gctggcactg gatccggcag  120
caccccggca agggcctgga atggatggcc cacatccact cctccggctc caccaactac  180
aaccccagcc tgaagtccag aatcaccatc agccgggaca cctccaagaa ccagttctcc  240
ctgaagctgt cctccgtgac cgccgctgac accgccgtgt actactgtgc cagaggcggc  300
gtgcaggcct tcgcttattg gggccagggc accctggtga cagtgtcctc cgctagcacc  360
aagggcccaa gtgtgtttcc cctggccccc agcagcaagt ctacttccgg cggaactgct  420
gccctgggtt gcctggtgaa ggactacttc cccgagcccg tgacagtgtc ctggaactct  480
ggggctctga cttccggcgt gcacaccttc cccgccgtgc tgcagagcag cggcctgtac  540
agcctgagca gcgtggtgac agtgccctcc agctctctgg gaacccagac ctatatctgc  600
aacgtgaacc acaagcccag caacaccaag gtggacaaga gagtggagcc caagagctgc  660
gacaagaccc acacctgccc cccctgccca gctccagaac tgctgggagg gccttccgtg  720
ttcctgttcc cccccaagcc caaggacacc ctgatgatca gcaggacccc cgaggtgacc  780
tgcgtggtgg tggccgtgtc ccacgaggac ccagaggtga agttcaactg gtacgtggac  840
ggcgtggagg tgcacaacgc caagaccaag cccagagagg agcagtacaa cagcacctac  900
agggtggtgt ccgtgctgac cgtgctgcac caggactggc tgaacggcaa agaatacaag  960
tgcaaagtct ccaacaaggc cctggctgcc ccaatcgaaa agacaatcag caaggccaag  1020
ggccagccac gggagcccca ggtgtacacc ctgcccccca gccgggagga gatgaccaag  1080
aaccaggtgt ccctgacctg tctggtgaag ggcttctacc ccagcgatat cgccgtggag  1140
tgggagagca acggccagcc cgagaacaac tacaagacca ccccccccagt gctggacagc  1200
gacggcagct tcttcctgta cagcaagctg accgtggaca agtccaggtg gcagcagggc  1260
aacgtgttca gctgcagcgt gatgcacgag gccctgcaca accactacac ccagaagtcc  1320
ctgagcctga gccccggcaa g                                          1341

SEQ ID NO: 516          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 516
SASSSVIYMH                                                       10

SEQ ID NO: 517          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 517
DTSKLAS                                                          7

SEQ ID NO: 518          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
```

```
SEQUENCE: 518
QQWSSNPLT                                                      9

SEQ ID NO: 519          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 519
SASSSVIYMH                                                     10

SEQ ID NO: 520          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 520
DTSKLAS                                                        7

SEQ ID NO: 521          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 521
QQWSSNPLT                                                      9

SEQ ID NO: 522          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 522
SSSVIY                                                         6

SEQ ID NO: 523          moltype =   length =
SEQUENCE: 523
000

SEQ ID NO: 524          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 524
WSSNPL                                                         6

SEQ ID NO: 525          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 525
SSVIY                                                          5

SEQ ID NO: 526          moltype =   length =
SEQUENCE: 526
000

SEQ ID NO: 527          moltype = AA  length = 9
FEATURE                 Location/Qualifiers
```

```
REGION                  1..9
                        note = source = /note="Description of Artificial Sequence:
                         Synthetic peptide"
source                  1..9
                        mol_type = protein
                        organism = synthetic construct
SEQUENCE: 527
QQWSSNPLT                                                            9

SEQ ID NO: 528          moltype = AA  length = 106
FEATURE                 Location/Qualifiers
REGION                  1..106
                        note = source = /note="Description of Artificial Sequence:
                         Synthetic polypeptide"
source                  1..106
                        mol_type = protein
                        organism = synthetic construct
SEQUENCE: 528
EIVLTQSPAT LSASPGERVT MSCSASSSVI YMHWYQQKPG QAPRRWIYDT SKLASGVPAR  60
FSGSGSGTDY TLTISSMEPE DAAVYYCQQW SSNPLTFGQG TKLEIK                 106

SEQ ID NO: 529          moltype = DNA  length = 318
FEATURE                 Location/Qualifiers
misc_feature            1..318
                        note = source = /note="Description of Artificial Sequence:
                         Synthetic polynucleotide"
source                  1..318
                        mol_type = other DNA
                        organism = synthetic construct
SEQUENCE: 529
gagatcgtgc tgacccagtc ccctgccacc ctgtctgcta gccctggcga gcgcgtgaca  60
atgtcctgct ccgcctcctc ctccgtgatc tacatgcact ggtatcagca gaagcccggc  120
caggcccctc ggcggtggat ctacgatacc tccaagctgg cctccggcgt gcccgccaga  180
ttctccggct ctggctctgg caccgactac accctgacca tctccagcat ggaacccgag  240
gacgccgccg tgtactactg ccagcagtgg tcctccaacc ccctgacctt cggccagggc  300
accaagctgg aaatcaag                                                318

SEQ ID NO: 530          moltype = AA  length = 213
FEATURE                 Location/Qualifiers
REGION                  1..213
                        note = source = /note="Description of Artificial Sequence:
                         Synthetic polypeptide"
source                  1..213
                        mol_type = protein
                        organism = synthetic construct
SEQUENCE: 530
EIVLTQSPAT LSASPGERVT MSCSASSSVI YMHWYQQKPG QAPRRWIYDT SKLASGVPAR  60
FSGSGSGTDY TLTISSMEPE DAAVYYCQQW SSNPLTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 531          moltype = DNA  length = 639
FEATURE                 Location/Qualifiers
misc_feature            1..639
                        note = source = /note="Description of Artificial Sequence:
                         Synthetic polynucleotide"
source                  1..639
                        mol_type = other DNA
                        organism = synthetic construct
SEQUENCE: 531
gagatcgtgc tgacccagtc ccctgccacc ctgtctgcta gccctggcga gcgcgtgaca  60
atgtcctgct ccgcctcctc ctccgtgatc tacatgcact ggtatcagca gaagcccggc  120
caggcccctc ggcggtggat ctacgatacc tccaagctgg cctccggcgt gcccgccaga  180
ttctccggct ctggctctgg caccgactac accctgacca tctccagcat ggaacccgag  240
gacgccgccg tgtactactg ccagcagtgg tcctccaacc ccctgacctt cggccagggc  300
accaagctgg aaatcaagcg tacggtggcc gctcccagcg tgttcatctt cccccccagc  360
gacgagcagc tgaagagtgg caccgccagc gtggtgtgcc tgctgaacaa cttctacccc  420
cgggaggcca aggtgcagtg gaaggtggac aacgccctgc agagcggcaa cagccaggag  480
agcgtcaccg agcaggacag caaggactcc acctacagcc tgagcagcac cctgaccctg  540
agcaaggccg actacgagaa gcataaggtg tacgcctgcg aggtgaccca ccagggcctg  600
tccagccccg tgaccaagag cttcaacagg ggcgagtgc                         639

SEQ ID NO: 532          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
```

```
                         organism = synthetic construct
SEQUENCE: 532
GFTFSTYAMS                                                          10

SEQ ID NO: 533           moltype = AA  length = 17
FEATURE                  Location/Qualifiers
REGION                   1..17
                         note = source = /note="Description of Artificial Sequence:
                          Synthetic peptide"
source                   1..17
                         mol_type = protein
                         organism = synthetic construct
SEQUENCE: 533
TISDAGSYSY YPDNVKG                                                  17

SEQ ID NO: 534           moltype = AA  length = 13
FEATURE                  Location/Qualifiers
REGION                   1..13
                         note = source = /note="Description of Artificial Sequence:
                          Synthetic peptide"
source                   1..13
                         mol_type = protein
                         organism = synthetic construct
SEQUENCE: 534
RGSRYEEYYV MDY                                                      13

SEQ ID NO: 535           moltype = AA  length = 5
FEATURE                  Location/Qualifiers
REGION                   1..5
                         note = source = /note="Description of Artificial Sequence:
                          Synthetic peptide"
source                   1..5
                         mol_type = protein
                         organism = synthetic construct
SEQUENCE: 535
TYAMS                                                               5

SEQ ID NO: 536           moltype = AA  length = 17
FEATURE                  Location/Qualifiers
REGION                   1..17
                         note = source = /note="Description of Artificial Sequence:
                          Synthetic peptide"
source                   1..17
                         mol_type = protein
                         organism = synthetic construct
SEQUENCE: 536
TISDAGSYSY YPDNVKG                                                  17

SEQ ID NO: 537           moltype = AA  length = 13
FEATURE                  Location/Qualifiers
REGION                   1..13
                         note = source = /note="Description of Artificial Sequence:
                          Synthetic peptide"
source                   1..13
                         mol_type = protein
                         organism = synthetic construct
SEQUENCE: 537
RGSRYEEYYV MDY                                                      13

SEQ ID NO: 538           moltype = AA  length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 538
GFTFSTY                                                             7

SEQ ID NO: 539           moltype = AA  length = 6
FEATURE                  Location/Qualifiers
REGION                   1..6
                         note = source = /note="Description of Artificial Sequence:
                          Synthetic peptide"
source                   1..6
                         mol_type = protein
                         organism = synthetic construct
SEQUENCE: 539
```

```
SDAGSY                                                       6

SEQ ID NO: 540          moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 540
RGSRYEEYYV MDY                                               13

SEQ ID NO: 541          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 541
GFTFSTYA                                                     8

SEQ ID NO: 542          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 542
ISDAGSYS                                                     8

SEQ ID NO: 543          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 543
ARRGSRYEEY YVMDY                                             15

SEQ ID NO: 544          moltype = AA  length = 122
FEATURE                 Location/Qualifiers
REGION                  1..122
                        note = source = /note="Description of Artificial Sequence:
                         Synthetic polypeptide"
source                  1..122
                        mol_type = protein
                        organism = synthetic construct
SEQUENCE: 544
EVQLVESGGG LVKPGGSLRL SCAASGFTFS TYAMSWVRQA PGKGLEWVAT ISDAGSYSYY  60
PDNVKGRFTI SRDNAKNSLY LQMNSLRAED TAVYYCARRG SRYEEYYVMD YWGQGTTVTV  120
SS                                                           122

SEQ ID NO: 545          moltype = DNA  length = 366
FEATURE                 Location/Qualifiers
misc_feature            1..366
                        note = source = /note="Description of Artificial Sequence:
                         Synthetic polynucleotide"
source                  1..366
                        mol_type = other DNA
                        organism = synthetic construct
SEQUENCE: 545
gaggtgcagc tggtggaatc tggcggaggc ctggtgaaac ccggcggatc cctgagactg  60
tcctgcgccg cctccggctt caccttctcc acctacgcca tgtcctgggt gcggcaggct  120
cccggcaagg gcctggaatg ggtggccacc atctccgacg ccggctccta ctcctactac  180
cccgacaacg tgaagggcag attcaccatc agccgggaca acgccaagaa ctccctgtac  240
ctgcagatga actccctgcg ggccgaggac accgccgtgt actactgtgc cagacggggc  300
tccagatacg aagagtacta cgtgatggac tattggggcc agggcaccac cgtgacagtg  360
tcctcc                                                       366

SEQ ID NO: 546          moltype = AA  length = 452
FEATURE                 Location/Qualifiers
REGION                  1..452
```

```
                        note = source = /note="Description of Artificial Sequence:
                         Synthetic polypeptide"
source                  1..452
                        mol_type = protein
                        organism = synthetic construct
SEQUENCE: 546
EVQLVESGGG LVKPGGSLRL SCAASGFTFS TYAMSWVRQA PGKGLEWVAT ISDAGSYSYY  60
PDNVKGRFTI SRDNAKNSLY LQMNSLRAED TAVYYCARRG SRYEEYYVMD YWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLMISR TPEVTCVVVA VSHEDPEVKF NWYVDGVEVH NAKTKPREEQ  300
YNSTYRVVSV LTVLHQDWLN GKEYKCKVSN KALAAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 547          moltype = DNA  length = 1356
FEATURE                 Location/Qualifiers
misc_feature            1..1356
                        note = source = /note="Description of Artificial Sequence:
                         Synthetic polynucleotide"
source                  1..1356
                        mol_type = other DNA
                        organism = synthetic construct
SEQUENCE: 547
gaggtgcagc tggtggaatc tggcggaggc ctggtgaaac ccggcggatc cctgagactg  60
tcctgcgccg cctccggctt caccttctcc acctacgcca tgtcctgggt gcggcaggct  120
cccggcaagg gcctggaatg ggtggccacc atctccgacg ccggctccta ctcctactac  180
cccgacaacg tgaagggcag attcaccatc agccgggaca acgccaagaa ctccctgtac  240
ctgcagatga actccctgcg ggccgaggac accgccgtgt actactgtgc cagacggggc  300
tccagatacg aagagtacta cgtgatggac tattggggcc agggcaccac cgtgacagtg  360
tcctccgcta gcaccaaggg cccaagtgtg tttcccctgg cccccagcag caagtctact  420
tccggcggaa ctgctgccct gggttgcctg gtgaaggact acttccccga gcccgtgaca  480
gtgtcctgga actctggggc tctgacttcc ggcgtgcaca ccttccccgc cgtgctgcag  540
agcagcggcc tgtacagcct gagcagcgtg gtgacagtgc cctccagctc tctgggaacc  600
cagacctata tctgcaacgt gaaccacaag cccagcaaca ccaaggtgga caagagagtg  660
gagcccaaga gctgcgacaa gacccacacc tgccccccct gcccagctcc agaactgctg  720
ggagggcctt ccgtgttcct gttccccccc aagcccaagg acaccctgat gatcagcagg  780
acccccgagg tgacctgcgt ggtggtggcc gtgtcccacg aggacccaga ggtgaagttc  840
aactggtacg tggacggcgt ggaggtgcac aacgccaaga ccaagcccag agaggagcag  900
tacaacagca cctacagggt ggtgtccgtg ctgaccgtgc tgcaccagga ctggctgaac  960
ggcaaagaat acaagtgcaa agtctccaac aaggccctgg ctgccccaat cgaaaagaca  1020
atcagcaagg ccaagggcca gccacgggag ccccaggtgt acaccctgcc ccccagccgg  1080
gaggagatga ccaagaacca ggtgtccctg acctgtctgg tgaagggctt ctaccccagc  1140
gatatcgccg tggagtggga gagcaacggc cagcccgaga acaactacaa gaccaccccc  1200
ccagtgctgg acagcgacgg cagcttcttc ctgtacagca agctgaccgt ggacaagtcc  1260
aggtggcagc agggcaacgt gttcagctgc agcgtgatgc acgaggccct gcacaaccac  1320
tacacccaga agtccctgag cctgagcccc ggcaag                            1356

SEQ ID NO: 548          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 548
RASQSISNNL H                                                       11

SEQ ID NO: 549          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 549
YASQSIS                                                            7

SEQ ID NO: 550          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 550
```

```
QQSSSWLT                                                                    8

SEQ ID NO: 551          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 551
RASQSISNNL H                                                                11

SEQ ID NO: 552          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 552
YASQSIS                                                                     7

SEQ ID NO: 553          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 553
QQSSSWLT                                                                    8

SEQ ID NO: 554          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 554
SQSISNN                                                                     7

SEQ ID NO: 555          moltype =   length =
SEQUENCE: 555
000

SEQ ID NO: 556          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 556
SSSWL                                                                       5

SEQ ID NO: 557          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 557
QSISNN                                                                      6

SEQ ID NO: 558          moltype =   length =
SEQUENCE: 558
000

SEQ ID NO: 559          moltype = AA  length = 8
FEATURE                 Location/Qualifiers
REGION                  1..8
```

```
                         note = source = /note="Description of Artificial Sequence:
                          Synthetic peptide"
source                   1..8
                         mol_type = protein
                         organism = synthetic construct
SEQUENCE: 559
QQSSSWLT                                                                    8

SEQ ID NO: 560           moltype = AA  length = 106
FEATURE                  Location/Qualifiers
REGION                   1..106
                         note = source = /note="Description of Artificial Sequence:
                          Synthetic polypeptide"
source                   1..106
                         mol_type = protein
                         organism = synthetic construct
SEQUENCE: 560
EIVLTQSPAT LSVSPGERVT LSCRASQSIS NNLHWYQQKP GQAPRLLIKY ASQSISGIPA  60
RFSGSGSGTD FTLTISSVEP EDFGVYFCQQ SSSWLTFGQG TKLEIK                 106

SEQ ID NO: 561           moltype = DNA  length = 318
FEATURE                  Location/Qualifiers
misc_feature             1..318
                         note = source = /note="Description of Artificial Sequence:
                          Synthetic polynucleotide"
source                   1..318
                         mol_type = other DNA
                         organism = synthetic construct
SEQUENCE: 561
gagatcgtgc tgacccagtc ccctgccacc ctgtccgtgt ctcccggcga gagagtgacc  60
ctgtcctgcc gggcctccca gtccatctcc aacaacctgc actggtatca gcagaagccc  120
ggccaggccc ctcggctgct gattaagtac gcctcccaga gcatctccgg catccctgcc  180
agattctccg gctccggcag cggcaccgac ttcaccctga ccatctccag cgtggaaccc  240
gaggacttcg gcgtgtactt ctgccagcag tcctcatcct ggctgacctt cggccagggc  300
accaagctgg aaatcaag                                                318

SEQ ID NO: 562           moltype = AA  length = 213
FEATURE                  Location/Qualifiers
REGION                   1..213
                         note = source = /note="Description of Artificial Sequence:
                          Synthetic polypeptide"
source                   1..213
                         mol_type = protein
                         organism = synthetic construct
SEQUENCE: 562
EIVLTQSPAT LSVSPGERVT LSCRASQSIS NNLHWYQQKP GQAPRLLIKY ASQSISGIPA  60
RFSGSGSGTD FTLTISSVEP EDFGVYFCQQ SSSWLTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 563           moltype = DNA  length = 639
FEATURE                  Location/Qualifiers
misc_feature             1..639
                         note = source = /note="Description of Artificial Sequence:
                          Synthetic polynucleotide"
source                   1..639
                         mol_type = other DNA
                         organism = synthetic construct
SEQUENCE: 563
gagatcgtgc tgacccagtc ccctgccacc ctgtccgtgt ctcccggcga gagagtgacc  60
ctgtcctgcc gggcctccca gtccatctcc aacaacctgc actggtatca gcagaagccc  120
ggccaggccc ctcggctgct gattaagtac gcctcccaga gcatctccgg catccctgcc  180
agattctccg gctccggcag cggcaccgac ttcaccctga ccatctccag cgtggaaccc  240
gaggacttcg gcgtgtactt ctgccagcag tcctcatcct ggctgacctt cggccagggc  300
accaagctgg aaatcaagcg tacggtggcc gctcccagcg tgttcatctt cccccccagc  360
gacgagcagc tgaagagtgg caccgccagc gtggtgtgcc tgctgaacaa cttctacccc  420
cgggaggcca aggtgcagtg gaaggtggac aacgccctgc agagcggcaa cagccaggag  480
agcgtcaccg agcaggacag caaggactcc acctacagcc tgagcagcac cctgaccctg  540
agcaaggccg actacgagaa gcataaggtg tacgcctgcg aggtgaccca ccagggcctg  600
tccagccccg tgaccaagag cttcaacagg ggcgagtgc                         639

SEQ ID NO: 564           moltype = AA  length = 10
FEATURE                  Location/Qualifiers
REGION                   1..10
                         note = source = /note="Description of Artificial Sequence:
                          Synthetic peptide"
source                   1..10
                         mol_type = protein
                         organism = synthetic construct
```

SEQUENCE: 564
GFTFSSYAMS 10

SEQ ID NO: 565 moltype = AA length = 17
FEATURE Location/Qualifiers
REGION 1..17
note = source = /note="Description of Artificial Sequence: Synthetic peptide"
source 1..17
mol_type = protein
organism = synthetic construct
SEQUENCE: 565
TISSGGSFTY YPDSVKG 17

SEQ ID NO: 566 moltype = AA length = 12
FEATURE Location/Qualifiers
REGION 1..12
note = source = /note="Description of Artificial Sequence: Synthetic peptide"
source 1..12
mol_type = protein
organism = synthetic construct
SEQUENCE: 566
RASTVVGTDF DV 12

SEQ ID NO: 567 moltype = AA length = 5
FEATURE Location/Qualifiers
REGION 1..5
note = source = /note="Description of Artificial Sequence: Synthetic peptide"
source 1..5
mol_type = protein
organism = synthetic construct
SEQUENCE: 567
SYAMS 5

SEQ ID NO: 568 moltype = AA length = 17
FEATURE Location/Qualifiers
REGION 1..17
note = source = /note="Description of Artificial Sequence: Synthetic peptide"
source 1..17
mol_type = protein
organism = synthetic construct
SEQUENCE: 568
TISSGGSFTY YPDSVKG 17

SEQ ID NO: 569 moltype = AA length = 12
FEATURE Location/Qualifiers
REGION 1..12
note = source = /note="Description of Artificial Sequence: Synthetic peptide"
source 1..12
mol_type = protein
organism = synthetic construct
SEQUENCE: 569
RASTVVGTDF DV 12

SEQ ID NO: 570 moltype = AA length = 7
FEATURE Location/Qualifiers
REGION 1..7
note = source = /note="Description of Artificial Sequence: Synthetic peptide"
source 1..7
mol_type = protein
organism = synthetic construct
SEQUENCE: 570
GFTFSSY 7

SEQ ID NO: 571 moltype = AA length = 6
FEATURE Location/Qualifiers
REGION 1..6
note = source = /note="Description of Artificial Sequence: Synthetic peptide"
source 1..6
mol_type = protein
organism = synthetic construct
SEQUENCE: 571
SSGGSF 6

```
SEQ ID NO: 572          moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 572
RASTVVGTDF DV                                                          12

SEQ ID NO: 573          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 573
GFTFSSYA                                                               8

SEQ ID NO: 574          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 574
ISSGGSFT                                                               8

SEQ ID NO: 575          moltype = AA  length = 14
FEATURE                 Location/Qualifiers
REGION                  1..14
                        note = source = /note="Description of Artificial Sequence:
                         Synthetic peptide"
source                  1..14
                        mol_type = protein
                        organism = synthetic construct
SEQUENCE: 575
ARRASTVVGT DFDV                                                        14

SEQ ID NO: 576          moltype = AA  length = 121
FEATURE                 Location/Qualifiers
REGION                  1..121
                        note = source = /note="Description of Artificial Sequence:
                         Synthetic polypeptide"
source                  1..121
                        mol_type = protein
                        organism = synthetic construct
SEQUENCE: 576
EVQLVESGGG LVKPGGSLRL SCAASGFTFS SYAMSWIRQA PGKGLEWVAT ISSGGSFTYY  60
PDSVKGRFTI SRDNAKNSLY LQMNSLRAED TAVYYCARRA STVVGTDFDV WGQGTTVTVS  120
S                                                                      121

SEQ ID NO: 577          moltype = DNA  length = 363
FEATURE                 Location/Qualifiers
misc_feature            1..363
                        note = source = /note="Description of Artificial Sequence:
                         Synthetic polynucleotide"
source                  1..363
                        mol_type = other DNA
                        organism = synthetic construct
SEQUENCE: 577
gaggtgcagc tggtggaatc tggcggaggc ctggtgaaac ccggcggatc cctgagactg  60
tcctgcgccg cctccggctt caccttctcc agctacgcca tgtcctggat ccggcaggct  120
cccggcaagg gcctggaatg ggtggccacc atctcctccg gcggcagctt cacctactac  180
cccgacagcg tgaagggcag attcaccatc agccgggaca acgccaagaa ctccctgtac  240
ctgcagatga actccctgcg ggccgaggac accgccgtgt actactgtgc cagacgggcc  300
tccaccgtcg tgggaaccga cttcgatgtg tggggccagg gcaccaccgt gacagtgtcc  360
tcc                                                                    363

SEQ ID NO: 578          moltype = AA  length = 451
FEATURE                 Location/Qualifiers
REGION                  1..451
                        note = source = /note="Description of Artificial Sequence:
```

```
                         Synthetic polypeptide"
source                  1..451
                        mol_type = protein
                        organism = synthetic construct
SEQUENCE: 578
EVQLVESGGG LVKPGGSLRL SCAASGFTFS SYAMSWIRQA PGKGLEWVAT ISSGGSFTYY  60
PDSVKGRFTI SRDNAKNSLY LQMNSLRAED TAVYYCARRA STVVGTDFDV WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVAV SHEDPEVKFN WYVDGVEVHN AKTKPREEQY  300
NSTYRVVSVL TVLHQDWLNG KEYKCKVSNK ALAAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 579          moltype = DNA  length = 1353
FEATURE                 Location/Qualifiers
misc_feature            1..1353
                        note = source = /note="Description of Artificial Sequence:
                         Synthetic polynucleotide"
source                  1..1353
                        mol_type = other DNA
                        organism = synthetic construct
SEQUENCE: 579
gaggtgcagc tggtggaatc tggcggaggc ctggtgaaac ccggcggatc cctgagactg  60
tcctgcgccg cctccggctt caccttctcc agctacgcca tgtcctggat ccggcaggct  120
cccggcaagg gcctggaatg ggtggccacc atctcctccg gcggcagctt cacctactac  180
cccgacagcg tgaagggcag attcaccatc agccgggaca acgccaagaa ctccctgtac  240
ctgcagatga actccctgcg ggccgaggac accgccgtgt actactgtgc cagacgggcc  300
tccaccgtcg tgggaaccga cttcgatgtg tggggccagg gcaccaccgt gacagtgtcc  360
tccgctagca ccaagggccc aagtgtgttt cccctggccc ccagcagcaa gtctacttcc  420
ggcggaactg ctgccctggg ttgcctggtg aaggactact tccccgagcc cgtgacagtg  480
tcctggaact ctggggctct gacttccggc gtgcacacct tccccgccgt gctgcagagc  540
agcggcctgt acagcctgag cagcgtggtg acagtgccct ccagctctct gggaacccag  600
acctatatct gcaacgtgaa ccacaagccc agcaacacca aggtggacaa gagagtggag  660
cccaagagct gcgacaagac ccacacctgc ccccctgcc cagctccaga actgctggga  720
gggccttccg tgttcctgtt cccccccaag cccaaggaca ccctgatgat cagcaggacc  780
cccgaggtga cctgcgtggt ggtggccgtg tcccacgagg acccagaggt gaagttcaac  840
tggtacgtgg acggcgtgga ggtgcacaac gccaagacca agcccagaga ggagcagtac  900
aacagcacct acagggtggt gtccgtgctg accgtgctgc accaggactg gctgaacggc  960
aaagaataca agtgcaaagt ctccaacaag gccctggctg ccccaatcga aaagacaatc  1020
agcaaggcca agggccagcc acgggagccc caggtgtaca ccctgccccc cagccgggag  1080
gagatgacca agaaccaggt gtccctgacc tgtctggtga agggcttcta ccccagcgat  1140
atcgccgtgg agtgggagag caacggccag cccgagaaca actacaagac cacccccccca  1200
gtgctggaca gcgacggcag cttcttcctg tacagcaagc tgaccgtgga caagtccagg  1260
tggcagcagg gcaacgtgtt cagctgcagc gtgatgcacg aggccctgca caaccactac  1320
acccagaagt ccctgagcct gagccccggc aag                               1353

SEQ ID NO: 580          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 580
RASQDIGSSL N                                                       11

SEQ ID NO: 581          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 581
ATSSLDS                                                            7

SEQ ID NO: 582          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 582
LQYASSPPT                                                          9
```

```
SEQ ID NO: 583          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 583
RASQDIGSSL N                                                        11

SEQ ID NO: 584          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 584
ATSSLDS                                                             7

SEQ ID NO: 585          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 585
LQYASSPPT                                                           9

SEQ ID NO: 586          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 586
SQDIGSS                                                             7

SEQ ID NO: 587          moltype =   length =
SEQUENCE: 587
000

SEQ ID NO: 588          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 588
YASSPP                                                              6

SEQ ID NO: 589          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 589
QDIGSS                                                              6

SEQ ID NO: 590          moltype =   length =
SEQUENCE: 590
000

SEQ ID NO: 591          moltype = AA  length = 9
FEATURE                 Location/Qualifiers
REGION                  1..9
                        note = source = /note="Description of Artificial Sequence:
```

```
                         Synthetic peptide"
source                  1..9
                        mol_type = protein
                        organism = synthetic construct
SEQUENCE: 591
LQYASSPPT                                                        9

SEQ ID NO: 592          moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 592
DIQMTQSPSS LSASVGDRVT LTCRASQDIG SSLNWLQQKP GKAIKRLIYA TSSLDSGVPS  60
RFSGSRSGTD YTLTISSLQP EDFVVYYCLQ YASSPPTFGG GTKLEIK                107

SEQ ID NO: 593          moltype = DNA  length = 321
FEATURE                 Location/Qualifiers
misc_feature            1..321
                        note = source = /note="Description of Artificial Sequence:
                         Synthetic polynucleotide"
source                  1..321
                        mol_type = other DNA
                        organism = synthetic construct
SEQUENCE: 593
gacatccaga tgacccagtc cccctccagc ctgtccgcct ccgtgggcga tagagtgacc  60
ctgacctgcc gggcctccca ggacatcggc tcctccctga actggctgca gcagaagccc  120
ggcaaggcca tcaagcggct gatctacgcc acctcctccc tggactccgg cgtgccctcc  180
cggttctccg gctctagatc cggcaccgac tacaccctga ccatctccag cctgcagccc  240
gaggacttcg tggtgtacta ctgcctgcag tacgcctcca gcccccccac ctttggcgga  300
ggcaccaagc tggaaatcaa g                                          321

SEQ ID NO: 594          moltype = AA  length = 214
FEATURE                 Location/Qualifiers
REGION                  1..214
                        note = source = /note="Description of Artificial Sequence:
                         Synthetic polypeptide"
source                  1..214
                        mol_type = protein
                        organism = synthetic construct
SEQUENCE: 594
DIQMTQSPSS LSASVGDRVT LTCRASQDIG SSLNWLQQKP GKAIKRLIYA TSSLDSGVPS  60
RFSGSRSGTD YTLTISSLQP EDFVVYYCLQ YASSPPTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 595          moltype = DNA  length = 642
FEATURE                 Location/Qualifiers
misc_feature            1..642
                        note = source = /note="Description of Artificial Sequence:
                         Synthetic polynucleotide"
source                  1..642
                        mol_type = other DNA
                        organism = synthetic construct
SEQUENCE: 595
gacatccaga tgacccagtc cccctccagc ctgtccgcct ccgtgggcga tagagtgacc  60
ctgacctgcc gggcctccca ggacatcggc tcctccctga actggctgca gcagaagccc  120
ggcaaggcca tcaagcggct gatctacgcc acctcctccc tggactccgg cgtgccctcc  180
cggttctccg gctctagatc cggcaccgac tacaccctga ccatctccag cctgcagccc  240
gaggacttcg tggtgtacta ctgcctgcag tacgcctcca gcccccccac ctttggcgga  300
ggcaccaagc tggaaatcaa gcgtacggtg gccgctccca gcgtgttcat cttccccccc  360
agcgacgagc agctgaagag tggcaccgcc agcgtggtgt gcctgctgaa caacttctac  420
cccCgggagg ccaaggtgca gtggaaggtg gacaacgccc tgcagagcgg caacagccag  480
gagagcgtca ccgagcagga cagcaaggac tccacctaca gcctgagcag caccctgacc  540
ctgagcaagg ccgactacga gaagcataag gtgtacgcct gcgaggtgac ccaccagggc  600
ctgtccagcc ccgtgaccaa gagcttcaac aggggcgagt gc                     642

SEQ ID NO: 596          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 596
```

```
GFTFSNFAMS                                                              10

SEQ ID NO: 597          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 597
TISTGGTYTY YPDSVKG                                                      17

SEQ ID NO: 598          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 598
RGYSGVDK                                                                8

SEQ ID NO: 599          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 599
SNFAMS                                                                  6

SEQ ID NO: 600          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 600
TISTGGTYTY YPDSVKG                                                      17

SEQ ID NO: 601          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 601
RGYSGVDK                                                                8

SEQ ID NO: 602          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 602
GFTFSNF                                                                 7

SEQ ID NO: 603          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 603
STGGTY                                                                  6
```

```
SEQ ID NO: 604          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 604
RGYSGVDK                                                                8

SEQ ID NO: 605          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 605
GFTFSNFA                                                                8

SEQ ID NO: 606          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 606
ISTGGTYT                                                                8

SEQ ID NO: 607          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 607
TRRGYSGVDK                                                              10

SEQ ID NO: 608          moltype = AA  length = 117
FEATURE                 Location/Qualifiers
REGION                  1..117
                        note = source = /note="Description of Artificial Sequence:
                         Synthetic polypeptide"
source                  1..117
                        mol_type = protein
                        organism = synthetic construct
SEQUENCE: 608
EVQLVESGGG LVKPGGSLRL SCAASGFTFS NFAMSWVRQA PGKGLEWVST ISTGGTYTYY  60
PDSVKGRFTI SRDNAKNSLY LQMNSLRAED TAVYYCARRG YSGVDKWGQG TTVTVSS     117

SEQ ID NO: 609          moltype = DNA  length = 351
FEATURE                 Location/Qualifiers
misc_feature            1..351
                        note = source = /note="Description of Artificial Sequence:
                         Synthetic polynucleotide"
source                  1..351
                        mol_type = other DNA
                        organism = synthetic construct
SEQUENCE: 609
gaggtgcagc tggtggaatc tggcggaggc ctggtgaaac ccggcggatc cctgagactg  60
tcctgcgccg cctccggctt caccttctcc aacttcgcca tgtcctgggt gcggcaggct  120
cccggcaagg gcctggaatg ggtgtccacc atctccaccg gcggcaccta cacctactac  180
cccgacagcg tgaagggcag attcaccatc agccgggaca acgccaagaa ctccctgtac  240
ctgcagatga actccctgcg ggccgaggac accgccgtgt actactgtgc cagacggggc  300
tactcaggcg tggacaaatg gggccagggc accaccgtga cagtgtcctc c           351

SEQ ID NO: 610          moltype = AA  length = 447
FEATURE                 Location/Qualifiers
REGION                  1..447
                        note = source = /note="Description of Artificial Sequence:
                         Synthetic polypeptide"
source                  1..447
                        mol_type = protein
```

```
                         organism = synthetic construct
SEQUENCE: 610
EVQLVESGGG LVKPGGSLRL SCAASGFTFS NFAMSWVRQA PGKGLEWVST ISTGGTYTYY  60
PDSVKGRFTI SRDNAKNSLY LQMNSLRAED TAVYYCARRG YSGVDKWGQG TTVTVSSAST  120
KGPSVFPLAP SSKSTSGGTA ALGCLVKDYF PCPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVAVSHED PEVKFNWYVD GVEVHNAKTK PREEQYNSTY  300
RVVSVLTVLH QDWLNGKEYK CKVSNKALAA PIEKTISKAK GQPREPQVYT LPPSREEMTK  360
NQVSLTCLVK GFYPCDIAVE WESNGQPENN YKTTPPVLDS DGSFFLYSKL TVDKSRWQQG  420
NVFSCSVMHE ALHNHYTQKS LSLSPGK                                     447

SEQ ID NO: 611           moltype = DNA  length = 1341
FEATURE                  Location/Qualifiers
misc_feature             1..1341
                         note = source = /note="Description of Artificial Sequence:
                          Synthetic polynucleotide"
source                   1..1341
                         mol_type = other DNA
                         organism = synthetic construct
SEQUENCE: 611
gaggtgcagc tggtggaatc tggcggaggc ctggtgaaac ccggcggatc cctgagactg  60
tcctgcgccg cctccggctt caccttctcc aacttcgcca tgtcctgggt gcggcaggct  120
cccggcaagg gcctggaatg ggtgtccacc atctccaccg gcggcaccta cacctactac  180
cccgacagcg tgaagggcag attcaccatc agccgggaca acgccaagaa ctccctgtac  240
ctgcagatga actccctgcg ggccgaggac accgccgtgt actactgtgc cagacggggc  300
tactcaggcg tggacaaatg gggccagggc accaccgtga cagtgtcctc cgctagcacc  360
aagggcccaa gtgtgtttcc cctggccccc agcagcaagt ctacttccgg cggaactgct  420
gccctgggtt gcctggtgaa ggactacttc ccctgtcccg tgacagtgtc ctggaactct  480
ggggctctga cttccggcgt gcacaccttc cccgccgtgc tgcagagcag cggcctgtac  540
agcctgagca gcgtggtgac agtgccctcc agctctctgg gaacccagac ctatatctgc  600
aacgtgaacc acaagcccag caacaccaag gtggacaaga gagtggagcc caagagctgc  660
gacaagaccc acacctgccc cccctgccca gctccagaac tgctgggagg gccttccgtg  720
ttcctgttcc cccccaagcc caaggacacc ctgatgatca gcaggacccc cgaggtgacc  780
tgcgtggtgg tggccgtgtc ccacgaggac ccagaggtga agttcaactg gtacgtggac  840
ggcgtggagg tgcacaacgc caagaccaag cccagagagg agcagtacaa cagcacctac  900
agggtggtgt ccgtgctgac cgtgctgcac caggactggc tgaacggcaa agaatacaag  960
tgcaaagtct ccaacaaggc cctggctgcc ccaatcgaaa agacaatcag caaggccaag  1020
ggccagccac gggagcccca ggtgtacacc ctgcccccca gccgggagga gatgaccaag  1080
aaccaggtgt ccctgacctg tctggtgaag ggcttctacc cctgtgatat cgccgtggag  1140
tgggagagca acggccagcc cgagaacaac tacaagacca cccccccagt gctggacagc  1200
gacggcagct tcttcctgta cagcaagctg accgtggaca agtccaggtg gcagcagggc  1260
aacgtgttca gctgcagcgt gatgcacgag gccctgcaca accactacac ccagaagtcc  1320
ctgagcctga gccccggcaa g                                           1341

SEQ ID NO: 612           moltype = AA  length = 16
FEATURE                  Location/Qualifiers
REGION                   1..16
                         note = source = /note="Description of Artificial Sequence:
                          Synthetic peptide"
source                   1..16
                         mol_type = protein
                         organism = synthetic construct
SEQUENCE: 612
KSGQSLLDST GKTYLN                                                 16

SEQ ID NO: 613           moltype = AA  length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 613
LVSKLDS                                                           7

SEQ ID NO: 614           moltype = AA  length = 9
FEATURE                  Location/Qualifiers
REGION                   1..9
                         note = source = /note="Description of Artificial Sequence:
                          Synthetic peptide"
source                   1..9
                         mol_type = protein
                         organism = synthetic construct
SEQUENCE: 614
WQGTHFPQT                                                         9

SEQ ID NO: 615           moltype = AA  length = 16
FEATURE                  Location/Qualifiers
```

```
REGION                  1..16
                        note = source = /note="Description of Artificial Sequence:
                         Synthetic peptide"
source                  1..16
                        mol_type = protein
                        organism = synthetic construct
SEQUENCE: 615
KSGQSLLDST GKTYLN                                                           16

SEQ ID NO: 616          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 616
LVSKLDS                                                                     7

SEQ ID NO: 617          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 617
WQGTHFPQT                                                                   9

SEQ ID NO: 618          moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 618
GQSLLDSTGK TY                                                               12

SEQ ID NO: 619          moltype =   length =
SEQUENCE: 619
000

SEQ ID NO: 620          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 620
GTHFPQ                                                                      6

SEQ ID NO: 621          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 621
QSLLDSTGKT Y                                                                11

SEQ ID NO: 622          moltype =   length =
SEQUENCE: 622
000

SEQ ID NO: 623          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
```

```
                        organism = synthetic construct
SEQUENCE: 623
WQGTHFPQT                                                       9

SEQ ID NO: 624          moltype = AA  length = 112
FEATURE                 Location/Qualifiers
REGION                  1..112
                        note = source = /note="Description of Artificial Sequence:
                         Synthetic polypeptide"
source                  1..112
                        mol_type = protein
                        organism = synthetic construct
SEQUENCE: 624
DVVMTQSPLS LPVTLGQPAS ISCKSGQSLL DSTGKTYLNW FLQRPGQSPR RLIYLVSKLD  60
SGVPDRFSGS GSGTDFTLKI SRVEAEDVGV YYCWQGTHFP QTFGGGTKLE IK          112

SEQ ID NO: 625          moltype = DNA  length = 336
FEATURE                 Location/Qualifiers
misc_feature            1..336
                        note = source = /note="Description of Artificial Sequence:
                         Synthetic polynucleotide"
source                  1..336
                        mol_type = other DNA
                        organism = synthetic construct
SEQUENCE: 625
gacgtggtga tgacccagtc ccccctgtcc ctgcctgtga ccctgggcca gcctgcctcc  60
atctcctgca agtccggcca gtccctgctg gactccactg gcaagaccta cctgaactgg  120
ttcctgcagc ggcctggcca gtcccctcgg cggctgatct acctggtgtc caagctggac  180
agcggcgtgc ccgacagatt ctccggctct ggctccggca ccgacttcac cctgaagatc  240
tcccgggtgg aagccgagga cgtgggcgtg tactactgct ggcagggcac ccacttcccc  300
cagaccttcg gcggaggcac caagctggaa atcaag                            336

SEQ ID NO: 626          moltype = AA  length = 219
FEATURE                 Location/Qualifiers
REGION                  1..219
                        note = source = /note="Description of Artificial Sequence:
                         Synthetic polypeptide"
source                  1..219
                        mol_type = protein
                        organism = synthetic construct
SEQUENCE: 626
DVVMTQSPLS LPVTLGQPAS ISCKSGQSLL DSTGKTYLNW FLQRPGQSPR RLIYLVSKLD  60
SGVPDRFSGS GSGTDFTLKI SRVEAEDVGV YYCWQGTHFP QTFGGGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 627          moltype = DNA  length = 657
FEATURE                 Location/Qualifiers
misc_feature            1..657
                        note = source = /note="Description of Artificial Sequence:
                         Synthetic polynucleotide"
source                  1..657
                        mol_type = other DNA
                        organism = synthetic construct
SEQUENCE: 627
gacgtggtga tgacccagtc ccccctgtcc ctgcctgtga ccctgggcca gcctgcctcc  60
atctcctgca agtccggcca gtccctgctg gactccactg gcaagaccta cctgaactgg  120
ttcctgcagc ggcctggcca gtcccctcgg cggctgatct acctggtgtc caagctggac  180
agcggcgtgc ccgacagatt ctccggctct ggctccggca ccgacttcac cctgaagatc  240
tcccgggtgg aagccgagga cgtgggcgtg tactactgct ggcagggcac ccacttcccc  300
cagaccttcg gcggaggcac caagctggaa atcaagcgta cggtggccgc tcccagcgtg  360
ttcatcttcc cccccagcga cgagcagctg aagagtggca ccgccagcgt ggtgtgcctg  420
ctgaacaact tctacccccg ggaggccaag gtgcagtgga aggtggacaa cgccctgcag  480
agcggcaaca gccaggagag cgtcaccgag caggacagca aggactccac ctacagcctg  540
agcagcaccc tgaccctgag caaggccgac tacgagaagc ataaggtgta cgcctgcgag  600
gtgacccacc agggcctgtc cagccccgtg accaagagct tcaacagggg cgagtgc     657

SEQ ID NO: 628          moltype = AA  length = 6
FEATURE                 Location/Qualifiers
REGION                  1..6
                        note = source = /note="Description of Artificial Sequence:
                         Synthetic 6xHis tag"
source                  1..6
                        mol_type = protein
                        organism = synthetic construct
SEQUENCE: 628
HHHHHH                                                          6

SEQ ID NO: 629          moltype = AA  length = 22
```

-continued

```
FEATURE                 Location/Qualifiers
REGION                  1..22
                        note = source = /note="Description of Artificial Sequence:
                         Synthetic peptide"
source                  1..22
                        mol_type = protein
                        organism = synthetic construct
SEQUENCE: 629
YGRKKRRQRR RLYRSPAMPE NL                                           22
```